US008673895B2

(12) United States Patent
Branstetter et al.

(10) Patent No.: US 8,673,895 B2
(45) Date of Patent: Mar. 18, 2014

(54) TETRAHYDRO-PYRIMIDOAZEPINES AS MODULATORS OF TRPV1

(75) Inventors: Bryan James Branstetter, Carlsbad, CA (US); James Guy Breitenbucher, Escondido, CA (US); Natalie A. Hawryluk, San Diego, CA (US); Alec D. Lebsack, San Diego, CA (US); Jeffrey E. Merit, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 1359 days.

(21) Appl. No.: 11/726,756

(22) Filed: Mar. 21, 2007

(65) Prior Publication Data

US 2007/0225275 A1    Sep. 27, 2007

Related U.S. Application Data

(60) Provisional application No. 60/785,415, filed on Mar. 21, 2006.

(51) Int. Cl.
*A61P 11/00* (2006.01)
*A61P 29/00* (2006.01)
*A61K 31/55* (2006.01)
*C07D 487/02* (2006.01)

(52) U.S. Cl.
USPC .......................................... 514/215; 540/578

(58) Field of Classification Search
USPC .......................................... 514/215; 540/578
See application file for complete search history.

(56) References Cited

U.S. PATENT DOCUMENTS

| 4,160,834 | A | 7/1979 | Miesel |
| 5,512,563 | A | 4/1996 | Albright et al. |
| 5,834,461 | A | 11/1998 | Albright et al. |
| 6,107,300 | A | 8/2000 | Bakthavatchalam et al. |
| 6,150,343 | A | 11/2000 | Curran et al. |
| 6,150,353 | A | 11/2000 | Broekkamp et al. |
| 6,232,320 | B1 | 5/2001 | Stewart et al. |
| 6,686,352 | B2 | 2/2004 | Masciadri et al. |
| 7,008,948 | B2 | 3/2006 | Bebbington et al. |
| 7,087,603 | B2 | 8/2006 | Bebbington et al. |
| 2001/0041673 | A1 | 11/2001 | Fossa |
| 2001/0041703 | A1 | 11/2001 | Carpino et al. |
| 2002/0002137 | A1 | 1/2002 | Busch et al. |
| 2002/0013320 | A1 | 1/2002 | Busch et al. |
| 2002/0016320 | A1 | 2/2002 | Fang et al. |
| 2002/0028838 | A1 | 3/2002 | MacLean et al. |
| 2002/0042419 | A1 | 4/2002 | Hakkinen |
| 2002/0045622 | A1 | 4/2002 | Carpino |
| 2002/0045635 | A1 | 4/2002 | Binggeli et al. |
| 2002/0072604 | A1 | 6/2002 | Carpino et al. |
| 2002/0086865 | A1 | 7/2002 | Friedman et al. |
| 2002/0094974 | A1 | 7/2002 | Castelhano et al. |
| 2002/0103221 | A1 | 8/2002 | Petrie et al. |
| 2002/0143177 | A1 | 10/2002 | Beck et al. |
| 2002/0151551 | A1 | 10/2002 | Fryburg |
| 2003/0055042 | A1 | 3/2003 | Masciadri et al. |
| 2003/0104974 | A1 | 6/2003 | Pitts et al. |
| 2003/0139427 | A1 | 7/2003 | Castelhano et al. |
| 2003/0191086 | A1 | 10/2003 | Hanus et al. |
| 2003/0191143 | A1 | 10/2003 | Pitts et al. |
| 2003/0199514 | A1 | 10/2003 | Fryburg et al. |
| 2003/0212059 | A1 | 11/2003 | Boyle et al. |
| 2004/0034250 | A1 | 2/2004 | Hartig et al. |
| 2004/0053908 | A1 | 3/2004 | Funahashi et al. |
| 2004/0142945 | A1 | 7/2004 | Barbosa et al. |
| 2004/0157845 | A1 | 8/2004 | Doherty et al. |
| 2005/0009754 | A1 | 1/2005 | Pan et al. |
| 2005/0020830 | A1 | 1/2005 | Allen et al. |
| 2005/0049263 | A1 | 3/2005 | Kasibhatla et al. |
| 2005/0165032 | A1 | 7/2005 | Norman et al. |
| 2005/0182063 | A1 | 8/2005 | Yohannes |
| 2005/0187217 | A1 | 8/2005 | Wilson et al. |
| 2005/0277643 | A1 | 12/2005 | Kelly et al. |
| 2006/0100194 | A1 | 5/2006 | Blackburn et al. |
| 2006/0128710 | A1 | 6/2006 | Lee et al. |
| 2006/0223868 | A1 | 10/2006 | Besidski et al. |
| 2007/0032473 | A1 | 2/2007 | Gerlach et al. |
| 2007/0032481 | A1 | 2/2007 | Dvorak et al. |
| 2007/0037834 | A1 | 2/2007 | Arai et al. |
| 2007/0136603 | A1 | 6/2007 | Kuecuekyan |
| 2007/0142386 | A1 | 6/2007 | Nordvall et al. |
| 2007/0149602 | A1 | 6/2007 | DuBois et al. |
| 2007/0232591 | A1 | 10/2007 | Gao et al. |
| 2008/0234252 | A1 | 9/2008 | Bryans et al. |

FOREIGN PATENT DOCUMENTS

| CA | 2116068 A1 | 8/1994 |
| CA | 2128955 A1 | 1/1995 |
| CL | 2007 00720 | 3/2007 |
| DE | 10 2000 5 62987 A1 | 7/2007 |
| EP | 612741 | 2/1994 |
| EP | 640592 | 7/1994 |
| EP | 1 731 523 A1 | 12/2006 |

(Continued)

OTHER PUBLICATIONS

Chen et al, Jour. Heterocyclic Chem. (1983), vol. 20 (3), pp. 663-666.
Eiden et al., Archiv der Pharmazie, (1979) 312(8), pp. 708-714.
Hirota et al, Heterocycles (1986), vol. 24 (1), pp. 143-154.
Hirota et al, Heterocycles (1986), vol. 24 (7), pp. 1997-2002.
Hirota et al, Heterocycles (1986), vol. 24 (11), pp. 3223-3228.
Nagamatsu et al, Jour. Heterocyclic Chem. (1993), vol. 30 (1), pp. 193-202.
Nagamatsu et al, Jour. Heterocyclic Chem. (1993), vol. 30 (1), pp. 233-240.
Nagamatsu et al, J. Synthesis, (1991), vol. 11, pp. 942-946.
Proctor et al, Jour. Chem. Society, (1978) vol. 8, pp. 862-870.
Yamamoto et al, Heterocycles (1978), vol. 11, pp. 275-280.
Yamamoto et al, Bulletin of the Chemical Society of Japan (1977), vol. 50 (2), pp. 453-458.

(Continued)

*Primary Examiner* — Brenda Coleman
(74) *Attorney, Agent, or Firm* — Michael J. Atkins

(57) ABSTRACT

Certain tetrahydro-pyrimidoazepine compounds are described, which are useful as TRPV1 modulators. Such compounds may be used in pharmaceutical compositions and methods for the treatment of disease states, disorders, and conditions mediated by TRPV1. Thus, the compounds may be administered to treat, e.g., pain, itch, cough, asthma, or inflammatory bowel disease.

12 Claims, No Drawings

(56) References Cited

FOREIGN PATENT DOCUMENTS

| | | |
|---|---|---|
| EP | 1818330 A1 | 8/2007 |
| EP | 2009003 A1 | 12/2008 |
| FR | 2874015 A1 | 2/2006 |
| JP | 3167178 A1 | 7/1991 |
| JP | 03255077 | 11/1991 |
| JP | 3255077 A | 11/1991 |
| JP | 06025243 | 2/1994 |
| JP | 6025243 A | 2/1994 |
| JP | 6172355 A | 6/1994 |
| JP | 03167178 | 7/1999 |
| JP | 11-513398 A | 11/1999 |
| JP | 06172355 | 3/2001 |
| JP | 2001 97979 | 4/2001 |
| JP | 2001294 572 A | 10/2001 |
| JP | 2001294572 | 10/2001 |
| JP | 2003 321 472 A | 11/2003 |
| JP | 2003321 472 A | 11/2003 |
| JP | 2003321472 | 11/2003 |
| JP | 2004 509117 A | 3/2004 |
| JP | 2005162 673 A | 6/2005 |
| JP | 2005162673 | 6/2005 |
| JP | 2000608 3085 A | 3/2006 |
| JP | 2006083085 | 3/2006 |
| JP | 2007 168879 A | 1/2009 |
| WO | WO 93/14080 | 7/1993 |
| WO | WO 95/06640 | 3/1995 |
| WO | WO 96/22282 | 7/1996 |
| WO | WO 97 13771 A1 | 4/1997 |
| WO | WO 97/19087 | 5/1997 |
| WO | WO 97/47601 | 12/1997 |
| WO | WO 97/47624 | 12/1997 |
| WO | WO 97/48702 | 12/1997 |
| WO | WO 98/40385 | 9/1998 |
| WO | WO 98 58947 A1 | 12/1998 |
| WO | WO 00 43394 A1 | 7/2000 |
| WO | WO 02 06288 A1 | 1/2002 |
| WO | WO 02 22602 A2 | 3/2002 |
| WO | WO 2002 32872 A1 | 4/2002 |
| WO | WO 02 051813 A2 | 7/2002 |
| WO | WO 02 094834 A1 | 11/2002 |
| WO | WO 03 037860 A2 | 5/2003 |
| WO | WO 03 062209 A2 | 7/2003 |
| WO | WO 2003 104230 A1 | 12/2003 |
| WO | WO 2004 026880 A1 | 4/2004 |
| WO | WO 2004/043367 | 5/2004 |
| WO | WO 2004 096784 A1 | 11/2004 |
| WO | WO 2005/007655 | 1/2005 |
| WO | WO 2005 014548 A1 | 2/2005 |
| WO | WO 2005 014558 A1 | 2/2005 |
| WO | WO 2005 023807 A2 | 3/2005 |
| WO | WO 2005 033105 A2 | 4/2005 |
| WO | WO 2005 033115 A1 | 4/2005 |
| WO | WO 2005 049613 A1 | 6/2005 |
| WO | WO 2005 066171 A1 | 7/2005 |
| WO | WO 2005 070929 A1 | 8/2005 |
| WO | WO 2005 082865 A1 | 9/2005 |
| WO | WO 2005 095419 A1 | 10/2005 |
| WO | WO 2005 117890 A2 | 12/2005 |
| WO | WO 2005 123666 A1 | 12/2005 |
| WO | WO 2006 010445 A1 | 2/2006 |
| WO | WO 2006/024776 | 3/2006 |
| WO | WO 2006 030031 A1 | 3/2006 |
| WO | WO 2006/041773 | 4/2006 |
| WO | WO 2006/044762 | 4/2006 |
| WO | WO 2006 062981 A2 | 6/2006 |
| WO | WO 2006 065484 A2 | 6/2006 |
| WO | WO 2006 081388 A2 | 8/2006 |
| WO | WO 2006/123242 | 11/2006 |
| WO | WO 2007/003536 | 1/2007 |
| WO | WO 2007 009963 A1 | 1/2007 |
| WO | WO 2007/019083 | 2/2007 |
| WO | WO 2007/032473 | 2/2007 |
| WO | WO 2007/093595 | 2/2007 |
| WO | WO 2007/062370 | 5/2007 |
| WO | WO 2007/079957 | 7/2007 |
| WO | WO 2007/098826 | 9/2007 |
| WO | WO 2007 109238 A1 | 9/2007 |
| WO | WO 2007/136603 | 11/2007 |
| WO | WO 2007/146122 | 12/2007 |
| ZA | 9802368 A | 9/1998 |

OTHER PUBLICATIONS

Yamamoto et al, Bulletin of the Chemical Society of Japan (1971), vol. 44 (1), pp. 153-158.
Barton et al., *Exp. Mol. Pathol.* 2006, vol. 81(2), pp. 166-170.
Agopyan et al., *Toxicol. App. Pharmacol.* 2003, vol. 192, pp. 21-35.
Agopyan et al., *Am. J. Physiol. Lung Cell Mol. Physiol.* 2004, vol. 286, pp. L563-572.
Akiba et al., *Biochem. Biophy. Res. Commun.* 2004, vol. 321(1), pp. 219-225.
Apostolidis et al., *Urology* 2005, vol. 65(2), pp. 400-405.
Asai et al., *Pain* 2005, vol. 117, pp. 19-29.
Balaban et al., *Hear. Res.* 2003, vol. 175, pp. 165-170.
Bodó et al., *Am. J. Pathol.* 2005, vol. 166(4), pp. 985-998.
Bölcskei et al., *Pain* 2005, vol. 117(3), pp. 368-376.
Calkins et al., *ARVO* 2006 Annual Meeting, Ft. Lauderdale, Florida, Program #1557, Poster #B93, Abstract.
Caterina, *Pain* 2003, vol. 105(1-2), pp. 5-9.
Caterina et al., *Annu. Rev. Neurosci.* 2001, vol. 24, pp. 487-517.
Chan et al., *Lancet* 2003, vol. 361, pp. 385-391.
Dinis et al., *J. Neurosci.* 2004, vol. 24(50), pp. 11253-11263.
Geppetti et al., *Br. J. Pharmacol.* 2004, vol. 141, pp. 1313-1320.
Ghilardi et al., *J. Neurosci.* 2005, vol. 25(12), pp. 3126-3131.
Goadsby, *Curr. Pain Headache Reports* 2004, vol. 8, pp. 393-398.
Greiff et al., *Thorax* 1995, vol. 50(3), pp. 225-229.
Honore et al., *J. Pharmacol. Exp. Ther.* 2005, vol. 314(1), pp. 410-421.
Iida et al., *Neurosci. Lett.* 2005, vol. 378, pp. 28-33.
Jancsó-Gábor et al., *J. Physiol.* 1970, vol. 206(3), pp. 495-507.
Kim et al., *Neurosci. Lett.* 2004, vol. 361, pp. 159-162.
Kimball et al., *Neurogastroenterol. Motil.* 2004, vol. 16(6), pp. 811-818.
Kwak et al., *Neuroscience* 1998, vol. 86(2), pp. 619-626.
Lalloo et al., *J. Appl. Physiol.* 1995, vol. 79(4), pp. 1082-1087.
Lazzeri et al., *Eur. Urology* 2004, vol. 46, pp. 792-798.
Marsch et al., *J. Neurosci.* 2007, vol. 27(4), pp. 832-839.
Menéndez et al., *Neurosci. Lett.* 2006, vol. 393(1), pp. 70-73.
Moore et al., *Am. J. Physiol. Gastrointest. Liver Physiol.* 2002, vol. 282(6), pp. G1045-G1051.
Morris et al., *Pain* 1997, vol. 71, pp. 179-186.
Pomonis et al., *J. Pharmacol. Exp. Ther.* 2003, vol. 306(1), pp. 387-393.
Razavi et al., *Cell* 2006, vol. 127(6), pp. 1123-1135.
Sánchez et al., *Eur. J. Pharmacol.* 2005, vol. 515(1-3), pp. 20-27.
Sculptoreanu et al., *Neurosci. Lett.* 2005, vol. 381(1-2), pp. 42-46.
Stucky et al., *Neuroscience* 1998, vol. 84(4), pp. 1257-1265.
Swanson et al., *J. Med. Chem.* 2005, vol. 48, pp. 1857-1872.
Szabó et al., *J. Pharmacol. Exp. Ther.* 2005, vol. 314(1), pp. 111-119.
Tominaga et al., *J. Neurobiol.* 2004, vol. 61(1), pp. 3-12.
Voets et al., *Nature* 2004, vol. 430, pp. 748-754.
Walker et al., *J. Pharmacol. Exp. Ther.* 2003, vol. 304(1), pp. 56-62.
Yiangou et al., *Lancet* 2001, vol. 357, pp. 1338-1339.
Zheng et al., *J. Neurophys.* 2003, vol. 90, pp. 444-455.
U.S. Appl. No. 60/705,719, filed Aug. 4, 2005, Dvorak et al.
Bagshawe et al. "Antibody-Directed Enzyme Prodrug Therapy: A Review" Drug Dev Res 1995 vol. 34 pp. 220-230.
Berge et al. "Pharmaceutical Salts". J. Pharm Sci 1977 vol. 66 pp. 1-19.
Bertolini et al."A New Rational Hypothesis for the Pharmacophore of the Active Metabolite of Leflunomide, a Potent Immunosuppressive Drug" J Med Chem 1997 vol. 40 pp. 2011-2016.
Bodor et al. "Novel Approaches to the Design of Safer Drugs: Soft Drugs and Site-Specific Chemical Delivery Systems" Adv Drug Res 1984 vol. 13 pp. 224-331.
Boechat et al "A Simple Reduction of Methyl Aromatic Esters to Alcohols Using Sodium Borohydride-Methanol System" Tetrahedron Lett 2004, vol. 45 pp. 6021-6022.

(56) References Cited

OTHER PUBLICATIONS

Bundgaard et al Design of Prodrugs H Bundgaard Ed. Elsevier 1985, p. 1 only.
Cordi et al "Novel Quinolinone-Phosphonic Acid AMPA Antagonists Devoid of Nephrotoxicity" Il Farmaco 2002 vol. 57 GPS 787-802.
Fleisher et al "Improved Review Oral Drug Delivery: Solubility Limitations of Prodrugs Overcome by the Use" Adv Drug Delivery Rev 1996 vol. 19 pp. 115-130.
Hamann et al "Synthesis and Biological Activity of a Novel Series of Nonsteroidal Peripherally Selective Androgen Receptor Antagonists Derived From 1,2-Dihydropyridono[5,6-g]Quinolines" J Med Chem 1998 vol. 41 (4) pp. 623-639.
Higuchi et al "4-Alkyl-and 3,4-Dialkyl-1,2,3,4-Tetrahydro-8-Pyridono[5,6g]Quinolines: Potent Nonsteroidal Androgen Receptor Agonists" Bioorg Med Chem Lett 1999 vol. 9 pp. 1335-1340.
Horikawa et al "A Practical Preparation of Methyl 2-Methoxy-6-Methylaminopyridine-3-Carboxylate From 2,6-Dichloro-3-Trifluoromethylpyridine" Chem Pharm Bull 2001 vol. 49(12) pp. 1621-1627.
Katritzky et al "Benzotriazole-Assisted Preparations of 2-(Substituted Amino)Pyridines and Pyrid-2-Ones" J Org Chem 1997 vol. 62(18) pp. 6210-6214.
Larsen et al Design and Application of Prodrugs Drug Design and Development Krogsgaard-Larsen et al Eds Harwood Academic Publishers 1991, Contents & Index Only.
Marsais et al "Directed Lithiation of 4-Halopyridines: Chemoselectivity, Regioselectivity and Application to Synthesis" J Heterocycl Chem 1988 vol. 25(1) pp. 81-87.
Ponticello et al "Synthesis of Novel 3-(Alkylthio)-2-Halopyridines and Related Derivatives" J Org Chem 1979 vol. 44(17) pp. 3080-3082.
Richardson et al "Synthesis and Structure-Activity Relationship of Novel Arylpiperazines as Potent and Selective Agonists of the Melanocortin Subtype-4 Receptor" J Med Chem 2004 vol. 47(3) pp. 744-755.
Robinson "Discovery of the Hemifumarate and (α-L-Alanyloxy)Methyl Ether as Prodrugs of an Antirheumatic Oxindole: Prodrugs for the Enolic OH Group" J Med Chem 1996 vol. 39 pp. 10-18.
Shan et al "Prodrug Strategies Based on Intramolecular Cyclization Reactions" J Pharm Sci 1997 vol. 86(7) pp. 765-767.
Stahl et al Handbook of Pharmaceutical Salts Properties Selection and Use Stahl and Wermuth Eds Wiley-VCH and VHCA Zurich 2002, Contents Only.
Baxter et al Hit-To-Lead Studies: The Discovery of Potent, Orally Bioavailable Thiazolopyrimidine CXCR2 Receptor Antagonists Bioorg Med Chem Lett 2006 vol. 16 pp. 960-963.
Liu et al "Single-Step Syntheses of 2-Amino-7-Chlorothiazolo[5,4-$_D$]Pyrimidines: Intermediates for Bivalent Thiazolopyrimidines" J Org Chem 2005 vol. 70 pgs. 10194-10197.
Makara et al "Synthesis of Bicyclic Pyrimidine Derivatives As ATP Analogues" J Org Chem 2001 vol. 66 pp. 5783-5789.
Xi et al "Synthesis and Evaluation of Thiazole Carboxamides As Vanilloid Receptor 1 (TRPV1) Antagonists" Bioorg Med Chem Lett 2005 vol. 15 pp. 5211-5217.
Banker et al Modern Pharmaceutics $3^{RD}$ ED 1996 pp. 415 and 596 Marcel Dekker New York.
Wolff et al Burger'S Medicinal Chemistry 1995 $5^{TH}$ ED Part 1, pp. 975-977.
Freeman et al "Reaction of Aminopropanedinitrile 4-Methylbenzenesulfonate (Aminomalononitrile P-Toluenesulfonante (Tosylate) With Isothyocyanates" J Org Chem 1991 vol. 56(15) pp. 4645-4648.
Hicks et al "Potential Antiinflammatory Compounds 1. Antiinflammatory Phenylpiperidine Derivatives" J Med Chem 1979 vol. 22(12) pp. 1460-1464.
Boechat et al "A Simple Reduction of Methyl Aromatic Esters to Alcohols Using Borohydride-Methanol System" Tetrahedron Lett 2004 vol. 45 pp. 6021-6022.
Jassal et al "Sialyation of Human $I_gG$-FC Carbohydrate by Transfected Rat A2,6-Sialyltransferase" Biochem Biophys Res Comm 2001 vol. 286(2) pp. 243-249.
Goldenberg-Furmanov et al "LYN is a Target Gene for Prostate Cancer: Sequence Based Inhibition Induces Regression of Human Xenografts" Cancer Res 2004 vol. 64 pp. 1058-1064.
Shah et al "Overriding Imatinib Resistance With a Novel ABL Kinase Inhibitor" Science 2004 vol. 305 pp. 399-401.
Donato et al "BCR-ABL Independence and LYN Kinase Overexpression in Chronic Myelogenous Leukemia Cells Selected Fro Resistance T STI571" Blood 2003 vol. 10(12) pp. 690-698.
Wobig et al "Darstellung Von Thiazolo[4,5,d]Pyrimidin-Derivativen" Liebigs Ann Chem 1989 pp. 409-412.
McKee et al "P-Substituted Phenyl Isothiocyanates and Some Related Thioureas" Jam Chem Soc 1946 vol. 68 pp. 2506-2507.
Paradisi et al "Stereoselective Synthesis of α-α'-Diamino-Dicarboxylic Acids, Part 2" Tetrahedron Assymetry 2000 vol. 11 pp. 4617-4622.
CAS Printout pp. 1-9 Downloaded Apr. 24, 2008.
Pyrimidinothiazole Search Results April 7, 2000.

TETRAHYDRO-PYRIMIDOAZEPINES AS MODULATORS OF TRPV1

CROSS-REFERENCE TO RELATED APPLICATION

This application claims priority to U.S. Provisional Application No. 60/785,415, filed Mar. 21, 2006.

FIELD OF THE INVENTION

The present invention relates to certain tetrahydro-pyrimidoazepine compounds, pharmaceutical compositions containing them, and methods of using them for the treatment of disease states, disorders, and conditions mediated by TRPV1 activity.

BACKGROUND OF THE INVENTION

Transient receptor-potential (TRP) channel proteins constitute a large and diverse family of proteins that are expressed in many tissues and cell types. One TRP channel protein of particular interest is the vanilloid receptor 1 (TRPV1 or VR1), a non-selective $Ca^{+2}$ channel that is the molecular target of vanilloid compounds (e.g., capsaicin and resiniferatoxin). Such vanilloid compounds are known to selectively depolarize nociceptors, specialized primary afferent neurons involved in the signaling pathway that leads to the sensation of pain. TRPV1 is activated by a diverse range of stimuli, including vanilloids, membrane depolarization, heat, stretch, low pH, inflammatory mediators (e.g., lipoxygenase metabolites), and endocannabinoid compounds. Because heightened activity of nociceptors contributes to unwanted pain, inflammatory conditions, thermoregulation, and control of smooth muscle tone and reflexes in mammals, modulation of signaling in this pathway is important in treatment and prophylaxis of various clinical syndromes (Caterina, M. J., *Pain* 2003, 105(1-2), 5-9; Caterina, M. J. et. al., *Annu. Rev. Neurosci.* 2001, 24, 487-517; Tominaga, M. et.al., *J. Neurobiol.* 2004, 61, 3-12; Voets, T. et.al., *Nature* 2004, 430, 748-754).

Because of TRPV1's connection with the sensory nervous system, TRPV1 agonists and antagonists may be therapeutically useful in the treatment or prophylaxis of disease states, disorders, and conditions mediated by TRPV1 activity, such as: i) pain (e.g., acute, chronic, inflammatory, or neuropathic pain); ii) itch (Kim et al., *Neurosci. Lett.* 2004, 361, 159) and various inflammatory disorders (Stucky, C. L. et.al., *Neuroscience* 1998, 84, 1257; Moore, B. A. et.al., *Am. J. Physiol. Gastrointest. Liver Physiol.* 2002, 282, G1045; Kwak, J. Y. et.al., *Neuroscience* 1998, 86, 619; Morris, V. H. et.al., *Pain* 1997, 71, 179; Greiff, L. et.al., *Thorax* 1995, 50, 225); iii) inner ear disorders (Balaban, C. D. et al., *Hear. Res.* 2003, 175, 165-70; Zheng, J. et al., *J. Neurophys.* 2003, 90, 444-55); iv) fever and other disorders or symptoms affected by thermoregulation (Jancso-Gabor et al., *J. Physiol.* 1970, 206, 495; Swanson et al., *J. Med. Chem.* 48, 1857; Iida et al., *Neurosci. Lett.* 2005, 378, 28); v) tracheobronchial and diaphragmatic dysfunction; and vi) gastrointestinal and urinary tract disorders (Lazzeri, M. et al., *Eur. Urology* 200, 792-798; Apostolidis, A. et.al., *Urology* 2005, 65, 400-405). Additionally, TRPV1 modulators may be therapeutically useful in the treatment or prophylaxis of anxiety (Marsch, R. et al., *J. Neurosci.* 2007, 27(4), 832-839); eye-related disorders (such as glaucoma, vision loss, and increased intraocular pressure) (Calkins, D. J. et al., Abstract from *ARVO 2006 Annual Meeting*, Program #1557, Poster #B93); baldness (e.g., by stimulating hair growth) (Bodo, E. et al., *Am. J. Pathol.* 2005, 166(4), 985-998); diabetes (including insulin-resistant diabetes or diabetic conditions mediated by insulin sensitivity or secretion) (Razavi, R. et al., *Cell* 2006, 127(6), 1097-1099; Akiba, Y. et al., *Biochem. Biophy. Res. Commun.* 2004, 321 (1), 219-225).

Acidosis is a well-established feature of cerebral ischaemia. Tissue pH may fall to 6 or lower, sufficient to activate TRPV1 channels expressed in the CNS. TRPV1 antagonists therefore may be useful in the treatment of disorders associated with reduced blood flow to the CNS or CNS hypoxia, such as head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

International Publication No. WO05/014558 (Feb. 17, 2005) describes certain aminopyrimidine inhibitors of voltage-gated sodium and potassium channel. Various bicyclic pyrimidines are disclosed as serotonin receptor modulators in U.S. patent application Ser. No. 11/460,294, filed Jul. 27, 2006. Condensed pyrimidine compounds are disclosed as inhibitors of voltage-gated ion channels in Intl. Publication No. WO 05/014558. Various bicyclic pyrimidines are also disclosed in Intl. Publication No. WO 05/066171 and U.S. Patent Appl. Publ. 2005/0165032 as inhibitors of the TRPV1 channel. However, there remains a need for potent TRPV1 modulators with desirable pharmaceutical properties.

SUMMARY OF THE INVENTION

Certain tetrahydro-pyrimidoazepine derivatives have now been found to have TRPV1-modulating activity. Thus, the invention is directed to the general and preferred embodiments defined, respectively, by the independent and dependent claims appended hereto, which are incorporated by reference herein.

Thus, in one general aspect the invention relates to compounds of the following Formula (I):

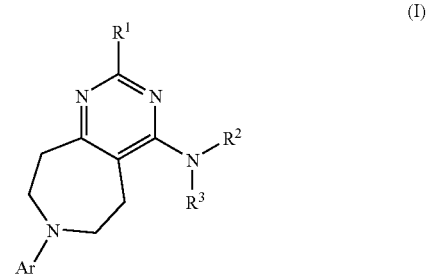

wherein:
$R^1$ is —H; —$NR^aR^b$; —OH; a —$C_{1-6}$alkyl, —$OC_{1-6}$alkyl, —O-(saturated monocyclic cycloalkyl), —$OC_1$alkyl-(saturated monocyclic cycloalkyl), —O-(saturated monocyclic heterocycloalkyl), —O-phenyl, —O-benzyl, —S—$C_{1-6}$alkyl, —S-(saturated monocyclic cycloalkyl), —$SC_1$alkyl-(saturated monocyclic cycloalkyl), —S-(saturated monocyclic heterocycloalkyl), —S-phenyl, —S-benzyl, or —$SO_2$—$C_{1-6}$alkyl group unsubstituted or substituted with one or two moieties independently selected from the group consisting of —$C_{1-6}$alkyl, —OH, —$OC_{1-4}$alkyl, —$NR^eR^f$, and halo substituents; or a phenyl, monocyclic cycloalkyl, or monocyclic heteroaryl group unsubstituted or substituted with a —$C_{1-6}$alkyl, —OH, —$OC_{1-4}$alkyl, —$NR^eR^f$, or halo substituent;

where $R^a$ and $R^b$ are each independently —H; —$C_{1-6}$alkyl; a —$C_{2-3}$alkyl group substituted with a —OH, —$OC_{1-4}$alkyl, —$NR^cR^d$, or halo substituent; or a saturated monocyclic cycloalkyl, —$C_1$alkyl-(saturated monocyclic cycloalkyl), saturated monocyclic heterocycloalkyl, —$C_1$alkyl-(saturated monocyclic heterocycloalkyl), phenyl, benzyl, or —$C_1$alkyl-(monocyclic heteroaryl) group unsubstituted or substituted with one, two, or three moieties independently selected from the group consisting of —$C_{1-6}$alkyl, —OH, —$OC_{1-4}$alkyl, —$NR^pR^q$, and halo substituents; or $R^a$ and $R^b$ taken together with their nitrogen of attachment form a saturated monocyclic heterocycloalkyl or bridged bicyclic heterocycloalkyl group unsubstituted or substituted with one, two, or three moieties independently selected from the group consisting of —$C_{1-6}$alkyl, —$C_{1-4}$alkyl—OH, —$C_{1-2}$alkyl-$OC_{1-2}$alkyl, —OH, —$OC_{1-4}$alkyl, —$NR^pR^q$, halo, —$CO_2H$, and benzyl substituents;

where $R^c$ and $R^d$ are each independently —H or —$C_{1-6}$alkyl; or $R^c$ and $R^d$ taken together with their nitrogen of attachment form a saturated monocyclic heterocycloalkyl;

where $R^p$ and $R^q$ are each independently —H or —$C_{1-6}$alkyl; or $R^p$ and $R^q$ taken together with their nitrogen of attachment form a saturated monocyclic heterocycloalkyl;

where $R^e$ and $R^f$ are each independently —H or —$C_{1-6}$alkyl; or $R^e$ and $R^f$ taken together with their nitrogen of attachment form a saturated monocyclic heterocycloalkyl;

$R^2$ is —H or —$C_{1-6}$alkyl;

$R^3$ is a monocyclic cycloalkyl, phenyl, benzyl, phenethyl, indanyl, thiazolyl, thiophenyl, pyridyl, pyridylmethyl, pyrimidinyl, pyrazinyl, pyridazinyl, benzothiadiazolyl, quinolinyl, isoquinolinyl, tetrahydroquinolinyl, or tetrahydroisoquinolinyl group unsubstituted or substituted with one, two, or three $R^g$ substituents;

where each $R^g$ substituent is —$C_{1-6}$alkyl; —$C_{1-4}$alkyl-OH unsubstituted or substituted with —$CF_3$; saturated monocyclic cycloalkyl; —OH; —$OC_{1-6}$alkyl; phenoxy; —CN; —$NO_2$; —$N(R^h)R^i$; —$C_{1-4}$alkyl-$N(R^h)R^i$; —$C(O)N(R^h)R^i$; —$N(R^h)C(O)R^i$; —$N(R^h)SO_2C_{1-6}$alkyl; —$C(O)C_{1-6}$alkyl; —$S(O)_{0-2}$—$C_{1-6}$alkyl; —$SO_2CF_3$; —$SO_2N(R^h)R^i$; —$SCF_3$; halo; —$CF_3$; —$OCF_3$; —$CO_2H$; —$CO_2C_{1-6}$alkyl; —$C(R^j)(R^x)$—CN; —$C(R^j)(R^x)$—OH; —$C(R^j)(R^x)$—$CO_2C_{1-6}$alkyl; —$C(R^j)(R^x)$—$CO_2H$; —$C(R^j)(R^x)$—$C(O)N(R^h)R^i$; phenyl; or monocyclic heteroaryl; or two adjacent $R^g$ substituents taken together form —$OC_{1-2}$alkylO—;

where $R^h$ and $R^i$ are each independently —H or —$C_{1-6}$alkyl; or $R^h$ and $R^i$ (when both are present) taken together with their nitrogen of attachment form a saturated monocyclic heterocycloalkyl group;

$R^j$ is independently —H, —$C_{1-6}$alkyl, or —$CF_3$;

$R^x$ is —H or —$C_{1-6}$alkyl; or $R^j$ and $R^x$ taken together with the carbon to which they are attached form a monocyclic cycloalkyl ring;

and

Ar is a phenyl, pyridyl, imidazolyl, pyrimidinyl, pyridazinyl, or fused-bicyclic heteroaryl group unsubstituted or substituted with one, two, or three $R^k$ substituents;

where each $R^k$ substituent is independently —$C_{1-6}$alkyl, —$C_{1-2}$alkyl-OH, —OH, —$OC_{1-6}$alkyl, phenoxy, —CN, —$NO_2$, —$N(R^l)R^m$, —$C(O)N(R^l)R^m$, —$N(R^l)C(O)R^m$, —$N(R^l)SO_2C_{1-6}$alkyl, —$N(R^l)SO_2CF_3$, —$C(O)C_{1-6}$alkyl, —$S(O)_{0-2}$—$C_{1-6}$alkyl, —$SO_2CF_3$, —$SO_2N(R^l)R^m$, —$SCF_3$, halo, —$CF_3$, —$OCF_3$, —$CO_2H$, or —$CO_2C_{1-6}$alkyl; or two adjacent $R^k$ substituents taken together form —$OC_{1-2}$alkylO—;

where $R^l$ and $R^m$ are each independently —H, —$C_{1-6}$alkyl, saturated monocyclic cycloalkyl, or —$CF_3$.

The invention also relates to pharmaceutically acceptable salts, pharmaceutically acceptable prodrugs, and pharmaceutically active metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) an effective amount of an agent selected from compounds of Formula (I) and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition mediated by TRPV1 activity, comprising administering to the subject in need of such treatment an effective amount of a compound of Formula (I), or a pharmaceutically acceptable salt, pharmaceutically acceptable prodrug, or pharmaceutically active metabolite of such compound. In certain preferred embodiments of the inventive method, the disease, disorder, or medical condition is selected from: pain (acute, chronic, inflammatory, or neuropathic pain); itch or various inflammatory disorders; inner ear disorders; fever and other conditions or disorders of thermoregulation; tracheobronchial and diaphragmatic dysfunction; gastrointestinal and urinary tract disorders; and disorders associated with reduced blood flow to the CNS or CNS hypoxia.

Additional embodiments, features, and advantages of the invention will be apparent from the following detailed description and through practice of the invention.

DETAILED DESCRIPTION OF INVENTION AND ITS PREFERRED EMBODIMENTS

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight—or branched-chain alkyl group having from 1 to 12 carbon atoms in the chain. Exemplary alkyl groups include methyl (Me, which also may be structurally depicted by a/symbol), ethyl (Et), n-propyl, isopropyl, butyl, isobutyl, sec-butyl, tert-butyl (tBu), pentyl, isopentyl, tert-pentyl, hexyl, isohexyl, and the like.

The term "alkenyl" refers to a straight- or branched-chain alkenyl group having from 2 to 12 carbon atoms in the chain. (The double bond of the alkenyl group is formed by two $sp^2$ hybridized carbon atoms.) Illustrative alkenyl groups include prop-2-enyl, but-2-enyl, but-3-enyl, 2-methylprop-2-enyl, hex-2-enyl, and the like.

The term "cycloalkyl" refers to a saturated or partially saturated, monocyclic, fused polycyclic, or bridged polycyclic carbocycle having from 3 to 12 ring atoms per carbocycle. Illustrative examples of cycloalkyl groups include the following moieties:

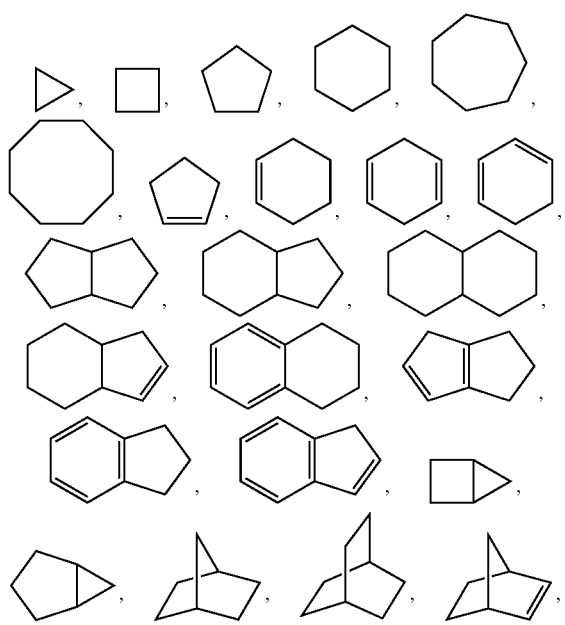

and the like.

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative examples of heterocycloalkyl groups include:

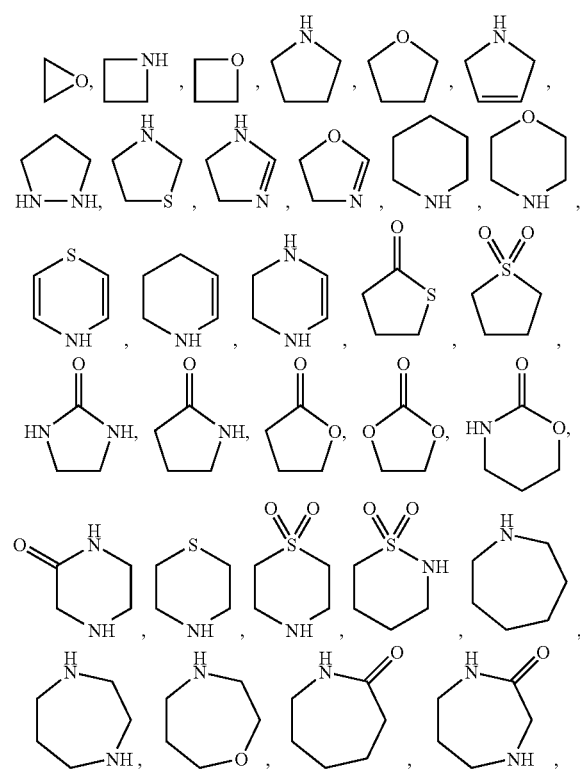

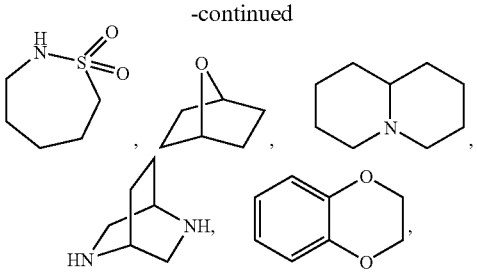

and the like.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following moieties:

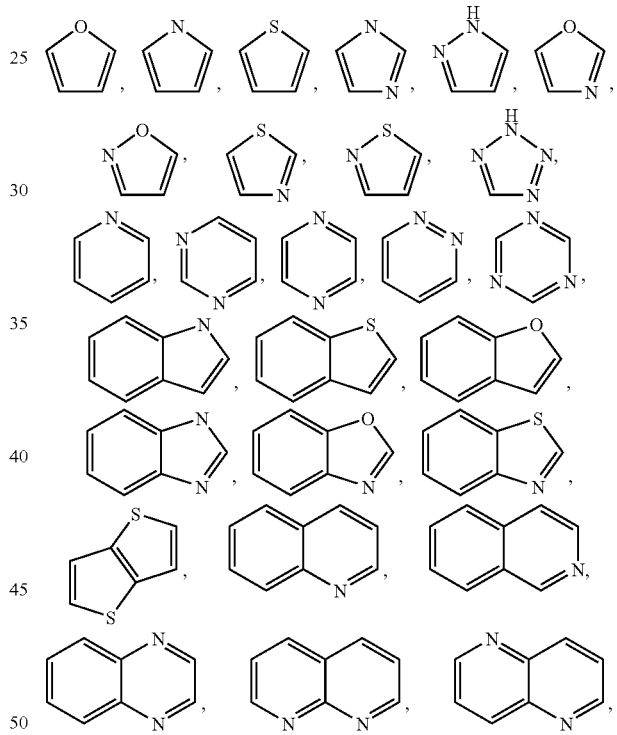

and the like.

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof.

Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of agents of Formula (I), $R^1$ is —H or —OH. In further preferred embodiments, $R^1$ is isopropyl or cyclopropyl. In further preferred embodiments, $R^1$ is a —O-(saturated monocyclic cycloalkyl), —OC$_1$alkyl-(saturated monocyclic cycloalkyl), —O-(saturated monocyclic heterocycloalkyl), —O-phenyl, or —O -benzyl group unsubstituted or substituted with one or two moieties independently selected from the group consisting of methyl, ethyl, and isopropyl substituents. In further preferred embodiments, $R^1$ is a —S—C$_{1-6}$alkyl, —S-(saturated monocyclic cycloalkyl), —SC$_1$alkyl-(saturated monocyclic cycloalkyl), —S-(saturated monocyclic heterocycloalkyl), —S-phenyl, or —S-benzyl group unsubstituted or substituted with a methyl, ethyl, or isopropyl substituent. In further preferred embodiments, $R^1$ is methylsulfanyl or methylsulfonyl. In further preferred embodiments, $R^1$ is a monocyclic heteroaryl group unsubstituted or substituted with a methyl substituent. In further preferred embodiments, $R^1$ is a furanyl, thiophenyl, thiazolyl, or pyridyl group unsubstituted or substituted with a methyl substituent.

In preferred embodiments, $R^a$ and $R^b$ are each independently —H; methyl, ethyl, propyl, isopropyl, butyl, isobutyl, sec-butyl, tert-butyl, pentyl, isopentyl, or hexyl; an ethyl or propyl group substituted with an —OC$_{1-4}$alkyl or —NR$^c$R$^d$ substituent; or a cyclopropyl, cyclobutyl, cyclopentyl, cyclohexyl, cycloheptyl, cyclopropylmethyl, cyclopentylmethyl, cyclohexylmethyl, aziridinyl, pyrrolidinyl, tetrahydrofuranyl, piperidinyl, tetrahydropyranyl, piperazinyl, morpholinyl, thiomorpholinyl, 1,1-dioxo-1$\lambda^6$-thiomorpholin-4-yl, phenyl, or furanylmethyl group unsubstituted or substituted with a methyl or methoxy substituent. In further preferred embodiments, $R^a$ and $R^b$ are each independently —H, methyl, isopropyl, methoxyethyl, cyclopropyl, cyclohexyl, cyclopropylmethyl, 2-piperidin-1-yl-ethyl, or 2-dimethylamino-ethyl. In further preferred embodiments, $R^a$ and $R^b$ taken together with their nitrogen of attachment form an aziridinyl, pyrrolidinyl, piperidinyl, 2-oxo-piperidin-1-yl, piperazinyl, oxo-piperazinyl, morpholinyl, thiomorpholinyl, 1,1-dioxo-1$\lambda^6$-thiomorpholin-4-yl, 1,1-dioxo-1$\lambda^6$-[1,2]thiazinan-2-yl, azepanyl, 1,4-oxazepanyl, or 7-azabicyclo[2.2.1]hept-7-yl group unsubstituted or substituted with a —C$_{1-6}$alkyl, hydroxymethyl, hydroxyethyl, methoxymethyl, methoxyethyl, fluoro, —OH, or —CO$_2$H substituent.

In preferred embodiments, $R^c$ and $R^d$ taken together with their nitrogen of attachment form piperidinyl, morpholinyl, or pyrrolidinyl.

In preferred embodiments, $R^3$ is a monocyclic cycloalkyl, pyridylmethyl, benzothiadiazolyl, tetrahydroquinolinyl, or tetrahydroisoquinolinyl group unsubstituted or substituted with one, two, or three $R^g$ substituents. In further preferred embodiments, $R^3$ is a 2-pyridyl group unsubstituted or substituted with one or two $R^g$ substituents. In further preferred embodiments, $R^3$ is a 2-pyridyl group unsubstituted or substituted with one or two $R^g$ substituents. In further preferred embodiments, $R^3$ is a 3-pyridyl group unsubstituted or substituted with one $R^g$ substituent.

In preferred embodiments, each $R^g$ substituent is independently methyl, isopropyl, tert-butyl, —CF$_3$, fluoro, chloro, bromo, —OCF$_3$, —SO$_2$NH$_2$, —OCH$_3$, phenoxy, —C(CH$_3$)$_2$—CN, —C(CH$_3$)$_2$—OH, —NO$_2$, —CN, —NH$_2$, —C(O)CH$_3$, —SO$_2$CF$_3$, —SCF$_3$, —CON(CH$_3$)$_2$, —CO$_2$H, phenyl, cyclohexyl, pyrrolidinyl, piperidinyl, morpholinyl, —SCH$_3$, oxazolyl, —SO$_2$—(pyrrolidinyl), —SO$_2$N(CH$_3$)$_2$, —C(CH$_3$)$_2$—CO$_2$CH$_3$, —C(CH$_3$)$_2$—CO$_2$H, 1-hydroxy-ethyl, 2-hydroxy-1,1-dimethyl-ethyl, 3,3,3-trifluoro-1-hydroxy-propyl, 3,3,3-trifluoro-1-hydroxy-1-methyl-propyl, or —SO$_2$CH$_3$; or two adjacent $R^g$ substituents taken together form —OC$_{1-2}$alkylO—. In further preferred embodiments, each $R^g$ substituent is independently methyl, isopropyl, tert-butyl, fluoro, —CF$_3$, chloro, —C(CH$_3$)$_2$—CN, —C(CH$_3$)$_2$—OH, —C(CH$_3$)$_2$—CH$_2$OH, —C(CH$_3$)$_2$—CO$_2$H, acetyl, —SO$_2$CH$_3$, or —SO$_2$CF$_3$.

In preferred embodiments, $R^h$ and $R^i$ taken together with their nitrogen of attachment form pyrrolidinyl, piperidinyl, piperazinyl, or morpholinyl.

In preferred embodiments, $R^j$ is —H, methyl, or —CF$_3$. In preferred embodiments, $R^x$ is —H or methyl. In further preferred embodiments, $R^j$ and $R^x$ taken together with the carbon to which they are attached form a cyclopropyl ring.

In preferred embodiments, Ar is 2-pyridyl substituted with —$CF_3$. In further preferred embodiments, Ar is 2-pyridyl substituted with —Cl, —Br, —F, methyl, —$SO_2CH_3$, or —$SO_2CH_2CH_3$. In further preferred embodiments, Ar is 2-pyridyl, substituted with one or two $R^k$ substituents independently selected from the group consisting of: —$CF_3$, fluoro, chloro, bromo, —$SO_2CH_3$, —$NH_2$, —$NO_2$, —$CO_2CH_3$, —$NHSO_2CH_3$, —CN, —$CONH_2$, —$SO_2CH_2CH_3$, —$SO_2NH_2$, —$SO_2NH$-cyclopropyl, —$SO_2NH$-isopropyl, —$CO_2H$, —$CH_2OH$, and methyl.

In preferred embodiments, $R^l$ and $R^m$ are each independently —H, methyl, ethyl, isopropyl, —$CF_3$, or cyclopropyl.

In preferred embodiments, $R^1$ is —H. In other preferred embodiments, $R^1$ is —$NR^aR^b$, and $R^a$ and $R^b$ are as previously defined. In further preferred embodiments, $R^1$ is a —$C_{1-6}$alkyl group unsubstituted or substituted with a —OH, —$OC_{1-4}$alkyl, —$NR^eR^f$, or halo substituent, and $R^e$ and $R^f$ are as previously defined. In further preferred embodiments, $R^1$ is methyl or isopropyl. In still further preferred embodiments, $R^1$ is a methyl group substituted with a —$OC_{1-4}$alkyl or —$NR^eR^f$ substituent, and $R^e$ and $R^f$ are as previously defined. In further preferred embodiments, $R^1$ is methoxymethyl or piperidinylmethyl. In other preferred embodiments, $R^1$ is methoxy, methylsulfanyl, or methylsulfonyl. In additional preferred embodiments, $R^1$ is cyclopropyl.

In preferred embodiments, $R^a$ and $R^b$ are each independently —H; methyl, ethyl, propyl, isopropyl, butyl, isobutyl, sec-butyl, tert-butyl, pentyl, isopentyl, or hexyl; an ethyl or propyl group substituted with an —$OC_{1-4}$alkyl or —$NR^cR^d$ substituent; or a cyclopropyl, cyclobutyl, cyclopentyl, cyclohexyl, cycloheptyl, cyclopropylmethyl, cyclopentylmethyl, aziridinyl, pyrrolidinyl, tetrahydrofuranyl, piperidinyl, tetrahydropyranyl, piperazinyl, morpholinyl, thiomorpholinyl, 1,1-dioxo-1$\lambda^6$-thiomorpholin-4-yl, or phenyl group unsubstituted or substituted with a —$C_{1-6}$alkyl, —$OC_{1-4}$alkyl, or halo substituent; and $R^c$ and $R^d$ are as previously defined. In other preferred embodiments, $R^a$ and $R^b$ are each independently —H, methyl, methoxyethyl, cyclopropyl, cyclopropylmethyl, 2-piperidin-1-yl-ethyl, or 2-dimethylamino-ethyl. Alternatively, $R^a$ and $R^b$ taken together with their nitrogen of attachment form an aziridinyl, pyrrolidinyl, piperidinyl, 2-oxo-piperidin-1-yl, piperazinyl, oxo-piperazinyl, morpholinyl, thiomorpholinyl, 1,1-dioxo-1$\lambda^6$-thiomorpholin-4-yl, 1,1-dioxo-1$\lambda^6$-[1,2]thiazinan-2-yl, or azepanyl group unsubstituted or substituted with a —$C_{1-6}$alkyl, —OH, or —$CO_2H$ substituent.

In preferred embodiments, $R^c$ and $R^d$ are each independently —H, methyl, or ethyl. Alternatively, $R^c$ and $R^d$ taken together with their nitrogen of attachment form piperidinyl.

In preferred embodiments, $R^p$ and $R^q$ are each independently —H, methyl, or ethyl.

In preferred embodiments, $R^e$ and $R^f$ are each independently —H, methyl, or ethyl.

Preferably, $R^2$ is —H or methyl; more preferably, $R^2$ is —H.

Preferably, $R^3$ is a phenyl, pyridyl, pyrimidinyl, pyrazinyl, quinolinyl, or isoquinolinyl group unsubstituted or substituted with one or two $R^g$ substituents, and each $R^g$ substituent is as previously defined. In further preferred embodiments, $R^3$ is a pyridyl, pyrimidinyl, pyrazinyl, quinolinyl, or isoquinolinyl group unsubstituted or substituted with one or two $R^g$ substituents, and each $R^g$ substituent is as previously defined. In additional preferred embodiments, $R^3$ is a pyridyl, thiazolyl, or pyridazinyl group unsubstituted or substituted with one or two $R^g$ substituents, and each $R^g$ substituent is as previously defined. In still further preferred embodiments, $R^3$ is a phenyl group substituted with one or two $R^g$ substituents, and each $R^g$ substituent is as previously defined. In still further preferred embodiments, $R^3$ is a benzyl or phenethyl group unsubstituted or substituted with one or two $R^g$ substituents, and each $R^g$ substituent is as previously defined. In still further preferred embodiments, $R^3$ is a 2-pyridyl group unsubstituted or substituted with one $R^g$ substituent, and $R^g$ substituent is as previously defined.

Preferably, each $R^g$ substituent is —$C_{1-6}$alkyl, —OH, —$OC_{1-6}$alkyl, phenoxy, —CN, —$NO_2$, —$N(R^h)R^i$, —$C(O)N(R^h)R^i$, —$N(R^h)C(O)R^i$, —$N(R^h)SO_2C_{1-6}$alkyl, —$C(O)C_{1-6}$alkyl, —$S(O)_{0-2}$—$C_{1-6}$alkyl, —$SO_2CF_3$, —$SO_2N(R^h)R^i$, —$SCF_3$, halo, —$CO_2H$, —$CO_2C_{1-6}$alkyl, —$C(R^j)_2$—CN, or —$C(R^j)_2$—OH, and $R^h$, $R^i$, and $R^j$ are as previously defined. Alternatively, two adjacent $R^g$ moieties taken together form —$OC_{1-2}$alkylO—. In further preferred embodiments, each $R^g$ substituent is isopropyl, tert-butyl, —$CF_3$, chloro, —$OCF_3$, —$SO_2NH_2$, —$OCH_3$, phenoxy, bromo, —$C(CH_3)_2$—CN, —$C(CH_3)_2$—OH, —$NO_2$, —CN, —$NH_2$, —$C(O)CH_3$, —$SO_2CF_3$, or —$SCF_3$; or two adjacent $R^g$ substituents taken together form —$OC_{1-2}$alkylO—. In still further preferred embodiments, each $R^g$ substituent is isopropyl, tert-butyl, —$CF_3$, chloro, —$C(CH_3)_2$—CN, —$C(CH_3)_2$—OH, or —$SO_2CF_3$.

In preferred embodiments, $R^h$ and $R^i$ are each independently —H, methyl, or ethyl.

In preferred embodiments, $R^j$ is —H, methyl, or ethyl.

In preferred embodiments, Ar is a phenyl group unsubstituted or substituted with one or two $R^k$ substituents, and each $R^k$ substituent is as previously defined. In further preferred embodiments, Ar is a phenyl group substituted with a —$NO_2$, —$N(R^l)R^m$, —$C(O)N(R^l)R^m$, —$N(R^l)C(O)R^m$, —$N(R^l)SO_2C_{1-6}$alkyl, —$N(R^l)SO_2CF_3$, —$SO_2CH_3$, or —$SO_2CF_3$ substituent, and $R^l$ and $R^m$ are as previously defined. In still further preferred embodiments, Ar is a fused-bicyclic heteroaryl group unsubstituted or substituted with one or two $R^k$ substituents, and each $R^k$ substituent is as previously defined. In still further preferred embodiments, Ar is 2-pyridyl substituted with —$CF_3$, —$NO_2$, or —$N(R^l)R^m$, and $R^l$ and $R^m$ are as previously defined. In still further preferred embodiments, Ar is 2-pyridyl substituted with —Cl, —Br, methyl, or —$SO_2CH_3$. In still further preferred embodiments, Ar is quinoxalinyl or phthalizinyl. In still further preferred embodiments, Ar is a phenyl, pyridyl, pyrimidinyl, or fused-bicyclic heteroaryl group substituted on a carbon ring atom at a position ortho to the point of attachment with an $R^k$ substituent, and the $R^k$ substituent is as previously defined.

In preferred embodiments, each $R^k$ substituent is —$C_{2-6}$alkyl, —OH, phenoxy, —CN, —$NO_2$, —$N(R^l)R^m$, —$C(O)N(R^l)R^m$, —$N(R^l)C(O)R^m$, —$N(R^l)SO_2C_{1-6}$alkyl, —$N(R^l)SO_2CF_3$, —$C(O)C_{1-6}$alkyl, —$S(O)_{0-2}$—$C_{1-6}$alkyl, —$SO_2CF_3$, —$SO_2N(R^l)R^m$, —$SCF_3$, —$OCF_3$, —$CO_2H$, or —$CO_2C_{1-6}$alkyl; or two adjacent $R^k$ substituents taken together form —$OC_{1-2}$alkylO—; and $R^l$ and $R^m$ are as previously defined. In still further preferred embodiments, each $R^k$ substituent is —$N(R^l)R^m$, —$NO_2$, —$N(R^l)SO_2CF_3$, or —$N(R^l)SO_2CH_3$, and $R^l$ and $R^m$ are as previously defined.

In preferred embodiments, $R^l$ and $R^m$ are each independently —H, methyl, ethyl, or —$CF_3$.

Further preferred embodiments of the present invention include compounds of Formula (I) wherein:

a) $R^1$ is —H, —$NR^aR^b$, —$C_{1-6}$alkyl, —O—$C_{1-6}$alkyl, —S—$C_{1-6}$alkyl, —$SO_2$—$C_{1-6}$alkyl, —$CH_2$—O—$C_{1-4}$alkyl, or —$CH_2$—$NR^eR^f$; $R^2$ is —H; $R^3$ is a pyridyl, pyrimidinyl, pyrazinyl, quinolinyl, or isoquinolinyl group unsubstituted or substituted with one or two $R^g$ substituents; and Ar is a phenyl group substituted with one or two $R^k$ substituents; and $R^a$, $R^b$, $R^e$, $R^f$, $R^g$, and $R^k$ are as previously defined; or b) $R^1$ is —H, —NR$^a$R$^b$, —C$_{1-6}$alkyl, —O—C$_{1-6}$alkyl, —S—C$_{1-6}$alkyl, —SO$_2$—C$_{1-6}$alkyl, —CH$_2$—O—C$_{1-4}$alkyl, or —CH$_2$—NR$^e$R$^f$; $R_2$ is —H; $R_3$ is a benzyl, phenethyl, indanyl, pyridyl, pyrimidinyl, pyrazinyl, quinolinyl, or isoquinolinyl group unsubstituted or substituted with one or two $R^g$ substituents; and Ar is a phenyl group substituted with one or two $R^k$ substituents, where each $R^k$ substituent is —C$_{2-6}$alkyl, —OH, phenoxy, —CN, —NO$_2$, —N(R$^l$)R$^m$, —C(O)N(R$^l$)R$^m$, —N(R$^l$)C(O)R$^m$, —N(R$^l$)SO$_2$C$_{1-6}$alkyl, —N(R$^l$)SO$_2$CF$_3$, —C(O)C$_{1-6}$alkyl, —S(O)$_{0-2}$—C$_{1-6}$alkyl, —SO$_2$CF$_3$, —SO$_2$N(R$^l$)$^m$, —SCF$_3$, —OCF$_3$, —CO$_2$H, or —CO$_2$C$_{1-6}$alkyl; or two adjacent $R^k$ substituents taken together form —OC$_{1-2}$alkylO—; and $R^a$, $R^b$, $R^e$, $R^f$, $R^g$, $R^l$, and $R^m$ are as previously defined; or c) $R^1$ is —H, —NR$^a$R$^b$, —C$_{1-6}$alkyl, —O—C$_{1-6}$alkyl, —S—C$_{1-6}$alkyl, —SO$_2$—C$_{1-6}$alkyl, —CH$_2$—O—C$_{1-4}$alkyl, or —CH$_2$—NR$^e$R$^f$; $R_2$ is —H; $R_3$ is a benzyl or phenethyl group unsubstituted or substituted with one or two $R^g$ substituents; and Ar is 2-pyridyl substituted with —CF$_3$, —NO$_2$, or —N(R$^l$)R$^m$; and $R^a$, $R^b$, $R^e$, $R^f$, $R^g$, $R^l$, and $R^m$ are as previously defined; or d) $R^1$ is —C$_{1-6}$alkyl; $R_2$ is —H; $R_3$ is a phenyl, pyridyl, pyrimidinyl, pyrazinyl, quinolinyl, or isoquinolinyl group unsubstituted or substituted with one or two $R^g$ substituents; and Ar is a phenyl, pyridyl, pyrimidinyl, or fused-bicyclic heteroaryl group unsubstituted or substituted with one or two $R^k$ substituents; and $R^g$ and $R^k$ are as previously defined; or e) $R^1$ is —H, —NR$^a$R$^b$, —C$_{1-6}$alkyl, —O—C$_{1-6}$alkyl, —S—C$_{1-6}$alkyl, —SO$_2$—C$_{1-6}$alkyl, —CH$_2$—O—C$_{1-4}$alkyl, or —CH$_2$—NR$^e$R$^f$; $R_2$ is —H; $R_3$ is a phenyl, benzyl, phenethyl, indanyl, pyridyl, pyrimidinyl, pyrazinyl, quinolinyl, or isoquinolinyl group unsubstituted or substituted with one or two $R^g$ substituents; and Ar is a fused-bicyclic heteroaryl group unsubstituted or substituted with one or two $R^k$ substituents; and $R^a$, $R^b$, $R^e$, $R^f$, $R^g$, and $R^k$ are as previously defined; or f) $R^1$ is —NR$^a$R$^b$; $R^2$ is —H; $R^3$ is a phenyl group substituted with one or two $R^g$ substituents, where each $R^g$ substituent is —C$_{1-6}$alkyl, —OH, —OC$_{1-6}$alkyl, phenoxy, —CN, —NO$_2$, —N(R$^h$)R$^i$, —C(O)N(R$^h$)R$^i$, —N(R$^h$)C(O)R$^i$, —N(R$^h$)SO$_2$C$_{1-6}$alkyl, —C(O)C$_{1-6}$alkyl, —S(O)$_{0-2}$—C$_{1-6}$alkyl, —SO$_2$CF$_3$, —SO$_2$N(R$^h$)R$^i$, —SCF$_3$, halo, —CO$_2$H, —CO$_2$C$_{1-6}$alkyl, —C(R$^j$)$_2$—CN, or —C(R$^j$)$_2$—OH; or two adjacent $R^g$ substituents taken together form —OC$_{1-2}$alkylO—; and Ar is a phenyl, pyridyl, pyrimidinyl, or fused-bicyclic heteroaryl group unsubstituted or substituted with one or two-$R^k$ substituents; and $R^a$, $R^b$, $R^h$, $R^i$, $R^j$, and $R^k$ are as previously defined; or g) $R^1$ is —NR$^a$R$^b$; $R^2$ is —H; $R^3$ is a phenyl, benzyl, phenethyl, indanyl, pyridyl, pyrimidinyl, pyrazinyl, quinolinyl, or isoquinolinyl group unsubstituted or substituted with one or two $R^g$ substituents; and Ar is a phenyl group unsubstituted or substituted with one or two $R^k$ substituents; and $R^a$, $R^b$, $R^g$, and $R^k$ are as previously defined.

The invention includes also pharmaceutically acceptable salts of the compounds represented by Formula (I), preferably of those described above. Pharmaceutically acceptable salts of the specific compounds exemplified herein are especially preferred.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Exemplary pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or the like.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

In preferred embodiments, the present invention relates to compounds of Formula (I) and to sulfate, hydrochloride, fumarate, tartrate, phosphate, methanesulfonic acid (mesylate), benzenesulfonic acid (besylate), and p-toluensulfonic acid (tosylate) salts thereof.

The invention also relates to treatment methods employing pharmaceutically acceptable prodrugs of the compounds of Formula (I). The term "prgdrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is not toxic, biologically intolerable, or otherwise biologically unsuitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Exemplary amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Preferred amides are derived from ammonia, $C_{1-3}$alkyl primary amines, and di($C_{1-2}$alkyl) amines. Exemplary esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

Pharmaceutically active metabolites may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I) and their pharmaceutically acceptable salts, pharmaceutically acceptable prodrugs, and pharmaceutically active metabolites (collectively, "agents") of the present invention are useful as TRPV1 modulators in the methods of the invention. The agents may be used in the inventive methods for the treatment or prevention of medical conditions, diseases, or disorders mediated through modulation of TRPV1, such as those described herein. Symptoms or disease states are intended to be included within the scope of "medical conditions, disorders, or diseases."

Accordingly, the invention relates to methods of using the pharmaceutical agents described herein to treat subjects diagnosed with or suffering from a disease, disorder, or condition mediated through TRPV1 activity, such as: i) pain (acute, chronic, inflammatory, or neuropathic pain); ii) itch or various inflammatory disorders; iii) inner ear disorders; iv) fever and other disorders of thermoregulation; v) tracheobronchial and diaphragmatic dysfunction; vi) gastrointestinal and urinary tract disorders; and vii) disorders associated with reduced blood flow to the CNS or CNS hypoxia.

In a preferred embodiment, an agent of the present invention is administered to treat pain. Pain may be associated with various diseases, disorders, or conditions, and may include various etiologies. Exemplary types of pain treatable with a TRPV1-modulating agent according to the invention include pain arising from or caused by: osteoarthritis, rotator cuff disorders, arthritis (e.g., rheumatoid arthritis or inflammatory arthritis), fibromyalgia, migraine and headache (e.g. cluster headache, sinus headache, or tension headache; see, Goadsby *Curr. Pain Headache Reports* 2004, 8, 393), sinusitis, oral mucositis, toothache, dental trauma, dental extractions, dental infections, burn, sunburn, dermatitis, psoriasis, eczema, insect sting or bite, burn pain (Bolkskei et al., *Pain* 2005, in press), musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, GI tract disorders, interstitial cystitis, urinary tract infection, urethral colic, renal colic, pharyngitis, cold sores, stomatitis, external otitis, otitis media (Chan et al., *Lancet* 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, cholecystitis, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J. Pharmacol. Exp. Ther.* 2005, 314,410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barré syndrome, Raynaud's syndrome, coronary artery spasm (Printzmetal's or variant angina), visceral hyperalgesia (Pomonis, J. D. et al. *J. Pharmacol. Exp. Ther.* 2003, 306, 387; Walker, K. M. et al., J. Pharmacol. Exp. Ther. 2003, 304(1), 56-62), thalamic pain, cancer (e.g. pain caused by cancer, by treatment of cancer by radiation or chemotherapy, or by nerve or bone lesions associated with cancer (see, Menendez, L. et al., Neurosci. Lett. 2005, 393 (1), 70-73; Asai, H. et al., Pain 2005,117, 19-29), or bone destruction pain (see, Ghilardi, J. R. et al., J. Neurosci. 2005, 25, 3126-31)), infection, or metabolic disease. Additionally, the compounds may be used to treat pain indications such as visceral pain, ocular pain, thermal pain, dental pain, capsaicin-induced pain (as well as other symptoms induced by capsaicin such as cough, lachrymation, and bronchospasm).

In another preferred embodiment, agents are administered to treat: itch, which may arise from various sources, such as dermatological or inflammatory disorders; or inflammatory disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBD), Crohn's disease, and ulcerative colitis (Geppetti, P. et al., Br. J. Pharmacol. 2004,141,1313-20; Yiangou, Y. et al., Lancet 2001, 357, 1338-39; Kimball, E. S. et al., Neurogastroenterol. Motil., 2004,16, 811), osteoarthritis (Szabo, A. et al., J. Pharmacol. Exp. Ther. 2005, 314,111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another preferred embodiment, inner ear disorders are treated with an inventive agent. Such disorders include, for example, hyperacusis, tinnitus, vestibular hypersensitivity, and episodic vertigo.

In another preferred embodiment, tracheobronchial and diaphragmatic dysfunctions are treated with an inventive agent, including, for example, asthma and allergy-related immune responses (Agopyan, N. et al., Am. J. Physiol. Lung Cell Mol. Physiol. 2004, 286, L563-72; Agopyan, N. et al., Toxicol. Appl. Pharmacol. 2003,192, 21-35), cough (e.g., acute or chronic cough, or cough caused by irritation from gastroesophageal reflux disease; see, Lailoo, U. G. et al., J. Appl. Physiol. 1995, 79(4), 1082-7), bronchospasm, chronic obstructive pulmonary disease, chronic bronchitis, emphysema, and hiccups (hiccoughs, singultus).

In yet another preferred embodiment, gastrointestinal and urinary tract disorders are treated with an inventive agent, such as, bladder overactivity, inflammatory hyperalgesia, visceral hyperreflexia of the urinary bladder, hemorrhagic cystitis (Dinis, P. et al., J. Neurosci. 2004, 24,11253-11263), interstitial cystitis (Sculptoreanu, A. et al., Neurosci. Lett. 2005, 381, 42-46), inflammatory prostate disease, prostatitis (Sanchez, M. et al., Eur. J. Pharmacol. 2005, 515, 20-27), nausea, vomiting, intestinal cramping, intestinal bloating, bladder spasms, urinary urgency, defecation urgency and urge incontinence.

In another preferred embodiment, disorders associated with reduced blood flow to the CNS or CNS hypoxia are treated with an inventive agent. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, agents are administered to treat other diseases, disorders, or conditions mediated through TRPV1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In especially preferred embodiments of the therapeutic methods of the invention, effective amounts of the TRPV1 modulators of the present invention are administered to treat pain, itch, cough, asthma, or inflammatory bowel disease.

The term "treat" or "treating" as used herein is intended to refer to administration of an agent or composition of the invention to a subject for the purpose of effecting a therapeutic or prophylactic benefit through modulation of TRPV1 activity. Treating includes reversing, ameliorating, alleviating, inhibiting the progress of, lessening the severity of, or preventing a disease, disorder, or condition, or one or more symptoms of such disease, disorder or condition mediated through modulation of TRPV1 activity. The term "subject" refers to a mammalian patient in need of such treatment, such as a human. "Modulators" include both inhibitors and activators, where "inhibitors" refer to compounds that decrease, prevent, inactivate, desensitize or down-regulate TRPV1 expression or activity, and "activators" are compounds that increase, activate, facilitate, sensitize, or up-regulate TRPV1 expression or activity.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 2.5 g/day. Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or included with such an agent as an additional active ingredient in a pharmaceutical composition according to the invention. In an exemplary embodiment, additional active compounds are those that are known or discovered to be effective in the treatment of conditions, disorders, or diseases mediated by TRPV1 activity, such as another TRPV1 modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The agents of the invention are used, alone or in combination with one or more other active ingredients, to formulate pharmaceutical compositions of the invention. A pharmaceutical composition of the invention comprises: (a) an effective amount of a pharmaceutical agent in accordance with the invention; and (b) a pharmaceutically acceptable excipient.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques known or that become available to those skilled in the art. The compositions may be administered in the inventive methods by a suitable route of delivery; e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the agent and any other active ingredients mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipiets include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil, sesame oil, or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Preferred agents useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

SCHEME A

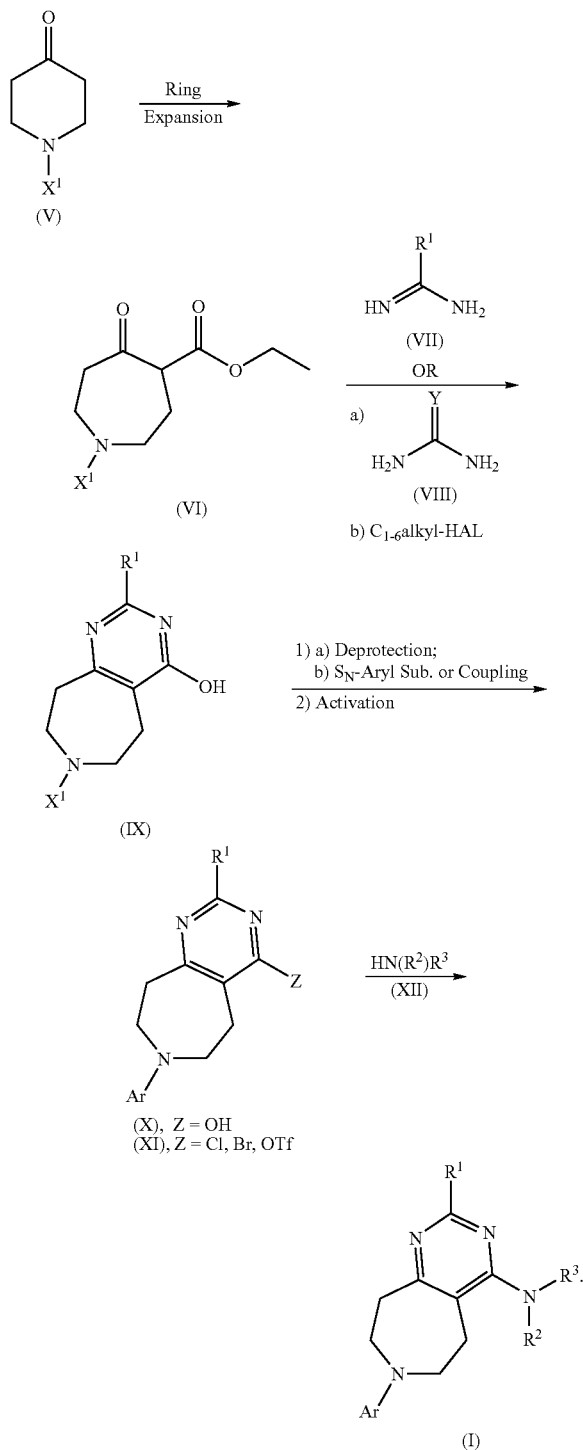

Referring to general Scheme A, compounds of Formula (I) may be prepared from β-ketoesters (VI), where $X^1$ is a suitable amino protecting group, such as a benzyl or carbamate group. Protected piperidones (V) are commercially available or may be prepared according to known methods. Preferred protecting groups for amines include, tert-butyl carbamate (Boc) or benzyl groups. β-Ketoesters (VI) may be prepared according to general techniques known in the art. For example, β-ketoesters (VI) may be accessed from piperidones (V) by ring expansion of piperidones (V) with ethyl diazoacetate in the presence of a Lewis acid, such as $BF_3 \cdot OEt$, in a suitable solvent, such as $Et_2O$ or $CH_2Cl_2$ or a mixture thereof, at temperatures ranging from about 0° C. to about room temperature (rt). β-Ketoesters (VI) may be reacted with amidines or carboximidamides (VII), or with ureas or thioureas (VIII), for example, in the presence of NaOEt or KOtBu, in a solvent such as EtOH or tBuOH or a mixture thereof, at temperatures between rt and the reflux temperature of the solvent, to form hydroxy pyrimidines (IX). Where the condensation is done with a urea or thiourea, in situ alkylation with an alkyl chloride or bromide provides pyrimidines (IX) where $R^1$ is $—S—C_{1-6}$alkyl or $—O—C_{1-6}$alkyl. The $X^1$ protecting group may be removed using known methods. For example, a Boc group may be removed with an acid such as TFA or HCl, in a solvent such as $Et_2O$, dioxane, EtOH, or MeOH or a mixture thereof, to form amines (IX) where $X^1$=—H. Where an acid salt is obtained, the corresponding free base may be obtained by suitable general methods known in the art. Preferably, the free base is obtained by filtration of the salt through resin-bound carbonate using an alcoholic solvent, preferably MeOH. Where $X^1$ is a benzyl group, the group may be removed according to standard methods, such as hydrogenation in the presence of a palladium catalyst such as Pd/C or $Pd(OH)_2/C$, in a solvent such as EtOH. Hydroxy pyrimidines (IX) where $X^1$ is —H may then be converted to amines (X) using known methods such as $S_N$-aryl substitution, or palladium-mediated cross-couplings. $S_N$-Aryl substitution may be accomplished by treatment of hydroxy pyrimidines (XI), where $X^1$ is —H, with Ar-HAL (where HAL is halo), such as 2-chloro-3-trifluoromethyl-pyridine, in the presence of a base such $K_2CO_3$, in a polar solvent such as DMSO, at temperatures between about rt and the reflux temperature of the solvent. Palladium-mediated cross-couplings are done by reacting Ar-HAL in the presence of a palladium catalyst. Preferably, hydroxy pyrimidines (IX), where $X^1$ is —H, are treated with $Et_3N$ or $(iPr)_2NEt$, in suitable solvents, such as n-BuOH, tBuOH, t-amyl alcohol, DMF, DMSO, DME, or NMP, or a mixture thereof, at temperatures from about 100 to about 200° C. Pyrimidines (X) can then be activated for use in palladium-mediated cross-coupling reactions or $S_N2$ reactions by general procedures known in the art. For example, treatment with $POCl_3$, $PCl_3$, $PBr_3$, or $POBr_3$ affords the corresponding halopyrimidines (XI) where Z is chloride or bromide. Treatment of pyrimidines (X) with trifluoromethane-sulfonic anhydride or N-phenyl-bis(trifluoromethanesulfonimide) in DCE, $CH_2Cl_2$, or THF, or a mixture thereof, in the presence of a base such as pyridine, $Et_3N$, $(iPr)_2NEt$, or KOtBu, provides triflates (XI) where Z is $—OSO_2CF_3$. In a preferred embodiment, pyrimidines (X) are treated with $POCl_3$ in $CH_3CN$ at temperatures from about 80 to about 100° C.

Substitution of pyrimidines (XI) with amines $HN(R^2)R^3$ to produce compounds of Formula (I) may be accomplished by various suitable methods within the routine purview of artisans. Where Z is Cl, substitution may involve heating chloropyrimidines (XI) with suitable amines (XII) in alcoholic solvents such as MeOH, EtOH, tBuOH, n-BuOH, or t-amyl-OH, or a mixture thereof, at temperatures from about rt to about the reflux temperature of the solvent. Preferably, the solvent is n-BuOH and the temperature is about 130° C. Alternatively, chloro-pyrimidines (XI) may be reacted with amines (XII) in the presence of an acid catalyst, preferably p-toluenesulfonic acid or TFA, in toluene or dioxane, at temperatures from about 100 to about 150° C., to provide compounds of Formula (I). Coupling of halides or triflates (XI) with amines (XII), in the presence of a catalyst such as $Pd(OAc)_2$, $Pd(PPh_3)_4$, $PdCl_2(PPh_3)_2$, or $PdCl_2(Po-tol_3)_2$, in a solvent such as THF, 1,4-dioxane, DMA, DMF, DME, or toluene, or mixtures thereof, in the presence of a base such as NaOtBu, $Na_2CO_3$, $K_2CO_3$, $Cs_2CO_3$, or $K_3PO_4$, with or without an additive such as 2-(dicyclohexylphosphanyl)biphenyl (DCPB), also affords pyrimidines (I). In a preferred embodiment, coupling is accomplished in the presence of $Pd(OAc)_2$ catalyst, DCPB, and NaOtBu in toluene at temperatures from about 100 to about 200° C. in a microwave reactor.

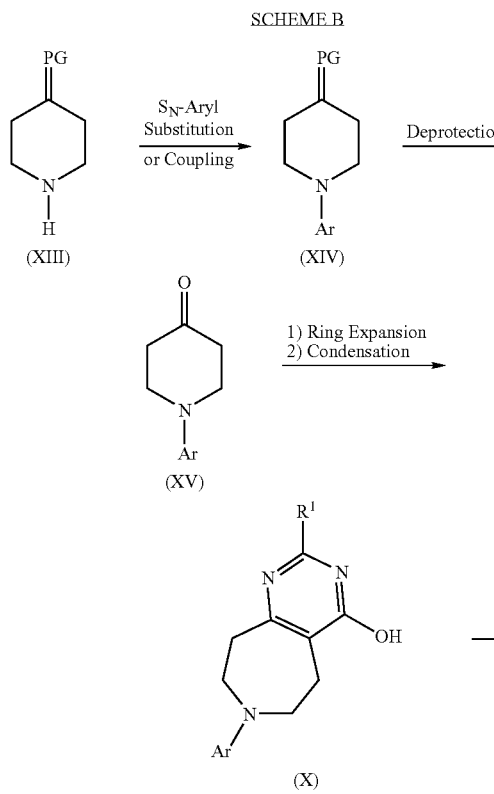

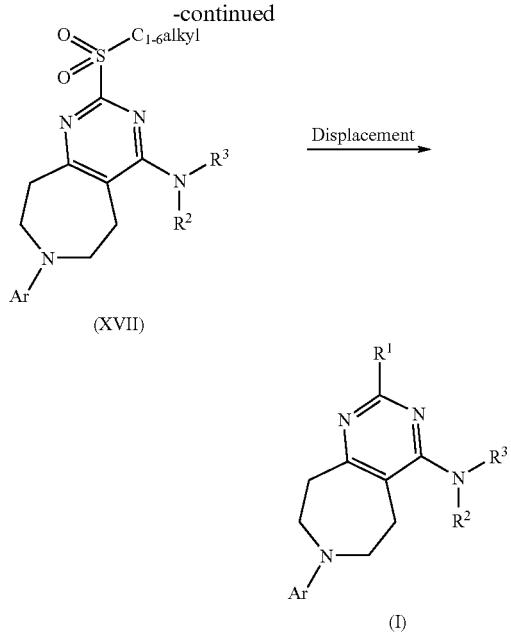

Referring to Scheme B, compounds of Formula (I) may be prepared by an alternate general route. Protected piperidones (XV), such as 1,4-dioxa-8-aza-spiro[4,5]decane (where PG is —O—$(CH_2)_2$—O—), may be converted to aryl amines (XIV) by $S_N$-aryl substitution or palladium-mediated cross-couplings as described in Scheme A. Deprotection of the protecting group using known general procedures, such as concentrated HCl, provides ketones (XV). Ketones (XV) may be processed into compounds of Formula (I) generally according to the ring expansion, condensation, activation, and displacements described in Scheme A.

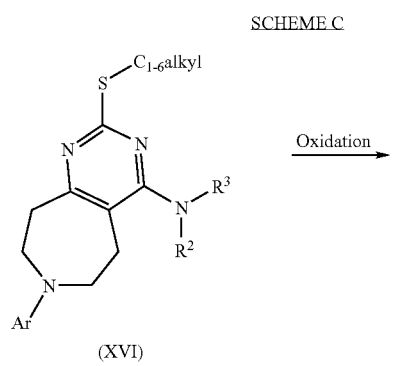

Referring to Scheme C, thioethers (XVI), obtained as described in Scheme A, may be oxidized using generally known methods to provide sulfones (XVII). Displacement of the sulfone substituent is attained by reaction with alcohols HO—$C_{1-6}$alkyl or amines $HN(R^a)R^b$ in solvents such as MeOH, EtOH, n-BuOH, THF, DMF, DMSO, or toluene, or a mixture thereof, with or without the presence of a suitable base, such as NaOMe, NaOEt, KOtBu, NaH, $Et_3N$, $(iPr)_2EtN$, or pyridine, at temperatures between rt and the reflux temperature of the solvent. Preferably, displacement with amines $HN(R^a)R^b$ is performed by heating with sulfones (XVII) in toluene in a sealed tube at 110° C.

Compounds of Formula (I) may be converted to their corresponding salts using methods known to those skilled in the art. For example, amines of Formula (I) may be treated with trifluoroacetic acid, HCl, citric acid, $H_2SO_4$, methanesulfonic acid (MsOH), benzenesulfonic acid, or p-toluenesulfonic acid (TsOH) in a solvent such as $Et_2O$, EtOAc, $CH_2Cl_2$, THF, or MeOH, or a mixture thereof, to provide the corresponding salt forms.

Compounds prepared according to the schemes described above may be obtained as single enantiomers, diastereomers, or regioisomers, or as racemic mixtures or mixtures of enantiomers, diastereomers, or regioisomers. Where regioisomeric or diastereomeric mixtures are obtained, isomers may be separated using conventional methods such as chromatography or crystallization. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, diastereomeric salt formation, or derivatization into diastereomeric adducts followed by separation.

The following examples are provided to further illustrate aspects of the invention and various preferred embodiments.

EXAMPLES

Chemistry

In obtaining the characterization data described in the examples below, the following analytical protocols were followed unless otherwise indicated.

NMR spectra were obtained on Bruker model DRX spectrometers. The format of $^1$H NMR data below is: chemical shift in ppm downfield of the tetramethylsilane reference (multiplicity, coupling constant J in Hz, integration).

Mass spectra were obtained on an Agilent series 1100 MSD using electrospray ionization (ESI) in either positive or negative modes as indicated. Calculated mass corresponds to the exact mass.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Normal phase purification was typically done by normal phase flash column chromatography (FCC) with RediSep® silica gel columns using EtOAc/hexanes as eluent unless otherwise specified.

Reverse phase high performance liquid chromatography (HPLC) was performed under the following conditions: Instrument, Shimadzu; Column, Phenomenex Gemini column 5 μm C18 (150×21.2 mm) or Waters Xterra RP18 OBD 5 μm (100×30 mm); Gradient, 95:5 to 0:100 water (0.05% TFA)/CH$_3$CN (0.05% TFA); Flow rate, 30 mL/min; Detection, UV at λ=254 nM.

Microwave reactions were carried out in either a CEM Discover® or a Biotage Initiator™ Microwave at specified temperatures.

Where solutions were "concentrated", they were concentrated using a rotary evaporator under reduced pressure. Unless otherwise specified, reaction solutions were stirred at room temperature (rt) under a $N_{2(g)}$ atmosphere.

Hydrochloride salts were obtained by treating the corresponding free bases with HCl (4 N in dioxane) at rt. The mixtures were either concentrated to obtain the HCl salt, or the resulting solid was isolated by filtration.

Trifluoroacetic acid salts were obtained by purification of the crude reaction product by preparative reverse phase HPLC.

Intermediate A: 5-Oxo-azepane-1,4-dicarboxylic acid 1-tert-butyl ester 4-ethyl ester

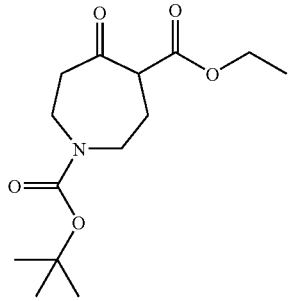 [SMILES: CCOC(=O)C1CCN(C(=O)OC(C)(C)C)CCC1=O]

To a 0° C. solution of 1-BOC-4-piperidone (20 g, 0.10 mol) in Et$_2$O (200 mL) was added BF$_3$.Et$_2$O (14 mL, 0.11 mol) followed by drop-wise addition of ethyl diazoacetate (13.7 mL, 0.11 mol) over 1 h. After addition was complete, the mixture was stirred at 0° C. for 1 h. The mixture was diluted with 30% aq. Na$_2$CO$_3$ and water at 0° C. and extracted with EtOAc. The combined organic layers were dried (Na$_2$SO$_4$) and concentrated. Purification of the residue (FCC) afforded the title compound (25.6 g, 98%). $^1$H NMR (CDCl$_3$): 4.25-2.03 (m, 11H), 1.47-1.45 (d, J=7.8 Hz, 9H), 1.31-1.24 (m, 3H).

Intermediate B: 5-Oxo-1-(3-trifluoromethyl-pyridin-2-yl)-azepane-4-carboxylic acid ethyl ester

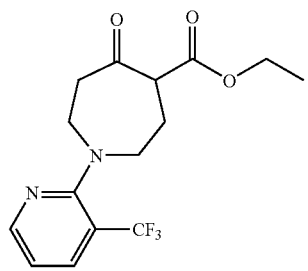 [SMILES: CCOC(=O)C1CCN(c2ncccc2C(F)(F)F)CCC1=O]

The title compound was prepared analogously to Intermediate A from 3'-trifluoromethyl-2,3,5,6-tetrahydro-[1,2']bipyridinyl-4-one (see U.S. Pat. Appl. Publ. US 2005/080095), using CH$_2$Cl$_2$ instead of Et$_2$O, and with a reaction time of 12 h at rt. MS (ESI): mass calcd. for C$_{15}$H$_{17}$F$_3$N$_2$O$_3$, 330.12; m/z found, 331.1 [M+H]$^+$. $^1$H NMR (mixture of enol and keto forms; CDCl$_3$): 12.75 (s, 1.4H), 8.44-8.41 (m, 1.0H), 8.40-8.38 (m, 1.4H), 7.90-7.83 (m, 2.5H), 7.04-6.99 (m, 1.0H), 6.97-6.92 (m, 1.5H), 4.26-4.19 (m, 5.6H), 3.77-3.65 (m, 3.1H), 3.51-3.45 (m, 4.4H), 3.39-3.33 (m, 4.2H), 3.02-2.94 (m, 1.0H), 2.83-2.75 (m, 4.1H), 2.70-2.66 (m, 3.1H), 2.34-2.15 (m, 2.0H), 1.36-1.23 (m, 8.9H).

Example 1

(4-tert-Butyl-phenyl)-[7-(3-trifluoromethyl-pyridin-2-yl)-6,7,8,9-tetrahydro-5H-pyrimido[4,5-d]azepin-4-yl]-amine

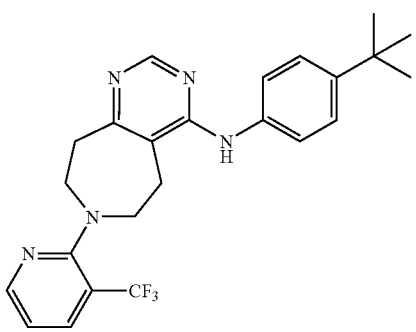 [SMILES: CC(C)(C)c1ccc(Nc2ncnc3c2CCN(c2ncccc2C(F)(F)F)CC3)cc1]

Step A. 4-Hydroxy-5,6,8,9-tetrahydro-pyrimido[4,5-d]azepine-7-carboxylic acid tert-butyl ester

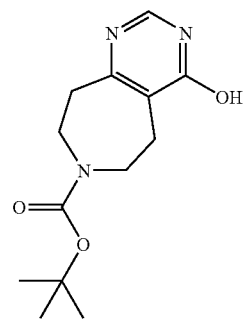 [SMILES: CC(C)(C)OC(=O)N1CCc2ncnc(O)c2CC1]

25

To solution of 5-oxo-azepane-1,4-dicarboxylic acid 1-tert-butyle ester 4-ethyl ester (8.8 g, 30.8 mmol) in EtOH (308 mL) was added NaOEt (21% in EtOH; 38 mL) followed by formamidine acetate (4.8 g, 45.9 mmol). The mixture was heated at reflux for 2 h, then was concentrated, azeotroping with toluene. The residue was dissolved in water and made basic via addition of 50% aq. NaOH. The aqueous layer was extracted with toluene and then acidified to pH=7 with HOAc (precipitate formed). The mixture was heated at 100° C. for 1 h, cooled to 0° C., and filtered to give the title compound (2.5 g, 31%), which was used without further purification.

Step B.
6,7,8,9-Tetrahydro-5H-pyrimido[4,5-d]azepin-4-ol

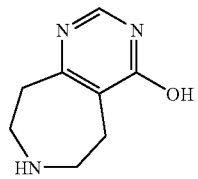

To a solution of 4-hydroxy-5,6,8,9-tetrahydro-pyrimido[4,5-d]azepine-7-carboxylic acid tert-butyl ester (1.0 g, 3.77 mmol) in CH$_2$Cl$_2$ (14 mL) was added 4 M HCl in dioxane (4 mL, 15 mmol). After 24 h, the mixture was concentrated to afford the HCl salt (923 mg). The salt (200 mg, 1.0 mmol) was dissolved in MeOH (10 mL) and filtered through quaternary amine resin, carbonate form (1.0 g) and concentrated to provide the title compound (159 mg, 97%).

Step C. 7-(3-Trifluoromethyl-pyridin-2-yl)-6,7,8,9-tetrahydro-5H-pyrimido[4,5-d]azepin-4-ol

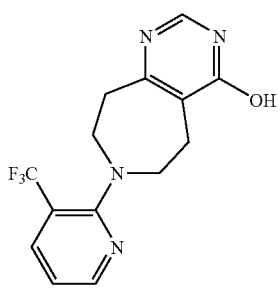 [SMILES: Oc1ncnc2c1CCN(c1ncccc1C(F)(F)F)CC2]

A solution of 6,7,8,9-tetrahydro-5H-pyrimido[4,5-d]azepin-4-ol (353 mg, 1.76 mmol), 2-fluoro-3-trifluoromethyl-pyridine (582 mg, 3.53 mmol), iPr$_2$NEt (0.9 mL, 5.28 mmol), and t-amyl alcohol (5 mL) was heated in a microwave at 180° C. for 5 h. The mixture was concentrated, diluted with water, and extracted with EtOAc. The combined organic layers were dried (Na$_2$SO$_4$) and concentrated to give the title compound (185 mg, 34%), which was used in the next step without further purification.

Step D. 4-Chloro-7-(3-trifluoromethyl-pyridin-2-yl)-6,7,8,9-tetrahydro-5H-pyrimido[4,5-d]azepine

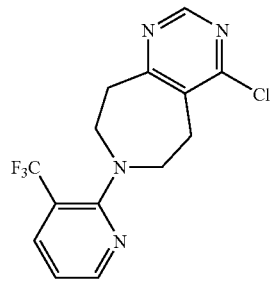 [SMILES: FC(F)(F)c1cccnc1N1CCc2ncnc(Cl)c2CC1]

To a solution of 7-(3-trifluoromethyl-pyridin-2-yl)-6,7,8,9-tetrahydro-5H-pyrimido[4,5-d]azepin-4-ol (185 mg, 0.60 mmol) in CH$_3$CN (2 mL) was added POCl$_3$ (0.11 mL, 1.19 mmol). The reaction mixture was heated at 90° C. for 2 h. The mixture was cooled to rt, diluted with EtOAc, and quenched slowly with saturated (satd.) aq. NaHCO$_3$. The combined organic layers were dried (Na$_2$SO$_4$) and concentrated. The crude residue was purified (FCC) to give the title compound (65 mg, 33%).

Step E. To a solution of 4-chloro-7-(3-trifluoromethyl-pyridin-2-yl)-6,7,8,9-tetrahydro-5H-pyrimido[4,5-d]azepine (27 mg, 0.085 mmol) in n-BuOH (1 mL) was added 4-tert-butylaniline (27 μL, 0.17 mmol). After 2 h at 135° C., the mixture was cooled to rt, quenched with saturated aqueous (satd. aq.) NaHCO$_3$, and extracted with EtOAc. The combined organic layers were dried (Na$_2$SO$_4$) and concentrated. The residue was purified (FCC) to give the title compound (33 mg, 89%). MS (ESI): mass calcd. for C$_{24}$H$_{26}$F$_3$N$_5$, 441.21; m/z found, 442.2 [M+H]$^+$. $^1$H NMR (CDCl$_3$): 8.50 (s, 1H), 8.40-8.37 (m, 1H), 7.90-7.85 (m, 1H), 7.46-7.36 (m, 4H), 6.98-6.93 (m, 1H), 6.45 (s, 1H), 3.70-3.65 (m, 2H), 3.64-3.60 (m, 2H), 3.26-3.20 (m, 2H), 3.02-2.95 (m, 2H), 1.32 (s, 9H). Alternatively, the reaction of this step may be performed in the microwave at 180° C. for 30 min.

Example 1A (4-tert-Butyl-phenyl)-[7-(3-trifluoromethyl-pyridin-2-yl)-6,7,8,9-tetrahydro-5H-pyrimido[4,5-d]azepin-4-yl]-amine hydrochloride salt The following Examples 2-16 were prepared using methods analogous to those described in Example 1, substituting the appropriate amidines in Step A and amines in Step E.

Example 2

(4-Trifluoromethyl-phenyl)-[7-(3-trifluoromethyl-pyridin-2-yl)-6,7,8,9-tetra-hydro-5H-pyrimido[4,5-d]azepin-4-yl]-amine

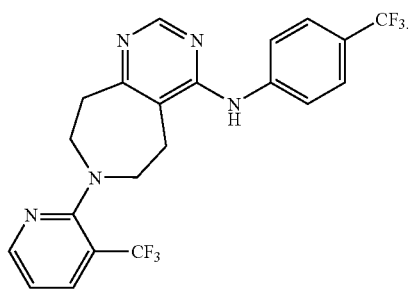 [SMILES: FC(F)(F)c1ccc(Nc2ncnc3c2CCN(c2ncccc2C(F)(F)F)CC3)cc1]

MS (ESI): mass calcd. for $C_{21}H_{17}F_6N_5$, 453.14; m/z found, 454.1 [M+H]$^+$. $^1$H NMR (CDCl$_3$): 8.56 (s, 1H), 8.39-8.36 (m, 1H), 7.89-7.86 (m, 1H), 7.68 (d, J=8.8 Hz, 2H), 7.59 (d, J=8.8 Hz, 2H), 6.98-6.94 (m, 1H), 6.65 (s, 1H), 3.68-3.64 (m, 2H), 3.63-3.59 (m, 2H), 3.27-3.22 (m, 2H), 3.04-3.00 (m, 2H).

Example 2A (4-Trifluoromethyl-phenyl)-[7-(3-trifluoromethyl-pyridin-2-yl)-6,7,8,9-tetrahydro-5H-pyrimido[4,5-d]azepin-4-yl]-amine hydrochloride salt Example 3

(4-tert-Butyl-phenyl)-[2-cyclopropyl-7-(3-trifluoromethyl-pyridin-2-yl)-6,7,8,9-tetrahydro-5H-pyrimido[4,5-d]azepin-4-yl]-amine

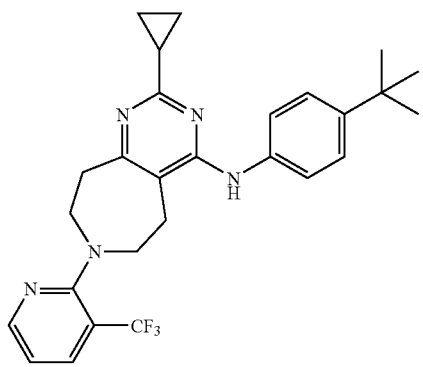 [SMILES: CC(C)(C)c1ccc(Nc2nc(C3CC3)nc3c2CCN(c2ncccc2C(F)(F)F)CC3)cc1]

MS (ESI): mass calcd. for $C_{27}H_{30}F_3N_5$, 481.25; m/z found, 482.2 [M+H]$^+$. $^1$H NMR (CDCl$_3$): 8.38-8.35 (m, 1H), 7.87-7.83 (m, 1H), 7.50-7.45 (m, 2H), 7.36-7.31 (m, 2H), 6.94-6.91 (m, 1H), 6.40 (s, 1H), 3.66-3.53 (m, 4H), 3.21-3.12 (m, 2H), 2.94-2.86 (m, 2H), 2.09-2.02 (m, 1H), 1.32 (s, 9H), 1.11-1.06 (m, 2H), 0.97-0.92 (m, 2H).

Example 4

(4-Chloro-phenyl)-[2-cyclopropyl-7-(3-trifluoromethyl-pyridin-2-yl)-6,7,8,9-tetrahydro-5H-pyrimido[4,5-d]azepin-4-yl]-amine

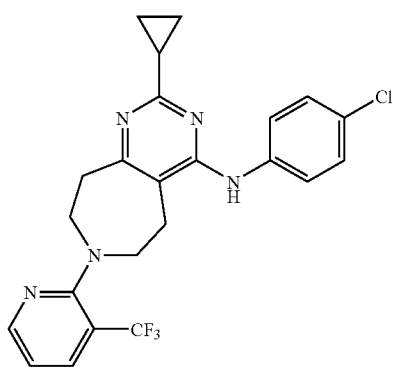 [SMILES: FC(F)(F)c1cccnc1N1CCc2nc(C3CC3)nc(Nc3ccc(Cl)cc3)c2CC1]

MS (ESI): mass calcd. for $C_{23}H_{21}ClF_3N_5$, 459.14; m/z found, 460.1 [M+H]$^+$. $^1$H NMR (CDCl$_3$): 8.39-8.35 (m, 1H), 7.88-7.83 (m, 1H), 7.50-7.45 (m, 2H), 7.30-7.26 (m, 2H), 6.97-6.91 (m, 1H), 6.41 (s, 1H), 3.65-3.55 (m, 4H), 3.20-3.15 (m, 2H), 2.94-2.89 (m, 2H), 2.08-2.01 (m, 1H), 1.05-1.01 (m, 2H), 0.97-0.92 (m, 2H).

Example 5

[2-Cyclopropyl-7-(3-trifluoromethyl-pyridin-2-yl)-6,7,8,9-tetrahydro-5H-pyrimido[4,5-d]azepin-4-yl]-(4-trifluoromethyl-phenyl)-amine

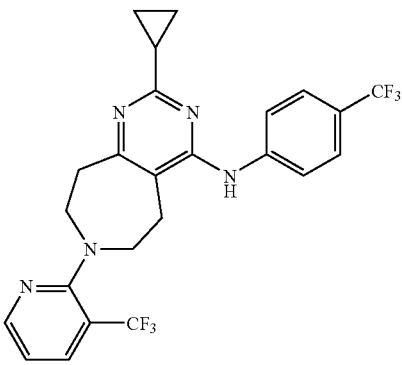 [SMILES: FC(F)(F)c1ccc(Nc2nc(C3CC3)nc3c2CCN(c2ncccc2C(F)(F)F)CC3)cc1]

MS (ESI): mass calcd. for $C_{24}H_{21}F_6N_5$, 493.17; m/z found, 494.1 [M+H]$^+$. $^1$H NMR (CDCl$_3$): 8.39-8.35 (m, 1H), 7.88-7.85 (m, 1H), 7.73-7.65 (m, 2H), 7.60-7.51 (m, 2H), 6.97-6.92 (m, 1H), 6.59 (s, 1H), 3.66-3.55 (m, 4H), 3.23-3.15 (m, 2H), 2.99-2.90 (m, 2H), 2.12-2.05 (m, 1H), 1.09-0.95 (m, 4H).

Example 5A

[2-Cyclopropyl-7-(3-trifluoromethyl-pyridin-2-yl)-6,7,8,9-tetrahydro-5H-pyrimido[4,5-d]azepin-4-yl]-(4-trifluoromethyl-phenyl)-amine hydrochloride salt Example 6

(4-tert-Butyl-phenyl)-[2-phenyl-7-(3-trifluoromethyl-pyridin-2-yl)-6,7,8,9-tetrahydro-5H-pyrimido[4,5-d]azepin-4-yl]-amine

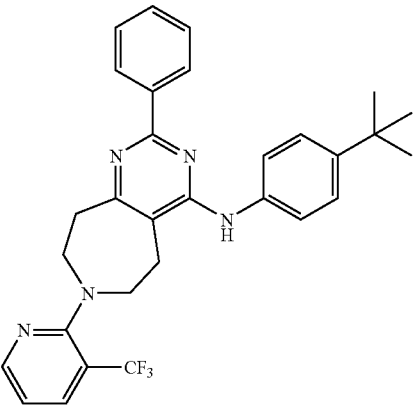 [SMILES: CC(C)(C)c1ccc(Nc2nc(-c3ccccc3)nc3c2CCN(c2ncccc2C(F)(F)F)CC3)cc1]

MS (ESI): mass calcd. for $C_{30}H_{30}F_3N_5$, 517.25; m/z found, 518.2 [M+H]+. 1H NMR (CDCl3): 8.41-8.37 (m, 3H), 7.89-7.86 (m, 1H), 7.65-7.59 (m, 2H), 7.49-7.39 (m, 5H), 6.97-6.91 (m, 1H), 6.54 (s, 1H), 3.73-3.69 (m, 2H), 3.68-3.64 (m, 2H), 3.35-3.29 (m, 2H), 3.06-3.00 (m, 2H), 1.35 (s, 3H).

Example 7

[2-Phenyl-7-(3-trifluoromethyl-pyridin-2-yl)-6,7,8,9-tetrahydro-5H-pyrimido[4,5-d]azepin-4-yl]-(4-trifluoromethyl-phenyl)-amine

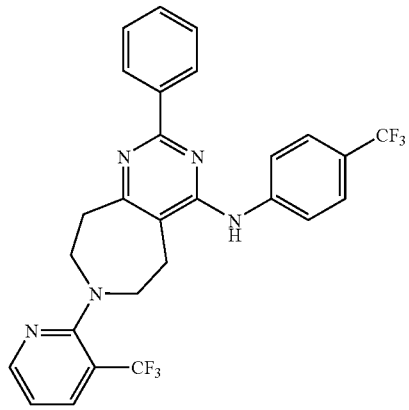 [SMILES: FC(F)(F)c1ccc(Nc2nc(-c3ccccc3)nc3c2CCN(c2ncccc2C(F)(F)F)CC3)cc1]

MS (ESI): mass calcd. for $C_{27}H_{21}F_6N_5$, 529.17; m/z found, 530.2 [M+H]+. 1H NMR (CDCl3): 8.41-8.33 (m, 3H), 7.89-7.85 (m, 1H), 7.81 (d, J=8.5 Hz, 2H), 7.65-7.63 (d, J=8.5 Hz, 2H), 7.49-7.43 (m, 3H), 6.98-6.93 (m, 1H), 6.72 (s, 1H), 3.72-3.67 (m, 2H), 3.66-3.62 (m, 2H), 3.36-3.32 (m, 2H), 3.11-3.02 (m, 2H).

Example 8

(4-tert-Butyl-phenyl)-[2-isopropyl-7-(3-trifluoromethyl-pyridin-2-yl)-6,7,8,9-tetrahydro-5H-pyrimido[4,5-d]azepin-4-yl]-amine

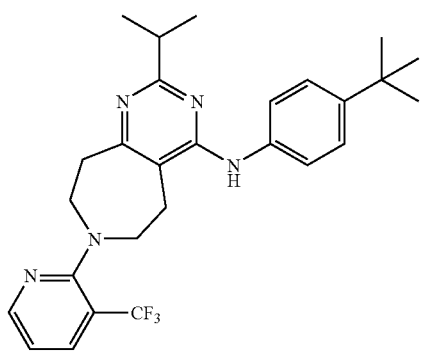 [SMILES: CC(C)c1nc2c(c(Nc3ccc(C(C)(C)C)cc3)n1)CCN(c1ncccc1C(F)(F)F)CC2]

MS (ESI): mass calcd. for $C_{27}H_{32}F_3N_5$, 483.26; m/z found, 484.2 [M+H]+. 1H NMR (CDCl3): 8.38-8.35 (m, 1H), 7.87-7.83 (m, 1H), 7.50-7.45 (m, 2H), 7.62-7.57 (m, 2H), 6.94-6.91 (m, 1H), 6.45 (s, 1H), 3.67-3.63 (m, 2H), 3.62-3.58 (m, 2H), 3.21-3.17 (m, 2H), 3.05-2.97 (m, 1H), 2.95-2.90 (m, 2H), 1.34-1.31 (m, 12H), 1.30 (s, 3H).

Example 9

[2-Isopropyl-7-(3-trifluoromethyl-pyridin-2-yl)-6,7,8,9-tetrahydro-5H-pyrimido[4,5-d]azepin-4-yl]-(4-trifluoromethyl-phenyl)-amine

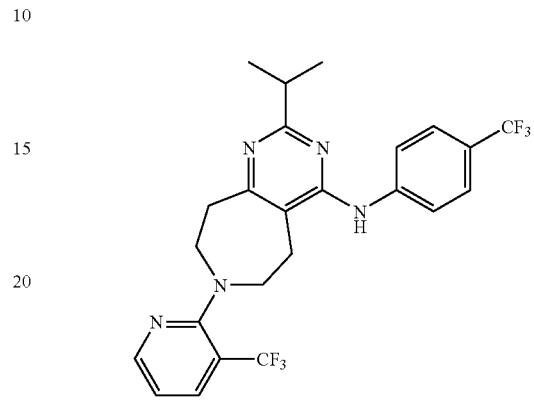

MS (ESI): mass calcd. for $C_{24}H_{23}F_6N_5$, 495.19; m/z found, 496.1 [M+H]+. 1H NMR (CDCl3): 8.39-8.36 (m, 1H), 7.88-7.84 (m, 1H), 7.79 (d, J=9.1 Hz, 2H), 7.58 (d, J=8.8 Hz, 2H), 6.97-6.93 (m, 1H), 6.64 (s, 1H), 3.67-3.63 (m, 2H), 3.61-3.57 (m, 2H), 3.24-3.20 (m, 2H), 3.09-3.00 (m, 1H), 3.00-2.95 (m, 2H), 1.31 (d, J=6.86 Hz, 6H).

Example 9A

[2-Isopropyl-7-(3-trifluoromethyl-pyridin-2-yl)-6,7,8,9-tetrahydro-5H-pyrimido[4,5-d]azepin-4-yl]-(4-trifluoromethyl-phenyl)-amine hydrochloride salt 1H NMR (CD3OD): 8.47-8.45 (m, 1H), 8.04 (dd, J=1.7, 7.8 Hz, 1H), 7.82 (d, J=8.6 Hz, 2H), 7.75 (d, J=8.6 Hz, 2H), 7.18-7.14 (m, 1H), 3.71-3.67 (m, 2H), 3.65-3.62 (m, 2H), 3.40-3.35 (m, 2H), 3.27-3.23 (m, 2H), 3.12 (td, J=6.8, 13.6 Hz, 1H), 1.32 (d, J=6.8 Hz, 6H).

Example 10

[2-Isopropyl-7-(3-trifluoromethyl-pyridin-2-yl)-6,7,8,9-tetrahydro-5H-pyrimido[4,5-d]azepin-4-yl]-(3-trifluoromethyl-phenyl)-amine

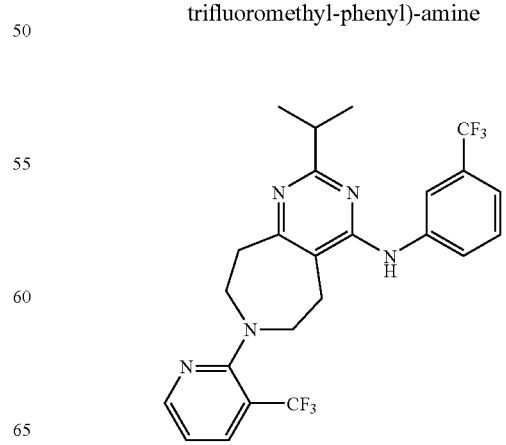

MS (ESI): mass calcd. for $C_{24}H_{23}F_6N_5$, 495.19; m/z found, 496.1 [M+H]⁺. ¹H NMR (CDCl₃): 8.41-8.39 (m, 1H), 8.30 (s, 1H), 7.91-7.88 (m, 1H), 7.69-7.66 (m, 1H), 7.47-7.43 (m, 1H), 7.32-7.31 (m, 1H), 6.99-6.95 (m, 1H), 6.63 (s, 1H), 3.70-3.66 (m, 2H), 3.64-3.61 (m, 2H), 3.26-3.22 (m, 2H), 3.10-3.02 (m, 1H), 3.01-2.97 (m, 2H), 1.33 (d, J=6.9 Hz, 6H).

Example 11

[2-Isopropyl-7-(3-trifluoromethyl-pyridin-2-yl)-6,7,8,9-tetrahydro-5H-pyrimido[4,5-d]azepin-4-yl]-(4-trifluoromethoxy-phenyl)-amine

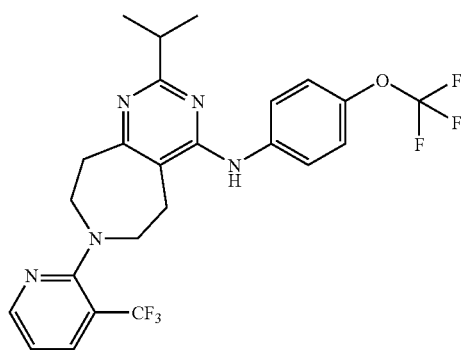 [SMILES: CC(C)c1nc2c(c(Nc3ccc(OC(F)(F)F)cc3)n1)CCN(c1ncccc1C(F)(F)F)CC2]

MS (ESI): mass calcd. for $C_{24}H_{23}F_6N_5O$, 511.18; m/z found, 512.1 [M+H]⁺. ¹H NMR (CDCl₃): 8.40-8.37 (m, 1H), 7.89-7.86 (m, 1H), 7.73-7.67 (m, 2H), 7.20 (d, J=8.3 Hz, 2H), 6.97-6.93 (m, 1H), 6.53 (s, 1H), 3.67-3.64 (m, 2H), 3.63-3.58 (m, 2H), 3.25-3.19 (m, 2H), 3.09-2.93 (m, 3H), 1.31 (d, J=6.8 Hz, 6H).

Example 12

[2-(4-Fluoro-phenyl)-ethyl]-[2-isopropyl-7-(3-trifluoromethyl-pyridin-2-yl)-6,7,8,9-tetrahydro-5H-pyrimido[4,5-d]azepin-4-yl]-amine

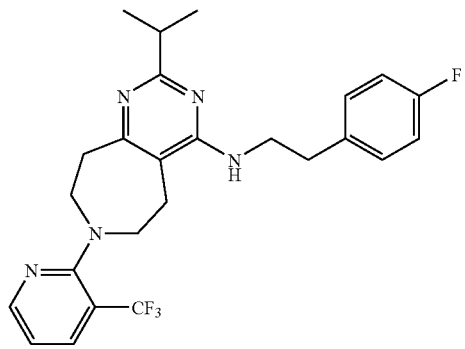 [SMILES: CC(C)c1nc2c(c(NCCc3ccc(F)cc3)n1)CCN(c1ncccc1C(F)(F)F)CC2]

MS (ESI): mass calcd. for $C_{25}H_{27}F_4N_5$, 473.22; m/z found, 474.2 [M+H]⁺. ¹H NMR (CDCl₃): 8.38-8.35 (m, 1H), 7.87-7.84 (m, 1H), 7.19-7.14 (m, 2H), 7.03-6.96 (m, 2H), 6.95-6.90 (m, 1H), 4.65-4.59 (m, 1H), 3.77-3.70 (m, 2H), 3.60-3.54 (m, 4H), 3.16-3.11 (m, 2H), 3.02-2.88 (m, 3H), 2.69-2.64 (m, 2H), 1.30 (d, J=7.1 Hz, 6H).

Example 13

[2-(2-Chloro-phenyl)-ethyl]-[2-isopropyl-7-(3-trifluoromethyl-pyridin-2-yl)-6,7,8,9-tetrahydro-5H-pyrimido[4,5-d]azepin-4-yl]-amine

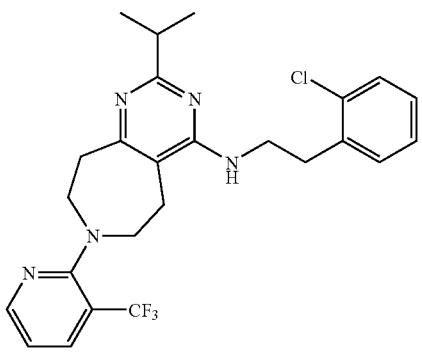 [SMILES: CC(C)c1nc2c(c(NCCc3ccccc3Cl)n1)CCN(c1ncccc1C(F)(F)F)CC2]

MS (ESI): mass calcd. for $C_{25}H_{27}ClF_3N_5$, 489.19; m/z found, 490.1 [M+H]⁺. ¹H NMR (CDCl₃): 8.40-8.37 (m, 1H), 7.89-7.86 (m, 1H), 7.40-7.37 (m, 1H), 7.25-7.16 (m, 3H), 6.96-6.92 (m, 1H), 4.73-4.67 (m, 1H), 3.84-3.78 (m, 2H), 3.61-3.56 (m, 4H), 3.17-3.07 (m, 4H), 3.02-2.93 (m, 1H), 2.72-2.67 (m, 2H), 1.31 (d, J=6.9 Hz, 6H).

Example 14

(3,4-Dichloro-benzyl)-[2-isopropyl-7-(3-trifluoromethyl-pyridin-2-yl)-6,7,8,9-tetrahydro-5H-pyrimido[4,5-d]azepin-4-yl]-amine

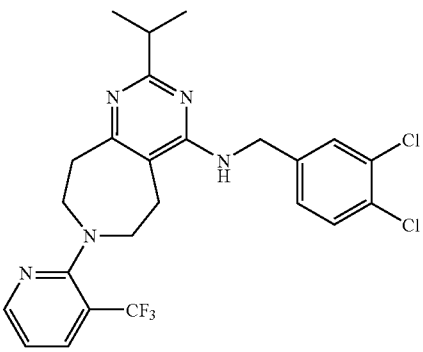 [SMILES: CC(C)c1nc2c(c(NCc3ccc(Cl)c(Cl)c3)n1)CCN(c1ncccc1C(F)(F)F)CC2]

MS (ESI): mass calcd. for $C_{24}H_{24}Cl_2F_3N_5$, 509.14; m/z found, 510.1 [M+H]⁺. ¹H NMR (CDCl₃): 8.39-8.36 (m, 1H), 7.89-7.86 (m, 1H), 7.50 (d, J=2.2 Hz, 1H), 7.40 (d, J=8.2 Hz, 1H), 7.22-7.19 (m, 1H), 6.96-6.93 (m, 1H), 4.99-4.94 (m, 1H), 4.68 (d, J=6.0 Hz, 2H), 3.64-3.57 (m, 4H), 3.18-3.14 (m, 2H), 2.99-2.91 (m, 1H), 2.82-2.79 (m, 2H), 1.26 (d, J=6.9 Hz, 6H).

Example 15

(4-tert-Butyl-phenyl)-[2-methyl-7-(3-trifluoromethyl-pyridin-2-yl)-6,7,8,9-tetrahydro-5H-pyrimido[4,5-d]azepin-4-yl]-amine

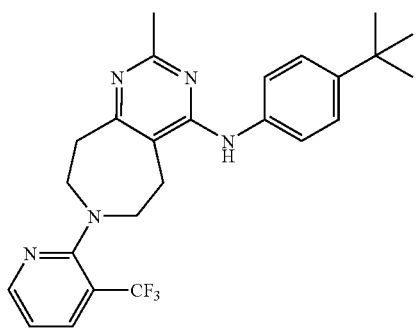 [SMILES: Cc1nc2c(c(Nc3ccc(C(C)(C)C)cc3)n1)CCN(c1ncccc1C(F)(F)F)CC2]

MS (ESI): mass calcd. for $C_{25}H_{28}F_3N_5$, 455.23; m/z found, 456.9 [M+H]$^+$. $^1$H NMR (CDCl$_3$): 8.40-8.38 (m, 1H), 7.89-7.86 (m, 1H), 7.53-7.50 (m, 2H), 7.39-7.35 (m, 2H), 6.97-6.93 (m, 1H), 6.50 (s, 1H), 3.66-3.59 (m, 4H), 3.22-3.18 (m, 2H), 2.96-2.93 (m, 2H), 2.55 (s, 3H), 1.34 (s, 9H).

Example 16

[2-Methyl-7-(3-trifluoromethyl-pyridin-2-yl)-6,7,8,9-tetrahydro-5H-pyrimido-[4,5-d]azepin-4-yl]-(4-trifluoromethyl-phenyl)-amine

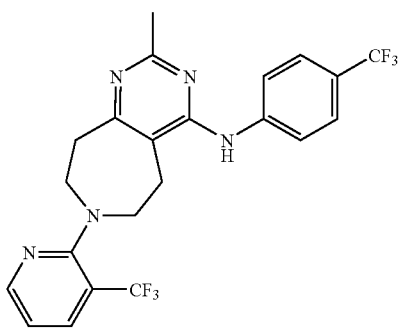

MS (ESI): mass calcd. for $C_{22}H_{19}F_6N_5$, 467.15; m/z found, 468.1 [M+H]$^+$. $^1$H NMR (CDCl$_3$): 8.41-8.39 (m, 1H), 7.90-7.87 (m, 1H), 7.74 (d, J=8.5 Hz, 2H), 7.60 (d, J=8.8 Hz, 2H), 7.00-6.95 (m, 1H), 6.66 (s, 1H), 3.67-3.64 (m, 2H), 3.63-3.59 (m, 2H), 3.25-3.20 (m, 2H), 3.02-2.98 (m, 2H), 2.59 (s, 3H).

Example 17

(5-Trifluoromethyl-pyridin-2-yl)-[7-(3-trifluoromethyl-pyridin-2-yl)-6,7,8,9-tetrahydro-5H-pyrimido[4,5-d]azepin-4-yl]-amine

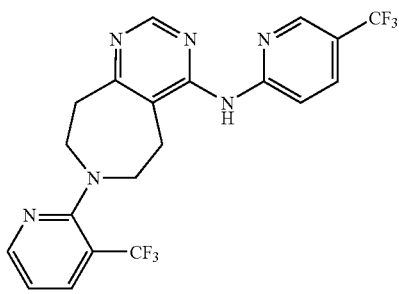 [SMILES: FC(F)(F)c1ccc(Nc2ncnc3c2CCN(c2ncccc2C(F)(F)F)CC3)nc1]

The title compound was synthesized in a manner similar to Example 1 with modifications to Step E as follows:

Step E. To a solution of 4-chloro-7-(3-trifluoromethyl-pyridin-2-yl)-6,7,8,9-tetrahydro-5H-pyrimido[4,5-d]azepine (38 mg, 0.12 mmol), 4-trifluoromethyl-amino-pyridine (28 mg, 0.17 mmol), and NaOtBu (16 mg, 0.16 mmol) in toluene (1.2 mL) in a microwave vial was added a solution of Pd(OAc)$_2$ (0.4 mg, 0.002 mmol) and 2-(dicyclohexylphosphino)biphenyl (DCPB) (1.2 mg, 0.004 mmol) in toluene (1 mL). The mixture was flushed with N$_{2(g)}$ and heated in a microwave at 200° C. for 30 min. The mixture was cooled, filtered through a plug of diatomaceous earth, and concentrated. The residue was purified (FCC) to afford the title compound (35 mg, 66%). MS (ESI): mass calcd. for $C_{20}H_{16}F_6N_6$, 454.13; m/z found, 453.2 [M+H]$^+$. $^1$H NMR (CDCl$_3$): 8.65 (s, 1H), 8.61 (d, J=8.8 Hz, 1H), 8.54-8.51 (m, 1H), 8.41-8.38 (m, 1H), 7.95-7.85 (m, 2H), 7.64 (s, 1H), 7.01-6.95 (m, 1H), 3.67-3.57 (m, 4H), 3.31-3.25 (m, 2H), 3.14-3.07 (m, 2H).

The following Examples 18-25 below were prepared using methods analogous to those described in Example 17, substituting the appropriate amidines in Step A and amines in Step E.

Example 18

Isoquinolin-1-yl-[7-(3-trifluoromethyl-pyridin-2-yl)-6,7,8,9-tetrahydro-5H-pyrimido[4,5-d]azepin-4-yl]-amine

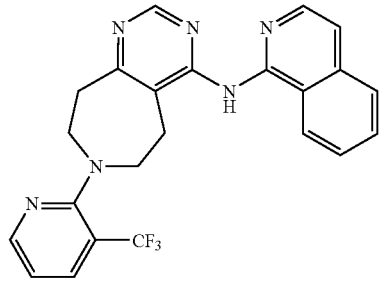 [SMILES: FC(F)(F)c1cccnc1N1CCc2ncnc(Nc3nccc4ccccc34)c2CC1]

MS (ESI): mass calcd. for $C_{23}H_{19}F_3N_6$, 436.16; m/z found, 437.1 [M+H]$^+$. $^1$H NMR (CDCl$_3$): 8.83 (d, J=8.0 Hz, 1H), 8.65 (s, 1H), 8.42-8.39 (m, 1H), 7.90-7.86 (m, 1H), 7.69-7.64

(m, 1H), 7.60-7.53 (m, 2H), 7.32-7.29 (m, 1H), 6.97-6.93 (m, 1H), 6.71 (d, J=6.9 Hz, 1H), 3.64-3.54 (m, 6H), 3.30-3.24 (m, 2H).

Example 19

[2-Cyclopropyl-7-(3-trifluoromethyl-pyridin-2-yl)-6,7,8,9-tetrahydro-5H-pyrimido[4,5-d]azepin-4-yl]-(5-trifluoromethyl-pyridin-2-yl)-amine

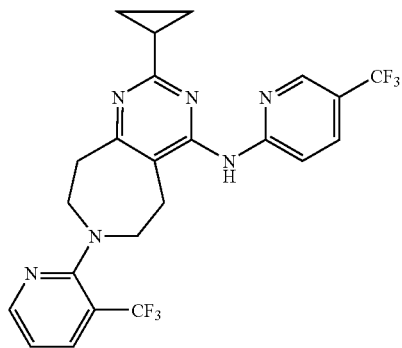 [SMILES: FC(F)(F)c1ccc(Nc2nc(C3CC3)nc3c2CCN(c2ncccc2C(F)(F)F)CC3)nc1]

MS (ESI): mass calcd. for C$_{23}$H$_{20}$F$_6$N$_6$, 494.17; m/z found, 495.1 [M+H]$^+$. $^1$H NMR (CDCl$_3$): 8.54-8.47 (m, 2H), 8.40-8.37 (m, 1H), 7.93-7.84 (m, 2H), 7.54 (s, 1H), 7.00-6.89 (m, 1H), 3.62-3.54 (m, 4H), 3.24-3.19 (m, 2H), 3.04-2.99 (m, 2H), 2.19-2.08 (m, 1H), 1.13-1.08 (m, 2H), 1.05-1.00 (m, 2H).

Example 20

[2-Isopropyl-7-(3-trifluoromethyl-pyridin-2-yl)-6,7,8,9-tetrahydro-5H-pyrimido[4,5-d]azepin-4-yl]-(5-trifluoromethyl-pyridin-2-yl)-amine

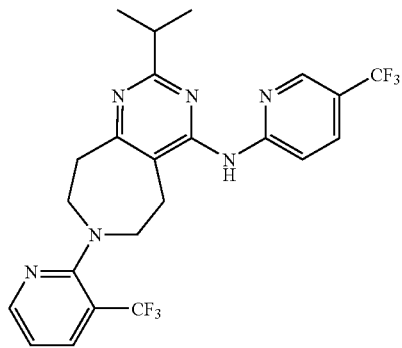 [SMILES: CC(C)c1nc2c(c(Nc3ccc(C(F)(F)F)cn3)n1)CCN(c1ncccc1C(F)(F)F)CC2]

MS (ESI): mass calcd. for C$_{23}$H$_{22}$F$_6$N$_6$, 496.18; m/z found, 497.1 [M+H]$^+$. $^1$H NMR (CDCl$_3$): 8.73 (d, J=9.1 Hz, 1H), 8.50 (s, 1H), 8.40-8.37 (m, 1H), 7.94-7.90 (m, 1H), 7.88-7.85 (m, 1H), 7.60 (s, 1H), 6.98-6.93 (m, 1H), 3.65-3.54 (m, 4H), 3.28-3.20 (m, 2H), 3.14-3.01 (m, 3H), 1.34 (d, J=6.9 Hz, 6H).

Example 20A

[2-Isopropyl-7-(3-trifluoromethyl-pyridin-2-yl)-6,7,8,9-tetrahydro-5H-pyrimido[4,5-d]azepin-4-yl]-(5-trifluoromethyl-pyridin-2-yl)-amine hydrochloride salt

Example 21

[2-Isopropyl-7-(3-trifluoromethyl-pyridin-2-yl)-6,7,8,9-tetrahydro-5H-pyrimido[4,5-d]azepin-4-yl]-quinolin-3-yl-amine

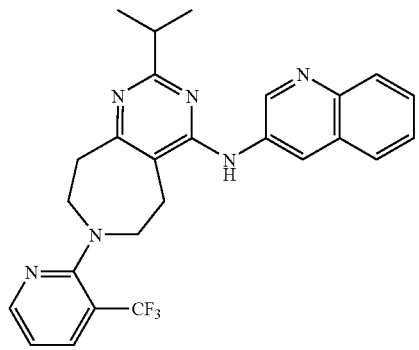 [SMILES: CC(C)c1nc2c(c(Nc3cnc4ccccc4c3)n1)CCN(c1ncccc1C(F)(F)F)CC2]

MS (ESI): mass calcd. for C$_{26}$H$_{25}$F$_3$N$_6$, 478.21; m/z found, 479.1 [M+H]$^+$. $^1$H NMR (CDCl$_3$): 8.99 (d, J=2.2 Hz, 1H), 8.86 (d, J=2.5 Hz, 1H), 8.43-8.40 (m, 1H), 8.07 (d, J=8.2 Hz, 1H), 7.92-7.88 (m, 1H), 7.83-7.80 (m, 1H), 7.65-7.61 (m, 1H), 7.58-7.54 (m, 1H), 7.00-6.95 (m, 1H), 6.75 (s, 1H), 3.74-3.70 (m, 2H), 3.67-3.63 (m, 2H), 3.29-3.25 (m, 2H), 3.14-3.05 (m, 3H), 1.38 (d, J=6.9 Hz, 6H).

Example 22

[2-Phenyl-7-(3-trifluoromethyl-pyridin-2-yl)-6,7,8,9-tetrahydro-5H-pyrimido[4,5-d]azepin-4-yl]-(5-trifluoromethyl-pyridin-2-yl)-amine

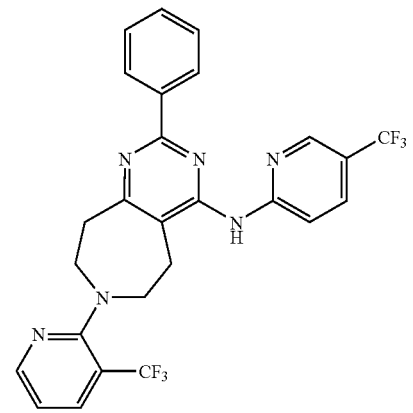 [SMILES: FC(F)(F)c1ccc(Nc2nc(-c3ccccc3)nc3c2CCN(c2ncccc2C(F)(F)F)CC3)nc1]

MS (ESI): mass calcd. for C$_{26}$H$_{20}$F$_6$N$_6$, 530.17; m/z found, 531.1 [M+H]$^+$. $^1$H NMR (CDCl$_3$): 8.76 (d, J=8.8 Hz, 1H), 8.57 (s, 1H), 8.44-8.39 (m, 3H), 8.04-8.00 (m, 1H), 7.91-7.88 (m, 1H), 7.67 (s, 1H), 7.55-7.48 (m, 3H), 7.00-6.96 (m, 1H), 3.72-3.62 (m, 4H), 3.41-3.36 (m, 2H), 3.18-3.11 (m, 2H).

Example 23

[2-Isopropyl-7-(3-trifluoromethyl-pyridin-2-yl)-6,7,8,9-tetrahydro-5H-pyrimido[4,5-d]azepin-4-yl]-(6-trifluoromethyl-pyridin-3-yl)-amine

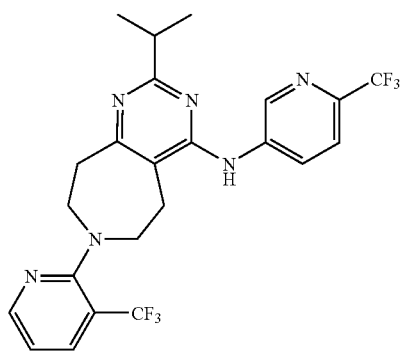 [SMILES: CC(C)c1nc2c(c(Nc3ccc(C(F)(F)F)nc3)n1)CCN(c1ncccc1C(F)(F)F)CC2]

MS (ESI): mass calcd. for $C_{23}H_{22}F_6N_6$, 496.18; m/z found, 497.1 [M+H]$^+$. $^1$H NMR (CDCl$_3$): 8.86 (d, J=2.5 Hz, 1H), 8.54-8.51 (m, 1H), 8.42-8.39 (m, 1H), 7.91-7.90 (m, 1H), 7.69 (d, J=8.5 Hz, 1H), 7.01-6.96 (m, 1H), 6.71 (s, 1H), 3.70-3.67 (m, 2H), 3.64-3.60 (m, 2H), 3.29-3.24 (m, 2H), 3.12-3.02 (m, 3H), 1.33 (d, J=6.6 Hz, 6H).

Example 24

2-Methyl-7-(3-(trifluoromethyl)pyridin-2-yl)-N-(6-(trifluoromethyl)pyridin-3-yl)6,7,8,9-tetrahydro-5H-pyrimido[4,5-d]azepin-4-amine

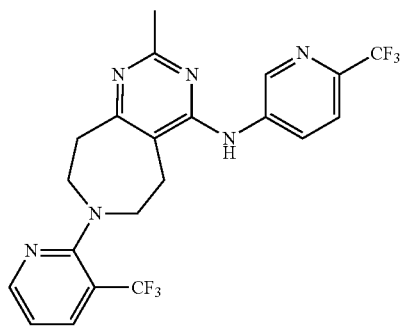 [SMILES: Cc1nc2c(c(Nc3ccc(C(F)(F)F)nc3)n1)CCN(c1ncccc1C(F)(F)F)CC2]

MS (ESI): mass calcd. for $C_{21}H_{18}F_6N_6$, 468.15; m/z found, 469.8 [M+H]$^+$. $^1$H NMR (CDCl$_3$): 8.84 (d, J=2.5 Hz, 1H), 8.47-8.43 (m, 1H), 8.40-8.38 (m, 1H), 7.90-7.87 (m, 1H), 7.68 (d, J=8.8 Hz, 1H), 7.00-6.96 (m, 1H), 6.81 (s, 1H), 3.67-3.63 (m, 2H), 3.62-3.59 (m, 2H), 3.25-3.22 (m, 2H), 3.06-3.03 (m, 2H), 2.58 (s, 3H).

Example 25

[2-Isopropyl-7-(3-trifluoromethyl-pyridin-2-yl)-6,7,8,9-tetrahydro-5H-pyrimido[4,5-d]azepin-4-yl]-(4-phenoxy-phenyl)-amine

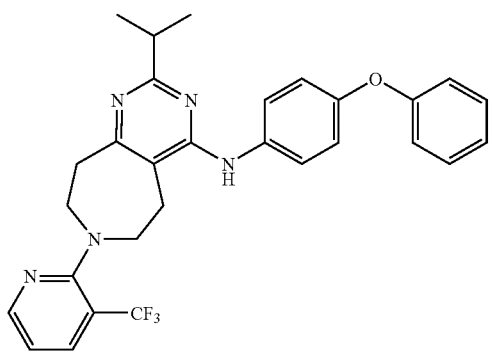 [SMILES: CC(C)c1nc2c(c(Nc3ccc(Oc4ccccc4)cc3)n1)CCN(c1ncccc1C(F)(F)F)CC2]

MS (ESI): mass calcd. for $C_{29}H_{28}F_3N_5O$, 519.22; m/z found, 520.2 [M+H]$^+$. $^1$H NMR (CDCl$_3$): 8.42-8.39 (m, 1H), 7.90-7.87 (m, 1H), 7.67-7.62 (m, 2H), 7.37-7.32 (m, 2H), 7.12-7.08 (m, 1H), 7.05-7.01 (m, 4H), 6.98-6.94 (m, 1H), 6.48 (s, 1H), 3.70-3.66 (m, 2H), 3.65-3.61 (m, 2H), 3.24-3.21 (m, 2H), 3.07-2.94 (m, 3H), 1.32 (d, J=6.9 Hz, 6H).

Example 26

(4-Trifluoromethyl-phenyl)-[7-(4-trifluoromethyl-pyrimidin-2-yl)-6,7,8,9-tetrahydro-5H-pyrimido[4,5-d]azepin-4-yl]-amine

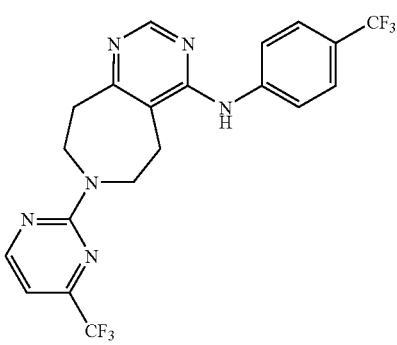 [SMILES: FC(F)(F)c1ccc(Nc2ncnc3c2CCN(c2nccc(C(F)(F)F)n2)CC3)cc1]

The title compound was synthesized a manner similar to Example 1 with modifications to Step C as follows and using 4-trifluoromethylaniline in Step E:

Step C. 7-(4-Trifluoromethyl-pyrimidin-2-yl)-6,7,8,9-tetrahydro-5H-pyrimido[4,5-d]azepin-4-ol. A solution of 6,7,8,9-tetrahydro-5H-pyrimido[4,5-d]azepin-4-ol (60 mg, 0.30 mmol), 2-chloro-4-tritrifluoropyrimidine (36 µL, 0.30 mmol), and Et$_3$N (0.11 mL, 0.81 mmol) in DMF (1.2 mL) was heated at 120° C. for 2 h. The mixture was cooled to rt, diluted with water, and extracted with EtOAc. The combined organic layers were dried (Na$_2$SO$_4$) and concentrated to give the title compound (69 mg, 68%), which was used without further purification.

Step E. MS (ESI): mass calcd. for $C_{20}H_{16}F_6N_6$, 454.13; m/z found, 455.1 [M+H]+. $^1$H NMR (CDCl$_3$): 8.56 (s, 1H), 8.53 (d, J=5.2 Hz, 1H), 7.67 (d, J=8.2 Hz, 2H), 7.59 (d, J=8.5 Hz, 2H), 6.80 (d, J=5.2 Hz, 1H), 6.60 (s, 1H), 4.30-4.26 (m, 2H), 4.13-4.09 (m, 2H), 3.31-3.26 (m, 2H), 2.96-2.90 (m, 2H).

Example 27

(7-Pyrimidin-2-yl-6,7,8,9-tetrahydro-5H-pyrimido[4,5-d]azepin-4-yl)-(4-trifluoromethyl-phenyl)-amine

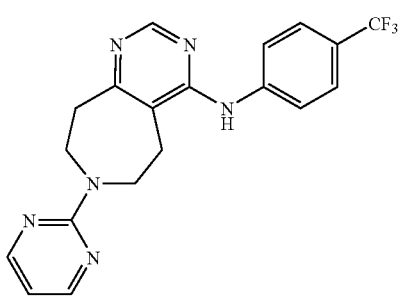 [SMILES: FC(F)(F)c1ccc(Nc2ncnc3c2CCN(c2ncccn2)CC3)cc1]

The title compound was prepared analogously to the methodology described in Example 26, substituting 2-chloropyrimidine in Step C. MS (ESI): mass calcd. for $C_{19}H_{17}F_3N_6$, 386.15; m/z found, 387.1 [M+H]+. $^1$H NMR (CDCl$_3$): 8.57 (s, 1H), 8.35 (d, J=4.8 Hz, 2H), 7.68 (d, J=8.8 Hz, 2H), 7.59 (d, J=8.8 Hz, 2H), 6.61 (s, 1H), 6.55-6.52 (m, 1H), 4.28-4.23 (m, 2H), 4.11-4.06 (m, 2H), 3.32-3.25 (m, 2H), 2.95-2.90 (m, 2H).

Example 28

(7-Pyrazin-2-yl-6,7,8,9-tetrahydro-5H-pyrimido[4,5-d]azepin-4-yl)-(4-trifluoromethyl-phenyl)-amine

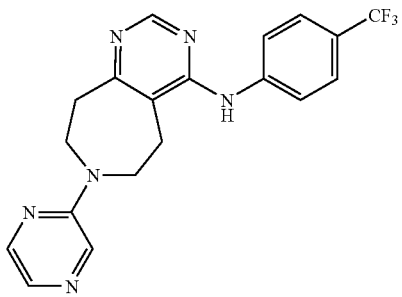 [SMILES: FC(F)(F)c1ccc(Nc2ncnc3c2CCN(c2cnccn2)CC3)cc1]

The title compound was prepared analogously to Example 26, substituting 2-chloropyrazine in Step C. MS (ESI): mass calcd. for $C_{19}H_{17}F_3N_6$, 386.15; m/z found, 387.1 [M+H]+. $^1$H NMR (CDCl$_3$): 8.56 (s, 1H), 8.12-8.10 (m, 1H), 8.08-8.06 (m, 1H), 7.86 (d, J=2.7 Hz, 1H), 7.67 (d, J=8.8 Hz, 2H), 7.59 (d, J=8.8 Hz, 2H), 6.57 (s, 1H), 4.25-4.20 (m, 2H), 3.92-3.88 (m, 2H), 3.38-3.34 (m, 2H), 2.96-2.91 (m, 2H).

Example 29

(7-Quinoxalin-2-yl-6,7,8,9-tetrahydro-5H-pyrimido[4,5-d]azepin-4-yl)-(4-trifluoromethyl-phenyl)-amine

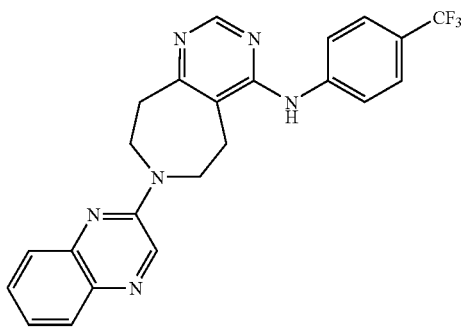 [SMILES: FC(F)(F)c1ccc(Nc2ncnc3c2CCN(c2cnc4ccccc4n2)CC3)cc1]

The title compound was prepared analogously to Example 26, substituting 2-chloroquinoxaline in Step C. MS (ESI): mass calcd. for $C_{23}H_{19}F_3N_6$, 436.16; m/z found, 437.1 [M+H]+. $^1$H NMR (CDCl$_3$): 8.58 (d, J=11.2 Hz, 2H), 7.92-7.89 (m, 1H), 7.73-7.66 (m, 3H), 7.63-7.58 (m, 3H), 7.44-7.39-(m, 1H), 6.61 (s, 1H), 4.42-4.3.5 (m, 2H), 4.16-4.07 (m, 2H), 3.46-3.38 (m, 2H), 3.09-3.02 (m, 2H).

Example 30

[7-(3-Chloro-pyridin-2-yl)-6,7,8,9-tetrahydro-5H-pyrimido[4,5-d]azepin-4-yl]-(4-trifluoromethyl-phenyl)-amine

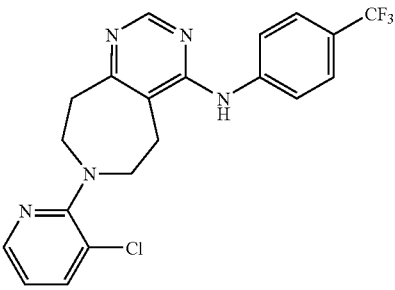 [SMILES: FC(F)(F)c1ccc(Nc2ncnc3c2CCN(c2ncccc2Cl)CC3)cc1]

The title compound was prepared analogously to Example 26, substituting 2,3-dichloropyridine in Step C. MS (ESI): mass calcd. for $C_{20}H_{17}ClF_3N_5$, 419.11; m/z found, 420.1 [M+H]+. $^1$H NMR (CDCl$_3$): 8.57 (s, 1H), 8.15-8.13 (m, 1H), 7.68 (d, J=9.3 Hz, 2H), 7.63-7.58 (m, 3H), 6.84-6.79 (m, 1H), 6.65 (s, 1H), 3.77-3.67 (m, 4H), 3.31-3.24 (m, 2H), 3.08-3.01 (m, 2H).

Example 31

(4-tert-Butyl-phenyl)-[7-(6-chloro-5-methyl-pyrimidin-4-yl)-6,7,8,9-tetrahydro-5H-pyrimido[4,5-d]azepin-4-yl]-amine

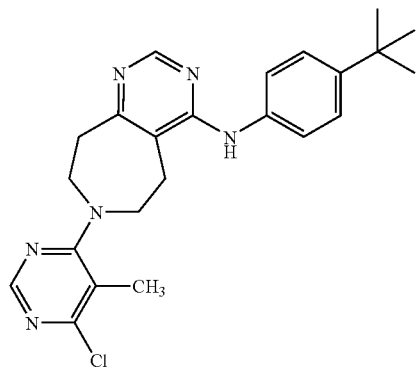 [SMILES: Cc1c(Cl)ncnc1N1CCc2ncnc(Nc3ccc(C(C)(C)C)cc3)c2CC1]

The title compound was prepared analogously to Example 26, substituting 4,6-dichloro-5-methylpyrimidine in Step C and 4-tert-butyl-aniline in Step E. MS (ESI−): mass calcd. for $C_{23}H_{27}ClN_6$, 422.20; m/z found, 421.2 [M−H]−. $^1$H NMR (CDCl$_3$): 8.50 (s, 1H), 8.33 (s, 1H), 7.44-7.36 (m, 4H), 6.43 (s, 1H), 3.91-3.84 (m, 2H), 3.81-3.75 (m, 2H), 3.26-3.19 (m, 2H), 3.04-2.98 (m, 2H), 2.31 (s, 3H), 1.32 (s, 9H).

Example 32

(4-tert-Butyl-phenyl)-[7-(3-methyl-quinoxalin-2-yl)-6,7,8,9-tetrahydro-5H-pyrimido[4,5-d]azepin-4-yl]-amine

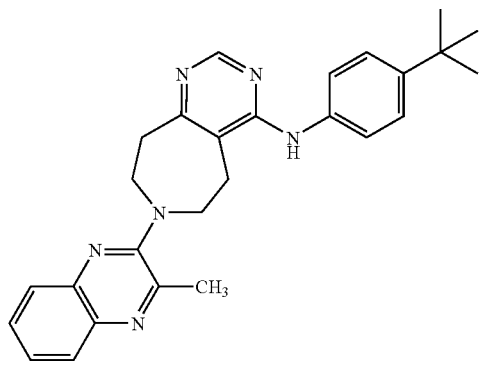 [SMILES: Cc1nc2ccccc2nc1N1CCc2ncnc(Nc3ccc(C(C)(C)C)cc3)c2CC1]

The title compound was prepared analogously to Example 26, substituting 2-chloro-3-methylquinoline in Step C and 4-tert-butyl-aniline in Step E. MS (ESI−): mass calcd. for $C_{27}H_{30}N_6$, 438.25; m/z found, 437.2 [M−H]−. $^1$H NMR (CDCl$_3$): 8.51 (s, 1H), 7.90-7.87 (m, 1H), 7.79-7.76 (m, 1H), 7.60-7.55 (m, 1H), 7.53-7.48 (m, 1H), 7.43-7.36 (m, 4H), 6.47 (s, 1H), 3.80-3.76 (m, 2H), 3.74-3.70 (m, 2H), 3.31-3.26 (m, 2H), 3.07-3.02 (m, 2H), 2.75 (s, 3H), 1.32 (s, 9H).

Example 33

(4-tert-Butyl-phenyl)-[2-isopropyl-7-(3-methyl-quinoxalin-2-yl)-6,7,8,9-tetrahydro-5H-pyrimido[4,5-d]azepin-4-yl]-amine

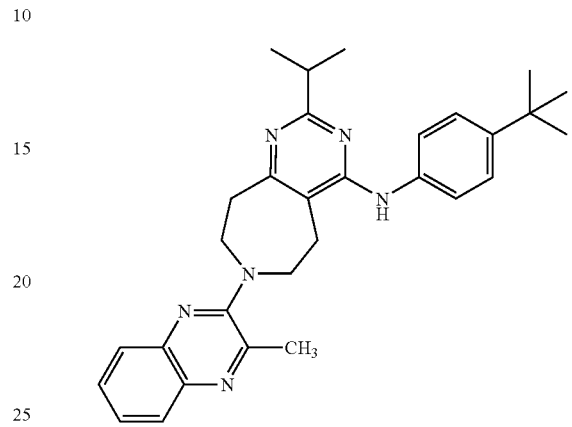

The title compound was prepared analogously to Example 26, substituting 2-chloro-3-methylquinoline in Step C and 4-tert-butyl-aniline in Step E. MS (ESI−): mass calcd. for $C_{30}H_{36}N_6$, 480.3; m/z found, 479.3 [M−H]−. $^1$H NMR (CDCl$_3$): 7.89-7.86 (m, 1H), 7.78-7.76 (m, 1H), 7.62-7.54 (m, 3H), 7.51-7.47 (m, 1H), 7.37-7.34 (m, 2H), 6.48 (s, 1H), 3.77-3.73 (m, 2H), 3.71-3.67 (m, 2H), 3.29-3.23 (m, 2H), 3.02-2.97 (m, 3H), 2.74 (s, 3H), 1.33-1.32 (m, 12H), 1.31 (s, 3H).

Example 34

[2-Isopropyl-7-(3-methyl-quinoxalin-2-yl)-6,7,8,9-tetrahydro-5H-pyrimido-[4,5-d]azepin-4-yl]-(4-trifluoromethyl-phenyl)-amine

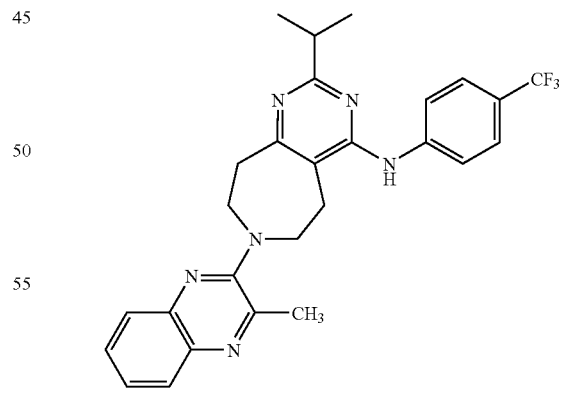

The title compound was prepared analogously to Example 26, substituting 2-chloro-3-methylquinoline in Step C. MS (ESI): mass calcd. for $C_{27}H_{27}F_3N_6$, 492.22; m/z found, 493.2 [M+H]+. $^1$H NMR (CDCl$_3$): 7.89-7.86 (m, 1H), 7.81-7.75 (m, 3H), 7.61-7.55 (m, 3H), 7.53-7.48 (m, 1H), 6.67 (s, 1H), 3.78-3.75 (m, 2H), 3.72-3.68 (m, 2H), 3.32-3.27 (m, 2H), 3.09-3.02 (m, 3H), 2.75 (s, 3H), 1.32 (d, J=7.1 Hz, 6H).

Example 35

[2-Isopropyl-7-(3-trifluoromethyl-quinoxalin-2-yl)-6,7,8,9-tetrahydro-5H-pyrimido[4,5-d]azepin-4-yl]-(4-trifluoromethyl-phenyl)-amine

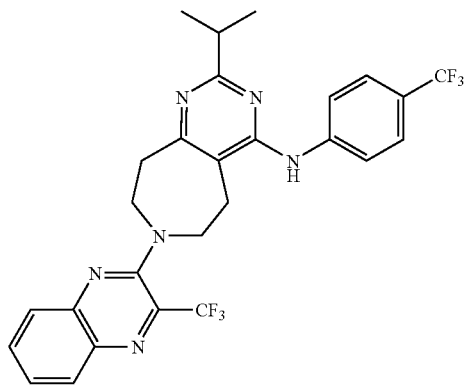 [SMILES: CC(C)c1nc2c(c(Nc3ccc(C(F)(F)F)cc3)n1)CCN(c1nc3ccccc3nc1C(F)(F)F)CC2]

The title compound was prepared analogously to Example 26, substituting 2-chloro-3-trifluoromethylquinoline in Step C. MS (ESI): mass calcd. for C$_{27}$H$_{24}$F$_6$N$_6$, 546.2; m/z found, 547.2 [M+H]$^+$. $^1$H NMR (CDCl$_3$): 8.06-8.03 (m, 1H), 7.88-7.71 (m, 4H), 7.65-7.57 (m, 3H), 6.66 (s, 1H), 3.87-3.77 (m, 4H), 3.33-3.27 (m, 2H), 3.10-3.00 (m, 3H), 1.32 (d, J=6.8 Hz, 6H).

Example 36

[2-Isopropyl-7-(3-methanesulfonyl-pyridin-2-yl)-6,7,8,9-tetrahydro-5H-pyrimido[4,5-d]azepin-4-yl]-(4-trifluoromethyl-phenyl)-amine

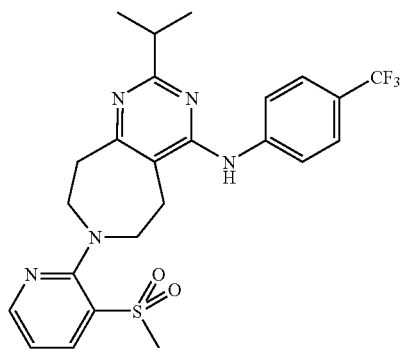 [SMILES: CC(C)c1nc2c(c(Nc3ccc(C(F)(F)F)cc3)n1)CCN(c1ncccc1S(C)(=O)=O)CC2]

The title compound was prepared analogously to Example 26, substituting 2-chloro-3-(methylsulfonyl)pyridine (see, Ponticello, G. S. et al., *J. Org. Chem.* 1979, 44(17), 3080-3082) in Step C. MS (ESI): mass calcd. for C$_{24}$H$_{26}$F$_3$N$_5$O$_2$S, 505.18; m/z found, 506.1 [M+H]$^+$. $^1$H NMR (CDCl$_3$): 8.54-8.51 (m, 1H), 8.38-8.34 (m, 1H), 7.80 (d, J=8.3 Hz, 2H), 7.60 (d, J=8.6 Hz, 2H), 7.25-7.21 (m, 1H), 6.89 (s, 1H), 3.60-3.55 (m, 2H), 3.54-3.50 (m, 2H), 3.24-3.20 (m, 2H), 3.11-2.99.(m, 6H), 1.32 (d, J=6.8 Hz, 6H).

Example 37

(4-tert-Butyl-phenyl)-(7-phthalazin-1-yl-6,7,8,9-tetrahydro-5H-pyrimido-[4,5-d]azepin-4-yl)-amine

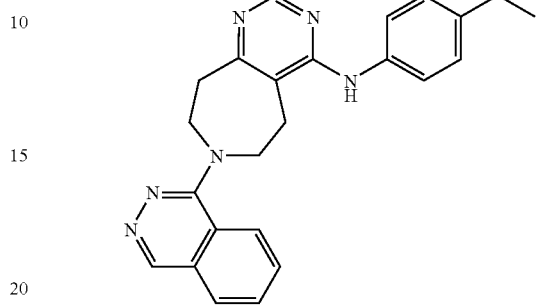

The title compound was synthesized in a manner similar to Example 1 with modifications to Step C as follows and using 4-tert-butyl-aniline in Step E:

Step C. 7-Phthalazin-1-yl-6,7,8,9-tetrahydro-5H-pyrimido-[4,5-d]azepin-4-ol. A solution of 6,7,8,9-tetrahydro-5H-pyrimido[4,5-d]azepin-4-ol (50 mg, 0.33 mmol), 1,4-dichlorophthalazine (55 mg, 0.28 mmol), and Et$_3$N (0.11 mL, 0.81 mmol) in DMF (5 mL) was heated at 120° C. for 2 h. The mixture was cooled to rt, diluted with water, and extracted with EtOAc. The combined organic layers were dried (Na$_2$SO$_4$) and concentrated to give 7-(4-chloro-phthalazin-1-yl)-6,7,8,9-tetrahydro-5H-pyrimido[4,5-d]azepin-4-ol (50 mg, 55%), of which 23 mg (0.14 mmol) was treated with ammonium formate (116 mg, 1.85 mmol) and Pd(OH)$_2$/C (14 mg, 0.08 mmol) in MeOH/dioxane (1:1; 4 mL). After 1 h at 100° C., the mixture was cooled rt, filtered through diatomaceous earth, and concentrated to give the title compound, which was carried on to Step D as in Example 1. MS (ESI−): mass calcd. for C$_{26}$H$_{28}$N$_6$, 424.24; m/z found, 423.2 [M−H]$^-$. $^1$H NMR (CDCl$_3$): 9.13 (s, 1H), 8.51 (s, 1H), 8.08-8.04 (m, 1H), 7.91-7.80 (m, 3H), 7.48-7.36 (m, 4H), 6.56 (s, 1H), 4.04-3.97 (m, 2H), 3.96-3.89 (m, 2H), 3.37-3.30 (m, 2H), 3.20-3.08 (m, 2H), 1.32 (s, 9H).

Example 38

(4-tert-Butyl-phenyl)-[7-(5-methyl-pyrimidin-4-yl)-6,7,8,9-tetrahydro-5H-pyrimido[4,5-d]azepin-4-yl]-amine

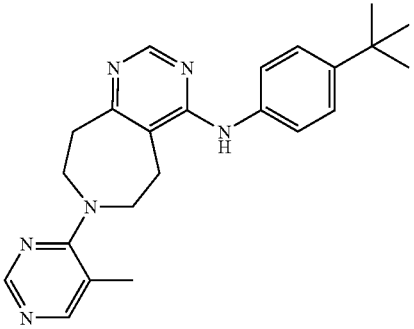 [SMILES: Cc1cncnc1N1CCc2ncnc(Nc3ccc(C(C)(C)C)cc3)c2CC1]

The title compound was prepared analogously to Example 37 using 4,6-dichloro-5-methyl pyrimidine in Step C. MS (ESI): mass calcd. for $C_{23}H_{28}N_6$, 388.24; m/z found, 389.2 [M+H]$^+$. $^1$H NMR (CDCl$_3$): 8.53 (s, 1H), 8.49 (s, 1H), 8.09 (s, 1H), 7.43-7.35 (m, 4H), 6.43 (s, 1H), 3.97-3.94 (m, 2H), 3.88-3.84 (m, 2H), 3.25-3.21 (m, 2H), 3.03-2.97 (m, 2H), 2.28 (s, 3H), 1.31 (s, 9H).

Example 39

[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine

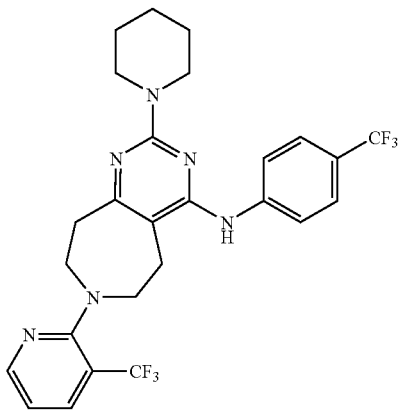 [SMILES: FC(F)(F)c1ccc(Nc2nc(N3CCCCC3)nc3c2CCN(c2ncccc2C(F)(F)F)CC3)cc1]

Step A. 2-Piperidin-1-yl-7-(3-trifluoromethyl-pyridin-2-yl)-6,7,8,9-tetrahydro-5H-pyrimido[4,5-d]azepin-4-ol. To solution of KOtBu (1.3 g, 5.77 mmol) in tBuOH (32 mL) was added 5-oxo-1-(3-trifluoromethyl-pyridin-2-yl)-azepane-4-carboxylic acid ethyl ester (Intermediate B; 1.27 g, 3.85 mmol), followed by piperidine-1-carboximidamide hydrobromide (1.2 g, 5.77 mmol). After heating at reflux for 24 h, the mixture was cooled and concentrated. The residue was dissolved in water and CH$_2$Cl$_2$. The aqueous layer was acidified to pH=7 with HOAc. The layers were separated and the aqueous layer was extracted with CH$_2$Cl$_2$. The combined organic layers were dried (Na$_2$SO$_4$) and concentrated. The residue was triturated with Et$_2$O and filtered. The filtrate was concentrated and the residue was purified (FCC) to give the title compound (776.4 g, 51%—combined filtered and chromatographed).

Step B. 4-Chloro-2-piperidin-1-yl-7-(3-trifluoromethyl-pyridin-2-yl)-6,7,8,9-tetrahydro-5H-pyrimido[4,5-d]azepine. To a solution of 2-piperidin-1-yl-7-(3-trifluoromethyl-pyridin-2-yl)-6,7,8,9-tetrahydro-5H-pyrimido[4,5-d]azepin-4-ol (435 mg, 1.11 mmol) in CH$_3$CN (9 mL) was added POCl$_3$ (0.41 mL, 4.43 mmol). After 1.5 h at 80° C., the mixture was cooled to rt, diluted with EtOAc, and quenched slowly with satd. aq. NaHCO$_3$. The organic layers were combined, dried (Na$_2$SO$_4$), and concentrated. The crude residue was purified (FCC) to give the title compound (160 mg, 35%).

Step C. [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine. To a solution of 4-chloro-2-piperidin-1-yl-7-(3-trifluoro-methyl-pyridin-2-yl)-6,7,8,9-tetrahydro-5H-pyrimido[4,5-d]azepine (50 mg, 0.12 mmol), 4-trifluoromethyl aniline (0.02 mL, 0.18 mmol), and NaOtBu (16 mg, 0.17 mmol) in toluene (1.5 mL) in a microwave vial was added a solution of Pd(OAc)$_2$ (0.4 mg, 0.002 mmol) and DCPB (1.3 mg, 0.004. mmol) in toluene (1 mL). The mixture was flushed with N$_{2(g)}$ and heated in a microwave at 200° C. for 50 min. The mixture was cooled and filtered through a plug of diatomaceous earth. The filtrate was concentrated and the residue was purified (FCC) to afford the title compound (48 mg, 89%). MS (ESI): mass calcd. for $C_{26}H_{26}F_6N_6$, 536.21; m/z found, 537.2 [M+H]$^+$. $^1$H NMR (CDCl$_3$): 8.40-8.37 (m, 1H), 7.87 (d, J=1.8 Hz, 1H), 7.65 (d, J=8.6 Hz, 2H), 7.55 (d, J=8.8 Hz, 2H), 6.97-6.91 (m, 1H), 6.49 (s, 1H), 3.77-3.71 (m, 4H), 3.62-3.54 (m, 4H), 3.10-3.06 (m, 2H), 2.89-2.84 (m, 2H), 1.70-1.56 (m, 6H).

Example 39A

[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine hydrochloride salt $^1$H NMR (CD$_3$OD): 8.47-8.45 (m, 1H), 8.05 (dd, J=7.8, 1.8 Hz, 1H), 7.74 (q, J=8.8 Hz, 4H), 7.16 (dd, J=7.8, 4.8 Hz, 1H), 3.74-3.69 (m, 4H), 3.64-3.59 (m, 2H), 3.57-3.54 (m, 2H), 3.31-3.27 (m, 2H), 3.13-3.02 (m, 2H), 1.80-1.72 (m, 2H), 1.72-1.65 (m, 4H).

Example 39B

[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine sulfate salt $^1$H NMR (CD$_3$OD): 8.48-8.45 (m, 1H), 8.05 (dd, J=7.8, 1.6 Hz, 1H), 7.78-7.68 (m, 4H), 7.19-7.13 (m, 1H), 3.75-3.69 (m, 4H), 3.65-3.59 (m, 2H), 3.58-3.53 (m, 2H), 3.33-3.28 (m, 2H), 3.13-3.09 (m, 2H), 1.79-1.62 (m, 6H).

The following Examples 40-45 were prepared using methodology similar to that described in Example 39, substituting the appropriate carboximidamides in Step A.

Example 40

[2-Morpholin-4-yl-7-(3-trifluoromethyl-pyridin-2-yl)-6,7,8,9-tetrahydro-5H-pyrimido[4,5-d]azepin-4-yl]-(4-trifluoromethyl-phenyl)-amine

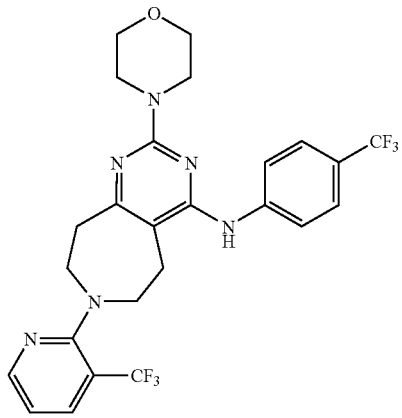 [SMILES: FC(F)(F)c1ccc(Nc2nc(N3CCOCC3)nc3c2CCN(c2ncccc2C(F)(F)F)CC3)cc1]

MS (ESI): mass calcd. for $C_{25}H_{24}F_6N_6O$, 538.19; m/z found, 539.2 [M+H]$^+$. $^1$H NMR (CDCl$_3$): 8.40-8.37 (m, 1H), 7.89-7.85 (m, 1H), 7.63 (d, J=9.1 Hz, 2H), 7.57 (d, J=9.1 Hz, 2H), 6.98-6.92 (m, 1H), 6.53 (s, 1H), 3.80-3.71 (m, 8H), 3.63-3.54 (m, 4H), 3.13-3.06 (m, 2H), 2.92-2.86 (m, 2H).

Example 40A

[2-Morpholin-4-yl-7-(3-trifluoromethyl-pyridin-2-yl)-6,7,8,9-tetrahydro-5H-pyrimido[4,5-d]azepin-4-yl]-(4-trifluoromethyl-phenyl)-amine hydrochloride salt $^1$H NMR (CD$_3$OD): 8.49-8.46 (m, 1H), 8.05 (dd, J=1.7, 7.4 Hz, 1H), 7.75 (s, 4H), 7.17 (dd, J=4.9, 7.4 Hz, 1H), 3.79-3.75 (m, 4H), 3.73-3.71 (m, 4H), 3.65-3.62 (m, 2H), 3.59-3.55 (m, 2H), 3.31-3.29 (m, 2H), 3.15-3.11 (m, 2H).

Example 41

[2-Morpholin-4-yl-7-(3-trifluoromethyl-pyridin-2-yl)-6,7,8,9-tetrahydro-5H-pyrimido[4,5-d]azepin-4-yl]-(5-trifluoromethyl-pyridin-2-yl)-amine

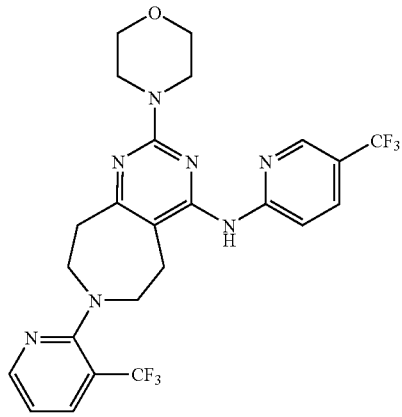 [SMILES: FC(F)(F)c1ccc(Nc2nc(N3CCOCC3)nc3c2CCN(c2ncccc2C(F)(F)F)CC3)nc1]

MS (ESI): mass calcd. for C$_{24}$H$_{23}$F$_6$N$_7$O, 539.19; m/z found, 540.2 [M+H]$^+$. $^1$H NMR (CDCl$_3$): 8.52-8.51 (m, 1H), 8.42-8.40 (m, 1H), 8.38 (d, J=8.8 Hz, 1H), 7.92-7.87 (m, 2H), 7.49-7.46 (m, 1H), 6.99-6.95 (m, 1H), 3.84-3.77 (m, 8H), 3.60-3.54 (m, 4H), 3.15-3.10 (m, 2H), 2.97-2.94 (m, 2H).

Example 42

(4-tert-Butyl-phenyl)-[2-piperidin-1-yl-7-(3-trifluoromethyl-pyridin-2-yl)-6,7,8,9-tetrahydro-5H-pyrimido[4,5-d]azepin-4-yl]-amine

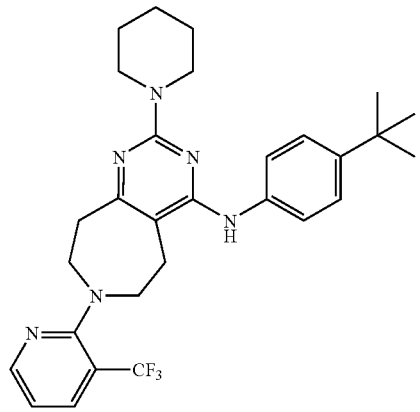 [SMILES: CC(C)(C)c1ccc(Nc2nc(N3CCCCC3)nc3c2CCN(c2ncccc2C(F)(F)F)CC3)cc1]

MS (ESI): mass calcd. for C$_{29}$H$_{35}$F$_3$N$_6$, 524.29; m/z found, 525.3 [M+H]$^+$. $^1$H NMR (CDCl$_3$): 8.39-8.36 (m, 1H), 7.87-7.84 (m, 1H), 7.50-7.46 (m, 2H), 7.35-7.31 (m, 2H), 6.94-6.89 (m, 1H), 6.31 (s, 1H), 3.76-3.71 (m, 4H), 3.63-3.55 (m, 4H), 3.09-3.03 (m, 2H), 2.86-2.81 (m, 2H), 1.67-1.57 (m, 6H), 1.32 (s, 9H).

Example 43

N$^2$,N$^2$-Dimethyl-N$^4$-(6-trifluoromethyl-pyridin-3-yl)-7-(3-trifluoro-methyl-pyridin-2-yl)-6,7,8,9-tetrahydro-5H-pyrimido[4,5-d]azepine-2,4-diamine

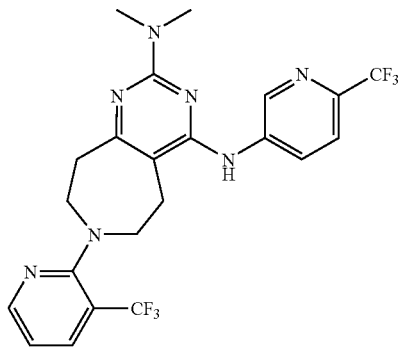 [SMILES: CN(C)c1nc2c(c(Nc3ccc(C(F)(F)F)nc3)n1)CCN(c1ncccc1C(F)(F)F)CC2]

Example 43B

N$^2$,N$^2$-Dimethyl-N$^4$-(6-trifluoromethyl-pyridin-3-yl)-7-(3-trifluoro-methyl-pyridin-2-yl)-6,7,8,9-tetrahydro-5H-pyrimido[4,5-d]azepine-2,4-diamine trifluoroacetic acid salt MS (ESI): mass calcd. for C$_{22}$H$_{21}$F$_6$N$_7$, 497.18; m/z found, 498.8 [M+H]$^+$. $^1$H NMR (CDCl$_3$): 9.04 (d, J=1.9 Hz, 1H), 8.76 (s, 1H), 8.39 (d, J=4.4 Hz, 1H), 8.16-8.13 (m, 1H), 8.03-8.00 (m, 1H), 7.74 (d, J=8.2 Hz, 1H), 7.12-7.08 (m, 1H), 3.67-3.62 (m, 4H), 3.38-3.33 (m, 2H), 3.22 (s, 6H), 3.12-3.08 (m, 2H).

Example 44

N$^2$,N$^2$-Dimethyl-N$^4$-(5-trifluoromethyl-pyridin-2-yl)-7-(3-trifluoro-methyl-pyridin-2-yl)-6,7,8,9-tetrahydro-5H-pyrimido[4,5-d]azepine-2,4-diamine

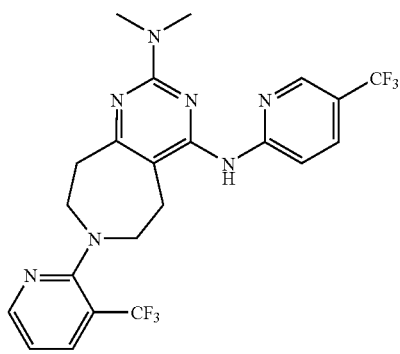 [SMILES: CN(C)c1nc2c(c(Nc3ccc(C(F)(F)F)cn3)n1)CCN(c1ncccc1C(F)(F)F)CC2]

MS (ESI): mass calcd. for C$_{22}$H$_{21}$F$_6$N$_7$, 497.18; m/z found, 498.8 [M+H]$^+$. $^1$H NMR (CDCl$_3$): 8.58 (d, J=9.1 Hz, 1H), 8.51-8.49 (m, 1H), 8.42-8.40 (m, 1H), 7.90-7.86 (m, 2H), 7.48 (s, 1H), 6.98-6.94 (m, 1H), 3.59-3.54 (m, 4H), 3.21 (s, 6H), 3.14-3.10 (m, 2H), 2.95-2.92 (m, 2H).

Example 45

N[4]-(3-Chloro-4-trifluoromethyl-phenyl)-N[2],N[2]-dimethyl-7-(3-trifluoro-methyl-pyridin-2-yl)-6,7,8,9-tetrahydro-5H-pyrimido[4,5-d]azepine-2,4-diamine

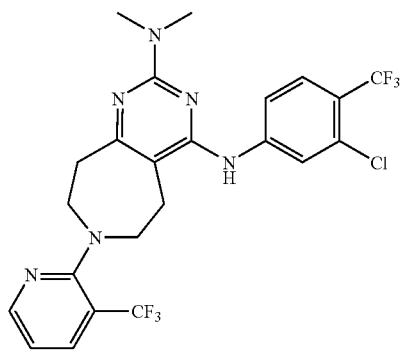 [SMILES: CN(C)c1nc2c(c(Nc3ccc(C(F)(F)F)c(Cl)c3)n1)CCN(c1ncccc1C(F)(F)F)CC2]

The title compound was synthesized like Example 39 with modifications to Step C as follows:

Step C. A mixture of [4-chloro-7-(3-trifluoromethyl-pyridin-2-yl)-6,7,8,9-tetrahydro-5H-pyrimido-[4,5-d]azepin-2-yl]-dimethyl-amine (50 mg, 0.14 mmol), 3-chloro-4-trifluoro-methylaniline (40 mg, 0.20 mmol), and p-toluenesulfonic acid (51 mg, 0.27 mmol) in toluene (2 mL) was heated in a sealed tube at 120° C. for 18 h. The mixture was cooled, diluted with satd. aq. NaHCO$_3$, and extracted with CH$_2$Cl$_2$. The organic layer was dried (MgSO$_4$) and concentrated. The residue was purified (FCC) to give the title compound (55 mg, 78%). MS (ESI): mass calcd. for C$_{23}$H$_{21}$ClF$_6$N$_6$, 530.14; m/z found, 531.8 [M+H]$^+$. $^1$H NMR (CD$_3$OD): 8.43-8.40 (m, 1H), 8.25 (d, J=1.9 Hz, 1H), 8.08-7.98 (m, 1H), 7.66-7.62 (m, 1H), 7.57 (d, J=8.8 Hz, 1H), 7.11-7.08 (m, 1H), 3.45-3.39 (m, 4H), 3.33-3.31 (m, 1H), 3.13 (s, 6H), 3.06-3.03 (m, 2H), 2.97-2.93 (m, 2H).

Example 46

(4-Bromo-phenyl)-[2-isopropyl-7-(3-trifluoromethyl-pyridin-2-yl)-6,7,8,9-tetrahydro6-5H-pyrimido[4,5-d]azepin-4-yl]-amine

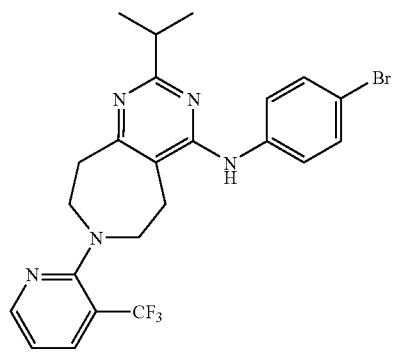 [SMILES: CC(C)c1nc2c(c(Nc3ccc(Br)cc3)n1)CCN(c1ncccc1C(F)(F)F)CC2]

The title compound was prepared using methods similar to those in Example 1 with modifications to Step E as follows:

Step E. A mixture of 4-chloro-2-isopropyl-7-(3-trifluoromethyl-pyridin-2-yl)-6,7,8,9-tetrahydro-5H-pyrimido[4,5-d]azepine (50 mg, 0.14 mmol), 4-bromoaniline (35 mg, 0.36 mmol), and p-toluenesulfonic acid (51 mg, 0.27 mmol) in toluene (2 mL) was heated in a sealed tube at 130° C. for 18 h. The mixture was cooled, diluted with satd. aq. NaHCO$_3$, and extracted with EtOAc. The organic layer was dried (Na$_2$SO$_4$) and concentrated. The residue was purified (FCC) to give the title compound (57 mg, 77%). MS (ESI): mass calcd. for C$_{23}$H$_{23}$BrF$_3$N$_5$, 505.11; m/z found, 506.1 [M+H]$^+$. $^1$H NMR (CDCl$_3$): 8.41-8.39 (m, 1H), 7.90-7.87 (m, 1H), 7.61-7.56 (m, 2H), 7.48-7.43 (m, 2H), 6.99-6.95 (m, 1H), 6.49 (s, 1H), 3.68-3.65 (m, 2H), 3.63-3.60 (m, 2H), 3.25-3.21 (m, 2H), 3.08-2.99 (m, 1H), 2.98-2.94 (m, 2H), 1.32 (d, J=6.9 Hz, 6H).

Example 47

(4-tert-Butyl-phenyl)-[2-morpholin-4-yl-7-(3-trifluoromethyl-pyridin-2-yl)-6,7,8,9-tetrahydro-5H-pyrimido[4,5-d]azepin-4-yl]-amine

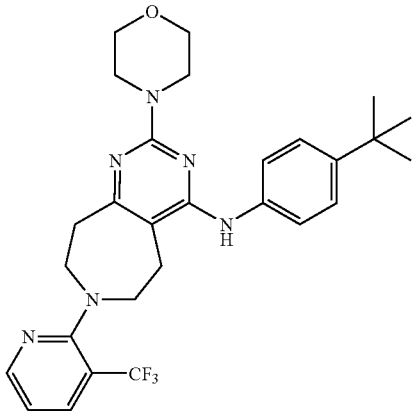 [SMILES: CC(C)(C)c1ccc(Nc2nc(N3CCOCC3)nc3c2CCN(c2ncccc2C(F)(F)F)CC3)cc1]

The title compound was synthesized in accordance with Example 39 with modifications to Step C as follows:

Step C. To a solution of 4-chloro-2-morpholin-4-yl-7-(3-trifluoromethyl-pyridin-2-yl)-6,7,8,9-tetrahydro-5H-pyrimido[4,5-d]azepine (30 mg, 0.08 mmol) in n-BuOH (2 mL) was added 4-tert-butylaniline (23 μL, 0.15 mmol). The mixture was heated in the microwave at 180° C. for 90 min, then was cooled to rt, diluted with MeOH, and filtered through quaternary amine resin, carbonate form (500 mg). The filtrate was concentrated and the residue was purified (FCC) to give the title compound (39 mg, 99%). MS (ESI): mass calcd. for C$_{28}$H$_{33}$F$_3$N$_6$O, 526.27; m/z found, 527.2 [M+H]$^+$. $^1$H NMR (CDCl$_3$): 8.40-8.37 (m, 1H), 7.87 (d, J=1.8 Hz, 1H), 7.48-7.43 (m, 2H), 7.37-7.31 (m, 2H), 6.96-6.89 (m, 1H), 6.35 (s, 1H), 3.80-3.70 (m, 8H), 3.64-3.54 (m, 4H), 3.11-3.04 (m, 2H), 2.88-2.82 (m, 2H), 1.33 (s, 9H).

The following Examples 48-51 were prepared analogously to the methods used in Example 47, substituting the appropriate carboximidamides in Step A and amines in Step C.

Example 48

N[4]-(4-tert-Butyl-phenyl)-N[2],N[2]-dimethyl-7-(3-trifluoromethyl-pyridin-2-yl)-6,7,8,9-tetrahydro-5H-pyrimido[4,5-d]azepine-2,4-diamine

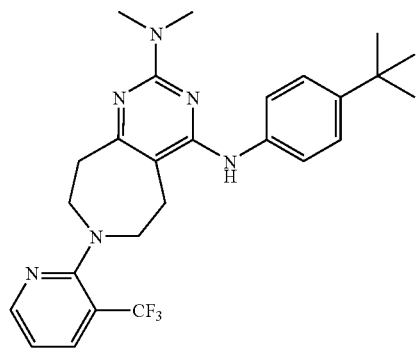 [SMILES: CN(C)c1nc2c(c(Nc3ccc(C(C)(C)C)cc3)n1)CCN(c1ncccc1C(F)(F)F)CC2]

MS (ESI): mass calcd. for $C_{26}H_{31}F_3N_6$, 484.26; m/z found, 485.9 [M+H]+.

Example 48

N[4](4-tert-Butyl-phenyl)-N[2],N[2]-dimethyl-7-(3-trifluoromethyl-pyridin-2-yl)-6,7,8,9-tetrahydro-5H-pyrimido[4,5-d]azepine-2,4-diamine trifluoroacetic acid salt

$^1$H NMR (CD$_3$OD): 8.47-8.45 (m, 1H), 8.05-8.02 (m, 1H), 7.51-7.47 (m, 2H), 7.46-7.42 (m, 2H), 7.17-7.13 (m, 1H), 3.64-3.60 (m, 2H), 3.57-3.53 (m, 2H), 3.30-3.27 (m, 2H), 3.18 (s, 6H), 3.11-3.06 (m, 2H), 1.35 (s, 9H).

Example 49

N[2],N[2]-Dimethyl-N[4]-(4-trifluoromethyl-phenyl)-7-(3-trifluoromethyl-pyridin-2-yl)-6,7,8,9-tetrahydro-5H-pyrimido[4,5-d]azepine-2,4-diamine

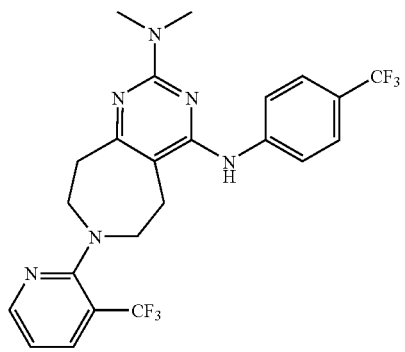 [SMILES: CN(C)c1nc2c(c(Nc3ccc(C(F)(F)F)cc3)n1)CCN(c1ncccc1C(F)(F)F)CC2]

MS (ESI): mass calcd. for $C_{23}H_{22}F_6N_6$, 496.18; m/z found, 497.8 [M+H]+. $^1$H NMR (CDCl$_3$): 8.41-8.39 (m, 1H), 7.89-7.86 (m, 1H), 7.73 (d, J=8.8 Hz, 2H), 7.57 (d, J=8.8 Hz, 2H), 6.97-6.93 (m, 1H), 6.55 (s, 1H), 3.62-3.56 (m, 4H), 3.18 (s, 6H), 3.13-3.09 (m, 2H), 2.90-2.87 (m, 2H).

Example 50

N[4]-([4]-Chloro-phenyl)-N[2],N[2]-dimethyl-7-(3-trifluoromethyl-pyridin-2-yl)-6,7,8,9-tetrahydro-5H-pyrimido[4,5-d]azepine-2,4-diamine

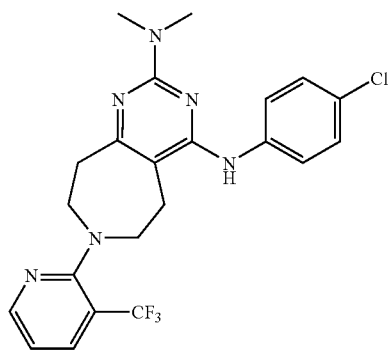 [SMILES: CN(C)c1nc2c(c(Nc3ccc(Cl)cc3)n1)CCN(c1ncccc1C(F)(F)F)CC2]

Example 50B

N[4]-(4-Chloro-phenyl)-N[2],N[2]-dimethyl-7-(3-trifluoromethyl-pyridin-2-yl)-6,7,8,9-tetrahydro-5H-pyrimido[4,5-d]azepine-2,4-diamine trifluoroacetic acid salt MS (ESI): mass calcd. for $C_{22}H_{22}ClF_3N_6$, 462.15; m/z found, 463.8 [M+H]+. $^1$H NMR (CD$_3$OD): 8.47-8.45 (m, 1H), 8.05-8.02 (m, 1H), 7.57-7.53 (m, 2H), 7.42-7.38 (m, 2H), 7.17-7.13 (m, 1H), 3.63-3.59 (m, 2H), 3.57-3.53 (m, 2H), 3.31-3.27 (m, 2H), 3.18 (s, 6H), 3.10-3.06 (m, 2H).

Example 51

N[4]-(4-Trifluoromethyl-phenyl)-7-(3-trifluoromethyl-pyridin-2-yl)-6,7,8,9-tetrahydro-5H-pyrimido[4,5-d]azepine-2,4-diamine

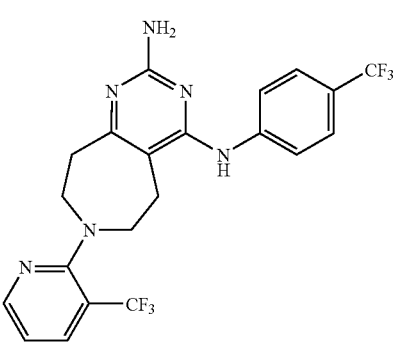 [SMILES: Nc1nc2c(c(Nc3ccc(C(F)(F)F)cc3)n1)CCN(c1ncccc1C(F)(F)F)CC2]

MS (ESI): mass calcd. for $C_{21}H_{18}F_6N_6$, 468.15; m/z found, 469.1 [M+H]+. $^1$H NMR (CDCl$_3$): 8.41-8.39 (m, 1H), 7.90-7.87 (m, 1H), 7.67 (d, J=8.2 Hz, 2H), 7.58 (d, J=8.5 Hz, 2H), 6.99-6.95 (m, 1H), 6.55 (s, 1H), 4.73 (s, 2H), 3.63-3.57 (m, 4H), 3.11-3.07 (m, 2H), 2.93-2.89 (m, 2H).

Example 52

[2-Methylsulfanyl-7-(3-trifluoromethyl-pyridin-2-yl)-6,7,8,9-tetrahydro-5H-pyrimido[4,5-d]azepin-4-yl]-(4-trifluoromethyl-phenyl)-amine

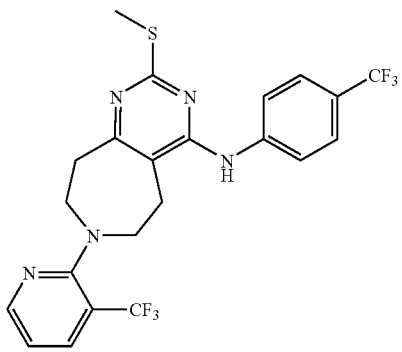

Step A. 2-Methylsulfanyl-7-(3-trifluoromethyl-pyridin-2-yl)-6,7,8,9-tetrahydro-5H-pyrimido[4,5-d]azepin-4-ol. To solution of 5-oxo-1-(3-trifluoromethyl-pyridin-2-yl)-azepane-4-carboxylic acid ethyl ester (3.0 g, 9.09 mmol) in EtOH (40 mL) was added NaOEt (1.97 g, 29.1 mmol) and thiourea (1.1 g, 13.6 mmol). The mixture was heated at reflux for 12 h. The mixture was cooled, treated with MeI (0.74 mL, 11.8 mmol) drop-wise, and stirred at rt for 1 h. Thee mixture was concentrated and the residue was dissolved in water and acidified to pH=7 with HOAc (a precipitate formed). The solid was filtered to give the title compound (3.3 g, >99%), which was used in the next step without further purification.

Step B. 4-Chloro-2-methylsulfanyl-7-(3-trifluoromethyl-pyridin-2-yl)-6,7,8,9-tetrahydro-5H-pyrimido[4,5-d]azepine. To a solution of 2-methylsulfanyl-7-(3-trifluoromethyl-pyridin-2-yl)-6,7,8,9-tetrahydro-5H-pyrimido[4,5-d]azepin-4-ol (1.8 g, 4.92 mmol) in $CH_3CN$ (40 mL) was added $POCl_3$ (1.4 mL, 14.8 mmol). After 15 min at 80° C., the mixture was cooled to rt, diluted with EtOAc, and quenched slowly with satd. aq. $NaHCO_3$. The organic layer was separated, dried ($MgSO_4$), and concentrated. The crude residue was purified (FCC) to give the title compound (1.6 g, 89%).

Step C. To a solution of 4-chloro-2-methylsulfanyl-7-(3-trifluoromethyl-pyridin-2-yl)-6,7,8,9-tetrahydro-5H-pyrimido[4,5-d]azepine (830 mg, 2.22 mmol) in n-BuOH (5 mL) was added 4-trifluoromethylaniline (0.4 mL, 3.30 mmol). The mixture was heated in the microwave at 160° C. for 30 min, then was cooled to rt, quenched with satd. aq. $NaHCO_3$, and extracted with EtOAc. The combined organic layers were dried ($MgSO_4$) and concentrated. The residue was purified (FCC) to give the title compound (950 mg, 86%). MS (ESI): mass calcd. for $C_{22}H_{19}F_6N_5S$, 499.13; m/z found, 500.1 $[M+H]^+$. $^1H$ NMR ($CDCl_3$): 8.40-8.37 (m, 1H), 7.89-7.86 (m, 1H), 7.69 (d, J=8.6 Hz, 2H), 7.58 (d, J=9.1 Hz, 2H), 6.99-6.94 (m, 1H), 6.65 (s, 1H), 3.66-3.62 (m, 2H), 3.60-3.56 (m, 2H), 3.21-3.16 (m, 2H), 2.99-2.94 (m, 2H), 2.53 (s, 3H).

Example 53

[2-Methanesulfonyl-7-(3-trifluoromethyl-pyridin-2-yl)-6,7,8,9-tetrahydro-5H-pyrimido[4,5-d]azepin-4-yl]-(4-trifluoromethyl-phenyl)-amine

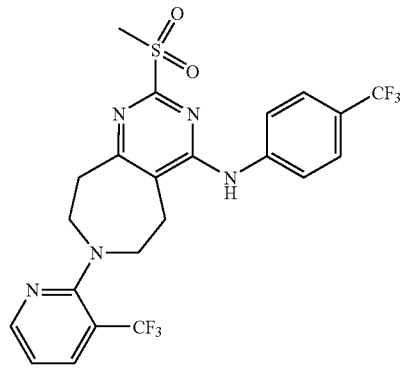 [SMILES: CS(=O)(=O)c1nc2c(c(Nc3ccc(C(F)(F)F)cc3)n1)CCN(c1ncccc1C(F)(F)F)CC2]

To a solution of [2-methylsulfanyl-7-(3-trifluoromethyl-pyridin-2-yl)-6,7,8,9-tetrahydro-5H-pyrimido[4,5-d]azepin-4-yl]-(4-trifluoromethyl-phenyl)-amine (Example 52; 513 mg, 1.02 mmol) in $CH_2Cl_2$ (10 mL) was added m-CPBA (77%; 480 mg, 2.22 mmol). After 2 h, the mixture was diluted with satd. aq. $NaHCO_3$ and extracted with $CH_2Cl_2$. The combined organic layers were dried ($MgSO_4$) and concentrated. The residue was purified (FCC; $MeOH/CH_2Cl_2$) to afford the title compound (500 mg, 92%). MS (ESI): mass calcd. for $C_{22}H_{19}F_6N_5O_2S$, 531.12; m/z found, 532.8 $[M+H]^+$. $^1H$ NMR ($CD_3OD$): 8.46-8.44 (m, 1H), 8.04-8.01 (m, 1H), 7.88 (d, J=8.8 Hz, 2H), 7.66 (d, J=8.5 Hz, 2H), 7.15-7.11 (m, 1H), 3.60-3.54 (m, 4H), 3.37-3.31 (m, 2H), 3.28-3.23 (m, 5H).

Example 54

$N^2$-phenyl-$N^4$(4-trifluoromethyl-phenyl)-7-(3-trifluoromethyl-pyridin-2-yl)-6,7,8,9-tetrahydro-5H-pyrimido[4,5-d]azepine-2,4-diamine

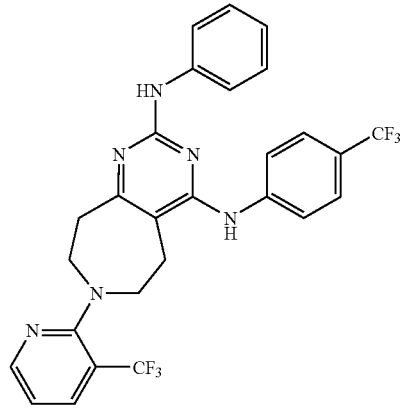 [SMILES: FC(F)(F)c1ccc(Nc2nc(Nc3ccccc3)nc3c2CCN(c2ncccc2C(F)(F)F)CC3)cc1]

A solution of [2-methanesulfonyl-7-(3-trifluoromethyl-pyridin-2-yl)-6,7,8,9-tetrahydro-5H-pyrimido[4,5-d]azepin- 4-yl]-(4-trifluoromethyl-phenyl)-amine (Example 53; 30 mg, 0.06 mmol), aniline (8 mg, 0.09 mmol), and p-toluenesulfonic acid (21.3 mg, 0.11 mmol) in toluene (2 mL) was heated at 125° C. for 12 h. The mixture was cooled and directly purified using Preparative HPLC to give the title compound (20 mg, 67%). MS (ESI): mass calcd. for $C_{27}H_{22}F_6N_6$, 544.18; m/z found, 545.9 [M+H]$^+$. $^1$H NMR (CD$_3$OD): 8.46-8.44 (m, 1H), 8.00-7.97 (m, 1H), 7.66-7.58 (m, 4H), 7.48 (s, 1H), 7.45-7.42 (m, 2H), 7.24-7.19 (m, 2H), 7.16-7.11 (m, 2H), 3.63-3.59 (m, 2H), 3.57-3.53 (m, 2H), 3.29-3.25 (m, 2H), 3.11-3.07 (m, 2H).

Example 55

N 2-Cyclopropyl-N$^4$-(4-trifluoromethyl-phenyl)-7-(3-trifluoromethyl-pyridin-2-yl)-6,7,8,9-tetrahydro-5H-pyrimido[4,5-d]azepine-2,4-diamine

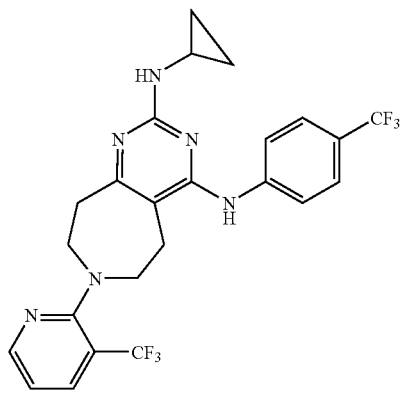 [SMILES: FC(F)(F)c1ccc(Nc2nc(NC3CC3)nc3c2CCN(c2ncccc2C(F)(F)F)CC3)cc1]

The title compound was prepared using methods analogous to those described in Example 54, with n-butanol or t-amyl alcohol as the solvent, in a sealed tube at 130° C., and without the addition of p-toluenesulfonic acid.

Example 55B

N$^2$-Cyclopropyl-N$^4$-(4-trifluoromethyl-phenyl)-7-(3-trifluoromethyl-pyridin-2-yl)-6,7,8,9-tetrahydro-5H-pyrimido[4,5-d]azepine-2,4-diamine trifluoroacetic acid salt MS (ESI): mass calcd. for $C_{24}H_{22}F_6N_6$, 508.18; m/z found, 509.8 [M+H]$^+$. $^1$H NMR (CD$_3$OD): 8.49-8.44 (m, 1H), 8.04 (d, J=7.7 Hz, 1H), 7.92 (s, 2H), 7.69 (d, J=8.8 Hz, 2H), 7.18-7.13 (m, 1H), 3.66-3.61 (m, 2H), 3.59-3.54 (m, 2H), 3.31-3.24 (m, 2H), 3.15-3.11 (m, 2H), 2.76-2.66 (m, 1H), 0.94-0.86 (m, 2H), 0.69-0.64 (m, 2H).

The compounds in Examples 56-61 were prepared using methods analogous to those described in Example 55.

Example 56

[2-Azetidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine

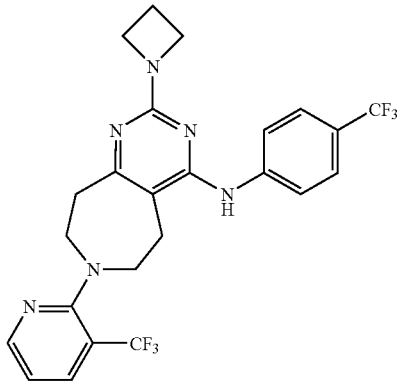 [SMILES: FC(F)(F)c1ccc(Nc2nc(N3CCC3)nc3c2CCN(c2ncccc2C(F)(F)F)CC3)cc1]

Example 56B

[2-Azetidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine trifluoroacetic acid salt MS (ESI): mass calcd. for $C_{24}H_{22}F_6N_6$, 508.18; m/z found, 509.8 [M+H]$^+$. $^1$H NMR (CD$_3$OD): 8.47-8.45 (m, 1H), 8.05-8.02 (m, 1H), 7.85 (d, J=8.5 Hz, 2H), 7.69 (d, J=8.8 Hz, 2H), 7.17-7.13 (m, 1H), 4.32-4.22 (m, 4H), 3.64-3.60 (m, 2H), 3.57-3.53 (m, 2H), 3.26-3.22 (m, 2H), 3.13-3.09 (m, 2H), 2.53-2.45 (m, 2H).

Example 57

1[-4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidine-4-carboxylic acid

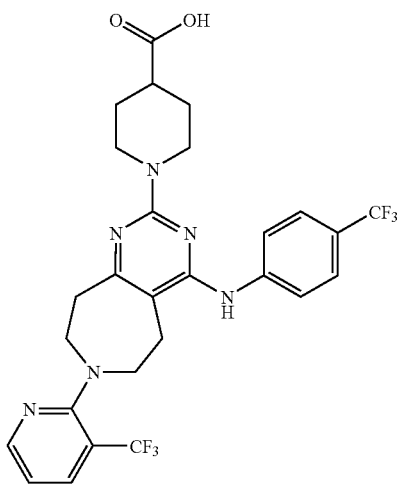 [SMILES: O=C(O)C1CCN(c2nc3c(c(Nc4ccc(C(F)(F)F)cc4)n2)CCN(c2ncccc2C(F)(F)F)CC3)CC1]

Example 57B

1-[4-(4-Trifluoromethyl-phenylamino)-7-(3-trifluoromethyl-pyridin-2-y-)-6,7,8,9-tetrahydro-5H-pyrimido[4,5-d]azepin-2-yl]-piperidine-4-carboxylic acid trifluoroacetic acid salt MS (ESI): mass calcd. for $C_{27}H_{26}F_6N_6O_2$, 580.2; m/z found, 581.9 [M+H]$^+$. $^1$H NMR (CD$_3$OD): 8.49-8.44 (m, 1H), 8.07-8.02 (m, 1H), 7.74-7.72 (m, 4H), 7.18-7.13 (m, 1H), 4.30-4.22 (m, 2H), 3.65-3.61 (m, 2H), 3.58-3.54 (m, 2H), 3.34-3.25 (m, 4H), 3.14-3.09 (m, 2H), 2.74-2.66 (m, 1H), 2.08-2.01 (m, 2H), 1.80-1.68 (m, 2H).

Example 58

N$^2$-(2-Piperidin-1-yl-ethyl)-N$^4$-(4-trifluoromethyl-phenyl)-7-(3-trifluoro-methyl-pridin-2-yl)-6,7,8,9-tetrahydro-5H-pyrimido[4,5-d]azepine-2,4-diamine

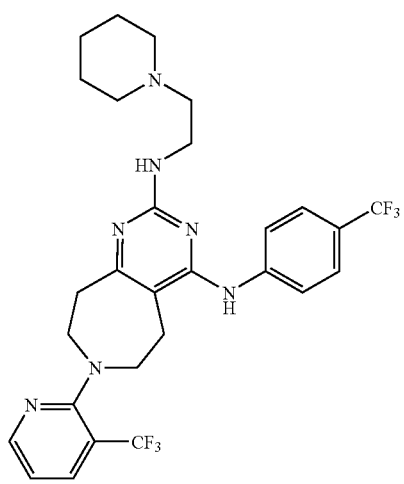 [SMILES: FC(F)(F)c1ccc(Nc2nc(NCCN3CCCCC3)nc3c2CCN(c2ncccc2C(F)(F)F)CC3)cc1]

Example 58B

N$^2$-(2-Piperidin-1-yl-ethyl)-N$^4$(4-trifluoromethyl-phenyl)-7-(3-trifluoro-methyl-pyridin-2-yl)-6,7,8,9-tetrahydro-5H-pyrimido[4,5-d]azepine-2,4-diamine trifluoroacetic acid salt MS (ESI): mass calcd. for $C_{28}H_{31}F_6N_7$, 579.25; m/z found, 581.0 [M+H]$^+$. $^1$H NMR (CD$_3$OD): 8.47-8.44 (m, 1H), 8.05-8.01 (m, 1H), 7.79-7.70 (m, 4H), 7.18-7.12 (m, 1H), 3.76-3.71 (m, 2H), 3.64-3.59 (m, 2H), 3.57-3.52 (m, 2H), 3.44-3.36 (m, 2H), 3.24-3.17 (m, 4H), 3.13-3.07 (m, 2H), 2.81-2.70 (m, 2H), 1.82-1.32 (m, 6H).

Example 59

1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-4-ol

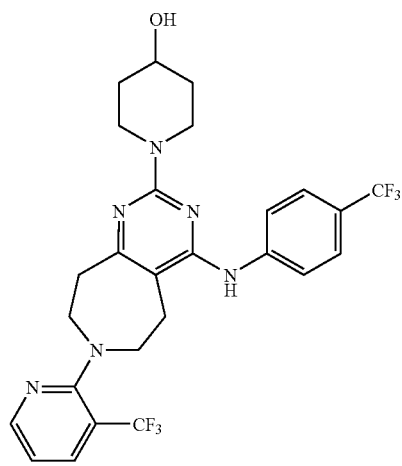 [SMILES: OC1CCN(c2nc3c(c(Nc4ccc(C(F)(F)F)cc4)n2)CCN(c2ncccc2C(F)(F)F)CC3)CC1]

Example 59B

1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-4-ol trifluoroacetic acid salt MS (ESI): mass calcd. for $C_{26}H_{26}F_6N_6O$, 552.21; m/z found, 553.9 [M+H]$^+$. $^1$H NMR (CD$_3$OD): 8.47-8.43 (m, 1H), 8.05-8.00 (m, 1H), 7.75-7.68 (m, 4H), 7.17-7.11 (m, 1H), 4.07-3.98 (m, 2H), 3.97-3.88 (m, 1H), 3.64-3.57 (m, 2H), 3.56-3.42 (m, 4H), 3.32-3.25 (m, 2H), 3.13-3.06 (m, 2H), 1.98-1.87 (m, 2H), 1.64-1.49 (m, 2H).

Example 60

[2-(4-Isopropyl-piperazin-1-yl)-7-(3-trifluoromethyl-pyridin-2-yl)-6,7,8,9-tetrahydro-5H-pyrimido[4,5-d]azepin-4-yl]-(4-trifluoromethyl-phenyl)-amine

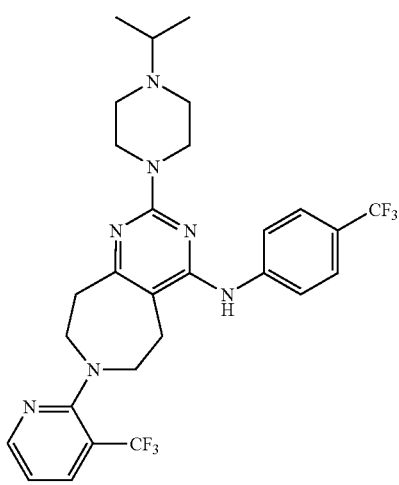 [SMILES: CC(C)N1CCN(c2nc3c(c(Nc4ccc(C(F)(F)F)cc4)n2)CCN(c2ncccc2C(F)(F)F)CC3)CC1]

Example 60B

[2-(4-Isopropyl-piperazin-1-yl)-7-(3-trifluoromethyl-pyridin-2-yl)-6,7,8,9-tetrahydro-5H-pyrimido[4,5-d]azepin-4-yl]-(4-trifluoromethyl-phenyl)-amine trifluoroacetic acid salt MS (ESI): mass calcd. for $C_{28}H_{31}F_6N_7$, 579.25; m/z found, 581.0 [M+H]$^+$. $^1$H NMR (CD$_3$OD): 8.47-8.44 (m, 1H), 8.05-8.01 (m, 1H), 7.73-7.71 (m, 4H), 7.18-7.12 (m, 1H), 3.66-3.24 (m, 15H), 3.18-3.07 (m, 2H), 1.38 (d, J=6.3 Hz, 6H).

Example 61

N$^2$-(Tetrahydro-pyran-4-yl)-N$^4$(4-trifluoromethyl-phenyl)-7-(3-trifluoro-methyl-pyridin-2-yl)-6,7,8,9-tetrahydro-5H-pyrimido[4,5-d]azepine-2,4-diamine

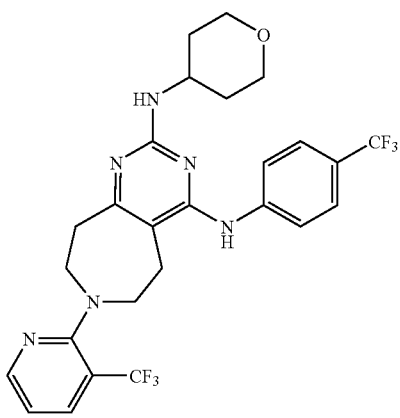 [SMILES: FC(F)(F)c1ccc(Nc2nc(NC3CCOCC3)nc3c2CCN(c2ncccc2C(F)(F)F)CC3)cc1]

Example 61B

N$^2$-(Tetrahydro-pyran-4-yl)-N$^4$-(4-trifluoromethyl-phenyl)-7-(3-trifluoro-methyl-pyridin-2-yl)-6,7,8,9-tetrahydro-5H-pyrimido[4,5-d]azepine-2,4-diamine trifluoroacetic acid salt MS (ESI): mass calcd. for $C_{26}H_{26}F_6N_6O$, 552.21; m/z found, 553.9 [M+H]$^+$. $^1$H NMR (CD$_3$OD): 8.48-8.45 (m, 1H), 8.06-8.03 (m, 1H), 7.77 (d, J=8.5 Hz, 2H), 7.72 (d, J=8.8 Hz, 2H), 7.18-7.14 (m, 1H), 3.98-3.84 (m, 3H), 3.64-3.60 (m, 2H), 3.58-3.54 (m, 2H), 3.43-3.35 (m, 2H), 3.21-3.17 (m, 2H), 3.12-3.09 (m, 2H), 1.92-1.84 (m, 2H), 1.65-1.54 (m, 2H).

Example 62

[2-Methoxy-7-(3-trifluoromethyl-pyridin-2-yl)-6,7,8,9-tetrahydro-5H-pyrimido[4,5-d]azepin-4-yl]-(4-trifluoromethyl-phenyl)-amine

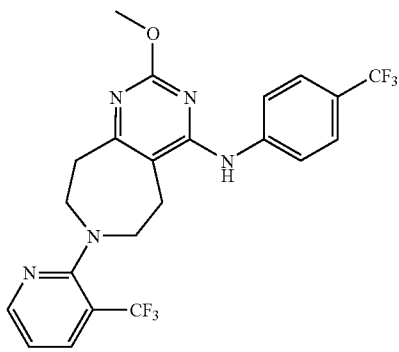 [SMILES: COc1nc2c(c(Nc3ccc(C(F)(F)F)cc3)n1)CCN(c1ncccc1C(F)(F)F)CC2]

A solution of [2-methanesulfonyl-7-(3-trifluoromethyl-pyridin-2-yl)-6,7,8,9-tetrahydro-5H-pyrimido[4,5-d]azepin-4-yl]-(4-trifluoromethyl-phenyl)-amine (Example 53; 44 mg, 0.08 mmol) and NaOMe (100 mg, 0.25 mmol) in MeOH (1.5 mL) was heated at 60° C. for 1 h. The mixture was cooled, acidified with HOAc (3 drops), and directly purified using Preparative HPLC (conditions as in Example 54) to give the title compound (35 mg, 89%). MS (ESI): mass calcd. for $C_{22}H_{19}F_6N_5O$, 483.15; m/z found, 484.8 [M+H]$^+$. $^1$H NMR (CDCl$_3$): 9.63 (s, 1H), 8.39 (d, J=3.3 Hz, 1H), 7.89 (d, J=7.7 Hz, 1H), 7.73 (d, J=8.5 Hz, 2H), 7.63 (d, J=8.5 Hz, 2H), 7.06-7.02 (m, 1H), 3.88 (s, 3H), 3.50-3.44 (m, 4H), 3.26-3.22 (m, 2H), 3.11-3.07 (m, 2H).

The following Examples 63-109 were prepared using methods analogous to those described in the preceding examples.

Example 63

N$^4$-(3,4-Dichloro-phenyl)-N$^2$,N$^2$-dimethyl-7-(3-trifluoromethyl-pyridin-2-yl)-6,7,8,9-tetrahydro-5H-pyrimido[4,5-d]azepine-2,4-diamine

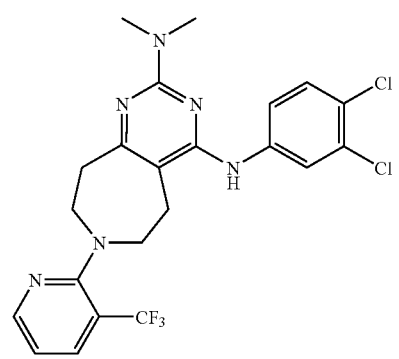 [SMILES: CN(C)c1nc2c(c(Nc3ccc(Cl)c(Cl)c3)n1)CCN(c1ncccc1C(F)(F)F)CC2]

MS (ESI): mass calcd. for $C_{22}H_{21}Cl_2F_3N_6$, 496.12; m/z found, 497.8 [M+H]$^+$.

Example 63B

N⁴-(3,4-Dichloro-phenyl)-N²,N²-dimethyl-7-(3-trifluoromethyl-pyridin-2-yl)-6,7,8,9-tetrahydro-5H-pyrimido[4,5-d]azepine-2,4-diamine trifluoroacetic acid salt ¹H NMR (CD$_3$OD): 8.46 (dd, J=4.7, 1.4 Hz, 1H), 8.03 (dd, J=7.8, 1.8 Hz, 1H), 7.93-7.92 (m, 1H), 7.53-7.52 (m, 2H), 7.17-7.12 (m, 1H), 3.64-3.58 (m, 2H), 3.56-3.52 (m, 2H), 3.32-3.29 (m, 2H), 3.22 (s, 6H), 3.11-3.06 (m, 2H).

Example 64

N⁴-(4-Methoxy-3-trifluoromethyl-phenyl)-N²,N²-dimethyl-7-(3-trifluoromethyl-pyridin-2-yl)-6,7,8,9-tetrahydro-5H-pyrimido[4,5-d]azepine-2,4-diamine

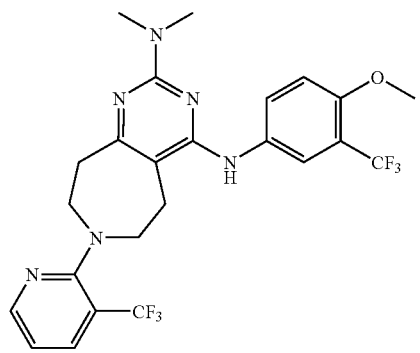 [SMILES: COc1ccc(Nc2nc(N(C)C)nc3c2CCN(c2ncccc2C(F)(F)F)CC3)cc1C(F)(F)F]

MS (ESI): mass calcd. for C$_{24}$H$_{24}$F$_6$N$_6$O, 526.19; m/z found, 527.9 [M+H]⁺. ¹H NMR (CD$_3$OD): 8.42 (dd, J=4.7, 1.6 Hz, 1H), 8.13 (d, J=2.7 Hz, 1H), 7.90 (dd, J=7.8, 1.8 Hz, 1H), 7.56 (dd, J=8.9, 2.7 Hz, 1H), 7.04-6.93 (m, 2H), 6.35 (s, 1H), 3.94 (s, 3H), 3.66-3.57 (m, 4H), 3.16 (s, 6H), 3.14-3.09 (m, 2H), 2.90-2.85 (m, 2H).

Example 65

2-{-4-[2-Dimethylamino-7-(3-trifluoromethyl-pyridin-2-yl)-6,7,8,9-tetrahydro-5H-pyrimido[4,5-d]azepin-4-ylamino]-phenyl}-2-methyl-propionitrile

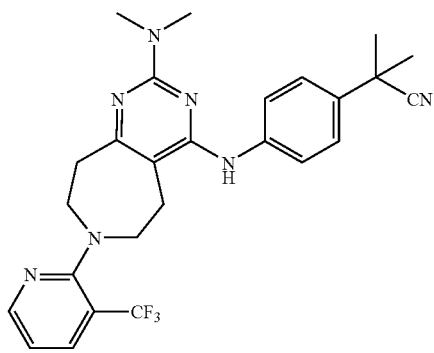 [SMILES: CN(C)c1nc2c(c(Nc3ccc(C(C)(C)C#N)cc3)n1)CCN(c1ncccc1C(F)(F)F)CC2]

MS (ESI): mass calcd. for C$_{26}$H$_{28}$F$_3$N$_7$, 495.24; m/z found, 496.9 [M+H]⁺.

Example 65B

2-{-4-[2-Dimethylamino-7-(3-trifluoromethyl-pyridin-2-yl)-6,7,8,9-tetrahydro-5H-pyrimido[4,5-d]azepin-4-ylamino]-phenyl}-2-methyl-propionitrile trifluoroacetic acid salt ¹H NMR (CD$_3$OD): 8.45 (dd, J=4.7, 1.4 Hz, 1H), 8.02 (dd, J=7.8, 1.8 Hz, 1H), 7.66-7.60 (m, 2H), 7.58-7.53 (m, 2H), 7.17-7.11 (m, 1H), 3.64-3.58 (m, 2H), 3.56-3.51 (m, 2H), 3.30-3.25 (m, 2H), 3.18 (s, 3H), 3.11-3.06 (m, 2H), 1.73 (s, 6H).

Example 66

(4-tert-Butyl-phenyl)-[2-piperidin-1-ylmethyl-7-(3-trifluoromethyl-pyridin-2-yl)-6,7,8,9-tetrahydro-5H-pyrimido[4,5-d]azepin-4-yl]-amine

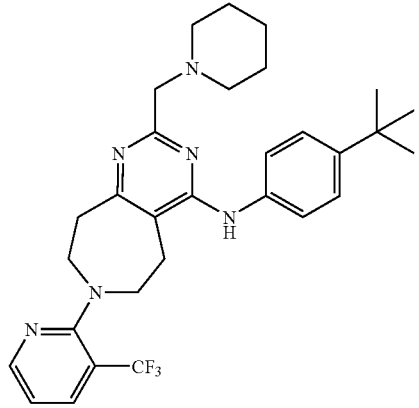 [SMILES: CC(C)(C)c1ccc(Nc2nc(CN3CCCCC3)nc3c2CCN(c2ncccc2C(F)(F)F)CC3)cc1]

MS (ESI): mass calcd. for C$_{30}$H$_{37}$F$_3$N$_6$, 538.30; m/z found, 540.0 [M+H]⁺.

Example 66B (4-tert-Butyl-phenyl)-[2-piperidin-1-ylmethyl-7-(3-trifluoromethyl-pyridin-2-yl)-6,7,8,9-tetrahydro-5H-pyrimido[4,5-d]azepin-4-yl]-amine trifluoroacetic acid salt ¹H NMR (CD$_3$OD): 8.46 (dd, J=4.7, 1.4 Hz, 1H), 8.04 (dd, J=7.8, 1.7 Hz, 1H), 7.53-7.49 (m, 2H), 7.39-7.35 (m, 2H), 7.17-7.13 (m, 1H), 4.41 (s, 2H), 3.65-3.60 (m, 4H), 3.33-3.31 (m, 2H), 3.23-3.18 (m, 2H), 1.80-1.69 (m, 4H), 1.68-1.58 (m, 2H), 1.36 (s, 9H), 1.29-1.21 (m, 2H).

Example 67

(4-tert-Butyl-phenyl)-[2-methoxymethyl-7-(3-trifluoromethyl-pyridin-2-yl)-6,7,8,9-tetrahydro-5H-pyrimido[4,5-d]azepin-4-yl]-amine

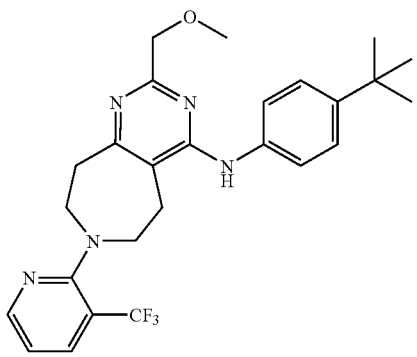 [SMILES: COCc1nc2c(c(Nc3ccc(C(C)(C)C)cc3)n1)CCN(c1ncccc1C(F)(F)F)CC2]

MS (ESI): mass calcd. for $C_{26}H_{30}F_3N_5O$, 485.24; m/z found, 468.9 [M+H]$^+$.

Example 67B (4-tert-Butyl-phenyl)-[2-methoxymethyl-7-(3-trifluoromethyl-pyridin-2-yl)-6,7,8,9-tetrahydro-5H-pyrimido[4,5-d]azepin-4-yl]-amine trifluoroacetic acid salt $^1$H NMR (CD$_3$OD): 8.66 (d, J=8.9 Hz, 1H), 8.52 (s, 1H), 8.40 (dd, J=4.7, 1.5 Hz, 1H), 7.93 (dd, J=8.9, 2.3 Hz, 1H), 7.88 (dd, J=7.8, 1.8 Hz, 1H), 7.63 (s, 1H), 7.00-6.95 (m, 1H), 3.65-3.56 (m, 4H), 3.28-3.21 (m, 2H), 3.09-3.03 (m, 2H), 2.63 (s, 3H).

Example 68

N$^4$-(2,3-Dihydro-benzo[1,4]dioxin-6-yl)-N$^2$,N$^2$-dimethyl-7-(3-trifluoromethyl-pyridin-2-yl)-6,7,8,9-tetrahydro-5H-pyrimido[4,5-d]azepine-2,4-diamine

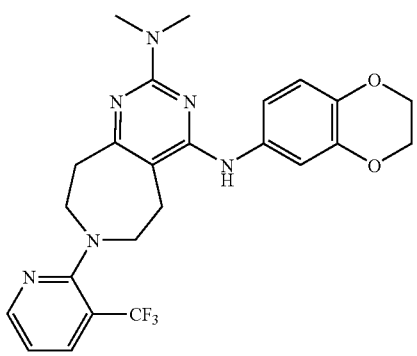 [SMILES: CN(C)c1nc2c(c(Nc3ccc4c(c3)OCCO4)n1)CCN(c1ncccc1C(F)(F)F)CC2]

MS (ESI): mass calcd. for $C_{24}H_{25}F_3N_6O_2$, 486.20; m/z found, 487.8 [M+H]$^+$.

Example 68B

N$^4$-(2,3-Dihydro-benzo[4,1]dioxin-6-yl)-N$^2$,N$^2$-dimethyl-7-(3-trifluoromethyl-pyridin-2-yl)-6,7,8,9-tetrahydro-5H-pyrimido[4,5-d]azepine-2,4-diamine trifluoroacetic acid salt $^1$H NMR (CD$_3$OD): 8.46-8.44 (m, 1H), 8.03 (dd, J=7.8, 1.7 Hz, 1H), 7.16-7.12 (m, 1H), 7.11 (d, J=2.4 Hz, 1H), 6.98 (dd, J=8.7, 2.5 Hz, 1H), 6.84 (d, J=8.7 Hz, 1H), 4.25 (s, 4H), 3.62-3.58 (m, 2H), 3.55-3.51 (m, 2H), 3.29-3.24 (m, 2H), 3.17 (s, 6H), 3.07-3.02 (m, 2H).

Example 69

[2-Methyl-7-(3-trifluoromethyl-pyridin-2-yl)-6,7,8,9-tetrahydro-5H-pyrimido[4,5-d]azepin-4-yl]-(5-trifluoromethyl-pyridin-2-yl)-amine

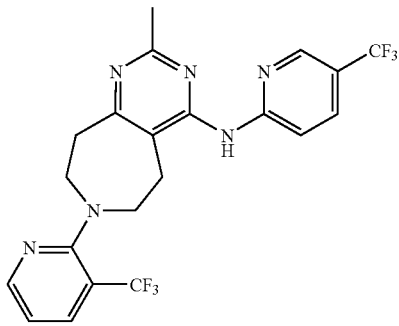 [SMILES: Cc1nc2c(c(Nc3ccc(C(F)(F)F)cn3)n1)CCN(c1ncccc1C(F)(F)F)CC2]

MS (ESI): mass calcd. for $C_{21}H_{18}F_6N_6$, 468.15; m/z found, 469.8 [M+H]$^+$. $^1$H NMR (CDCl$_3$): 8.66 (d, J=8.9 Hz, 1H), 8.52 (s, 1H), 8.40 (dd, J=4.7, 1.5 Hz, 1H), 7.93 (dd, J=8.9, 2.3 Hz, 1H), 7.88 (dd, J=7.8, 1.8 Hz, 1H), 7.63 (s, 1H), 7.00-6.95 (m, 1H), 3.65-3.56 (m, 4H), 3.28-3.21 (m, 2H), 3.09-3.03 (m, 2H), 2.63 (s, 3H).

Example 70

N$^4$-Benzyl-N$^2$,N$^2$-dimethyl-7-(3-trifluoromethyl-pyridin-2-yl)-6,7,8,9-tetrahydro-5H-pyrimido[4,5-d]azepine-2,4-diamine

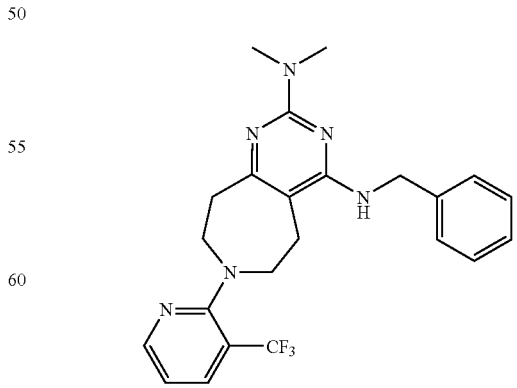

MS (ESI): mass calcd. for $C_{23}H_{25}F_3N_6$, 442.21; m/z found, 443.8 [M+H]$^+$.

Example 70B

N[4]-Benzyl-N[2],N[2]-dimethyl-7-(3-trifluoromethyl-pyridin-2-yl)-6,7,8,9-tetrahydro-5H-pyrimido[4,5-d]azepine-2,4-diamine trifluoroacetic acid salt $^1$H NMR (CD$_3$OD): 8.40-8.38 (m, 1H), 8.00-7.97 (m, 1H), 7.34-7.26 (m, 4H), 7.25-7.20 (m, 1H), 7.10-7.06 (m, 1H), 4.70 (s, 2H), 3.60-3.56 (m, 2H), 3.54-3.50 (m, 2H), 3.26-3.20 (m, 2H), 3.15 (s, 6H), 2.97-2.93 (m, 2H).

Example 71

4-[2-Dimethylamino-7-(3-trifluoromethyl-pyridin-2-yl)-6,7,8,9-tetrahydro-5H-pyrimido[4,5-d]azepin-4-ylamino]-benzenesulfonamide

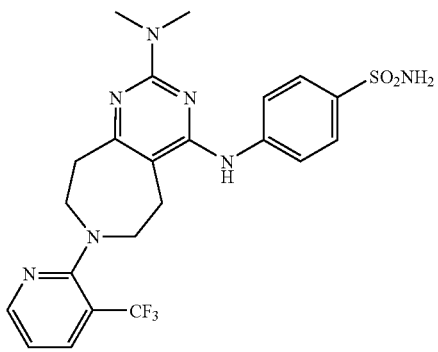 [SMILES: CN(C)c1nc2c(c(Nc3ccc(S(N)(=O)=O)cc3)n1)CCN(c1ncccc1C(F)(F)F)CC2]

MS (ESI): mass calcd. for C$_{22}$H$_{24}$F$_3$N$_7$O$_2$S, 507.17; m/z found, 508.8 [M+H]$^+$.

Example 71B

4-[2-Dimethylamino-7-(3-trifluoromethyl-pyridin-2-yl)-6,7,8,9-tetrahydro-5H-pyrimido[4,5-d]azepin-4-ylamino]-benzenesulfonamide trifluoroacetic acid salt $^1$H NMR (CD$_3$OD): 8.47-8.45 (m, 1H), 8.04 (dd, J=7.8, 1.7 Hz, 1H), 7.94-7.91 (m, 2H), 7.81-7.77 (m, 2H), 7.19-7.11 (m, 1H), 3.66-3.58 (m, 2H), 3.58-3.52 (m, 1H), 3.34-3.29 (m, 2H), 3.21 (s, 6H), 3.13-3.10 (m, 2H).

Example 72

N[2],N[2]-Dimethyl-N[4]-(4-nitro-phenyl)-7-(3-trifluoromethyl-pyridin-2-yl)-6,7,8,9-tetrahydro-5H-pyrimido[4,5-d]azepine-2,4-diamine

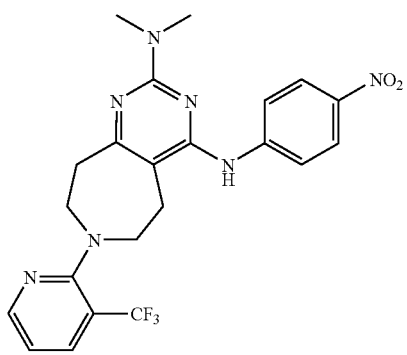 [SMILES: CN(C)c1nc2c(c(Nc3ccc([N+](=O)[O-])cc3)n1)CCN(c1ncccc1C(F)(F)F)CC2]

MS (ESI): mass calcd. for C$_{22}$H$_{22}$F$_3$N$_7$O$_2$, 473.18; m/z found, 474.8.[M+H]$^+$.

Example 72B

N[2],N[2]-Dimethyl-N[4]-(4-nitro-phenyl)-7-(3-trifluoromethyl-pyridin-2-yl)-6,7,8,9-tetrahydro-5H-pyrimido[4,5-d]azepine-2,4-diamine trifluoroacetic acid salt $^1$H NMR (CD$_3$OD): 8.48-8.45 (m, 1H), 8.31-8.26 (m, 2H), 8.04 (dd, J=7.8, 1.8 Hz, 1H), 7.92-7.87 (m, 2H), 7.19-7.12 (m, 1H), 3.66-3.59 (m, 2H), 3.58-3.54 (m, 2H), 3.37-3.33 (m, 2H), 3.24 (s, 3H), 3.16-3.12 (m, 2H).

Example 73

N[4]-(3,4-Dichloro-benzyl)-N[2],N[2]-dimethyl-7-(3-trifluoromethyl-pyridin-2-yl)-6,7,8,9-tetrahydro-5H-pyrimido[4,5-d]azepine-2,4-diamine

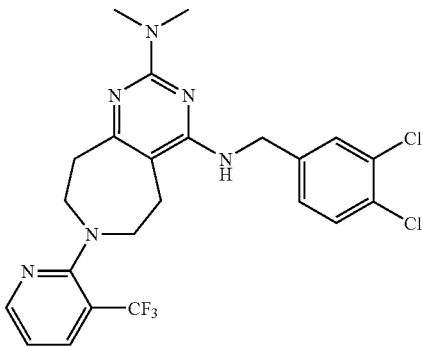 [SMILES: CN(C)c1nc2c(c(NCc3ccc(Cl)c(Cl)c3)n1)CCN(c1ncccc1C(F)(F)F)CC2]

MS (ESI): mass calcd. for C$_{23}$H$_{23}$Cl$_2$F$_3$N$_6$, 510.13; m/z found, 511.1 [M+H]$^+$.

Example 73B

N[4]-(3,4-Dichloro-benzyl)-N[2],N[2]-dimethyl-7-(3-trifluoromethyl-pyridin-2-yl)-6,7,8,9-tetrahydro-5H-pyrimido[4,5-d]azepine-2,4-diamine trifluoroacetic acid salt $^1$H NMR (CD$_3$OD): 8.40 (dd, J=4.7, 1.3 Hz, 1H), 7.99 (dd, J=7.8, 1.8 Hz, 1H), 7.48-7.46 (m, 1H), 7.44 (s, 1H), 7.24 (dd, J=8.3, 2.0 Hz, 1H), 7.12-7.06 (m, 1H), 4.65 (s, 2H), 3.61-3.55 (m, 2H), 3.54-3.49 (m, 2H), 3.25-3.18 (m, 2H), 3.14 (s, 6H), 2.97-2.91 (m, 2H).

Example 74

[2-Methylsulfanyl-7-(3-trifluoromethyl-pyridin-2-yl)-6,7,8,9-tetrahydro-5H-pyrimido[4,5-d]azepin-4-yl]-(5-trifluoromethyl-pyridin-2-yl)-amine

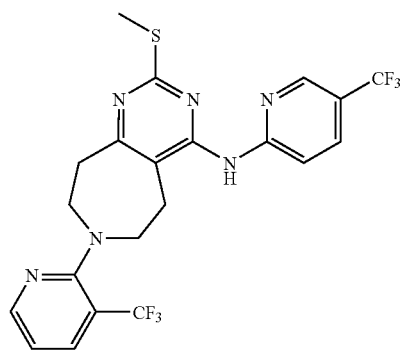 [SMILES: CSc1nc2c(c(Nc3ccc(C(F)(F)F)cn3)n1)CCN(c1ncccc1C(F)(F)F)CC2]

MS (ESI): mass calcd. for C$_{21}$H$_{18}$F$_6$N$_6$S, 500.12; m/z found, 501.8 [M+H]$^+$.

Example 74B

[2-Methylsulfanyl-7-(3-trifluoromethyl-pyridin-2-yl)-6,7,8,9-tetrahydro-5H-pyrimido[4,5-d]azepin-4-yl]-(5-trifluoromethyl-pyridin-2-yl)-amine trifluoroacetic acid salt $^1$H NMR (CD$_3$OD): 8.84-8.81 (m, 1H), 8.35 (dd, J=8.0, 1.5 Hz, 1H), 8.19 (s, 1H), 7.75-7.65 (m, 2H), 6.71 (d, J=9.0 Hz, 1H), 4.32-4.24 (m, 2H), 3.90-3.84 (m, 2H), 3.30-3.23 (m, 2H), 2.98 (t, J=6.3 Hz, 2H), 2.32 (s, 3H).

Example 75

[2-Methylsulfanyl-7-(3-trifluoromethyl-pyridin-2-yl)-6,7,8,9-tetrahydro-5H-pyrimido[4,5-d]azepin-4-yl]-(6-trifluoromethyl-pyridin-3-yl)-amine

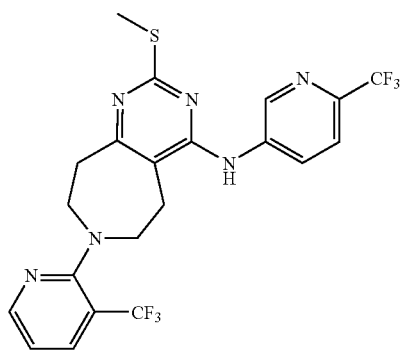 [SMILES: CSc1nc2c(c(Nc3ccc(C(F)(F)F)nc3)n1)CCN(c1ncccc1C(F)(F)F)CC2]

MS (ESI): mass calcd. for C$_{21}$H$_{18}$F$_6$N$_6$S, 500.12; m/z found, 501.8 [M+H]$^+$.

Example 75B

[2-Methylsulfanyl-7-(3-trifluoromethyl-pyridin-2-yl)-6,7,8,9-tetrahydro-5H-pyrimido[4,5-d]azepin-4-yl]-(6-trifluoromethyl-pyridin-3-yl)-amine trifluoroacetic acid salt $^1$H NMR (CD$_3$OD): 9.00 (d, J=2.4 Hz, 1H), 8.46-8.43 (m, 1H), 8.36 (dd, J=8.6, 2.4 Hz, 1H), 8.02 (dd, J=7.8, 1.8 Hz, 1H), 7.78 (d, J=8.6 Hz, 1H), 7.16-7.10 (m, 1H), 3.56-3.48 (m, 4H), 3.20-3.10 (m, 4H), 2.50 (s, 3H).

Example 76

[2-Methoxymethyl-7-(3-trifluoromethyl-pyridin-2-yl)-6,7,8,9-tetrahydro-5H-pyrimido[4,5-d]azepin-4-yl]-(4-trifluoromethyl-phenyl)-amine

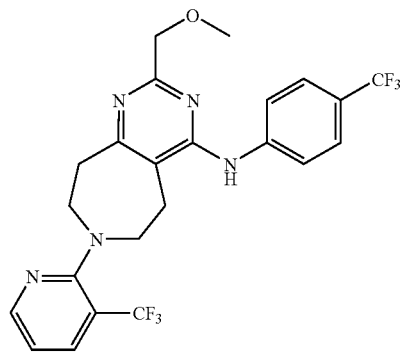 [SMILES: COCc1nc2c(c(Nc3ccc(C(F)(F)F)cc3)n1)CCN(c1ncccc1C(F)(F)F)CC2]

MS (ESI): mass calcd. for C$_{23}$H$_{21}$F$_6$N$_5$O, 497.17; m/z found, 489.3 [M+H]$^+$.

Example 76B

[2-Methoxymethyl-7-(3-trifluoromethyl-pyridin-2-yl)-6,7,8,9-tetrahydro-5H-pyrimido[4,5-d]azepin-4-yl]-(4-trifluoromethyl-phenyl)-amine trifluoroacetic acid salt $^1$H NMR (CD$_3$OD): 8.46-8.44 (m, 1H), 8.03 (dd, J=7.9, 1.7 Hz, 1H), 7.79-7.68 (m, 4H), 7.18-7.11 (m, 1H), 4.57 (s, 2H), 3.68-3.59 (m, 4H), 3.52 (s, 3H), 3.46-3.42 (m, 2H), 3.28-3.23 (m, 2H).

Example 77

4-[2-Dimethylamino-7-(3-trifluoromethyl-pridin-2-yl)-6,7,8,9-tetrahydro-5H-pyrimido[4,5-d]azepin-4-ylamino]-benzoic acid methyl ester

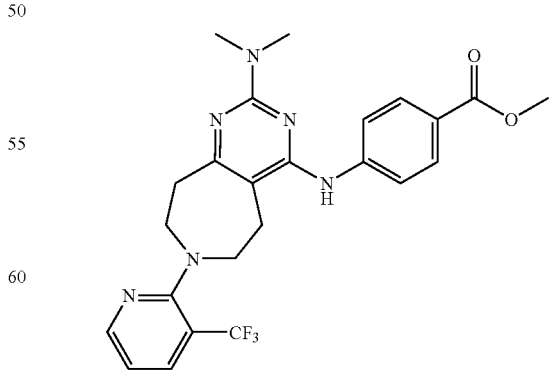

MS (ESI): mass calcd. for C$_{24}$H$_{25}$F$_3$N$_6$O$_2$, 486.20; m/z found, 487.8 [M+H]$^+$.

Example 77B

4-[2-Dimethylamino-7-(3-trifluoromethyl-pyridin-2-yl)-6,7,8,9-tetrahydro-5H-pyrimido[4,5-d]azepin-4-ylamino]-benzoic acid methyl ester trifluoroacetic acid salt $^1$H NMR (CD$_3$OD): 8.47 (dd, J=4.7, 1.5 Hz, 1H), 8.08-8.04 (m, 2H), 8.04 (d, J=1.8 Hz, 1H), 7.75-7.72 (m, 2H), 7.18-7.13 (m, 1H), 3.92 (s, 3H), 3.64-3.60 (m, 2H), 3.58-3.53 (m, 2H), 3.32-3.29 (m, 2H), 3.22 (s, 6H), 3.15-3.09 (m, 2H).

Example 78

4-[2-Dimethylamino-7-(3-trifluoromethyl-pyridin-2-yl)-6,7,8,9-tetrahydro-5H-pyrimido[4,5-d]azepin-4-ylamino]-benzonitrile

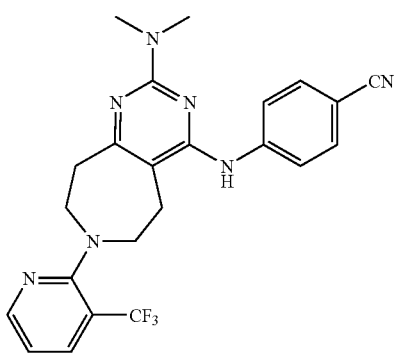 [SMILES: CN(C)c1nc2c(c(Nc3ccc(C#N)cc3)n1)CCN(c1ncccc1C(F)(F)F)CC2]

MS (ESI): mass calcd. for C$_{23}$H$_{22}$F$_3$N$_7$, 453.19; m/z found, 454.8 [M+H]$^+$.

Example 78B

4-[2-Dimethylamino-7-(3-trifluoromethyl-pyridin-2-yl)-6,7,8,9-tetrahydro-5H-pyrimido[4,5-d]azepin-4-ylamino]-benzonitrile trifluoroacetic acid salt $^1$H NMR (CD$_3$OD): 8.46 (dd, J=4.7, 1.4 Hz, 1H), 8.04 (dd, J=7.8, 1.8 Hz, 1H), 7.85-7.81 (m, 2H), 7.79-7.76 (m, 2H), 7.18-7.13 (m, 1H), 3.65-3.59 (m, 2H), 3.57-3.52 (m, 2H), 3.34-3.32 (m, 2H), 3.23 (s, 6H), 3.15-3.09 (m, 2H).

Example 79

N$^4$-(4-Dimethylamino-phenyl)-N$^2$,N$^2$-dimethyl-7-(3-trifluoromethyl-pyridin-2-yl)-6,7,8,9-tetrahydro-5H-pyrimido[4,5-d]azepine-2,4-diamine

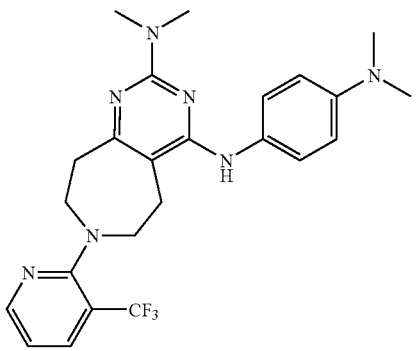 [SMILES: CN(C)c1ccc(Nc2nc(N(C)C)nc3c2CCN(c2ncccc2C(F)(F)F)CC3)cc1]

MS (ESI): mass calcd. for C$_{24}$H$_{28}$F$_3$N$_7$, 471.24; m/z found, 472.2 [M+H]$^+$.

Example 79B

N$^4$-(4-Dimethylamino-phenyl)-N$^2$,N$^2$-dimethyl-7-(3-trifluoromethyl-pyridin-2-yl)-6,7,8,9-tetrahydro-5H-pyrimido[4,5-d]azepine-2,4-diamine trifluoroacetic acid salt $^1$H NMR (CD$_3$OD): 8.46-8.43 (m, 1H), 8.02 (dd, J=7.8, 1.7 Hz, 1H), 7.82-7.76 (m, 2H), 7.62-7.58 (m, 2H), 7.17-7.10 (m, 1H), 3.64-3.57 (m, 2H), 3.56-3.51 (m, 2H), 3.31-3.28 (m, 2H), 3.27 (s, 6H), 3.19 (s, 6H), 3.12-3.06 (m, 2H).

Example 80

(3-Chloro-4-trifluoromethyl-phenyl)-[2-methoxymethyl-7-(3-trifluoromethyl-pyridin-2-yl)-6,7,8,9-tetrahydro-5H-pyrimido[4,5-d]azepin-4-yl]-amine

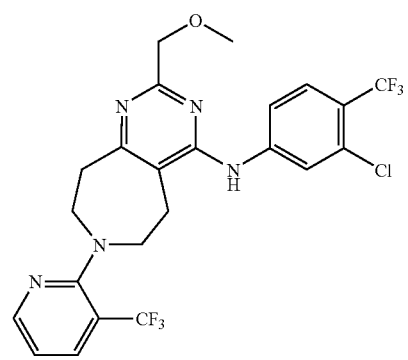 [SMILES: COCc1nc2c(c(Nc3ccc(C(F)(F)F)c(Cl)c3)n1)CCN(c1ncccc1C(F)(F)F)CC2]

MS (ESI): mass calcd. for $C_{23}H_{20}ClF_6N_5O$, 531.13; m/z found, 532.3 [M+H]⁺.

Example 80B (3-Chloro-4-trifluoromethyl-phenyl)-[2-methoxym-ethyl-7-(3-trifluoromethyl-pyridin-2-yl)-6,7,8,9-tet-rahydro-5H-pyrimido[4,5-d]azepin-4-yl]-amine trifluoroacetic acid salt ¹H NMR (CD₃OD): 8.44 (dd, J=4.8, 1.4 Hz, 1H), 8.02 (dd, J=7.8, 1.8 Hz, 1H), 7.44-7.38 (m, 2H), 7.16-7.10 (m, 1H), 6.96-6.91 (m, 2H), 3.80 (s, 3H), 3.62-3.57 (m, 2H), 3.56-3.50 (m, 2H), 3.29-3.23 (m, 2H), 3.14 (s, 3H), 3.08-3.02 (m, 2H).

Example 81

N⁴-(4-Methoxy-phenyl)-N²,N²-dimethyl-7-(3-trifluoromethyl-pyridin-2-yl)-6,7,8,9-tetrahydro-5H-pyrimido[4,5-d]azepine-2,4-diamine

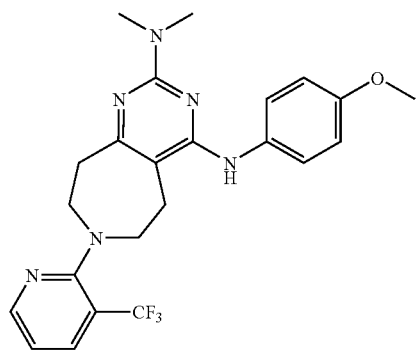 [SMILES: COc1ccc(Nc2nc(N(C)C)nc3c2CCN(c2ncccc2C(F)(F)F)CC3)cc1]

MS (ESI): mass calcd. for $C_{23}H_{25}F_3N_6O$, 458.20; m/z found, 459.8 [M+H]⁺.

Example 81B

N⁴-(4-Methoxy-phenyl)-N²,N²-dimethyl-7-(3-trifluoromethyl-pyridin-2-yl)-6,7,8,9-tetrahydro-5H-pyrimido[4,5-d]azepine-2,4-diamine trifluoroacetic acid salt ¹H NMR (CD₃OD): 8.44 (dd, J=4.8, 1.4 Hz, 1H), 8.02 (dd, J=7.8, 1.8 Hz, 1H), 7.44-7.38 (m, 2H), 7.16-7.10 (m, 1H), 6.96-6.91 (m, 2H), 3.80 (s, 3H), 3.62-3.57 (m, 2H), 3.56-3.50 (m, 2H), 3.29-3.23 (m, 2H), 3.14 (s, 3H), 3.08-3.02 (m, 2H).

Example 82

N⁴-Indan-2-yl-N²,N²-dimethyl-7-(3-trifluoromethyl-pyridin-2-yl)-6,7,8,9-tetrahydro-5H-pyrimido[4,5-d]azepine-2,4-diamine

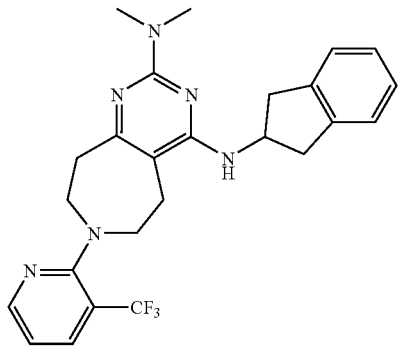 [SMILES: CN(C)c1nc2c(c(NC3Cc4ccccc4C3)n1)CCN(c1ncccc1C(F)(F)F)CC2]

MS (ESI): mass calcd. for $C_{25}H_{27}F_3N_6$, 468.22; m/z found, 469.9 [M+H]⁺.

Example 82B

N⁴-Indan-2-yl-N²,N²-dimethyl-7-(3-trifluoromethyl-pyridin-2-yl)-6,7,8,9-tetrahydro-5H-pyrimido[4,5-d]azepine-2,4-diamine trifluoroacetic acid salt ¹H NMR (CD₃OD): 8.44-8.41 (m, 1H), 8.02 (dd, J=7.8, 1.7 Hz, 1H), 7.25-7.20 (m, 2H), 7.18-7.15 (m, 2H), 7.15-7.11 (m, 1H), 5.04-4.95 (m, 1H), 3.60-3.54 (m, 2H), 3.47-3.43 (m, 2H), 3.42-3.35 (m, 2H), 3.24 (s, 6H), 3.23-3.20 (m, 2H), 3.10-3.02 (m, 2H), 2.95-2.90 (m, 2H).

Example 83

[7-(5-Amino-3-methyl-pyridin-2-yl)-2-isopropyl-6,7,8,9-tetrahydro-5H-pyrimido[4,5-d]azepin-4-yl]-(4-trifluoromethyl-phenyl)-amine

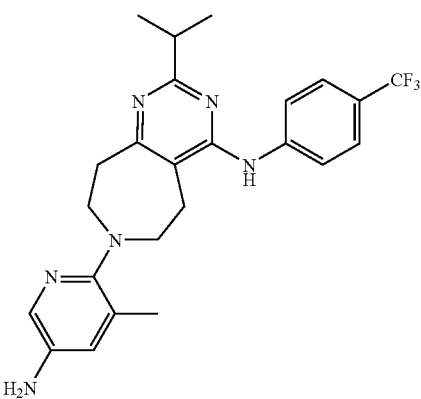

MS (ESI): mass calcd. for $C_{24}H_{27}F_3N_6$, 456.22; m/z found, 455.2 [M–H]⁻. ¹H NMR (CDCl₃): 7.79 (d, J=8.6 Hz, 2H), 7.67 (d, J=2.9 Hz, 1H), 7.58 (d, J=8.7 Hz, 2H), 6.90-6.85 (m, 1H), 6.69-6.65 (m, 1H), 3.46-3.37 (m, 2H), 3.34-3.29 (m, 2H), 3.26-3.22 (m, 2H), 3.21-3.17 (m, 2H), 3.10-3.03 (m, 1H), 2.96-2.90 (m, 2H), 2.27 (s, 3H), 1.34 (d, J=6.9 Hz, 6H).

Example 84

[7-(2-Amino-phenyl)-2-isopropyl-6,7,8,9-tetrahydro-5H-pyrimido[4,5-d]azepin-4-yl]-(4-trifluoromethyl-phenyl)-amine

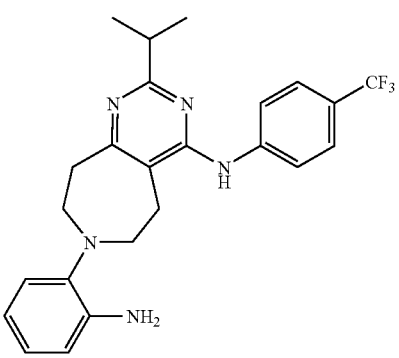 [SMILES: CC(C)c1nc2c(c(Nc3ccc(C(F)(F)F)cc3)n1)CCN(c1ccccc1N)CC2]

MS (ESI): mass calcd. for C$_{24}$H$_{26}$F$_3$N$_5$, 441.21; m/z found, 442.2 [M+H]$^+$. $^1$H NMR (CDCl$_3$): 7.44-7.33 (m, 2H), 7.17-7.09 (m, 2H), 6.89-6.81 (m, 2H), 6.67-6.59 (m, 2H), 4.10-3.97 (m, 2H), 3.60-3.47((m, 2H), 3.13-3.03 (m, 2H), 3.02-2.92 (m, 1H), 2.90-2.85 (m, 2H), 1.28-1.26 (m, 6H).

Example 85

[2-Isopropyl-7-(2-nitro-phenyl)-6,7,8,9-tetrahydro-5H-pyrimido[4,5-d]azepin-4-yl]-(4-trifluoromethyl-phenyl)-amine

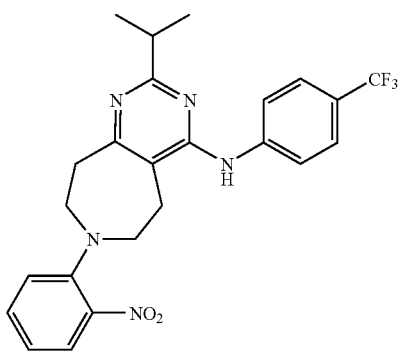 [SMILES: CC(C)c1nc2c(c(Nc3ccc(C(F)(F)F)cc3)n1)CCN(c1ccccc1[N+](=O)[O-])CC2]

MS (ESI): mass calcd. for C$_{24}$H$_{24}$F$_3$N$_5$O$_2$, 471.19; m/z found, 472.1 [M+H]$^+$. $^1$H NMR (CDCl$_3$): 7.99 (dd, J=8.2, 1.5 Hz, 1H), 7.66-7.56 (m, 1H), 7.42-7.35 (m, 2H), 7.34-7.28 (m, 2H), 6.67-6.51 (m, 2H), 4.22-4.02 (m, 2H), 3.62-3.47 (m, 2H), 3.15-3.04 (m, 2H), 2.96-2.83 (m, 3H), 1.21 (d, J=6.9 Hz, 6H).

Example 86

[7-(3-Amino-pyridin-2-yl)-2-isopropyl-6,7,8,9-tetrahydro-5H-pyrimido[4,5-d]azepin-4-yl]-(4-trifluoromethyl-phenyl)-amine

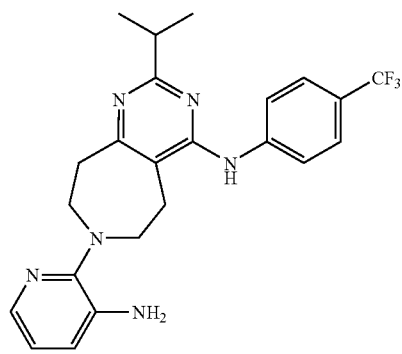

MS (ESI): mass calcd. for C$_{23}$H$_{25}$F$_3$N$_6$, 442.21; m/z found, 443.1 [M+H]$^+$. $^1$H NMR (CDCl$_3$): 7.86-7.72 (m, 3H), 7.64-7.57 (m, 2H), 7.04-6.95 (m, 1H), 6.90-6.85 (m, 1H), 6.71-6.67 (m, 1H), 3.89-3.77 (m, 2H), 3.47-3.40 (m, 2H), 3.39-3.35 (m, 2H), 3.26-3.21 (m, 2H), 3.13-3.04 (m, 1H), 3.01-2.94 (m, 2H), 1.36 (d, J=6.9 Hz, 6H).

Example 87

[2-Isopropyl-7-(3-methyl-5-nitro-pyridin-2-yl)-6,7,8,9-tetrahydro-5H-pyrimido[4,5-d]azepin-4-yl]-(4-trifluoromethyl-phenyl)-amine

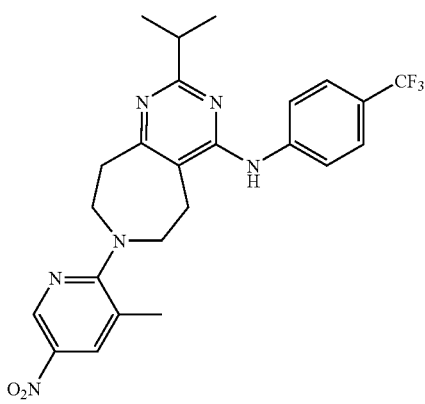 [SMILES: Cc1cc([N+](=O)[O-])cnc1N1CCc2nc(C(C)C)nc(Nc3ccc(C(F)(F)F)cc3)c2CC1]

MS (ESI): mass calcd. for C$_{24}$H$_{25}$F$_3$N$_6$O$_2$, 486.20; m/z found, 487.1 [M+H]$^+$. $^1$H NMR (CDCl$_3$): 8.93 (d, J=2.6 Hz, 1H), 8.16-8.05 (m, 1H), 7.81 (d, J=8.5 Hz, 2H), 7.62 (d, J=8.4 Hz, 2H), 7.35-7.28 (m, 1H), 6.76-6.60 (m, 1H), 4.04-3.90 (m, 2H), 3.89-3.82 (m, 2H), 3.35-3.22 (m, 2H), 3.12-3.02 (m, 3H), 2.41 (s, 3H), 1.33 (d, J=6.9 Hz, 6H).

Example 88

[2-Isopropyl-7-(3-nitro-pyridin-2-yl)-6,7,8,9-tetrahydro-5H-pyrimido[4,5-d]azepin-4-yl]-(4-trifluoromethyl-phenyl)-amine

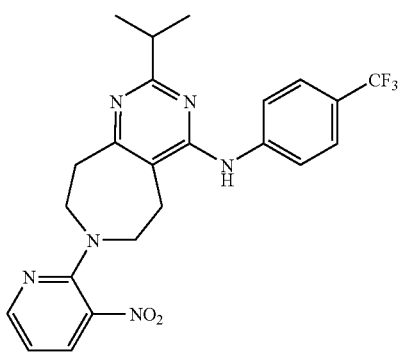 [SMILES: CC(C)c1nc2c(c(Nc3ccc(C(F)(F)F)cc3)n1)CCN(c1ncccc1[N+](=O)[O-])CC2]

MS (ESI): mass calcd. for $C_{23}H_{23}F_3N_6O_2$, 472.18; m/z found, 473.1 [M+H]$^+$. $^1$H NMR (CDCl$_3$): 8.41-8.28 (m, 1H), 8.15-8.12 (m, 1H), 7.36-7.21 (m, 4H), 6.84-6.69 (m, 1H), 3.81-3.67 (m, 4H), 3.47-3.37 (m, 2H), 3.36-3.30 (m, 2H), 3.22-3.07 (m, 1H), 1.32 (d, J=6.9 Hz, 6H).

Example 89

N-{2-[2-Isopropyl-4-(4-trifluoromethyl-phenylamino)-5,6,8,9-tetrahydro-pyrimido[4,5-d]azepin-7-yl]-phenyl}-methanesulfonamide

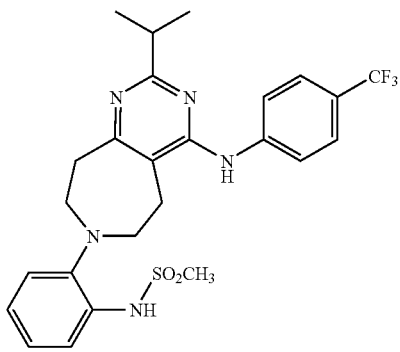 [SMILES: CC(C)c1nc2c(c(Nc3ccc(C(F)(F)F)cc3)n1)CCN(c1ccccc1NS(C)(=O)=O)CC2]

MS (ESI): mass calcd. for $C_{25}H_{28}F_3N_5O_2S$, 519.19; m/z found, 520.1 [M+H]$^+$. $^1$H NMR (CDCl$_3$): 9.03-8.84 (m, 1H), 7.63-7.54 (m, 1H), 7.43-7.37 (m, 2H), 7.32-7.28 (m, 2H), 6.69-6.57 (m, 2H), 4.18-4.01 (m, 2H), 3.65-3.52 (m, 2H), 3.13-2.97 (m, 3H), 2.93-2.84 (m, 4H), 1.31 (d, J=6.9 Hz, 6H).

Example 90

4-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperazin-2-one

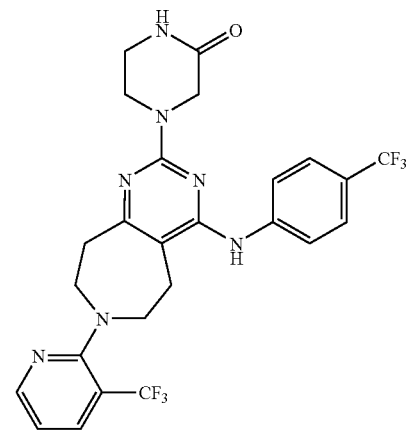 [SMILES: O=C1CN(c2nc3c(c(Nc4ccc(C(F)(F)F)cc4)n2)CCN(c2ncccc2C(F)(F)F)CC3)CCN1]

MS (ESI): mass calcd. for $C_{25}H_{23}F_6N_7O$, 551.19; m/z found, 552.9 [M+H]$^+$.

Example 90B

4-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperazin-2-one trifluoroacetic acid salt H NMR (CDCl$_3$): 8.41 (dd, J=4.8, 1.4 Hz, 1H), 7.91 (dd, J=7.8, 1.8 Hz, 1H), 7.70 (d, J=8.7 Hz, 2H), 7.61 (d, J=8.6 Hz, 2H), 7.34-7.31 (m, 1H), 7.05-7.01 (m, 1H), 6.53-6.45 (m, 1H), 4.39-4.31 (m, 2H), 4.14-4.09 (m, 2H), 3.65-3.57 (m, 4H), 3.57-3.52 (m, 2H), 3.40-3.31 (m, 2H), 3.02-2.90 (m, 2H).

Example 91

(R)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol

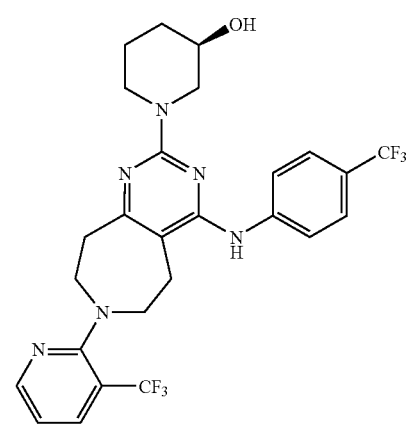 [SMILES: O[C@@H]1CCCN(c2nc3c(c(Nc4ccc(C(F)(F)F)cc4)n2)CCN(c2ncccc2C(F)(F)F)CC3)C1]

MS (ESI): mass calcd. for $C_{26}H_{26}F_6N_6O$, 552.21; m/z found, 553.9 [M+H]$^+$.

Example 91B (R)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol trifluoroacetic acid salt $^1$H NMR (CDCl$_3$): 8.42-8.38 (m, 1H), 7.89 (dd, J=7.8, 1.6 Hz, 1H), 7.67-7.59 (m, 5H), 7.02 (dd, J=7.7, 4.8 Hz, 1H), 4.33-4.23 (m, 1H), 4.20-4.11 (m, 1H), 4.08-4.00 (m, 1H), 3.63-3.49 (m, 5H), 3.39-3.33 (m, 2H), 3.31-3.22 (m, 1H), 2.99-2.90 (m, 2H), 2.03-1.90 (m, 1H), 1.89-1.73 (m, 2H), 1.58-1.49 (m, 1H).

Example 92

[2-(4-Methyl-piperazin-1-yl)-7-(3-trifluoromethyl-pyridin-2-yl)-6,7,8,9-tetrahydro-5H-pyrimido[4,5-d]azepin-4-yl]-(4-trifluoromethyl-phenyl)-amine

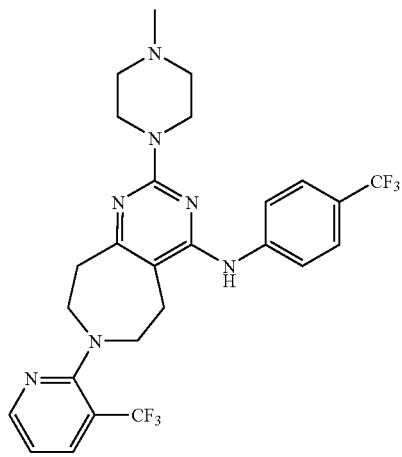 [SMILES: CN1CCN(c2nc3c(c(Nc4ccc(C(F)(F)F)cc4)n2)CCN(c2ncccc2C(F)(F)F)CC3)CC1]

MS (ESI): mass calcd. for C$_{26}$H$_{27}$F$_6$N$_7$, 551.22; m/z found, 552.9 [M+H]$^+$.

Example 92B

[2-(4-Methyl-piperazin-1-yl)-7-(3-trifluoromethyl-pyridin-2-yl)-6,7,8,9-tetrahydro-5H-pyrimido[4,5-d]azepin-4-yl]-(4-trifluoromethyl-phenyl)-amine trifluoroacetic acid salt $^1$H NMR (CDCl$_3$): 8.38 (dd, J=4.6, 1.4 Hz, 1H), 7.87 (dd, J=7.8, 1.8 Hz, 1H), 7.64 (d, J=8.6 Hz, 2H), 7.56 (d, J=8.7 Hz, 2H), 6.97-6.91 (m, 1H), 6.52 (s, 1H), 3.83-3.75 (m, 4H), 3.62-3.53 (m, 4H), 3.13-3.04 (m, 2H), 2.90-2.84 (m, 2H), 2.52-2.42 (m, 4H), 2.34 (s, 3H).

Example 93

N$^2$-(2-Methoxy-ethyl)-N$^2$-methyl-N$^4$(4-trifluoromethyl-phenyl)-7-(3-trifluoromethyl-pyridin-2-yl)-6,7,8,9-tetrahydro-5H-pyrimido[4,5-d]azepine-2,4-diamine

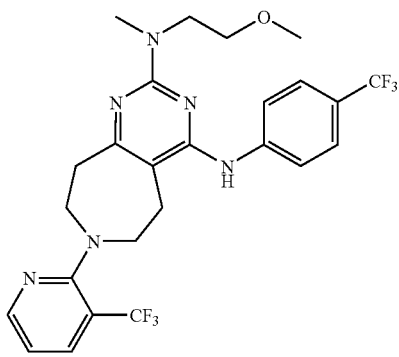 [SMILES: COCCN(C)c1nc2c(c(Nc3ccc(C(F)(F)F)cc3)n1)CCN(c1ncccc1C(F)(F)F)CC2]

MS (ESI): mass calcd. for C$_{25}$H$_{26}$F$_6$N$_6$O, 540.21; m/z found, 541.3 [M+H]$^+$.

Example 93B

N$^2$(2-Methoxy-ethyl)-N$^2$-methyl-N$^4$-(4-trifluoromethyl-phenyl)-7-(3-trifluoromethyl-pyridin-2-yl)-6,7,8,9-tetrahydro-5H-pyrimido[4,5-d]azepine-2,4-diamine trifluoroacetic acid salt $^1$H NMR (CD$_3$OD): 8.45 (dd, J=4.8, 1.3 Hz, 1H), 8.03 (dd, J=7.8, 1.8 Hz, 1H), 7.76 (d, J=8.6 Hz, 2H), 7.70 (d, J=8.7 Hz, 2H), 7.17-7.11 (m, 1H), 3.78-3.76 (m, 2H), 3.64-3.59 (m, 2H), 3.59-3.52 (m, 4H), 3.21 (s, 3H), 3.13-3.08 (m, 2H).

Example 94

(S)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol

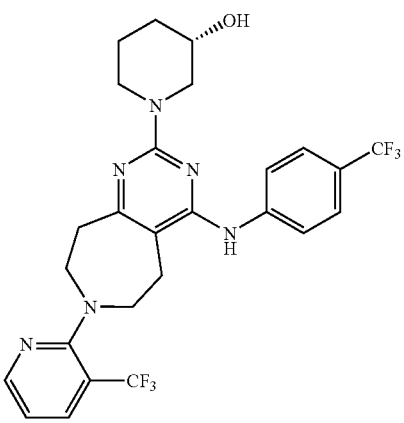 [SMILES: O[C@H]1CCCN(c2nc3c(c(Nc4ccc(C(F)(F)F)cc4)n2)CCN(c2ncccc2C(F)(F)F)CC3)C1]

MS (ESI): mass calcd. for $C_{26}H_{26}F_6N_6O$, 552.21; m/z found, 553.3 [M+H]$^+$.

Example 94B (S)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol trifluoroacetic acid salt $^1$H NMR (CD$_3$OD): 8.45 (dd, J=4.7, 1.4 Hz, 1H), 8.03 (dd, J=7.8, 1.8 Hz, 1H), 7.77-7.68 (m, 4H), 7.14 (dd, J=7.6, 4.8 Hz, 1H), 3.88-3.76 (m, 2H), 3.70-3.51 (m, 7H), 3.30-3.25 (m, 2H), 3.13-3.07 (m, 2H), 2.00-1.86 (m, 2H), 1.74-1.50 (m, 2H), 1.36-1.24 (m, 1H).

Example 95

N$^2$-Cyclopropylmethyl-N$^4$-(4-trifluoromethyl-phenyl)-7-(3-trifluoromethyl-pyridin-2-yl)-6,7,8,9-tetrahydro-5H-pyrimido[4,5-d]azepine-2,4-diamine

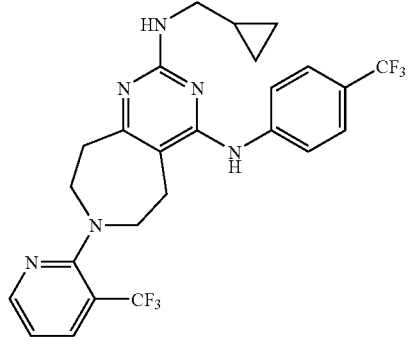 [SMILES: FC(F)(F)c1ccc(Nc2nc(NCC3CC3)nc3c2CCN(c2ncccc2C(F)(F)F)CC3)cc1]

MS (ESI): mass calcd. for $C_{25}H_{24}F_6N_6$, 522.20; m/z found, 523.3 [M+H]$^+$.

Example 95B

N$^2$-Cyclopropylmethyl-N$^4$(4-trifluoromethyl-phenyl)-7-(3-trifluoromethyl-pyridin-2-yl)-6,7,8,9-tetrahydro-5H-pyrimido[4,5-d]azepine-2,4-diamine trifluoroacetic acid salt $^1$H NMR (CD$_3$OD): 8.45 (dd, J=4.7, 1.4 Hz, 1H), 8.04-8.01 (m, 1H), 7.81-7.67 (m, 4H), 7.16-7.11 (m, 1H), 3.65-3.51 (m, 4H), 3.26-3.13 (m, 4H), 3.11-3.06 (m, 2H), 1.10-1.00 (m, 1H), 0.52-0.45 (m, 2H), 0.22-0.15 (m, 2H).

Example 96

1-{4-[2-Isopropyl-7-(3-trifluoromethyl-pyridin-2-yl)-6,7,8,9-tetrahydro-5H-pyrimido[4,5-d]azepin-4-ylamino]-phenyl}-ethanone

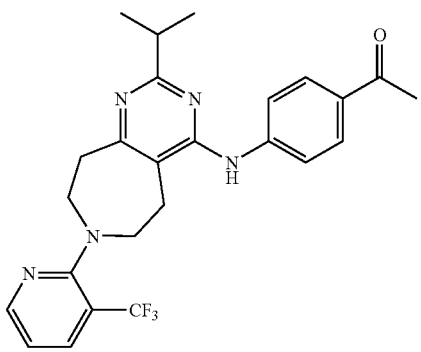 [SMILES: CC(=O)c1ccc(Nc2nc(C(C)C)nc3c2CCN(c2ncccc2C(F)(F)F)CC3)cc1]

MS (ESI): mass calcd. for $C_{25}H_{26}F_3N_5O$, 469.21; m/z found, 470.2 [M+H]$^+$. $^1$H NMR (CDCl$_3$): 8.40-8.37 (m, 1H), 8.00-7.95 (m, 2H), 7.87 (dd, J=7.8, 1.8 Hz, 1H), 7.81-7.77 (m, 2H), 6.98-6.94 (m, 1H), 6.73 (s, 1H), 3.68-3.57 (m, 4H), 3.25-3.21 (m, 2H), 3.10-3.03 (m, 1H), 3.02-2.96 (m, 2H), 2.59 (s, 3H), 1.34 (d, J=6.9 Hz, 6H).

Example 97

4-[2-Isopropyl-7-(3-trifluoromethyl-pyridin-2-yl)-6,7,8,9-tetrahydro-5H-pyrimido[4,5-d]azepin-4-ylamino]-benzonitrile

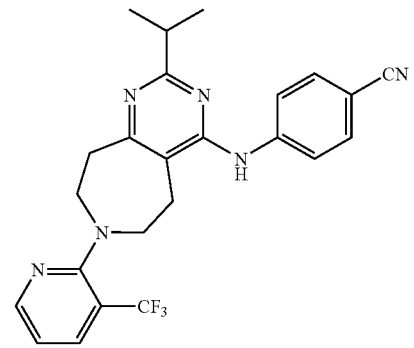 [SMILES: CC(C)c1nc2c(c(Nc3ccc(C#N)cc3)n1)CCN(c1ncccc1C(F)(F)F)CC2]

MS (ESI): mass calcd. for $C_{24}H_{23}F_3N_6$, 452.19; m/z found, 453.1 [M+H]$^+$. $^1$H NMR (CDCl$_3$): 8.41-8.38 (m, 1H), 7.89 (dd, J=7.8, 1.8 Hz, 1H), 7.85-7.81 (m, 2H), 7.66-7.61 (m, 2H), 7.00-6.95 (m, 1H), 6.72 (s, 1H), 3.69-3.57 (m, 4H), 3.28-3.23 (m, 2H), 3.13-3.04 (m, 1H), 3.03-2.98 (m, 2H), 1.34 (d, J=6.9 Hz, 6H).

Example 98

(3,4-Dichloro-benzyl)-[2-methylsulfanyl-7-(3-trifluoromethyl-pyridin-2-yl)-6,7,8,9-tetrahydro-5H-pyrimido[4,5-d]azepin-4-yl]-amine

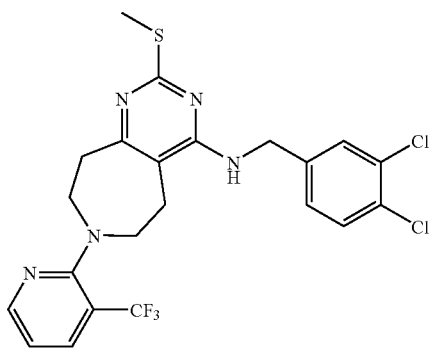 [SMILES: CSc1nc2c(c(NCc3ccc(Cl)c(Cl)c3)n1)CCN(c1ncccc1C(F)(F)F)CC2]

MS (ESI): mass calcd. for $C_{22}H_{20}Cl_2F_3N_5S$, 513.08; m/z found, 514.0 [M+H]$^+$. $^1$H NMR (CDCl$_3$): 8.38-8.34 (m, 1H), 7.88-7.84 (m, 1H), 7.43-7.38 (m, 2H), 7.18-7.14 (m, 1H), 6.96-6.91 (m, 1H), 5.05-4.97 (m, 1H), 4.66 (d, J=5.7 Hz, 2H), 3.63-3.50 (m, 4H), 3.14-3.08 (m, 2H), 2.80-2.76 (m, 2H), 2.44 (s, 3H).

Example 99

[2-Piperazin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine

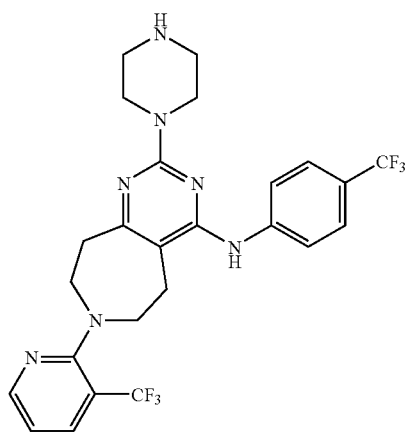 [SMILES: FC(F)(F)c1ccc(Nc2nc(N3CCNCC3)nc3c2CCN(c2ncccc2C(F)(F)F)CC3)cc1]

MS (ESI): mass calcd. for $C_{25}H_{25}F_6N_7$, 537.21; m/z found, 538.2 [M+H]$^+$.

Example 99B

[2-Piperazin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine trifluoroacetic acid salt $^1$H NMR (CD$_3$OD): 8.47-8.44 (m, 1H), 8.03 (dd, J=7.8, 1.8 Hz, 1H), 7.74-7.67 (m, 4H), 7.17-7.13 (m, 1H), 4.02-3.93 (m, 4H), 3.59-3.50 (m, 4H), 3.35-3.21 (m, 6H), 3.13-3.07 (m, 2H).

Example 100

[2-Thiomorpholin-4-yl-7-(3-trifluoromethyl-pyridin-2-yl)-6,7,8,9-tetrahydro-5H-pyrimido[4,5-d]azepin-4-yl]-(4-trifluoromethyl-phenyl)-amine

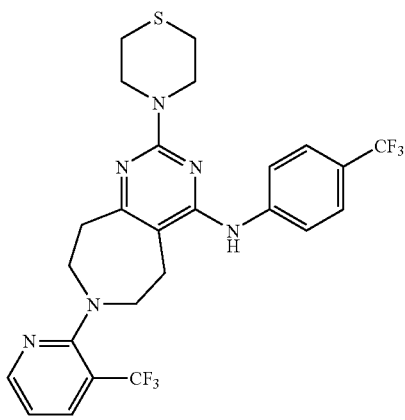 [SMILES: FC(F)(F)c1ccc(Nc2nc(N3CCSCC3)nc3c2CCN(c2ncccc2C(F)(F)F)CC3)cc1]

MS (ESI): mass calcd. for $C_{25}H_{24}F_6N_6S$, 554.17; m/z found, 555.2 [M+H]$^+$. $^1$H NMR (CDCl$_3$): 8.44-8.41 (m, 1H), 7.91 (dd, J=7.8, 1.8 Hz, 1H), 7.67-7.57 (m, 4H), 7.02-6.96 (m, 1H), 6.56 (s, 1H), 4.20-4.08 (m, 4H), 3.68-3.57 (m, 4H), 3.16-3.08 (m, 2H), 2.95-2.89 (m, 2H), 2.71-2.66 (m, 4H).

Example 101

[2-Isopropyl-7-(3-trifluoromethyl-pyridin-2-yl)-6,7,8,9-tetrahydro-5-H-pyrimido[4,5-d]azepin-4-yl]-(4-trifluoromethanesulfonyl-phenyl)-amine

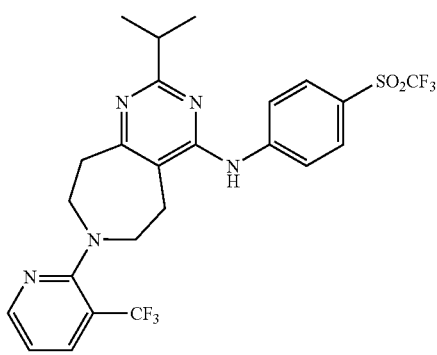

MS (ESI): mass calcd. for $C_{24}H_{23}F_6N_5O_2S$, 559.15; m/z found, 560.1 [M+H]$^+$.

Example 101B

[2-Isopropyl-7-(3-trifluoromethyl-pyridin-2-yl)-6,7,8,9-tetrahydro-5H-pyrimido[4,5-d]azepin-4-yl]-(4-trifluoromethanesulfonyl-phenyl)-amine trifluoroacetic acid salt $^1$H NMR (CD$_3$OD): 8.44-8.42 (m, 1H), 8.02-7.94 (m, 3H), 7.88-7.84 (m, 2H), 7.14-7.09 (m, 1H), 3.83-3.76 (m, 1H), 3.69-3.60 (m, 6H), 3.29-3.22 (m, 2H), 1.32-1.27 (m, 6H).

Example 102

[2-(4-Benzyl-piperazin-1-yl)-7-(3-trifluoromethyl-pyridin-2-yl)-6,7,8,9-tetrahydro-5H-pyrimido[4,5-d]azepin-4-yl]-(4-trifluoromethyl-phenyl)-amine

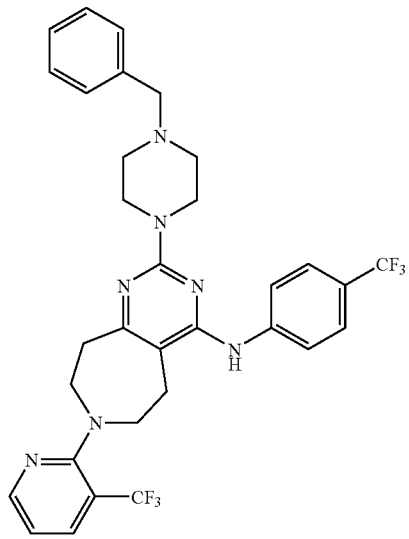 [SMILES: FC(F)(F)c1ccc(Nc2nc(N3CCN(Cc4ccccc4)CC3)nc3c2CCN(c2ncccc2C(F)(F)F)CC3)cc1]

MS (ESI): mass calcd. for C$_{32}$H$_{31}$F$_6$N$_7$, 627.25; m/z found, 628.2 [M+H]$^+$. $^1$H NMR (CDCl$_3$): 8.41-8.38 (m, 1H), 7.88 (dd, J=7.8, 1.9 Hz, 1H), 7.66-7.61 (m, 2H), 7.57-7.53 (m, 2H), 7.39-7.28 (m, 5H), 6.98-6.93 (m, 1H), 6.51 (s, 1H), 3.82-3.76 (m, 4H), 3.63-3.55 (m, 6H), 3.12-3.07 (m, 2H), 2.91-2.86 (m, 2H), 2.54-2.49 (m, 4H).

Example 103

4-[2-Isopropyl-7-(3-trifluoromethyl-pyridin-2-yl)-6,7,8,9-tetrahydro-5H-pyrimido[4,5-d]azepin-4-ylamino]-benzoic acid methyl ester

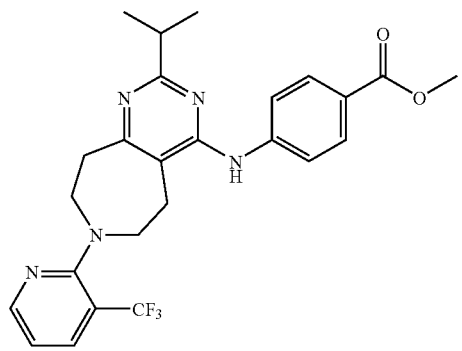 [SMILES: COC(=O)c1ccc(Nc2nc(C(C)C)nc3c2CCN(c2ncccc2C(F)(F)F)CC3)cc1]

MS (ESI): mass calcd. for C$_{25}$H$_{26}$F$_3$N$_5$O$_2$, 485.20; m/z found, 486.2 [M+H]$^+$. $^1$H NMR (CDCl$_3$): 8.41-8.39 (m, 1H), 8.07-8.02 (m, 2H), 7.89 (dd, J=7.8, 1.8 Hz, 1H), 7.80-7.75 (m, 2H), 6.99-6.95 (m, 1H), 6.71 (s, 1H), 3.92 (s, 3H), 3.68-3.59 (m, 4H), 3.27-3.22 (m, 2H), 3.11-3.03 (m, 1H), 3.02-2.98 (m, 2H), 1.35 (d, J=6.9 Hz, 6H).

Example 104

[2-Isopropyl-7-(3-trifluoromethyl-pyridin-2-yl)-6,7,8,9-tetrahydro-5H-pyrimido[4,5-d]azepin-4-yl]-(4-trifluoromethylsulfanyl-phenyl)-amine

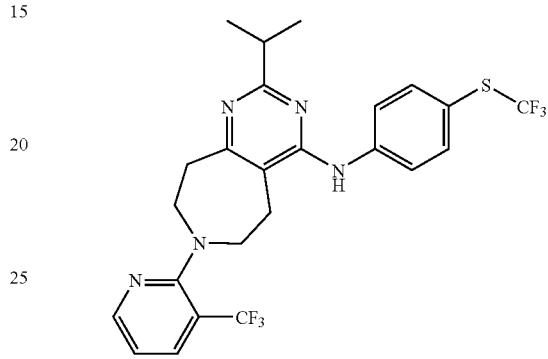

MS (ESI): mass calcd. for C$_{24}$H$_{23}$F$_6$N$_5$S, 527.16; m/z found, 528.1 [M+H]$^+$. $^1$H NMR (CDCl$_3$): 8.41-8.39 (m, 1H), 7.89 (dd, J=7.8, 1.8 Hz, 1H), 7.81-7.77 (m, 2H), 7.65-7.61 (m, 2H), 6.99-6.95 (m, 1H), 6.65 (s, 1H), 3.70-3.58 (m, 4H), 3.27-3.22 (m, 2H), 3.12-3.03 (m, 1H), 3.02-2.97 (m, 2H), 1.34 (d, J=6.9 Hz, 6H).

Example 105

[2-Isopropyl-7-(3-trifluoromethyl-pyridin-2-yl)-6,7,8,9-tetrahydro-5H-pyrimido[4,5-d]azepin-4-yl]-pyrimidin-4-yl-amine

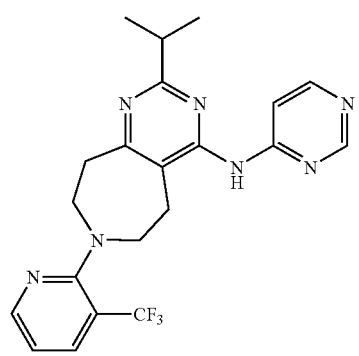 [SMILES: CC(C)c1nc2c(c(Nc3ccncn3)n1)CCN(c1ncccc1C(F)(F)F)CC2]

MS (ESI): mass calcd. for C$_{21}$H$_{22}$F$_3$N$_7$, 429.19; m/z found, 430.1 [M+H]$^+$. $^1$H NMR (CDCl$_3$): 8.83-8.81 (m, 1H), 8.60 (d, J=5.9 Hz, 1H), 8.58-8.55 (m, 1H), 8.42-8.40 (m, 1H), 7.89 (dd, J=7.8, 1.8 Hz, 1H), 7.51 (s, 1H), 7.01-6.97 (m, 1H), 3.65-3.56 (m, 4H), 3.29-3.25 (m, 2H), 3.17-3.10 (m, 1H), 3.08-3.04 (m, 2H), 1.38 (d, J=6.9 Hz, 6H).

Example 106

[2-Pyrrolidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine

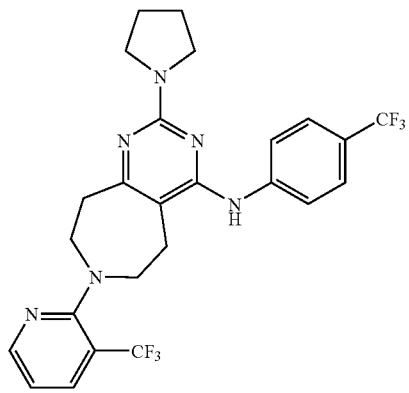 [SMILES: FC(F)(F)c1ccc(Nc2nc(N3CCCC3)nc3c2CCN(c2ncccc2C(F)(F)F)CC3)cc1]

MS (ESI): mass calcd. for $C_{25}H_{24}F_6N_6$, 522.20; m/z found, 523.1 [M+H]+. $^1$H NMR (CDCl$_3$): 8.41-8.38 (m, 1H), 7.88 (dd, J=7.8, 1.8 Hz, 1H), 7.82-7.77 (m, 2H), 7.59-7.54 (m, 2H), 6.97-6.92 (m, 1H), 6.55 (s, 1H), 3.64-3.53 (m, 8H), 3.13-3.08 (m, 2H), 2.91-2.87 (m, 2H), 2.02-1.94 (m, 4H).

Example 107

[2-Isopropyl-7-(3-trifluoromethyl-pyridin-2-yl)-6,7,8,9-tetrahydro-5H-pyrimido[4,5-d]azepin-4-yl]-pyrimidin-2-yl-amine

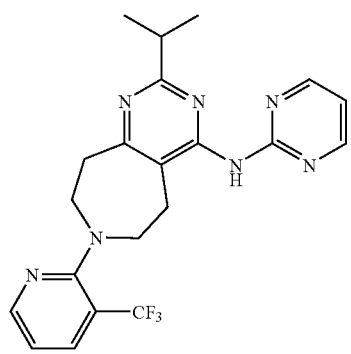 [SMILES: CC(C)c1nc2c(c(Nc3ncccn3)n1)CCN(c1ncccc1C(F)(F)F)CC2]

MS (ESI): mass calcd. for $C_{21}H_{22}F_3N_7$, 429.19; m/z found, 430.1 [M+H]+. $^1$H NMR (CDCl$_3$): 8.45 (d, J=4.8 Hz, 2H), 8.43-8.41 (m, 1H), 7.88 (dd, J=7.8, 1.8 Hz, 1H), 7.36 (s, 1H), 7.00-6.95 (m, 1H), 6.85-6.83 (m, 1H), 3.65-3.58 (m, 2H), 3.55-3.50 (m, 2H), 3.35-3.30 (m, 2H), 3.14-3.06 (m, 1H), 2.93-2.88 (m, 2H), 1.33 (d, J=6.9 Hz, 6H).

Example 108

[2-(3,4-Dichloro-phenyl)-ethyl]-[2-isopropyl-7-(3-trifluoromethyl-pyridin-2-yl)-6,7,8,9-tetrahydro-5H-pyrimido[4,5-d]azepin-4-yl]-amine

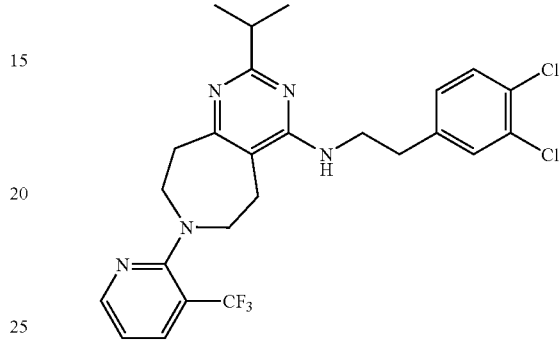

MS (ESI): mass calcd. for $C_{25}H_{26}Cl_2F_3N_5$, 523.15; m/z found, 524.1 [M+H]+. $^1$H NMR (CDCl$_3$): 8.40-8.37 (m, 1H), 7.87 (dd, J=7.8, 1.8 Hz, 1H), 7.38 (d, J=8.2 Hz, 1H), 7.32 (d, J=2.0 Hz, 1H), 7.06 (dd, J=8.1, 2.0 Hz, 1H), 6.96-6.92 (m, 1H), 4.68-4.63 (m, 1H), 3.80-3.70 (m, 2H), 3.61-3.57 (m, 4H), 3.18-3.13 (m, 2H), 3.03-2.95 (m, 1H), 2.95-2.89 (m, 2H), 2.72-2.68 (m, 2H), 1.32 (d, J=6.8 Hz, 6H).

Example 109

(3,4-Dichloro-phenyl)-[2-isopropyl-7-(3-trifluoromethyl-pyridin-2-yl)-6,7,8,9-tetrahydro-5H-pyrimido[4,5-d]azepin-4-yl]-amine

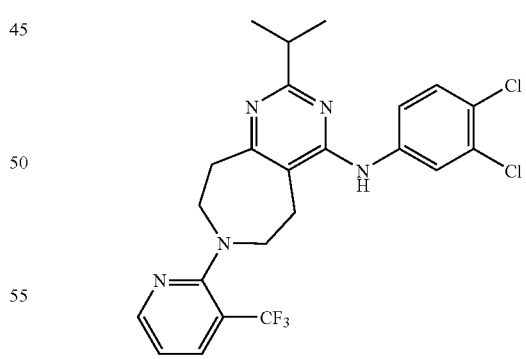

MS (ESI): mass calcd. for $C_{23}H_{22}Cl_2F_3N_5$, 495.12; m/z found, 496.1 [M+H]+. $^1$H NMR (CDCl$_3$): 8.41-8.38 (m, 1H), 8.10 (d, J=2.4 Hz, 1H), 7.89 (dd, J=7.8, 1.8 Hz, 1H), 7.43-7.37 (m, 2H), 6.99-6.95 (m, 1H), 6.50 (s, 1H), 3.69-3.57 (m, 4H), 3.26-3.21 (m, 2H), 3.10-3.01 (m, 1H), 2.98-2.94 (m, 2H), 1.34 (d, J=6.9 Hz, 6H).

The following compounds in Examples 110-114 are prepared according to the procedures described above.

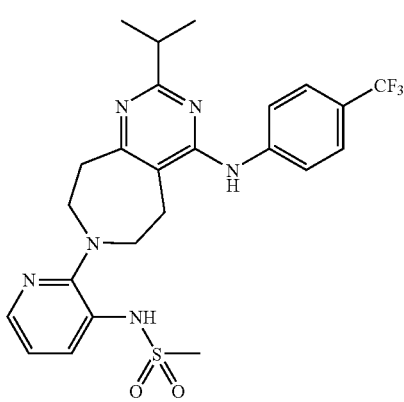 [SMILES: CC(C)c1nc2c(c(Nc3ccc(C(F)(F)F)cc3)n1)CCN(c1ncccc1NS(C)(=O)=O)CC2]

Example 110

N-{2-[2-Isopropyl-4-(4-trifluoromethyl-phenylamino)-5,6,8,9-tetrahydro-pyrimido[4,5-d]azepin-7-yl]-pyridin-3-yl}-methanesulfonamide

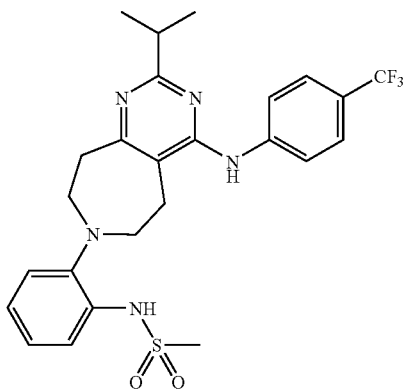

Example 111

N-{2-[2-Isopropyl-4-(4-trifluoromethyl-phenylamino)-5,6,8,9-tetrahydro-pyrimido[4,5-d]azepin-7-yl]-phenyl}-methanesulfonamide

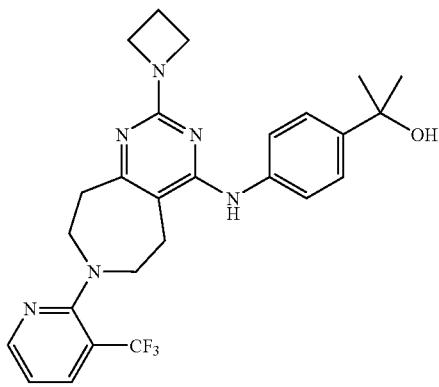 [SMILES: CC(C)(O)c1ccc(Nc2nc(N3CCC3)nc3c2CCN(c2ncccc2C(F)(F)F)CC3)cc1]

Example 112

2-{4-[2-Azetidin-1-yl-7-(3-trifluoromethyl-pyridin-2-yl)-6,7,8,9-tetrahydro-5H-pyrimido[4,5-d]azepin-4-ylamino]-phenyl}-propan-2-ol

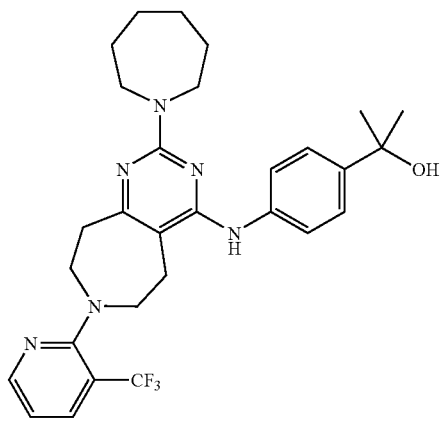 [SMILES: CC(C)(O)c1ccc(Nc2nc(N3CCCCCC3)nc3c2CCN(c2ncccc2C(F)(F)F)CC3)cc1]

Example 113

2-{4-[2-Azepan-1-yl-7-(3-trifluoromethyl-pyridin-2-yl)-6,7,8,9-tetrahydro-5H-pyrimido[4,5-d]azepin-4-ylamino]-phenyl}-propan-2-ol

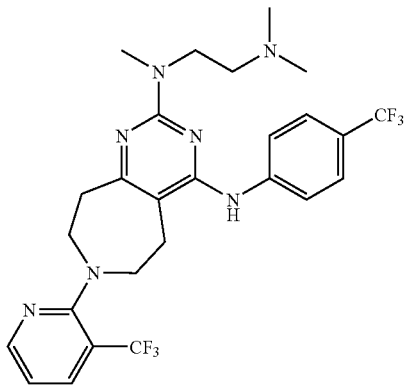 [SMILES: CN(C)CCN(C)c1nc2c(c(Nc3ccc(C(F)(F)F)cc3)n1)CCN(c1ncccc1C(F)(F)F)CC2]

Example 114

$N^2$(2-Dimethylamino-ethyl)-$N^2$-methyl-$N^4$-(4-trifluoromethyl-phenyl)-7-(3-trifluoromethyl-pyridin-2-yl)-6,7,8,9-tetrahydro-5H-pyrimido[4,5-d]azepine-2,4-diamine Intermediate C:
5-Trifluoromethyl-pyrazin-2-ylamine

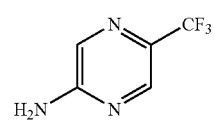

The title compound was prepared using known procedures (See: U.S. Pat. No. 4,160,834).

Intermediate D:
6-Chloro-5-trifluoromethyl-pyridin-2-ylamine

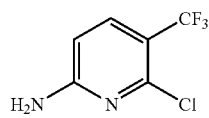

The title compound was prepared from 2,6-dichloro-3-trifluoromethyl-pyridine using methods analogous to Intermediate C (See: Hirokawa et al. *Chem. Pharm. Bull.* 2001, 49(12), 1621; Katritzky, A. R. et al. *J. Org. Chem.* 1997, 62, 6412).

Intermediate E:
6-Methoxy-5-trifluoromethyl-pyridin-2-ylamine

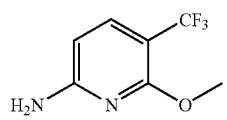

The title compound was prepared as described by Hirokawa et al. *Chem. Pharm. Bull.* 2001, 49(12), 1621 and WO 2006/081388.

Intermediate F:
1-Methyl-1,2,3,4-tetrahydro-quinolin-7-ylamine

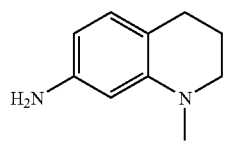

The title compound was prepared using methods analogous to those described by Hamann, L. G. et al. *J. Med. Chem.* 1998, 41, 623 and Higuchi, R. I. et al. *Bioorg. Med. Chem. Lett.* 1999, 9, 1335.

Intermediate G: 1,4,4-Trimethyl-1,2,3,4-tetrahydro-quinolin-7-ylamine

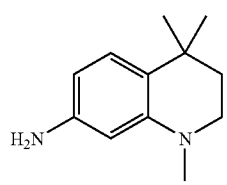

The title compound was prepared using methods analogous to Intermediate F.

Intermediate H:
2-(4-Amino-phenyl)-2-methyl-propionic acid methyl ester

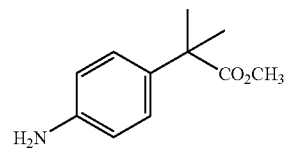

Step A: 2-Methyl-2-(4-nitrophenyl)-propionic acid methyl ester. To a solution of 2-methyl-2-(4-nitrophenyl)-propionic acid (1.0014 g, 4.76 mmol) in 10% MeOH/benzene (20 mL) was added dropwise (trimethylsilyl)-diazomethane (2.0 M in hexanes, 3.5 mL, 7.0 mmol). The reaction mixture was stirred at rt until evolution of $N_2$ ceased (<5 min) and then concentrated. The crude residue was purified (FCC) to give the title compound (937.6 mg, 88%).

Step B. To a solution of 2-methyl-2-(4-nitrophenyl)-propionic acid methyl ester (932.2 mg, 4.16 mmol) and ammonium formate (1.58 g, 25.1 mmol) in MeOH was added Pd/C (10%, 441.2 mg, 0.414 mmol). The reaction mixture was stirred at rt until gas evolution ceased, then filtered through a plug of diatomaceous earth and concentrated. The residue was redissolved in $H_2O$ and extracted with EtOAc. The organic layers were combined, dried, and concentrated to provide the title compound which was used without further purification.

The following Examples 115-126 were prepared using methods analogous to those described in Example 1, substituting the appropriate amidines in Step A and amines in Step E.

Example 115

N-{[4-Chloro-3-(trifluoromethyl)phenyl]methyl}-2-(1-methylethyl)-7-[3-(trifluoromethyl)pyridin-2-yl]-6,7,8,9-tetrahydro-5H-pyrimido[4,5-d]azepin-4-amine

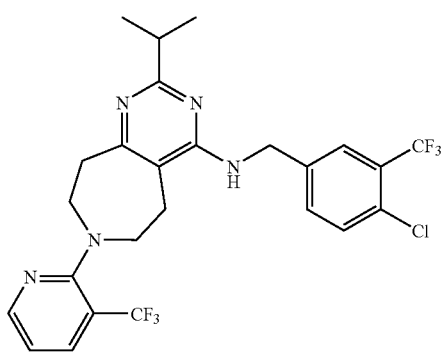 [SMILES: CC(C)c1nc2c(c(NCc3ccc(Cl)c(C(F)(F)F)c3)n1)CCN(c1ncccc1C(F)(F)F)CC2]

MS (ESI): mass calcd. for $C_{25}H_{24}ClF_6N_5$, 543.16; m/z found, 544.1 [M+H]$^+$. $^1$H NMR (CDCl$_3$): 8.37-8.35 (m, 1H), 7.87-7.84 (m, 1H), 7.73-7.71 (m, 1H), 7.49-7.43 (m, 2H), 6.95-6.91 (m, 1H), 5.05-4.99 (m, 1H), 4.72 (d, J=5.8 Hz, 2H), 3.63-3.55 (m, 4H), 3.18-3.12 (m, 2H), 2.98-2.89 (m, 1H), 2.82-2.77 (m, 2H), 1.22 (d, J=6.9 Hz, 6H).

Example 116

2-(1-Methylethyl)-7-[3-(trifluoromethyl)pyridin-2-yl]-N-{[6-(trifluoromethyl)pyridin-3-yl]methyl}-6,7,8,9-tetrahydro-5H-pyrimido[4,5-d]azepin-4-amine

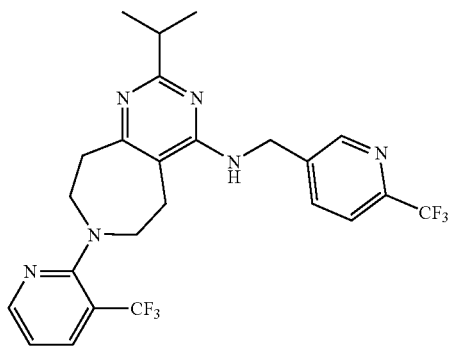 [SMILES: CC(C)c1nc2c(c(NCc3ccc(C(F)(F)F)nc3)n1)CCN(c1ncccc1C(F)(F)F)CC2]

MS (ESI): mass calcd. for $C_{24}H_{24}F_6N_6$, 510.20; m/z found, 511.1 [M+H]$^+$. $^1$H NMR (CDCl$_3$): 8.75-8.73 (m, 1H), 8.38-8.35 (m, 1H), 7.89-7.84 (m, 2H), 7.62 (d, J=8.1 Hz, 1H), 6.95-6.92 (m, 1H), 5.11-5.07 (m, 1H), 4.81 (d, J=5.8 Hz, 2H), 3.62-3.55 (m, 4H), 3.18-3.13 (m, 2H), 2.97-2.87 (m, 1H), 2.84-2.79 (m, 2H), 1.20 (d, J=6.9 Hz, 6H).

Example 117

2-(1-Methylethyl)-N-{[4-(trifluoromethyl)phenyl]methyl}-7-[3-(trifluoromethyl)pyridin-2-yl]-6,7,8,9-tetrahydro-5H-pyrimido[4,5-d]azepin-4-amine

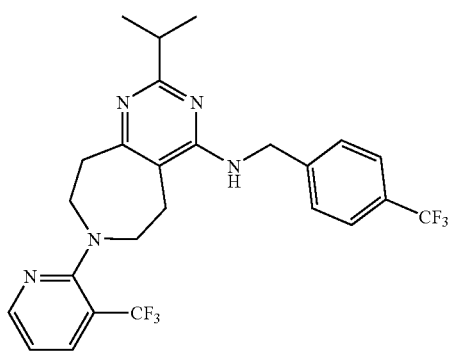

MS (ESI): mass calcd. for $C_{25}H_{25}F_6N_5$, 509.20; m/z found, 510.1 [M+H]$^+$. $^1$H NMR (CDCl$_3$): 8.38-8.35 (m, 1H), 7.86 (dd, J=7.8, 1.8 Hz, 1H), 7.58 (d, J=8.1 Hz, 2H), 7.47 (d, J=8.1 Hz, 2H), 6.95-6.91 (m, 1H), 5.00-4.95 (m, 1H), 4.79 (d, J=5.7

Hz, 2H), 3.63-3.56 (m, 4H), 3.17-3.13 (m, 2H), 2.98-2.88 (m, 1H), 2.82-2.77 (m, 2H), 1.23 (d, J=6.9 Hz, 6H).

Example 118

N-[2-(2-Fluorophenyl)ethyl]-2-(1-methylethyl)-7-[3-(trifluoromethyl)pyridin-2-yl]-6,7,8,9-tetrahydro-5H-pyrimido[4,5-d]azepin-4-amine

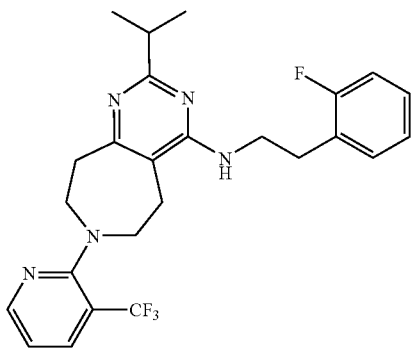

MS (ESI): mass calcd. for $C_{25}H_{27}F_4N_5$, 473.22; m/z found, 474.1 [M+H]$^+$. $^1$H NMR (CDCl$_3$): 8.38-8.36 (m, 1H), 7.86 (dd, J=7.8, 1.8 Hz, 1H), 7.24-7.17 (m, 2H), 7.10-7.02 (m, 2H), 6.95-6.91 (m, 1H), 4.73-4.69 (m, 1H), 3.78-3.74 (m, 2H), 3.59-3.56 (m, 4H), 3.14-3.12 (m, 2H), 3.01-2.93 (m, 3H), 2.69-2.67 (m, 2H), 1.30 (d, J=6.9 Hz, 6H).

Example 119

N-[2-(2-Bromophenyl)ethyl]-2-(1-methylethyl)-7-[3-(trifluoromethyl)pyridin-2-yl]-6,7,8,9-tetrahydro-5H-pyrimido[4,5-d]azepin-4-amine

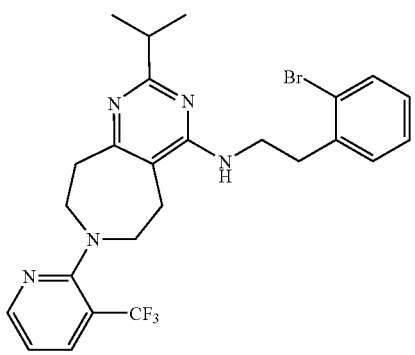 [SMILES: CC(C)c1nc2c(c(NCCc3ccccc3Br)n1)CCN(c1ncccc1C(F)(F)F)CC2]

MS (ESI): mass calcd. for $C_{25}H_{27}BrF_3N_5$, 534.14; m/z found, 536.1 [M+H]$^+$. $^1$H NMR (CDCl$_3$): 8.38-8.36 (m, 1H), 7.85 (dd, J=7.8, 1.8 Hz, 1H), 7.57-7.54 (m, 1H), 7.25-7.20 (m, 2H), 7.11-7.07 (m, 1H), 6.94-6.90 (m, 1H), 4.70-4.67 (m, 1H), 3.82-3.77 (m, 2H), 3.60-3.54 (m, 4H), 3.16-3.08 (m, 4H), 3.02-2.93 (m, 1H), 2.71-2.68 (m, 2H), 1.31 (d, J=6.9 Hz, 6H).

Example 120

N-[(2,6-Dichlorophenyl)methyl]-2-(1-methylethyl)-7-[3-(trifluoromethyl)pyridin-2-yl]-6,7,8,9-tetrahydro-5H-pyrimido[4,5-d]azepin-4-amine

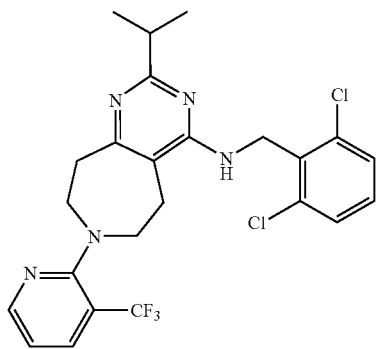 [SMILES: CC(C)c1nc2c(c(NCc3c(Cl)cccc3Cl)n1)CCN(c1ncccc1C(F)(F)F)CC2]

MS (ESI): mass calcd. for $C_{24}H_{24}Cl_2F_3N_5$, 509.14; m/z found, 510.1 [M+H]$^+$. $^1$H NMR (CDCl$_3$): 8.36-8.34 (m, 1H), 7.84 (dd, J=7.8, 1.8 Hz, 1H), 7.33 (d, J=8.0 Hz, 2H), 7.20-7.16 (m, 1H), 6.93-6.90 (m, 1H), 5.05 (d, J=5.5 Hz, 2H), 4.95-4.92 (m, 1H), 3.61-3.54 (m, 4H), 3.16-3.10 (m, 2H), 3.01-2.94 (m, 1H), 2.75-2.72 (m, 2H), 1.31 (d, J=6.9 Hz, 6H).

Example 121

N-[(2-Chlorophenyl)methyl]-2-(1-methylethyl)-7-[3-(trifluoromethyl)pyridin-2-yl]-6,7,8,9-tetrahydro-5H-pyrimido[4,5-d]azepin-4-amine trifluoroacetic acid salt

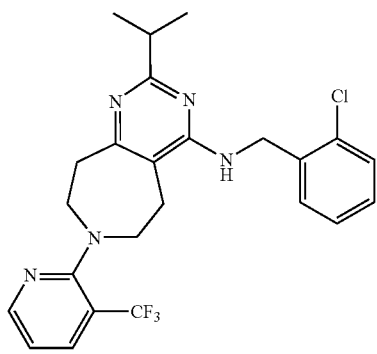 [SMILES: CC(C)c1nc2c(c(NCc3ccccc3Cl)n1)CCN(c1ncccc1C(F)(F)F)CC2]

MS (ESI): mass calcd. for $C_{24}H_{25}ClF_3N_5$, 475.18; m/z found, 477.1 [M+H]$^+$. $^1$H NMR (CD$_3$OD): 8.40-8.38 (m, 1H), 8.02-7.98 (m, 1H), 7.42-7.39 (m, 1H), 7.29-7.20 (m, 3H), 7.10-7.06 (m, 1H), 3.67-3.64 (m, 2H), 3.61-3.57 (m, 2H), 3.31-3.26 (m, 4H), 3.09-3.06 (m, 2H), 3.01-2.92 (m, 1H), 1.20 (d, J=6.8 Hz, 6H).

Example 122

N-[4-(1,1-Dimethylethyl)cyclohexyl]-2-(1-methylethyl)-7-[3-(trifluoromethyl)pyridin-2-yl]-6,7,8,9-tetrahydro-5H-pyrimido[4,5-d]azepin-4-amine

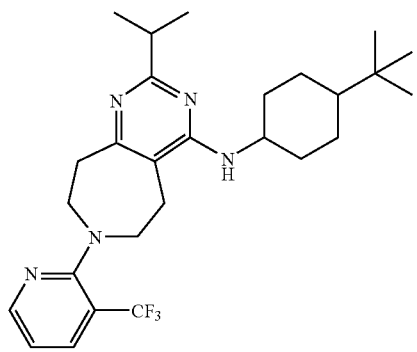 [SMILES: CC(C)c1nc2c(c(NC3CCC(C(C)(C)C)CC3)n1)CCN(c1ncccc1C(F)(F)F)CC2]

MS (ESI): mass calcd. for $C_{27}H_{38}F_3N_5$, 489.31; m/z found, 490.2 [M+H]$^+$. $^1$H NMR (CDCl$_3$): 8.38-8.36 (m, 1H), 7.85 (dd, J=7.8, 1.8 Hz, 1H), 6.94-6.90 (m, 1H), 4.34-4.31 (m, 1H), 3.96-3.86 (m, 1H), 3.64-3.54 (m, 4H), 3.14-3.09 (m, 2H), 2.96-2.89 (m, 1H), 2.74-2.69 (m, 2H), 2.25-2.18 (m, 2H), 1.88-1.80 (m, 2H), 1.27 (d, J=6.9 Hz, 6H), 1.25-0.95 (m, 5H), 0.89 (s, 9H).

Example 123

N-[2-(3-Chlorophenyl)ethyl]-2-(1-methylethyl)-7-[3-(trifluoromethyl)pyridin-2-yl]-6,7,8,9-tetrahydro-5H-pyrimido[4,5-d]azepin-4-amine

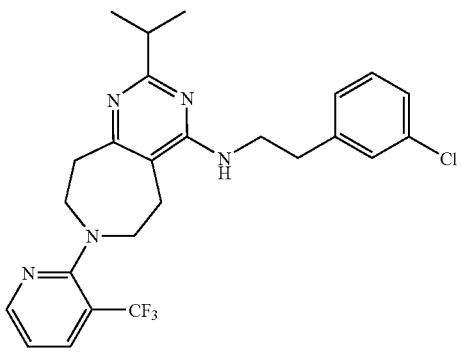 [SMILES: CC(C)c1nc2c(c(NCCc3cccc(Cl)c3)n1)CCN(c1ncccc1C(F)(F)F)CC2]

MS (ESI): mass calcd. for $C_{25}H_{27}ClF_3N_5$, 489.19; m/z found, 490.1 [M+H]$^+$. $^1$H NMR (CDCl$_3$): 8.39-8.36 (m, 1H), 7.85 (dd, J=7.8, 1.8 Hz, 1H), 7.25-7.20 (m, 3H), 7.11-7.08 (m, 1H), 6.95-6.90 (m, 1H), 4.68-4.60 (m, 1H), 3.77-3.73 (m, 2H), 3.61-3.55 (m, 4H), 3.18-3.11 (m, 2H), 3.02-2.88 (m, 3H), 2.69-2.64 (m, 2H), 1.31 (d, J=6.9 Hz, 6H).

Example 124

N-[2-(4-Chlorophenyl)ethyl]-2-(1-methylethyl)-7-[3-(trifluoromethyl)pyridin-2-yl]-6,7,8,9-tetrahydro-5H-pyrimido[4,5-d]azepin-4-amine

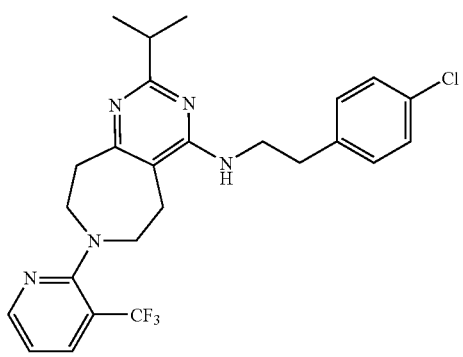 [SMILES: CC(C)c1nc2c(c(NCCc3ccc(Cl)cc3)n1)CCN(c1ncccc1C(F)(F)F)CC2]

MS (ESI): mass calcd. for $C_{25}H_{27}ClF_3N_5$, 489.19; m/z found, 490.4 [M+H]$^+$. $^1$H NMR (CDCl$_3$): 8.38-8.36 (m, 1H), 7.86-7.85 (m, 1H), 7.29-7.26 (m, 2H), 7.15-7.13 (m, 2H), 6.95-6.92 (m, 1H), 4.64-4.61 (m, 1H), 3.73 (dd, J=13.2, 6.7 Hz, 2H), 3.61-3.54 (m, 4H), 3.16-3.11 (m, 2H), 3.00-2.93 (m, 1H), 2.91 (t, J=7.1 Hz, 2H), 2.68-2.65 (m, 2H), 1.31 (d, J=6.9 Hz, 6H).

Example 125

N-[2-(2,6-Dichlorophenyl)ethyl]-2-(1-methylethyl)-7-[3-(trifluoromethyl)pyridin-2-yl]-6,7,8,9-tetrahydro-5H-pyrimido[4,5-d]azepin-4-amine

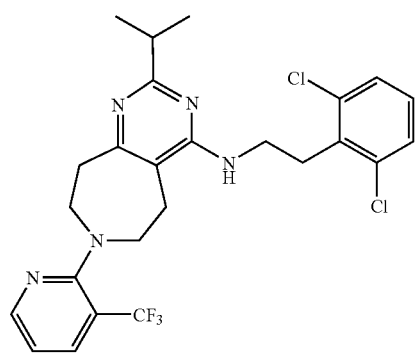 [SMILES: CC(C)c1nc2c(c(NCCc3c(Cl)cccc3Cl)n1)CCN(c1ncccc1C(F)(F)F)CC2]

MS (ESI): mass calcd. for $C_{25}H_{26}Cl_2F_3N_5$, 523.15; m/z found, 524.4 [M+H]$^+$. $^1$H NMR (CDCl$_3$): 8.39-8.37 (m, 1H), 7.86 (dd, J=7.8, 1.8 Hz, 1H), 7.29 (d, J=8.0 Hz, 2H), 7.11-7.07 (m, 1H), 6.95-6.91 (m, 1H), 4.79-4.75 (m, 1H), 3.85 (dd, J=6.8, 12.8 Hz, 2H), 3.62-3.54 (m, 4H), 3.30 (t, J=13.8, 6.9 Hz, 2H), 3.14-3.10 (m, 2H), 2.96-2.90 (m, 1H), 2.74-2.70 (m, 2H), 1.28 (d, J=6.9 Hz, 6H).

Example 126

2-(1-Methylethyl)-N-{2-[2-(methyloxy)phenyl]ethyl}-7-[3-(trifluoromethyl)pyridin-2-yl]-6,7,8,9-tetrahydro-5H-pyrimido[4,5-d]azepin-4-amine

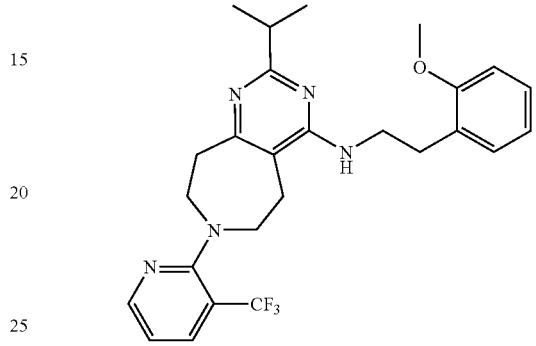

MS (ESI): mass calcd. for $C_{26}H_{30}F_3N_5O$, 485.24; m/z found, 486.5 [M+H]$^+$. $^1$H NMR (CDCl$_3$): 8.37-8.35 (m, 1H), 7.85 (dd, J=7.8, 1.7 Hz, 1H), 7.25-7.20 (m, 1H), 7.16-7.14 (m, 1H), 6.94-6.87 (m, 3H), 5.03-4.99 (m, 1H), 3.86 (s, 3H), 3.72-3.68 (m, 2H), 3.58-3.56 (m, 4H), 3.13-3.10 (m, 2H), 2.97-2.90 (m, 3H), 2.69-2.65 (m, 2H), 1.29 (d, J=6.9 Hz, 6H).

Example 127

N,N-Dimethyl-4-({2-(1-methylethyl)-7-[3-(trifluoromethyl)pyridin-2-yl]-6,7,8,9-tetrahydro-5H-pyrimido[4,5-d]azepin-4-yl}amino)benzamide

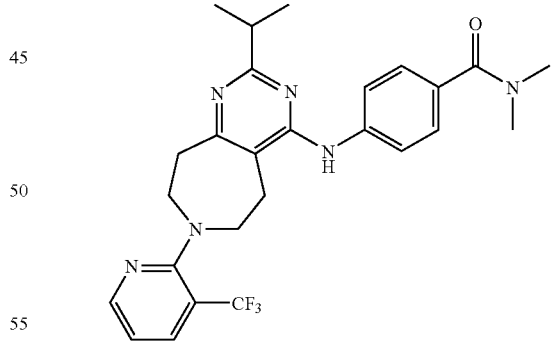

The title compound was prepared using methods analogous to those described in Example 1, using isobutyramidine in Step A, 4-amino-N,N-dimethyl-benzamide in Step E, and substituting t-amyl alcohol for n-butanol in Step E. MS (ESI): mass calcd. for $C_{26}H_{29}F_3N_6O$, 498.24; m/z found, 499.3 [M+H]$^+$. $^1$H NMR (CDCl$_3$): 8.41-8.39 (m, 1H), 7.89 (dd, J=7.8, 1.8 Hz, 1H), 7.75-7.72 (m, 2H), 7.47-7.44 (m, 2H), 6.99-6.95 (m, 1H), 6.63 (s, 1H), 3.72-3.60 (m, 4H), 3.27-3.21 (m, 2H), 3.16-3.02 (m, 7H), 3.00-2.97 (m, 2H), 1.34 (d, 6.9 Hz, 6H).

The following Examples 128-175 were prepared using methods analogous to those described in Example 46, substituting the appropriate amidines in Step A and amines in Step E.

Example 128

N-[3-Chloro-4-(trifluoromethyl)phenyl]-2-(1-methylethyl)-7-[3-(trifluoromethyl)pyridin-2-yl]-6,7,8,9-tetrahydro-5H-pyrimido[4,5-d]azepin-4-amine

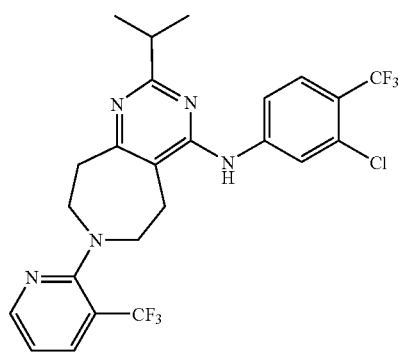 [SMILES: CC(C)c1nc2c(c(Nc3ccc(C(F)(F)F)c(Cl)c3)n1)CCN(c1ncccc1C(F)(F)F)CC2]

MS (ESI): mass calcd. for $C_{24}H_{22}ClF_6N_5$, 529.14; m/z found, 530.1 [M+H]$^+$. $^1$H NMR (CDCl$_3$): 8.39-8.38 (m, 1H), 8.16 (d, J=2.0 Hz,$_1$H), 7.88 (dd, J=7.8, 1.8 Hz, 1H), 7.62 (d, 8.7 Hz, 1H), 7.55-7.52 (m, 1H), 6.99-6.95 (m, 1H), 6.66 (s, 1H),

Example 129

2-Methyl-2-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]propanenitrile

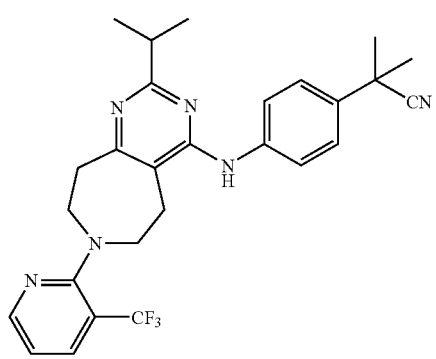 [SMILES: CC(C)c1nc2c(c(Nc3ccc(C(C)(C)C#N)cc3)n1)CCN(c1ncccc1C(F)(F)F)CC2]

MS (ESI): mass calcd. for $C_{27}H_{29}F_3N_6$, 494.24; m/z found, 495.2 [M+H]$^+$. $^1$H NMR (CDCl$_3$): 8.39-8.38 (m, 1H), 7.87 (dd, J=7.8, 1.8 Hz, 1H), 7.74-7.70 (m, 2H), 7.45-7.42 (m, 2H), 6.97-6.93 (m, 1H), 6.53 (s, 1H), 3.67-3.60 (m, 4H), 3.24-3.21 (m, 2H), 3.06-3.01 (m, 1H), 2.98-2.94 (m, 2H), 1.74 (s, 6H), 1.32 (d, J=6.9 Hz, 6H).

Example 130

4-({2-(1-Methylethyl)-7-[3-(trifluoromethyl)pyridin-2-yl]-6 7,8,9-tetrahydro-5H-pyrimido[4,5-d]azepin-4-yl}amino)benzoic acid

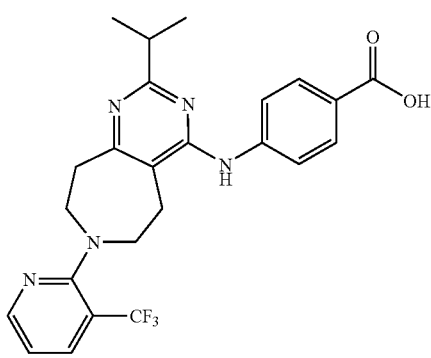 [SMILES: CC(C)c1nc2c(c(Nc3ccc(C(=O)O)cc3)n1)CCN(c1ncccc1C(F)(F)F)CC2]

MS (ESI): mass calcd. for $C_{24}H_{24}F_3N_5O_2$, 471.19; m/z found, 472.1 [M+H]$^+$. $^1$H NMR (CD$_3$OD): 8.46-8.43 (m, 1H), 8.07-8.01 (m, 3H), 7.76-7.72 (m, 2H), 7.16-7.12 (m, 1H), 3.68-3.58 (m, 4H), 3.34-3.30 (m, 2H), 3.24-3.20 (m, 2H), 3.12-3.05 (m, 1H), 1.31 (d, J=6.8 Hz, 6H).

Example 131

N-Biphenyl-4-yl-2-(1-methylethyl)-7-[3-(trifluoromethyl)pyridin-2-yl]-6,7,8,9-tetrahydro-5H-pyrimido[4,5-d]azepin-4-amine

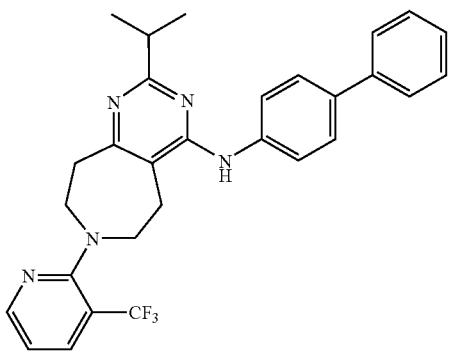 [SMILES: CC(C)c1nc2c(c(Nc3ccc(-c4ccccc4)cc3)n1)CCN(c1ncccc1C(F)(F)F)CC2]

MS (ESI): mass calcd. for $C_{29}H_{28}F_3N_5$, 503.23; m/z found, 504.5 [M+H]$^+$. $^1$H NMR (CDCl$_3$): 8.40-8.38 (m, 1H), 7.89-7.86 (m, 1H), 7.77-7.74 (m, 2H), 7.64-7.58 (m, 4H), 7.46-7.42 (m, 2H), 7.35-7.30 (m, 1H), 6.97-6.93 (m, 1H), 6.57 (s, 1H), 3.70-3.65 (m, 2H), 3.64-3.60 (m, 2H), 3.24-3.20 (m, 2H), 3.08-3.01 (m, 1H), 2.99-2.96 (m, 2H), 1.34 (d, J=6.9 Hz, 6H).

Example 132

N-(4-Cyclohexylphenyl)-2-(1-methylethyl)-7-[3-(trifluoromethyl)pyridin-2-yl]-6,7,8,9-tetrahydro-5H-pyrimido[4,5-d]azepin-4-amine

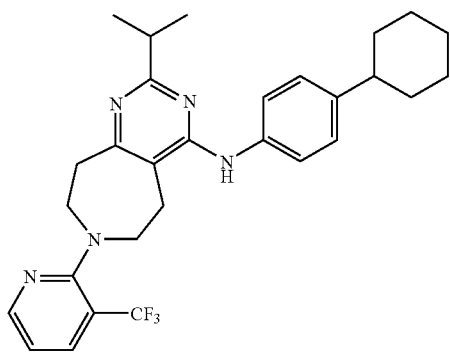

MS (ESI): mass calcd. for $C_{29}H_{34}F_3N_5$, 509.27; m/z found, 510.5 [M+H]$^+$. $^1$H NMR (CDCl$_3$): 8.39-8.37 (m, 1H), 7.86 (dd, J=7.8, 1.8 Hz, 1H), 7.60-7.57 (m, 2H), 7.20-7.16 (m, 2H), 6.95-6.92 (m, 1H), 6.44 (s, 1H), 3.68-3.58 (m, 4H), 3.22-3.18 (m, 2H), 3.05-2.97 (m, 1H), 2.95-2.91 (m, 2H), 2.52-2.44 (m, 1H), 1.93-1.80 (m, 4H), 1.78-1.70 (m, 2H), 1.46-1.36 (m, 4H), 1.31 (d, J=6.9 Hz, 6H).

Example 133

2-(1-Methylethyl)-N-(4-piperidin-1-ylphenyl)-7-[3-(trifluoromethyl)pyridin-2-yl]-6,7,8,9-tetrahydro-5H-pyrimido[4,5-d]azepin-4-amine

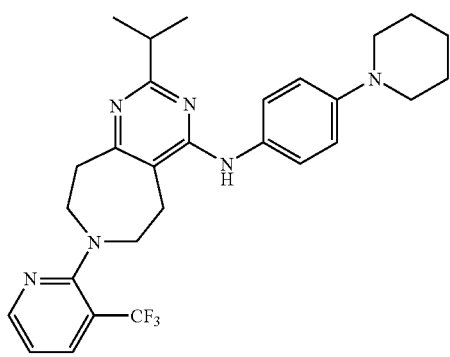 [SMILES: CC(C)c1nc2c(c(Nc3ccc(N4CCCCC4)cc3)n1)CCN(c1ncccc1C(F)(F)F)CC2]

MS (ESI): mass calcd. for $C_{28}H_{33}F_3N_6$, 510.27; m/z found, 511.5 [M+H]$^+$. $^1$H NMR (CDCl$_3$): 8.40-8.37 (m, 1H), 7.88-7.85 (m, 1H), 7.53-7.49 (m, 2H), 6.97-6.91 (m, 3H), 6.35 (s, 1H), 3.68-3.57 (m, 4H), 3.22-3.17 (m, 2H), 3.15-3.09 (m, 4H), 3.03-2.95 (m, 1H), 2.93-2.88 (m, 2H), 1.76-1.71 (m, 4H), 1.60-1.54 (m, 2H), 1.29 (d, J=6.9 Hz, 6H).

Example 134

2-(1-Methylethyl)-N-(4-morpholin-4-ylphenyl)-7-[3-(trifluoromethyl)pyridin-2-yl]-6,7,8,9-tetrahydro-5H-pyrimido[4,5-d]azepin-4-amine

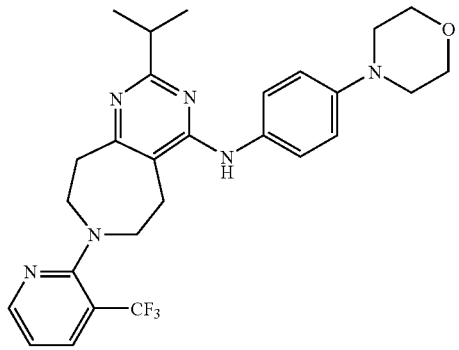 [SMILES: CC(C)c1nc2c(c(Nc3ccc(N4CCOCC4)cc3)n1)CCN(c1ncccc1C(F)(F)F)CC2]

MS (ESI): mass calcd. for $C_{27}H_{31}F_3N_6O$, 512.25; m/z found, 513.5 [M+H]$^+$. $^1$H NMR (CDCl$_3$): 8.39-8.37 (m, 1H), 7.86 (dd, J=7.8, 1.8 Hz, 1H), 7.57-7.53 (m, 2H), 6.95-6.90 (m, 3H), 6.37 (s, 1H), 3.90-3.86 (m, 4H), 3.67-3.59 (m, 4H), 3.21-3.17 (m, 2H), 3.15-3.12 (m, 4H), 3.03-2.96 (m, 1H), 2.93-2.90 (m, 2H), 1.29 (d, J=6.9 Hz, 6H).

Example 135

2-(1-Methylethyl)-N-[4-(methylsulfanyl)phenyl]-7-[3-(trifluoromethyl)pyridin-2-yl]-6,7,8,9-tetrahydro-5H-pyrimido[4,5-d]azepin-4-amine

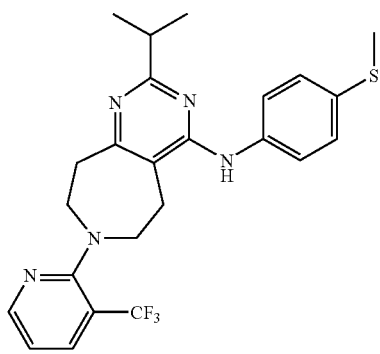 [SMILES: CSc1ccc(Nc2nc(C(C)C)nc3c2CCN(c2ncccc2C(F)(F)F)CC3)cc1]

MS (ESI): mass calcd. for $C_{24}H_{26}F_3N_5S$, 473.19; m/z found, 474.4 [M+H]$^+$. $^1$H NMR (CDCl$_3$): 8.40-8.37 (m, 1H), 7.87 (dd, J=7.8, 1.8 Hz, 1H), 7.63-7.60 (m, 2H), 7.30-7.26 (m, 2H), 6.97-6.92 (m, 1H), 6.46 (s, 1H), 3.69-3.57 (m, 4H), 3.24-3.18 (m, 2H), 3.06-2.97 (m, 1H), 2.95-2.92 (m, 2H), 2.49 (s, 3H), 1.31 (d, J=6.9 Hz, 6H).

Example 136

2-(1-Methylethyl)-N-(4-nitrophenyl)-7-[3-(trifluoromethyl)pyridin-2-yl]-6,7,8,9-tetrahydro-5H-pyrimido[4,5-d]azepin-4-amine

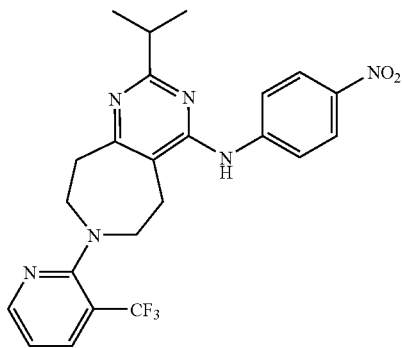 [SMILES: CC(C)c1nc2c(c(Nc3ccc([N+](=O)[O-])cc3)n1)CCN(c1ncccc1C(F)(F)F)CC2]

MS (ESI): mass calcd. for $C_{23}H_{23}F_3N_6O_2$, 472.18; m/z found, 473.4 [M+H]$^+$. $^1$H NMR (CDCl$_3$): 8.40-8.38 (m, 1H), 8.26-8.23 (m, 2H), 7.89-7.84 (m, 3H), 6.98-6.95 (m, 1H), 6.85 (s, 1H), 3.66-3.63 (m, 2H), 3.61-3.59 (m, 2H), 3.27-3.23 (m, 2H), 3.13-3.05 (m, 1H), 3.04-2.99 (m, 2H), 1.34 (d, J=6.9 Hz, 6H).

Example 137

2-(1-Methylethyl)-N-[4-(1-methylethyl)phenyl]-7-[3-(trifluoromethyl)pyridin-2-yl]-6,7,8,9-tetrahydro-5H-pyrimido[4,5-d]azepin-4-amine

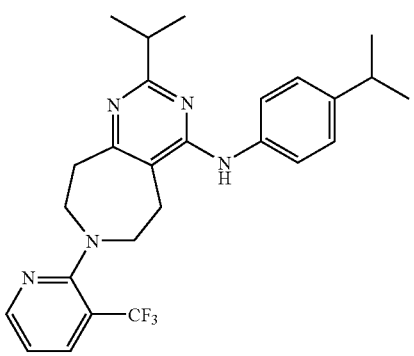 [SMILES: CC(C)c1ccc(Nc2nc(C(C)C)nc3c2CCN(c2ncccc2C(F)(F)F)CC3)cc1]

MS (ESI): mass calcd. for $C_{26}H_{30}F_3N_5$, 469.25; m/z found, 470.2 [M+H]$^+$. $^1$H NMR (CDCl$_3$): 8.39-8.37 (m, 1H), 7.86 (dd, J=7.8, 1.8 Hz, 1H), 7.60-7.57 (m, 2H), 7.23-7.18 (m, 2H), 6.96-6.92 (m, 1H), 6.45 (s, 1H), 3.69-3.58 (m, 4H), 3.24-3.17 (m, 2H), 3.06-2.97 (m, 1H), 2.96-2.85 (m, 3H), 1.32 (d, J=6.9 Hz, 6H), 1.26 (d, J=6.8 Hz, 6H).

Example 138

2-(1,1-Dimethylethyl)-N-[4-(1,1-dimethylethyl)phenyl]-7-[3-(trifluoromethyl)pyridin-2-yl]-6,7,8,9-tetrahydro-5H-pyrimido[4,5-d]azepin-4-amine

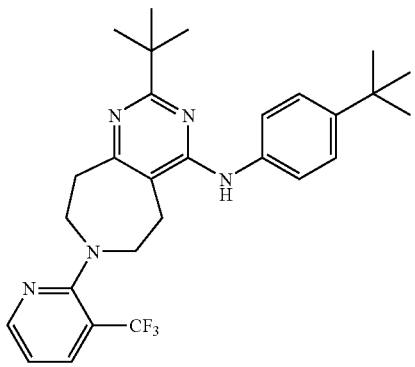 [SMILES: CC(C)(C)c1ccc(Nc2nc(C(C)(C)C)nc3c2CCN(c2ncccc2C(F)(F)F)CC3)cc1]

MS (ESI): mass calcd. for $C_{28}H_{34}F_3N_5$, 497.28; m/z found, 498.2 [M+H]$^+$. $^1$H NMR (CDCl$_3$): 8.39-8.37 (m, 1H), 7.86 (d, J=7.8, 1.8 Hz, 1H), 7.64-7.60 (m, 2H), 7.39-7.33 (m, 2H), 6.96-6.91 (m, 1H), 6.43 (s, 1H), 3.71-3.58 (m, 4H), 3.24-3.18 (m, 2H), 2.96-2.92 (m, 2H), 1.38 (s, 9H), 1.33 (s, 9H).

Example 139

2-(1,1-Dimethylethyl)-N-[4-(trifluoromethyl)phenyl]-7-[3-(trifluoromethyl)pyridin-2-yl]-6,7,8,9-tetrahydro-5H-pyrimido[4,5-d]azepin-4-amine

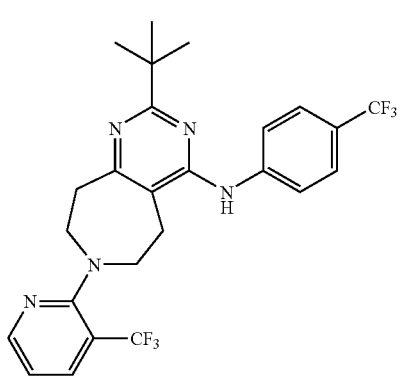 [SMILES: CC(C)(C)c1nc2c(c(Nc3ccc(C(F)(F)F)cc3)n1)CCN(c1ncccc1C(F)(F)F)CC2]

MS (ESI): mass calcd. for $C_{25}H_{25}F_6N_5$, 509.20; m/z found, 510.1 [M+H]$^+$. $^1$H NMR (CDCl$_3$): 8.39-8.37 (m, 1H), 7.90-7.86 (m, 1H), 7.80 (d, J=8.5 Hz, 2H), 7.59 (d, J=8.6 Hz, 2H), 6.98-6.93 (m, 1H), 6.62 (s, 1H), 3.69-3.64 (m, 2H), 3.63-3.58 (m, 2H), 3.27-3.21 (m, 2H), 3.02-2.95 (m, 2H), 1.38 (s, 9H).

Example 140

N-[3-Fluoro-4-(trifluoromethyl)phenyl]-2-(1-methylethyl)-7-[3-(trifluoromethyl)pyridin-2-yl]-6,7,8,9-tetrahydro-5H-pyrimido[4,5-d]azepin-4-amine

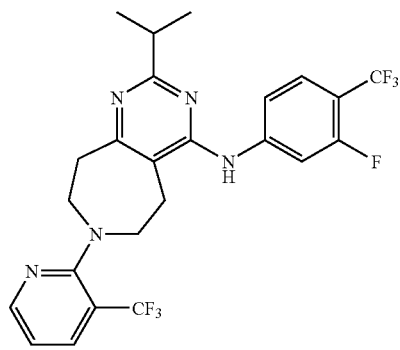 [SMILES: CC(C)c1nc2c(c(Nc3ccc(C(F)(F)F)c(F)c3)n1)CCN(c1ncccc1C(F)(F)F)CC2]

MS (ESI): mass calcd. for $C_{24}H_{22}F_7N_5$, 513.18; m/z found, 514.1 [M+H]+. $^1$H NMR (CDCl$_3$): 8.39-8.38 (m, 1H), 8.05-8.00 (m, 1H), 7.88 (dd, J=7.8, 1.8 Hz, 1H), 7.54-7.49 (m, 1H), 7.27-7.25 (m, 1H), 6.99-6.94 (m, 1H), 6.71 (s, 1H), 3.69-3.57 (m, 4H), 3.27-3.21 (m, 2H), 3.12-3.03 (m, 1H), 3.01-2.95 (m, 2H), 1.34 (d, J=6.9 Hz, 6H).

Example 141

N-(2,3-Dihydro-1H-inden-5-yl)-2-(1-methylethyl)-7-[3-(trifluoromethyl)pyridin-2-yl]-6,7,8,9-tetrahydro-5H-pyrimido[4,5-d]azepin-4-amine hydrochloride salt

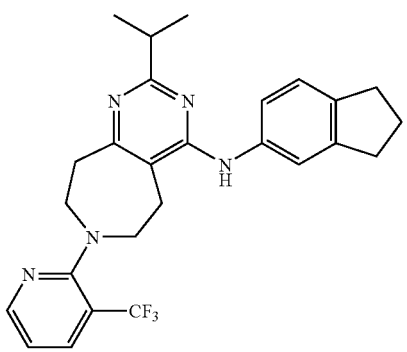 [SMILES: CC(C)c1nc2c(c(Nc3ccc4c(c3)CCC4)n1)CCN(c1ncccc1C(F)(F)F)CC2]

MS (ESI): mass calcd. for $C_{26}H_{28}F_3N_5$, 467.23; m/z found, 468.2 [M+H]+. $^1$H NMR (CD$_3$OD): 8.46-8.43 (m, 1H), 8.02 (dd, J=7.8, 1.7 Hz, 1H), 7.40-7.38 (m, 1H), 7.26-7.21 (m, 2H), 7.14-7.11 (m, 1H), 3.66-3.63 (m, 2H), 3.61-3.57 (m, 2H), 3.19-3.14 (m, 2H), 3.06-2.97 (m, 1H), 2.96-2.90 (m, 6H), 2.15-2.08 (m, 2H), 1.26 (d, J=6.8 Hz, 6H).

Example 142

2-(1-Methylethyl)-N-[4-(1,3-oxazol-5-yl)phenyl]-7-[3-(trifluoromethyl)pyridin-2-yl]-6,7,8,9-tetrahydro-5H-pyrimido[4,5-d]azepin-4-amine

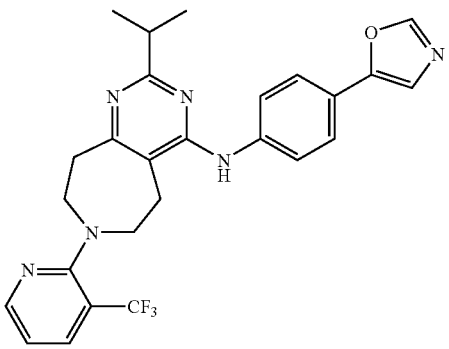 [SMILES: CC(C)c1nc2c(c(Nc3ccc(-c4cnco4)cc3)n1)CCN(c1ncccc1C(F)(F)F)CC2]

MS (ESI): mass calcd. for $C_{26}H_{25}F_3N_6O$, 494.20; m/z found, 495.1 [M+H] +. $^1$H NMR (CDCl$_3$): 8.40-8.38 (m, 1H), 7.90-7.86 (m, 2H), 7.78-7.75 (m, 2H), 7.66-7.62 (m, 2H), 7.30 (s, 1H), 6.98-6.93 (m, 1H), 6.61 (s, 1H), 3.70-3.58 (m, 4H), 3.26-3.19 (m, 2H), 3.10-2.94 (m, 3H), 1.33 (d, J=6.9 Hz, 6H).

Example 143

N-[4-(1,1-Dimethylethyl)-3-nitrophenyl]-2-(1-methylethyl)-7-[3-(trifluoromethyl)pyridin-2-yl]-6,7,8,9-tetrahydro-5H-pyrimido[4,5-d]azepin-4-amine

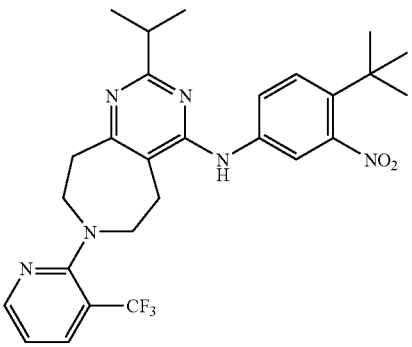 [SMILES: CC(C)c1nc2c(c(Nc3ccc(C(C)(C)C)c([N+](=O)[O-])c3)n1)CCN(c1ncccc1C(F)(F)F)CC2]

MS (ESI): mass calcd. for $C_{27}H_{31}F_3N_6O_2$, 528.24; m/z found, 529.2 [M+H]+. $^1$H NMR (CDCl$_3$): 8.39-8.37 (m, 1H), 8.10 (d, J=2.4 Hz, 1H), 7.87 (dd, J=7.8, 1.8 Hz, 1H), 7.53 (dd, J=8.8, 2.4 Hz, 1H), 7.47 (d, J=8.8 Hz, 1H), 6.99-6.94 (m, 1H), 6.57 (s, 1,H), 3.68-3.56 (m, 4H), 3.26-3.17 (m, 2H), 3.07-2.99 (m, 1H), 2.98-2.93 (m, 2H), 1.41 (s, 9H), 1.31 (d, J=6.9 Hz, 6H).

Example 144

2-Furan-2-yl-N-[4-(trifluoromethyl)phenyl]-7-[3-(trifluoromethyl)pyridin-2-yl]-6,7,8,9-tetrahydro-5H-pyrimido[4,5-d]azepin-4-amine

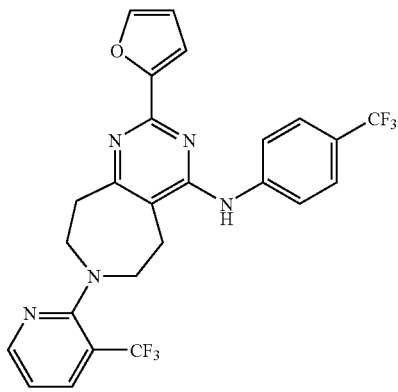 [SMILES: FC(F)(F)c1ccc(Nc2nc(-c3ccco3)nc3c2CCN(c2ncccc2C(F)(F)F)CC3)cc1]

MS (ESI): mass calcd. for C$_{25}$H$_{19}$F$_6$N$_5$O, 519.15; m/z found, 520.1 [M+H]$^+$. $^1$H NMR (CDCl$_3$): 8.32-8.31 (m, 1H), 7.81 (dd, J=7.8, 1.8 Hz, 1H), 7.73 (d, J=8.6 Hz, 2H), 7.56 (d, J=8.6 Hz, 2H), 7.53-7.52 (m, 1H), 7.14-7.11 (m, 1H), 6.92-6.87 (m, 1H), 6.68 (s, 1H), 6.49-6.46 (m, 1H), 3.64-3.52 (m, 4H), 3.30-3.23 (m, 2H), 3.01-2.95 (m, 2H).

Example 145

N-[4-(1,1-Dimethylethyl)phenyl]-2-furan-2-yl-7-[3-(trifluoromethyl)pyridin-2-yl]-6,7,8,9-tetrahydro-5H-pyrimido[4,5-d]azepin-4-amine

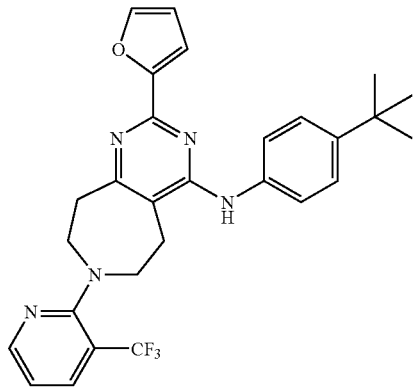 [SMILES: CC(C)(C)c1ccc(Nc2nc(-c3ccco3)nc3c2CCN(c2ncccc2C(F)(F)F)CC3)cc1]

MS (ESI): mass calcd. for C$_{28}$H$_{28}$F$_3$N$^5$O, 507.22; m/z found, 508.2 [M+H]$^+$. $^1$H NMR (CDCl$_3$): 8.33-8.31 (m, 1H), 7.80 (dd, J=7.8, 1.9 Hz, 1H), 7.54!-7.50 (m, 3H), 7.35-7.31 (m, 2H), 7.13-7.11 (m, 1H), 6.89-6.85 (m, 1H), 6.48 (s, 1H), 6.46-6.44 (m, 1H), 3.63-3.53 (m, 4H), 3.27-3.21 (m, 2H), 2.96-2.90 (m, 2H), 1.27 (s, 9H).

Example 146

2-Furan-3-yl-N-[4-(trifluoromethyl)phenyl]-7-[3-(trifluoromethyl)pyridin-2-yl]-6,7,8,9-tetrahydro-5H-pyrimido[4,5-d]azepin-4-amine

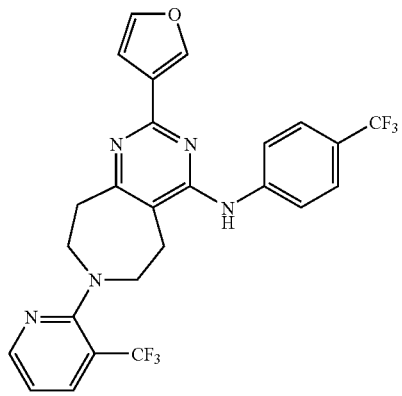 [SMILES: FC(F)(F)c1ccc(Nc2nc(-c3ccoc3)nc3c2CCN(c2ncccc2C(F)(F)F)CC3)cc1]

MS (ESI): mass calcd. for C$_{25}$H$_{19}$F$_6$N$_5$O, 519.15; m/z found, 520.1 [M+H]$^+$. $^1$H NMR (CDCl$_3$): 8.33-8.31 (m, 1H), 8.10-8.08 (m, 1H), 7.81 (dd, J=7.8, 1.8 Hz, 1H), 7.70 (d, J=8.5 Hz, 2H), 7.55 (d, J=8.7 Hz, 2H), 7.41-7.39 (m, 1H), 6.94-6.92 (m, 1H), 6.91-6.87 (m, 1H), 6.62 (s, 1H), 3.64-3.52 (m, 4H), 3.24-3.17 (m, 2H), 2.99-2.93 (m, 2H).

Example 147

N-[4-(1,1-Dimethylethyl)phenyl]-2-furan-3-yl-7-[3-(trifluoromethyl)pyridin-2-yl]-6,7,8,9-tetrahydro-5H-pyrimido[4,5-d]azepin-4-amine

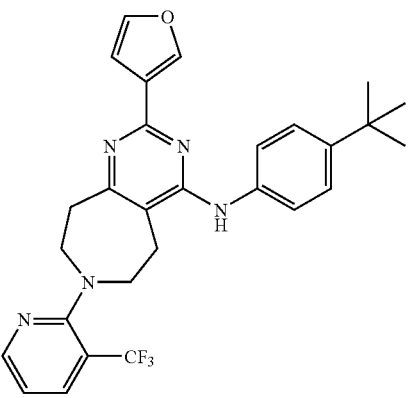 [SMILES: CC(C)(C)c1ccc(Nc2nc(-c3ccoc3)nc3c2CCN(c2ncccc2C(F)(F)F)CC3)cc1]

MS (ESI): mass calcd. for C$_{28}$H$_{28}$F$_3$N$_5$O, 507.22; m/z found, 508.2 [M+H]$^+$. $^1$H NMR (CDCl$_3$): 8.33-8.31 (m, 1H), 8.09-8.07 (m, 1H), 7.80 (dd, J=7.8, 1.8 Hz, 1H), 7.52-7.48 (m, 2H), 7.39-7.37 (m, 1H), 7.34-7.30 (m, 2H), 6.95-6.93 (m, 1H), 6.89-6.86 (m, 1H), 6.42 (s, 1H), 3.64-3.52 (m, 4H), 3.21-3.14 (m, 2H), 2.95-2.88 (m, 2H), 1.28 (s, 9H).

Example 148

Benzo[1,2,5]thiadiazol-5-yl-[2-isopropyl-7-(3-trifluoromethyl-pyridin-yl)-6,7,8,9-tetrahydro-5H-pyrimido[4,5-d]azepin-4-yl]-amine

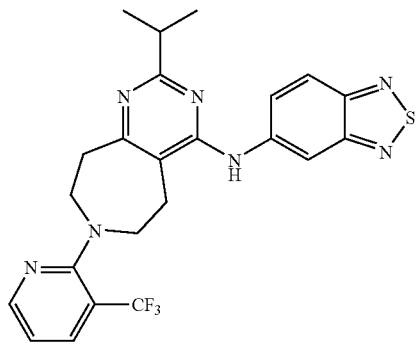 [SMILES: CC(C)c1nc2c(c(Nc3ccc4nsnc4c3)n1)CCN(c1ncccc1C(F)(F)F)CC2]

MS (ESI): mass calcd. for $C_{23}H_{22}F_3N_7S$, 485.16; m/z found, 486.1 [M+H]$^+$. $^1$H NMR (CDCl$_3$): 8.56-8.53 (m, 1H), 8.34-8.31 (m, 1H), 7.85 (d, J=9.4 Hz, 1H), 7.81 (dd, J=7.8, 1.8 Hz, 1H), 7.59 (dd, J=9.4, 2.2 Hz, 1H), 6.91-6.87 (m, 1H), 6.68 (s, 1H), 3.63-3.59 (m, 2H), 3.57-3.54 (m, 2H), 3.21-3.16 (m, 2H), 3.07-2.99 (m, 1H), 2.98-2.95 (m, 2H), 1.30 (d, J=6.9 Hz, 6H).

Example 149

2-(2-Thienyl)-N-[4-(trifluoromethyl)phenyl]-7-[3-(trifluoromethyl)pyridin-2-yl]-6,7,8,9-tetrahydro-5H-pyrimido[4,5-d]azepin-4-amine

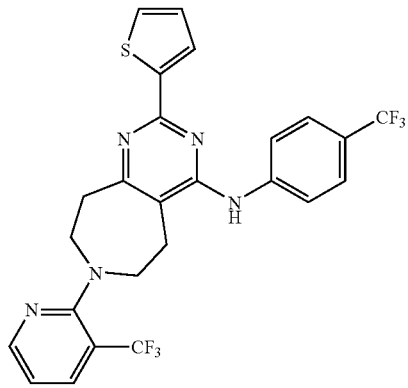 [SMILES: FC(F)(F)c1ccc(Nc2nc(-c3cccs3)nc3c2CCN(c2ncccc2C(F)(F)F)CC3)cc1]

MS (ESI): mass calcd. for $C_{25}H_{19}F_6N_5S$, 535.13; m/z found, 536.1 [M+H]$^+$. $^1$H NMR (CDCl$_3$): 8.33-8.31 (m, 1H), 7.86-7.83 (m, 1H), 7.81 (dd, J=7.8, 1.8 Hz, 1H), 7.76 (d, J=8.5 Hz, 2H), 7.57 (d, J=8.6 Hz, 2H), 7.37-7.34 (m, 1H), 7.06-7.04 (m, 1H), 6.91-6.87 (m, 1H), 6.64 (s, 1H), 3.65-3.53 (m, 4H), 3.26-3.20 (m, 2H), 3.00-2.94 (m, 2H).

Example 150

2-(3-Thienyl)-N-[4-(trifluoromethyl)phenyl]-7-[3-(trifluoromethyl)pyridin-2-yl]-6,7,8,9-tetrahydro-5H-pyrimido[4,5-d]azepin-4-amine

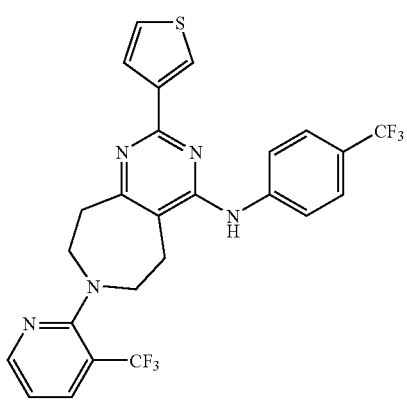 [SMILES: FC(F)(F)c1ccc(Nc2nc(-c3ccsc3)nc3c2CCN(c2ncccc2C(F)(F)F)CC3)cc1]

MS (ESI): mass calcd. for $C_{25}H_{19}F_6N_5S$, 535.13; m/z found, 536 [M+H]$^+$. $^1$H NMR (CDCl$_3$): 8.40-8.38 (m, 1H), 8.20-8.18 (m, 1H), 7.90-7.86 (m, 1H), 7.84-7.78 (m, 3H), 7.65-7.63 (m, 2H), 7.36-7.34 (m, 1H), 6.99-6.94 (m, 1H), 6.69 (s, 1H), 3.72-3.60 (m, 4H), 3.35-3.26 (m, 2H), 3.08-3.02 (m, 2H).

Example 151

2-(1-Methylethyl)-N-(4-methylphenyl)-7-[3-(trifluoromethyl)pyridin-2-yl]-6,7,8,9-tetrahydro-5H-pyrimido[4,5-d]azepin-4-amine hydrochloride salt

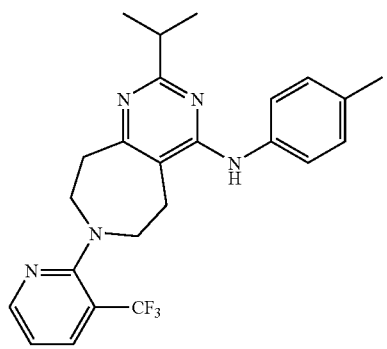 [SMILES: Cc1ccc(Nc2nc(C(C)C)nc3c2CCN(c2ncccc2C(F)(F)F)CC3)cc1]

MS (ESI): mass calcd. for $C_{24}H_{26}F_3N_5$, 441.21; m/z found, 442.2 [M+H]$^+$. $^1$H NMR (CD$_3$OD): 8.46-8.44 (mi, 1H), 8.03 (dd, J=7.8, 1.7 Hz, 1H), 7.42-7.39 (m, 2H), 7.24-7.22 (m, 2H), 7.17-7.13 (m, 1H), 3.68-3.58 (m, 4H), 3.35-3.30 (m, 2H), 3.21-3.15 (m, 2H), 3.10-3.00 (m, 1H), 2.37 (s, 3H), 1.26 (d, J=6.8 Hz, 6H).

Example 152

2-(1-Methylethyl)-N-[4-(pyrrolidin-1-ylsulfonyl)phenyl]-7-[3-(trifluoromethyl)pyridin-2-yl]-6,7,8,9-tetrahydro-5H-pyrimido[4,5-d]azepin-4-amine

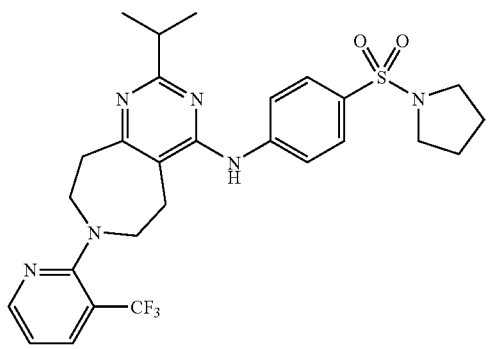 [SMILES: CC(C)c1nc2c(c(Nc3ccc(S(=O)(=O)N4CCCC4)cc3)n1)CCN(c1ncccc1C(F)(F)F)CC2]

MS (ESI): mass calcd. for $C_{27}H_{31}F_3N_6O_2S$, 560.22; m/z found, 561.1 [M+H]+. $^1$H NMR (CDCl$_3$): 8.40-8.38 (m, 1H), 7.90-7.85 (m, 3H), 7.82-7.78 (m, 2H), 6.99-6.94 (m, 1H), 6.74 (s, 1H), 3.66-3.57 (m, 4H), 3.29-3.21 (m, 6H), 3.11-2.97 (m, 3H), 1.81-1.74 (m, 4H), 1.34 (d, J=6.9 Hz, 6H).

Example 153

2-(2-Methyl-1,3-thiazol-4-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

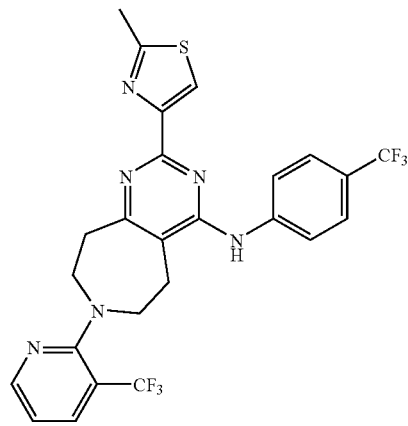 [SMILES: Cc1nc(-c2nc3c(c(Nc4ccc(C(F)(F)F)cc4)n2)CCN(c2ncccc2C(F)(F)F)CC3)cs1]

MS (ESI): mass calcd. for $C_{25}H_{20}F_6N_6S$, 550.14; m/z found, 551.2 [M+H]+. $^1$H NMR (CD$_3$OD): 8.48-8.44 (m, 1H), 8.34 (s, 1H), 8.07-8.02 (m, 1H), 7.89-7.86 (m, 2H), 7.82-7.77 (m, 2H), 7.18-7.13 (m, 1H), 3.72-3.62 (m, 4H), 3.56-3.53 (m, 2H), 3.33-3.30 (m, 2H), 2.84 (s, 3H).

Example 154

N,N-Dimethyl-4-({2-(1-methylethyl)-7-[3-(trifluoromethyl)pyridin-2-yl]-6,7,8,9-tetrahydro-5H-pyrimido[4,5-d]azepin-4-yl}amino)benzenesulfonamide

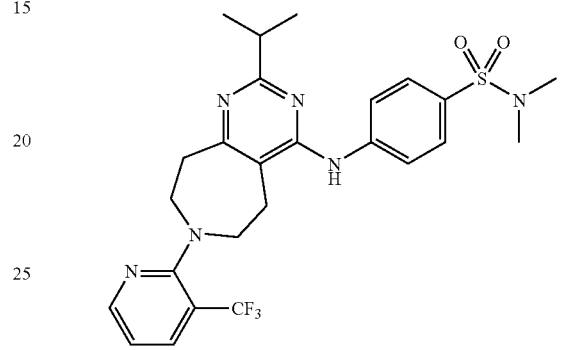

MS (ESI): mass calcd. for $C_{25}H_{29}F_3N_6O_2S$, 534.20; m/z found, 535.3 [M+H]+. $^1$H NMR (CDCl$_3$): 8.42-8.40 (m, 1H), 7.92-7.89 (m, 3H), 7.78-7.75 (m, 2H), 7.01-6.96 (m, 1H), 6.77 (s, 1H), 3.69-3.60 (m, 4H), 3.29-3.24 (m, 2H), 3.14-3.06 (m, 1H), 3.04-3.00 (m, 2H), 2.74 (s, 6H), 1.36 (d, 6.9 Hz, 6H).

Example 155

N-[2-Fluoro-4-(trifluoromethyl)phenyl]-2-(1-methylethyl)-7-[3-(trifluoromethyl)pyridin-2-yl]-6,7,8,9-tetrahydro-5H-pyrimido[4,5-d]azepin-4-amine

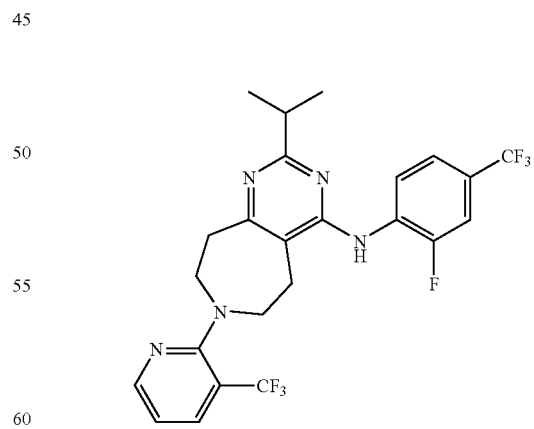

MS (ESI): mass calcd. for $C_{24}H_{22}F_7N_5$, 513.18; m/z found, 514.2 [M+H]+. $^1$H NMR (CDCl$_3$): 8.93-8.88 (m, 1H), 8.42-8.40 (m, 1H), 7.89 (dd, J=7.8, 1.8 Hz, 1H), 7.49-7.46 (m, 1H), 7.41-7.38 (m, 1H), 7.00-6.97 (m, 2H), 3.70-3.67 (m, 2H), 3.63-3.60 (m, 2H), 3.28-3.25 (m, 2H), 3.13-3.06 (m, 1H), 3.04-3.01 (m, 2H), 1.36 (d, J=6.9 Hz, 6H).

Example 156

1-[4-({2-Piperidin-1-yl-7-[3-(trifluoromethyl)pyridin-2-yl]-6,7,8,9-tetrahydro-5H-pyrimido[4,5-d]azepin-4-yl}amino)phenyl]ethanone

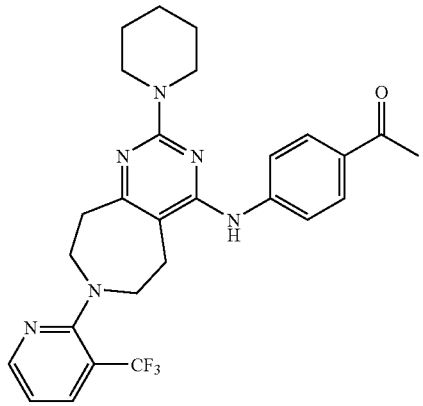 [SMILES: CC(=O)c1ccc(Nc2nc(N3CCCCC3)nc3c2CCN(c2ncccc2C(F)(F)F)CC3)cc1]

MS (ESI): mass calcd. for $C_{27}H_{29}F_3N_6O$, 510.24; m/z found, 511.2 [M+H]$^+$. $^1$H NMR (CDCl$_3$): 8.41-8.39 (m, 1H), 7.98-7.95 (m, 2H), 7.88 (dd, J=7.8, 1.8 Hz, 1H), 7.66-7.64 (m, 2H), 6.98-6.94 (m, 1H), 6.60 (s, 1H), 3.81-3.74 (m, 4H), 3.64-3.55 (m, 4H), 3.14-3.08 (m, 2H), 2.92-2.86 (m, 2H), 2.60 (s, 3H), 1.71-1.60 (m, 6H).

Example 157

N-[3-Fluoro-4-(trifluoromethyl)phenyl]-2-piperidin-1-yl-7-[3-(trifluoromethyl)pyridin-2-yl]-6,7,8,9-tetrahydro-5H-pyrimido[4,5-d]azepin-4-amine

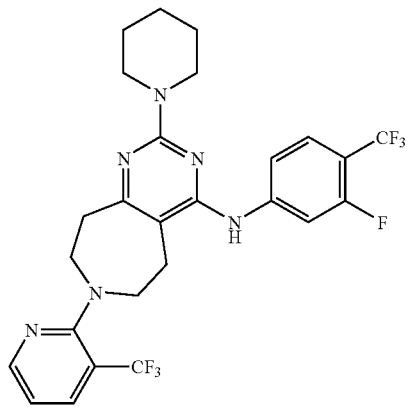 [SMILES: Fc1cc(Nc2nc(N3CCCCC3)nc3c2CCN(c2ncccc2C(F)(F)F)CC3)ccc1C(F)(F)F]

MS (ESI): mass calcd. for $C_{26}H_{25}F_7N_6$, 554.20; m/z found, 555.2 [M+H]$^+$. $^1$H NMR (CDCl$_3$): 8.41-8.39 (m, 1H), 7.88 (dd, J=7.8, 1.8 Hz, 1H), 7.84-7.81 (m, 1H), 7.50 (t, J=8.4 Hz, 1H), 7.18-7.14 (m, 1H), 6.98-6.95 (m, 1H), 6.57 (s, 1H), 3.81-3.73 (m, 4H), 3.63-3.55 (m, 4H), 3.13-3.07 (m, 2H), 2.91-2.85 (m, 2H), 1.73-1.60 (m, 6H).

Example 158

N,N-Dimethyl-4-({2-piperidin-1-yl-7-[3-(trifluoromethyl)pyridin-2-yl]-6,7,8,9-tetrahydro-5H-pyrimido[4,5-d]azepin-4-yl}amino)benzenesulfonamide

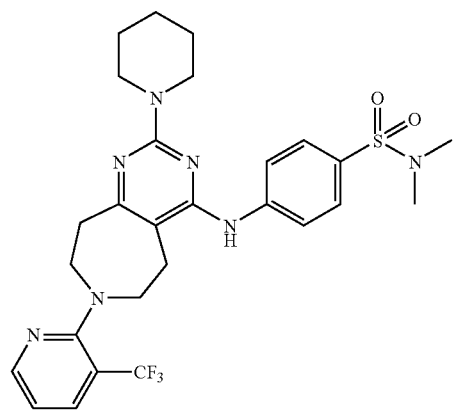 [SMILES: CN(C)S(=O)(=O)c1ccc(Nc2nc(N3CCCCC3)nc3c2CCN(c2ncccc2C(F)(F)F)CC3)cc1]

MS (ESI): mass calcd. for $C_{27}H_{32}F_3N_7O_2S$, 575.23; m/z found, 576.3 [M+H]$^+$. $^1$H NMR (CDCl$_3$): 8.42-8.40 (m, 1H), 7.90-7.88 (m, 1H), 7.76-7.72 (m, 4H), 6.98-6.95 (m, 1H), 6.60 (s, 1H), 3.79-3.75 (m, 4H), 3.61-3.56 (m, 4H), 3.12-3.08 (m, 2H), 2.92-2.87 (m, 2H), 2.73 (s, 6H), 1.72-1.63 (m, 6H).

Example 159

N-[4-(1,1-Dimethylethyl)-3-nitrophenyl]-2-piperidin-1-yl-7-[3-(trifluoromethyl)pyridin-2-yl]-6,7,8,9-tetrahydro-5H-pyrimido[4,5-d]azepin-4-amine

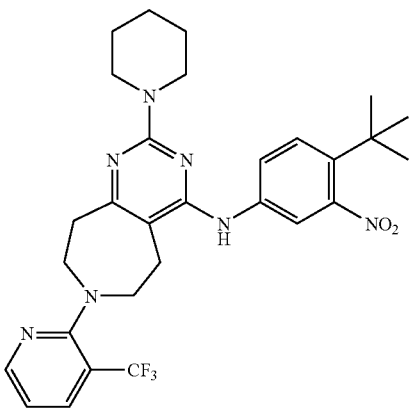 [SMILES: CC(C)(C)c1ccc(Nc2nc(N3CCCCC3)nc3c2CCN(c2ncccc2C(F)(F)F)CC3)cc1[N+](=O)[O-]]

MS (ESI): mass calcd. for $C_{29}H_{34}F_3N_7O_2$, 569.27; m/z found, 570.3 [M+H]$^+$. $^1$H NMR (CDCl$_3$): 8.41-8.39 (m, 1H), 8.08 (d, J=2.5 Hz, 1H), 7.88 (dd, J=7.8, 1.8 Hz, 1H), 7.45 (d, J=8.8 Hz, 1H), 7.31-7.28 (m, 1H), 6.97-6.93 (m, 1H), 6.42 (s, 1H), 3.77-3.71 (m, 4H), 3.64-3.55 (m, 4H), 3.11-3.06 (m, 2H), 2.88-2.83 (m, 2H), 1.71-1.59 (m, 6H), 1.41 (s, 9H).

Example 160

N-[4-(Methylsulfanyl)phenyl]-2-piperidin-1-yl-7-[3-(trifluoromethyl)pyridin-2-yl]-6,7,8,9-tetrahydro-5H-pyrimido[4,5-d]azepin-4-amine

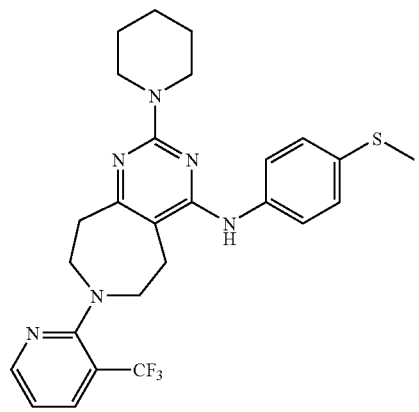 [SMILES: CSc1ccc(Nc2nc(N3CCCCC3)nc3c2CCN(c2ncccc2C(F)(F)F)CC3)cc1]

MS (ESI): mass calcd. for $C_{26}H_{29}F_3N_6S$, 514.21; m/z found, 515.2 [M+H]$^+$. $^1$H NMR (CDCl$_3$): 8.40-8.39 (m, 1H), 7.87 (dd, J=7.8, 1.8 Hz, 1H), 7.52-7.47 (m, 2H), 7.30-7.26 (m, 2H), 6.97-6.92 (m, 1H), 6.32 (s, 1H), 3.77-3.70 (m, 4H), 3.65-3.56 (m, 4H), 3.11-3.06 (m, 2H), 2.87-2.84 (m, 2H), 2.50 (s, 3H), 1.69-1.57 (m, 6H).

Example 161

[2-Isopropyl-7-(3-trifluoromethyl-pyridin-2-yl)-6,7,8,9-tetrahydro-5H-pyrimido[4,5-d]azepin-4-yl]-(1-methyl-1,2,3,4-tetrahydro-quinolin-7-yl)-amine

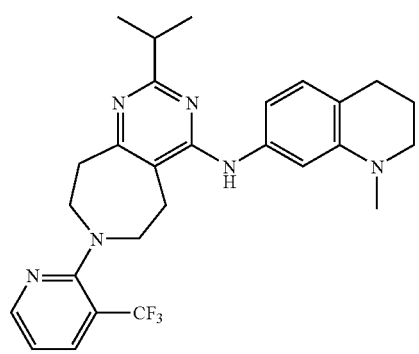 [SMILES: CC(C)c1nc2c(c(Nc3ccc4c(c3)N(C)CCC4)n1)CCN(c1ncccc1C(F)(F)F)CC2]

MS (ESI): mass calcd. for $C_{27}H_{31}F_3N_6$, 496.26; m/z found, 497.3 [M+H]$^+$. $^1$H NMR (CDCl$_3$): 8.39-8.36 (m, 1H), 7.86 (dd, J=7.8, 1.8 Hz, 1H), 7.20 (d, J=2.0 Hz, 1H), 6.96-6.86 (m, 2H), 6.68 (dd, J=8.0, 2.1 Hz, 1H), 6.40 (s, 1H), 3.72-3.56 (m, 4H), 3.27-3.16 (m, 4H), 3.05-2.90 (m, 6H), 2.74 (t, J=6.4 Hz, 2H), 2.02-1.94 (m, 2H), 1.32 (d, J=6.9 Hz, 6H).

Example 162

[2-Isopropyl-7-(3-trifluoromethyl-pyridin-2-yl)-6,7,8,9-tetrahydro-5H-pyrimido[4,5-d]azepin-4-yl]-(1,4,4-trimethyl-1,2,3,4-tetrahydro-quinolin-7-yl)-amine

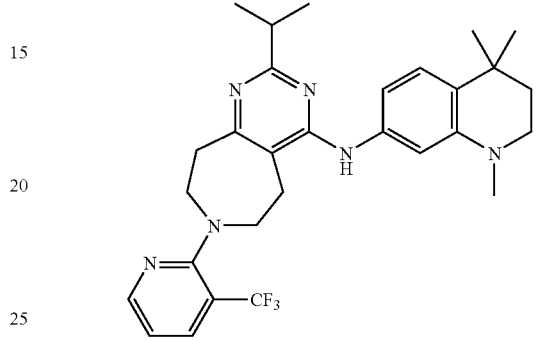

MS (ESI): mass calcd. for $C_{29}H_{35}F_3N_6$, 524.29; m/z found, 525.3 [M+H]$^+$. $^1$H NMR (CDCl$_3$): 8.40-8.38 (m, 1H), 7.88 (dd, J=7.8, 1.8 Hz, 1H), 7.23 (d, J=2.2 Hz, 1H), 7.14 (d, J=8.3 Hz, 1H), 6.97-6.92 (m, 1H), 6.78 (dd, J=8.2, 2.2 Hz, 1H), 6.43 (s, 1H), 3.70-3.60 (m, 4H), 3.29-3.25 (m, 2H), 3.23-3.20 (m, 2H), 3.06-3.00 (m, 1H), 2.98-2.93 (m, 5H), 1.80-1.77 (m, 2H), 1.35 (d, J=6.9 Hz, 6H), 1.30 (s, 6H).

Example 163

(1-Methyl-1,2,3,4-tetrahydro-quinolin-7-yl)-[2-piperidin-1-yl-7-(3-trifluoromethyl-pyridin-2-yl)-6,7,8,9-tetrahydro-5H-pyrimido[4,5-d]azepin-4-yl]-amine hydrochloride salt

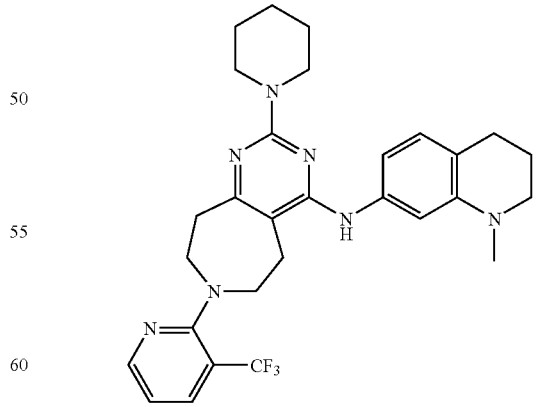

MS (ESI): mass calcd. for $C_{29}H_{34}F_3N_7$, 537.28; m/z found, 538.3 [M+H]$^+$. $^1$H NMR (CDCl$_3$): 8.41-8.39 (m, 1H), 7.89 (dd, J=7.8, 1.7 Hz, 1H), 7.02-6.98 (m, 1H), 6.97-6.94 (m, 2H), 6.75-6.72 (m, 1H), 6.66-6.62 (m, 1H), 4.09-3.78 (m, 6H), 3.69-3.61 (m, 4H), 3.31-3.25 (m, 2H), 2.92-2.87 (m, 5H), 2.80-2.75 (m, 2H), 2.04-1.97 (m, 2H), 1.74-1.66 (m, 6H).

Example 164

[2-Piperidin-1-yl-7-(3-trifluoromethyl-pyridin-2-yl)-6,7,8,9-tetrahydro-5H-pyrimido[4,5-d]azepin-4-yl]-(1,4,4-trimethyl-1,2,3,4-tetrahydro-quinolin-7-yl)-amine hydrochloride salt

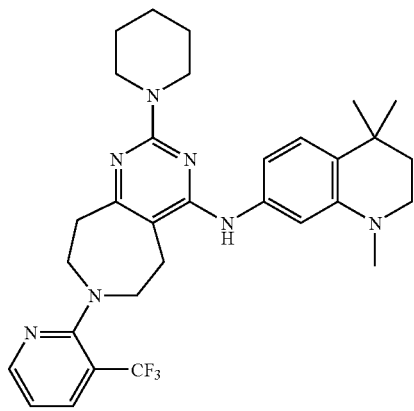 [SMILES: CN1CCC(C)(C)c2ccc(Nc3nc(N4CCCCC4)nc4c3CCN(c3ncccc3C(F)(F)F)CC4)cc21]

MS (ESI): mass calcd. for $C_{31}H_{38}F_3N_7$, 565.31; m/z found, 566.3 [M+H]$^+$. $^1$H NMR (CDCl$_3$): 8.41-8.39 (m, 1H), 7.90-7.88 (m, 1H), 7.19 (d, J=8.2 Hz, 1H), 7.02-6.93 (m, 2H), 6.78-6.69 (m, 2H), 4.10-3.90 (m, 4H), 3.87-3.80 (m, 2H), 3.69-3.61 (m, 4H), 3.33-3.26 (m, 2H), 2.94-2.87 (m, 5H), 1.82-1.77 (m, 2H), 1.75-1.67 (m, 6H), 1.31 (s, 6H).

Example 165

[2-Isopropyl-7-(3-trifluoromethyl-pyridin-2-yl)-6,7,8,9-tetrahydro-5H-pyrimido[4,5-d]azepin-4-yl]-(6-pyrrolidin-1-yl-pyridin-3-yl)-amine

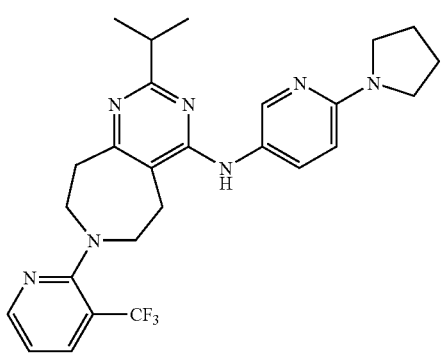 [SMILES: CC(C)c1nc2c(c(Nc3ccc(N4CCCC4)nc3)n1)CCN(c1ncccc1C(F)(F)F)CC2]

MS (ESI): mass calcd. for $C_{26}H_{30}F_3N_7$, 497.25; m/z found, 498.3 [M+H]$^+$. $^1$H NMR (CDCl$_3$): 8.41-8.39 (m, 1H), 8.20 (d, J=2.6 Hz, 1H), 7.88 (dd, J=7.8, 1.8 Hz, 1H), 7.85 (dd, J=9.0, 2.7 Hz, 1H), 6.98-6.94 (m, 1H), 6.41 (d, J=9.0 Hz, 1H), 6.21

(s, 1H), 3.70-3.66 (m, 2H), 3.64-3.62 (m, 2H), 3.50-3.48 (m, 4H), 3.23-3.18 (m, 2H), 2.99-2.92 (m, 3H), 2.07-2.01 (m, 4H), 1.27 (d, J=6.9 Hz, 6H).

Example 166

(2-Fluoro-4-trifluoromethyl-phenyl)-[2-piperidin-1-yl-7-(3-trifluoromethyl-pyridin-2-yl)-6,7,8,9-tetrahydro-5H-pyrimido[4,5-d]azepin-4-yl]-amine

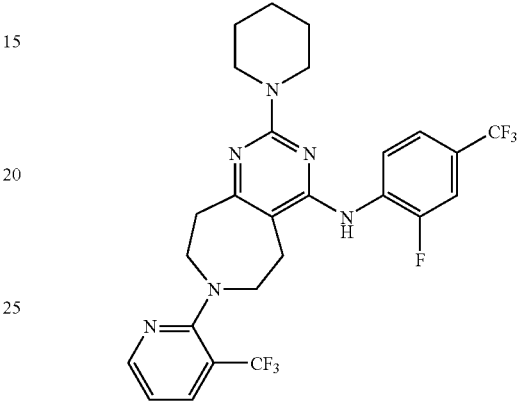

MS (ESI): mass calcd. for $C_{26}H_{25}F_7N_6$, 554.25; m/z found, 555.2 [M+H]$^+$. $^1$H NMR (CDCl$_3$): 8.40-8.36 (m, 1H), 7.87 (dd, J=7.8, 1.8 Hz, 1H), 7.84-7.78 (m, 1H), 7.48 (t, J=8.4 Hz, 1H), 7.16-7.11 (m, 1H), 6.97-6.91 (m, 1H), 6.55 (s, 1H), 3.78-3.70 (m, 4H), 3.61-3.52 (m, 4H), 3.11-3.05 (m, 2H), 2.88-2.83 (m, 2H), 1.72-1.56 (m, 6H).

Example 167

2-Pyridin-4-yl-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

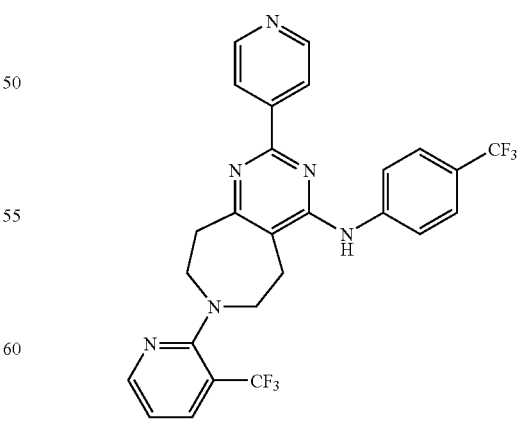

MS (ESI): mass calcd. for $C_{26}H_{20}F_6N_6$, 530.17; m/z found, 531.5 [M+H]$^+$. $^1$H NMR (MeOD): 8.90 (d, J=6.6 Hz, 2H), 8.81 (d, J=6.7 Hz, 1H), 8.45-8.42 (m, 1H), 8.02 (dd, J=7.8, 1.8

Hz, 1H), 7.87 (d, J=8.5 Hz, 2H), 7.69 (d, J=8.6 Hz, 2H), 7.12 (dd, J=7.7, 4.9 Hz, 1H), 3.62-3.56 (m, 4H), 3.42-3.37 (m, 2H), 3.29-3.25 (m, 2H).

Example 168

N-[4-(1,1-Dimethylethyl)phenyl]-2-pyridin-4-yl-7-[3-(trifluoromethyl)pyridin-2-yl]-6,7,8,9-tetrahydro-5H-pyrimido[4,5-d]azepin-4-amine trifluoroacetic acid salt

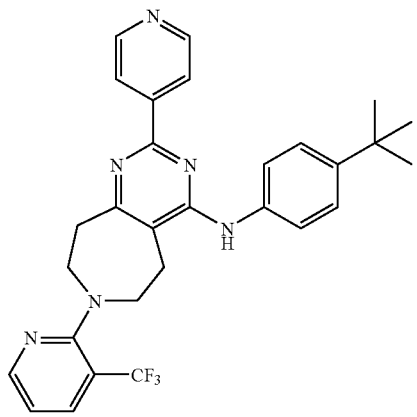 [SMILES: CC(C)(C)c1ccc(Nc2nc(-c3ccncc3)nc3c2CCN(c2ncccc2C(F)(F)F)CC3)cc1]

MS (ESI): mass calcd. for $C_{29}H_{29}F_3N_7$, 518.24; m/z found, 519.5 [M+H]$^+$. $^1$H NMR (MeOD): 8.89 (d, J=6.6 Hz, 2H), 8.72 (d, J=6.7 Hz, 2H), 8.44 (dd, J=4.7, 1.4 Hz, 1H), 8.02 (dd, J=7.8, 1.8 Hz, 1H), 7.58-7.54 (m, 2H), 7.47-7.44 (m, 2H), 7.12 (dd, J=7.8, 4.8 Hz, 1H), 3.63-3.57 (m, 4H), 3.40-3.35 (m, 2H), 3.26-3.21 (m, 2H), 1.36 (s, 9H).

Example 169

N-[3-Chloro-4-(trifluoromethyl)phenyl]-2-pyridin-4-yl-7-[3-(trifluoromethyl)pyridin-2-yl]-6,7,8,9-tetrahydro-5H-pyrimido[4,5-d]azepin-4-amine

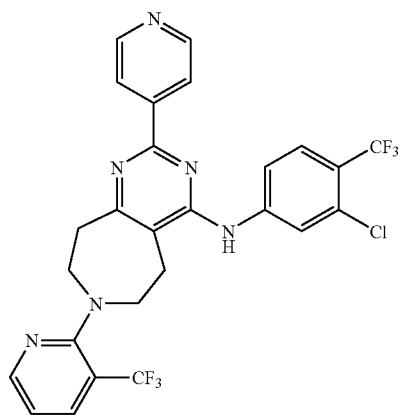 [SMILES: FC(F)(F)c1ccc(Nc2nc(-c3ccncc3)nc3c2CCN(c2ncccc2C(F)(F)F)CC3)cc1Cl]

MS (ESI): mass calcd. for $C_{26}H_{19}ClF_6N_6$, 564.13; m/z found, 565.4 [M+H]$^+$. $^1$H NMR (CDCl$_3$): 8.76 (d, J=5.1 Hz, 2H), 8.40 (d, J=3.7 Hz, 1H), 8.22 (d, J=5.3 Hz, 2H), 8.09 (s, 1H), 7.91-7.87 (m, 1H), 7.70 (d, J8.8 Hz, 1H), 7.58 (d, J=9.0 Hz, 1H), 7.01-6.95 (m, 1H), 6.81 (s, 1H), 3.75-3.61 (m, 4H), 3.41-3.32 (m, 2H), 3.13-3.06 (m, 2H).

Example 170

2-Pyridin-4-yl-7-[3-(trifluoromethyl)pyridin-2-yl]-N-[6-(trifluoromethyl)pyridin-3-yl]-6,7,8,9-tetrahydro-5H-pyrimido[4,5-d]azepin-4-amine trifluoroacetic acid salt

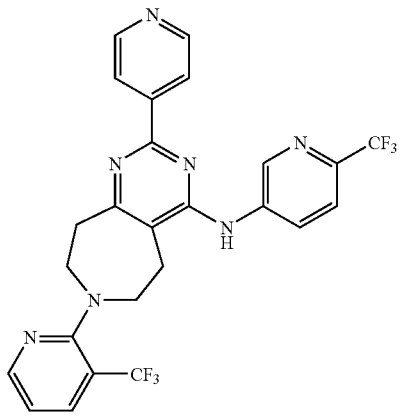 [SMILES: FC(F)(F)c1ccc(Nc2nc(-c3ccncc3)nc3c2CCN(c2ncccc2C(F)(F)F)CC3)cn1]

MS (ESI): mass calcd. for $C_{25}H_{19}F_6N_7$, 531.16; m/z found, 532.1 [M+H]$^+$. $^1$H NMR (CDCl$_3$): 9.04 (d, J=2.3 Hz, 1H), 8.90 (d, J=6.4 Hz, 2H), 8.73 (d, J=6.4 Hz, 2H), 8.43-8.41 (m, 1H), 8.21 (dd, J=8.5, 2.3 Hz, 1H), 7.94 (dd, J=7.8, 1.6 Hz, 1H), 7.79 (d, J=8.6 Hz, 1H), 7.33 (s, 1H), 7.06-7.02 (m, 1H), 3.77-3.72 (m, 2H), 3.71-3.65 (m, 2H), 3.43-3.38 (m, 2H), 3.25-3.19 (m, 2H).

Example 171

N-[4-(1,1-Dimethylethyl)phenyl]-2-pyridin-2-yl-7-[3-(trifluoromethyl)pyridin-2-yl]-6,7,8,9-tetrahydro-5H-pyrimido[4,5-d]azepin-4-amine trifluoroacetic acid salt

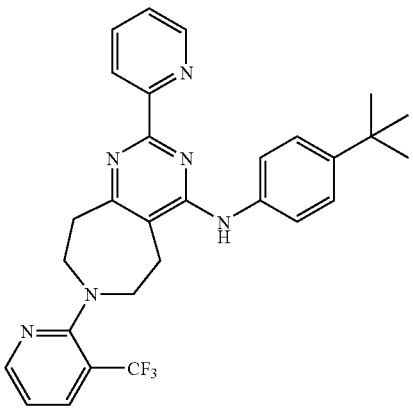 [SMILES: CC(C)(C)c1ccc(Nc2nc(-c3ccccn3)nc3c2CCN(c2ncccc2C(F)(F)F)CC3)cc1]

MS (ESI): mass calcd. for $C_{29}H_{29}F_3N_6$, 518.24; m/z found, 519.5 [M+H]$^+$. $^1$H NMR (MeOD): 8.84-8.82 (m, 1H), 8.45 (dd, J=4.7, 1.5 Hz, 1H), 8.27-8.23 (m, 1H), 8.09-8.00 (m, 2H), 7.72-7.65 (m, 1H), 7.54 (s, 4H), 7.16-7.12 (m, 1H), 3.72-3.63 (m, 4H), 3.57-3.52 (m, 2H), 3.30-3.26 (m, 2H), 1.39 (s, 9H).

Example 172

2-Pyridin-2-yl-N-[4-(trifluoromethyl)phenyl]-7-[3-(trifluoromethyl)pyridin-2-yl]-6,7,8,9-tetrahydro-5H-pyrimido[4,5-d]azepin-4-amine le 1 trifluoroacetic acid salt

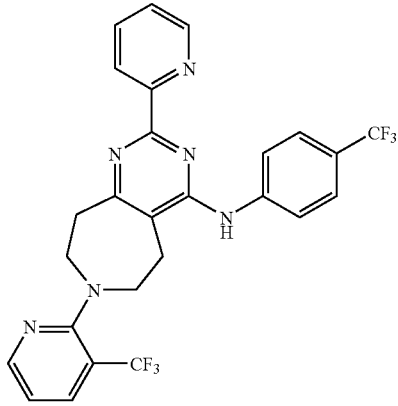 [SMILES: FC(F)(F)c1ccc(Nc2nc(-c3ccccn3)nc3c2CCN(c2ncccc2C(F)(F)F)CC3)cc1]

MS (ESI): mass calcd. for $C_{26}H_{20}F_6N_6$, 530.17; m/z found, 531.5 [M+H]$^+$. $^1$H NMR (MeOD): 8.88-8.81 (m, 1H), 8.47-8.44 (m, 1H), 8.34-8.31 (m, 1H), 8.16 (dt, J=7.8, 1.6 Hz, 1H), 8.03 (dd, J=7.8, 1.7 Hz, 1H), 7.86 (d, J=8.6 Hz, 2H), 7.80 (d, J=8.6 Hz, 2H), 7.77-7.73 (m, 1H), 7.17-7.12 (m, 1H), 3.71-3.64 (m, 4H), 3.60-3.55 (m, 2H), 3.35-3.31 (m, 2H).

Example 173

N-[3-Chloro-4-(trifluoromethyl)phenyl]-2-pyridin-2-yl-7-[3-(trifluoromethyl)pyridin-2-yl]-6,7,8,9-tetrahydro-5H-pyrimido[4,5-d]azepin-4-amine trifluoroacetic ac id salt

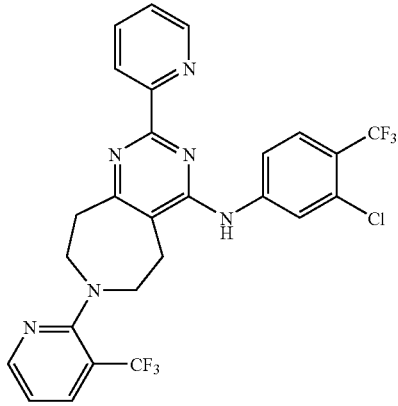 [SMILES: FC(F)(F)c1ccc(Nc2nc(-c3ccccn3)nc3c2CCN(c2ncccc2C(F)(F)F)CC3)cc1Cl]

MS (ESI): mass calcd. for $C_{26}H_{19}ClF_6N_6$, 564.13; m/z found, 565.1 [M+H]$^+$. $^1$H NMR (MeOD): 8.92-8.82 (m, 1H), 8.47-8.44 (m, 1H), 8.44-8.41 (m, 1H), 8.27 (dt, J=7.8, 1.6 Hz, 1H), 8.05-8.01 (m, 2H), 7.88 (d, J=8.7 Hz, 1H), 7.84-7.80 (m, 2H), 7.17-7.13 (m, 1H), 3.70-3.62 (m, 4H), 3.60-3.55 (m, 2H), 3.35-3.31 (m, 2H).

Example 174

Methyl 2-methyl-2-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]propanoate

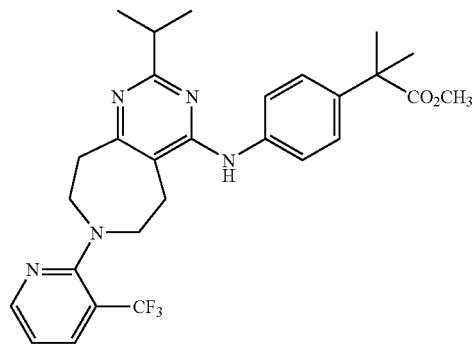 [SMILES: COC(=O)C(C)(C)c1ccc(Nc2nc(C(C)C)nc3c2CCN(c2ncccc2C(F)(F)F)CC3)cc1]

MS (ESI): mass calcd. for $C_{28}H_{32}F_3N_5O_2$, 527.25; m/z found, 528.2 [M+H]$^+$. $^1$H NMR (CDCl$_3$): 8.40-8.39 (m, 1H), 7.88 (dd, J=7.8, 1.8 Hz, 1H), 7.69-7.65 (m, 2H), 7.35-7.31 (m, 2H), 6.98-6.94 (m, 1H), 6.51 (s, 1H), 3.70-3.60 (m, 7H), 3.25-3.20 (m, 2H), 3.08-3.00 (m, 1H), 2.98-2.95 (m, 2H), 1.61 (s, 6H), 1.34 (d, J=6.9 Hz, 6H).

Example 175

Methyl 2-methyl-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propanoate

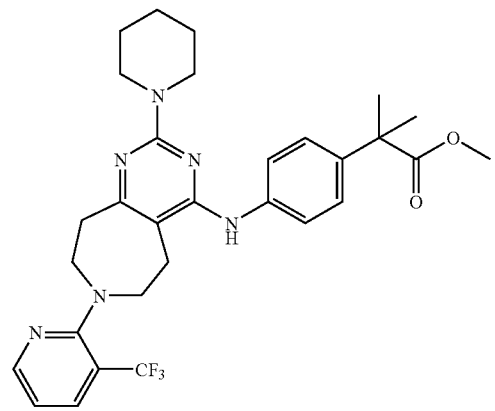 [SMILES: COC(=O)C(C)(C)c1ccc(Nc2nc(N3CCCCC3)nc3c2CCN(c2ncccc2C(F)(F)F)CC3)cc1]

MS (ESI): mass calcd. for $C_{30}H_{35}F_3N_6O_2$, 568.27; m/z found, 569.3 [M+H]$^+$. $^1$H NMR (CDCl$_3$): 8.40-8.39 (m, 1H), 7.87 (dd, J=7.8, 1.8 Hz, 1H), 7.56-7.52 (m, 2H), 7.32-7.28 (m, 2H), 6.97-6.92 (m, 1H), 6.36 (s, 1H), 3.78-3.72 (m, 4H), 3.67 (s, 3H), 3.64-3.56 (m, 4H), 3.11-3.05 (m, 2H), 2.88-2.83 (m, 2H), 1.70-1.58 (m, 12H).

Example 176

2-Pyridin-3-yl-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

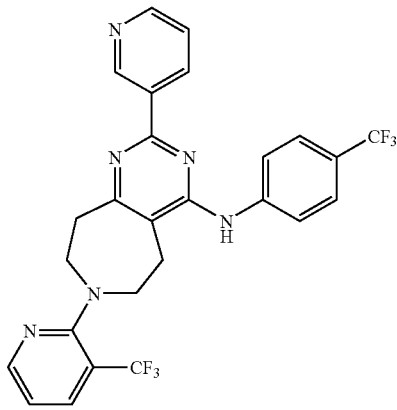 [SMILES: FC(F)(F)c1ccc(Nc2nc(-c3cccnc3)nc3c2CCN(c2ncccc2C(F)(F)F)CC3)cc1]

A microwave vial containing [2-methylsulfanyl-7-(3-trifluoromethyl-pyridin-2-yl)-6,7,8,9-tetrahydro-5H-pyrimido[4,5-d]azepin-4-yl]-(4-trifluoromethyl-phenyl)-amine (Example 53; 100 mg, 0.20 mmol), Pd$_2$(dba)$_3$ (7.3 mg, 0.008 mmol), tri-(2-furyl)phosphine (7.4 mg, 0.032 mmol), copper (I) thiophene-2-carboxylate (49 mg, 0.260 mmol), and 3-pyridyl boronic acid (27 mg, 0.22 mmol) was sealed and evacuated under N$_2$. Upon complete flushing with N$_2$, THF (3 mL) was added. The reaction mixture was stirred at 50° C. for 18 h. The reaction mixture was filtered through a plug of diatomaceous earth, concentrated, and purified directly using Preparative HPLC (conditions as in Example 54) to give the title compound (40 mg, 40%). MS (ESI): mass calcd. for C$_{26}$H$_{20}$F$_6$N$_6$, 530.17; m/z found, 531.2 [M+H]$^+$. $^1$H NMR (MeOD): 9.32-9.28 (m, 1H), 8.54-8.36 (m, 1H), 8.03 (dd, J=7.8, 1.6 Hz, 1H), 7.88 (d, J=8.0 Hz, 2H), 7.73-7.69 (m, 1H), 7.17-7.11 (m, 1H), 3.64-3.57 (m, 4H), 3.42-3.37 (m, 2H), 3.29-3.24 (m, 2H).

Example 177

2-[4-({2-Piperidin-1-yl-7-[3-(trifluoromethyl)pyridin-2-yl]-6,7,8,9-tetrahydro-5H-pyrimido[4,5-d]azepin-4-yl}amino)phenyl]propan-2-ol

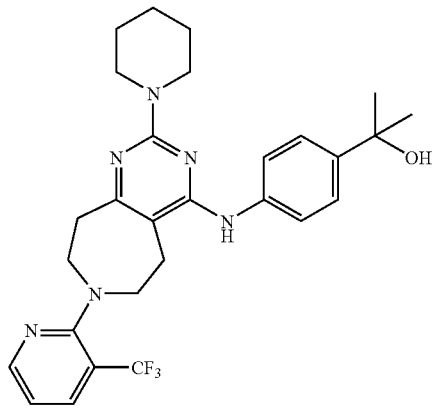 [SMILES: CC(C)(O)c1ccc(Nc2nc(N3CCCCC3)nc3c2CCN(c2ncccc2C(F)(F)F)CC3)cc1]

To a solution of methylmagnesium bromide (170 mL of a 3.0 M solution in Et$_2$O, 0.51 mmol) in THF at 0° C. was added a solution of 1-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]ethanone (Example 156; 59.8 mg, 0.117 mmol) in THF. The solution was allowed to warm to rt over 1 h, and stirred at rt for an additional 5 min. The reaction mixture was then quenched with satd. aq. NH$_4$Cl and extracted with EtOAc. The organic layers were combined, dried, and concentrated. The crude residue was purified (FCC) to give the title compound (51 mg, 83%). MS (ESI): mass calcd. for C$_{28}$H$_{33}$F$_3$N$_6$O, 526.27; m/z found, 527.3 [M+H]$^+$. $^1$H NMR (CDCl$_3$): 8.39-8.37 (m, 1H), 7.86 (dd, J=7.8, 1.8 Hz, 1H), 7.55-7.51 (m, 2H), 7.46-7.41 (m, 2H), 6.94-6.90 (m, 1H), 6.35 (s, 1H), 3.77-3.69 (m, 4H), 3.63-3.53 (m, 4H), 3.10-3.03 (m, 2H), 2.87-2.80 (m, 2H), 1.70 (s, 1H), 1.66-1.60 (m, 6H), 1.54 (s, 6H).

Example 178

2-[4-({2-(1-Methylethyl)-7-[3-(trifluoromethyl)pyridin-2-yl]-6,7,8,9-tetrahydro-5H-pyrimido[4,5-d]azepin-4-yl}amino)phenyl]propan-2-ol

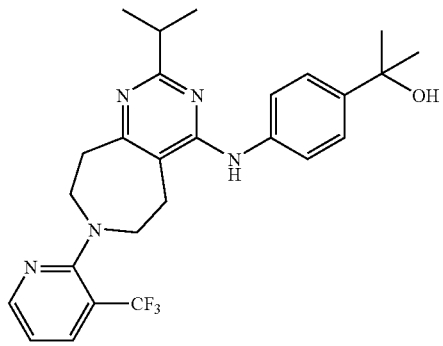 [SMILES: CC(C)c1nc2c(c(Nc3ccc(C(C)(C)O)cc3)n1)CCN(c1ncccc1C(F)(F)F)CC2]

The title compound was prepared using methods analogous to those described in Example 167, starting with 1-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]ethanone (Example 96). MS (ESI): mass calcd. for C$_{26}$H$_{30}$F$_3$N$_5$O, 485.24; m/z found, 486.2 [M+H]$^+$. $^1$H NMR (CDCl$_3$): 8.39-8.37 (m, 1H), 7.87 (dd, J=7.8, 1.8 Hz, 1H), 7.68-7.63 (m, 2H), 7.48-7.45 (m, 2H), 6.97-6.92 (m, 1H), 6.50 (s, 1H), 3.69-3.58 (m, 4H), 3.25-3.17 (m, 2H), 3.08-2.98 (m, 1H), 2.98-2.92 (m, 2H), 1.61 (s, 6H), 1.32 (d, J=6.9 Hz, 6H).

Example 179

1,1,1-Trifluoro-2-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]propan-2-ol

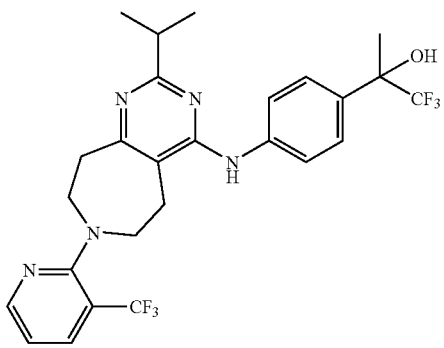 [SMILES: CC(C)c1nc2c(c(Nc3ccc(C(C)(O)C(F)(F)F)cc3)n1)CCN(c1ncccc1C(F)(F)F)CC2]

The title compound was prepared using methods analogous to those described in Example 167, starting with 2,2,2-trifluoro-1-{4-[2-isopropyl-7-(3-trifluoromethyl-pyridin-2-yl)-6,7,8,9-tetrahydro-5H-pyrimido[4,5-d]azepin-4-ylamino]-phenyl}-ethanone (prepared analogously to Example 1). MS (ESI): mass calcd. for $C_{26}H_{27}F_6N_5O$, 539.21; m/z found, 540.1 [M+H]$^+$. $^1$H NMR (CDCl$_3$): 8.41-8.40 (m, 1H), 7.89 (dd, J=7.8, 1.8 Hz, 1H), 7.77-7.73 (m, 2H), 7.59-7.54 (m, 2H), 6.99-6.95 (m, 1H), 6.58 (s, 1H), 3.71-3.60 (m, 4H), 3.27-3.21 (m, 2H), 3.09-3.02 (m, 1H), 3.01-2.96 (m, 2H), 2.42 (s, 1H), 1.82 (s, 3H), 1.34 (d, J=6.9 Hz, 6H).

Example 180

1,1,1-Trifluoro-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propan-2-ol

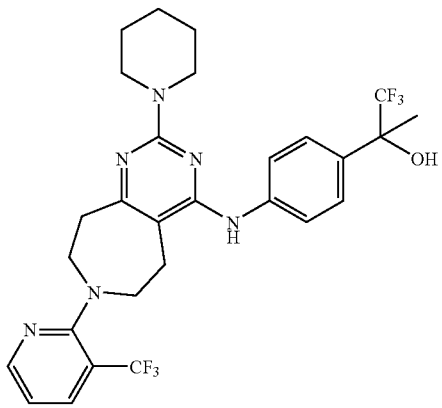 [SMILES: CC(O)(c1ccc(Nc2nc(N3CCCCC3)nc3c2CCN(c2ncccc2C(F)(F)F)CC3)cc1)C(F)(F)F]

The title compound was prepared using methods analogous to those described in Example 167, starting with 2,2,2-trifluoro-1-{4-[2-isopropyl-7-(3-trifluoromethyl-pyridin-2-yl)-6,7,8,9-tetrahydro-5H-pyrimido[4,5-d]azepin-4-ylamino]-phenyl}-ethanone (prepared analogously to Example 1). MS (ESI): mass calcd. for $C_{28}H_{30}F_6N_6O$, 580.24; m/z found, 581.3 [M+H]$^+$. $^1$H NMR (CDCl$_3$): 8.40-8.38 (m, 1H), 7.88 (dd, J=7.8, 1.8 Hz, 1H), 7.63-7.60 (m, 2H), 7.54-7.51 (m, 2H), 6.97-6.92 (m, 1H), 6.42 (s, 1H), 3.80-3.71 (m, 4H), 3.66-3.56 (m, 4H), 3.12-3.06 (m, 2H), 2.90-2.84 (m, 2H), 2.37 (s, 1H), 1.81 (s, 3H), 1.70-1.59 (m, 6H).

Example 181

2-Methyl-2-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]propan-1-ol

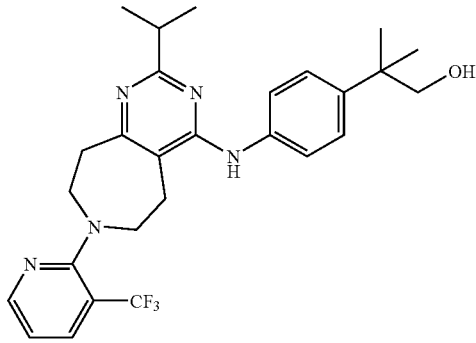 [SMILES: CC(C)c1nc2c(c(Nc3ccc(C(C)(C)CO)cc3)n1)CCN(c1ncccc1C(F)(F)F)CC2]

To a solution of methyl 2-methyl-2-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]propanoate (Example 174, 73 mg, 0.14 mmol) in THF was added LiAlH$_4$ (14.2 mg, 0.374 mmol). After stirring at rt for 4 h, the reaction mixture was quenched with satd. aq. Na$_2$SO$_4$. The reaction mixture was then filtered through a plug of diatomaceous earth and concentrated. The crude residue was purified (FCC) to give the title compound (45.4 mg, 66%). MS (ESI): mass calcd. for $C_{27}H_{32}F_3N_5O$, 499.26; m/z found, 500.3 [M+H]$^+$. $^1$H NMR (CDCl$_3$): 8.41-8.39 (m, 1H), 7.89 (dd, J=7.8, 1.8 Hz, 1H), 7.70-7.66 (m, 2H), 7.40-7.36 (m, 2H), 6.98-6.94 (m, 1H), 6.51 (s, 1H), 3.70-3.60 (m, 6H), 3.26-3.20 (m, 2H), 3.08-3.00 (m, 1H), 2.98-2.94 (m, 2H), 1.37 (s, 6H), 1.34 (d, 6.9 Hz, 6H).

Example 182

1-[4-({2-(1-Methylethyl)-7-[3-(trifluoromethyl)pyridin-2-yl]-6,7,8,9-tetrahydro-5H-pyrimido[4,5-d]azepin-4-yl}amino)phenyl]ethanol

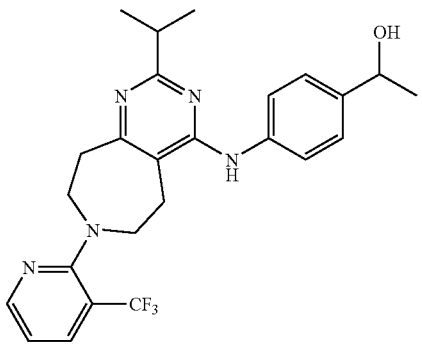 [SMILES: CC(C)c1nc2c(c(Nc3ccc(C(C)O)cc3)n1)CCN(c1ncccc1C(F)(F)F)CC2]

To a solution of 1-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]ethanone (Example 96; 37 mg, 0.079 mmol) in MeOH was added NaBH$_4$ (4.1 mg, 0.11 mmol). The mixture was stirred at rt for 4 h, then concentrated. The residue was redissolved in water and extracted with EtOAc. The organic layers were combined, dried, and concentrated. The crude residue was purified (FCC) to give the title compound (32.1 mg, 86%). MS (ESI): mass calcd. for $C_{25}H_{28}F_3N_5O$, 471.22; m/z found, 472.2 [M+H]$^+$. $^1$H NMR (CDCl$_3$): 8.40-8.38 (m, 1H), 7.87 (dd, J=7.8, 1.8 Hz, 1H), 7.67-7.64 (m, 2H), 7.38-7.34 (m, 2H), 6.97-6.92 (m, 1H), 6.51 (s, 1H), 4.93-4.88 (m, 1H), 3.69-3.60 (m, 4H), 3.24-3.18 (m, 2H), 3.06-2.98 (m, 1H), 2.98-2.94 (m, 2H), 1.76 (d, J=3.6 Hz, 1H), 1.52 (d, J=6.4 Hz, 3H), 1.31 (d, J=6.9 Hz, 6H).

Example 183

2,2,2-Trifluoro-1-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]ethanol

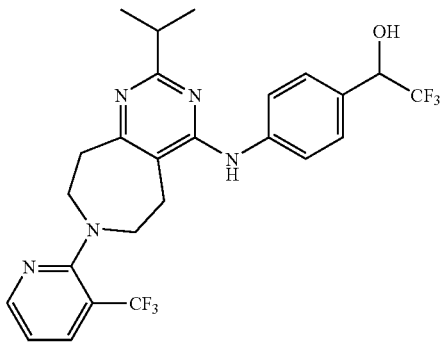 [SMILES: CC(C)c1nc2c(c(Nc3ccc(C(O)C(F)(F)F)cc3)n1)CCN(c1ncccc1C(F)(F)F)CC2]

The title compound was prepared using methods analogous to those described in Example 172, starting with 2,2,2-trifluoro-1-{4-[2-isopropyl-7-(3-trifluoromethyl-pyridin-2-yl)-6,7,8,9-tetrahydro-5H-pyrimido[4,5-d]azepin-4-ylamino]-phenyl}-ethanone (prepared analogously to Example 1). MS (ESI): mass calcd. for $C_{25}H_{25}F_6N_5O$, 525.20; m/z found, 526.1 [M+H]$^+$. $^1$H NMR (CDCl$_3$): 8.32-8.30 (m, 1H), 7.80 (dd, J=7.8, 1.8 Hz, 1H), 7.69-7.65 (m, 2H), 7.40-7.36 (m, 2H), 6.90-6.86 (m, 1H), 6.51 (s, 1H), 4.97-4.91 (m, 1H), 3.59-3.56 (m, 2H), 3.54-3.51 (m, 2H), 3.17-3.12 (m, 2H), 3.00-2.92 (m, 1H), 2.90-2.87 (m, 2H), 2.66-2.60 (m, 1H), 1.26-1.23 (m, 6H).

Example 184

2-Methyl-2-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]propanoic acid

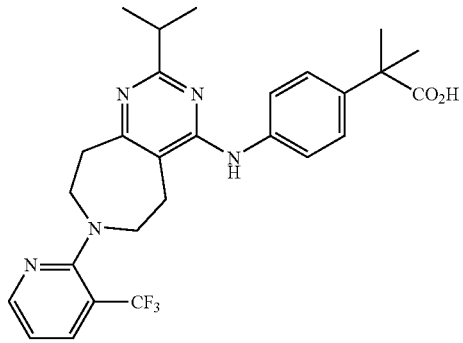 [SMILES: CC(C)c1nc2c(c(Nc3ccc(C(C)(C)C(=O)O)cc3)n1)CCN(c1ncccc1C(F)(F)F)CC2]

To a solution of methyl 2-methyl-2-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]propanoate (Example 174; 63 mg, 0.12 mmol) in 1:2 THF:H$_2$O (3 mL:6 mL) was added lithium hydroxide monohydrate (8.0 mg, 0.19 mmol). The mixture was heated at 60° C. for 5 h. The THF was removed under reduced pressure, and the resulting solution was acidified to neutral pH with 10% aq. HCl. The solution was then extracted with EtOAc. The organic layers were combined, dried, and concentrated. The crude residue was purified (FCC) to give the title compound (37 mg, 60%). MS (ESI): mass calcd. for $C_{27}H_{30}F_3N_5O_2$, 513.24; m/z found, 514.1 [M+H]$^+$. $^1$H NMR (CD$_3$OD): 8.45-8.42 (m, 1H), 8.01 (dd, J=7.9, 1.7 Hz, 1H), 7.69-7.63 (m, 2H), 7.38-7.33 (m, 2H), 7.13-7.09 (m, 1H), 3.57-3.50 (m, 4H), 3.21-3.16 (m, 2H), 3.13-3.08 (m, 2H), 3.01-2.93 (m, 1H), 1.57 (s, 6H), 1.28 (d, J=6.9 Hz, 6H).

Example 185

4-({2-(1-Methylethyl)-7-[3-(trifluoromethyl)pyridin-2-yl]-6,7,8,9-tetrahydro-5H-pyrimido[4,5-d]azepin-4-yl}amino)benzoic acid trifluoroacetic acid salt

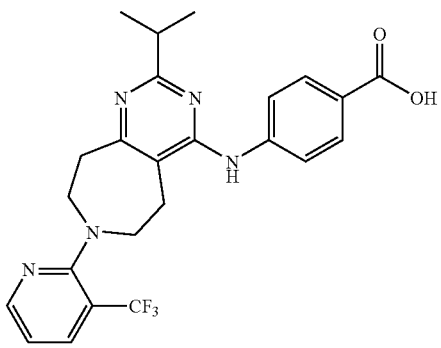 [SMILES: CC(C)c1nc2c(c(Nc3ccc(C(=O)O)cc3)n1)CCN(c1ncccc1C(F)(F)F)CC2]

The title compound was prepared using methods analogous to those described in Example 184, starting with methyl 4-({2-(1-methylethyl)-7-[3-(trifluoromethyl)pyridin-2-yl]-6,7,8,9-tetrahydro-5H-pyrimido[4,5-d]azepin-4-yl}amino)benzoate (Example 103) and purified using preparative HPLC. MS (ESI): mass calcd. for $C_{24}H_{24}F_3N_5O_2$, 471.19; m/z found, 472.1 [M+H]$^+$. $^1$H NMR (CD$_3$OD): 8.46-8.43 (m, 1H), 8.07-8.01 (m, 3H), 7.76-7.72 (m, 2H), 7.16-7.12 (m, 1H), 3.68-3.58 (m, 4H), 3.34-3.30 (m, 2H), 3.24-3.20 (m, 2H), 3.12-3.05 (m, 1H), 1.31 (d, J=6.8 Hz, 6H).

Example 186

2-Methyl-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propanoic acid

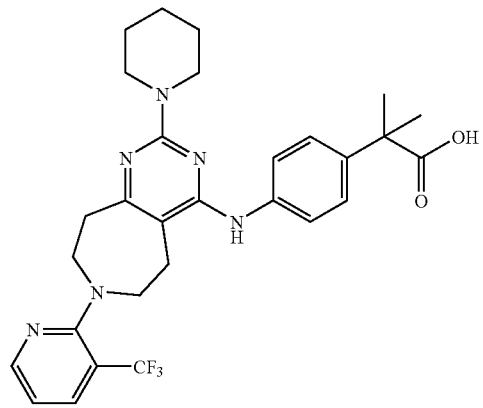 [SMILES: CC(C)(C(=O)O)c1ccc(Nc2nc(N3CCCCC3)nc3c2CCN(c2ncccc2C(F)(F)F)CC3)cc1]

The title compound was prepared using methods analogous to those described in Example 184, starting with of methyl 2-methyl-2-[4-({2-(1-methylethyl)-7-[3-(trifluoromethyl)pyridin-2-yl]-6,7,8,9-tetrahydro-5H-pyrimido[4,5-d]azepin-4-yl}amino)phenyl]propanoate (Example 174). MS (ESI): mass calcd. for $C_{29}H_{33}F_3N_6O_2$, 554.26; m/z found, 555.3 [M+H]+. 1H NMR (CDCl3): 8.39-8.37 (m, 1H), 7.86 (dd, J=7.8, 1.8 Hz, 1H), 7.56-7.52 (m, 2H), 7.37-7.32 (m, 2H), 6.95-6.90 (m, 1H), 6.35 (s, 1H), 3.76-3.70 (m, 4H), 3.62-3.54 (m, 4H), 3.07-3.03 (m, 2H), 2.85-2.80 (m, 2H), 1.68-1.56 (m, 12H).

The following Examples 187-190 were prepared using methods analogous to those described in Example 17, substituting the appropriate amidines in Step A and amines in Step E.

Example 187

2-(1-Methylethyl)-N-(5-methylpyrazin-2-yl)-7-[3-(trifluoromethyl)pyridin-2-yl]-6,7,8,9-tetrahydro-5H-pyrimido[4,5-d]azepin-4-amine hydrochloride salt

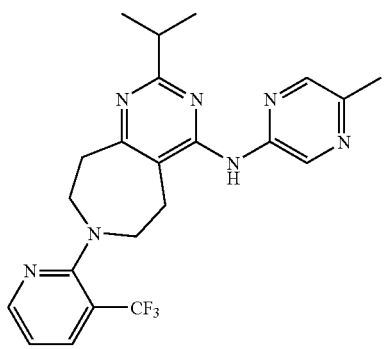 [SMILES: Cc1cnc(Nc2nc(C(C)C)nc3c2CCN(c2ncccc2C(F)(F)F)CC3)cn1]

MS (ESI): mass calcd. for $C_{22}H_{24}F_3N_7$, 443.20; m/z found, 444.1 [M+H]+. 1H NMR (CD3OD): 9.15-9.13 (m, 1H), 8.44-8.41 (m, 1H), 8.39-8.38 (m, 1H), 8.00 (dd, J=7.8, 1.6 Hz, 1H), 7.15-7.09 (m, 1H), 3.66-3.53 (m, 4H), 3.39-3.33 (m, 2H), 3.27-3.21 (m, 2H), 3.19-3.09 (m, 1H), 2.55 (s, 3H), 1.32 (d, J=6.8 Hz, 6H).

Example 188

N-[6-Chloro-5-(trifluoromethyl)pyridin-2-yl]-2-(1-methylethyl)-7-[3-(trifluoromethyl)pyridin-2-yl]-6,7,8,9-tetrahydro-5H-pyrimido[4,5-d]azepin-4-amine hydrochloride salt

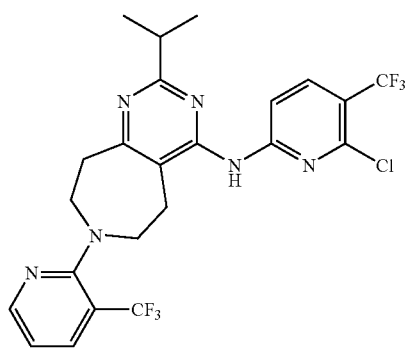 [SMILES: CC(C)c1nc2c(c(Nc3ccc(C(F)(F)F)c(Cl)n3)n1)CCN(c1ncccc1C(F)(F)F)CC2]

MS (ESI): mass calcd. for $C_{23}H_{21}ClF_6N_6$, 530.14; m/z found, 531.2 [M+H]+. 1H NMR (CDCl3): 8.57-8.52 (m, 1H), 8.47-8.44 (m, 1H), 8.18 (d, J=8.6 Hz, 1H), 8.12 (s, 1H), 7.95-7.91 (m, 1H), 7.02-7.07 (m, 1H), 4.09-3.99 (m, 1H), 3.93-3.84 (m, 2H), 3.71-3.64 (m, 4H), 3.21-3.13 (m, 2H), 1.48 (d, J=6.7 Hz, 6H).

Example 189

[2-Isopropyl-7-(3-trifluoromethyl-pyridin-2-yl)-6,7,8,9-tetrahydro-5H-pyrimido[4,5-d]azepin-4-yl]-(6-methoxy-5-trifluoromethyl-pyridin-2-yl)-amine hydrochloride salt

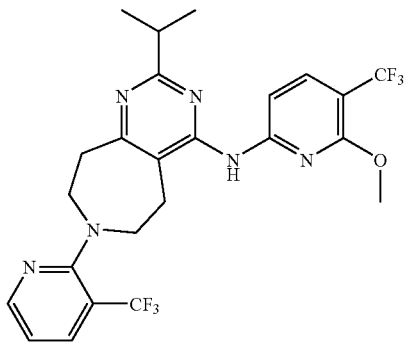 [SMILES: COc1nc(Nc2nc(C(C)C)nc3c2CCN(c2ncccc2C(F)(F)F)CC3)ccc1C(F)(F)F]

MS (ESI): mass calcd. for $C_{24}H_{24}F_6N_6O$, 526.19; m/z found, 527.2 [M+H]+. 1H NMR (CD3OD): 8.48-8.45 (m, 1H), 8.10-8.02 (m, 2H), 7.89-7.85 (m, 1H), 7.19-7.14 (m, 1H), 4.06 (s, 3H), 3.71-3.66 (m, 2H), 3.64-3.59 (m, 2H), 3.44-3.39 (m, 2H), 3.34-3.28 (m, 2H), 3.24-3.17 (m, 1H), 1.41-1.39 (m, 6H).

Example 190

2-Pyridin-4-yl-7-[3-(trifluoromethyl)pyridin-2-yl]-N-[5-(trifluoromethyl)pyridin-2-yl]-6,7,8,9-tetrahydro-5H-pyrimido[4,5-d]azepin-4-amine trifluoroacetic acid salt

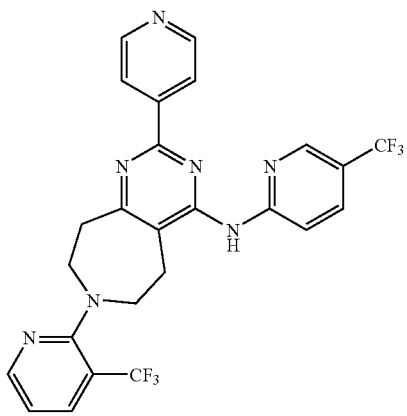 [SMILES: FC(F)(F)c1ccc(Nc2nc(-c3ccncc3)nc3c2CCN(c2ncccc2C(F)(F)F)CC3)nc1]

MS (ESI): mass calcd. for $C_{25}H_{19}F_6N_7$, 531.16; m/z found, 532.5 [M+H]+. 1H NMR (MeOD): 8.96-8.92 (m, 2H), 8.92-8.89 (m, 2H), 8.66-8.63 (m, 1H), 8.44 (dd, J=4.8, 1.4 Hz, 1H), 8.30 (d, J=8.8 Hz, 1H), 8.12 (dd, J=9.0, 2.3 Hz, 1H), 8.02 (dd, J=7.9, 1.8 Hz, 1H), 7.15-7.10 (m, 1H), 3.64-3.55 (m, 4H), 3.48-3.40 (m, 2H), 3.30-3.27 (m, 2H).

Examples 191-192 were prepared using methods analogous to those described in Example 17, substituting the appropriate amidines in Step A, amines in Step E, and substituting Pd$_2$(dba)$_3$ (5 mol %) for Pd(OAc)$_2$ and 1,2,3,4,5-pentaphenyl-1'-(di-tbutylphosphino)ferrocene (Qphos, 10 mol %) for DCPB.

Example 191

[2-Isopropyl-7-(3-trifluoromethyl-pyridin-2-yl)-6,7,8,9-tetrahydro-5H-pyrimido[4,5-d]azepin-4-yl]-(5-trifluoromethyl-pyrazin-2-yl)-amine

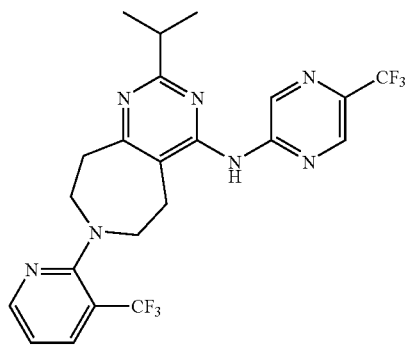 [SMILES: CC(C)c1nc2c(c(Nc3cnc(C(F)(F)F)cn3)n1)CCN(c1ncccc1C(F)(F)F)CC2]

MS (ESI): mass calcd. for C$_{22}$H$_{21}$F$_6$N$_7$, 497.18; m/z found, 498.2 [M+H]$^+$. $^1$H NMR (CDCl$_3$): 10.02-10.01 (m, 1H), 8.56-8.55 (m, 1H), 8.40-8.38 (m, 1H), 7.88 (dd, J=7.8, 1.8 Hz, 1H), 7.56 (s, 1H), 7.01-6.96 (m, 1H), 3.67-3.55 (m, 4H), 3.31-3.24 (m, 2H), 3.16-3.04 (m, 3H), 1.36 (d, J=6.9 Hz, 6H).

Example 192

[2-Piperidin-1-yl-7-(3-trifluoromethyl-pyridin-2-yl)-6,7,8,9-tetrahydro-5H-pyrimido[4,5-d]azepin-4-yl]-(5-trifluoromethyl-pyrazin-2-yl)-amine

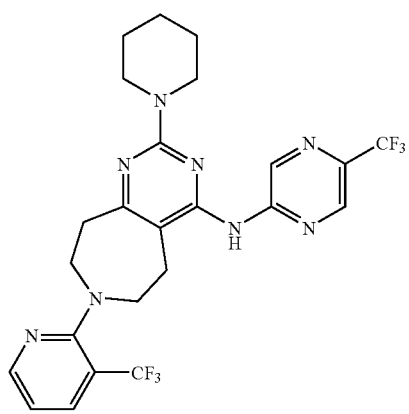 [SMILES: FC(F)(F)c1cnc(Nc2nc(N3CCCCC3)nc3c2CCN(c2ncccc2C(F)(F)F)CC3)cn1]

MS (ESI): mass calcd. for C$_{24}$H$_{24}$F$_6$N$_8$, 538.20; m/z found, 539.2 [M+H]$^+$. $^1$H NMR (CDCl$_3$): 9.76-9.73 (m, 1H), 8.56-8.54 (m, 1H), 8.42-8.40 (m, 1H), 7.89 (dd, J=7.8, 1.8 Hz, 1H), 7.43 (s, 1H), 6.99-6.95 (m, 1H), 3.81-3.75 (m, 4H), 3.62-3.53 (m, 4H), 3.15-3.09 (m, 2H), 2.98-2.92 (m, 2H), 1.75-1.58 (m, 6H).

The following Examples 193-197 were prepared using methods analogous to those described in Example 39, substituting the appropriate carboximidamidines in Step A and amines in Step C.

Example 193

2-(4-Methylpiperazin-1-yl)-7-[3-(trifluoromethyl)pyridin-2-yl]-N-[5-(trifluoromethyl)pyridin-2-yl]-6,7,8,9-tetrahydro-5H-pyrimido[4,5-d]azepin-4-amine

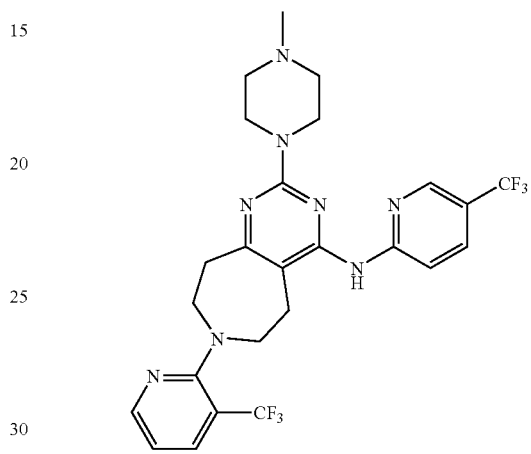

MS (ESI): mass calcd. for C$_{25}$H$_{26}$F$_6$N$_8$, 552.22; m/z found, 553.2 [M+H]$^+$. $^1$H NMR (CDCl$_3$): 8.50-8.48 (m, 1H), 8.41-8.38 (m, 2H), 7.90-7.86 (m, 2H), 7.44 (s, 1H), 6.97-6.94 (m, 1H), 3.86-3.79 (m, 4H), 3.58-3.52 (m, 4H), 3.13-3.08 (m, 2H), 2.95-2.91 (m, 2H), 2.51-2.47 (m, 4H), 2.35 (s, 3H).

Example 194

2-Azepan-1-yl-7-[3-(trifluoromethyl)pyridin-2-yl]-N-[5-(trifluoromethyl)pyridin-2-yl]-6,7,8,9-tetrahydro-5H-pyrimido[4,5-d]azepin-4-amine

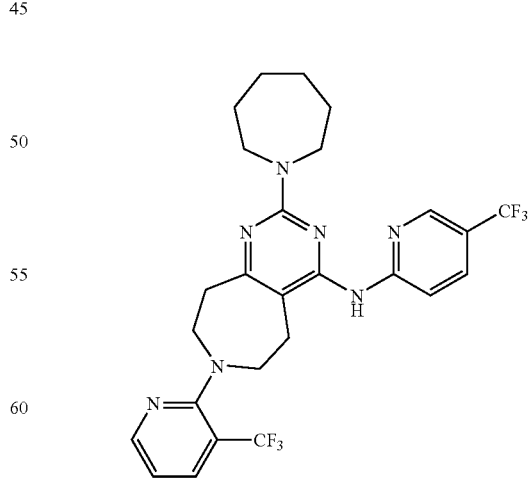

MS (ESI): mass calcd. for C$_{26}$H$_{27}$F$_6$N$_7$, 551.22; m/z found, 552.2 [M+H]$^+$. $^1$H NMR (CDCl$_3$): 8.80 (d, J=8.8 Hz, 1H), 8.49-8.48 (m, 1H), 8.40-8.38 (m, 1H), 7.88-7.84 (m, 2H), 7.44 (s, 1H), 6.96-6.92 (m, 1H), 3.81-3.72 (m, 4H), 3.59-3.52 (m, 4H), 3.12-3.08 (m, 2H), 2.94-2.90 (m, 2H), 1.84-1.78 (m, 4H), 1.59-1.55 (m, 4H).

Example 195

N²-[2-(Dimethylamino)ethyl]-N²-methyl-7-[3-(trifluoromethyl)pyridin-2-yl]-N⁴-[5-(trifluoromethyl)pyridin-2-yl]-6,7,8,9-tetrahydro-5H-pyrimido[4,5-d]azepine-2,4-diamine

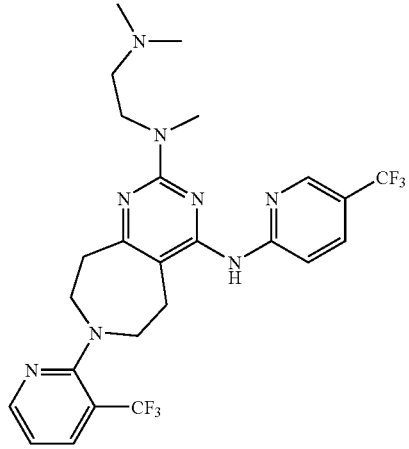 [SMILES: CN(C)CCN(C)c1nc2c(c(Nc3ccc(C(F)(F)F)cn3)n1)CCN(c1ncccc1C(F)(F)F)CC2]

MS (ESI): mass calcd. for C$_{25}$H$_{28}$F$_6$N$_8$, 554.23; m/z found, 555.2 [M+H]$^+$. $^1$H NMR (CDCl$_3$): 8.56 (d, J=8.9 Hz, 1H), 8.49-8.48 (m, 1H), 8.40-8.38 (m, 1H), 7.87 (dd, J=7.8, 1.8 Hz, 1H), 7.84-7.82 (m, 1H), 7.45 (s, 1H), 6.96-6.94 (m, 1H), 3.79-3.73 (m, 2H), 3.57-3.52 (m, 4H), 3.19 (s, 3H), 3.11-3.09 (m, 2H), 2.93-2.90 (m, 2H), 2.55-2.50 (m, 2H), 2.30 (s, 6H).

Example 196

N²-Methyl-N²-[2-(methyloxy)ethyl]-7-[3-(trifluoromethyl)pyridin-2-yl]-N²-[5-(trifluoromethyl)pyridin-2-yl]-6,7,8,9-tetrahydro-5H-pyrimido[4,5-d]azepine-2,4-diamine

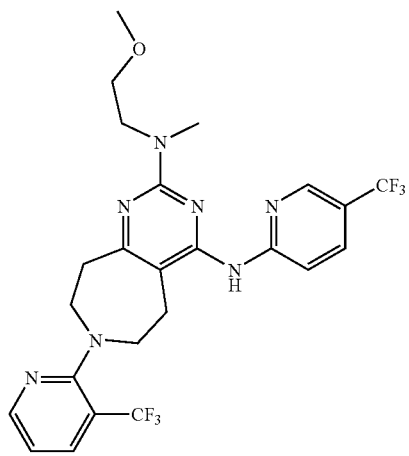 [SMILES: COCCN(C)c1nc2c(c(Nc3ccc(C(F)(F)F)cn3)n1)CCN(c1ncccc1C(F)(F)F)CC2]

MS (ESI): mass calcd. for C$_{24}$H$_{25}$F$_6$N$_7$O, 541.20; m/z found, 542.1 [M+H]$^+$. $^1$H NMR (CDCl$_3$): 8.55 (d, J=8.8 Hz, 1H), 8.49-8.48 (m, 1H), 8.40-8.39 (m, 1H), 7.88-7.84 (m, 2H), 7.46 (s, 1H), 6.97-6.94 (m, 1H), 3.84-3.80 (m, 2H), 3.64-3.61 (m, 2H), 3.56-3.53 (m, 4H), 3.38 (s, 3H), 3.23 (s, 3H), 3.11-3.09 (m, 2H), 2.93-2.91 (m, 2H).

Example 197

2-Azetidin-1-yl-7-[3-(trifluoromethyl)pyridin-2-yl]-N-[5-(trifluoromethyl)pyridin-2-yl]-6,7,8,9-tetrahydro-5H-pyrimido[4,5-d]azepin-4-amine trifluoroacetic acid salt

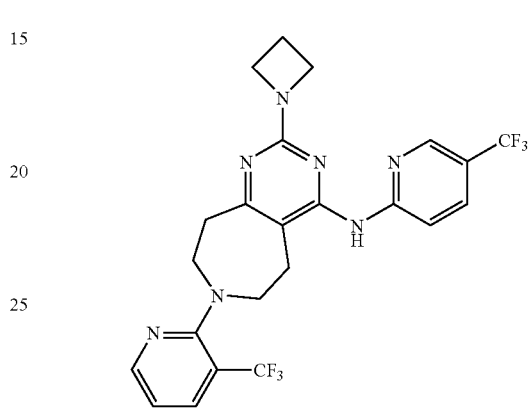

MS (ESI): mass calcd. for C$_{23}$H$_{21}$F$_6$N$_7$, 509.18; m/z found, 510.5 [M+H]$^+$. $^1$H NMR (MeOD): 8.69 (s, 1H), 8.47-8.42 (m, 1H), 8.41 (d, J=8.8 Hz, 1H), 8.14 (dd, J=8.9, 2.3 Hz, 1H), 8.02 (dd, J=7.8, 1.7 Hz, 1H), 7.16-7.11 (m, 1H), 4.37-4.32 (m, 4H), 3.63-3.58 (m, 2H), 3.55-3.51 (m, 2H), 3.29-3.24 (m, 2H), 3.15-3.10 (m, 2H), 2.57-2.48 (m, 2H).

The following Examples 198-201 were prepared using reduction methods analogous to those described in International Publication No. WO2005/117890:

Example 198

N-{2-(1-Methylethyl)-7-[3-(trifluoromethyl)pyridin-2-yl]-6,7,8,9-tetrahydro-5H-pyrimido[4,5-d]azepin-4-yl}benzene-1,4-diamine trifluoroacetic acid salt

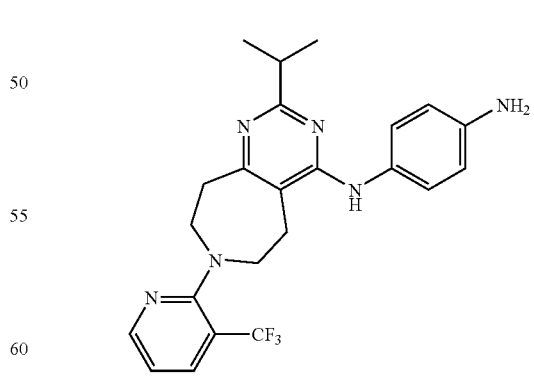

The title compound was prepared from 2-(1-methylethyl)-N-(4-nitrophenyl)-7-[3-(trifluoromethyl)pyridin-2-yl]-6,7,8,9-tetrahydro-5H-pyrimido[4,5-d]azepin-4-amine (Example 136). MS (ESI): mass calcd. for C$_{23}$H$_{25}$F$_3$N$_6$, 442.21; m/z found, 443.1 [M+H]$^+$. $^1$H NMR (CD$_3$OD): 8.38-8.36 (m, 1H), 7.97-7.94 (m, 1H), 7.59-7.53 (m, 2H), 7.27-7.19 (m, 2H), 7.10-7.06 (m, 1H), 3.60-3.51 (m, 4H), 3.27-3.24 (m, 2H), 3.14-3.11 (m, 2H), 3.03-2.96.(m, 1H), 1.20 (d, J=6.8 Hz, 6H).

Example 199

4-(1,1-Dimethylethyl)-N1-{2-(1-methylethyl)-7-[3-(trifluoromethyl)pyridin-2-yl]-6,7,8,9-tetrahydro-5H-pyrimido[4,5-d]azepin-4-yl}benzene-1,3-diamine

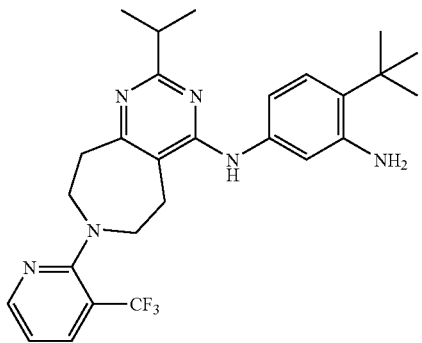 [SMILES: CC(C)c1nc2c(c(Nc3ccc(C(C)(C)C)c(N)c3)n1)CCN(c1ncccc1C(F)(F)F)CC2]

The title compound was prepared from N-[4-(1,1-dimethylethyl)-3-nitrophenyl]-2-(1-methylethyl)-7-[3-(trifluoromethyl)pyridin-2-yl]-6,7,8,9-tetrahydro-5H-pyrimido[4,5-d]azepin-4-amine (Example 143). MS (ESI): mass calcd. for $C_{27}H_{33}F_3N_6$, 498.27; m/z found, 499.2 [M+H]$^+$. $^1$H NMR (CDCl$_3$): 8.31-8.29 (m, 1H), 7.80-7.78 (m, 1H), 7.21 (d, J=2.3 Hz, 1H), 7.10 (d, J=8.5 Hz, 1H), 6.87-6.84 (m, 1H), 6.82 (dd, J=8.5, 2.3 Hz, 1H), 6.31 (s, 1H), 3.82-3.70 (brs, 2H), 3.59-3.51 (m, 4H), 3.16-3.10 (m, 2H), 3.02-2.91 (m, 1H), 2.87-2.82 (m, 2H), 1.35 (s, 9H), 1.26 (d, J=6.9 Hz, 6H).

Example 200

4-(1,1-Dimethylethyl)-N1-{2-piperidin-1-yl-7-[3-(trifluoromethyl)pyridin-2-yl]-6,7,8,9-tetrahydro-5H-pyrimido[4,5-d]azepin-4-yl}benzene-1,3-diamine

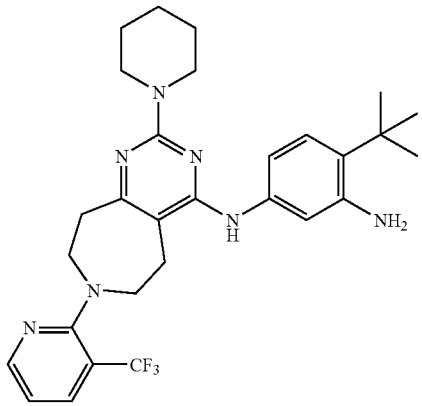 [SMILES: CC(C)(C)c1ccc(Nc2nc(N3CCCCC3)nc3c2CCN(c2ncccc2C(F)(F)F)CC3)cc1N]

The title compound was prepared from N-[4-(1,1-dimethylethyl)-3-nitrophenyl]-2-piperidin-1-yl-7-[3-(trifluoromethyl)pyridin-2-yl]-6,7,8,9-tetrahydro-5H-pyrimido[4,5-d]azepin-4-amine (Example 159). MS (ESI): mass calcd. for $C_{29}H_{36}F_3N_7$, 539.30; m/z found, 540.3 [M+H]$^+$. $^1$H NMR (CDCl$_3$): 8.40-8.38 (m, 1H), 7.87 (dd, J=7.8, 1.8 Hz, 1H), 7.16 (d, J=8.5 Hz, 1H), 7.08 (d, J=2.3 Hz, 1H), 6.95-6.91 (m, 1H), 6.85 (dd, J=2.3, 8.5 Hz, 1H), 6.24 (s, 1H), 3.83-3.74 (m, 6H), 3.63-3.56 (m, 4H), 3.10-3.05 (m, 2H), 2.85-2.80 (m, 2H), 1.70-1.59 (m, 6H), 1.43 (s, 9H).

Example 201

7-[5-Amino-3-(trifluoromethyl)pyridin-2-yl]-N-[4-(1,1-dimethylethyl)phenyl]-2-(1-methylethyl)-6,7,8,9-tetrahydro-5H-pyrimido[4,5-d]azepin-4-amine

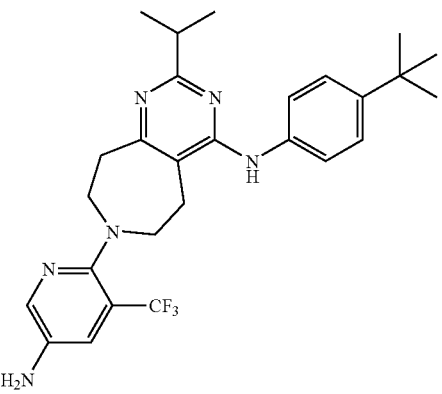 [SMILES: CC(C)c1nc2c(c(Nc3ccc(C(C)(C)C)cc3)n1)CCN(c1ncc(N)cc1C(F)(F)F)CC2]

The title compound was prepared from N-[4-(1,1-dimethylethyl)phenyl]-2-(1-methylethyl)-7-[5-nitro-3-(trifluoromethyl)pyridin-2-yl]-6,7,8,9-tetrahydro-5H-pyrimido[4,5-d]azepin-4-amine (Example 290). MS (ESI): mass calcd. for $C_{27}H_{33}F_3N_6$, 498.27; m/z found, 499.5 [M+H]$^+$. $^1$H NMR (CDCl$_3$): 7.99-7.95 (m, 1H), 7.63-7.56 (m, 2H), 7.38-7.32 (m, 2H), 7.26-7.24 (m, 1H), 6.48 (s, 1H), 3.75-3.68 (m, 2H), 3.25-3.18 (m, 4H), 3.19-3.12 (m, 2H), 3.08-2.97 (m, 1H), 2.91-2.84 (m, 2H), 1.61-1.48 (m, 9H), 1.35-1.30 (m, 6H).

The following Examples 202-206 were prepared using methods analogous to those described in Example 52, substituting the appropriate amidines in Step A and amines in Step C.

Example 202

N-[4-(1,1-Dimethylethyl)phenyl]-2-(methylsulfanyl)-7-[3-(trifluoromethyl)pyridin-2-yl]-6,7,8,9-tetrahydro-5H-pyrimido[4,5-d]azepin-4-amine

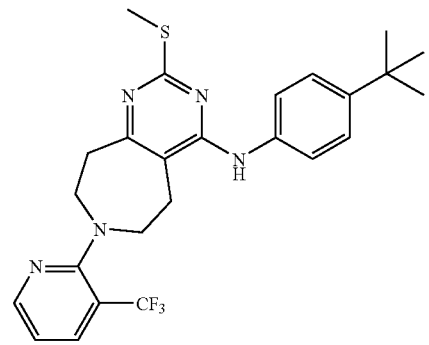 [SMILES: CSc1nc2c(c(Nc3ccc(C(C)(C)C)cc3)n1)CCN(c1ncccc1C(F)(F)F)CC2]

MS (ESI): mass calcd. for $C_{25}H_{28}F_3N_5S$, 487.20; m/z found, 488.1 [M+H]$^+$. $^1$H NMR (CDCl$_3$): 8.40-8.37 (m, 1H), 7.88-7.86 (m, 1H), 7.51-7.47 (m, 2H), 7.36-7.34 (m, 2H), 6.97-6.93 (m, 1H), 6.48 (s, 1H), 3.65-3.62 (m, 2H), 3.60-3.57 (m, 2H), 3.18-3.14 (m, 2H), 2.94-2.90 (m, 2H), 2.52 (s, 3H), 1.33 (s, 9H).

Example. 203

N-[2-Chloro-4-(trifluoromethyl)phenyl]-2-(methylsulfanyl)-7-[3-(trifluoromethyl)pyridin-2-yl]-6,7,8,9-tetrahydro-5H-pyrimido[4,5-d]azepin-4-amine

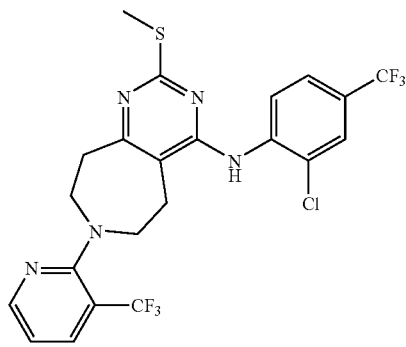 [SMILES: CSc1nc2c(c(Nc3ccc(C(F)(F)F)cc3Cl)n1)CCN(c1ncccc1C(F)(F)F)CC2]

MS (ESI): mass calcd. for $C_{22}H_{18}ClF_6N_5S$, 533.09; m/z found, 534.1 [M+H]$^+$. $^1$H NMR (DMSO): 9.48 (s, 1H), 9.16-9.14 (m, 1H), 8.74-8.71 (m, 1H), 8.60 (d, J=2.0 Hz, 1H), 8.48 (d, J=8.5 Hz, 1H), 8.41-8.39 (m, 1H), 7.81-7.78 (m, 1H), 4.20-4.17 (m, 4H), 3.78-3.72 (m, 4H), 2.91 (s, 3H).

Example 204

2-(Methylsulfanyl)-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

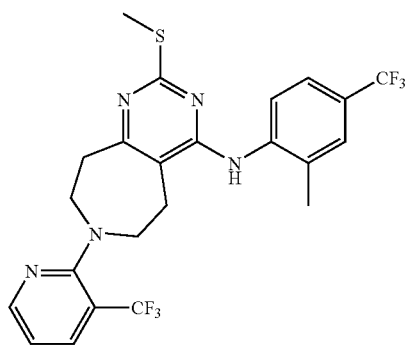 [SMILES: CSc1nc2c(c(Nc3ccc(C(F)(F)F)cc3C)n1)CCN(c1ncccc1C(F)(F)F)CC2]

MS (ESI): mass calcd. for $C_{23}H_{21}F_6N_5S$, 513.14; m/z found, 514 [M+H]$^+$. $^1$H NMR (CDCl$_3$): 8.38 (dd, J=4.7, 1.5 Hz, 1H), 8.08 (d, J=8.6 Hz, 1H), 7.88 (dd, J=7.8, 1.8 Hz, 1H), 7.49-7.44 (m, 2H), 6.99-6.92 (m, 1H), 6.42 (bs, 1H), 3.68-3.62 (m, 2H), 3.62-3.54 (m, 2H), 3.21-3.15 (m, 2H), 2.98-2.92 (m, 2H), 2.45 (s, 3H), 2.36 (s, 3H).

Example 205

2-(Methylsulfanyl)-N-(1-methyl-1,2,3,4-tetrahydroquinolin-7-yl)-7-[3-(trifluoromethyl)pyridin-2-yl]-6,7,8,9-tetrahydro-5H-pyrimido[4,5-d]azepin-4-amine

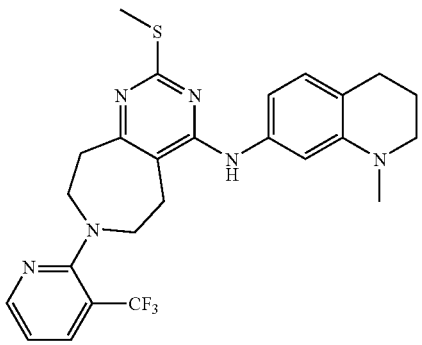 [SMILES: CSc1nc2c(c(Nc3ccc4c(c3)N(C)CCC4)n1)CCN(c1ncccc1C(F)(F)F)CC2]

MS (ESI): mass calcd. for $C_{25}H_{27}F_3N_6S$, 500.20; m/z found, 501 [M+H]$^+$. $^1$H NMR (CDCl$_3$): 8.38 (dd, J=4.7, 1.5 Hz, 1H), 7.86 (dd, J=7.8, 1.8 Hz, 1H), 6.97-6.91 (m, 1H), 6.89 (d, J=7.9 Hz, 1H), 6.78 (d, J=2.0 Hz, 1H), 6.74 (dd, J=7.9, 2.1 Hz, 1H), 6.41 (bs, 1H), 3.66-3.61 (m, 2H), 3.61-3.55 (m, 2H), 3.23 (t, J=5.6 Hz, 2H), 3.19-3.11 (m, 2H), 2.93-2.83 (m, 2H), 2.89 (s, 3H), 2.73 (t, J=6.4 Hz, 2H), 2.52 (s, 3H), 2.03-1.93 (m, 2H).

Example 206

2-(Methylsulfanyl)-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine

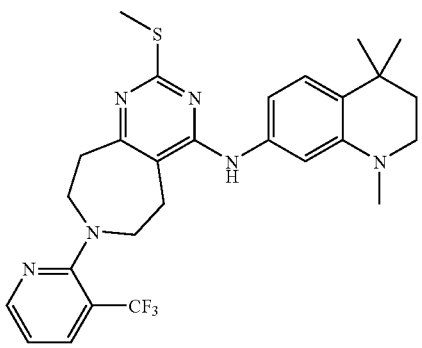 [SMILES: CSc1nc2c(c(Nc3ccc4c(c3)N(C)CCC4(C)C)n1)CCN(c1ncccc1C(F)(F)F)CC2]

MS (ESI): mass calcd. for $C_{27}H_{31}F_3N_6S$, 528.23; m/z found, 529 [M+H]$^+$. $^1$H NMR (CDCl$_3$): 8.38 (dd, J=4.7, 1.5 Hz, 1H), 7.86 (dd, J=7.8, 1.8 Hz, 1H), 7.12 (d, J=8.2 Hz, 1H), 6.93 (dd, J=7.4, 4.7 Hz, 1H), 6.84-6.78 (m, 2H), 6.41 (bs, 1H), 3.66-3.61 (m, 2H), 3.61-3.55 (m, 2H), 3.27-3.21 (m, 2H), 3.17-3.11 (m, 2H), 2.93-2.86 (m, 2H), 2.91 (s, 3H), 2.53 (s, 3H), 1.78-1.72 (m, 2H), 1.28 (s, 6H).

Examples 207-211 synthesized in a manner similar to Example 53 substituting the appropriate amines in Step C of Example 52.

Example 207

N-[4-(1,1-Dimethylethyl)phenyl]-2-(methylsulfonyl)-7-[3-(trifluoromethyl)pyridin-2-yl]-6,7,8,9-tetrahydro-5H-pyrimido[4,5-d]azepin-4-amine

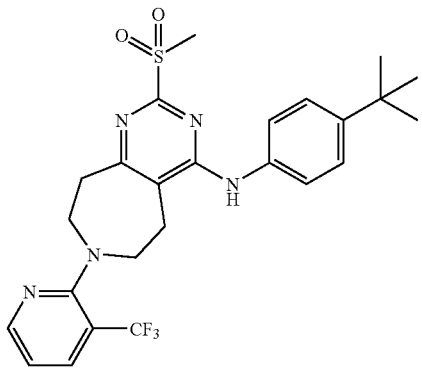 [SMILES: CC(C)(C)c1ccc(Nc2nc(S(C)(=O)=O)nc3c2CCN(c2ncccc2C(F)(F)F)CC3)cc1]

The title compound was prepared starting with N-[4-(1,1-dimethylethyl)phenyl]-2-(methylsulfanyl)-7-[3-(trifluoromethyl)pyridin-2-yl]-6,7,8,9-tetrahydro-5H-pyrimido[4,5-d]azepin-4-amine (Example 202). MS (ESI): mass calcd. for $C_{25}H_{28}F_3N_5O_2S$, 519.19; m/z found, 520.2 [M+H]$^+$. $^1$H NMR (CDCl$_3$): 8.40-8.38 (m, 1H), 7.88 (dd, J=7.8, 1.8 Hz, 1H), 7.49-7.45 (m, 2H), 7.41-7.38 (m, 2H), 7.00-6.96 (m, 1H), 6.77 (s, 1H), 3.72-3.67 (m, 2H), 3.64-3.59 (m, 2H), 3.36-3.31 (m, 2H), 3.25 (s, 3H), 3.07-3.02 (m, 2H), 1.33 (s, 9H).

Example 208

2-(Methylsulfonyl)-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine

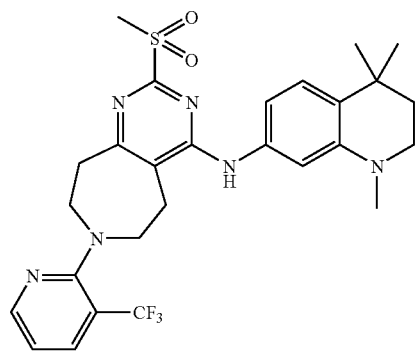 [SMILES: CN1CCC(C)(C)c2ccc(Nc3nc(S(C)(=O)=O)nc4c3CCN(c3ncccc3C(F)(F)F)CC4)cc21]

The title compound was prepared starting with 2-(methylsulfanyl)-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine (Example 206). MS (ESI): mass calcd. for $C_{27}H_{31}F_3N_6O_2S$, 560.22; m/z found, 561 [M+H]$^+$. $^1$H NMR (CDCl$_3$): 8.57 (d, J=2.2 Hz, 0.6 H), 8.51 (d, J=2.0 Hz, 0.4H), 8.43-8.37 (m, 1H), 8.07-7.94 (m, 1H), 7.91-7.85 (m, 1H), 7.30-7.20 (m, 1H), 7.02-6.95 (m, 1H), 5.75-5.40 (m, 1H), 3.93-3.78 (m, 2H), 3.68-3.47 (m, 7H), 3.44-3.21 (m, 4H), 2.90 (s, 1.5 H), 2.87 (s, 1.5H), 2.05-1.90 (m, 2H), 1.39 (s, 3H), 1.37 (s, 1.5H), 1.35 (s, 1.5H).

Example 209

2-(Methylsulfonyl)-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

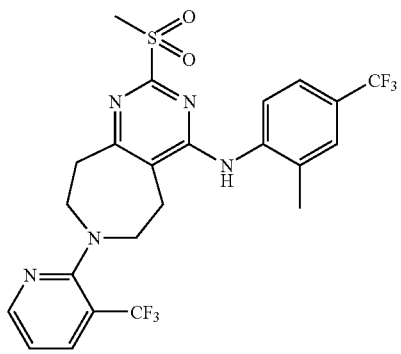 [SMILES: Cc1cc(C(F)(F)F)ccc1Nc1nc(S(C)(=O)=O)nc2c1CCN(c1ncccc1C(F)(F)F)CC2]

The title compound was prepared starting with 2-(methylsulfanyl)-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine (Example 204). MS (ESI): mass calcd. for $C_{23}H_{21}F_6N_5O_2S$, 545.13; m/z found, 546 [M+H]$^+$. $^1$H NMR (CDCl$_3$): 8.38 (dd, J=4.6, 1.4 Hz, 1H), 7.96 (d, J=8.2 Hz, 1H), 7.89 (dd, J=7.8, 1.8 Hz, 1H), 7.55-7.48 (m, 2H), 7.00 (dd, J=7.4, 4.7 Hz, 1H), 6.71 (bs, 1H), 3.74-3.67 (m, 2H), 3.66-3.59 (m, 2H), 3.38-3.32 (m, 2H), 3.20 (s, 3H), 3.11-3.05 (m, 2H), 2.37 (s, 3H).

Example 210

2-(1-Methylethyl)-N-[4-(methylsulfonyl)phenyl]-7-[3-(trifluoromethyl)pyridin-2-yl]-6,7,8,9-tetrahydro-5H-pyrimido[4,5-d]azepin-4-amine

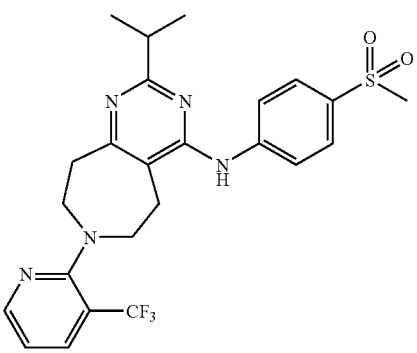 [SMILES: CC(C)c1nc2c(c(Nc3ccc(S(C)(=O)=O)cc3)n1)CCN(c1ncccc1C(F)(F)F)CC2]

The title compound was prepared starting with 2-(1-methylethyl)-N-[4-(methylsulfanyl)phenyl]-7-[3-(trifluoromethyl)pyridin-2-yl]-6,7,8,9-tetrahydro-5H-pyrimido[4,5-d]azepin-4-amine (Example 135). MS (ESI): mass calcd. for $C_{24}H_{26}F_3N_5O_2S$, 505.18; m/z found, 506.4 [M+H]$^+$. $^1$H NMR (CDCl$_3$): 8.40-8.37 (m, 1H), 7.92-7.86 (m, 5H), 6.99-6.94 (m, 1H), 6.77 (s, 1H), 3.69-3.57 (m, 4H), 3.28-3.21 (m, 2H), 3.11-3.04 (m, 4H), 3.02-2.99 (m, 2H), 1.33 (d, J=6.9 Hz, 6H).

Example 211

Methyl 5-chloro-6-[2-(methylsulfonyl)-4-{[4-(trifluoromethyl)phenyl]amino}MM-5,6,8,9-tetrahydro-7H-pyrimido[4,5-d]azepin-7-yl]pyridine-3-carboxylate

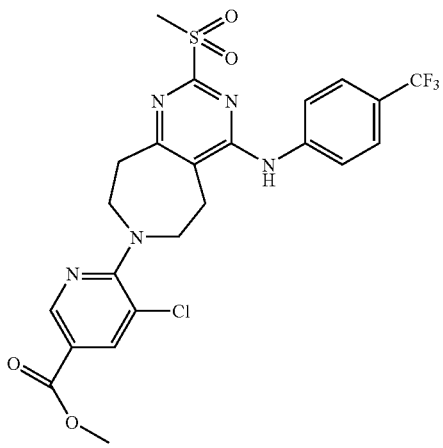 [SMILES: COC(=O)c1cnc(N2CCc3nc(S(C)(=O)=O)nc(Nc4ccc(C(F)(F)F)cc4)c3CC2)c(Cl)c1]

The title compound was prepared starting from methyl 5-chloro-6-[2-(methylsulfanyl)-4-{[4-(trifluoromethyl)phenyl]amino}-5,6,8,9-tetrahydro-7H-pyrimido[4,5-d]azepin-7-yl]pyridine-3-carboxylate (Example 303). MS (ESI): mass calcd. for $C_{23}H_{21}ClF_3N_5O_4S$, 555.10; m/z found, 556.1 [M+H]+. 1H NMR (CD3OD): 8.50 (d, J=2.00 Hz, 1H), 7.96 (d, J=2.00 Hz, 1H), 7.54 (d, J=8.55 Hz, 2H), 7.44 (d, J=8.64 Hz, 2H), 6.93 (s, 1H), 3.86-3.71 (m, 4H), 3.70 (s, 3H), 3.26-3.11 (m, 2H), 3.02-2.95 (m, 2H).

The following Examples 212-277 were prepared using methods analogous to those described in Example 55, substituting the appropriate amines.

Example 212

2-(1,1-Dioxido-1,2-thiazinan-2-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

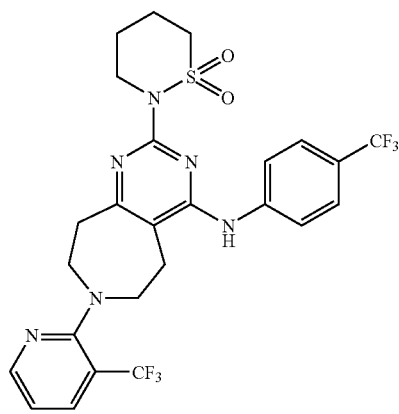 [SMILES: O=S1(=O)CCCCN1c1nc2c(c(Nc3ccc(C(F)(F)F)cc3)n1)CCN(c1ncccc1C(F)(F)F)CC2]

MS (ESI): mass calcd. for $C_{25}H_{24}F_6N_6O_2S$, 586.16; m/z found, 587.5 [M+H]+. 1H NMR (CDCl3): 9.89-9.69 (m, 1H), 8.49-8.34 (m, 1H), 7.92 (d, J=7.0 Hz, 1H), 7.68-7.54 (m, 4H), 7.05 (dd, J=7.6, 4.7 Hz, 1H), 4.15-4.08 (m, 2H), 3.68-3.52 (m, 4H), 3.43-3.34 (m, 2H), 3.28-3.08 (m, 4H), 2.39-2.23 (m, 2H), 1.82-1.65 (m, 2H).

Example 213

N²-[2-(Methyloxy)ethyl]-N -[4-(trifluoromethyl)phenyl]-7-[3-(trifluoromethyl)pyridin-2-yl]-6,7,8,9-tetrahydro-5H-pyrimido[4,5-d]azepine-2,4-diamine trifluoroacetic acid salt

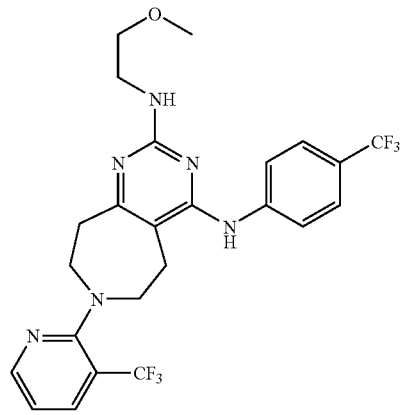 [SMILES: COCCNc1nc2c(c(Nc3ccc(C(F)(F)F)cc3)n1)CCN(c1ncccc1C(F)(F)F)CC2]

MS (ESI): mass calcd. for $C_{24}H_{24}F_6N_6O$, 526.19; m/z found, 527.5 [M+H]+. 1H NMR (CD3OD): 8.45 (dd, J=4.7, 1.4 Hz, 1H), 8.02 (dd, J=7.8, 1.8 Hz, 1H), 7.79 (d, J=8.5 Hz, 2H), 7.69 (d, J=8.6 Hz, 2H), 7.14 (dd, J=7.7, 4.8 Hz, 1H), 3.65-3.59 (m, 2H), 3.58-3.47 (m, 6H), 3.33-3.31 (m, 3H), 3.20-3.15 (m, 2H), 3.11-3.07 (m, 2H).

Example 214

2-[3-(Methyloxy)piperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

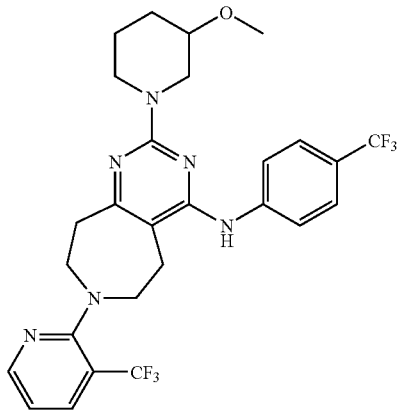 [SMILES: COC1CCCN(c2nc3c(c(Nc4ccc(C(F)(F)F)cc4)n2)CCN(c2ncccc2C(F)(F)F)CC3)C1]

MS (ESI): mass calcd. for $C_{27}H_{28}F_6N_6O$, 566.22; m/z found, 567.6 [M+H]⁺. ¹H NMR (CD₃OD): 8.47-8.43 (m, 1H), 8.03 (dd, J=7.8, 1.7 Hz, 1H), 7.71 (s, 4H), 7.17-7.10 (m, 1H), 3.91-3.67 (m, 3H), 3.65-3.50 (m, 5H), 3.43-3.36 (m, 1H), 3.29-3.26 (m, 2H), 3.20 (s, 3H), 3.12-3.07 (m, 2H), 1.95-1.73 (m, 3H), 1.61-1.50 (m, 1H).

Example 215

2-{(2S)-2-[(Methyloxy)methyl]pyrrolidin-1-yl}-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

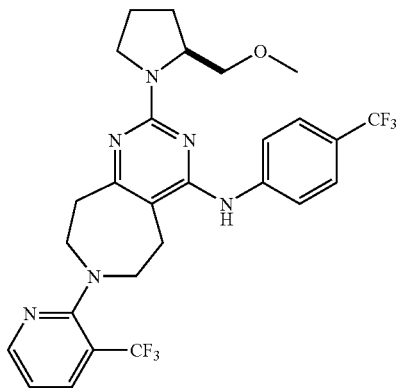 [SMILES: COC[C@@H]1CCCN1c1nc2c(c(Nc3ccc(C(F)(F)F)cc3)n1)CCN(c1ncccc1C(F)(F)F)CC2]

MS (ESI): mass calcd. for $C_{27}H_{28}F_6N_6O$, 566.22; m/z found, 567.6 [M+H]⁺. ¹H NMR (CD₃OD): 8.46-8.43 (m, 1H), 8.03 (dd, J=7.8, 1.7 Hz, 1H), 7.80 (d, J=8.5 Hz, 2H), 7.69 (d, J=8.6 Hz, 2H), 7.14 (dd, J=7.8, 4.8 Hz, 1H), 4.34-4.25 (m, 1H), 3.66-3.37 (m, 9H), 3.29-3.20 (m, 4H), 3.14-3.07 (m, 2H), 2.23-1.90 (m, 4H).

Example 216

N²(Furan-2-ylmethyl)-N²-methyl-N⁴-[4-(trifluoromethyl)phenyl]-7-[3-(trifluoromethyl)pyridin-2-yl]-6,7,8,9-tetrahydro-5H-pyrimido[4,5-d]azepine-2,4-diamine trifluoroacetic acid salt

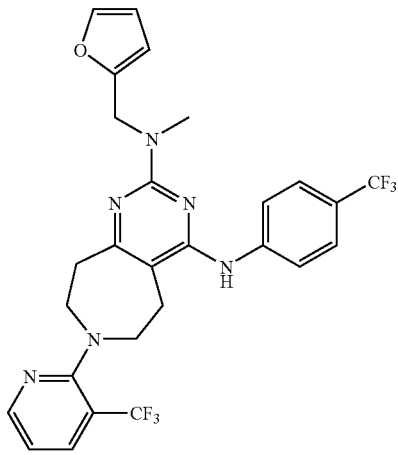 [SMILES: CN(Cc1ccco1)c1nc2c(c(Nc3ccc(C(F)(F)F)cc3)n1)CCN(c1ncccc1C(F)(F)F)CC2]

MS (ESI): mass calcd. for $C_{27}H_{24}F_6N_6O$, 562.19; m/z found, 563.5 [M+H]⁺. ¹H NMR (CD₃OD): 8.46-8.43 (m, 1H), 8.03 (dd, J=7.8, 1.7 Hz, 1H), 7.74 (d, J=8.6 Hz, 2H), 7.66 (d, J=8.7 Hz, 2H), 7.50-7.46 (m, 1H), 7.14 (dd, J=7.8, 4.8 Hz, 1H), 6.37 (dd, J=3.2, 1.9 Hz, 1H), 6.17 (d, J=2.5 Hz, 1H), 4.76 (s, 2H), 3.65-3.58 (m, 2H), 3.58-3.53 (m, 2H), 3.34-3.30 (m, 2H), 3.21 (s, 3H), 3.14-3.09 (m, 2H).

Example 217

2-Azetidin-1-yl-7-[3-(trifluoromethyl)pyridin-2-yl]-N-[6-(trifluoromethyl)pyridin-3-yl]-6,7,8,9-tetrahydro-5H-pyrimido[4,5-d]azepin-4-amine

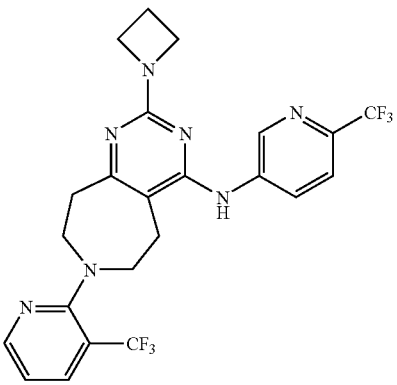 [SMILES: FC(F)(F)c1ccc(Nc2nc(N3CCC3)nc3c2CCN(c2ncccc2C(F)(F)F)CC3)cn1]

MS (ESI): mass calcd. for $C_{23}H_{21}F_6N_7$, 509.18; m/z found, 510.1 [M+H]⁺. ¹H NMR (DMSO): 9.07 (d, J=2.4 Hz, 1H), 8.89 (s, 1H), 8.45 (dd, J=4.7, 1.5 Hz, 1H), 8.43 (dd, J=8.7, 2.4 Hz, 1H), 8.03 (dd, J=7.8, 1.8 Hz, 1H), 7.77 (d, J=8.7 Hz, 1H), 7.10 (dd, J=7.6, 4.7 Hz, 1H), 3.97 (t, J=7.4 Hz, 4H), 3.45-3.38 (m, 4H), 3.00-2.96 (m, 4H), 2.27-2.22 (m, 2H).

Example 218

N²,N²-Dimethyl-7-[3-(trifluoromethyl)pyridin-2-yl]-N⁴-{[6-(trifluoromethyl)pyridin-3-yl]methyl}-6,7,8,9-tetrahydro-5H-pyrimido[4,5-d]azepine-2,4-diamine trifluoroacetic acid salt

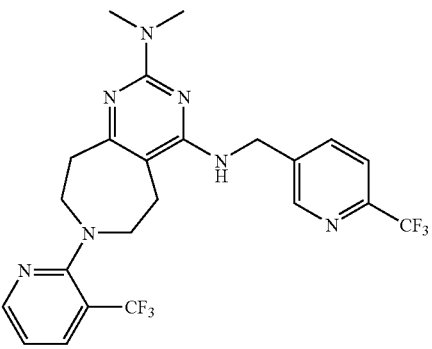 [SMILES: CN(C)c1nc2c(c(NCc3ccc(C(F)(F)F)nc3)n1)CCN(c1ncccc1C(F)(F)F)CC2]

MS (ESI): mass calcd. for $C_{23}H_{23}F_6N_7$, 511.19; m/z found, 512.4 [M+H]⁺. ¹H NMR (MeOD): 8.69 (d, J=1.6 Hz, 1H), 8.40 (dd, J=4.8, 1.5 Hz, 1H), 8.02-7.96 (m, 2H), 7.77 (d, J=8.0

Hz, 1H), 7.10 (dd, J=7.5, 4.7 Hz, 1H), 4.80 (s, 2H), 3.60-3.55 (m, 2H), 3.54-3.49 (m, 2H), 3.24-3.20 (m, 2H), 3.13 (s, 6H), 2.96-2.93 (m, 2H).

Example 219

N²-[2-(Dimethylamino)ethyl]-N²-methyl-N⁴-[4-(trifluoromethyl)phenyl]-7-[3-(trifluoromethyl)pyridin-2-yl]-6,7,8,9-tetrahydro-5H-pyrimido[4,5-d]azepine-2,4-diamine trifluoroacetic acid salt

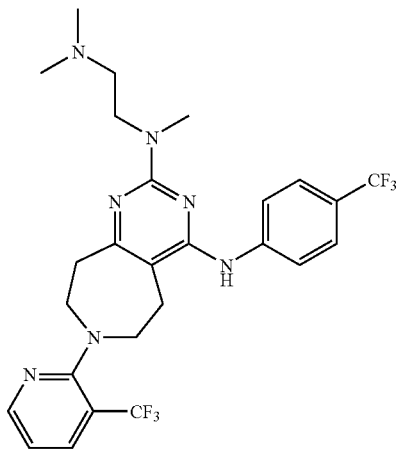 [SMILES: CN(C)CCN(C)c1nc2c(c(Nc3ccc(C(F)(F)F)cc3)n1)CCN(c1ncccc1C(F)(F)F)CC2]

MS (ESI): mass calcd. for $C_{26}H_{29}F_6N_7$, 553.24; m/z found, 554.2 [M+H]⁺. ¹H NMR (MeOD): 8.48-8.45 (m, 1H), 8.04 (dd, J=7.9, 1.7 Hz, 1H), 7.78 (d, J=8.6 Hz, 2H), 7.67 (d, J=8.4 Hz, 2H), 7.19-7.12 (m, 1H), 3.93 (t, J=6.1 Hz, 2H), 3.63-3.59 (m, 2H), 3.58-3.53 (m, 2H), 3.36-3.31 (m, 2H), 3.29-3.24 (m, 2H), 3.23 (s, 3H), 3.12-3.08 (m, 2H), 2.57 (s, 6H).

Example 220

2-(4-Methylpiperazin-1-yl)-7-[3-(trifluoromethyl)pyridin-2-yl]-N-[6-(trifluoromethyl)pyridin-3-yl]-6,7,8,9-tetrahydro-5H-pyrimido[4,5-d]azepin-4-amine

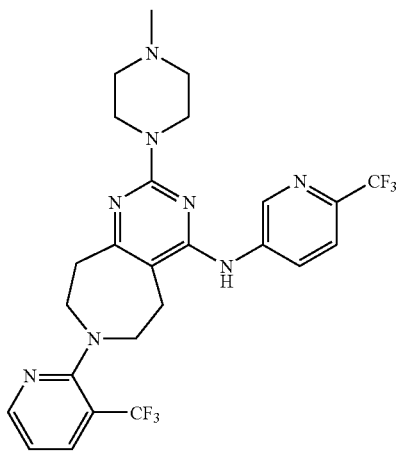 [SMILES: CN1CCN(c2nc3c(c(Nc4ccc(C(F)(F)F)nc4)n2)CCN(c2ncccc2C(F)(F)F)CC3)CC1]

MS (ESI): mass calcd. for $C_{25}H_{26}F_6N_8$, 552.22; m/z found, 553.5 [M+H]⁺. ¹H NMR (CDCl₃): 8.86 (d, J=2.4 Hz, 1H), 8.40-8.37 (m, 1H), 8.14 (dd, J=8.4, 2.3 Hz, 1H), 7.87 (dd, J=7.8, 1.8 Hz, 1H), 7.65 (d, J=8.6 Hz, 1H), 6.98-6.93 (m, 1H), 6.55 (s, 1H), 3.82-3.75 (m, 4H), 3.63-3.53 (m, 4H), 3.14-3.05 (m, 2H), 2.95-2.87 (m, 2H), 2.50-2.43 (m, 4H), 2.34 (s, 3H).

Example 221

N-[3-Chloro-4-(trifluoromethyl)phenyl]-2-(4-methylpiperazin-1-yl)-7-[3-(trifluoromethyl)pyridin-2-yl]-6,7,8,9-tetrahydro-5H-pyrimido[4,5-d]azepin-4-amine

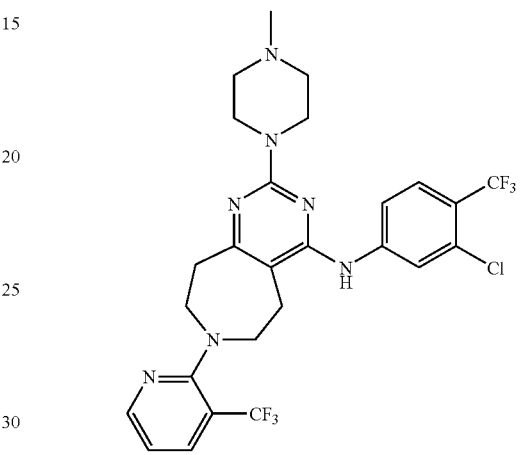

MS (ESI): mass calcd. for $C_{26}H_{26}ClF_6N_7$, 585.18; m/z found, 586.5 [M+H]⁺. ¹H NMR (CDCl₃): 8.38 (dd, J=4.6, 1.5 Hz, 1H), 8.01 (d, J=1.9 Hz, 1H), 7.87 (dd, J=7.8, 1.8 Hz, 1H), 7.59 (d, J=8.7 Hz, 1H), 7.37-7.31 (m, 1H), 6.95 (dd, J=7.5, 4.9 Hz, 1H), 6.53 (s, 1H), 3.84-3.77 (m, 4H), 3.62-3.52 (m, 4H), 3.13-3.03 (m, 2H), 2.90-2.83 (m, 2H), 2.51-2.46 (m, 4H), 2.35 (s, 3H).

Example 222

2-Azepan-1-yl-N-[4-(trifluoromethyl)phenyl]-7-[3-(trifluoromethyl)pyridin-2-yl]-6,7,8,9-tetrahydro-5H-pyrimido[4,5-d]azepin-4-amine

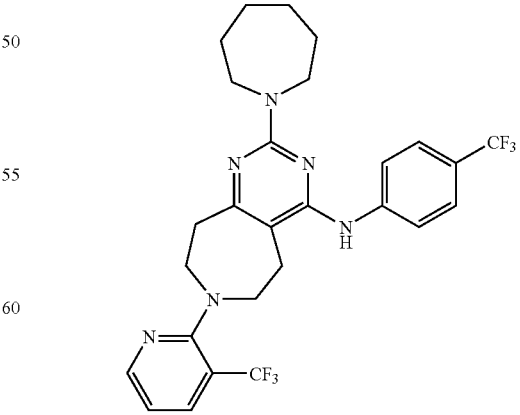

MS (ESI): mass calcd. for $C_{27}H_{28}F_6N_6$, 550.23; m/z found, 551.5 [M+H]⁺. ¹H NMR (CDCl₃): 8.39-8.36 (m, 1H), 7.86

(dd, J=7.8, 1.8 Hz, 1H), 7.72 (d, J=8.5 Hz, 2H), 7.54 (d, J=8.6 Hz, 2H), 6.93 (dd, J=7.5, 4.9 Hz, 1H), 6.50 (s, 1H), 3.78-3.67 (m, 4H), 3.63-3.53 (m, 4H), 3.12-3.01 (m, 2H), 2.89-2.83 (m, 2H), 1.83-1.74 (m, 4H), 1.65-1.47 (m, 4H).

Example 223

2-Azepan-1-yl-7-[3-(trifluoromethyl)pyridin-2-yl]-N-[6-(trifluoromethyl)pyridin-3-yl]-6,7,8,9-tetrahydro-5H-pyrimido[4,5-d]azepin-4-amine

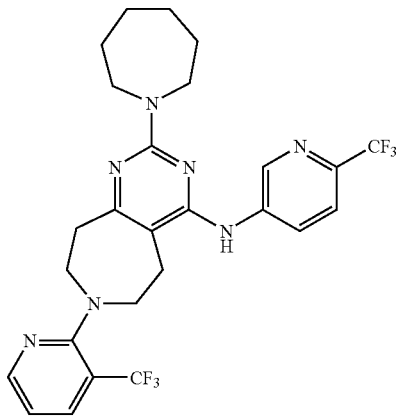 [SMILES: FC(F)(F)c1ccc(Nc2nc(N3CCCCCC3)nc3c2CCN(c2ncccc2C(F)(F)F)CC3)cn1]

MS (ESI): mass calcd. for $C_{26}H_{27}F_6N_7$, 551.22; m/z found, 552.5 [M+H]$^+$. $^1$H NMR (CDCl$_3$): 8.78 (d, J=2.5 Hz, 1H), 8.40-8.34 (m, 2H), 7.87 (dd, J=7.8, 1.8 Hz, 1H), 7.62 (d, J=8.7 Hz, 1H), 6.97-6.91 (m, 1H), 6.54 (s, 1H), 3.76-3.68 (m, 4H), 3.63-3.52 (m, 4H), 3.13-3.05 (m, 2H), 2.93-2.87 (m, 1H), 1.83-1.72 (m, 4H), 1.60-1.49 [(m, 4H) coincidental with water peak].

Example 224

2-Azepan-1-yl-N-[3-chloro-4-(trifluoromethyl)phenyl]-7-[3-(trifluoromethyl)pyridin-2-yl]-6,7,8,9-tetrahydro-5H-pyrimido[4,5-d]azepin-4-amine

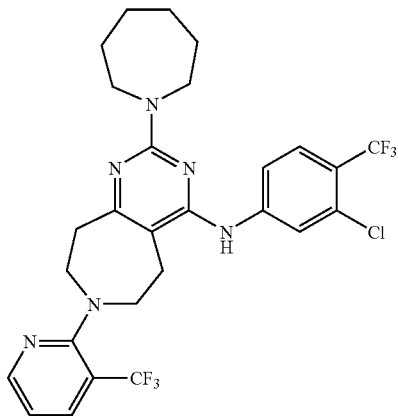 [SMILES: FC(F)(F)c1ccc(Nc2nc(N3CCCCCC3)nc3c2CCN(c2ncccc2C(F)(F)F)CC3)cc1Cl]

MS (ESI): mass calcd. for $C_{27}H_{27}ClF_6N_6$, 584.19; m/z found, 585.5 [M+H]$^+$. $^1$H NMR (CDCl$_3$): 8.39-8.36 (m, 1H), 8.25 (d, J=1.9 Hz, 1H), 7.86 (dd, J=7.8, 1.8 Hz, 1H), 7.56 (d, J=8.7 Hz, 1H), 7.32-7.28 (m, 1H), 6.96-6.91 (m, 1H), 6.52 (s, 1H), 3.80-3.68 (m, 4H), 3.62-3.52 (m, 4H), 3.12-3.03 (m, 2H), 2.89-2.83 (m, 2H), 1.86-1.76 (m, 4H), 1.61-1.50 [(m, 4H) coincidental with water peak].

Example 225

$N^2$-[2-(Dimethylamino)ethyl]-$N^2$-methyl-7-[3-(trifluoromethyl)pyridin-2-yl]-$N^4$-[6-(trifluoromethyl)pyridin-3-yl]-6,7,8,9-tetrahydro-5H-pyrimido[4,5-d]azepine-2,4-diamine

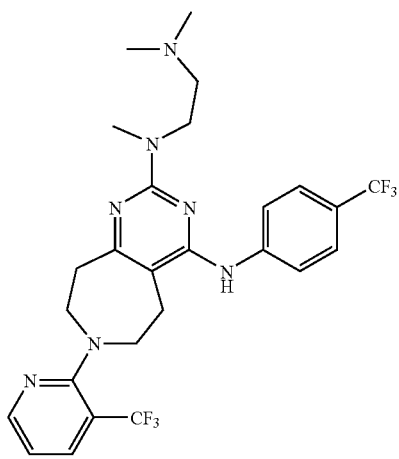 [SMILES: CN(C)CCN(C)c1nc2c(c(Nc3ccc(C(F)(F)F)cc3)n1)CCN(c1ncccc1C(F)(F)F)CC2]

MS (ESI): mass calcd. for $C_{25}H_{28}F_6N_8$, 554.23; m/z found, 555.5 [M+H]$^+$. $^1$H NMR (CDCl$_3$): 8.77 (s, 1H), 8.40-8.37 (m, 1H), 8.36-8.32 (m, 1H), 7.87 (dd, J=7.8, 1.8 Hz, 1H), 7.61 (d, J=8.6 Hz, 1H), 6.98-6.92 (m, 1H), 6.54 (s, 1H), 3.78-3.67 (m, 2H), 3.63-3.52 (m, 4H), 3.15 (s, 3H), 3.12-3.06 (m, 2H), 2.94-2.87 (m, 2H), 2.54-2.46 (m, 2H), 2.28 (s, 6H).

Example 226

$N^4$-[3-Chloro-4-(trifluoromethyl)phenyl]-$N^2$-[2-(dimethylamino)ethyl]-$N^2$-methyl-7-[3-(trifluoromethyl)pyridin-2-yl]-6,7,8,9-tetrahydro-5H-pyrimido[4,5-d]azepine-2,4-diamine

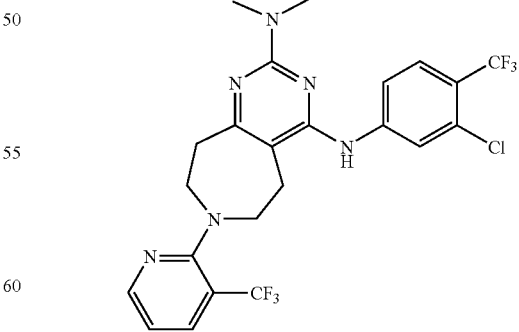

MS (ESI): mass calcd. for $C_{26}H_{28}ClF_6N_7$, 587.20; m/z found, 588.5 [M+H]$^+$. $^1$H NMR (CDCl$_3$): 8.38 (dd, J=4.6, 1.4 Hz, 1H), 8.02 (s, 1H), 7.87 (dd, J=7.8, 1.8 Hz, 1H), 7.57 (d, J=8.7 Hz, 1H), 7.43 (d, J=8.6 Hz, 1H), 6.94 (dd, J=7.4, 4.9 Hz, 1H), 6.53 (s, 1H), 3.78-3.69 (m, 2H), 3.61-3.49 (m, 4H), 3.17 (s, 3H), 3.11-3.05 (m, 2H), 2.89-2.82 (m, 2H), 2.54-2.48 (m, 2H), 2.28 (s, 6H).

Example 227

N$^4$-[(3,4-Dichlorophenyl)methyl]-N$^2$-[2-(dimethylamino)ethyl]-N$^2$-methyl-7-[3-(trifluoromethyl)pyridin-2-yl]-6,7 8,9-tetrahydro-5H-pyrimido[4,5-d]azepine-2,4-diamine trifluoroacetic acid salt

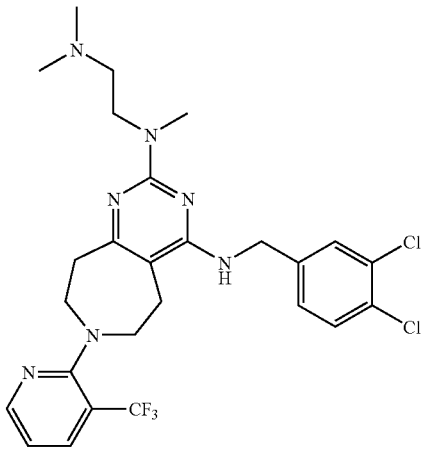 [SMILES: CN(C)CCN(C)c1nc2c(c(NCc3ccc(Cl)c(Cl)c3)n1)CCN(c1ncccc1C(F)(F)F)CC2]

MS (ESI): mass calcd. for $C_{26}H_{30}Cl_2F_3N_7$, 567.19; m/z found, 568.5 [M+H]$^+$. $^1$H NMR (MeOD): 8.42 (dd, J=4.7, 1.4 Hz, 1H), 8.01 (dd, J=7.8, 1.8 Hz, 1H), 7.51 (d, J=8.3 Hz, 1H), 7.47-7.44 (m, 1.H), 7.22 (dd, J=8.3, 2.1 Hz, 1H), 7.14-7.08 (m, 1H), 4.73 (s, 2H), 4.00-3.93 (m, 2H), 3.62-3.58 (m, 2H), 3.57-3.52 (m, 2H), 3.29-3.22 (m, 2H), 3.21 (s, 3H), 3.01-2.96 (m, 2H), 2.78 (s, 6H).

Example 228

N$^2$-Methyl-N$^2$-[2-(methyloxy)ethyl]-7-[3-(trifluoromethyl)pyridin-2-yl]-N$^4$-[6-(trifluoromethyl)pyridin-3-yl]-6,7,8 9-tetrahydro-5H-pyrimido[4,5-d]azepine-2,4-diamine trifluoroacetic acid salt

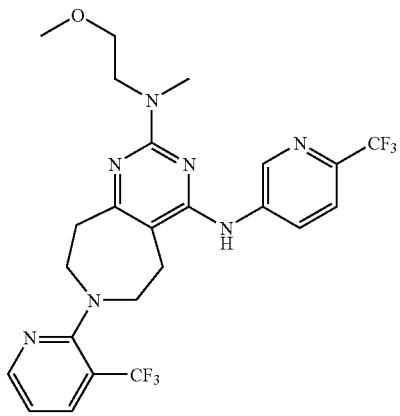 [SMILES: COCCN(C)c1nc2c(c(Nc3ccc(C(F)(F)F)nc3)n1)CCN(c1ncccc1C(F)(F)F)CC2]

MS (ESI): mass calcd. for $C_{24}H_{25}F_6N_7O$, 541.20; m/z found, 542.5 [M+H]$^+$. $^1$H NMR (MeOD): 8.47-8.44 (m, 1H), 8.26 (dd, J=8.5, 2.2 Hz, 1H), 8.03 (dd, J=7.8, 1.7 Hz, 1H), 7.86 (d, J=8.6 Hz, 1H), 7.18-7.12 (m, 1H), 3.79 (t, J=5.1 Hz, 2H), 3.65-3.53 (m, 6H), 3.32 (s, 3H), 3.32-3.29 (m, 2H), 3.23 (s, 3H), 3.15-3.11 (m, 2H).

Example 229

N$^4$-[3-Chloro-4-(trifluoromethyl)phenyl]-N$^2$-methyl-N$^2$-[2-(methyloxy)ethyl]-7-[3-(trifluoromethyl)pyridin-2-yl]-6,7,8,9-tetrahydro-5H-pyrimido[4,5-d]azepine-2,4-diamine trifluoroacetic acid salt

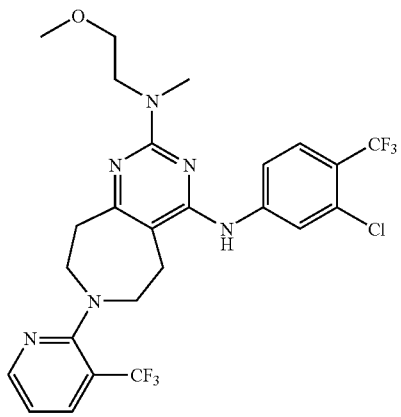 [SMILES: COCCN(C)c1nc2c(c(Nc3ccc(C(F)(F)F)c(Cl)c3)n1)CCN(c1ncccc1C(F)(F)F)CC2]

MS (ESI): mass calcd. for $C_{25}H_{25}ClF_6N_6O$, 574.17; m/z found, 575.5 [M+H]$^+$. $^1$H NMR (MeOD): 8.45 (dd, J=4.7, 1.3 Hz, 1H), 8.05 (d, J=1.8 Hz, 1H), 8.03 (dd, J=7.9, 1.7 Hz, 1H), 7.80-7.76 (m, 1H), 7.64 (d, J=8.7 Hz, 1H), 7.18-7.11 (m, 1H), 3.86-3.79 (m, 2H), 3.65-3.58 (m, 4H), 3.56-3.51 (m, 2H), 3.34 (s, 3H), 3.33-3.30 (m, 2H), 3.25 (s, 3H), 3.12-3.07 (m, 2H).

Example 230

N$^4$-[(3,4-Dichlorophenyl)methyl]-N$^2$-methyl-N$^2$-[2-(methyloxy)ethyl]-7-[3-(trifluoromethyl)pyridin-2yl]-6,7,8,9-tetrahydro-5H-pyrimido[4,5-d]azepine-2,4-diamine trifluoroacetic acid salt

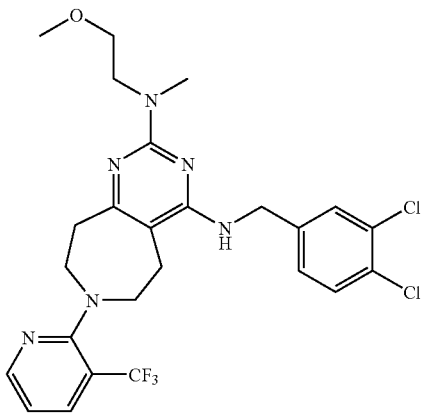 [SMILES: COCCN(C)c1nc2c(c(NCc3ccc(Cl)c(Cl)c3)n1)CCN(c1ncccc1C(F)(F)F)CC2]

MS (ESI): mass calcd. for $C_{25}H_{27}Cl_2F_3N_6O$, 554.16; m/z found, 554.2 [M+H]$^+$. $^1$H NMR (MeOD): 8.42-8.39 (m, 1H), 8.00 (dd, J=7.8, 1.7 Hz, 1H), 7.46 (d, J=8.3 Hz, 1H), 7.44-7.42 (m, 1H), 7.21 (dd, J=8.3, 2.0 Hz, 1H), 7.12-7.07 (m, 1H), 4.62 (s, 2H), 3.70 (t, J=5.1 Hz, 2H), 3.61-3.57 (m, 2H), 3.56-3.50 (m, 2H), 3.38-3.32 (m, 2H), 3.25 (s, 3H), 3.24-3.19 (m, 2H), 3.15 (s, 3H), 2.98-2.93 (m, 2H).

Example 231

2-Azetidin-1-yl-N-[3-chloro-4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

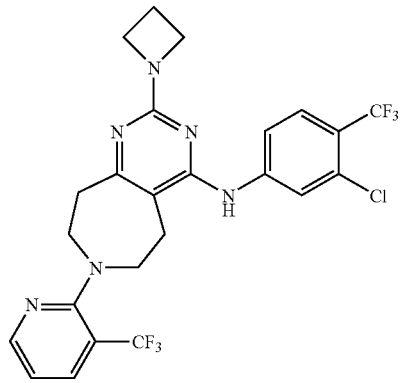 [SMILES: FC(F)(F)c1ccc(Nc2nc(N3CCC3)nc3c2CCN(c2ncccc2C(F)(F)F)CC3)cc1Cl]

MS (ESI): mass calcd. for C$_{24}$H$_{21}$ClF$_6$N$_6$, 542.14; m/z found, 543.5 [M+H]$^+$. $^1$H NMR (MeOD): 8.46-8.43 (m, 1H), 8.16-8.13 (m, 1H), 8.02 (dd, J=7.8, 1.8 Hz, 1H), 7.76-7.73 (m, 2H), 7.16-7.11 (m, 1H), 4.30 (t, J=7.7 Hz, 4H), 3.62-3.58 (m, 2H), 3.55-3.49 (m, 2H), 3.27-3.21 (m, 2H), 3.12-3.07 (m, 2H), 2.55-2.45 (m, 2H).

Example 232

2-Azetidin-1-yl-N-[(3,4-dichlorophenyl)methyl]-7-[3-(trifluoromethyl)pyridin-2-yl]-6,7,8,9-tetrahydro-5H-pyrimido[4,5-d]azepin-4-amine trifluoroacetic acid salt

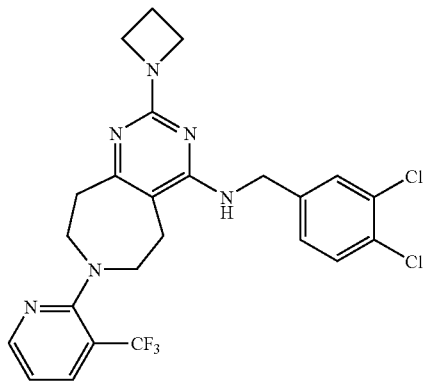 [SMILES: FC(F)(F)c1cccnc1N1CCc2nc(N3CCC3)nc(NCc3ccc(Cl)c(Cl)c3)c2CC1]

MS (ESI): mass calcd. for C$_{24}$H$_{23}$Cl$_2$F$_3$N$_6$, 522.13; m/z found, 523.5 [M+H]$^+$. $^1$H NMR (MeOD): 8.43-8.35 (m, 1H), 7.98 (dd, J=7.8, 1.7 Hz, 1H), 7.50-7.42 (m, 2H), 7.27-7.20 (m, 1H), 7.11-7.05 (m, 1H), 4.62-4.55 (m, 2H), 4.23-4.13 (m, 4H), 3.61-3.53 (m, 2H), 3.51-3.46 (m, 2H), 3.16-3.09 (m, 2H), 2.94-2.86 (m, 2H), 2.49-2.37 (m, 2H).

Example 233

N-[3-Chloro-4-(trifluoromethyl)phenyl]-2-piperidin-1-yl-7-[3-(trifluoromethyl)pyridin-2-yl]-6,7,8,9-tetrahydro-5H-pyrimido[4,5-d]azepin-4-amine trifluoroacetic acid salt

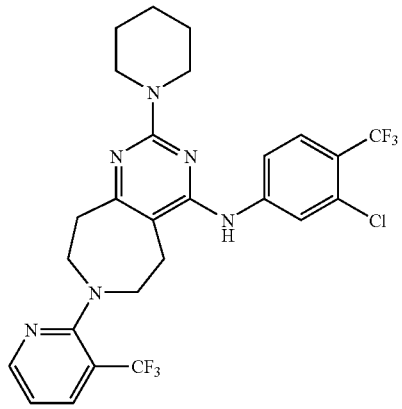 [SMILES: FC(F)(F)c1ccc(Nc2nc(N3CCCCC3)nc3c2CCN(c2ncccc2C(F)(F)F)CC3)cc1Cl]

MS (ESI): mass calcd. for C$_{26}$H$_{25}$ClF$_6$N$_6$, 570.17; m/z found, 571.5 [M+H]$^+$. $^1$H NMR (MeOD): 8.47-8.44 (m, 1H), 8.06-7.98 (m, 2H), 7.79 (d, J=8.7 Hz, 1H), 7.62 (dd, J=8.6, 1.3 Hz, 1H), 7.18-7.12 (m, 1H), 3.79-3.71 (m, 4H), 3.63-3.56 (m, 2H), 3.56-3.51 (m, 2H), 3.32-3.25 (m, 2H), 3.12-3.07 (m, 2H), 1.81-1.66 (m, 6H).

Example 234

2-Piperidin-1-yl-7-[3-(trifluoromethyl)pyridin-2-yl]-N-[6-(trifluoromethyl)pyridin-3-yl]-6,7,8,9-tetrahydro-5H-pyrimido[4,5-d]azepin-4-amine trifluoroacetic acid salt

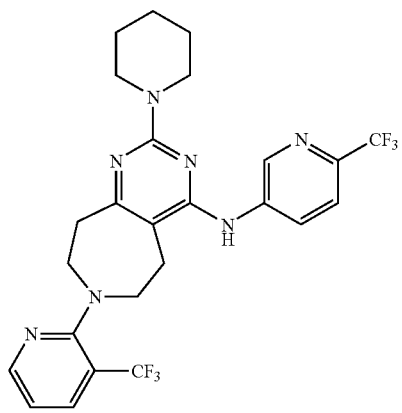 [SMILES: FC(F)(F)c1ccc(Nc2nc(N3CCCCC3)nc3c2CCN(c2ncccc2C(F)(F)F)CC3)cn1]

MS (ESI): mass calcd. for C$_{25}$H$_{25}$F$_6$N$_7$, 537.21; m/z found, 538.5 [M+H]$^+$. $^1$H NMR (MeOD): 8.94 (d, J=2.4 Hz, 1H), 8.46 (dd, J=4.7, 1.3 Hz, 1H), 8.20 (dd, J=8.3, 2.2 Hz, 1H), 8.04 (dd, J=7.9, 1.7 Hz, 1H), 7.87 (d, J=8.6 Hz, 1H), 7.18-7.13

(m, 1H), 3.74-3.68 (m, 4H), 3.64-3.58 (m, 2H), 3.58-3.52 (m, 2H), 3.32-3.27 (m, 2H), 3.14-3.09 (m, 2H), 1.78-1.62 (m, 6H).

Example 235

2-(2,6-Dimethylmorpholin-4-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

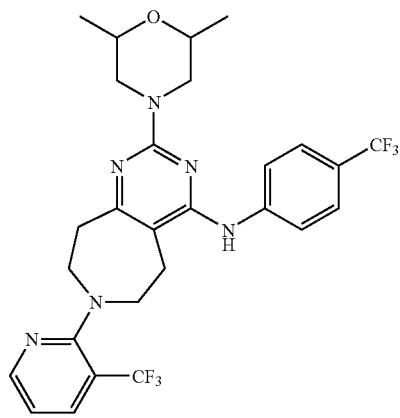 [SMILES: CC1CN(c2nc3c(c(Nc4ccc(C(F)(F)F)cc4)n2)CCN(c2ncccc2C(F)(F)F)CC3)CC(C)O1]

MS (ESI): mass calcd. for $C_{27}H_{28}F_6N_6O$, 566.22; m/z found, 566.2 [M+H]$^+$. $^1$H NMR (MeOD): 8.45 (d, J=4.7 Hz, 1H), 8.03 (dd, J=7.8, 1.6 Hz, 1H), 7.74-7.67 (m, 4H), 7.18-7.12 (m, 1H), 4.19 (d, J=13.1 Hz, 2H), 3.69-3.58 (m, 4H), 3.58-3.52 (m, 2H), 3.30-3.25 (m, 2H), 3.14-3.08 (m, 2H), 2.80-2.69 (m, 2H), 1.19 (d, J=6.2 Hz, 6H).

Example 236

2-[(2R,6S)-2,6-Dimethylmorpholin-4-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

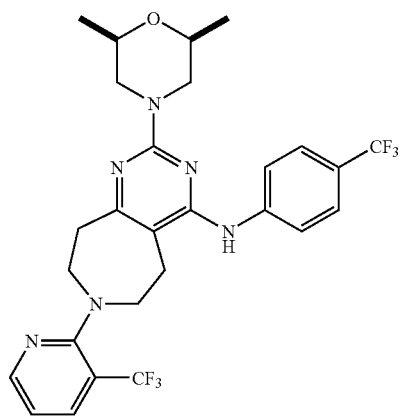 [SMILES: C[C@@H]1CN(c2nc3c(c(Nc4ccc(C(F)(F)F)cc4)n2)CCN(c2ncccc2C(F)(F)F)CC3)C[C@H](C)O1]

MS (ESI): mass calcd. for $C_{27}H_{28}F_6N_6O$, 566.22; m/z found, 567.5 [M+H]$^+$. $^1$H NMR (MeOD): 8.47-8.44 (m, 1H), 8.03 (dd, J=7.8, 1.7 Hz, 1H), 7.74-7.68 (m, 4H), 7.17-7.12 (m, 1H), 4.20 (d, J=13.0 Hz, 2H), 3.71-3.58 (m, 4H), 3.58-3.52 (m, 2H), 3.30-3.26 (m, 2H), 3.14-3.08 (m, 2H), 2.80-2.68 (m, 2H), 1.19 (d, J=6.2 Hz, 6H).

Example 237

2-(1,4-Oxazepan-4-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

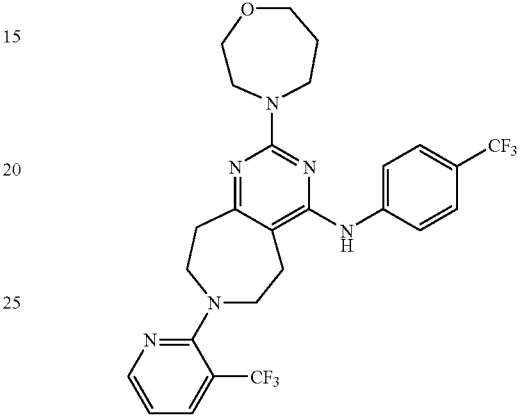

MS (ESI): mass calcd. for $C_{26}H_{26}F_6N_6O$, 552.20; m/z found, 553.2 [M+H]$^+$. $^1$H NMR (CDCl$_3$): 8.40-8.37 (m, 1H), 7.86 (dd, J=7.8, 1.8 Hz, 1H), 7.66 (d, J=8.4 Hz, 2H), 7.54 (d, J=8.6 Hz, 1H), 6.97-6.89 (m, 1H), 6.52 (s, 1H), 3.94-3.85 (m, 4H), 3.84-3.78 (m, 2H), 3.74-3.70 (m, 2H), 3.63-3.54 (m, 4H), 3.11-3.04 (m, 2H), 2.91-2.85 (m, 2H), 2.04-1.95 (m, 2H).

Example 238

2-(3,3-Difluoropiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

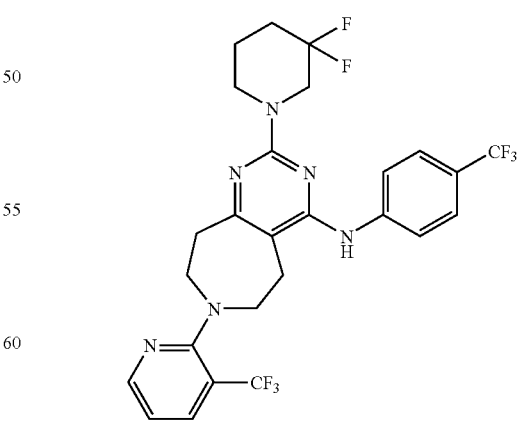

MS (ESI): mass calcd. for $C_{26}H_{24}F_8N_6$, 572.19; m/z found, 573.1 [M+H]$^+$. $^1$H NMR (MeOD): 8.46-8.43 (m, 1H), 8.02 (dd, J=7.8, 1.7 Hz, 1H), 7.73-7.67 (m, 4H), 7.16-7.11 (m, 1H), 4.02 (t, J=11.4 Hz, 2H), 3.79-3.74 (m, 2H), 3.64-3.59 (m, 2H), 3.57-3.53 (m, 2H), 3.30-3.27 (m, 2H), 3.13-3.08 (m, 2H), 2.21-2.09 (m, 2H), 1.91-1.80 (m, 2H).

Example 239

2-(4-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

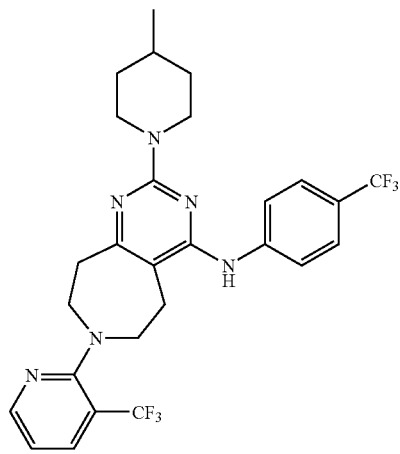 [SMILES: CC1CCN(c2nc3c(c(Nc4ccc(C(F)(F)F)cc4)n2)CCN(c2ncccc2C(F)(F)F)CC3)CC1]

MS (ESI): mass calcd. for $C_{27}H_{28}F_6N_6$, 550.2; m/z found, 551.5 [M+H]$^+$. $^1$H NMR (MeOD): 8.47-8.43 (m, 1H), 8.03 (dd, J=7.8, 1.7 Hz, 1H), 7.75-7.67 (m, 4H), 7.18-7.10 (m, 1H), 4.34 (d, J=13.5 Hz, 2H), 3.66-3.57 (m, 2H), 3.57-3.51 (m, 2H), 3.30-3.24 (m, 2H), 3.15-3.02 (m, 4H), 1.85-1.67 (m, 3H), 1.29-1.09 (m, 2H), 0.99 (d, J=6.3 Hz, 3H).

Example 240

2-(3-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

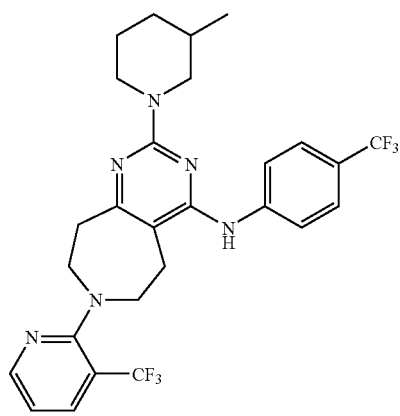 [SMILES: CC1CCCN(c2nc3c(c(Nc4ccc(C(F)(F)F)cc4)n2)CCN(c2ncccc2C(F)(F)F)CC3)C1]

MS (ESI): mass calcd. for $C_{27}H_{28}F_6N_6$, 550.2; m/z found, 551.6 [M+H]$^+$. $^1$H NMR (MeOD): 8.47-8.43 (m, 1H), 8.03 (dd, J=7.8, 1.7 Hz, 1H), 7.75-7.67 (m, 4H), 7.19-7.10 (m, 1H), 4.32-4.15 (m, 2H), 3.63-3.57 (m, 2H), 3.57-3.51 (m, 2H), 3.30-3.24 (m, 2H), 3.13-3.01 (m, 3H), 2.82-2.66 (m, 1H), 1.93-1.73 (m, 2H), 1.73-1.45 (m, 2H), 1.34-1.17 (m, 1H), 0.94 (d, J=6.6 Hz, 3H).

Example 241

2-(3,3-Difluoroazetidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine

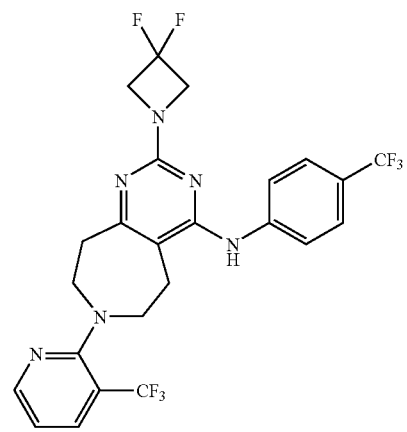 [SMILES: FC1(F)CN(c2nc3c(c(Nc4ccc(C(F)(F)F)cc4)n2)CCN(c2ncccc2C(F)(F)F)CC3)C1]

MS (ESI): mass calcd. for $C_{24}H_{20}F_8N_6$, 544.16; m/z found, 545.5 [M+H]$^+$. $^1$H NMR (MeOD): 8.45 (dd, J=4.8, 1.4 Hz, 1H), 8.03 (dd, J=7.8, 1.8 Hz, 1H), 7.80 (d, J=8.5 Hz, 2H), 7.71 (d, J=8.6 Hz, 2H), 7.18-7.11 (m, 1H), 4.64-4.59 (m, 4H), 3.65-3.59 (m, 2H), 3.58-3.53 (m, 2H), 3.29-3.23 (m, 2H), 3.16-3.10 (m, 2H).

Example 242

2-(4,4-Difluoropiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine

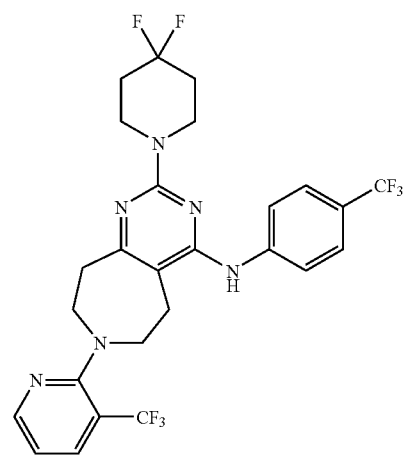 [SMILES: FC1(F)CCN(c2nc3c(c(Nc4ccc(C(F)(F)F)cc4)n2)CCN(c2ncccc2C(F)(F)F)CC3)CC1]

MS (ESI): mass calcd. for $C_{26}H_{24}F_8N_6$, 572.19; m/z found, 573.1 [M+H]$^+$. $^1$H NMR (CDCl$_3$): 8.39 (dd, J=4.7, 1.6 Hz, 1H), 7.87 (dd, J=7.8, 1.8 Hz, 1H), 7.63-7.55 (m, 4H), 6.98-

6.91 (m, 1H), 6.53 (s, 1H), 3.95-3.88 (m, 4H), 3.62-3.58 (m, 2H), 3.58-3.54 (m, 2H), 3.11-3.06 (m, 2H), 2.91-2.86 (m, 2H), 2.04-1.93 (m, 4H).

Example 243

2-(3,3-Difluoropyrrolidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

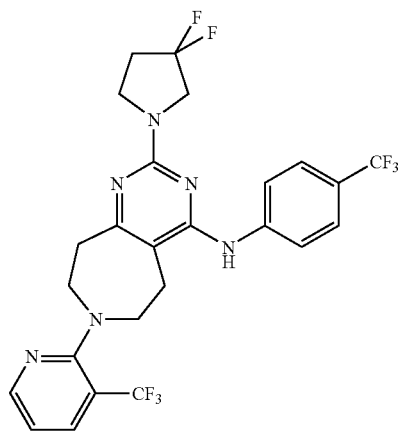 [SMILES: FC1(F)CCN(c2nc3c(c(Nc4ccc(C(F)(F)F)cc4)n2)CCN(c2ncccc2C(F)(F)F)CC3)C1]

MS (ESI): mass calcd. for $C_{25}H_{22}F_8N_6$, 558.18 m/z found, 559.5 [M+H]$^+$. $^1$H NMR (MeOD): 8.45 (dd, J=4.4, 1.4 Hz, 1H), 8.02 (dd, J=7.8, 1.8 Hz, 1H), 7.81 (d, J=8.6 Hz, 2H), 7.71 (d, J=8.661 Hz, 2H), 7.16-7.11 (m, 1H), 3.99-3.92 (m, 2H), 3.84 (t, J=7.4 Hz, 2H), 3.64-3.58 (m, 2H), 3.57-3.52 (m, 2H), 3.31-3.27 (m, 2H), 3.15-3.10 (m, 2H), 2.62-2.50 (m, 2H).

Example 244

2-(2-Methylpyrrolidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine

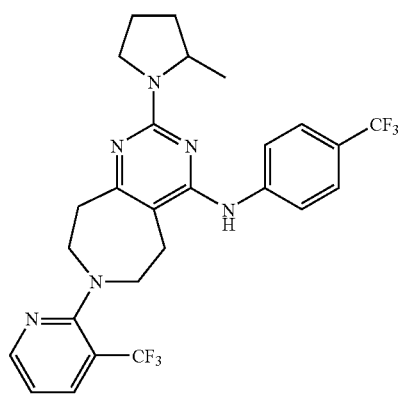 [SMILES: CC1CCCN1c1nc2c(c(Nc3ccc(C(F)(F)F)cc3)n1)CCN(c1ncccc1C(F)(F)F)CC2]

MS (ESI): mass calcd. for $C_{26}H_{26}F_6N_6$, 536.21; m/z found, 537.6 [M+H]$^+$. $^1$H NMR (CDCl$_3$): 8.38 (dd, J=4.7, 1.6 Hz, 1H), 7.86 (dd, J=7.8, 1.8 Hz, 1H), 7.77 (d, J=8.6 Hz, 2H), 7.55 (d, J=8.6 Hz, 2H), 6.95-6.91 (m, 1H), 6.52 (s, 1H), 4.33-4.24 (m, 1H), 3.68-3.49 (m, 6H), 3.13-3.05 (m, 2H), 2.90-2.85 (m, 2H), 2.13-2.00 (m, 2H), 1.97-1.88 (m, 1H), 1.74-1.65 (m, 1H), 1.26 (d, J=6.3 Hz, 3H).

Example 245

N-[3-Chloro-4-(trifluoromethyl)phenyl]-2-(1,4-oxazepan-4-yl)-7-[3-(trifluoromethyl)pyridin-2-yl]-6,7,8,9-tetrahydro-5H-pyrimido[4,5-d]azepin-4-amine trifluoroacetic acid salt

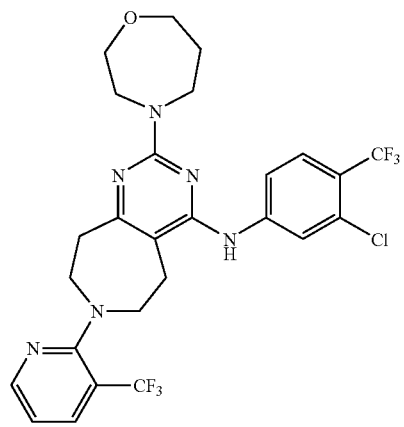 [SMILES: FC(F)(F)c1ccc(Nc2nc(N3CCCOCC3)nc3c2CCN(c2ncccc2C(F)(F)F)CC3)cc1Cl]

MS (ESI): mass calcd. for $C_{26}H_{25}ClF_6N_6O$, 586.17; m/z found, 587.5 [M+H]$^+$. $^1$H NMR (MeOD): 8.46-8.44 (m, 1H), 8.04-8.00 (m, 2H), 7.79 (d, J=8.7 Hz, 1H), 7.64-7.59 (m, 1H), 7.17-7.11 (m, 1H), 3.92-3.81 (m, 6H), 3.80-3.76 (m, 2H), 3.64-3.59 (m, 2H), 3.57-3.52 (m, 2H), 3.36-3.32 (m, 2H), 3.13-3.09 (m, 2H).

Example 246

2-(2-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine hydrochloride salt

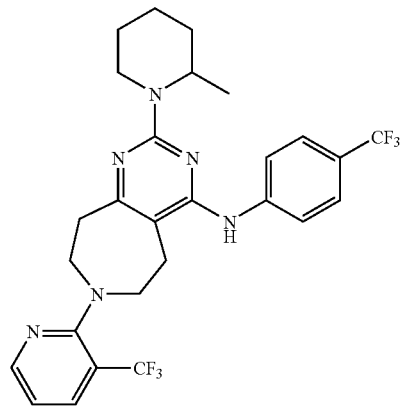 [SMILES: CC1CCCCN1c1nc2c(c(Nc3ccc(C(F)(F)F)cc3)n1)CCN(c1ncccc1C(F)(F)F)CC2]

MS (ESI): mass calcd. for $C_{27}H_{28}F_6N_6$, 550.23; m/z found, 551.6 [M+H]$^+$. $^1$H NMR (MeOD): 8.45 (dd, J=4.7, 1.4 Hz, 1H), 8.03 (dd, J=7.8, 1.8 Hz, 1H), 7.74-7.68 (m, 4H), 7.17-7.11 (m, 1H), 4.70-4.63 (m, 1H), 4.19-4.11 (m, 1H), 3.64-

3.58 (m, 2H), 3.56-3.52 (m, 2H), 3.30-3.26 (m, 2H), 3.24-3.15 (m, 1H), 3.12-3.07 (m, 2H), 1.85-1.62 (m, 5H), 1.58-1.46 (m, 1H), 1.27 (d, J=6.9 Hz, 3H).

Example 247

2-(1,1-Dioxidothiomorpholin-4-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

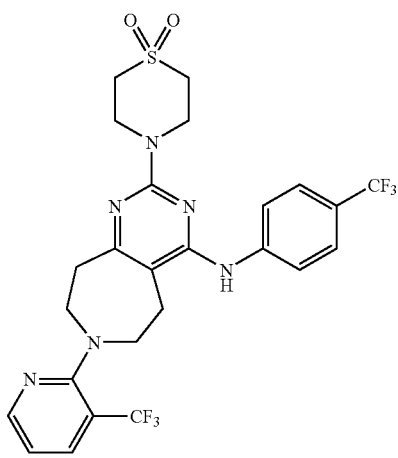 [SMILES: O=S1(=O)CCN(c2nc3c(c(Nc4ccc(C(F)(F)F)cc4)n2)CCN(c2ncccc2C(F)(F)F)CC3)CC1]

MS (ESI): mass calcd. for $C_{25}H_{24}F_6N_6O_2S$, 586.16; m/z found, 587.1 [M+H]$^+$. $^1$H NMR ((CD$_3$)$_2$CO): 8.46-8.44 (m, 1H), 8.02-8.00 (m, 1H), 7.88-7.84 (m, 2H), 7.64-7.62 (m, 2H), 7.13-7.08 (m, 1H), 4.31-4.25 (m, 4H), 3.56-3.48 (m, 4H), 3.14-3.04 (m, 6H), 2.07-2.04 (m, 2H).

Example 248

N-[4-(1,1-Dimethylethyl)phenyl]-2-pyrrolidin-1-yl-7-[3-(trifluoromethyl)pyridin-2-yl]-6,7,8,9-tetrahydro-5H-pyrimido[4,5-d]azepin-4-amine

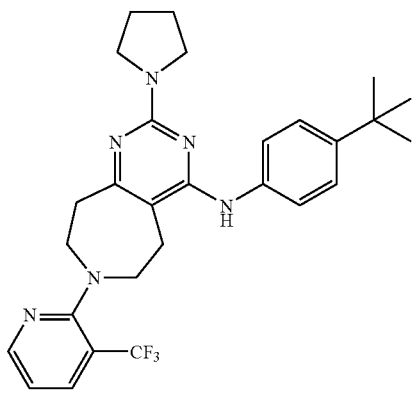 [SMILES: CC(C)(C)c1ccc(Nc2nc(N3CCCC3)nc3c2CCN(c2ncccc2C(F)(F)F)CC3)cc1]

MS (ESI): mass calcd. for $C_{28}H_{33}F_3N_6$, 510.27; m/z found, 511.2 [M+H]$^+$. $^1$H NMR (CDCl$_3$): 8.38-8.36 (m, 1H), 7.85 (dd, J=7.8, 1.8 Hz, 1H), 7.62-7.58 (m, 2H), 7.34-7.31 (m, 2H), 6.94-6.90 (m, 1H), 6.35 (s, 1H), 3.61-3.56 (m, 8H), 3.09-3.06 (m, 2H), 2.86-2.82 (m, 2H), 1.99-1.92 (m, 4H), 1.32 (s, 9H).

Example 249

2-Azetidin-1-yl-N-[4-(1,1-dimethylethyl)phenyl]-7-[3-(trifluoromethyl)pyridin-2-yl]-6,7,8,9-tetrahydro-5H-pyrimido[4,5-d]azepin-4-amine

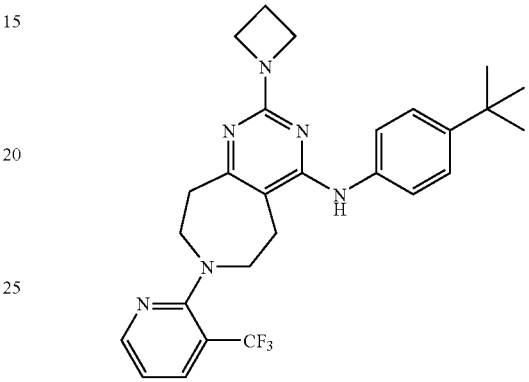

MS (ESI): mass calcd. for $C_{27}H_{31}F_3N_6$, 496.26; m/z found, 497.2 [M+H]$^+$. $^1$H NMR (CDCl$_3$): 8.38-8.37 (m, 1H), 7.85 (dd, J=7.7, 1.9 Hz, 1H), 7.58-7.54 (m, 2H), 7.33-7.30 (m, 2H), 6.94-6.90 (m, 1H), 6.37 (s, 1H), 4.15-4.10 (m, 4H), 3.62-3.54 (m, 4H), 3.10-3.05 (m, 2H), 2.86-2.81 (m, 2H), 2.35-2.28 (m, 2H), 1.31 (s, 9H).

Example 250

2-Piperidin-1-yl-7-[3-(trifluoromethyl)pyridin-2-yl]-N-[5-(trifluoromethyl)pyridin-2-yl]-6,7,8,9-tetrahydro-5H-pyrimido[4,5-d]azepin-4-amine

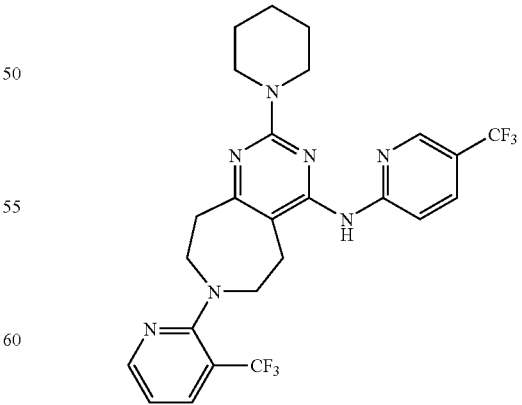

MS (ESI): mass calcd. for $C_{25}H_{25}F_6N_7$, 537.21; m/z found, 538.2 [M+H]$^+$. $^1$H NMR (CDCl$_3$): 8.49-8.47 (m, 1H), 8.43 (d, J=8.9 Hz, 1H), 8.40-8.39 (m, 1H), 7.89-7.85 (m, 2H), 7.42 (s, 1H), 6.97-6.92 (m, 1H), 3.79-3.74 (m, 4H), 3.58-3.52 (m, 4H), 3.12-3.06 (m, 2H), 2.95-2.88 (m, 2H), 1.73-1.59 (m, 6H).

Example 251

N-[(3,4-Dichlorophenyl)methyl]-2-piperidin-1-yl-7-[3-(trifluoromethyl)pyridin-2-yl]-6,7,8,9-tetrahydro-5H-pyrimido[4 5-d]azepin-4-amine

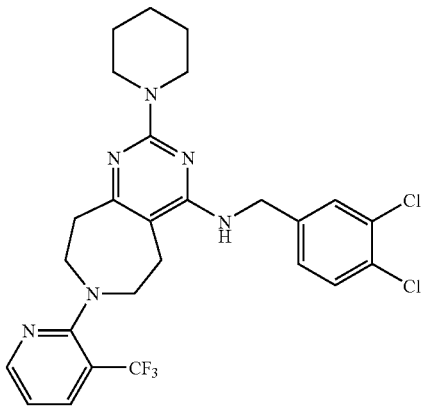 [SMILES: FC(F)(F)c1cccnc1N1CCc2nc(N3CCCCC3)nc(NCc3ccc(Cl)c(Cl)c3)c2CC1]

MS (ESI): mass calcd. for $C_{26}H_{27}Cl_2F_3N_6$, 551.16; m/z found, 551.1 [M+H]$^+$. $^1$H NMR (CDCl$_3$): 8.36-8.35 (m, 1H), 7.84 (dd, J=7.8, 1.8 Hz, 1H), 7.44-7.43 (m, 1H), 7.37 (d, J=8.2 Hz, 1H), 7.18-7.16 (m, 1H), 6.92-6.89 (m, 1H), 4.82-4.79 (m, 1H), 4.59 (d, J=5.7 Hz, 2H), 3.69-3.65 (m, 4H), 3.57-3.52 (m, 4H), 3.03-2.99 (m, 2H), 2.72-2.69 (m, 2H), 1.64-1.59 (m, 2H), 1.56-1.50 (m, 4H).

Example 252

N-[4-(1,1-Dimethylethyl)phenyl]-2-(4-methylpiperazin-1-yl)-7-[3-(trifluoromethyl)pyridin-2-yl]-6,7,8,9-tetrahydro-5H-pyrimido[4,5-d]azepin-4-amine

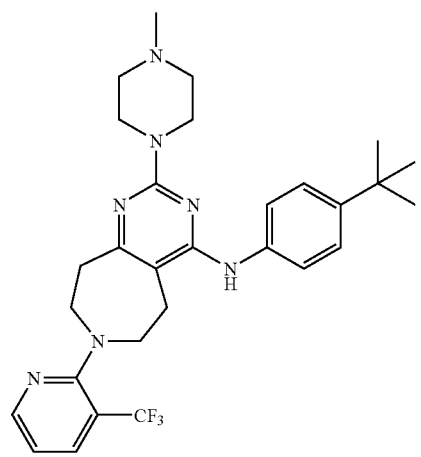 [SMILES: CN1CCN(c2nc3c(c(Nc4ccc(C(C)(C)C)cc4)n2)CCN(c2ncccc2C(F)(F)F)CC3)CC1]

MS (ESI): mass calcd. for $C_{29}H_{36}F_3N_7$, 539.30; m/z found, 540.2 [M+H]$^+$. $^1$H NMR (CDCl$_3$): 8.39-8.37 (m, 1H), 7.86 (dd, J=7.8, 1.7 Hz, 1H), 7.48-7.45 (m, 2H), 7.36-7.32 (m, 2H), 6.94-6.90 (m, 1H), 6.34 (s, 1H), 3.84-3.76 (m, 4H), 3.64-3.55 (m, 4H), 3.09-3.04 (m, 2H), 2.87-2.81 (m, 2H), 2.51-2.42 (m, 4H), 2.34 (s, 3H), 1.33 (s, 9H).

Example 253

2-Azepan-1-yl-N-[4-(1,1-dimethylethyl)phenyl]-7-[3-(trifluoromethyl)pyridin-2-yl]-6,7,8,9-tetrahydro-5H-pyrimido[4,5-d]azepin-4-amine

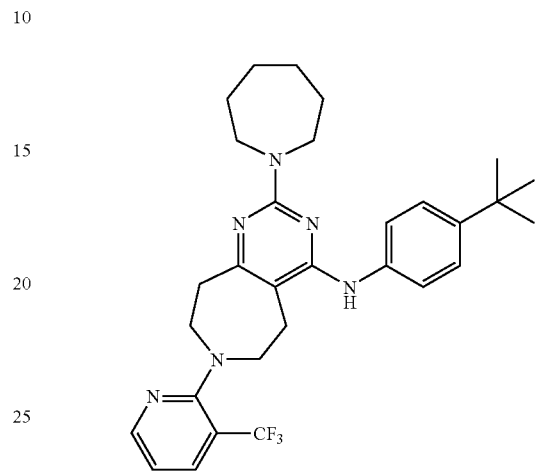

MS (ESI): mass calcd. for $C_{30}H_{37}F_3N_6$, 538.30; m/z found, 539.2 [M+H]$^+$. $^1$H NMR (CDCl$_3$): 8.39-8.37 (m, 1H), 7.85 (dd, J=7.8, 1.7 Hz, 1H), 7.56-7.53 (m, 2H), 7.33-7.30 (m, 2H), 6.93-6.90 (m, 1H), 6.31 (s, 1H), 3.76-3.70 (m, 4H), 3.63-3.56 (m, 4H), 3.08-3.04 (m, 2H), 2.86-2.82 (m, 2H), 1.83-1.74 (m, 4H), 1.58-1.52 (m, 4H), 1.32 (s, 9H).

Example 254

N$^2$-[22-(Dimethylamino)ethyl]-N$^4$-[4-(1,1-dimethylethyl)phenyl]-N$^2$-methyl-7-[3-(trifluoromethyl)pyridin-2-yl]-6,7,8,9-tetrahydro-5H-pyrimido[4,5-d]azepine-2,4-diamine

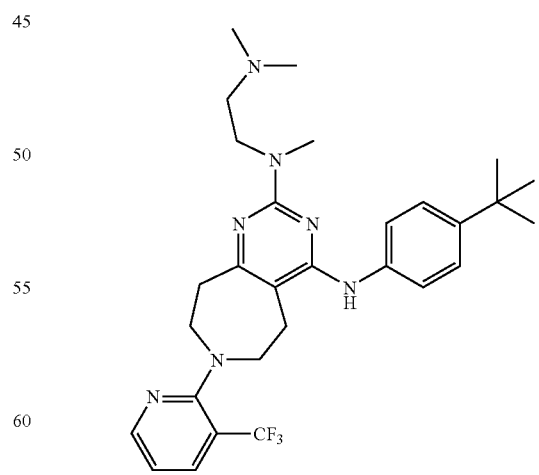

MS (ESI): mass calcd. for $C_{29}H_{38}F_3N_7$, 541.31; m/z found, 542.3 [M+H]$^+$. $^1$H NMR (CDCl$_3$): 8.38-8.37 (m, 1H), 7.86-7.85 (m, 1H), 7.50-7.46 (m, 2H), 7.33-7.30 (m, 2H), 6.94-6.90 (m, 1H), 6.29 (s, 1H), 3.72-3.70, (m, 2H), 3.63-3.55 (m, 4H), 3.15 (s, 3H), 3.08-3.04 (m, 2H), 2.86-2.82 (m, 2H), 2.52-2.46 (m, 2H), 2.26 (s, 6H), 1.31 (s, 9H).

Example 255

2-Azepan-1-yl-N-[(3,4-dichlorophenyl)methyl]-7-[3-(trifluoromethyl)pyridin-2-yl]-6,7,8,9-tetrahydro-5H-pyrimido[4,5-d]azepin-4-amine

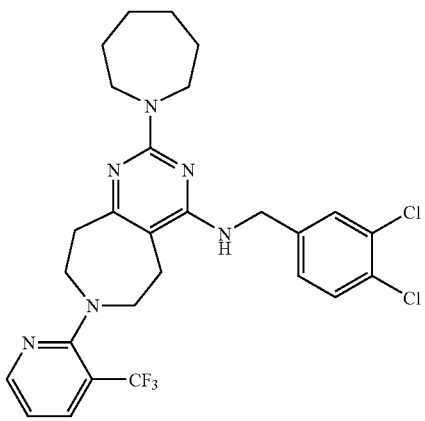 [SMILES: FC(F)(F)c1cccnc1N1CCc2nc(N3CCCCCC3)nc(NCc3ccc(Cl)c(Cl)c3)c2CC1]

MS (ESI): mass calcd. for $C_{27}H_{29}Cl_2F_3N_6$, 564.18; m/z found, 565.1 [M+H]$^+$. $^1$H NMR (CDCl$_3$): 8.37-8.35 (m, 1H), 7.86-7.83 (m, 1H), 7.43-7.42 (m, 1H), 7.36 (d, J=8.2 Hz, 1H), 7.17-7.15 (m, 1H), 6.91-6.89 (m, 1H), 4.83-4.79 (m, 1H), 4.59 (d, J=5.7 Hz, 2H), 3.69-3.52 (m, 8H), 3.03-3.00 (m, 2H), 2.72-2.69 (m, 2H), 1.72-1.61 (m, 4H), 1.52-1.47 (m, 4H).

Example 256

N-[(3,4-Dichlorophenyl)methyl]-2-(4-methylpiperazin-1-yl)-7-[3-(trifluoromethyl)pyridin-2-yl]-6,7,8,9-tetrahydro-5H-pyrimido[4,5-d]azepin-4-amine

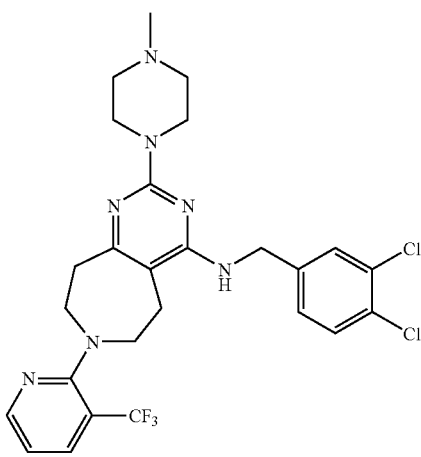 [SMILES: CN1CCN(c2nc3c(c(NCc4ccc(Cl)c(Cl)c4)n2)CCN(c2ncccc2C(F)(F)F)CC3)CC1]

MS (ESI): mass calcd. for $C_{26}H_{28}Cl_2F_3N_7$, 565.17; m/z found, 566.1 [M+H]$^+$. $^1$H NMR (CDCl$_3$): 8.37-8.35 (m, 1H), 7.86-7.84 (m, 1H), 7.44-7.43 (m, 1H), 7.38 (d, J=8.2 Hz, 1H), 7.17-7.15 (m, 1H), 6.93-6.90 (m, 1H), 4.86-4.82 (m, 1H), 4.60 (d, J=5.7 Hz, 2H), 3.77-3.69 (m, 4H), 3.57-3.52 (m, 4H), 3.04-3.00 (m, 2H), 2.73-2.69 (m, 2H), 2.43-2.39 (m, 4H), 2.32 (s, 3H).

Example 257

$N^4$-[4-(1,1-Dimethylethyl)phenyl]-$N^2$-methyl-$N^2$-[2-(methyloxy)ethyl]-7-[3-(trifluoromethyl)pyridin-2-yl]-6,7,8,9-tetrahydro-5H-pyrimido[4,5-d]azepine-2,4-diamine

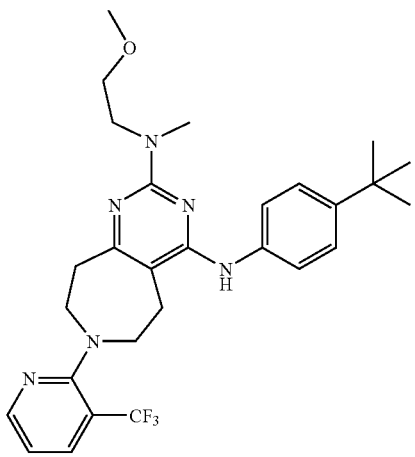 [SMILES: COCCN(C)c1nc2c(c(Nc3ccc(C(C)(C)C)cc3)n1)CCN(c1ncccc1C(F)(F)F)CC2]

MS (ESI): mass calcd. for $C_{28}H_{35}F_3N_6O$, 528.28; m/z found, 529.2 [M+H]$^+$. $^1$H NMR (CDCl$_3$): 8.38-8.37 (m, 1H), 7.86 (dd, J=7.8, 1.9 Hz, 1H), 7.52-7.49 (m, 2H), 7.34-7.30 (m, 2H), 6.94-6.90 (m, 1H), 6.32 (s, 1H), 3.77 (t, J=6.1 Hz, 2H), 3.62-3.56 (m, 6H), 3.34 (s, 3H), 3.19 (s, 3H), 3.07-3.05 (m, 2H), 2.86-2.82 (m, 2H), 1.32 (s, 9H).

Example 258

N-[3-Chloro-4-(trifluoromethyl)phenyl]-2-pyrrolidin-1-yl-7-[3-(trifluoromethyl)pyridin-2-yl]-6,7,8,9-tetrahydro-5H-pyrimido[4,5-d]azepin-4-amine

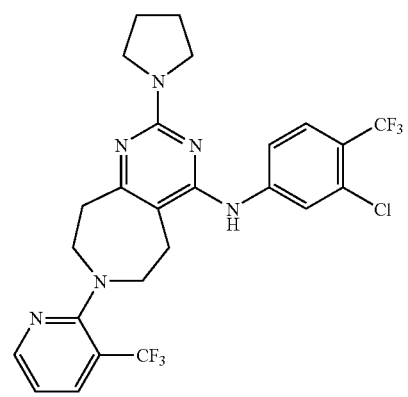 [SMILES: FC(F)(F)c1ccc(Nc2nc(N3CCCC3)nc3c2CCN(c2ncccc2C(F)(F)F)CC3)cc1Cl]

MS (ESI): mass calcd. for $C_{25}H_{23}ClF_6N_6$, 556.16; m/z found, 557.4 [M+H]$^+$. $^1$H NMR (CDCl$_3$): 8.39-8.38 (m, 1H), 8.23 (d, J=1.9 Hz, 1H), 7.87 (dd, J=7.8, 1.8 Hz, 1H), 7.58 (d, J=8.7 Hz, 1H), 7.46-7.42 (m, 1H), 6.97-6.93 (m, 1H), 6.54 (s, 1H), 3.65-3.53 (m, 8H), 3.14-3.06 (m, 2H), 2.90-2.84 (m, 2H), 2.02-1.94 (m, 4H).

Example 259

[1-(4-{[4-(Trifluoromethyl)phenyl]amino}-7-[3-(trifluoromethyl)pyridin-2-yl]-6,7,8,9-tetrahydro-5H-pyrimido[4,5-d]azepin-2-yl)piperidin-2-yl]methanol

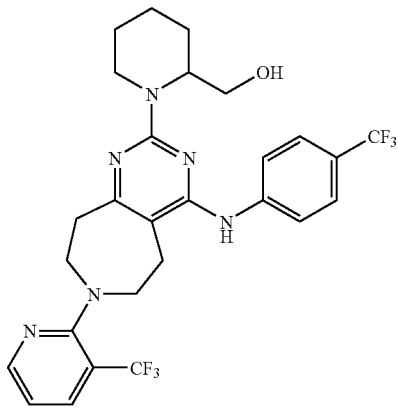 [SMILES: OCC1CCCCN1c1nc2c(c(Nc3ccc(C(F)(F)F)cc3)n1)CCN(c1ncccc1C(F)(F)F)CC2]

MS (ESI): mass calcd. for $C_{27}H_{28}F_6N_6O$, 566.22; m/z found, 567.5 [M+H]$^+$. $^1$H NMR (CDCl$_3$): 8.40-8.37 (m, 1H), 7.87 (dd, J=7.8, 1.8 Hz, 1H), 7.65-7.61 (m, 2H), 7.59-7.56 (m, 2H), 6.97-6.92 (m, 1H), 6.52 (s, 1H), 4.94-4.87 (m, 1H), 4.58-4.51 (m, 1H), 4.05-4.00 (m, 1H), 3.74-3.65 (m, 2H), 3.61-3.53 (m, 4H), 3.15-3.04 (m, 3H), 2.89-2.84 (m, 2H), 1.78-1.57 (m, 5H).

Example 260

[(2S)-1-(4-{[4-(Trifluoromethyl)phenyl]amino}-7-[3-(trifluoromethyl)pyridin-2-yl]-6,7,8,9-tetrahydro-5H-pyrimido[4,5-d]azepin-2-yl)pyrrolidin-2-yl]methanol hydrochloride salt

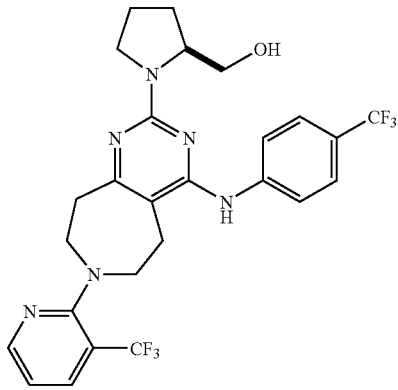 [SMILES: OC[C@@H]1CCCN1c1nc2c(c(Nc3ccc(C(F)(F)F)cc3)n1)CCN(c1ncccc1C(F)(F)F)CC2]

MS (ESI): mass calcd. for $C_{26}H_{26}F_6N_6O$, 552.21; m/z found, 553.1 [M+H]$^+$. $^1$H NMR (CD$_3$OD): 8.48-8.45 (m, 1H), 8.06-8.01 (m, 1H), 7.86-7.81 (m, 2H), 7.72-7.67 (m, 2H), 7.1,9-7.12 (m, 1H), 4.26-4.14 (m, 1H), 3.87-3.49 (m, 8H), 3.30-3.19 (m, 2H), 3.15-3.08 (m, 2H), 2.23-1.85 (m, 4H).

Example 261

[(2R)-1-(4-{[4-(Trifluoromethyl)phenyl]amino}-7-[3-(trifluoromethyl)pyridin-2-yl]-6,7,8,9-tetrahydro-5H-pyrimido[4,5-d]azepin-2-yl)pyrrolidin-2-yl]methanol hydrochloride salt

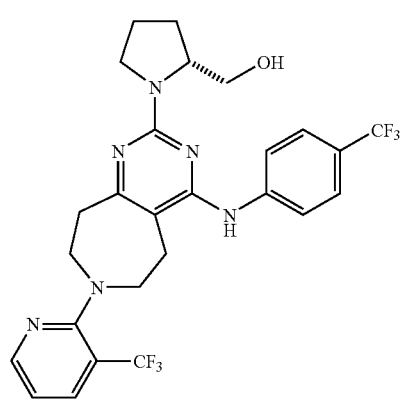 [SMILES: OC[C@H]1CCCN1c1nc2c(c(Nc3ccc(C(F)(F)F)cc3)n1)CCN(c1ncccc1C(F)(F)F)CC2]

MS (ESI): mass calcd. for $C_{26}H_{26}F_6N_6O$, 552.21; m/z found, 553.1 [M+H]$^+$. $^1$H NMR (CD$_3$OD): 8.47-8.44 (m, 1H), 8.04-8.01 (m, 1H), 7.84-7.81 (m, 2H), 7.71-7.69 (m, 2H), 7.16-7.12 (m, 1H), 4.24-4.16 (m, 1H), 3.84-3.52 (m, 8H), 3.28-3.20 (m, 2H), 3.13-3.10 (m, 2H), 2.22-1.85 (m, 4H).

Example 262

[(2S)-1-(7-[3-(Trifluoromethyl)pyridin-2-yl]-4-{[5-(trifluoromethyl)pyridin-2-yl]amino}-6,7,8,9-tetrahydro-5H-pyrimido[4,5-d]azepin-2-yl]pyrrolidin-2-yl]methanol hydrochloride salt

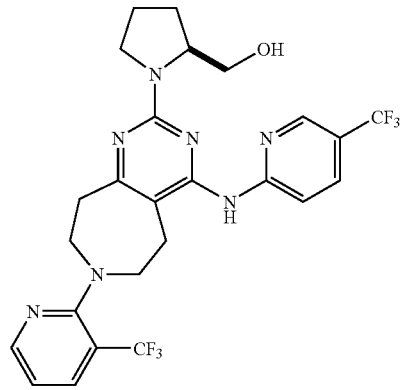 [SMILES: OC[C@@H]1CCCN1c1nc2c(c(Nc3ccc(C(F)(F)F)cn3)n1)CCN(c1ncccc1C(F)(F)F)CC2]

MS (ESI): mass calcd. for $C_{25}H_{25}F_6N_7O$, 553.20; m/z found, 554.1 [M+H]$^+$. $^1$H NMR (CDCl$_3$): 8.66-8.62 (m, 1H), 8.50-8.40 (m, 2H), 8.07-8.01 (m, 1H), 7.94-7.89 (m, 1H), 7.07-7.02 (m, 1H), 5.15-5.03 (m, 1H), 3.91-3.56 (m, 10H), 3.09-2.98 (m, 2H), 2.16-1.99 (m, 4H).

Example 263

N²-[(3R)-Tetrahydrofuran-3-yl]-7-[3-(trifluoromethyl)pyridin-2-yl]-N⁴-[5-(trifluoromethyl)pyridin-2-yl]-6,7,8,9-tetrahydro-5H-pyrimido[4,5-d]azepine-2,4-diamine

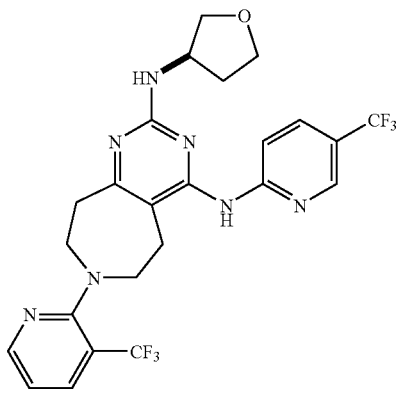

MS (ESI): mass calcd. for $C_{24}H_{23}F_6N_7O$, 539.19; m/z found, 540.2 [M+H]⁺. ¹H NMR (CD₃OD): 8.56-8.54 (m, 1H), 8.46-8.43 (m, 2H), 8.04-7.99 (m, 2H), 7.14-7.10 (m, 1H), 4.55-4.49 (m, 1H), 4.01-3.95 (m, 2H), 3.90-3.83 (m, 1H), 3.73-3.69 (m, 1H), 3.51-3.44 (m, 4H), 3.10-3.01 (m, 4H), 2.36-2.26 (m, 1H), 2.01-1.92 (m, 1H).

Example 264

N⁴-[4-(1,1-Dimethylethyl)phenyl]-N²-[(3R)-tetrahydrofuran-3-yl]-7-[3-(trifluoromethyl)pyridin-2-yl]-6,7,8,9-tetrahydro-5H-pyrimido[4,5-d]azepine-2,4-diamine

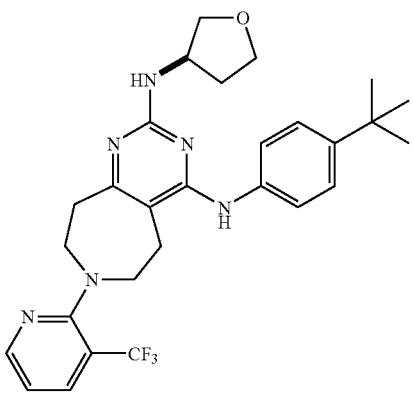

MS (ESI): mass calcd. for $C_{28}H_{33}F_3N_6O$, 526.27; m/z found, 527.3 [M+H]⁺. ¹H NMR (CD₃OD): 8.33-8.32 (m, 1H), 7.90 (dd, J=7.8, 1.8 Hz, 1H), 7.41-7.37 (m, 2H), 7.25-7.22 (m, 2H), 7.02-6.99 (m, 1H), 4.32-4.27 (m, 1H), 3.85-3.76 (m, 2H), 3.73-3.68 (m, 1H), 3.52 (dd, J=9.0, 3.9 Hz, 1H), 3.37-3.34 (m, 4H), 2.92-2.84 (m, 4H), 2.17-2.09 (m, 1H), 1.81-1.74 (m, 1H), 1.22 (s, 9H).

Example 265

N²-(Tetrahydro-furan-3-yl)-N⁴-(4-trifluoromethyl-phenyl)-7-(3-trifluoromethyl-pyridin-2-yl)-6,7,8,9-tetrahydro-5H-pyrimido[4,5-d]azepine-2,4-diamine trifluoroacetic acid salt

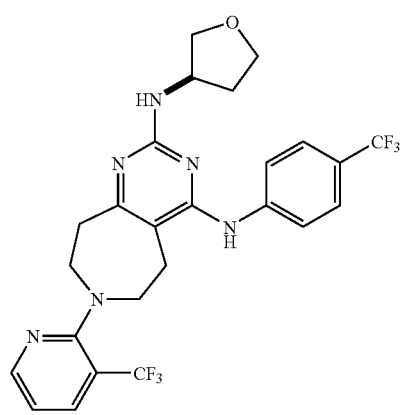

MS (ESI): mass calcd. for $C_{25}H_{24}F_6N_6O$, 538.19; m/z found, 539.2 [M+H]⁺. ¹H NMR (CD₃OD): 8.49-8.46 (m, 1H), 8.04 (dd, J=7.8, 1.7 Hz, 1H), 7.78 (d, J=8.6 Hz, 2H), 7.73 (d, J=8.7 Hz, 2H), 7.19-7.15 (m, 1H), 4.42-4.38 (m, 1H), 3.98-3.92 (m, 1H), 3.84-3.78 (m, 2H), 3.71 (dd, J=9.5, 3.2 Hz, 1H), 3.65-3.62 (m, 2H), 3.57-3.55 (m, 2H), 3.23-3.18 (m, 2H), 3.14-3.10 (m, 2H), 2.31-2.22 (m, .1H), 1.98-1.92 (m, 1H).

Example 266

N²-Methyl-N²-(1-methylethyl)-7-[3-(trifluoromethyl)pyridin-2-yl]-N⁴-[6-(trifluoromethyl)pyridin-3-yl]-6,7,8,9-tetrahydro-5H-pyrimido[4,5-d]azepine-2,4-diamine

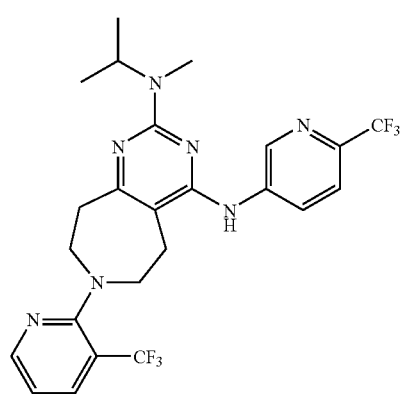 [SMILES: CC(C)N(C)c1nc2c(c(Nc3ccc(C(F)(F)F)nc3)n1)CCN(c1ncccc1C(F)(F)F)CC2]

MS (ESI): mass calcd. for $C_{24}H_{25}F_6N_7$, 525.21; m/z found, 526.2 [M+H]$^+$.

Example 267

$N^2$-Cyclohexyl-$N^2$-methyl-$N^4$-[2-methyl-4-(trifluoromethyl)phenyl]-7-[3-(trifluoromethyl)pyridin-2-yl]-6,7,8,9-tetrahydro-5H-pyrimido[4,5-d]azepine-2,4-diamine

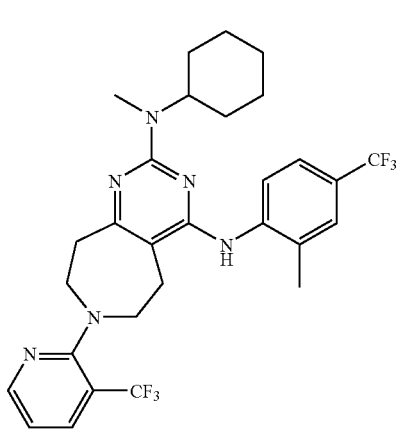 [SMILES: Cc1cc(C(F)(F)F)ccc1Nc1nc(N(C)C2CCCCC2)nc2c1CCN(c1ncccc1C(F)(F)F)CC2]

MS (ESI): mass calcd. for $C_{29}H_{32}F_6N_6$, 578.26; m/z found, 579.3 [M+H]$^+$.

Example 268

2-(7-Azabicyclo[2.2.1]hept-7-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine

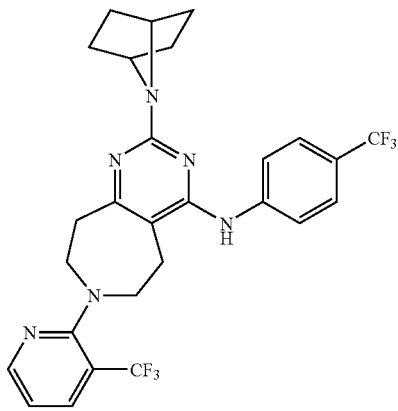 [SMILES: FC(F)(F)c1ccc(Nc2nc(N3C4CCC3CC4)nc3c2CCN(c2ncccc2C(F)(F)F)CC3)cc1]

MS (ESI): mass calcd. for $C_{27}H_{26}F_6N_6$, 548.521 m/z found, 549.2 [M+H]$^+$. $^1$H NMR (CDCl$_3$): 8.40-8.38 (m, 1H), 7.89-7.87 (m, 1H), 7.71 (d, J=8.5 Hz, 2H), 7.59 (d, J=8.5 Hz, 2H), 6.97-6.94 (m, 1H), 6.55 (s, 1H), 4.63 (s, 2H), 3.62-3.56 (m, 4H), 3.12-3.10 (m, 2H), 2.91-2.89 (m, 2H), 1.84-1.80 (m, 4H), 1.51-1.46 (m, 4H).

Example 269

2-[2-(1-Methylethyl)pyrrolidin-1-yl]-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

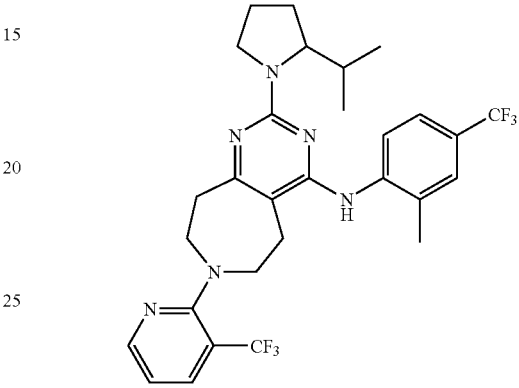

MS (ESI): mass calcd. for $C_{29}H_{32}F_6N_6$, 578.26; m/z found, 579.3 [M+H]$^+$. $^1$H NMR (CDCl$_3$): 8.40-8.37 (m, 2H), 7.88-7.85 (m, 1H), 7.45-7.42 (m, 2H), 6.95-6.91 (m, 1H), 6.33 (s, 1H), 4.04-4.02 (m, 1H), 3.76-3.69 (m, 1H), 3.65-3.56 (m, 4H), 3.54-3.48 (m, 1H), 3.11-3.08 (m, 2H), 2.89-2.86 (m, 2H), 2.42-2.37 (m, 1H), 2.35 (s, 3H), 1.96-1.87 (m, 1H), 1.86-1.80 (m, 3H), 0.86 (d, J=9.0 Hz, 3H), 0.77 (d, J=9.0 Hz, 3H).

Example 270

$N^2$-(Cyclohexylmethyl)-7-[3-(trifluoromethyl)pyridin-2-yl]-$N^4$-[6-(trifluoromethyl)pyridin-3-yl]-6,7,8,9-tetrahydro-5H-pyrimido[4,5-d]azepine-2,4-diamine

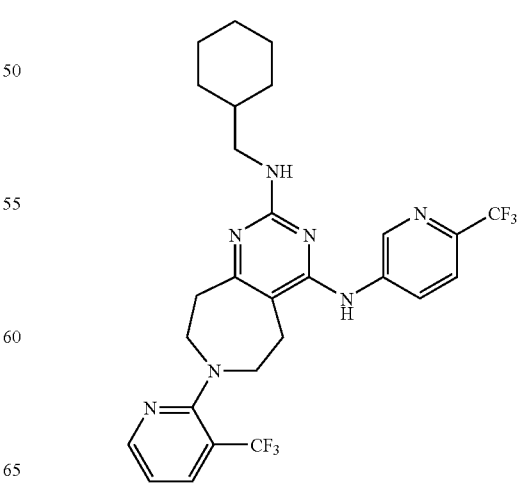

MS (ESI): mass calcd. for $C_{27}H_{29}F_6N_7$, 565.24; m/z found, 566.3 [M+H]$^+$. $^1$H NMR (CDCl$_3$): 8.75 (s, 1H), 8.40-8.38 (m, 2H), 7.88-7.86 (m, 1H), 7.62 (d, J=8.5 Hz, 1H), 6.97-6.94 (m, 1H), 6.60 (s, 1H), 3.60-3.55 (m, 4H), 3.22 (t, J=6.0 Hz, 2H), 3.08-3.05 (m, 2H), 2.91-2.89 (m, 2H), 1.80-1.72 (m, 3H), 1.68-1.64 (m, 1H), 1.63-1.51 (m, 3H), 1.27-1.22 (m, 3H), 1.02-0.94 (m, 2H).

Example 271

[4-(4-{[4-(Trifluoromethyl)phenyl]amino}-7-[3-(trifluoromethyl)pyridin-2-yl]-6,7,8,9-tetrahydro-5H-pyrimido[4,5-d]azepin-2-yl)morpholin-2-yl]methanol

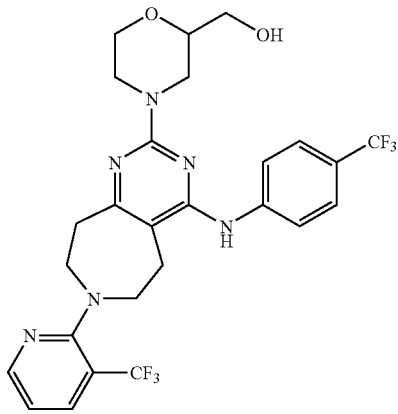 [SMILES: OCC1CN(c2nc3c(c(Nc4ccc(C(F)(F)F)cc4)n2)CCN(c2ncccc2C(F)(F)F)CC3)CCO1]

MS (ESI): mass calcd. for $C_{26}H_{26}F_6N_6O_2$, 568.20; m/z found, 569.3 [M+H]$^+$. $^1$H NMR (CDCl$_3$): 8.39-8.38 (m, 1H), 7.88-7.86 (m, 1H), 7.62 (d, J=11.0 Hz, 2H), 7.56 (d, J=11.0 Hz, 2H), 6.97-6.93 (m, 1H), 6.54 (s, 1H), 4.48-4.38 (m, 2H), 4.04-4.01 (m, 1H), 3.76-3.72 (m, 1H), 3.70-3.62 (m, 3H), 3.61-3.52 (m, 4H), 3.10-3.06 (m, 3H), 2.89-2.86 (m, 3H), 2.03-1.95 (m, 1H).

Example 272

N$^2$-Methyl-N$^2$-(1-methylethyl)-N$^4$-[4-(trifluoromethyl)phenyl]-7-[3-(trifluoromethyl)pyridin-2-yl]-6,7,8,9-tetrahydro-5H-pyrimido[4,5-d]azepine-2,4-diamine

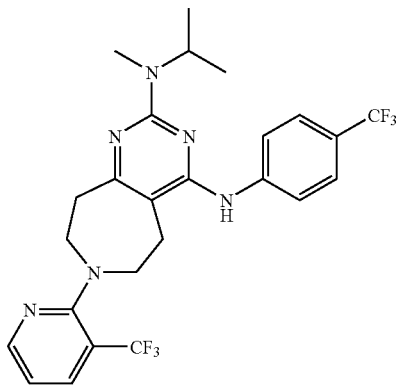 [SMILES: CC(C)N(C)c1nc2c(c(Nc3ccc(C(F)(F)F)cc3)n1)CCN(c1ncccc1C(F)(F)F)CC2]

MS (ESI): mass calcd. for $C_{25}H_{26}F_6N_6$, 524.21; m/z found, 525.3 [M+H]$^+$. $^1$H NMR (CDCl$_3$): 8.39-8.37 (m, 1H), 7.88-7.85 (m, 1H), 7.70 (d, J=8.5 Hz, 2H), 7.55 (d, J=8.5 Hz, 2H), 6.95-6.92 (m, 1H), 6.50 (s, 1H), 5.05-5.00 (m, 1H), 3.61-3.56 (m, 4H), 3.11-3.07 (m, 2H), 2.98 (s, 3H), 2.90-2.84 (m, 2H), 1.18 (d, J=6.5 Hz, 6H).

Example 273

[4-(4-{[2-Methyl-4-(trifluoromethyl)phenyl]amino}-7-[3-(trifluoromethyl)pyridin-2-yl]-6,7,8,9-tetrahydro-5H-pyrimido[4,5-d]azepin-2-yl)morpholin-2-yl]methanol

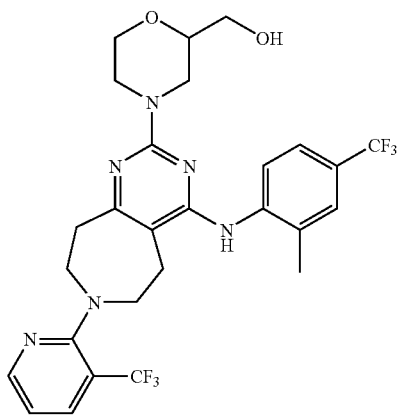 [SMILES: Cc1cc(C(F)(F)F)ccc1Nc1nc(N2CCOC(CO)C2)nc2c1CCN(c1ncccc1C(F)(F)F)CC2]

MS (ESI): mass calcd. for $C_{27}H_{28}F_6N_6O_2$, 582.22; m/z found, 583.3 [M+H]$^+$. $^1$H NMR (CDCl$_3$): 8.39-8.37 (m, 1H), 8.04 (d, J=11.5 Hz, 1H), 7.88-7.86 (m, 1H), 7.45 (d, J=9.0 Hz, 2H), 6.96-6.93 (m, 1H), 6.31 (s, 1H), 4.43-4.34 (m, 2H), 4.02-3.98 (m, 1H), 3.74-3.71 (m, 1H), 3.66-3.55 (m, 7H), 3.11-3.08 (m, 2H), 3.07-2.99 (m, 1H), 2.89-2.80 (m, 3H), 2.34 (s, 3H), 1.99 (br s, 1H).

Example 274

2-[2-(1-Methylethyl)pyrrolidin-1-yl]-7-[3-(trifluoromethyl)pyridin-2-yl]-N-[6-(trifluoromethyl)pyridin-3-yl]-6,7,8,9-tetrahydro-5H-pyrimido[4,5-d]azepin-4-amine

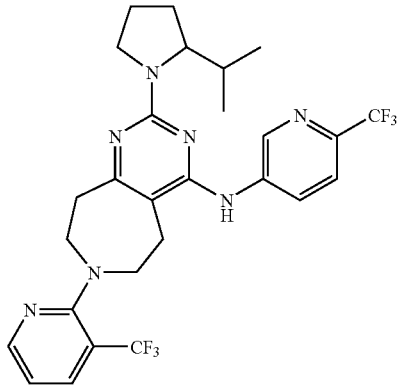 [SMILES: CC(C)C1CCCN1c1nc2c(c(Nc3ccc(C(F)(F)F)nc3)n1)CCN(c1ncccc1C(F)(F)F)CC2]

MS (ESI): mass calcd. for $C_{27}H_{29}F_6N_7$, 565.24; m/z found, 566.3 [M+H]+. $^1$H NMR (CDCl$_3$): 8.86 (d, J=2.5 Hz, 1H), 8.41-8.40 (m, 1H), 8.14-8.11 (m, 1H), 7.90-7.88 (m, 1H), 7.66 (d, J=9.0 Hz, 1H), 6.99-6.96 (m, 1H), 6.60 (s, 1H), 4.47 (d, J=13.0 Hz, 1H), 4.39 (d, J=13.0 Hz, 1H), 4.06-4.03 (m, 1H), 3.79-3.75 (m, 1H), 3.71-3.56 (m, 7H), 3.13-3.05 (m, 3H), 2.95-2.85 (m, 3H), 2.07 (2.04 (m, 1H).

Example 275

$N^2$-Cyclohexyl-$N^2$-methyl-7-[3-(trifluoromethyl)pyridin-2-yl]-$N^4$-[6-(trifluoromethyl)pyridin-3-yl]-6,7,8,9-tetrahydro-5H-pyrimido[4,5-d]azepine-2,4-diamine

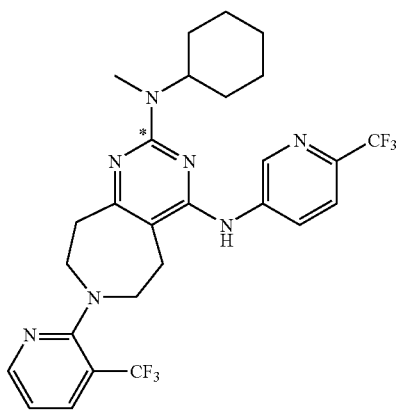 [SMILES: CN(c1nc2c(c(Nc3ccc(C(F)(F)F)nc3)n1)CCN(c1ncccc1C(F)(F)F)CC2)C1CCCCC1]

MS (ESI): mass calcd. for $C_{27}H_{29}F_6N_7$, 565.24; m/z found, 566.3 [M+H]+. $^1$H NMR (CDCl$_3$): 8.70 (s, 1H), 8.42 (d, J=10.0 Hz, 1H), 8.39-8.38 (m, 1H), 7.88-7.86 (m, 1H), 7.61 (d, J=10.0 Hz, 1H), 7.00-6.93 (m, 1H), 6.55 (s, 1H), 4.49 (br s, 1H), 3.61-3.55 (m, 4H), 3.11-3.08 (m, 2H), 3.01 (s, 3H), 2.91-2.88 (m, 2H), 1.87-1.84 (m, 2H), 1.75-1.71 (m, 3H), 1.52-1.12 (m, 5H).

Example 276

2-(2R)-2-Methylpiperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine

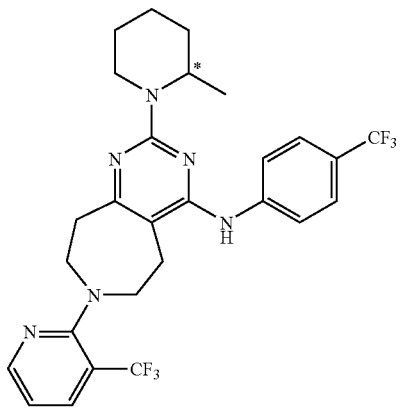 [SMILES: CC1CCCCN1c1nc2c(c(Nc3ccc(C(F)(F)F)cc3)n1)CCN(c1ncccc1C(F)(F)F)CC2]

MS (ESI): mass calcd. for $C_{27}H_{28}F_6N_6$, 550.23; m/z found, 551.3 [M+H]+. $^1$H NMR (CD$_3$OD): 8.53-8.35 (m, 1H), 8.08-7.97 (m, 1H), 7.80 (d, J=8.8 Hz, 2H), 7.55 (d, J=8.4 Hz, 2H), 7.18-7.07 (m, 1H), 3.59-2.87 (m, 12H), 2.02-1.52 (m, 4H), 1.20 (d, J=6.8 Hz, 3H). $[\alpha]^P{}_{20}$=+58.2 (c=0.005, MeOH).

Example 277

2-[(2S)-2-Methylpiperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine

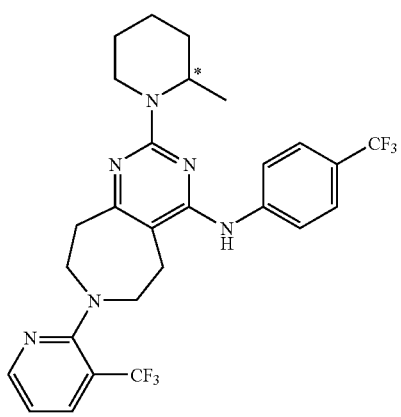 [SMILES: CC1CCCCN1c1nc2c(c(Nc3ccc(C(F)(F)F)cc3)n1)CCN(c1ncccc1C(F)(F)F)CC2]

MS (ESI): mass calcd. for $C_{27}H_{28}F_6N_6$, 550.23; m/z found, 551.3 [M+H]+. $^1$H NMR (CD$_3$OD): 8.54-8.33 (m, 1H), 8.02 (dd, J=7.9, 1.8 Hz, 1H), 7.80 (d, J=8.5 Hz, 2H), 7.54 (d, J=8.6 Hz, 2H), 7.17-7.07 (m, 1H), 3.60-3.37 (m, 2H), 3.36-3.31 (m, 2H), 3.11-2.97 (m, 4H), 1.80-1.68 (m, 4H), 1.66-1.60 (m, 4H), 1.20 (d, J=6.89 Hz, 3H). $[\alpha]^P{}_{20}$=−53.8 (c=0.005, MeOH).

The following Examples 278-280 were prepared using methods analogous to those described in Example 54, substituting the appropriate amines.

Example 278

$N^2$(2-Methylphenyl)-$N^4$-[4-(trifluoromethyl)phenyl]-7-[3-(trifluoromethyl)pyridin-2-yl]-6,7,8,9-tetrahydro-5H-pyrimido[4,5-d]azepine-2,4-diamine trifluoroacetic acid salt

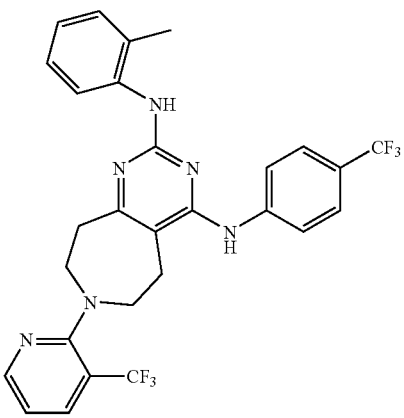 [SMILES: Cc1ccccc1Nc1nc2c(c(Nc3ccc(C(F)(F)F)cc3)n1)CCN(c1ncccc1C(F)(F)F)CC2]

MS (ESI): mass calcd. for $C_{28}H_{24}F_6N_6$, 558.19; m/z found, 559.4 [M+H]+. $^1$H NMR (MeOD): 8.45 (dd, J=4.7, 1.5 Hz, 1H), 8.02 (dd, J=7.8, 1.8 Hz, 1H), 7.58 (d, J=8.5 Hz, 2H), 7.41 (d, J=8.6 Hz, 2H), 7.33-7.28 (m, 3H), 7.28-7.22 (m, 1H), 7.14 (dd, J=7.7, 4.8 Hz, 1H), 3.66-3.62 (m, 2H), 3.57-3.54 (m, 2H), 3.27-3.23 (m, 2H), 3.14-3.09 (m, 2H), 2.21 (s, 3H).

Example 279

N²-(3-Methylphenyl)-N⁴-[4-(trifluoromethyl)phenyl]-7-[3-(trifluoromethyl)pyridin-2-yl]-6,7,8,9-tetrahydro-5H-pyrimido[4,5-d]azepine-2,4-diamine trifluoroacetic acid salt

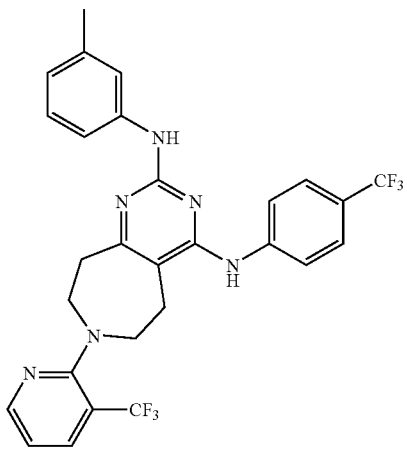 [SMILES: Cc1cccc(Nc2nc3c(c(Nc4ccc(C(F)(F)F)cc4)n2)CCN(c2ncccc2C(F)(F)F)CC3)c1]

MS (ESI): mass calcd. for $C_{28}H_{24}F_6N_6$, 558.20; m/z found, 559.1 [M+H]⁺. ¹H NMR (MeOD): 8.45 (dd, J=4.7, 1.4 Hz, 1H), 8.02 (dd, J=7.8, 1.8 Hz, 1H), 7.67 (d, J=8.5 Hz, 2H), 7.61 (d, J=8.7 Hz, 2H), 7.17-7.11 (m, 3H), 7.01-6.96 (m, 1H), 3.67-3.59 (m, 2H), 3.59-3.55 (m, 2H), 3.35 (s, 1H), 3.26-3.23 (m, 2H), 3.14-3.09 (m, 2H), 2.20 (s, 3H).

Example 280

N²-(4-Methylphenyl)-N⁴-[4-(trifluoromethyl)phenyl]-7-[3-(trifluoromethyl)pyridin-2-yl]-6,7,8,9-tetrahydro-5H-pyrimido[4,5-d]azepine-2,4-diamine trifluoroacetic acid salt

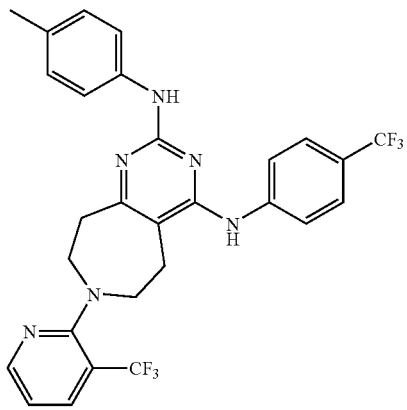 [SMILES: Cc1ccc(Nc2nc3c(c(Nc4ccc(C(F)(F)F)cc4)n2)CCN(c2ncccc2C(F)(F)F)CC3)cc1]

MS (ESI): mass calcd. for $C_{28}H_{24}F_6N_6$, 558.20; m/z found, 559.5 [M+H]⁺. ¹H NMR (MeOD): 8.46 (dd, J=4.7, 1.3 Hz, 1H), 8.03 (dd, J=7.8, 1.7 Hz, 1H), 7.65 (d, J=8.6 Hz, 2H), 7.58 (d, J=8.6 Hz, 2H), 7.21 (d, J=8.4 Hz, 2H), 7.18-7.12 (m, 1H), 7.10 (d, J=8.2 Hz, 2H), 3.66-3.60 (m, 2H), 3.59-3.53 (m, 2H), 3.25-3.19 (m, 2H), 3.14-3.08 (m, 2H), 2.33 (s, 3H).

The following Examples 281-295 were prepared using methods analogous to those described in Example 26, substituting the appropriate 2-chloro pyridines in Step C and anilines in Step E:

Example 281

N-{2-[2-(1-Methylethyl)-4-{[4-(trifluoromethyl)phenyl]amino}-5,6,8,9-tetrahydro-7H-pyrimido[4,5-d]azepin-7-yl]pyridin-3-yl}methanesulfonamide

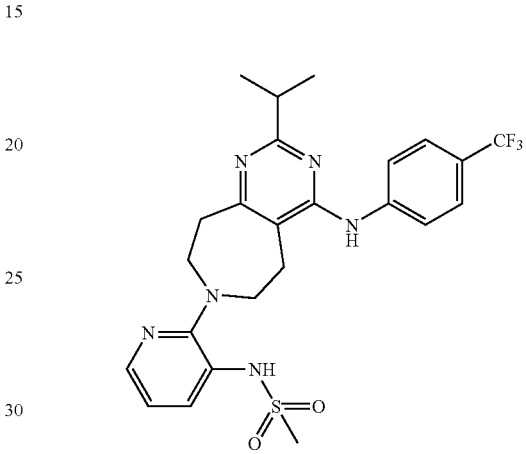

The title compound was prepared using methods analogous to those described by Richardson, T. I. et al. *J. Med. Chem.* 2004, 47, 744) starting from [7-(2-amino-phenyl)-2-isopropyl-6,7,8,9-tetrahydro-5H-pyrimido[4,5-d]azepin-4-yl]-(4-trifluoromethyl-phenyl)-amine (Example 84). MS (ESI): mass calcd. for $C_{24}H_{27}F_3N_6O_2S$, 520.20; m/z found, 521.1 [M+H]⁺. ¹H NMR (CDCl₃): 8.11 (dd, J=4.8, 1.6 Hz, 1H), 7.82-7.76 (m, 3H), 7.61-7.58 (m, 2H), 7.09 (dd, J=8.1, 4.8 Hz, 1H), 6.81-6.51 (m, 1H), 3.36-3.30 (m, 4H), 3.28-3.20 (m, 2H), 3.15-3.13 (m, 3H), 3.11-3.03 (m, 1H), 3.03-2.96 (m, 2H), 1.34 (d, J=6.9 Hz, 6H).

Example 282

2-(1-Methylethyl)-7-[3-(methylsulfonyl)pyridin-2-yl]-N-[6-(trifluoromethyl)pyridin-3-yl]-6,7,8,9-tetrahydro-5H-pyrimido[4,5-d]azepin-4-amine

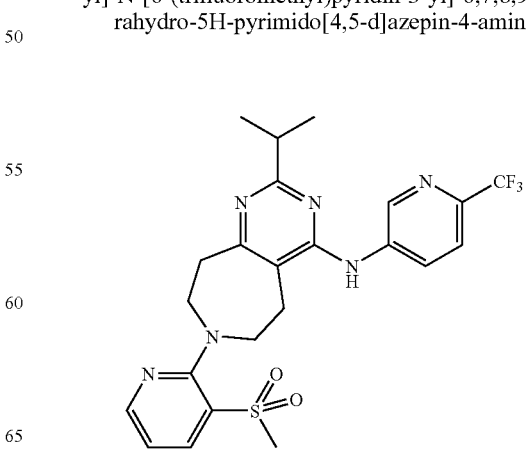

The title compound was prepared analogously to the methods described in Example 26, substituting 2-chloro-3-methanesulfonyl-pyridine (*J. Org. Chem.* 1979, 44(17), 3080-3082) in Step C. MS (ESI): mass calcd. for $C_{23}H_{25}F_3N_6O_2S$, 506.17; m/z found, 507.1 [M+H]$^+$. $^1$H NMR (CDCl$_3$): 8.78 (dd, J=4.8, 1.9 Hz, 1H), 8.48 (dd, J=7.9, 1.9 Hz, 1H), 8.09-8.07 (m, 1H), 7.53 (dd, J=7.9, 4.8 Hz, 1H), 7.45 (d, J=8.6 Hz, 1H), 6.90 (dd, J=8.5, 2.7 Hz, 1H), 5.96-5.78 (m, 1H), 4.25-4.00 (m, 2H), 3.58-3.52 (m, 2H), 3.24 (s, 3H), 3.20-3.13 (m, 2H), 2.95-2.91 (m, 2H), 2.91-2.81 (m, 1H), 1.18 (d, J=6.9 Hz, 6H).

Example 283

7-[3-(Methylsulfonyl)pyridin-2-yl]-N-[4-(trifluoromethyl)phenyl]-6,7,8,9-tetrahydro-5H-pyrimido[4,5-d]azepin-4-amine

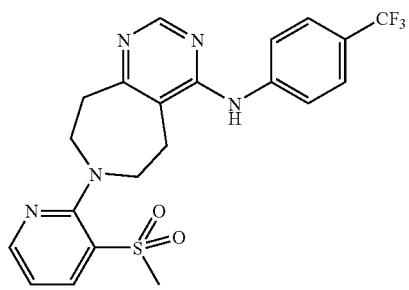 [SMILES: CS(=O)(=O)c1cccnc1N1CCc2ncnc(Nc3ccc(C(F)(F)F)cc3)c2CC1]

The title compound was prepared analogously to the methods described in Example 26, substituting 2-chloro-3-methanesulfonyl-pyridine (*J. Org. Chem.* 1979, 44(17), 3080-3082) in Step C. MS (ESI): mass calcd. for $C_{21}H_{20}F_3N_5O_2S$, 463.13; m/z found, 464 [M+H]$^+$. $^1$H NMR (CDCl$_3$): 8.66-8.60 (m, 1H), 8.55 (dd, J=4.8, 1.9 Hz, 1H), 8.38 (dd, J=7.8, 1.9 Hz, 1H), 7.73 (d, J=8.6 Hz, 2H), 7.65 (d, J=8.6 Hz, 2H), 7.28-7.24 (m, 1H), 3.67-3.59 (m, 2H), 3.59-3.54 (m, 2H), 3.39-3.28 (m, 2H), 3.14-3.05 (m, 2H), 2.99 (s, 3H).

Example 284

7-(3-Aminopyridin-2-yl)-N-[4-(1,1-dimethylethyl)phenyl]-2-(1-methylethyl)-6,7,8,9-tetrahydro-5H-pyrimido[4,5-d]azepin-4-amine

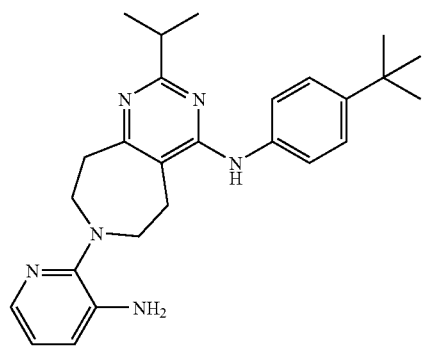 [SMILES: CC(C)c1nc2c(c(Nc3ccc(C(C)(C)C)cc3)n1)CCN(c1ncccc1N)CC2]

MS (ESI): mass calcd. for $C_{26}H_{34}N_6$, 430.28; m/z found, 431.2 [M+H]$^+$. $^1$H NMR (CDCl$_3$): 7.78 (dd, J=4.8, 1.6 Hz, 1H), 7.63-7.56 (m, 2H), 7.39-7.32 (m, 2H), 7.01-6.95 (m, 1H), 6.88-6.83 (m, 1H), 6.51-6.47 (m, 1H), 3.87-3.75 (m, 2H), 3.44-3.30 (m, 4H), 3.23-3.15 (m, 2H), 3.08-2.99 (m, 1H), 2.94-2.88 (m, 2H), 1.37-1.30 (m, 1H).

Example 285

7-[3-Chloro-5-(trifluoromethyl)pyridin-2-yl]-N-[4-(1,1-dimethylethyl)phenyl]-2-(1-methylethyl)-6,7,8,9-tetrahydro-5H-pyrimido[4,5-d]azepin-4-amine

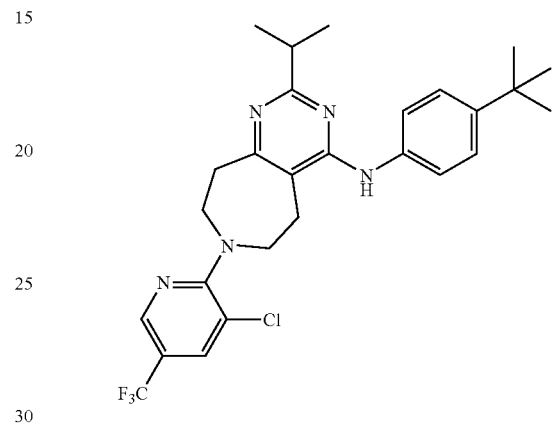

MS (ESI): mass calcd. for $C_{27}H_{31}ClF_3N_5$, 517.22; m/z found, 518.2 [M+H]$^+$. $^1$H NMR (CDCl$_3$): 8.41-8.26 (m, 1H), 7.64-7.55 (m, 2H), 7.40-7.33 (m, 2H), 7.28-7.23 (m, 1H), 3.99-3.78 (m, 4H), 3.28-3.17 (m, 2H), 3.08-2.94 (m, 3H), 1.43-1.26 (m, 6H).

Example 286

7-(5-Bromo-3-chloropyridin-2-yl)-N-[4-(1,1-dimethylethyl)phenyl]-2-(1-methylethyl)-6,7,8,9-tetrahydro-5H-pyrimido[4,5-d]azepin-4-amine

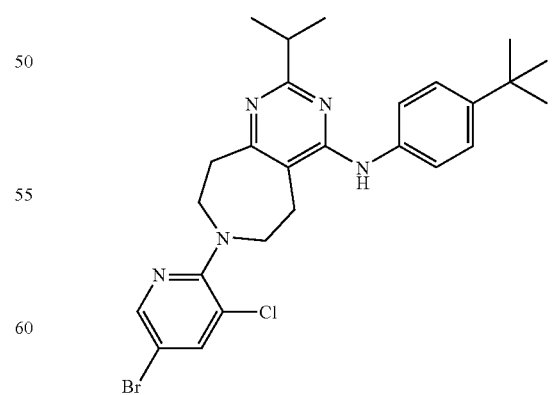

MS (ESI): mass calcd. for $C_{26}H_{31}BrClN_5$, 527.15; m/z found, 530.1 [M+H]$^+$. $^1$H NMR (CDCl$_3$): 8.21-8.08 (m, 1H), 7.73-7.68 (m, 1H), 7.63-7.57 (m, 2H), 7.40-7.31 (m, 2H), 6.46 (s, 1H), 3.79-3.58 (m, 4H), 3.26-3.15 (m, 2H), 3.06-2.98 (m, 1H), 2.96-2.91 (m, 2H), 1.37-1.30 (m, 6H).

Example 287

7-[3-Chloro-5-(trifluoromethyl)pyridin-2-yl]-2-(1-methylethyl)-N-[4-(trifluoromethyl)phenyl]-6,7,8,9-tetrahydro-5H-pyrimido[4,5-d]azepin-4-amine

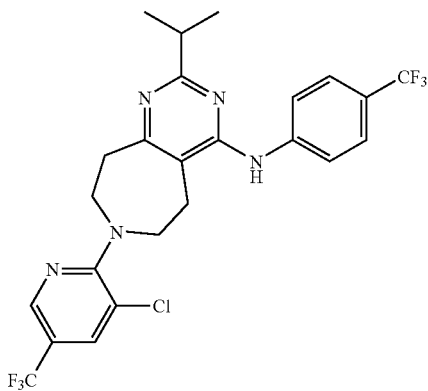 [SMILES: CC(C)c1nc2c(c(Nc3ccc(C(F)(F)F)cc3)n1)CCN(c1ncc(C(F)(F)F)cc1Cl)CC2]

MS (ESI): mass calcd. for $C_{24}H_{22}ClF_6N_5$, 529.15; m/z found, 530.1 [M+H]$^+$. $^1$H NMR (CDCl$_3$): 8.40-8.28 (m, 1H), 7.83-7.77 (m, 2H), 7.77-7.74 (m, 1H), 7.62-7.57 (m, 2H), 3.99-3.81 (m, 4H), 3.33-3.18 (m, 2H), 3.11-2.98 (m, 3H), 1.32 (d, J=6.9 Hz, 6H).

Example 288

5-Chloro-6-[2-(1-methylethyl)-4-{[4-(trifluoromethyl)phenyl]amino}-5,6,8,9-tetrahydro-7H-pyrimido[4 5-d]azepin-7-yl]pyridine-3-carboxylic acid trifluoroacetic acid salt

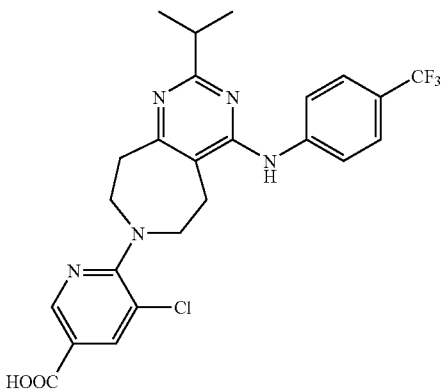 [SMILES: CC(C)c1nc2c(c(Nc3ccc(C(F)(F)F)cc3)n1)CCN(c1ncc(C(=O)O)cc1Cl)CC2]

MS (ESI): mass calcd. for $C_{24}H_{23}ClF_3N_5O_2$, 505.15; m/z found, 506.1 [M+H]$^+$. $^1$H NMR (CD$_3$OD): 8.75-8.57 (m, 1H), 8.18-8.10 (m, 1H), 7.87-7.78 (m, 2H), 7.72-7.67 (m, 2H), 4.08-3.82 (m, 4H), 3.43-3.34 (m, 2H), 3.28-3.22 (m, 2H), 3.10-3.02 (m, 1H), 1.29 (d, J=6.8 Hz, 6H).

Example 289

N-[4-(1,1-Dimethylethyl)phenyl]-2-(1-methylethyl)-7-(3-methyl-5-nitropyridin-2-yl)-6,7,8,9-tetrahydro-5H-pyrimido[4,5-d]azepin-4-amine

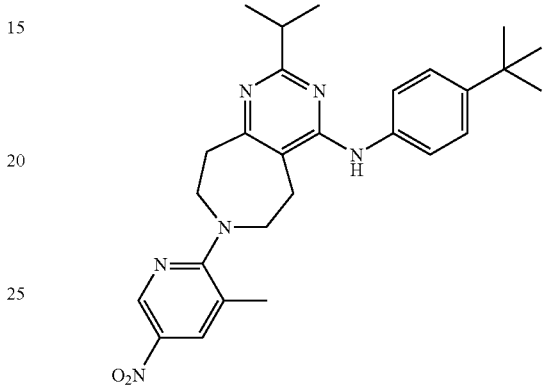

MS (ESI): mass calcd. for $C_{27}H_{34}N_6O_2$, 474.27; m/z found, 475.5 [M+H]$^+$. $^1$H NMR (CDCl$_3$): 8.97-8.85 (m, 1H), 8.16-8.02 (m, 1H), 7.63-7.54 (m, 2H), 7.39-7.33 (m, 2H), 6.45 (s, 1H), 3.99-3.88 (m, 2H), 3.86-3.81 (m, 2H), 3.27-3.16 (m, 2H), 3.05-2.94 (m, 3H), 2.39 (s, 3H), 1.34-1.33 (m, 9H), 1.31 (d, J=6.9 Hz, 6H).

Example 290

N-[4-(1,1-Dimethylethyl)phenyl]-2-(1-methylethyl)-7-[5-nitro-3-(trifluoromethyl)pyridin-2-yl]-6,7,8,9-tetrahydro-5H-pyrimido[4,5-d]azepin-4-amine

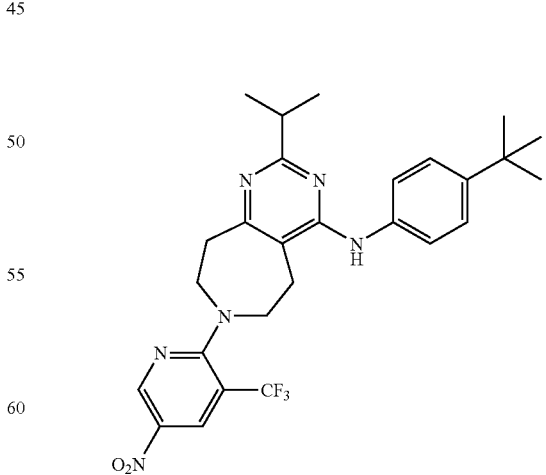

MS (ESI): mass calcd. for $C_{27}H_{31}F_3N_6O_2$, 528.25; m/z found, 529.5 [M+H]$^+$. $^1$H NMR (CDCl$_3$): 9.12-9.01 (m, 1H), 8.63-8.57 (m, 1H), 7.67-7.50 (m, 2H), 7.40-7.32 (m, 2H), 6.38 (s, 1H), 4.22-4.14 (m, 2H), 4.00-3.95 (m, 2H), 3.32-3.22 (m, 2H), 3.06-3.02 (m, 2H), 3.02-2.95 (m, 1H), 1.34-1.32 (m, 9H), 1.29 (d, J=6.9 Hz, 6H).

Example 291

2-(1-Methylethyl)-7-[5-nitro-3-(trifluoromethyl)pyridin-2-yl]-N-[4-(trifluoromethyl)phenyl]-6,7,8,9-tetrahydro-5H-pyrimido[4,5-d]azepin-4-amine

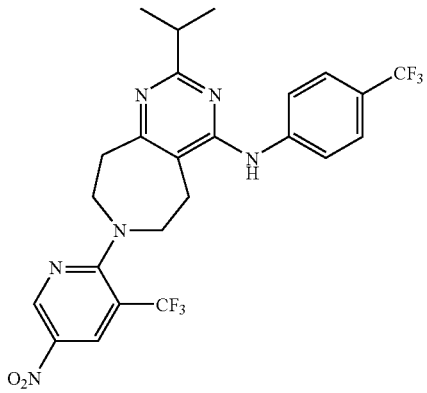 [SMILES: CC(C)c1nc2c(c(Nc3ccc(C(F)(F)F)cc3)n1)CCN(c1ncc([N+](=O)[O-])cc1C(F)(F)F)CC2]

MS (ESI): mass calcd. for $C_{24}H_{22}F_6N_6O_2$, 540.17; m/z found, 541.5 [M+H]+. $^1$H NMR (CDCl$_3$): 9.14-9.04 (m, 1H), 8.64-8.56 (m, 1H), 7.86-7.74 (m, 2H), 7.63-7.58 (m, 2H), 6.57 (s, 1H), 4.23-4.15 (m, 2H), 4.02-3.94 (m, 2H), 3.35-3.24 (m, 2H), 3.12-3.06 (m, 2H), 3.07-2.97 (m, 1H), 1.30 (d, J=6.9 Hz, 6H).

Example 292

N-[4-(1,1-Dimethylethyl)phenyl]-7-(5-fluoro-3-methylpyridin-2-yl)-2-(1-methylethyl)-6,7,8,9-tetrahydro-5H-pyrimido[4,5-d]azepin-4-amine

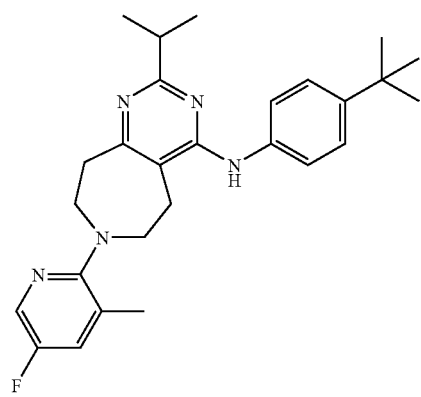 [SMILES: Cc1cc(F)cnc1N1CCc2nc(C(C)C)nc(Nc3ccc(C(C)(C)C)cc3)c2CC1]

The title compound was prepared from N-[4-(1,1-dimethylethyl)phenyl]-2-(1-methylethyl)-7-(3-methyl-5-nitropyridin-2-yl)-6,7,8,9-tetrahydro-5H-pyrimido[4,5-d]azepin-4-amine (Example 289) using procedures analogous to those reported in US 2000/006150343 and Marsais, F. et al. *J. Heterocycl. Chem.* 1988, 25(1), 81. MS (ESI): mass calcd. for $C_{27}H_{34}FN_5$, 447.28; m/z found, 448.5 [M+H]+. $^1$H NMR (CDCl$_3$): 8.03-7.92 (m, 1H), 7.66-7.55 (m, 2H), 7.40-7.31 (m, 2H), 7.24-7.17 (m, 1H), 6.54-6.43 (m, 1H), 3.45-3.36 (m, 2H), 3.36-3.31 (m, 2H), 3.21-3.14 (m, 2H), 3.07-2.98 (m, 1H), 2.93-2.88 (m, 2H), 2.33 (s, 3H), 1.60-1.53 (m, 9H), 1.37-1.31 (m, 6H).

Example 293

2-(4-{[4-(Trifluoromethyl)phenyl]amino}-5,6,8,9-tetrahydro-7H-pyrimido[4,5-d]azepin-7-yl)pyridine-3-carbonitrile

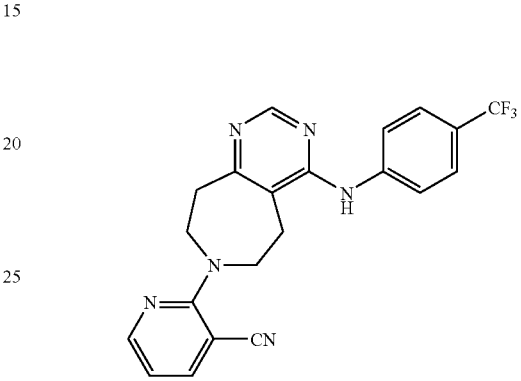

MS (ESI): mass calcd. for $C_{21}H_{17}F_3N_6$, 410.15; m/z found, 411.1 [M+H]+. $^1$H NMR (CDCl$_3$): 8.60 (s, 1H), 8.34 (dd, J=4.7, 1.9 Hz, 1H), 7.78 (dd, J=7.6, 1.9 Hz, 1H), 7.73 (d, J=8.7 Hz, 2H), 7.64 (d, J=8.4 Hz, 2H), 6.78-6.66 (m, 1H), 4.25-4.14 (m, 2H), 4.11-4.07 (m, 2H), 3.47-3.30 (m, 2H), 3.20-3.13 (m, 2H).

Example 294

2-(4-{[4-(Trifluoromethyl)phenyl]amino}-5,6,8,9-tetrahydro-7H-pyrimido[4,5-d]azepin-7-yl)pyridine-3-carboxamide trifluoroacetic acid salt

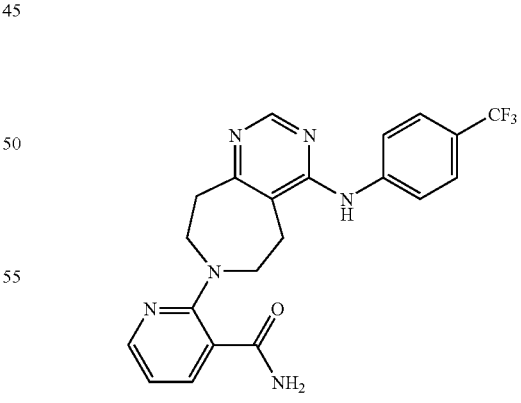

MS (ESI): mass calcd. for $C_{21}H_{19}F_3N_6O$, 428.16; m/z found, 429.1 [M+H]+. $^1$H NMR (CD$_3$OD): 8.62 (s, 1H), 8.22 (dd, J=5.0, 1.9 Hz, 1H), 7.83 (dd, J=7.5, 1.9 Hz, 1H), 7.78 (d, J=8.7 Hz, 2H), 7.73 (d, J=8.7 Hz, 2H), 6.89 (dd, J=7.5, 5.0 Hz, 1H), 3.94-3.80 (m, 4H), 3.51-3.38 (m, 2H), 3.31-3.26 (m, 2H).

Example 295

7-(3-Fluoropyridin-2-yl)-N-[4-(trifluoromethyl)phenyl]-6,7,8,9-tetrahydro-5H-pyrimido[4,5-d]azepin-4-amine

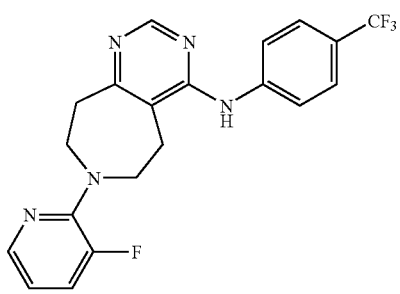 [SMILES: Fc1cccnc1N1CCc2ncnc(Nc3ccc(C(F)(F)F)cc3)c2CC1]

MS (ESI): mass calcd. for $C_{20}H_{17}F_4N_5$, 403.14; m/z found, 404.2 [M+H]$^+$. $^1$H NMR (CDCl$_3$): 8.62 (s, 1H), 8.11-7.79 (m, 2H), 7.77-7.62 (m, 4H), 7.34-7.22 (m, 1H), 6.86-6.60 (m, 1H), 4.15-3.90 (m, 4H), 3.26-2.96 (m, 4H).

Example 296

N-[4-(1,1-Dimethylethyl)phenyl]-7-[3-(ethylsulfonyl)pyridin-2-yl]-2-(1-methylethyl)-6,7,8,9-tetrahydro-5H-pyrimido[4,5-d]azepin-4-amine

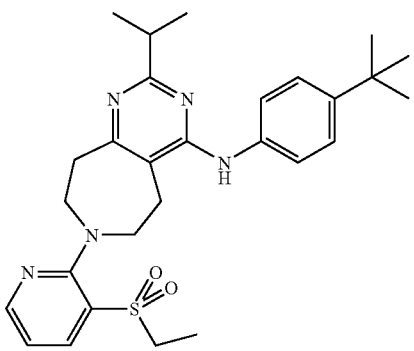 [SMILES: CCS(=O)(=O)c1cccnc1N1CCc2nc(C(C)C)nc(Nc3ccc(C(C)(C)C)cc3)c2CC1]

The title compound was prepared analogously to the methods described in Example 26, substituting 2-chloro-3-ethanesulfonyl-pyridine (prepared using methods analogous to those reported in *J. Org. Chem.* 1979, 44(17), 3080-3082) in Step C. MS (ESI): mass calcd. for $C_{28}H_{37}N_5O_2S$, 507.27; m/z found, 508.2 [M+H]$^+$. $^1$H NMR (CDCl$_3$): 8.44 (dd, J=4.7, 1.9 Hz, 1H), 8.27 (dd, J=7.8, 1.9 Hz, 1H), 7.61-7.47 (m, 2H), 7.32-7.24 (m, 2H), 7.14 (dd, J=7.8, 4.8 Hz, 1H), 6.56 (s, 1H), 3.53-3.43 (m, 2H), 3.45-3.41 (m, 2H), 3.22 (q, J=7.4 Hz, 2H), 3.15-3.08 (m, 2H), 3.01-2.92 (m, 1H), 2.91-2.86 (m, 2H), 1.29-1.22 (m, 15H).

Example 297

7-[3-(Ethylsulfonyl)pyridin-2-yl]-2-piperidin-1-yl-N-[4-(trifluoromethyl)phenyl]-6,7,8,9-tetrahydro-5H-pyrimido[4,5-d]azepin-4-amine

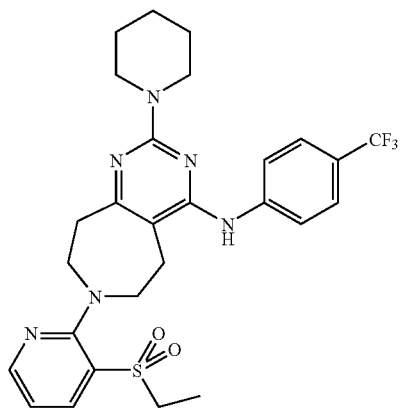 [SMILES: CCS(=O)(=O)c1cccnc1N1CCc2nc(N3CCCCC3)nc(Nc3ccc(C(F)(F)F)cc3)c2CC1]

The title compound was prepared analogously to the methods described in Example 26, substituting 2-chloro-3-ethanesulfonyl-pyridine (prepared using methods analogous to those reported in *J. Org. Chem.* 1979, 44(17), 3080-3082) in Step C. MS (ESI): mass calcd. for $C_{27}H_{31}F_3N_6O_2S$, 560.22; m/z found, 561.1 [M+H]$^+$. $^1$H NMR (CDCl$_3$): 8.44 (dd, J=4.7, 1.9 Hz, 1H), 8.27 (dd, J=7.8, 1.9 Hz, 1H), 7.58 (d, J=8.5 Hz, 2H), 7.49 (d, J=8.7 Hz, 2H), 7.13 (dd, J=7.8, 4.8 Hz, 1H), 6.60 (s, 1H), 3.76-3.58 (m, 4H), 3.49-3.42 (m, 2H), 3.41-3.37 (m, 2H), 3.28 (q, J=7.4 Hz, 2H), 3.03-2.96 (m, 2H), 2.85-2.78 (m, 2H), 1.65-1.49 (m, 4H), 1.02 (t, J=7.5 Hz, 3H).

The following Examples 298-302 were prepared using methods analogous to those described in Example 26, substituting the appropriate 2-chloro pyridines (see Cordi, A. A. et al. *Il Farmaco*, 2002, 57, 787) in Step C and anilines in-Step E.

Example 298

2-(2-Piperidin-1-yl-4-{[4-(trifluoromethyl)phenyl]amino}-5,6,8,9-tetrahydro-7H-pyrimido[4,5-d]azepin-7-yl)pyridine-3-sulfonamide

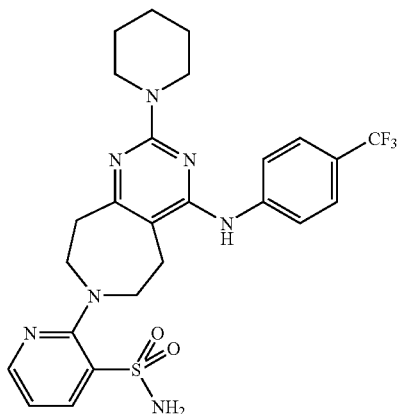 [SMILES: NS(=O)(=O)c1cccnc1N1CCc2nc(N3CCCCC3)nc(Nc3ccc(C(F)(F)F)cc3)c2CC1]

MS (ESI): mass calcd. for C25H28F3N7O2S, 547.20; m/z found, 548.1 [M+H]+. 1H NMR (CDCl3): 8.45 (dd, J=4.8, 1.9 Hz, 1H), 8.23 (dd, J=7.8, 1.9 Hz, 1H), 7.57 (d, J=8.6 Hz, 2H), 7.49 (d, J=8.6 Hz, 2H), 7.15 (dd, J=7.8, 4.8 Hz, 1H), 6.60 (s, 1H), 3.72-3.61 (m, 4H), 3.46-3.38 (m, 2H), 3.36-3.31 (m, 2H), 3.05-2.95 (m, 2H), 2.85-2.80 (m, 2H), 1.66-1.51 (m, 4H).

Example 299

N-Cyclopropyl-2-(2-piperidin-1-yl-4-{[4-(trifluoromethyl)phenyl]amino}-5,6,8,9-tetrahydro-7H-pyrimido[4,5-d]azepin-7-yl)pyridine-3-sulfonamide

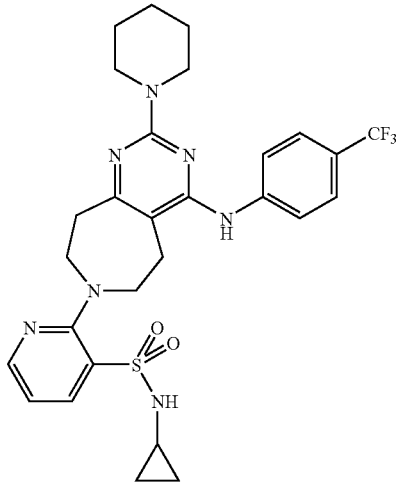 [SMILES: O=S(=O)(NC1CC1)c1cccnc1N1CCc2nc(N3CCCCC3)nc(Nc3ccc(C(F)(F)F)cc3)c2CC1]

MS (ESI): mass calcd. for C28H32F3N7O2S, 587.23; m/z found, 588.1 [M+H]+. 1H NMR (CDCl3): 8.44 (dd, J=4.8, 1.9 Hz, 1H), 8.26 (dd, J=7.8, 1.9 Hz, 1H), 7.56 (d, J=8.6 Hz, 2H), 7.49 (d, J=8.8 Hz, 2H), 7.13 (dd, J=7.8, 4.8 Hz, 1H), 6.62 (s, 1H), 5.68-5.41 (m, 1H), 3.72-3.64 (m, 3H), 3.46-3.39 (m, 2H), 3.36-3.32 (m, 2H), 3.03-2.93 (m, 2H), 2.84-2.78 (m, 2H), 1.68-1.50 (m, 4H), 0.41-0.16 (m, 4H).

Example 300

N-(1-Methylethyl)-2-(2-piperidin-1-yl-4-{[4-(trifluoromethyl)phenyl]amino}-5,6,8,9-tetrahydro-7H-pyrimido[4,5-d]azepin-7-yl)pyridine-3-sulfonamide

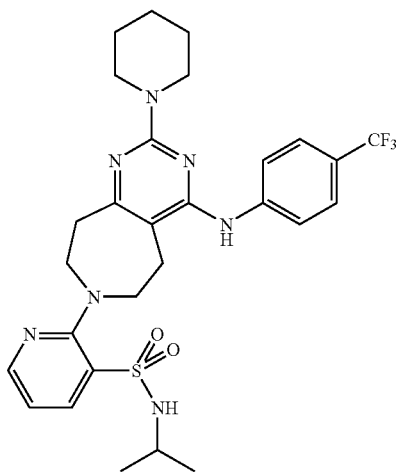 [SMILES: CC(C)NS(=O)(=O)c1cccnc1N1CCc2nc(N3CCCCC3)nc(Nc3ccc(C(F)(F)F)cc3)c2CC1]

MS (ESI): mass calcd. for C28H34F3N7O2S, 589.24; m/z found, 590.2 [M+H]+. 1H NMR (CDCl3): 8.41 (dd, J=4.8, 1.9 Hz, 1H), 8.21 (dd, J=7.7, 1.9 Hz, 1H), 7.58 (d, J=8.5 Hz, 2H), 7.49 (d, J=8.6 Hz, 2H), 7.10 (dd, J=7.7, 4.8 Hz, 1H), 6.72 (s, 1H), 3.72-3.63 (m, 4H), 3.45-3.38 (m, 2H), 3.36-3.31 (m, 2H), 3.11-3.02 (m, 1H), 3.00-2.95 (m, 2H), 2.86-2.79 (m, 2H), 1.67-1.48 (m, 4H), 0.70 (d, J=6.5 Hz, 6H).

Example 301

7-[3-(Ethylsulfonyl)pyridin-2-yl]-N-[4-(trifluoromethyl)phenyl]-6,7,8,9-tetrahydro-5H-pyrimido[4,5-d]azepin-4-amine

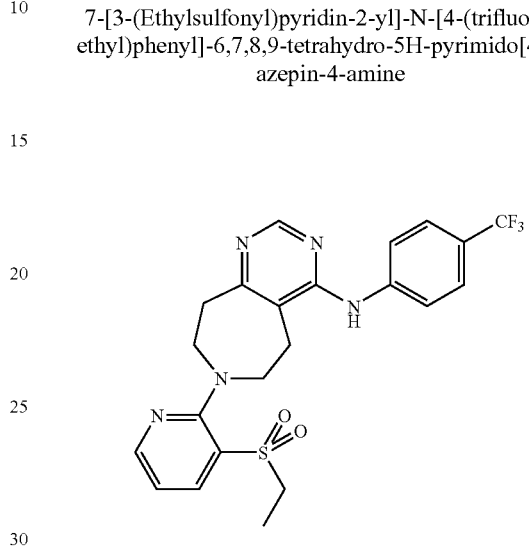

MS (ESI): mass calcd. for C22H22F3N5O2S, 477.14; m/z found, 478.1 [M+H]+. 1H NMR (CDCl3): 8.63 (s, 1H), 8.55 (dd, J=4.7, 1.9 Hz, 1H), 8.35 (dd, J=7.8, 1.8 Hz, 1H), 7.72 (d, J=8.6 Hz, 2H), 7.65 (d, J=8.5 Hz, 2H), 7.27-7.24 (m, 1H), 3.66-3.58 (m, 2H), 3.58-3.54 (m, 2H), 3.41-3.30 (m, 2H), 3.17-3.06 (m, 4H), 1.04 (t, J=7.4 Hz, 3H).

Example 302

2-(4-{[4-(Trifluoromethyl)phenyl]amino}-5,6,8,9-tetrahydro-7H-pyrimido[4,5-d]azepin-7-yl)pyridine-3-sulfonamide

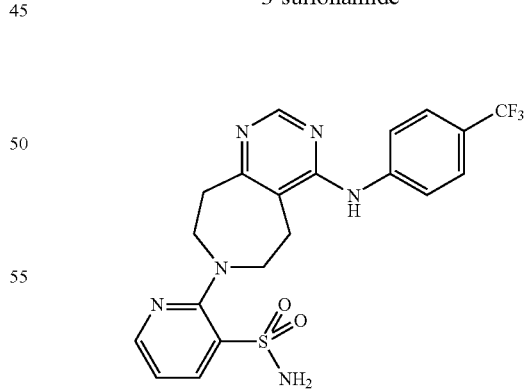

MS (ESI): mass calcd. for C20H19F3N6O2S, 464.12; m/z found, 465.1 [M+H]+. 1H NMR (MeOD): 8.45-8.34 (m, 2H), 8.23 (dd, J=7.8, 1.8 Hz, 1H), 7.63 (d, J=8.5 Hz, 2H), 7.52 (d, J=8.6 Hz, 2H), 7.15 (dd, J=7.8, 4.8 Hz, 1H), 3.49-3.39 (m, 2H), 3.39-3.34 (m, 2H), 3.23-3.17 (m, 2H), 3.07-3.02 (m, 2H).

Example 303

Methyl 5-chloro-6-[2-(methylsulfanyl)-4-{[4-(trifluoromethyl)phenyl]amino}-5,6,8,9-tetrahydro-7H-pyrimido[4,5-d]azepin-7-yl]pyridine-3-carboxylate

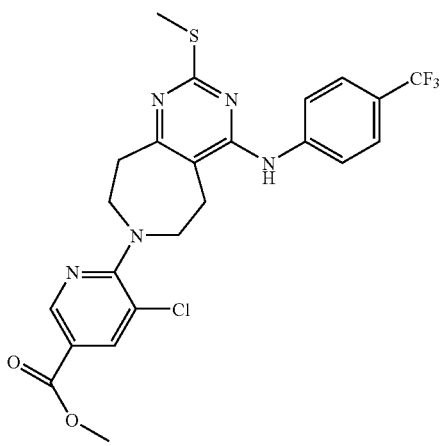 [SMILES: COC(=O)c1cnc(N2CCc3nc(SC)nc(Nc4ccc(C(F)(F)F)cc4)c3CC2)c(Cl)c1]

Step A. 4-Hydroxy-2-methylsulfanyl-5,6,8,9-tetrahydro-pyrimido[4,5-d]azepine-7-carboxylic acid tert-butyl ester. To solution of 5-oxo-azepane-1,4-dicarboxylic acid 1-tert-butyl ester 4-ethyl ester (10.5 g, 0.04 mol) in EtOH (168 mL) was added NaOEt (8.1 g, 0.12 mol) and thiourea (4.2 g, 0.06 mol). The mixture was heated at reflux for 12 h. The mixture was cooled, treated with MeI (3.0 mL, 0.05 mol) drop-wise, and stirred at rt for 1 h. The mixture was concentrated and the residue was dissolved in water and acidified to pH=7 with HOAc (a precipitate formed). The solid was filtered to give the title compound (8.4 g, 73%), which was used in the next step without further purification.

Step B: 2-Methylsulfanyl-4-trifluoromethanesulfonyloxy-5,6,8,9-tetrahydro-pyrimido[4,5-d]azepine-7-carboxylic acid tert-butyl ester. To a solution of 4-hydroxy-2-methylsulfanyl-5,6,8,9-tetrahydro-pyrimido[4,5-d]azepine-7-carboxylic acid tert-butyl ester (1.2g, 3.86 mmol) in THF (129 mL) was added KOtBu (518 mg, 4.63 mmol) at rt. After 20 min, N-phenyl-bis(trifluoromethanesulfonimide) (1.9 g, 5.40 mmol) was added. The reaction mixture was stirred for an additional 24 h at rt and then concentrated. The residue was purified (FCC) to afford the title compound (1.4 g, 82%)

Step C: (2-Methylsulfanyl-6,7,8,9-tetrahydro-5H-pyrimido[4,5-d]azepin-4-yl)-(4-trifluoromethyl-phenyl)-amine. A solution containing methylsulfanyl-4-trifluoromethanesulfonyloxy-5,6,8,9-tetrahydro-pyrimido[4,5-d]azepine-7-carboxylic acid tert-butyl ester (950 mg, 2.15 mmol), 4-trifluoromethylaniline (0.6 mL, 4.74 mmol) and DMSO (8 mL) was heated at 100° C. for 24 h. The reaction mixture was cooled to rt and diluted with water and extracted with EtOAc. The combined organic extracts were dried and concentrated. The residue was purified (FCC; MeOH/CH$_2$Cl$_2$) to give the title compound (422 mg, 55%).

Step D. A solution of (2-methylsulfanyl-6,7,8,9-tetrahydro-5H-pyrimido[4,5-d]azepin-4-yl)-(4-trifluoromethyl-phenyl)-amine (187 mg, 0.53 mmol), 5,6-dichloro-nicotinic acid methyl ester (129 mg, 0.58 mmol), and Et$_3$N (0.2 mL, 1.58 mmol) in DMF (1.2 mL) was heated at 120° C. for 2 h. The mixture was cooled to rt, diluted with water, and extracted with EtOAc. The combined organic layers were dried and concentrated. The residue was purified (FCC) to give the title compound (203 mg, 74%). MS (ESI): mass calcd. for C$_{23}$H$_{21}$ClF$_3$N$_5$O$_2$S, 523.11; m/z found, 524.1 [M+H]$^+$. $^1$H NMR (CDCl$_3$): 8.57 (d, J=2.0 Hz, 1H), 8.00 (d, J=2.0 Hz, 1H), 7.59 (d, J=8.6 Hz, 2H), 7.48 (d, J=8.6 Hz, 2H), 6.73-6.59 (m, 1H), 3.89-3.65 (m, 7H), 3.19-3.07 (m, 2H), 2.95-2.87 (m, 2H), 2.40 (s, 3H).

The following Examples 304-306 were prepared using methods analogous to those described in Example 303, substituting the appropriate anilines in Step C and 2-chloro pyridines in Step D.

Example 304

2-(Methylsulfanyl)-7-[3-(methylsulfonyl)pyridin-2-yl]-N-[4-(trifluoromethyl)phenyl]-6,7,8,9-tetrahydro-5H-pyrimido[4,5-d]azepin-4-amine

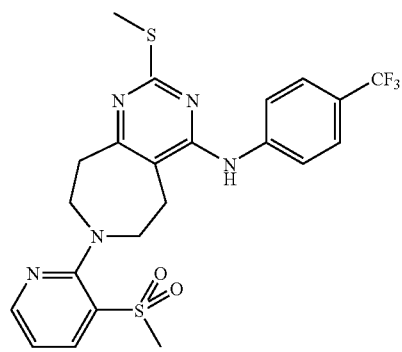

MS (ESI): mass calcd. for C$_{22}$H$_{22}$F$_3$N$_5$O$_2$S$_2$, 509.11; m/z found, 510.1 [M+H]$^+$. $^1$H NMR (CDCl$_3$): 8.62-8.49 (m, 1H), 8.40-8.35 (m, 1H), 7.73 (d, J=8.5 Hz, 2H), 7.62 (d, J=8.5 Hz, 2H), 7.25 (dd, J=7.8, 4.7 Hz, 1H), 7.05-6.94 (m, 1H), 3.61-3.54 (m, 2H), 3.55-3.50 (m, 2H), 3.28-3.17 (m, 2H), 3.06 (s, 3H), 3.04-2.99 (m, 2H), 2.55 (s, 3H).

Example 305

[7-(3-Ethanesulfonyl-pyridin-2-yl)-2-methylsulfanyl-6,7,8,9-tetrahydro-5H-pyrimido[4,5-d]azepin-4-yl]-(4-trifluoromethyl-phenyl)-amine

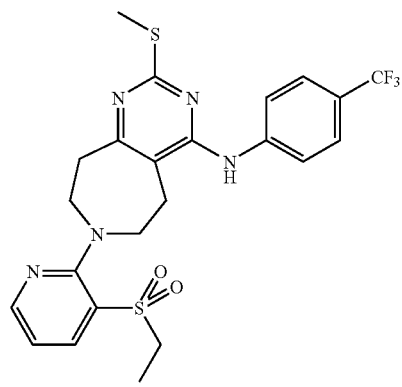 [SMILES: CCS(=O)(=O)c1cccnc1N1CCc2nc(SC)nc(Nc3ccc(C(F)(F)F)cc3)c2CC1]

MS (ESI): mass calcd. for C$_{23}$H$_{24}$F$_3$N$_5$O$_2$S$_2$, 523.13; m/z found, 524.1 [M+H]$^+$. $^1$H NMR (CDCl$_3$): 8.62-8.46 (m, 1H), 8.38-8.31 (m, 1H), 7.72 (d, J=8.5 Hz, 2H), 7.62 (d, J=8.5 Hz, 2H), 7.26-7.22 (m, 1H), 3.63-3.42 (m, 4H), 3.30-3.17 (m, 4H), 3.05-2.96 (m, 2H), 2.54 (s, 3H), 1.10-1.05 (m, 3H).

Example 306

{5-Chloro-6-[2-(methylsulfanyl)-4-{[4-(trifluoromethyl)phenyl]amino}-5,6,8,9-tetrahydro-7H-pyrimido[4,5-d]azepin-7-yl]pyridin-3-yl}methanol

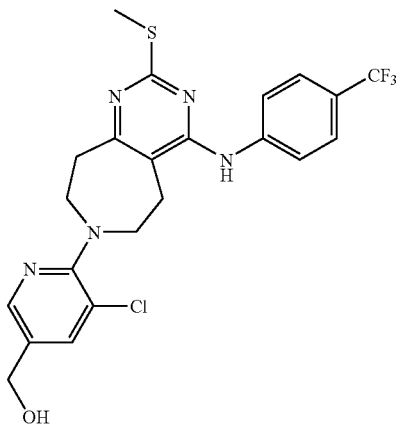 [SMILES: CSc1nc2c(c(Nc3ccc(C(F)(F)F)cc3)n1)CCN(c1ncc(CO)cc1Cl)CC2]

The title compound was prepared analogously to that reported starting methyl 5-chloro-6-[2-(methylsulfanyl)-4-{[4-(trifluoromethyl)-phenyl]amino}-5,6,8,9-tetrahydro-7H-pyrimido[4,5-d]azepin-7-yl]pyridine-3-carboxylate (Example 303) (Boechat, N. et al. *Tetrahedron Lett.* 2004, 45, 6021). MS (ESI): mass calcd. for $C_{22}H_{21}ClF_3N_5OS$, 495.11; m/z found, 496.1 [M+H]$^+$. $^1$H NMR (MeOD): 8.38-8.26 (m, 1H), 8.03 (d, J=8.6 Hz, 2H), 7.96-7.92 (m, 1H), 7.80 (d, J=8.6 Hz, 2H), 4.79-4.69 (m, 2H), 3.86-3.69 (m, 4H), 3.41-3.27 (m, 4H), 2.68 (s, 3H).

Example 307

2-({[(4S)-2,2-Dimethyl-1,3-dioxolan-4-yl]methyl}oxy)-N-[4-(trifluoromethyl)phenyl]-7-[3-(trifluoromethyl)pyridin-2-yl]-6,7,8,9-tetrahydro-5H-pyrimido[4,5-d]azepin-4-amine

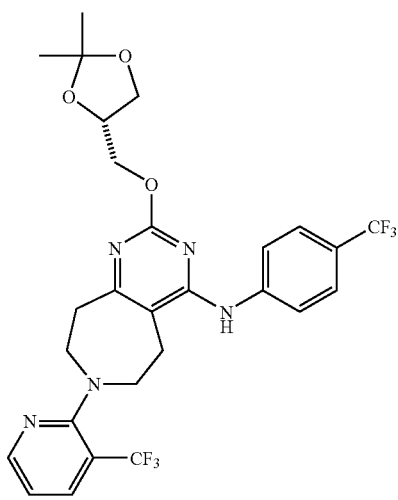 [SMILES: CC1(C)OC[C@H](COc2nc3c(c(Nc4ccc(C(F)(F)F)cc4)n2)CCN(c2ncccc2C(F)(F)F)CC3)O1]

A dispersion of NaH in mineral oil (12.0 mg, 0.28 mmol) was added to a flask containing (2,2-dimethyl-[1,3]dioxolan-4-yl)-methanol (116µL, 0.94 mmol) and DMF (1.0 mL). After 30 min, the mixture was transferred to a flask containing [2-methanesulfonyl-7-(3-trifluoromethyl-pyridin-2-yl)-6,7,8,9-tetrahydro-5H-pyrimido[4,5-d]azepin-4-yl]-(4-trifluoromethyl-phenyl)-amine (Example 53; 50 mg, 0.094 mmol). The resulting mixture was then heated at 70° C. for 24 h. The mixture was cooled, diluted with MeOH (1.0 mL) and purified by reverse phase HPLC, yielding 39 mg (70%) of the title compound. MS (ESI): mass calcd. for $C_{27}H_{27}F_6N_5O_3$, 583.20; m/z found, 584.2 [M+H]$^+$. $^1$H NMR (CDCl$_3$): 8.39-8.37 (m, 1H), 7.89-7.86 (m, 1H), 7.69 (d, J=11.0 Hz, 2H), 7.59 (d, J=11.0 Hz, 2H), 6.98-6.94 (m, 1H), 6.68 (s, 1H), 4.52-4.56 (m, 1H), 4.42-4.38 (m, 1H), 4.28-4.24 (m, 1H), 4.16-4.12 (m, 1H), 3.94-3.90 (m, 1H), 3.63-3.56 (m, 4H), 3.18-3.15 (m, 2H), 2.96-2.93 (m, 2H), 1.46 (s, 3H), 1.38 (s, 3H).

The following Examples 308-340 were prepared using methods analogous to those described in Example 307, substituting the appropriate alcohols.

Example 308

2-(Cyclohexyloxy)-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

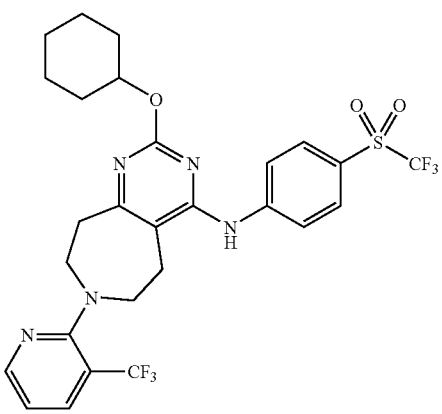 [SMILES: O=S(=O)(c1ccc(Nc2nc(OC3CCCCC3)nc3c2CCN(c2ncccc2C(F)(F)F)CC3)cc1)C(F)(F)F]

MS (ESI): mass calcd. for $C_{27}H_{27}F_6N^5O_3S$, 615.17; m/z found, 616.2 [M+H]$^+$. $^1$H NMR (CDCl$_3$): 8.40-8.38 (d, J=5.0 Hz, 1H), 7.98 (d, J=9.0 Hz, 2H), 7.93-7.87 (m, 3H), 7.00-6.97 (m, 1H), 6.96 (s, 1H), 4.92-4.87 (m, 1H), 3.64-3.57 (m, 4H), 3.22-3.18 (m, 2H), 3.00-2.95 (m, 2H), 2.11-2.08 (m, 2H), 1.89-1.86 (m, 2H), 1.69-1.63(m, 2H), 1.46-1.25 (m, 4H).

Example 309

2-[(1-Cyclohexylethyl)oxy]-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

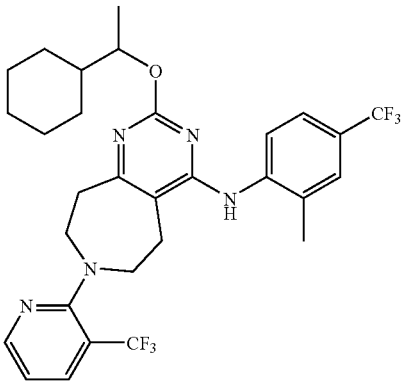 [SMILES: Cc1cc(C(F)(F)F)ccc1Nc1nc(OC(C)C2CCCCC2)nc2c1CCN(c1ncccc1C(F)(F)F)CC2]

MS (ESI): mass calcd. for $C_{30}H_{33}F_6N_5O$, 593.26; m/z found, 594.3 [M+H]$^+$. $^1$H NMR (CDCl$_3$): 8.39-8.37 (m, 1H), 8.08 (d, J=11.0 Hz, 1H), 7.89-7.86 (m, 1H), 7.46 (s, 2H), 6.97-6.94 (m, 1H), 6.42 (s, 1H), 4.84-4.78 (m, 1H), 3.66-3.53 (m, 4H), 3.19-3.16 (m, 2H), 2.94-2.91 (m, 2H), 2.36 (s, 3H), 1.80-1.72 (m, 4H), 1.68-1.57 (m, 2H), 1.24 (d, J=8.0 Hz, 3H), 1.21-0.97 (m, 5H).

Example 310

2-(Cyclopentyloxy)-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

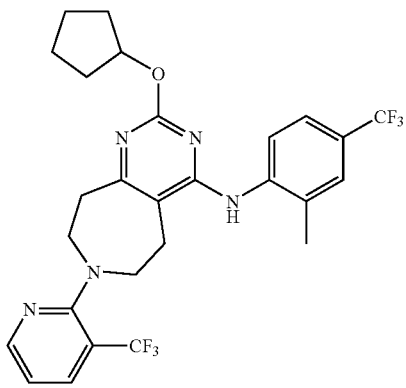 [SMILES: Cc1cc(C(F)(F)F)ccc1Nc1nc(OC2CCCC2)nc2c1CCN(c1ncccc1C(F)(F)F)CC2]

MS (ESI): mass calcd. for $C_{27}H_{27}F_6N_5O$, 551.21; m/z found, 552.3 [M+H]$^+$. $^1$H NMR (CDCl$_3$): 8.40-8.38 (m, 1H), 8.17 (d, J=11.0 Hz, 1H), 7.89-7.87 (m, 1H), 7.46 (s, 2H), 6.97-6.94 (m, 1H), 6.44 (s, 1H), 5.25-5.20 (m, 1H), 3.66-3.57 (m, 4H), 3.18-3.15 (m, 2H), 2.95-2.92 (m, 2H), 2.36 (s, 3H), 1.88-1.76 (m, 6H), 1.63-1.54 (m, 2H).

Example 311

2-[(1-Methylpiperidin-4-yl)oxy]-N-[4-(trifluoromethyl)phenyl]-7-[3-(trifluoromethyl)pyridin-2-yl]-6,7,8,9-tetrahydro-5H-pyrimido[4,5-d]azepin-4-amine

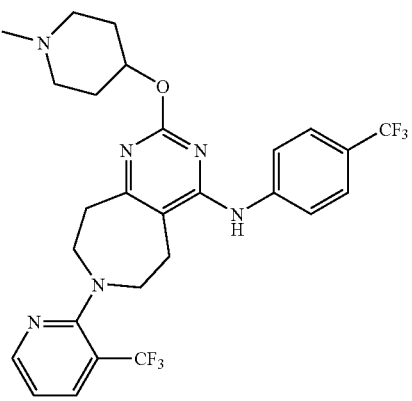 [SMILES: CN1CCC(Oc2nc3c(c(Nc4ccc(C(F)(F)F)cc4)n2)CCN(c2ncccc2C(F)(F)F)CC3)CC1]

MS (ESI): mass calcd. for $C_{27}H_{28}F_6N_6O$, 566.22; m/z found, 567.3 [M+H]$^+$. $^1$H NMR (CDCl$_3$): 8.40-8.37 (m, 2H), 7.88-7.86 (m, 1H), 7.60 (s, 3H), 7.00-6.97 (m, 1H), 5.24 (br s, 1H), 3.57-3.52 (m, 4H), 3.46-3.05 (m, 6H), 3.05-3.02 (m, 2H), 2.79 (s, 3H), 2.65 (s, 1H), 2.37-2.30 (m, 2H), 2.18-2.13 (m, 2H).

Example 312

N-[2-Methyl-4-(trifluoromethyl)phenyl]-2-(tetrahydro-2H-pyran-4-yloxy)-7-[3-(trifluoromethyl)pyridin-2-yl]-6,7,8,9-tetrahydro-5H-pyrimido[4,5-d]azepin-4-amine

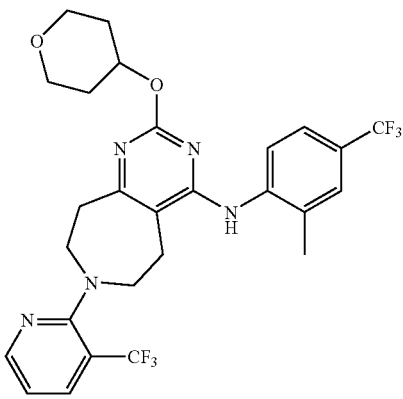 [SMILES: Cc1cc(C(F)(F)F)ccc1Nc1nc(OC2CCOCC2)nc2c1CCN(c1ncccc1C(F)(F)F)CC2]

MS (ESI): mass calcd. for $C_{27}H_{27}F_6N_5O_2$, 567.21; m/z found, 568.2 [M+H]$^+$. $^1$H NMR (CDCl$_3$): 8.39-8.38 (m, 1H), 8.01 (d, J=10.5 Hz, 1H), 7.89-7.86 (m, 1H), 7.48-7.46 (m, 2H), 6.98-6.95 (m, 1H), 6.43 (s, 1H), 4.99-4.92 (m, 1H), 4.02-3.96 (m, 2H), 3.90 (s, 1H), 3.65-3.57 (m, 4H), 3.53-3.47 (m, 2H), 3.19-3.16 (m, 2H), 2.96-2.93 (m, 2H), 2.36 (s, 2H), 2.03-1.98 (m, 2H), 1.86-1.77 (m, 2H).

Example 313

N-[2-Methyl-4-(trifluoromethyl)phenyl]-2-(tetrahydrofuran-3-yloxy)-7-[3-(trifluoromethyl)pyridin-2-yl]-6,7,8,9-tetrahydro-5H-pyrimido[4,5-d]azepin-4-amine

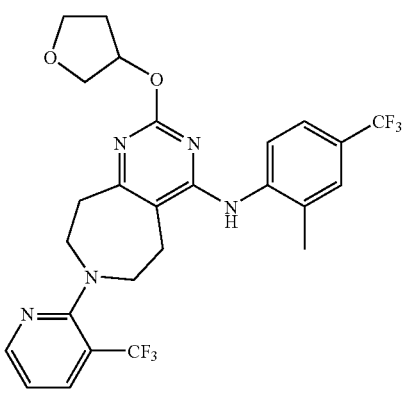 [SMILES: Cc1cc(C(F)(F)F)ccc1Nc1nc(OC2CCOC2)nc2c1CCN(c1ncccc1C(F)(F)F)CC2]

MS (ESI): mass calcd. for $C_{26}H_{25}F_6N_5O_2$, 553.19; m/z found, 554.2 [M+H]$^+$. $^1$H NMR (CDCl$_3$): 8.40-8.38 (m, 1H), 7.97 (d, J=11.0 Hz, 1H), 7.89-7.86 (m, 1H), 7.49 (s, 2H), 6.98-6.95 (m, 1H), 6.42 (s, 1H), 5.33-5.28 (m, 1H), 3.97-3.85

(m, 4H), 3.66-3.57 (m, 4H), 3.19-3.16 (m, 2H), 2.96-2.93 (m, 2H), 2.35 (s, 3H), 2.20-2.08 (m, 2H).

Example 314

N-[4-(Pyrrolidin-1-ylsulfonyl)phenyl]-2-(tetrahydrofuran-3-yloxy)-7-[3-(trifluoromethyl)pyridin-2-yl]-6,7,8,9-tetrahydro-5H-pyrimido[4,5-d]azepin-4-amine

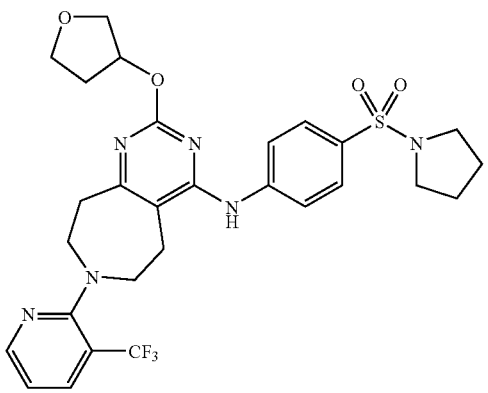 [SMILES: O=S(=O)(c1ccc(Nc2nc(OC3CCOC3)nc3c2CCN(c2ncccc2C(F)(F)F)CC3)cc1)N1CCCC1]

MS (ESI): mass calcd. for $C_{28}H_{31}F_3N_6O_4S$, 604.21; m/z found, 605.2 [M+H]⁺. ¹H NMR (CDCl₃): 8.40-8.38 (m, 1H), 7.89-7.87 (m, 1H), 7.79 (d, J=11.0 Hz, 2H), 7.72 (d, J=11.0 Hz, 2H), 6.99-6.96 (m, 1H), 6.81 (s, 1H), 5.46-5.42 (m, 1H), 4.70-3.90 (m, 4H), 3.63-3.56 (m, 4H), 3.27-3.24 (m, 4H), 3.19-3.16 (m, 2H), 2.98-2.95 (m, 2H), 2.25-2.20 (m, 2H), 1.80-1.76 (m, 4H).

Example 315

2-{[1-(1-Methylethyl)pyrrolidin-3-yl]oxy}-N-[4-(trifluoromethyl)phenyl]-7-[3-(trifluoromethyl)pyridin-2-yl]-6,7,8,9-tetrahydro-5H-pyrimido[4,5-d]azepin-4-amine

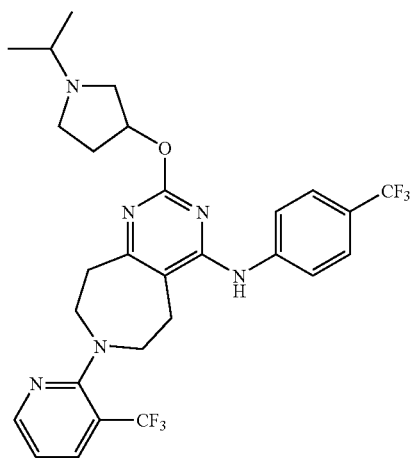 [SMILES: CC(C)N1CCC(Oc2nc3c(c(Nc4ccc(C(F)(F)F)cc4)n2)CCN(c2ncccc2C(F)(F)F)CC3)C1]

MS (ESI): mass calcd. for $C_{28}H_{30}F_6N_6O$, 580.24; m/z found, 581.3 [M+H]⁺. ¹H NMR (CDCl₃): 8.41-8.39 (m, 1H), 7.90-7.88 (m, 1H), 7.70 (d, J=9.0 Hz, 2H), 7.61 (d, J=9.0 Hz, 2H), 6.99-6.96 (m, 1H), 6.67 (s, 1H), 5.37-5.33 (m, 1H), 3.65-3.58 (m, 4H), 3.31-3.28 (m, 1H), 3.20-3.17 (m, 2H), 2.97-2.94 (m, 2H), 2.83-2.79 (m, 1H), 2.69-2.62 (m, 2H), 2.47-2.42 (m, 1H), 2.34-2.27 (m, 1H), 2.08-2.02 (m, 1H), 1.12-1.10 (m, 6H).

Example 316

[2-r(1-Cyclohexylethyl)oxy]-N-(1-methyl-1,2,3,4-tetrahydroquinolin-7-yl)-7-[3-(trifluoromethyl)pyridin-2-yl]-6,7,8,9-tetrahydro-5H-pyrimido[4,5-d]azepin-4-amine

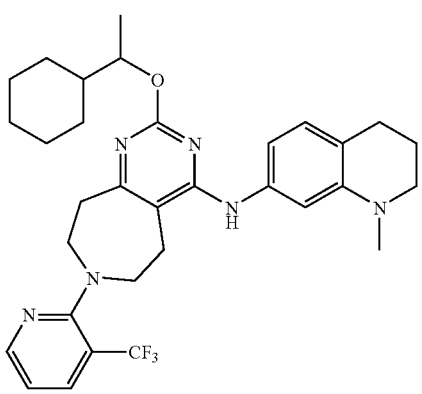 [SMILES: CC(Oc1nc2c(c(Nc3ccc4c(c3)N(C)CCC4)n1)CCN(c1ncccc1C(F)(F)F)CC2)C1CCCCC1]

MS (ESI): mass calcd. for $C_{32}H_{39}F_3N_6O$, 580.31; m/z found, 581.4 [M+H]⁺.

Example 317

2-[(1-Cyclopropylethyl)oxy]-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

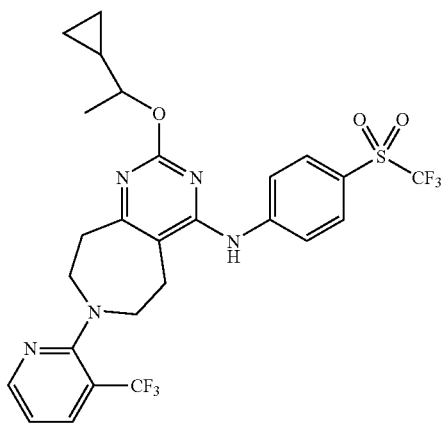 [SMILES: CC(Oc1nc2c(c(Nc3ccc(S(=O)(=O)C(F)(F)F)cc3)n1)CCN(c1ncccc1C(F)(F)F)CC2)C1CC1]

MS (ESI): mass calcd. for $C_{26}H_{25}F_6N_5O_3S$, 601.16; m/z found, 602.2 [M+H]⁺. ¹H NMR (CDCl₃): 8.41-8.39 (m, 1H), 7.97 (d, J=9.0 Hz, 2H), 7.90-7.88 (m, 1H), 7.88 (d, J=9.0 Hz, 2H), 7.00-6.97 (m, 1H), 6.95 (s, 1H), 4.64-4.58 (m, 1H), 3.63-3.57 (m, 4H), 3.21-3.19 (m, 2H), 3.00-2.98 (m, 2H), 1.45 (d, J=1.5 Hz, 3H), 1.24-1.17 (m, 1H), 0.61-0.51 (m, 2H), 0.47-0.42 (m, 1H), 0.34-0.29 (m, 1H).

Example 318

2-[(1-Cyclohexylethyl)oxy]-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

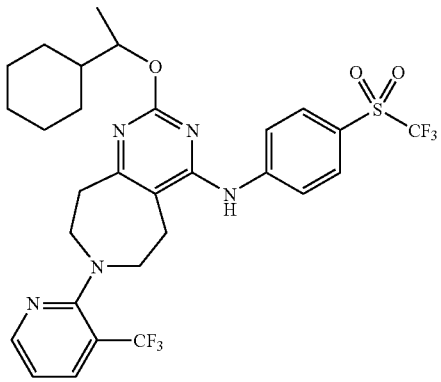 [SMILES: CC(Oc1nc2c(c(Nc3ccc(S(=O)(=O)C(F)(F)F)cc3)n1)CCN(c1ncccc1C(F)(F)F)CC2)C1CCCCC1]

MS (ESI): mass calcd. for $C_{29}H_{31}F_6N_5O_3S$, 643.21; m/z found, 644.2 [M+H]⁺. ¹H NMR (CDCl₃): 8.41-8.39 (m, 1H), 7.98 (d, J=9.0 Hz, 2H), 7.92-7.88 (m, 1H), 7.90 (d, J=9.0 Hz, 2H), 7.00-6.98 (m, 1H), 6.95 (s, 1H), 4.95-4.90 (m, 1H), 3.63-3.58 (m, 4H), 3.22-3.20 (m, 2H), 3.00-2.97 (m, 2H), 1.91-1.88 (m, 1H), 1.83-1.76 (m, 3H), 1.72-1.66 (m, 2H), 1.33 (d, J=1.5 Hz, 3H), 1.30-1.08 (m, 5H).

Example 319

2-(Cyclopentyloxy)-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

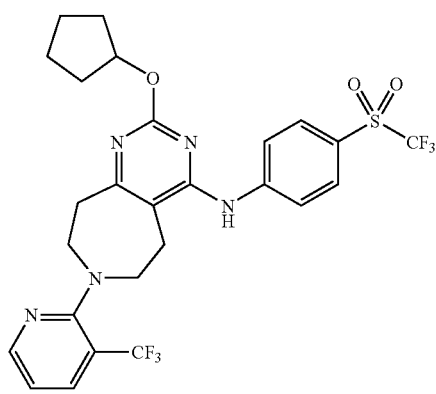 [SMILES: O=S(=O)(c1ccc(Nc2nc(OC3CCCC3)nc3c2CCN(c2ncccc2C(F)(F)F)CC3)cc1)C(F)(F)F]

MS (ESI): mass calcd. for $C_{26}H_{25}F_6N_5O_3S$, 601.16; m/z found, 602.2 [M+H]⁺. ¹H NMR (CDCl₃): 8.41-8.39 (m, 1H), 7.99 (d, J=9.0 Hz, 2H), 7.94 (d, J=9.0 Hz, 2H), 7.90-7.88 (m, 1H), 7.00-6.97 (m, 1H), 6.97 (s, 1H), 5.37-5.33 (m, 1H), 3.63-3.57 (m, 4H), 3.22-3.19 (m, 2H), 3.00-2.98 (m, 2H), 2.00-1.91 (m, 4H), 1.91-1.85 (m, 2H), 1.69-1.63 (m, 2H).

Example 320

2-[(1-Cyclohexylethyl)oxy]-N-[4-(pyrrolidin-1-ylsulfonyl)phenyl]-7-[3-(trifluoromethyl)pyridin-2-yl]-6,7,8,9-tetrahydro-5H-pyrimido[4,5-d]azepin-4-amine

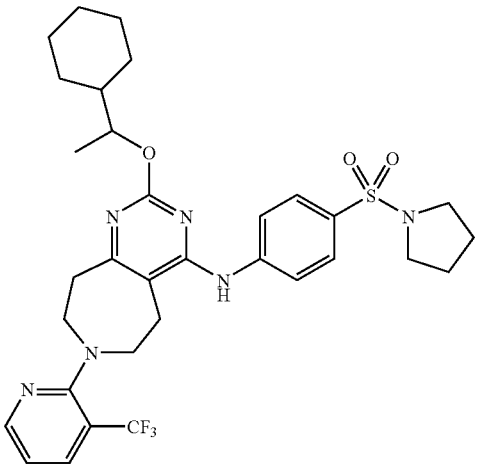 [SMILES: CC(Oc1nc2c(c(Nc3ccc(S(=O)(=O)N4CCCC4)cc3)n1)CCN(c1ncccc1C(F)(F)F)CC2)C1CCCCC1]

MS (ESI): mass calcd. for $C_{32}H_{39}F_3N_6O_3S$, 644.28; m/z found, 645.5 [M+H]⁺. ¹H NMR (CDCl₃): 8.40-8.38 (m, 1H), 7.89-7.86 (m, 1H), 7.80 (d, J=9.0 Hz, 2H), 7.74 (d, J=9.0 Hz, 2H), 6.96 (m, 1H), 6.75 (s, 1H), 4.93-4.87 (m, 1H), 3.62-3.54 (m, 4H), 3.27-3.23 (m, 4H), 3.19-3.16 (m, 2H), 2.95-2.93 (m, 2H), 1.89-1.85 (m, 1H), 1.82-1.71 (m, 7H), 1.68-1.62 (m, 2H), 1.29 (d, J=1.5 Hz, 3H), 1.27-1.04 (m, 5H).

Example 321

2-[(1-Cyclopropylethyl)oxy]-N-(1-methyl-1,2,3,4-tetrahydroquinolin-7-yl)-7-[3-(trifluoromethyl)pyridin-2-yl]-6,7,8,9-tetrahydro-5H-pyrimido[4,5-d]azepin-4-amine

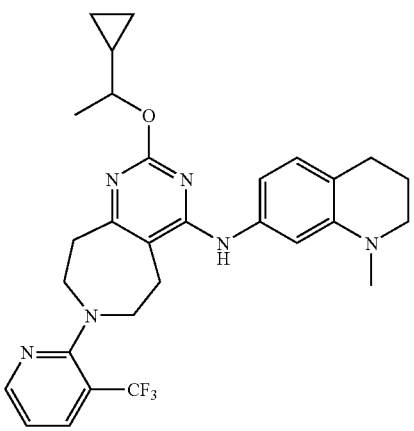 [SMILES: CC(Oc1nc2c(c(Nc3ccc4c(c3)N(C)CCC4)n1)CCN(c1ncccc1C(F)(F)F)CC2)C1CC1]

MS (ESI): mass calcd. for C$_{32}$H$_{39}$F$_3$N$_6$O, 580.7; m/z found, 581.4 [M+H]$^+$.

Example 322

2-(Tetrahydro-2H-pyran-4-yloxy)-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

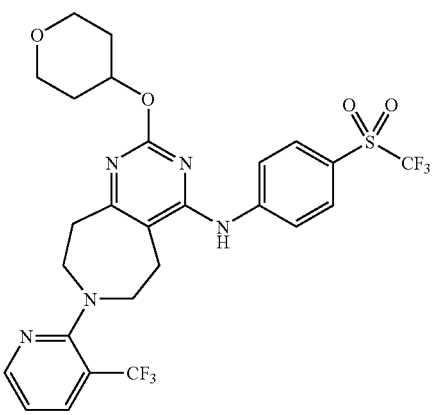 [SMILES: O=S(=O)(c1ccc(Nc2nc(OC3CCOCC3)nc3c2CCN(c2ncccc2C(F)(F)F)CC3)cc1)C(F)(F)F]

MS (ESI): mass calcd. for C$_{26}$H$_{25}$F$_6$N$_5$O$_4$S, 617.15; m/z found, 618.2 [M+H]$^+$. $^1$H NMR (CDCl$_3$): 8.41-8.40 (m, 1H), 7.99 (d, J=9.0 Hz, 2H), 7.91-7.87 (m, 3H), 7.01-6.98 (m, 1H), 6.95 (s, 1H), 5.16-5.11 (m, 1H), 4.07-4.03 (m, 2H), 3.64-3.58 (m, 6H), 3.23-3.21 (m, 2H), 3.01-2.99 (m, 2H), 2.13-2.08 (m, 2H), 1.94-1.87 (m, 2H).

Example 323

N-(1-Methyl-1,2,3,4-tetrahydroquinolin-7-yl)-2-(tetrahydrofuran-3-yloxy)-7-[3-(trifluoromethyl)pyridin-2-yl]-6,7,8,9-tetrahydro-5H-pyrimido[4,5-d]azepin-4-amine

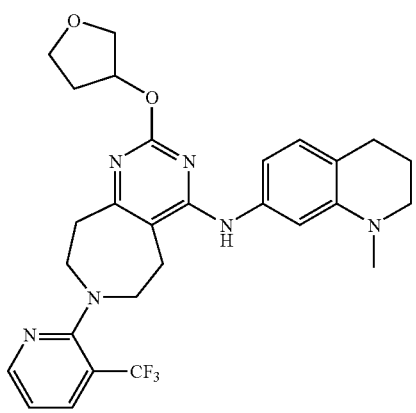 [SMILES: CN1CCCc2ccc(Nc3nc(OC4CCOC4)nc4c3CCN(c3ncccc3C(F)(F)F)CC4)cc21]

MS (ESI): mass calcd. for C$_{28}$H$_{31}$F$_3$N$_6$O$_2$, 540.24; m/z found, 541.3 [M+H]$^+$. $^1$H NMR (CDCl$_3$): 8.41-8.39 (m, 1H), 7.89-7.87 (m, 1H), 6.97-6.94 (m, 1H), 6.92 (d, J=8.0 Hz, 1H), 6.81-6.79 (m, 1H), 6.60 (d, J=2.0 Hz, 1H), 6.44 (s, 1H), 5.45-5.42 (m, 1H), 4.10-4.06 (m, 1H), 4.00-3.95 (m, 1H), 3.93-3.88 (m, 2H), 3.65-3.58 (m, 4H), 3.26-3.23 (m, 2H), 3.16-3.14 (m, 2H), 2.92-2.89 (m, 4H), 2.76 (t, J=6.0 Hz, 2H), 2.23-2.13 (m, 3H), 2.02-1.97 (m, 2H).

Example 324

2-(Cyclopentyloxy)-N-(1-methyl-1,2,3,4-tetrahydroquinolin-7-yl)-7-[3-(trifluoromethyl)pyridin-2-yl]-6,7,8,9-tetrahydro-5H-pyrimido[4,5-d]azepin-4-amine

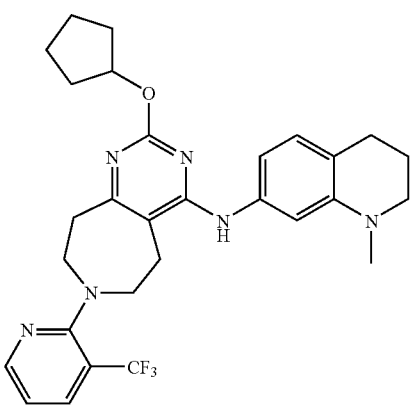 [SMILES: CN1CCCc2ccc(Nc3nc(OC4CCCC4)nc4c3CCN(c3ncccc3C(F)(F)F)CC4)cc21]

MS (ESI): mass calcd. for C$_{29}$H$_{33}$F$_3$N$_6$O, 538.27; m/z found, 539.3 [M+H]$^+$.

Example 325

2-[(1-Cyclopropylethyl)oxy]-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

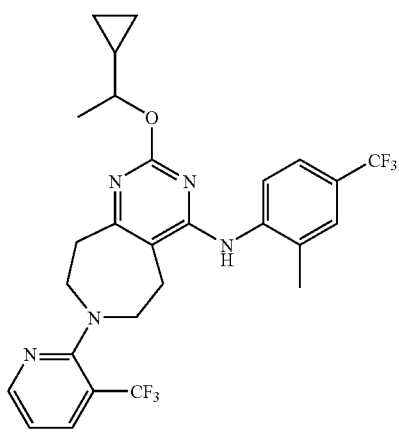 [SMILES: Cc1cc(C(F)(F)F)ccc1Nc1nc(OC(C)C2CC2)nc2c1CCN(c1ncccc1C(F)(F)F)CC2]

MS (ESI): mass calcd. for C$_{27}$H$_{27}$F$_6$N$_5$O, 551.21; m/z found, 552.3 [M+H]$^+$. $^1$H NMR (CDCl$_3$): 8.39-8.37 (m, 1H), 8.03 (d, J=11.5 Hz, 1H), 7.89-7.86 (m, 1H), 7.47 (s, 1H), 7.45 (s, 1H), 6.97-6.94 (m, 1H), 6.39 (s, 1H), 4.52-4.45 (m, 1H), 3.65-3.57 (m, 4H), 3.18-3.15 (m, 2H), 2.93-2.90 (m, 2H), 2.35 (s, 3H), 1.37 (d, J=8.0 Hz, 3H), 1.18-1.09 (m, 1H), 0.55-0.43 (m, 2H), 0.40-0.33 (m, 1H), 0.25-0.19 (m, 1H).

Example 326

2-(Cyclohexyloxy)-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

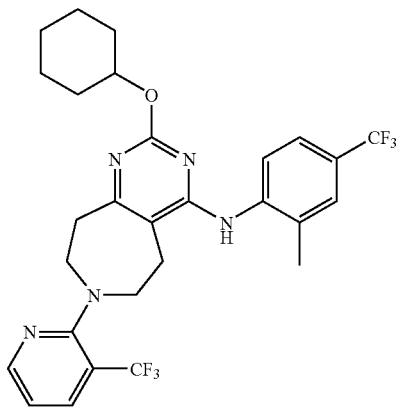 [SMILES: Cc1cc(C(F)(F)F)ccc1Nc1nc(OC2CCCCC2)nc2c1CCN(c1ncccc1C(F)(F)F)CC2]

MS (ESI): mass calcd. for $C_{28}H_{29}F_6N_5O$, 565.23; m/z found, 566.3 [M+H]$^+$. $^1$H NMR (CDCl$_3$): 8.41-8.39 (m, 1H), 8.16 (d, J=9.0 Hz, 1H), 7.90-7.88 (m, 1H), 7.49-7.48 (m, 2H), 6.99-6.96 (m, 1H), 6.46 (s, 1H), 4.81-4.76 (m, 1H), 3.67-3.65 (m, 2H), 3.61-3.59 (m, 2H), 3.20-3.17 (m, 2H), 2.96-2.94 (m, 2H), 2.38 (s, 3H), 2.05-2.01 (m, 2H), 1.85-1.80 (m, 2H), 1.63-1.51 (m, 1H), 1.38-1.27 (m, 5H).

Example 327

2-(Butyloxy)-7-[3-(trifluoromethyl)pyridin-2-yl]-N-[6-(trifluoromethyl)pyridin-3-yl]-6,7,8,9-tetrahydro-5H-pyrimido[4,5-d]azepin-4-amine

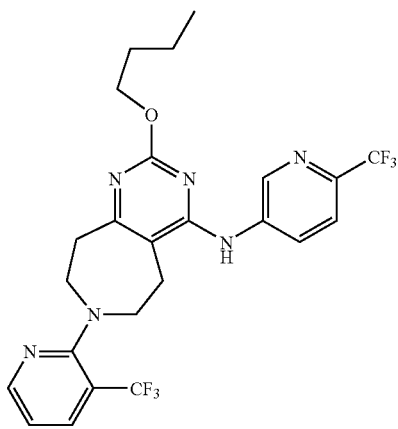 [SMILES: CCCCOc1nc2c(c(Nc3ccc(C(F)(F)F)nc3)n1)CCN(c1ncccc1C(F)(F)F)CC2]

MS (ESI): mass calcd. for $C_{24}H_{24}F_6N_6O$, 526.19; m/z found, 527.2 [M+H]$^+$. $^1$H NMR (CDCl$_3$): 8.82 (d, J=2.5 Hz, 1H), 8.39-8.34 (m, 2H), 7.89-7.87 (m, 1H), 7.67 (d, J=8.5 Hz, 1H), 6.98-6.95 (m, 1H), 6.83 (br s, 1H), 4.29 (t, J=6.5 Hz, 2H), 3.64-3.61 (m, 2H), 3.59-3.56 (m, 2H), 3.21-3.19 (m, 2H), 3.01-2.98 (m, 2H), 1.80-1.74 (m, 2H), 1.55-1.47 (m, 2H), 0.96 (t, J=7.0 Hz, 3H).

Example 328

2-(Cyclohexyloxy)-N-(1-methyl-1,2,3,4-tetrahydroquinolin-7-yl)-7-[3-(trifluoromethyl)pyridin-2-yl]-6,7,8,9-tetrahydro-5H-pyrimido[4,5-d]azepin-4-amine

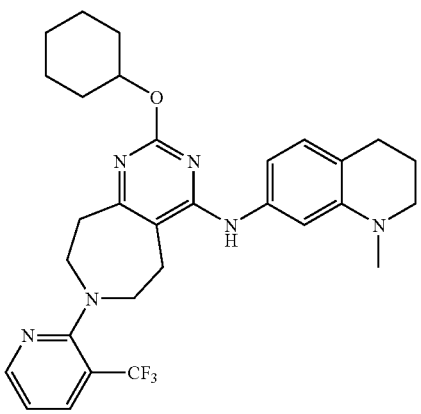

MS (ESI): mass calcd. for $C_{30}H_{35}F_3N_6O$, 552.28; m/z found, 553.3 [M+H]$^+$. $^1$H NMR (CDCl$_3$): 8.39-8.37 (m, 1H), 7.87-7.84 (m, 1H), 6.94-6.88 (m, 3H), 6.56 (d, J=2.5 Hz, 1H), 6.41 (s, 1H), 4.93-4.86 (m, 1H), 3.63-3.56 (m, 4H), 3.23 (t, J=7.0 Hz, 2H), 3.14-3.11 (m, 2H), 2.89 (s, 3H), 2.88-2.86 (m, 2H), 2.74 (t, J=8.0 Hz, 2H), 2.0-1.94 (m, 4H), 1.81-1.78 (m, 2H), 1.59-1.53 (m, 3H), 1.37-1.26 (m, 3H).

Example 329

N-(1-Methyl-1,2,3,4-tetrahydroquinolin-7-yl)-2-(tetrahydro-2H-pyran-4-yloxy)-7-[3-(trifluoromethyl)pyridin-2-yl]-6,7,8,9-tetrahydro-5H-pyrimido[4,5-d]azepin-4-amine

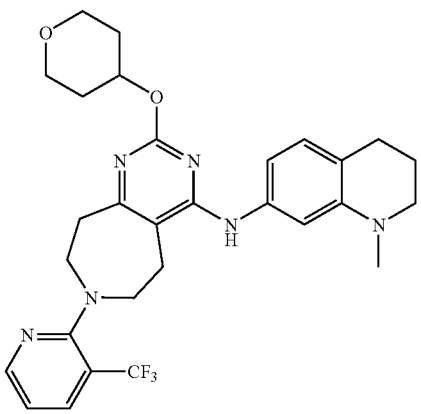 [SMILES: CN1CCCc2ccc(Nc3nc(OC4CCOCC4)nc4c3CCN(c3ncccc3C(F)(F)F)CC4)cc21]

MS (ESI): mass calcd. for $C_{29}H_{33}F_3N_6O_2$, 554.26; m/z found, 555.3 [M+H]$^+$. $^1$H NMR (CDCl$_3$): 8.41-8.39 (m, 1H), 7.89-7.87 (m, 1H), 6.97-6.94 (m, 1H), 6.91 (d, J=8.0 Hz, 1H), 6.86-6.83 (m, 1H), 6.59 (d, J=2.0 Hz, 1H), 6.43 (s, 1H), 5.13-5.08 (m, 1H), 4.03-3.99 (m, 2H), 3.65-3.53 (m, 6H), 3.26-3.24 (m, 2H), 3.17-3.14 (m, 2H), 2.92-2.89 (m, 5H), 2.76 (t, J=6.5 Hz, 2H), 2.08-1.97 (m, 4H), 1.89-1.81 (m, 2H).

Example 330

2-({[(4R)-2,2-Dimethyl-1,3-dioxolan-4-yl]methyl}oxy)-N-[4-(trifluoromethyl)phenyl]-7-[3-(trifluoromethyl)pyridin-2-yl]-6,7,8,9-tetrahydro-5H-pyrimido[4,5-d]azepin-4-amine

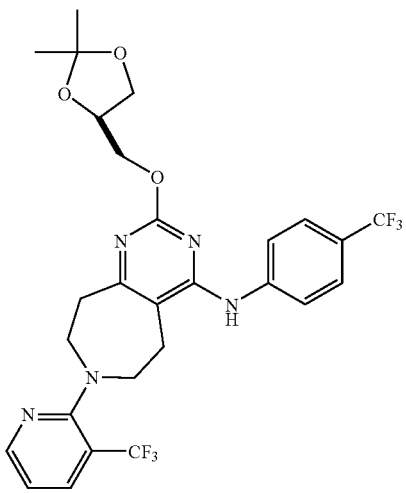 [SMILES: CC1(C)OC[C@@H](COc2nc3c(c(Nc4ccc(C(F)(F)F)cc4)n2)CCN(c2ncccc2C(F)(F)F)CC3)O1]

MS (ESI): mass calcd. for C$_{27}$H$_{27}$F$_6$N$_5$O$_3$, 583.20; m/z found, 584.2 [M+H]$^+$. $^1$H NMR (CDCl$_3$): 8.39-8.37 (m, 1H), 7.89-7.86 (m, 1H), 7.69 (d, J=11.0 Hz, 2H), 7.59 (d, J=11.0 Hz, 2H), 6.98-6.94 (m, 1H), 6.68 (s, 1H), 4.52-4.56 (m, 1H), 4.42-4.38 (m, 1H), 4.28-4.24 (m, 1H), 4.16-4.12 (m, 1H), 3.94-3.90 (m, 1H), 3.63-3.56 (m, 4H), 3.18-3.15 (m, 2H), 2.96-2.93 (m, 2H), 1.46 (s, 3H), 1.38 (s, 3H).

Example 331

2-(Tetrahydrofuran-3-yloxy)-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

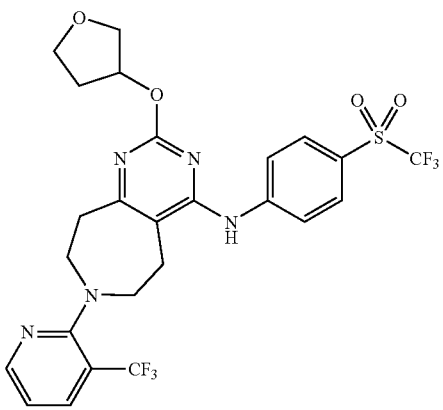 [SMILES: O=S(=O)(c1ccc(Nc2nc(OC3CCOC3)nc3c2CCN(c2ncccc2C(F)(F)F)CC3)cc1)C(F)(F)F]

MS (ESI): mass calcd. for C$_{25}$H$_{23}$F$_6$N$_5$O$_4$S, 603.14; m/z found, 604.2 [M+H]$^+$. $^1$H NMR (CDCl$_3$): 8.40-8.39 (m, 1H), 7.99 (d, J=9.0 Hz, 2H), 7.91-7.87 (m, 3H), 7.01-6.98 (m, 2H), 5.50-5.46 (m, 1H), 4.12-4.08 (m, 1H), 4.06-3.93 (m, 3H), 3.64-3.58 (m, 4H), 3.23-3.20 (m, 2H), 3.02-2.99 (m, 2H), 2.28-2.24 (m, 2H).

Example 332

2-[(1-Cyclohexylethyl)oxy]-N-[4-(trifluoromethyl)phenyl]-7-[3-(trifluoromethyl)pyridin-2-yl]-6,7,8,9-tetrahydro-5H-pyrimido[4,5-d]azepin-4-amine

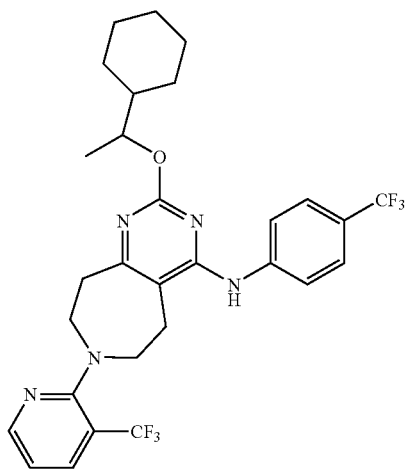 [SMILES: CC(Oc1nc2c(c(Nc3ccc(C(F)(F)F)cc3)n1)CCN(c1ncccc1C(F)(F)F)CC2)C1CCCCC1]

MS (ESI): mass calcd. for C$_{29}$H$_{31}$F$_6$N$_5$O, 579.24; m/z found, 580.2 [M+H]$^+$. $^1$H NMR (CDCl$_3$): 8.41-8.39 (m, 1H), 7.90-7.88 (m, 1H), 7.70 (d, J=8.5 Hz, 2H), 7.59 (d, J=8.5 Hz, 2H), 6.99-6.96 (m, 1H), 6.67 (s, 1H), 4.94-4.88 (m, 1H), 3.65-3.58 (m, 4H), 3.20-3.17 (m, 2H), 2.96-2.94 (m, 2H), 1.90-1.87 (m, 1H), 1.83-1.75 (m, 3H), 1.72-1.65 (m, 2H), 1.31 (d, J=6.5 Hz, 3H), 1.28-1.07 (m, 5H).

Example 333

2-(Cyclopentyloxy)-N-[4-(pyrrolidin-1-ylsulfonyl)phenyl]-7-[3-(trifluoromethyl)pyridin-2-yl]-6,7,8,9-tetrahydro-5H-pyrimido[4,5-d]azepin-4-amine

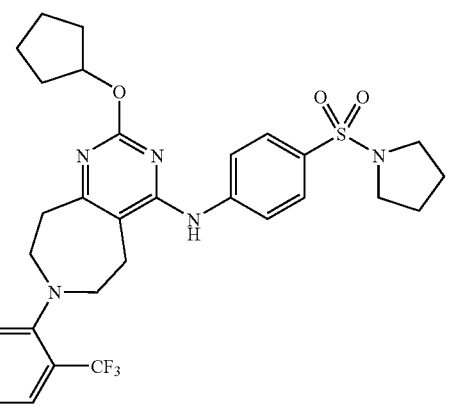

MS (ESI): mass calcd. for C$_{29}$H$_{33}$F$_3$N$_6$O$_3$S, 602.23; m/z found, 603.3 [M+H]$^+$. $^1$H NMR (CDCl$_3$): 8.39-8.37 (m, 1H), 7.89-7.86 (m, 1H), 7.79 (s, 4H), 6.98-6.94 (m, 1H), 6.77 (s, 1H), 5.33-5.30 (m, 1H), 3.62-3.55 (m, 4H), 3.27-3.23 (m, 4H), 3.18-3.16 (m, 2H), 2.96-2.93 (m, 2H), 1.96-1.75 (m, 9H), 1.66-1.58 (m, 3H).

Example 334

2-[(1-Cyclopropylethyl)oxy]-N-[4-(pyrrolidin-1-ylsulfonyl)phenyl]-7-[3-(trifluoromethyl)pyridin-2-yl]-6,7,8,9-tetrahydro-5H-pyrimido[4,5-d]azepin-4-amine

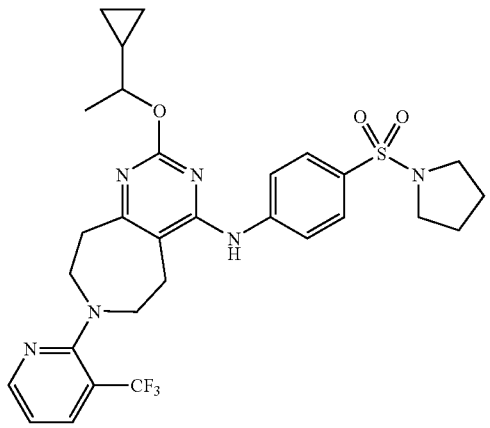 [SMILES: CC(Oc1nc2c(c(Nc3ccc(S(=O)(=O)N4CCCC4)cc3)n1)CCN(c1ncccc1C(F)(F)F)CC2)C1CC1]

MS (ESI): mass calcd. for $C_{29}H_{33}F_3N_6O_3S$, 602.23; m/z found, 603.3 [M+H]$^+$. $^1$H NMR (CDCl$_3$): 8.39-8.37 (m, 1H), 7.89-7.86 (m, 1H), 7.78 (d, J=11.0 Hz, 2H), 7.71 (d, J=11.0 Hz, 2H), 6.98-6.94 (m, 1H), 6.74 (s, 1H), 4.61-4.54 (m, 1H), 3.62-3.55 (m, 4H), 3.27-3.23 (m, 4H), 3.18-3.15 (m, 2H), 2.95-2.93 (m, 2H), 1.79-1.75 (m, 4H), 1.42 (d, J=8.0 Hz, 3H), 1.21-1.15 (m, 1H), 0.58-0.39 (m, 3H), 0.30-0.24 (m, 1H).

Example 335

N-[4-(Pyrrolidin-1-ylsulfonyl)phenyl]-2-(tetrahydro-2H-pyran-4-yloxy)-7-[3-(trifluoromethyl)pyridin-2-yl]-6,7,8,9-tetrahydro-5H-pyrimido[4,5-d]azepin-4-amine

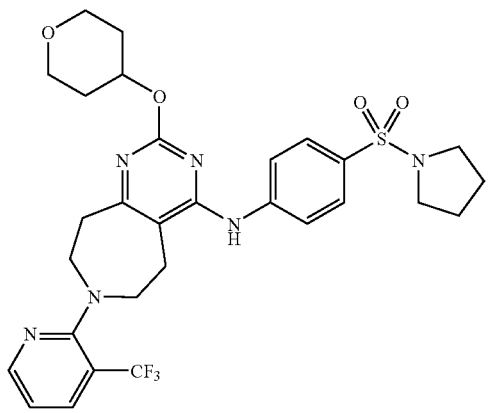 [SMILES: O=S(=O)(c1ccc(Nc2nc(OC3CCOCC3)nc3c2CCN(c2ncccc2C(F)(F)F)CC3)cc1)N1CCCC1]

MS (ESI): mass calcd. for $C_{29}H_{33}F_3N_6O_4S$, 618.22; m/z found, 619.3 [M+H]$^+$. $^1$H NMR (CDCl$_3$): 8.40-8.38 (m, 1H), 7.89-7.86 (m, 1H), 7.79 (d, J=11.0 Hz, 2H), 7.72 (d, J=11.0 Hz, 2H), 6.99-6.95 (m, 1H), 6.80 (s, 1H), 5.13-5.06 (m, 1H), 4.06-4.00 (m, 2H), 3.62-3.54 (m, 6H), 3.27-3.24 (m, 4H), 3.19-3.16 (m, 2H), 2.97-2.94 (m, 2H), 2.11-2.06 (m, 2H), 1.92-1.83 (m, 2H), 1.80-1.75 (m, 4H).

Example 336

2-(Cycloheptyloxy)-N-[4-(trifluoromethyl)phenyl]-7-[3-(trifluoromethyl)pyridin-2-yl]-6,7,8,9-tetrahydro-5H-pyrimido[4,5-d]azepin-4-amine

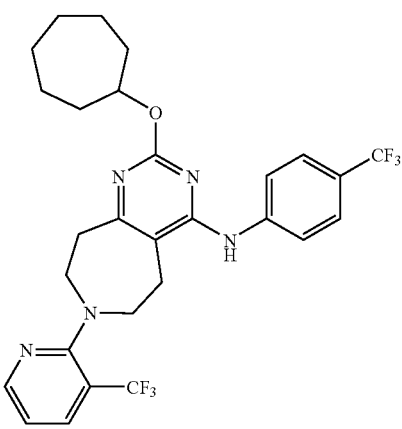 [SMILES: FC(F)(F)c1ccc(Nc2nc(OC3CCCCCC3)nc3c2CCN(c2ncccc2C(F)(F)F)CC3)cc1]

MS (ESI): mass calcd. for $C_{28}H_{29}F_6N_5O$, 565.23; m/z found, 566.2 [M+H]$^+$. $^1$H NMR (CDCl$_3$): 8.41-8.39 (m, 1H), 7.90-7.88 (m, 1H), 7.71 (d, J=9.0 Hz, 2H), 7.60 (d, J=9.0 Hz, 2H), 6.99-6.96 (m, 1H), 6.68 (s, 1H), 5.08-5.03 (m, 1H), 3.65-3.58 (m, 4H), 3.19-3.17 (m, 2H), 2.96-2.94 (m, 2H), 2.13-2.07 (m, 2H), 1.88-1.74 (m, 4H), 1.64-1.58 (m, 4H), 1.51-1.44 (m, 2H).

Example 337

2-(Cyclopentyloxy)-N-[4-(trifluoromethyl)phenyl]-7-[3-(trifluoromethyl)pyridin-2-yl]-6,7,8,9-tetrahydro-5H-pyrimido[4,5-d]azepin-4-amine

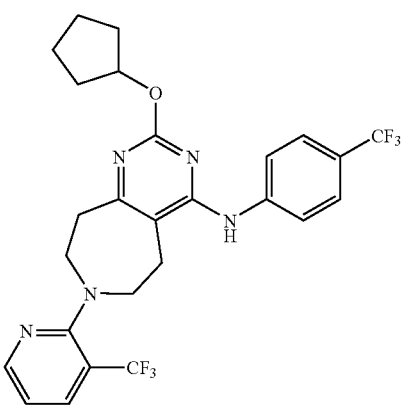 [SMILES: FC(F)(F)c1ccc(Nc2nc(OC3CCCC3)nc3c2CCN(c2ncccc2C(F)(F)F)CC3)cc1]

MS (ESI): mass calcd. for $C_{26}H_{25}F_6N_5O$, 537.20; m/z found, 538.2 [M+H]$^+$. $^1$H NMR (CDCl$_3$): 8.41-8.39 (m, 1H), 7.90-7.87 (m, 1H), 7.74 (d, J=8.5 Hz, 2H), 7.60 (d, J=8.5 Hz, 2H), 6.99-6.96 (m, 1H), 6.70 (s, 1H), 5.34-5.30 (m, 1H), 3.64-3.57 (m, 4H), 3.19-3.17 (m, 2H), 2.97-2.94 (m, 2H), 1.97-1.92 (m, 4H), 1.88-1.83 (2H), 1.65-1.62 (m, 2H).

Example 338

2-(Cyclohexyloxy)-N-[4-(trifluoromethyl)phenyl]-7-[3-(trifluoromethyl)pyridin-2-yl]-6,7,8,9-tetrahydro-5H-pyrimido[4,5-d]azepin-4-amine

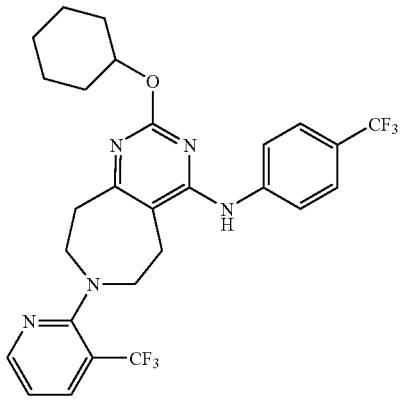 [SMILES: FC(F)(F)c1ccc(Nc2nc(OC3CCCCC3)nc3c2CCN(c2ncccc2C(F)(F)F)CC3)cc1]

MS (ESI): mass calcd. for $C_{27}H_{27}F_6N_5O$, 551.21; m/z found, 552.2 [M+H]$^+$. $^1$H NMR (CDCl$_3$): 8.41-8.39 (m, 1H), 7.90-7.87 (m, 1H), 7.72 (d, J=8.5 Hz, 2H), 7.59 (d, J=8.5 Hz, 2H), 6.98-6.96 (m, 1H), 6.71 (s, 1H), 4.90-4.84 (m, 1H), 3.64-3.57 (m, 4H), 3.19-3.17 (m, 2H), 2.96-2.94 (m, 2H), 2.10-2.07 (m, 2H), 1.88-1.84 (m, 2H), 1.65-1.55 (m, 3H), 1.44-1.27 (m, 3H).

Example 339

2-(Tetrahydro-2H-pyran-4-yloxy)-N-[4-(trifluoromethyl)phenyl]-7-[3-(trifluoromethyl)pyridin-2-yl]-6,7,8,9-tetrahydro-5H-pyrimido[4,5-d]azepin-4-amine

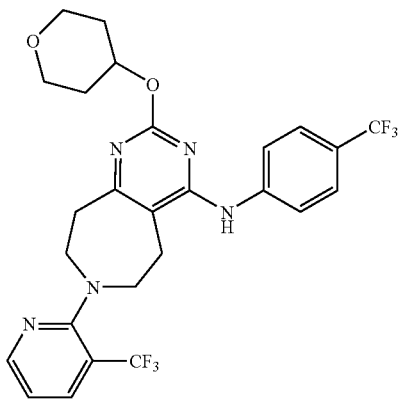 [SMILES: FC(F)(F)c1ccc(Nc2nc(OC3CCOCC3)nc3c2CCN(c2ncccc2C(F)(F)F)CC3)cc1]

MS (ESI): mass calcd. for $C_{26}H_{25}F_6N_5O_2$, 553.19; m/z found, 554.2 [M+H]$^+$. $^1$H NMR (CDCl$_3$): 8.41-8.40 (m, 1H), 7.91-7.88 (m, 1H), 7.68 (d, J=8.5 Hz, 2H), 7.60 (d, J=8.5 Hz, 2H), 6.99-6.96 (m, 1H), 6.69 (s, 1H), 5.12-5.06 (m, 1H), 4.06-4.02 (m, 2H), 3.97 (s, 1H), 3.65-3.56 (m, 5H), 3.20-3.18 (m, 2H), 2.97-2.95 (m, 2H), 2.11-2.04 (m, 2H), 1.93-1.85 (m, 2H).

Example 340

2-(Tetrahydrofuran-3-yloxy)-N-[4-(trifluoromethyl)phenyl]-7-[3-(trifluoromethyl)pyridin-2-yl]-6,7,8,9-tetrahydro-5H-pyrimido[4,5-d]azepin-4-amine

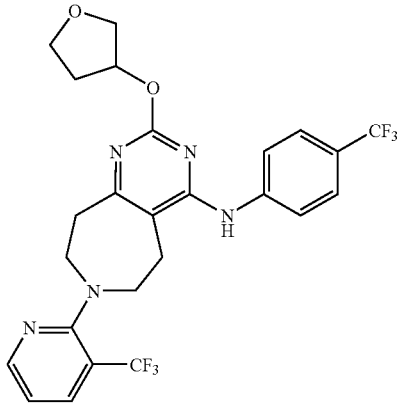 [SMILES: FC(F)(F)c1ccc(Nc2nc(OC3CCOC3)nc3c2CCN(c2ncccc2C(F)(F)F)CC3)cc1]

MS (ESI): mass calcd. for $C_{25}H_{23}F_6N_5O_2$, 539.18; m/z found, 540.2 [M+H]$^+$. $^1$H NMR (CDCl$_3$): 8.40-8.38 (m, 1H), 7.89-7.86 (m, 1H), 7.65 (d, J=11.0 Hz, 2H), 7.60 (d, J=11.0 Hz, 2H), 6.98-6.95 (m, 1H), 6.67 (s, 1H), 5.43-5.39 (m, 1H), 4.09-4.05 (m, 1H), 4.00-3.89 (m, 3H), 3.64-3.56 (m, 4H), 3.19-3.15 (m, 2H), 2.96-2.93 (m, 2H), 2.24-2.17 (m, 2H).

The following Examples 341-343 were prepared using methods analogous to those described in Example 307, substituting the appropriate alcohols and using the appropriate alcohol as the solvent.

Example 341

2-[(1-Methylethyl)oxy]-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

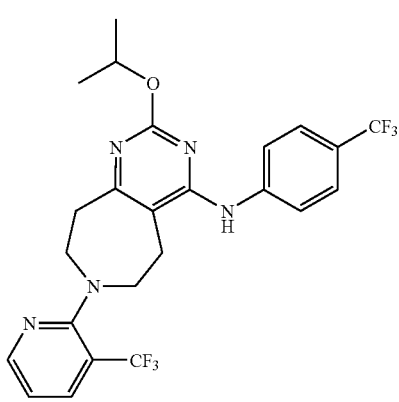 [SMILES: CC(C)Oc1nc2c(c(Nc3ccc(C(F)(F)F)cc3)n1)CCN(c1ncccc1C(F)(F)F)CC2]

MS (ESI): mass calcd. for $C_{24}H_{23}F_6N_5O$, 511.18; m/z found, 512.5 [M+H]$^+$. $^1$H NMR (MeOD): 8.46-8.44 (m, 1H), 8.03 (dd, J=7.8, 1.7 Hz, 1H), 7.74 (s, 4H), 7.17-7.12 (m, 1H), 5.22-5.16 (m, 1H), 3.65-3.61 (m, 2H), 3.60-3.56 (m, 2H), 3.26-3.21 (m, 2H), 3.19-3.14 (m, 2H), 1.37 (d, J=6.2 Hz, 6H).

Example 342

2-(Phenyloxy)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

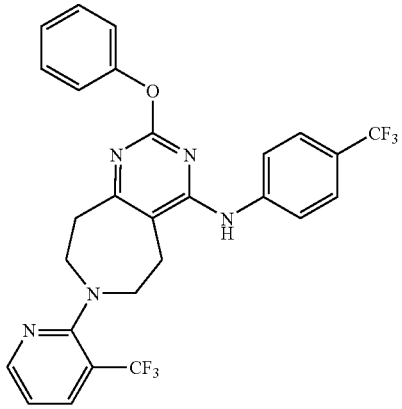 [SMILES: FC(F)(F)c1ccc(Nc2nc(Oc3ccccc3)nc3c2CCN(c2ncccc2C(F)(F)F)CC3)cc1]

MS (ESI): mass calcd. for $C_{27}H_{21}F_6N_5O$, 545.17; m/z found, 546.5 [M+H]$^+$. $^1$H NMR (MeOD): 8.48-8.46 (m, 1H), 8.04 (dd, J=7.8, 1.7 Hz, 1H), 7.51-7.46 (m, 2H), 7.44 (d, J=8.6 Hz, 2H), 7.40-7.34 (m, 3H), 7.24 (d, J=7.7 Hz, 2H), 7.16 (dd, J=7.7, 4.8 Hz, 1H), 3.69-3.64 (m, 2H), 3.61-3.55 (m, 2H), 3.35-3.31 (m, 2H), 3.21-3.16 (m, 2H).

Example 343

2-(Butyloxy)-N-[4-(trifluoromethyl)phenyl]-7-[3-(trifluoromethyl)pyridin-2-yl]-6,7,8,9-tetrahydro-5H-pyrimido[4,5-d]azepin-4-amine

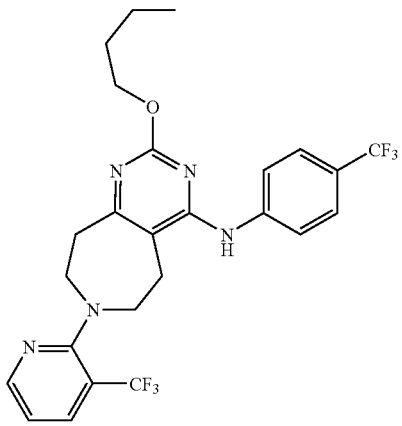 [SMILES: CCCCOc1nc2c(c(Nc3ccc(C(F)(F)F)cc3)n1)CCN(c1ncccc1C(F)(F)F)CC2]

MS (ESI): mass calcd. for $C_{25}H_{25}F_6N_5O$, 525.20; m/z found, 526.1 [M+H]$^+$. $^1$H NMR (CDCl$_3$): 8.40-8.37 (m, 1H), 7.88 (dd, J=7.8, 1.8 Hz, 1H), 7.72-7.69 (m, 2H), 7.61-7.57 (m, 2H), 6.98-6.94 (m, 1H), 6.66 (s, 1H), 4.29 (t, J=6.6 Hz, 2H), 3.64-3.56 (m, 4H), 3.20-3.15 (m, 2H), 2.97-2.94 (m, 2H), 1.81-1.75 (m, 2H), 1.54-1.47 (m, 2H), 0.96 (t, J=7.4 Hz, 3H).

Example 344

4-{[4-(Trifluoromethyl)phenyl]amino}-7-[3-(trifluoromethyl)pyridin-2-yl]-6,7,8,9-tetrahydro-5H-pyrimido[4,5-d]azepin-2-ol trifluoroacetic acid salt

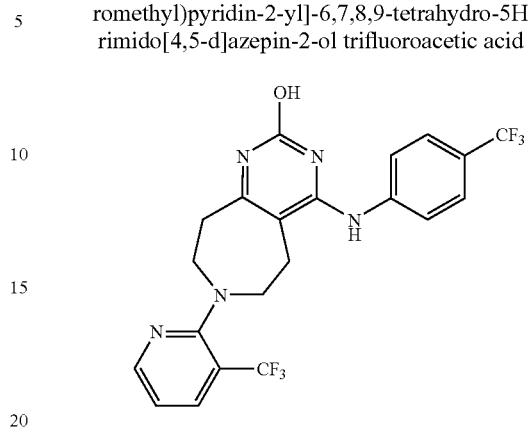

A solution of [2-methanesulfonyl-7-(3-trifluoromethyl-pyridin-2-yl)-6,7,8,9-tetrahydro-5H-pyrimido[4,5-d]azepin-4-yl]-(4-trifluoromethyl-phenyl)-amine (Example 53; 112 mg, 0.21 mmol) and NaOH (25 mg, 0.63 mmol) in 1:3 H$_2$O/dioxane (4 mL) was heated at 60° C. for 1 h. The mixture was cooled, acidified with TFA (3 drops), and directly purified using Preparative HPLC (conditions as in Example 54) to give the title compound (60 mg, 98%). MS (ESI): mass calcd. for $C_{21}H_{17}F_6N_5O$, 469.13; m/z found, 470.5 [M+H]$^+$. $^1$H NMR (CDCl$_3$): 8.46-8.41 (m, 1H), 7.97 (dd, J=7.8, 1.5 Hz, 1H), 7.64 (s, 4H), 7.09 (dd, J=7.7, 4.9 Hz, 1H), 3.63-3.58 (m, 2H), 3.58-3.53 (m, 2H), 3.18-3.12 (m, 2H), 2.89-2.84 (m, 2H).

Example 345

2-(Ethyloxy)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt

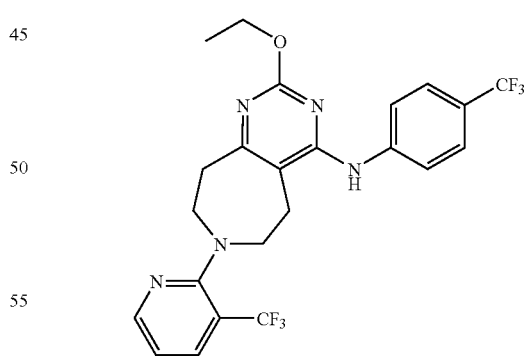

The title compound was prepared using methods analogous to those described in Example 62. MS (ESI): mass calcd. for $C_{23}H_{21}F_6N_5O$, 497.17; m/z found, 498.4 [M+H]$^+$. $^1$H NMR (MeOD): 8.45 (dd, J=4.7, 1.5 Hz, 1H), 8.03 (dd, J=7.8, 1.8 Hz, 1H), 7.75 (q, J=8.9 Hz, 4H), 7.15 (dd, J=7.5, 4.8 Hz, 1H), 4.45 (q, J=7.1 Hz, 2H), 3.64-3.61 (m, 2H), 3.59-3.56 (m, 2H), 3.25-3.22 (m, 2H), 3.17-3.15 (m, 2H), 1.38 (t, J=7.1 Hz, 3H).

Example 346

2-[(Methyloxy)methyl]-7-[3-(trifluoromethyl)pyridin-2-yl]-N-[6-(trifluoromethyl)pyridin-3-yl]-6,7,8,9-tetrahydro-5H-pyrimido[4,5-d]azepin-4-amine trifluoroacetic acid salt

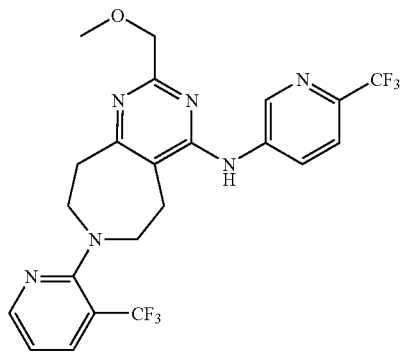 [SMILES: COCc1nc2c(c(Nc3ccc(C(F)(F)F)nc3)n1)CCN(c1ncccc1C(F)(F)F)CC2]

The title compound was prepared using methods analogous to those described for Example 39 with modifications to Step A as follows:

Step A. 2-Hydroxymethyl-7-(3-trifluoromethyl-pyridin-2-yl)-6,7,8,9-tetrahydro-5H-pyrimido[4,5-d]azepin-4-ol. To solution of NaOMe (1.9 mL) in MeOH (0.5 mL) was added 5-oxo-1-(3-trifluoromethyl-pyridin-2-yl)-azepane-4-carboxylic acid ethyl ester (Intermediate B; 285 mg, 0.96 mmol), followed by 2-chloro-acetamidine (149 mg, 1.16 mmol). After heating at 100° C. in a microwave for 15 min, the mixture was cooled and concentrated. The residue was dissolved in water and extracted with $CH_2Cl_2$. The combined organic layers were dried, concentrated, and directly purified using Preparative HPLC (conditions as in Example 54) to give the title compound (86 mg, 26%). MS (ESI): mass-calcd. for $C_{22}H_{20}F_6N_6O$, 498.16; m/z found, 499.3 [M+H]$^+$. $^1$H NMR (MeOD): 8.95 (d, J=2.3 Hz, 1H), 8.47-8.45 (m, 1H), 8.29 (dd, J=8.5, 2.2 Hz, 1H), 8.04 (dd, J=7.8, 1.7 Hz, 1H), 7.88 (d, J=8.6 Hz, 1H), 7.16 (dd, J=7.7, 4.9 Hz, 1H), 4.61 (s, 2H), 3.68-3.61 (m, 4H), 3.53 (s, 3H), 3.49-3.45 (m, 2H), 3.30-3.28 (m, 2H).

Example 347

2-Methyl-2-[4-({2-[(methyloxy)methyl]-7-[3-(trifluoromethyl)pyridin-2-yl]-6,7,8,9-tetrahydro-5H-pyrimido[4,5-d]azepin-4-yl}amino)phenyl]propanenitrile trifluoroacetic acid salt

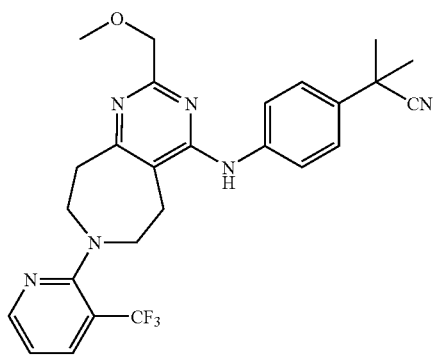 [SMILES: COCc1nc2c(c(Nc3ccc(C(C)(C)C#N)cc3)n1)CCN(c1ncccc1C(F)(F)F)CC2]

The title compound was prepared using methods analogous to those described in Example 346, substituting the appropriate anilines in Step E. MS (ESI): mass calcd. for $C_{26}H_{27}F_3N_6O$, 496.22; m/z found, 497.5 [M+H]$^+$. $^1$H NMR (MeOD): 8.45 (dd, J=4.7, 1.4 Hz, 1H), 8.03 (dd, J=7.8, 1.8 Hz, 1H), 7.58 (s, 4H), 7.14 (dd, J=7.4, 4.8 Hz, 1H), 4.54 (s, 2H), 3.68-3.60 (m, 4H), 3.51 (s, 3H), 3.44-3.40 (m, 2H), 3.25-3.21 (m, 2H), 1.75 (s, 6H).

Example 348

2-(Methylsulfonyl)-7-[3-(trifluoromethyl)pyridin-2-yl]-N-[5-(trifluoromethyl)pyridin-2-yl]-6,7,8,9-tetrahydro-5H-pyrimido[4,5-d]azepin-4-amine

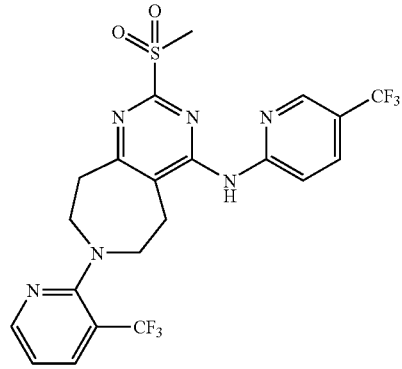 [SMILES: CS(=O)(=O)c1nc2c(c(Nc3ccc(C(F)(F)F)cn3)n1)CCN(c1ncccc1C(F)(F)F)CC2]

The title compound was synthesized in a manner similar to Example 53 with modifications to Step C in Example 52 as follows:

Step C. To a solution of 4-chloro-2-methylsulfanyl-7-(3-trifluoromethyl-pyridin-2-yl)-6,7,8,9-tetrahydro-5H-pyrimido[4,5-d]azepine (400 mg, 1.07 mmol), 4-trifluoromethyl-amino-pyridine (208 mg, 1.28 mmol), and NaOtBu (144 mg, 1.5 mmol) in toluene (4 mL) in a microwave vial was added a solution of Pd(OAc)$_2$ (3.7 mg, 0.016 mmol) and 2-(dicyclohexylphosphino)biphenyl (DCPB) (11.9 mg, 0.034 mmol) in toluene (1 mL). The mixture was flushed with $N_{2(g)}$ and heated in a microwave at 200° C. for 2 h. The mixture was cooled, filtered through a plug of diatomaceous earth, and concentrated. The residue was purified (FCC) to afford the title compound (230 mg, 48%). MS (ESI): mass calcd. for $C_{21}H_{18}F_6N_6O_2S$, 532.11; m/z found, 533.1 [M+H]$^+$. $^1$H NMR (CDCl$_3$): 8.67 (d, J=8.9 Hz, 1H), 8.56-8.54 (m, 1H), 8.42-8.40 (m, 1H), 8.03-8.00 (m, 1H), 7.89 (dd, J=7.8, 1.8 Hz, 1H), 7.85 (s, 1H), 7.03-6.98 (m, 1H), 3.70-3.65 (m, 2H), 3.63-3.59 (m, 2H), 3.39-3.36 (m, 2H), 3.32 (s, 3H), 3.19-3.15 (m, 2H).

Example 349

2-(Phenylsulfanyl)-N-[4-(trifluoromethyl)phenyl]-7-[3-(trifluoromethyl)pyridin-2-yl]-6,7,8,9-tetrahydro-5H-pyrimido[4,5-d]azepin-4-amine

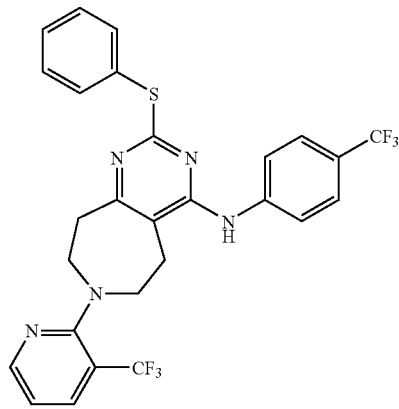 [SMILES: FC(F)(F)c1ccc(Nc2nc(Sc3ccccc3)nc3c2CCN(c2ncccc2C(F)(F)F)CC3)cc1]

To a microwave reaction vial were added [2-methanesulfonyl-7-(3-trifluoromethyl-pyridin-2-yl)-6,7,8,9-tetrahydro-5H-pyrimido[4,5-d]azepin-4-yl]-(4-trifluoromethyl-phenyl)-amine (53 mg, 0.1 mmol), thiophenol (16 mg, 0.15 mmol), p-toluenesulfonic acid monohydrate (10 mg, 0.05 mmol), and DMF (0.4 mL). The vial was capped, and the mixture was heated via microwave irradiation at 100° C. for 10 min, filtered through a 0.45 μm filter, and the filtrate was purified by reversed phase HPLC (Phenomenex Gemini 30 mm×100 mm column, gradient of acetonitrile in 20 mM aqueous NH$_4$OH). The title compound was obtained as a white solid (27 mg, 48%). MS (ESI): mass calcd. for $C_{27}H_{21}F_6N_5S$, 561.14; m/z found, 562 [M+H]$^+$. $^1$H NMR (CDCl$_3$): 8.38 (dd, J=4.7, 1.5 Hz, 1H), 7.88 (dd, J=7.8, 1.8 Hz, 1H), 7.68-7.62 (m, 2H), 7.56-7.50 (m, 1H), 7.50-7.42 (m, 2H), 7.23 (d, J=8.7 Hz, 2H), 7.16 (d, J=8.7 Hz, 2H), 6.96 (dd, J=7.4, 4.6 Hz, 1H), 6.58 (bs, 1H), 3.66-3.55 (m, 4H), 3.23-3.17 (m, 2H), 2.96-2.90 (m, 2H).

Examples 350-352 were synthesized in a manner similar to Example 349 substituting the appropriate thiols.

Example 350

2-(Phenylsulfanyl)-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

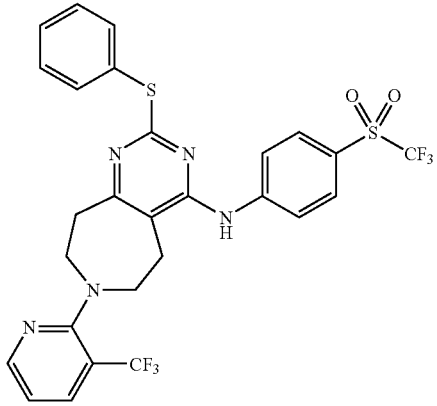 [SMILES: O=S(=O)(c1ccc(Nc2nc(Sc3ccccc3)nc3c2CCN(c2ncccc2C(F)(F)F)CC3)cc1)C(F)(F)F]

MS (ESI): mass calcd. for $C_{27}H_{21}F_6N_5O_2S_2$, 625.10; m/z found, 626 [M+H]$^+$. $^1$H NMR (CDCl$_3$): 8.38 (dd, J=4.7, 1.4 Hz, 1H), 7.89 (dd, J=7.8, 1.8 Hz, 1H), 7.70-7.64 (m, 2H), 7.63-7.53 (m, 3H), 7.50-7.44 (m, 2H), 6.98 (dd, J=7.9, 5.0 Hz, 1H), 6.81 (bs, 1H), 3.65-3.53 (m, 4H), 3.25-3.18 (m, 2H), 3.00-2.92 (m, 2H).

Example 351

N-[2-Methyl-4-(trifluoromethyl)phenyl]-2-(phenylsulfanyl)-7-[3-(trifluoromethyl)pyridin-2-yl]-6,7,8,9-tetrahydro-5H-pyrimido[4,5-d]azepin-4-amine

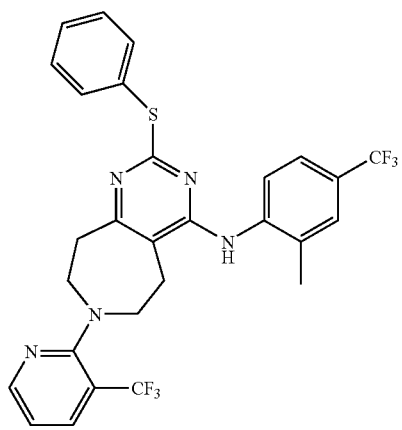 [SMILES: Cc1cc(C(F)(F)F)ccc1Nc1nc(Sc2ccccc2)nc2c1CCN(c1ncccc1C(F)(F)F)CC2]

MS (ESI): mass calcd. for $C_{28}H_{23}F_6N_5S$, 575.16; m/z found, 576 [M+H]$^+$. $^1$H NMR (CDCl$_3$): 8.38 (dd, J=4.7, 1.4 Hz, 1H), 7.88 (dd, J=7.8, 1.8 Hz, 1H), 7.61-7.56 (m, 2H), 7.48-7.42 (m, 2H), 7.42-7.33 (m, 2H), 7.32-7.28 (m, 1H), 7.02-6.93 (m, 2H), 6.43 (bs, 1H), 3.70-3.62 (m, 2H), 3.62-3.56 (m, 2H), 3.23-3.16 (m, 2H), 2.97-2.91 (m, 2H), 2.22 (s, 3H).

Example 352

2-(Phenylsulfanyl)-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine

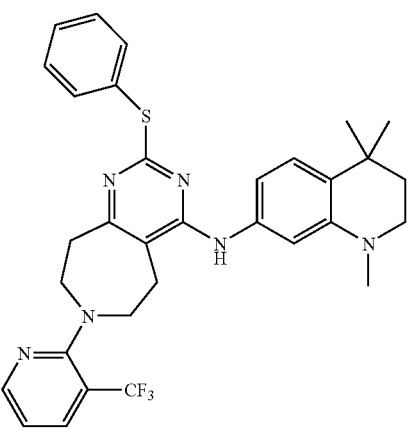 [SMILES: CN1CCC(C)(C)c2ccc(Nc3nc(Sc4ccccc4)nc4c3CCN(c3ncccc3C(F)(F)F)CC4)cc21]

MS (ESI): mass calcd. for $C_{32}H_{33}F_3N_6S$, 590.24; m/z found, 591 [M+H]$^+$. $^1$H NMR (CDCl$_3$): 8.37 (dd, J=4.7, 1.6

Hz, 1H), 7.86 (dd, J=7.8, 1.8 Hz, 1H), 7.66-7.60 (m, 2H), 7.43-7.33 (m, 3H), 6.94 (dd, J=7.7, 4.8 Hz, 1H), 6.77 (d, J=8.3 Hz, 1H), 6.53 (dd, J=. 8.3, 2.2 Hz, 1H), 6.35 (bs, 1H), 6.23 (d, J=2.2 Hz, 1H), 3.65-3.54 (m, 4H), 3.22-3.10 (m, 4H), 2.91-2.83 (m, 2H), 2.77 (s, 3H), 1.76-1.70.(m, 2H), 1.25 (s, 6H).

Examples 353-375 were synthesized in a manner similar to Example 349 substituting the appropriate thiols and substituting Cs$_2$CO$_3$ (4 molar equivalents) for p-toluenesulfonic acid.

Example 353

2-[(Phenylmethyl)sulfanyl]-N-[4-(trifluoromethyl)phenyl]-7-[3-(trifluoromethyl)pyridin-2-yl]-6,7,8,9-tetrahydro-5H-pyrimido[4,5-d]azepin-4-amine

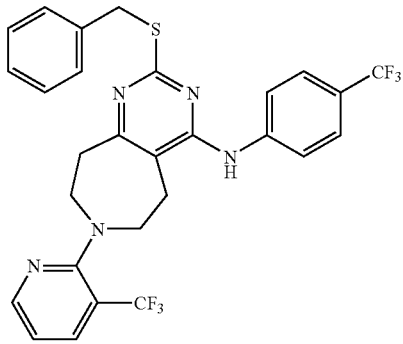 [SMILES: FC(F)(F)c1ccc(Nc2nc(SCc3ccccc3)nc3c2CCN(c2ncccc2C(F)(F)F)CC3)cc1]

MS (ESI): mass calcd. for C$_{28}$H$_{23}$F$_6$N$_5$S, 575.16; m/z found, 576 [M+H]$^+$. $^1$H NMR (CDCl$_3$): 8.38 (dd, J=4.6, 1.4 Hz, 1H), 7.88 (dd, J=7.8, 1.8 Hz, 1H), 7.59 (d, J=8.6 Hz, 2H), 7.52 (d, J=8.7 Hz, 2H), 7.37-7.32 (m, 2H), 7.30-7.20 (m, 3H), 6.96 (dd, J=7.4, 4.8 Hz, 1H), 6.62 (bs, 1H), 4.36 (s, 2H), 3.67-3.60 (m, 2H), 3.60-3.54 (m, 2H), 3.21-3.15 (m, 2H), 2.98-2.91 (m, 2H).

Example 354

2-(Cyclohexylsulfanyl)-N-[4-(trifluoromethyl)phenyl]-7-[3-(trifluoromethyl)pyridin-2-yl]-6,7,8,9-tetrahydro-5H-pyrimido[4,5-d]azepin-4-amine

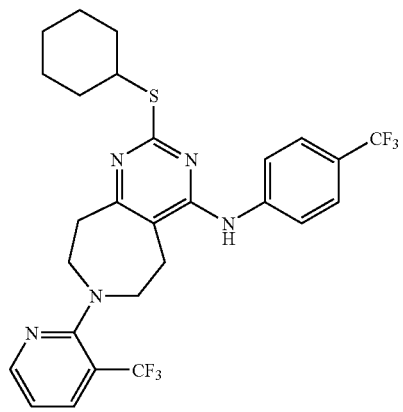 [SMILES: FC(F)(F)c1ccc(Nc2nc(SC3CCCCC3)nc3c2CCN(c2ncccc2C(F)(F)F)CC3)cc1]

MS (ESI): mass calcd. for C$_{27}$H$_{27}$F$_6$N$_5$S, 567.19; m/z found, 568 [M+H]$^+$. $^1$H NMR (CDCl$_3$): 8.38 (dd, J=4.6, 1.4 Hz, 1H), 7.87 (dd, J=7.8, 1.8 Hz, 1H), 7.67 (d, J=8.6 Hz, 2H), 7.58 (d, J=8.6 Hz, 2H), 6.96 (dd, J=7.5, 4.6 Hz, 1H), 6.63 (bs, 1H), 3.73-3.61 (m, 1H), 3.68-3.60 (m, 2H), 3.60-3.53 (m, 2H), 3.19-3.12 (m, 2H), 2.98-2.92 (m, 2H), 2.14-2.05 (m, 2H), 1.82-1.73 (m, 2H), 1.68-1.60 (m, 1H), 1.56-1.43 (m, 2H), 1.43-1.23 (m, 3H).

Example 355

2-[(1-Methylethyl)sulfanyl]-N-[4-(trifluoromethyl)phenyl]-7-[3-(trifluoromethyl)pyridin-2-yl]-6,7,8,9-tetrahydro-5H-pyrimido[4,5-d]azepin-4-amine

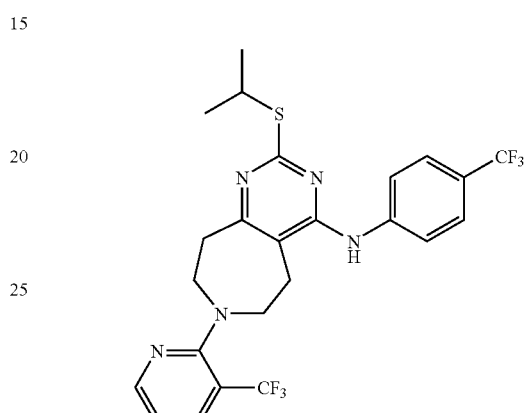

MS (ESI): mass calcd. for C$_{24}$H$_{23}$F$_6$N$_5$S, 527.16; m/z found, 528 [M+H]$^+$. $^1$H NMR (CDCl$_3$): 8.38 (dd, J=4.6, 1.4 Hz, 1H), 7.87 (dd, J=7.8, 1.8 Hz, 1H), 7.68 (d, J=8.6 Hz, 2H), 7.58 (d, J=8.6 Hz, 2H), 6.96 (dd, J=7.8, 5.1 Hz, 1H), 6.63 (bs, 1H), 3.87 (sept, J=6.8 Hz, 1H), 3.67-3.61 (m, 2H), 3.61-3.54 (m, 2H), 3.20-3.14 (m, 2H), 2.98-2.92 (m, 2H), 1.41 (d, J=6.8 Hz, 6H).

Example 356

1-[(4-{[4-(Trifluoromethyl)phenyl]amino}-7-[3-(trifluoromethyl)pyridin-2-yl]-6,7,8,9-tetrahydro-5H-pyrimido[4,5-d]azepin-2-yl)sulfanyl]propan-2-ol

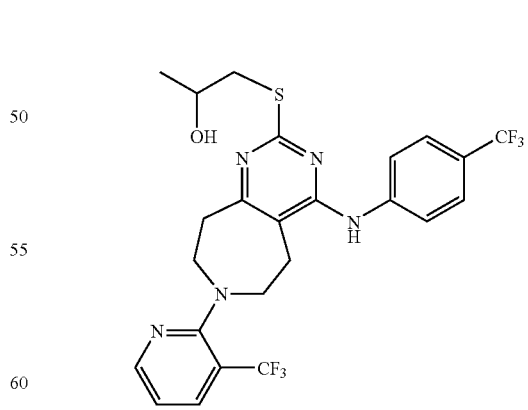

MS (ESI): mass calcd. for C$_{24}$H$_{23}$F$_6$N$_5$OS, 543.15; m/z found, 544 [M+H]$^+$. $^1$H NMR (CDCl$_3$): 8.39 (dd, J=4.7, 1.5 Hz, 1H), 7.88 (dd, J=7.8, 1.8 Hz, 1H), 7.65 (d, J=8.8 Hz, 2H), 7.60 (d, J=8.8 Hz, 2H), 6.97 (dd, J=7.5, 4.7 Hz, 1H), 6.67 (bs, 1H), 4.24 (bs, 1H), 4.15-4.05 (m, 1H), 3.65-3.60 (m, 2H), 3.60-3.53 (m, 2H), 3.29 (dd, J=14.6, 3.0 Hz, 1H), 3.19-3.12 (m, 2H), 3.08 (dd, J=14.6, 7.4 Hz, 1H), 2.99-2.92 (m, 2H), 1.26 (d, J=6.2 Hz, 3H).

Example 357

[2-(2-Methyl-tetrahydro-furan-3-ylsulfanyl)-7-(3-trifluoromethyl-pyridin-2-yl)-6,7,8,9-tetrahydro-5H-pyrimido[4,5-d]azepin-4-yl]-(4-trifluoromethyl-phenyl)-amine

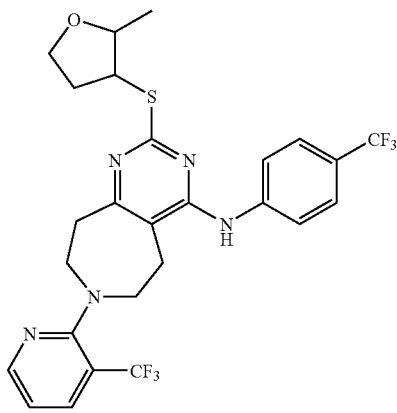 [SMILES: CC1OCCC1Sc1nc2c(c(Nc3ccc(C(F)(F)F)cc3)n1)CCN(c1ncccc1C(F)(F)F)CC2]

The title compound was isolated as a mixture of isomers. MS (ESI): mass calcd. for $C_{26}H_{25}F_6N_5OS$, 569.17; m/z found, 570 [M+H]$^+$. $^1$H NMR (CDCl$_3$): 8.38 (dd, J=4.6, 1.3 Hz, 1H), 7.88 (dd, J=7.8, 1.8 Hz, 1H), 7.65 (d, J=8.6 Hz, 2H), 7.54 (d, J=8.7 Hz, 2H), 6.97 (dd, J=7.4, 4.8 Hz, 1H), 6.63 (bs, 1H), 4.35-4.23 (m, 2H), 4.06-3.98 (m, 1H), 3.82-3.74 (m, 1H), 3.68-3.61 (m, 2H), 3;61-3.54 (m, 2H), 3.20-3.14 (m, 2H), 2.98-2.92 (m, 2H), 2.55-2.43 (m, 1H), 2.11-2.02 (m, 1H), 1.27 (d, J=6.1 Hz, 3H).

Example 358

[2-(2-Methyl-tetrahydro-furan-3-ylsulfanyl)-7-(3-trifluoromethyl-pyridin-2-yl)-6,7,8,9-tetrahydro-5H-pyrimido[4,5-d]azepin-4-yl]-(4-trifluoromethyl-phenyl)-amine

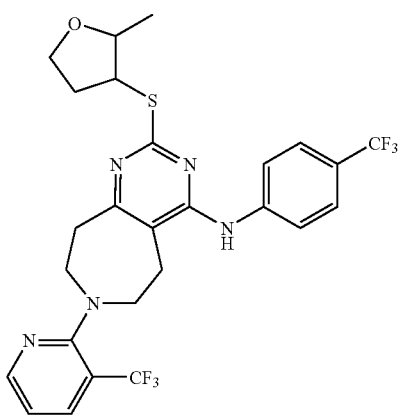 [SMILES: CC1OCCC1Sc1nc2c(c(Nc3ccc(C(F)(F)F)cc3)n1)CCN(c1ncccc1C(F)(F)F)CC2]

The title compound was isolated as a mixture of isomers. MS (ESI): mass calcd. for $C_{26}H_{25}F_6N_5OS$, 569.17; m/z found, 570 [M+H]$^+$. $^1$H NMR (CDCl$_3$): 8.39 (dd, J=4.6, 1.4 Hz, 1H), 7.88 (dd, J=7.8, 1.8 Hz, 1H), 7.64 (d, J=8.7 Hz, 2H), 7.59 (d, J=8.7 Hz, 2H), 6.97 (dd, J=7.2, 4.8 Hz, 1H), 6.63 (bs, 1H), 4.00-3.92 (m, 1H), 3.90-3.81 (m, 2H), 3.81-3.74 (m, 1H), 3.67-3.60 (m, 2H), 3.60-3.53 (m, 2H), 3.31-3.25 (m, 2H), 2.99-2.92 (m, 2H), 2.59-2.46 (m, 1H), 2.04-1.93 (m, 1H), 1.30 (d, J=6.0 Hz, 3H).

Example 359

2-[(Phenylmethyl)sulfanyl]-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

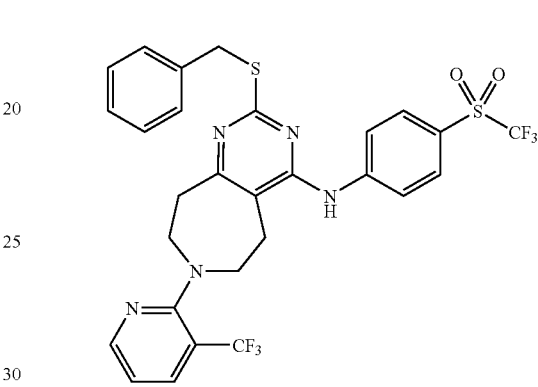

MS (ESI): mass calcd. for $C_{28}H_{23}F_6N_5O_2S_2$, 639.12; m/z found, 640 [M+H]$^+$. $^1$H NMR (CDCl$_3$): 8.38 (dd, J=4.7, 1.5 Hz, 1H), 7.91-7.85 (m, 3H), 7.79-7.74 (m, 2H), 7.42-7.37 (m, 2H), 7.33-7.26 (m, 2H), 7.26-7.22 (m, 1H), 6.98 (dd, J=8.2, 5.2 Hz, 1H), 6.86 (bs, 1H), 4.40 (s, 2H), 3.65-3.55 (m, 4H), 3.25-3.20 (m, 2H), 3.01-2.96 (m, 2H).

Example 360

2-(Cyclohexylsulfanyl)-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

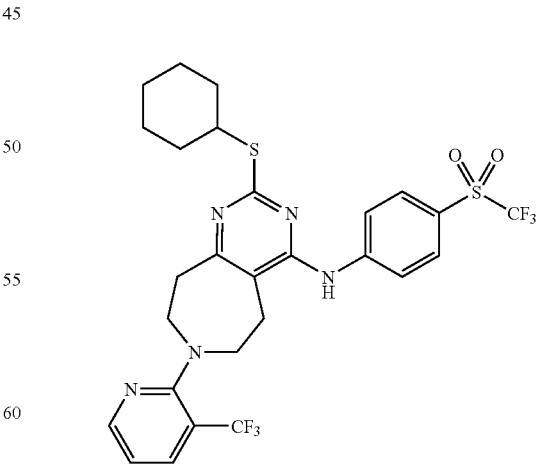

MS (ESI): mass calcd. for $C_{27}H_{27}F_6N_5O_2S_2$, 631.15; m/z found, 632 [M+H]$^+$. $^1$H NMR (CDCl$_3$): 8.38 (dd, J=4.8, 1.6 Hz, 1H), 7.97 (d, J=8.9 Hz, 2H), 7.90-7.84 (m, 3H), 6.98 (dd, J=7.6, 4.7 Hz, 1H), 6.88 (bs, 1H), 3.75-3.67 (m, 1H), 3.64-

3.60 (m, 2H), 3.60-3.54 (m, 2H), 3.21-3.15 (m, 2H), 3.02-2.95 (m, 2H), 2.16-2.07 (m, 2H), 1.85-1.74 (m, 2H), 1.69-1.61 (m, 1H), 1.57-1.45 (m, 2H), 1.45-1.25 (m, 3H).

Example 361

2-[(1-Methylethyl)sulfanyl]-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

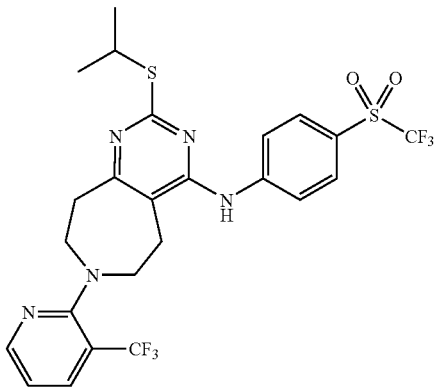 [SMILES: CC(C)Sc1nc2c(c(Nc3ccc(S(=O)(=O)C(F)(F)F)cc3)n1)CCN(c1ncccc1C(F)(F)F)CC2]

MS (ESI): mass calcd. for $C_{24}H_{23}F_6N_5O_2S_2$, 591.12; m/z found, 592 [M+H]+. $^1$H NMR (CDCl$_3$): 8.38 (dd, J=4.7, 1.5 Hz, 1H), 7.96 (d, J=8.9 Hz, 2H), 7.90-7.84 (m, 3H), 6.98 (dd, J=7.4, 4.8 Hz, 1H), 6.90 (bs, 1H), 3.90 (sept, J=6.8 Hz, 1H), 3.66-3.60 (m, 2H), 3.60-3.54 (m, 2H), 3.23-3.18 (m, 2H), 3.03-2.95 (m, 2H), 1.43 (d, J=6.8 Hz, 3H).

Example 362

1-({7-[3-(Trifluoromethyl)pyridin-2-yl]-4-{4-[(trifluoromethyl)sulfonyl]phenyl}amino)-6,7,8,9-tetrahydro-5H-pyrimido[4,5-d]azepin-2-yl}sulfanyl)propan-2-ol

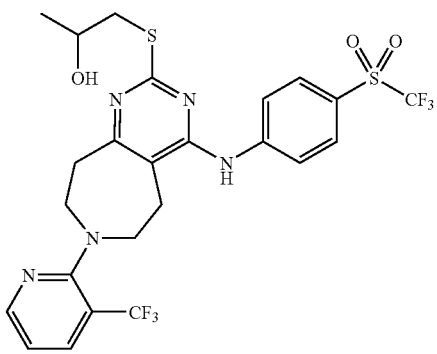 [SMILES: CC(O)CSc1nc2c(c(Nc3ccc(S(=O)(=O)C(F)(F)F)cc3)n1)CCN(c1ncccc1C(F)(F)F)CC2]

MS (ESI): mass calcd. for $C_{24}H_{23}F_6N_5O_3S_2$, 607.11; m/z found, 608 [M+H]+. $^1$H NMR (CDCl$_3$): 8.38 (dd, J=4.7, 1.6 Hz, 1H), 8.01-7.95 (m, 2H), 7.91-7.84 (m, 3H), 7.02-6.94 (m, 2H), 4.19 (bs, 1H), 4.19-4.10 (m, 1H), 3.65-3.58 (m, 2H), 3.58-3.52 (m, 2H), 3.33 (dd, J=14.6, 3.1 Hz, 1 H), 3.21-3.13 (m, 2H), 3.15 (dd, J=14:6, 7.2 Hz, 1H), 3.03, 2.95 (m, 2H), 1.30 (d, J6.2 Hz, 3 H).

Example 363

[2-(2-Methyl-tetrahydro-furan-3-ylsulfanyl)-7-(3-trifluoromethyl-pyridin-2-yl)-6,7,8,9-tetrahydro-5H-pyrimido[4,5-d]azepin-4-yl]-(4-trifluoromethane-sulfonyl-phenyl)-amine

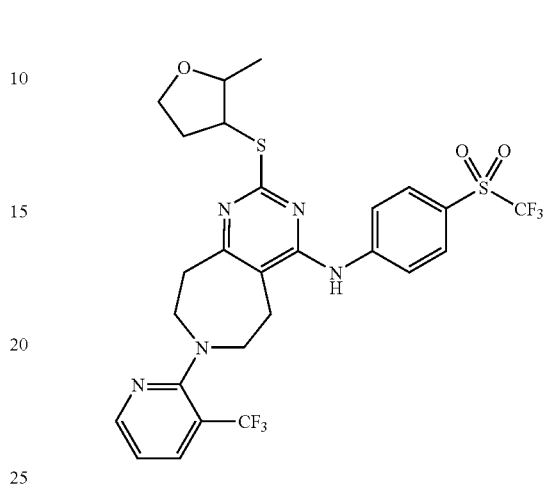

The title compound was prepared using 2-methyltetrahydrofuran-3-thiol, obtained as a mixture of isomers from Acros Organics (cat. #33270 0010). Upon purification by reverse phase HPLC (Phenomenex Gemini 5 μm $C_{18}$ column, 30×100 mm, gradient of acetonitrile in 20 mM aqueous NH$_4$OH), the title compound was isolated as a single diastereomer of unknown stereochemistry. Analytical HPLC: Waters Xterra MS $C_{18}$ 5 μm column, 4.6×100 mm, gradient over 7 min from 1 to 99% acetonitrile in water modified with 0.05% TFA, 1.0 mL/min; $t_R$=8.07 min. MS (ESI): mass calcd. for $C_{26}H_{25}F_6N_5O_3S_2$, 633.13; m/z found, 634 [M+H]+. $^1$H NMR (CDCl$_3$): 8.38 (dd, J=4.6, 1.5 Hz, 1H), 7.97 (d, J=8.9 Hz, 2H), 7.89 (dd, J=7.8, 1.8 Hz, 1H), 7.85 (d, J=9.0 Hz, 2H), 6.98 (dd, J=8.1, 5.4 Hz, 1H), 6.89 (bs, 1H), 4.03-3.96 (m, 1H), 3.93-3.84 (m, 2H), 3.84-3.78 (m, 1H), 3.66-3.61 (m, 2H), 3.23-3.18 (m, 2H), 3.03-2.95 (m, 2H), 2.61-2.50 (m, 1H), 2.06-1.95 (m, 1H), 1.33 (d, J=6.0 Hz, 3H).

Example 364

N-[2-Methyl-4-(trifluoromethyl)phenyl]-2-[(phenylmethyl)sulfanyl]-7-[3-(trifluoromethyl)pyridin-2-yl]-6,7,8,9-tetrahydro-5H-pyrimido[4,5-d]azepin-4-amine

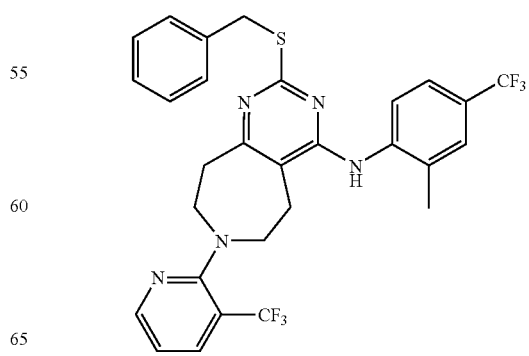

MS (ESI): mass calcd. for $C_{29}H_{25}F_6N_5S$, 589.17; m/z found, 590 [M+H]$^+$. $^1$H NMR (CDCl$_3$): 8.38 (dd, J=4.6, 1.4 Hz, 1H), 7.88 (dd, J=7.8, 1.8 Hz, 1H), 7.86 (d, J=8.3 Hz, 1H), 7.48-7.45 (m, 1H), 7.42-7.37 (m, 1H), 7.26-7.16 (m, 5H), 6.96 (dd, J=7.7, 4.8 Hz, 1H), 6.35 (bs, 1H), 4.25 (s, 2H), 3.68-3.61 (m, 2H), 3.61-3.54 (m, 2H), 3.21-3.15 (m, 2H), 2.97-2.91 (m, 2H), 2.31 (s, 3H).

Example 365

2-(Cyclohexylsulfanyl)-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

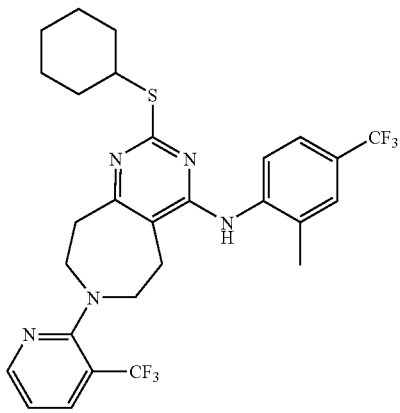 [SMILES: Cc1cc(C(F)(F)F)ccc1Nc1nc(SC2CCCCC2)nc2c1CCN(c1ncccc1C(F)(F)F)CC2]

MS (ESI): mass calcd. for $C_{28}H_{29}F_6N_5S$, 581.20; m/z found, 582 [M+H]$^+$. $^1$H NMR (CDCl$_3$): 8.38 (dd, J=4.8, 1.6 Hz, 1H), 7.98 (d, J=9.0 Hz, 1H), 7.87 (dd, J=7.8, 1.8 Hz, 1H), 7.49-7.44 (m, 2H), 6.96 (dd, J=7.6, 4.7 Hz, 1H), 6.37 (bs, 1H), 3.68-3.61 (m, 2H), 3.61-3.45 (m, 3H), 3.19-3.12 (m, 2H), 2.98-2.92 (m, 2H), 2.34 (s, 3H), 2.05-1.95 (m, 2H), 1.77-1.65 (m, 2H), 1.65-1.53 (m, 1H), 1.48-1.34 (m, 2H), 1.33-1.17 (m, 3H).

Example 366

2-[(1-Methylethyl)sulfanyl]-N-[2-methyl-4-(trifluoromethyl)phenyl]-7-[3-(trifluoromethyl)pyridin-2-yl]-6,7,8,9-tetrahydro-5H-pyrimido[4,5-d]azepin-4-amine

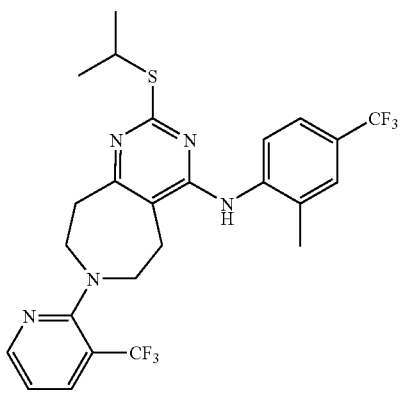 [SMILES: Cc1cc(C(F)(F)F)ccc1Nc1nc(SC(C)C)nc2c1CCN(c1ncccc1C(F)(F)F)CC2]

MS (ESI): mass calcd. for $C_{25}H_{25}F_6N_5S$, 541.17; m/z found, 542 [M+H]$^+$. $^1$H NMR (CDCl$_3$): 8.38 (dd, J=4.7, 1.5 Hz, 1H), 8.03 (d, J=9.0 Hz, 1H), 7.88 (dd, J=7.8, 1.8 Hz, 1H), 7.49-7.43 (m, 2H), 6.96 (dd, J=7.8, 5.1 Hz, 1H), 6.38 (bs, 1H), 3.74 (sept, J=6.8 Hz, 1H), 3.69-3.62 (m, 2H), 3.62-3.55 (m, 2H), 3.21-3.14 (m, 2H), 2.98-2.91 (m, 2H), 2.35 (s, 3H), 1.34 (d, J=6.8 Hz, 6H).

Example 367

1-[(4-{[2-Methyl-4-(trifluoromethyl)phenyl]amino}-7-[3-(trifluoromethyl)pyridin-2-yl]-6,7,8,9-tetrahydro-5H-pyrimido[4,5-d]azepin-2-yl)sulfanyl]propan-2-ol

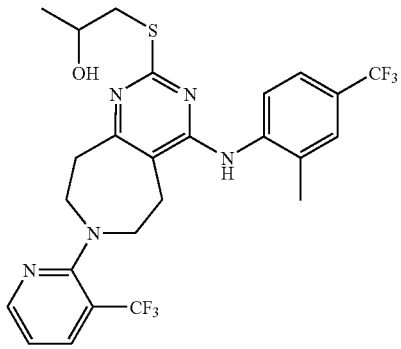 [SMILES: Cc1cc(C(F)(F)F)ccc1Nc1nc(SCC(C)O)nc2c1CCN(c1ncccc1C(F)(F)F)CC2]

MS (ESI): mass calcd. for $C_{25}H_{25}F_6N_5OS$, 557.17; m/z found, 558 [M+H]$^+$. $^1$H NMR (CDCl$_3$): 8.39 (dd, J=4.7, 1.5 Hz, 1H), 7.88 (dd, J=7.7, 1.8 Hz, 1H), 7.86 (d, J=8.6 Hz, 1H), 7.53-7.47 (m, 2H), 6.97 (dd, J=7.6, 4.8 Hz, 1H), 6.39 (bs, 1H), 4.02-3.93 (m, 1H), 3.67-3.61 (m, 2H), 3.61-3.53 (m, 2H), 3.22-3.13 (m, 3H), 2.33 (s, 3H), 1.17 (d, J=6.2 Hz, 3H).

Example 368

2,5-Anhydro-1,4-dideoxy-3-S-(4-{[2-methyl-4-(trifluoromethyl)phenyl]amino}-7-[3-(trifluoromethyl)pyridin-2-yl]-6,7,8,9-tetrahydro-5H-pyrimido[4,5-d]azepin-2-yl)-3-thiopentitol

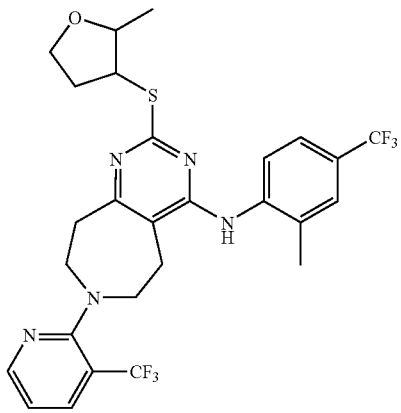 [SMILES: Cc1cc(C(F)(F)F)ccc1Nc1nc(SC2CCOC2C)nc2c1CCN(c1ncccc1C(F)(F)F)CC2]

The title compound was isolated as a mixture of isomers. MS (ESI): mass calcd. for $C_{27}H_{27}F_6N_5OS$, 583.18; m/z found, 584 [M+H]$^+$. $^1$H NMR (CDCl$_3$): 8.41-8.37 (m, 1H), 7.91-7.85 (m, 2H), 7.48. (s, 2H), 6.97 (dd, J=7.8, 4.8 Hz, 1H), 6.37 (bs, 1H), 4.20-4.15 (m, 1H), 3.92-3.83 (m, 1H), 3.83-3.76 (m, 2H), 3.68-3.55 (m, 4H), 3.20-3.14 (m, 2H), 2.99-2.92 (m, 2H), 2.42-2.32 (m, 1H), 2.34 (s, 3H), 1.96-1.88 (m, 1H), 1.23 (d, J=6.1 Hz, 3H).

Example 369

2,5-Anhydro-1,4-dideoxy-3-S-(4-{[2-methyl-4-(trifluoromethyl)phenyl]amino}-7-[3-(trifluoromethyl)pyridin-2-yl]-6,7,8,9-tetrahydro-5H-pyrimido[4,5-d]azepin-2-yl)-3-thiopentitol

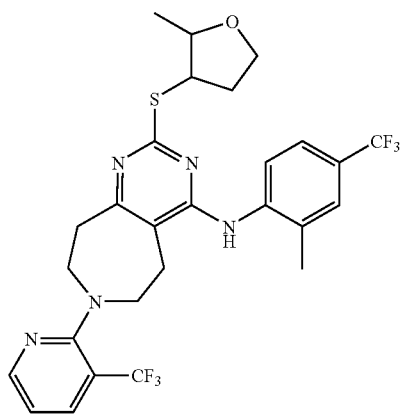 [SMILES: Cc1cc(C(F)(F)F)ccc1Nc1nc(SC2CCOC2C)nc2c1CCN(c1ncccc1C(F)(F)F)CC2]

The title compound was isolated as a mixture of isomers. MS (ESI): mass calcd. for $C_{27}H_{27}F_6N_5OS$, 583.18; m/z found, 584 [M+H]$^+$. $^1$H NMR (CDCl$_3$): 8.39 (dd, J=4.8, 1.5 Hz, 1H), 7.92-7.85 (m, 2H), 7.50-7.45 (m, 2H), 6.97 (dd, J=7.4, 4.8 Hz, 1H), 6.37 (bs, 1H), 3.92-3.83 (m, 1H), 3.85-3.76 (m, 2H), 3.68-3.55 (m, 5H), 3.21-3.15 (m, 2H), 3.00-2.93 (m, 2H), 2.42-2.32 (m, 1H), 2.34 (s, 3H), 1.96-1.87 (m, 1H), 1.23 (d, J=6.1 Hz, 3H).

Example 370

2-[(Phenylmethyl)sulfanyl]-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine

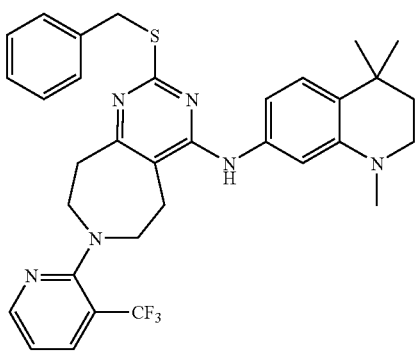 [SMILES: CN1CCC(C)(C)c2ccc(Nc3nc(SCc4ccccc4)nc4c3CCN(c3ncccc3C(F)(F)F)CC4)cc21]

MS (ESI): mass calcd. for $C_{33}H_{35}F_3N_6S$, 604.26; m/z found, 605 [M+H]$^+$. $^1$H NMR (CDCl$_3$): 8.38 (dd, J=4.7, 1.5 Hz, 1H), 7.86 (dd, J=7.8, 1.8 Hz, 1H), 7.29-7.14 (m, 5H), 7.11 (d, J=8.0 Hz, 1H), 6.94 (dd, J=7.4, 4.5 Hz, 1H), 6.77-6.71 (m, 2H), 6.37 (bs, 1H), 4.33 (s, 2H), 3.68-3.54 (m, 4H), 3.27-3.19 (m, 2H), 3.19-3.11 (m, 2H), 2.93-2.84 (m, 2H), 2.89 (s, 3H), 1.78-1.71 (m, 2H), 1.26 (s, 6H).

Example 371

2-(Cyclohexylsulfanyl)-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine

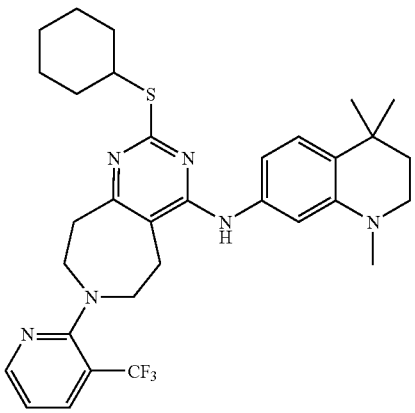 [SMILES: CN1CCC(C)(C)c2ccc(Nc3nc(SC4CCCCC4)nc4c3CCN(c3ncccc3C(F)(F)F)CC4)cc21]

MS (ESI): mass calcd. for $C_{32}H_{39}F_3N_6S$, 596.29; m/z found, 597 [M+H]$^+$. $^1$H NMR (CDCl$_3$): 8.38 (dd, J=4.7, 1.5 Hz, 1H), 7.86 (dd, J=7.8, 1.8 Hz, 1H), 7.13 (d, J=8.2 Hz, 1H), 6.93 (dd, J=7.6, 4.6 Hz, 1H), 6.88 (dd, J=8.2, 2.0 Hz, 1H), 6.51 (d, J=2.0 Hz, 1H), 6.33 (bs, 1H), 3.69-3.59 (m, 3H), 3.59-3.53 (m, 2H), 3.26-3.21 (m, 2H), 3.17-3.10 (m, 2H), 2.92-2.84 (m, 2H), 2.90 (s, 3H), 2.09-2.01 (m, 2H), 1.79-1.65 (m, 4H), 1.62-1.53 (m, 1H), 1.48-1.37 (m, 2H), 1.37-1.15 (m, 3H), 1.28 (s, 6H).

Example 372

2-[(1-Methylethyl)sulfanyl]-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine

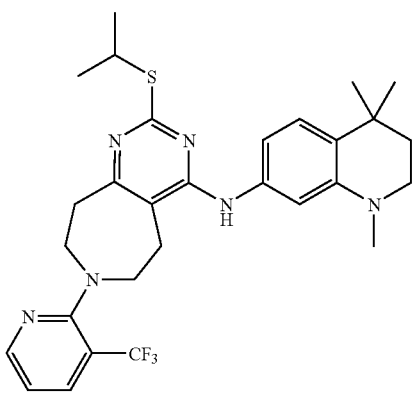 [SMILES: CC(C)Sc1nc2c(c(Nc3ccc4c(c3)N(C)CCC4(C)C)n1)CCN(c1ncccc1C(F)(F)F)CC2]

MS (ESI): mass calcd. for $C_{29}H_{35}F_3N_6S$, 556.26; m/z found, 557 [M+H]$^+$. $^1$H NMR (CDCl$_3$): 8.38 (dd, J=4.6, 1.4 Hz, 1H), 7.86 (dd, J=7.8, 1.9 Hz, 1H), 7.11 (d, J=8.2 Hz, 1H), 6.96-6.90 (m, 1H), 6.87-6.82 (m, 1H), 6.69-6.65 (m, 1H), 6.37 (bs, 1H), 3.95-3.85 (m, 1H), 3.65-3.60 (m, 2H), 3.60-

3.54 (m, 2H), 3.26-3.20 (m, 2H), 3.17-3.10 (m, 2H), 2.93-2.85 (m, 5H), 1.79-1.74 (m, 2H), 1.37 (d, J=6.8 Hz, 6H), 1.28 (s, 6H).

Example 373

1-({7-[3-(Trifluoromethyl)pyridin-2-yl]-4-[(1,4,4-trimethyl-1,2,3,4-tetrahydroquinolin-7-yl)amino]-6,7,8,9-tetrahydro-5H-pyrimido[4,5-d]azepin-2-yl}sulfanyl)propan-2-ol

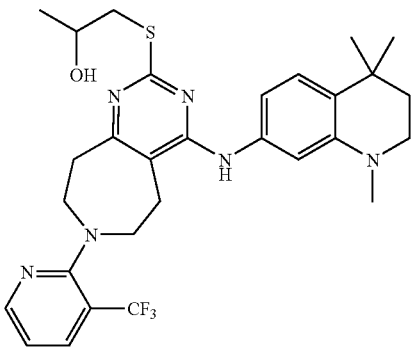 [SMILES: CC(O)CSc1nc2c(c(Nc3ccc4c(c3)N(C)CCC4(C)C)n1)CCN(c1ncccc1C(F)(F)F)CC2]

MS (ESI): mass calcd. for $C_{29}H_{35}F_3N_6OS$, 572.25; m/z found, 573 [M+H]$^+$. H NMR (CDCl$_3$): 8.38 (dd, J=4.6, 1.4 Hz, 1H), 7.86 (dd, J=7.8, 1.8 Hz, 1H), 7.14 (d, J=8.2 Hz, 1H), 6.95 (dd, J=7.7, 4.8 Hz, 1H), 6.75 (d, J=2.1 Hz, 1H), 6.68 (dd, J=8.2, 2.2 Hz, 1H), 6.40 (bs, 1H), 4.33 (bs, 1H), 4.07-3.99 (m, 1H), 3.66-3.60 (m, 2H), 3.60-3.52 (m, 2H), 3.27-3.21 (m, 2H), 3.20-3.10 (m, 3H), 3.05 (dd, J=14.5, 7.0 Hz, 1H), 2.92 (s, 3H), 2.91-2.84 (m, 2H), 1.78-1.71 (m, 2H), 1.27 (s, 6H), 1.20 (d, J=6.2 Hz, 3H).

Example 374

2,5-Anhydro-1,4-dideoxy-3-thio-3-S-{7-[3-(trifluoromethyl)pyridin-2-yl]-4-[(1,4,4-trimethyl-1,2,3,4-tetrahydroquinolin-7-yl)amino]-6,7,8,9-tetrahydro-5H-pyrimido[4,5-d]azepin-2-yl}pentitol

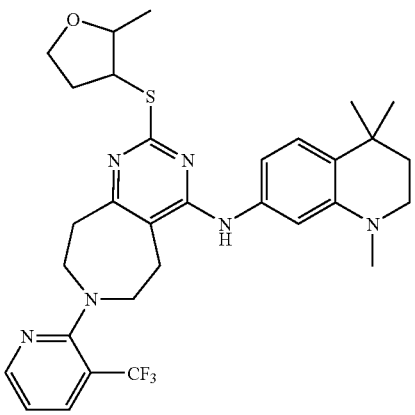 [SMILES: CC1OCCC1Sc1nc2c(c(Nc3ccc4c(c3)N(C)CCC4(C)C)n1)CCN(c1ncccc1C(F)(F)F)CC2]

The title compound was isolated as a mixture of isomers. MS (ESI): mass calcd. for $C_{31}H_{37}F_3N_6OS$, 598.27; m/z found, 599 [M+H]$^+$. $^1$H NMR (CDCl$_3$): 8.38 (dd, J=4.6, 1.7 Hz, 12H), 7.86 (dd, J=7.7, 1.8 Hz, 1H), 7.12 (d, J=8.2 Hz, 1H), 6.94 (dd, J=7.8, 4.2 Hz, 1H), 6.75 (dd, J=8.2, 2.2 Hz, 1H), 6.64 (d, J=2.1 Hz, 1H), 6.36 (bs, 1H), 3.93-3.80 (m, 3H), 3.78-3.71 (m, 1H), 3.66-3.61 (m, 2H), 3.61-3.54 (m, 2H), 3.24 (t, J=5.9 Hz, 2H), 3.17-3.11 (m, 2H), 2.93-2.87 (m, 2H), 2.91 (s, 3H), 2.52-2.42 (m, 1H), 2.00-1.90 (m, 1H), 1.76 (t, J=5.9 Hz, 2H), 1.27 (s, 6H), 1.24 (d, J=6.1 Hz, 3H).

Example 375

2-(Propylsulfanyl)-N-[4-(trifluoromethyl)phenyl]-7-[3-(trifluoromethyl)pyridin-2-yl]-6,7,8,9-tetrahydro-5H-pyrimido[4,5-d]azepin-4-amine

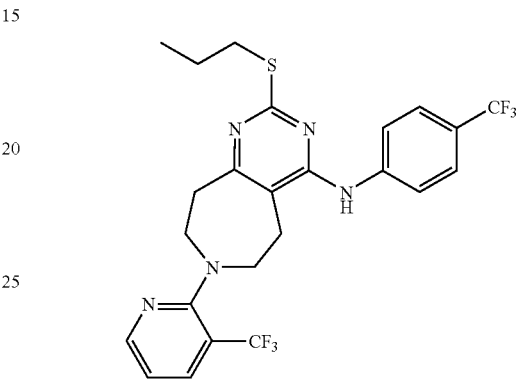

MS (ESI): mass calcd. for $C_{24}H_{23}F_6N_5S$, 527.16; m/z found, 528 [M+H]$^+$. $^1$H NMR (CDCl$_3$): 8.38 (dd, J=4.7, 1.4 Hz, 1H), 7.88 (dd, J=7.8, 1.8 Hz, 1H), 7.67 (d, J=8.6 Hz, 2H), 7.58 (d, J=8.6 Hz, 2H), 6.96 (dd, J=7.2, 4.8 Hz, 1H), 6.62 (bs, 1H), 3.66-3.61 (m, 2H), 3.61-3.54 (m, 2H), 3.20-3.13 (m, 2H), 3.08-3.02 (m, 2H), 2.98-2.91 (m, 2H), 1.73 (sextet, J=7.4 Hz, 2H), 1.00 (t, J=7.3 Hz, 3H).

The compounds in Examples 376-394 were prepared using methods analogous to those described in the preceding examples.

Example 376

2-Methyl-2-{4-[2-morpholin-4-yl-7-(3-trifluoromethyl-pyridin-2-yl)-6,7,8,9-tetrahydro-5H-pyrimido[4,5-d]azepin-4-ylamino]-phenyl}-propionic acid methyl ester

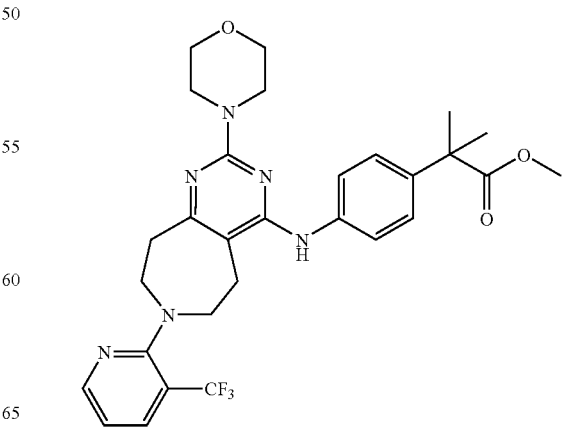

MS: mass calcd. for C$_{29}$H$_{33}$F$_3$N$_6$O$_3$, 570.2567; m/z found, 571.3 [M+H]$^+$. $^1$H NMR (CDCl$_3$): 8.41-8.38 (m, 1H), 7.88 (dd, J=1.8, 7.8 Hz, 1H), 7.53-7.48 (m, 2H), 7.33-7.29 (m, 2H), 6.98-6.92 (m, 1H), 6.40 (s, 1H), 3.80-3.72 (m, 8H), 3.67 (s, 3H), 3.64-3.56 (m, 4H), 3.11-3.06 (m, 2H), 2.89-2.85 (m, 2H), 1.60 (s, 6H).

Example 377

2-(1-Methylethyl)-N-(4-pyrrolidin-1-ylphenyl)-7-[3-(trifluoromethyl)pyridin-2-yl]-6,7,8,9-tetrahydro-5H-pyrimido[4,5-d]azepin-4-amine

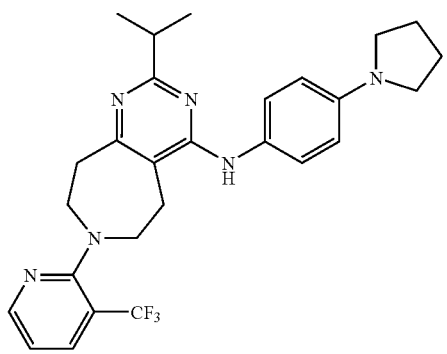 [SMILES: CC(C)c1nc2c(c(Nc3ccc(N4CCCC4)cc3)n1)CCN(c1ncccc1C(F)(F)F)CC2]

MS: mass calcd. for C$_{27}$H$_{31}$F$_3$N$_6$, 496.2562; m/z found, 497.3 [M+H]$^+$. $^1$H NMR (CDCl$_3$): 8.41-8.38 (m, 1H), 7.88 (dd, J=1.8, 7.8 Hz, 1H), 7.47-7.43 (m, 2H), 6.97-6.92 (m, 1H), 6.60-6.55 (m, 2H), 6.31 (s, 1H), 3.69-3.59 (m, 4H), 3.34-3.28 (m, 4H), 3.22-3.17 (m, 2H), 3.02-2.94 (m, 1H), 2.93-2.87 (m, 2H), 2.07-1.98 (m, 4H), 1.30 (d, J=6.9 Hz, 6H).

Example 378

2-Piperidin-1-yl-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine

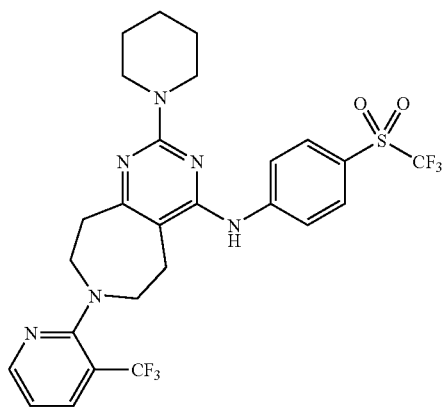 [SMILES: O=S(=O)(c1ccc(Nc2nc(N3CCCCC3)nc3c2CCN(c2ncccc2C(F)(F)F)CC3)cc1)C(F)(F)F]

MS: mass calcd. for C$_{26}$H$_{26}$F$_6$N$_6$O$_2$S, 600.1742; m/z found, 601.2 [M+H]$^+$. $^1$H NMR (CDCl$_3$): 8.42-8.38 (m, 1H), 7.97-7.93 (m, 2H), 7.89 (dd, J=1.8, 7.8 Hz, 1H), 7.86-7.82 (m, 2H), 6.99-6.95 (m, 1H), 6.78 (s, 1H), 3.81-3.72. (m, 4H), 3.63-3.52 (m, 4H), 3.14-3.09 (m, 2H), 2.94-2.88 (m, 2H), 1.74-1.60 (m, 6H).

Example 379

N,N-Dimethyl-4-({2-morpholin-4-yl-7-[3-(trifluoromethyl)pyridin-2-yl]-6,7,8,9-tetrahydro-5H-pyrimido[4,5-d]azepin-4-yl}amino)benzenesulfonamide

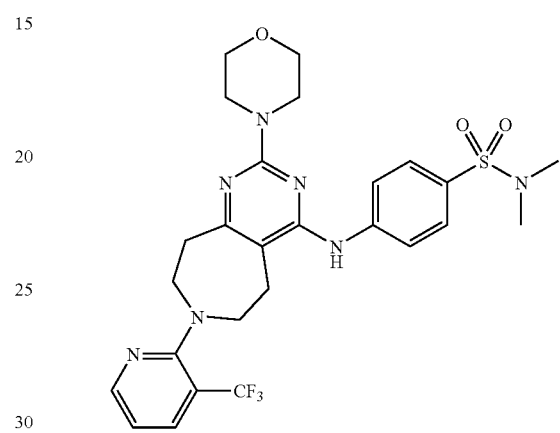

MS: mass calcd. for C$_{26}$H$_{30}$F$_3$N$_7$O$_3$S, 577.2083; m/z found, 578.2 [M+H]$^+$. $^1$H NMR (CDCl$_3$): 8.42-8.39 (m, 1H), 7.89 (dd, J=1.8, 7.8 Hz, 1H), 7.79-7.67 (m, 4H), 7.00-6.95 (m, 1H), 6.64 (s, 1H), 3.82-3.73 (m, 8H), 3.64-3.55 (m, 4H), 3.15-3.09 (m, 2H), 2.95-2.88 (m, 2H), 2.73 (s, 6H).

Example 380

1-[4-({2-Morpholin-4-yl-7-[3-(trifluoromethyl)pyridin-2-yl]-6,7,8,9-tetrahydro-5H-pyrimido[4,5-d]azepin-4-yl}amino)phenyl]ethanone

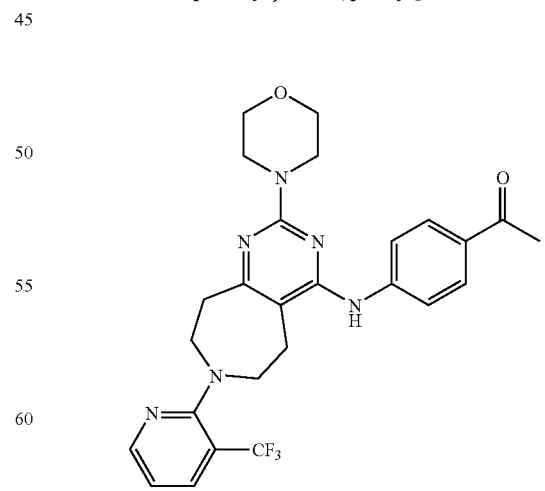

MS: mass calcd. for C$_{26}$H$_{27}$F$_3$N$_6$O$_2$, 512.2148; m/z found, 513.2 [M+H]$^+$. $^1$H NMR (CDCl$_3$): 8.42-8.39 (m, 1H), 7.99-7.94 (m, 2H), 7.89 (dd, J=1.8, 7.8 Hz, 1H), 7.66-7.60 (m, 2H), 6.99-6.94 (m, 1H), 6.63 (s, 1H), 3.82-3.74 (m, 8H), 3.64-3.55 (m, 4H), 3.14-3.09 (m, 2H), 2.93-2.89 (m, 2H), 2.60 (s, 3H).

Example 381

(3-Chloro-4-trifluoromethyl-phenyl)-[2-morpholin-4-yl-7-(3-trifluoromethyl-pyridin-2-yl)-6,7,8,9-tetrahydro-5H-pyrimido[4,5-d]azepin-4-yl]-amine

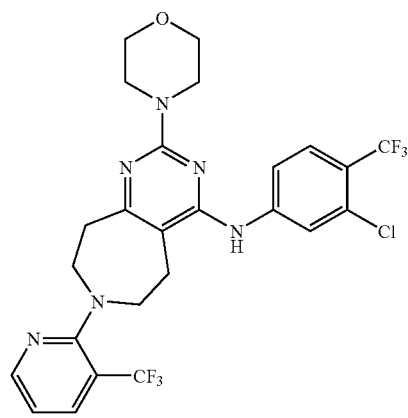 [SMILES: FC(F)(F)c1ccc(Nc2nc(N3CCOCC3)nc3c2CCN(c2ncccc2C(F)(F)F)CC3)cc1Cl]

MS: mass calcd. for $C_{25}H_{23}ClF_6N_6O$, 572.1526; m/z found, 573.2 [M+H]$^+$. $^1$H NMR (CDCl$_3$): 8.42-8.39 (m, 1H), 8.00 (d, J=2.0 Hz, 1H), 7.89 (dd, J=1.8, 7.8 Hz, 1H), 7.61 (d, J=8.6 Hz, 1H), 7.38-7.35 (m, 1H), 7.00-6.95 (m, 1H), 6.55 (s, 1H), 3.83-3.74 (m, 8H), 3.63-3.55 (m, 4H), 3.14-3.08 (m, 2H), 2.92-2.87 (m, 2H).

Example 382

2-Methyl-2-{4-[2-morpholin-4-yl-7-(3-trifluoromethyl-pyridin-2-yl)-6,7,8,9-tetrahydro-5H-pyrimido[4,5-d]azepin-4-ylamino]-phenyl}-propionitrile

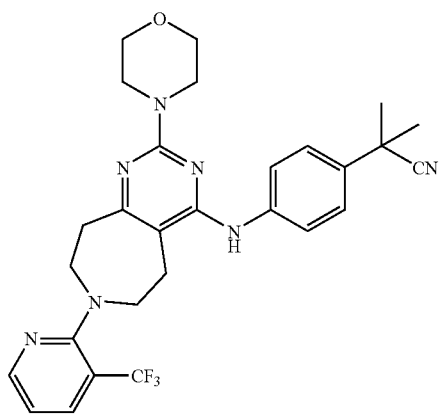 [SMILES: CC(C)(C#N)c1ccc(Nc2nc(N3CCOCC3)nc3c2CCN(c2ncccc2C(F)(F)F)CC3)cc1]

MS: mass calcd. for $C_{28}H_{30}F_3N_7O$, 537.2464; m/z found, 538.2 [M+H]$^+$. $^1$H NMR (CDCl$_3$): 8.40-8.36 (m, 1H), 7.87 (dd, J=1.8, 7.8 Hz, 1H), 7.58-7.52 (m, 2H), 7.44-7.39 (m, 2H), 6.97-6.90 (m, 1H), 6.42 (s, 1H), 3.81-3.69 (m, 8H), 3.64-3.53 (m, 4H), 3.11-3.05 (m, 2H), 2.90-2.84 (m, 2H), 1.73 (s, 6H).

Example 383

2-Methyl-2-{4-[2-piperidin-1-yl-7-(3-trifluoromethyl-pyridin-2-yl)-6,7,8,9-tetrahydro-5H-pyrimido[4,5-d]azepin-4-ylamino]-phenyl}-propan-1-ol

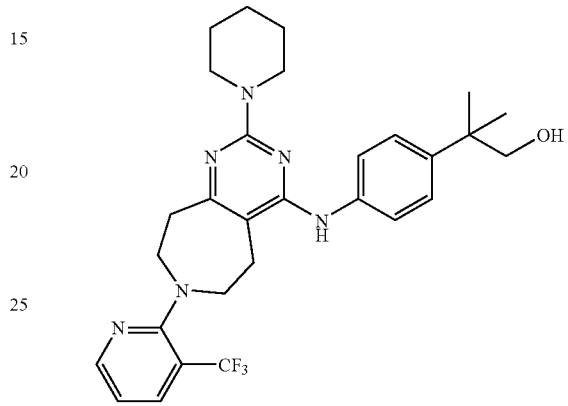

MS: mass calcd. for $C_{29}H_{35}F_3N_6O$, 540.2825; m/z found, 541.3 [M+H]$^+$. $^1$H NMR (CDCl$_3$): 8.43-8.36 (m, 1H), 7.87 (dd, J=1.8, 7.8 Hz, 1H), 7.58-7.53 (m, 2H), 7.36-7.32 (m, 2H), 6.96-6.91 (m, 1H), 6.35 (s, 1H), 3.78-3.72 (m, 4H), 3.65-3.56 (m, 6H), 3.11-3.05 (m, 2H), 2.89-2.83 (m, 2H), 1.71-1.58 (m, 6H), 1.36 (s, 6H).

Example 384

2-Methyl-2-{4-[2-piperidin-1-yl-7-(3-trifluoromethyl-pyridin-2-yl)-6,7,8,9-tetrahydro-5H-pyrimido[4,5-d]azepin-4-ylamino]-phenyl}-propionitrile

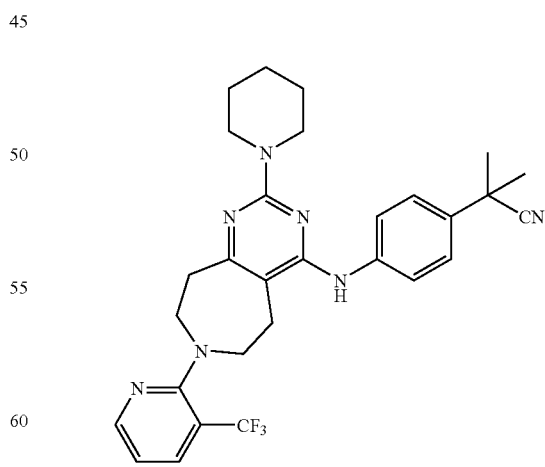

MS: mass calcd. for $C_{29}H_{32}F_3N_7$, 535.2672; m/z found, 536.3 [M+H]$^+$. $^1$H NMR (CDCl$_3$): 8.42-8.36 (m, 1H), 7.88 (dd, J=1.8, 7.8 Hz, 1H), 7.62-7.57 (m, 2H), 7.44-7.40 (m, 2H), 6.96-6.92 (m, 1H), 6.40 (s, 1H), 3.78-3.72 (m, 4H), 3.65-3.54 (m, 4H), 3.11-3.06 (m, 2H), 2.89-2.84 (m, 2H), 1.75 (s, 6H), 1.71-1.58 (m, 6H).

Example 385

2-Fluoro-4-[2-piperidin-1-yl-7-(3-trifluoromethyl-pyridin-2-yl)-6,7,8,9-tetrahydro-5H-pyrimido[4,5-d]azepin-4-ylamino]-benzoic acid methyl ester

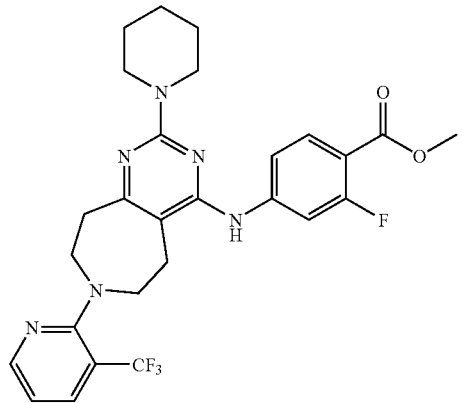 [SMILES: COC(=O)c1ccc(Nc2nc(N3CCCCC3)nc3c2CCN(c2ncccc2C(F)(F)F)CC3)cc1F]

MS: mass calcd. for $C_{27}H_{28}F_4N_6O_2$, 544.221; m/z found, 545.2 [M+H]$^+$. $^1$H NMR (CDCl$_3$): 8.43-8.37 (m, 1H), 7.93-7.86 (m, 2H), 7.75 (dd, J=2.1, 14.0 Hz, 1H), 7.14 (dd, J=2.1, 8.7 Hz, 1H), 6.98-6.94 (m, 1H), 6.60 (s, 1H), 3.93 (s, 3H), 3.79-3.75 (m, 4H), 3.61-3.55 (m, 4H), 3.13-3.06 (m, 2H), 2.90-2.85 (m, 2H), 1.73-1.59 (m, 6H).

Example 386

(6-Methoxy-5-trifluoromethyl-pyridin-2-yl)-[2-piperidin-1-yl-7-(3-trifluoromethyl-pyridin-2-yl)-6,7,8,9-tetrahydro-5H-pyrimido[4,5-d]azepin-4-yl]-amine

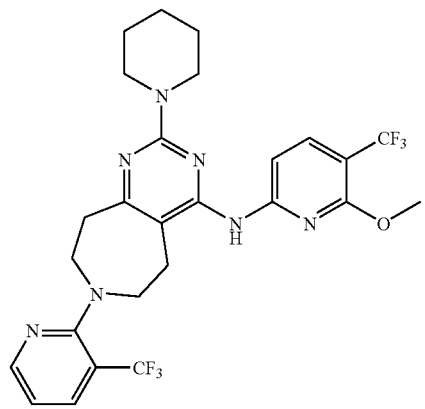 [SMILES: COc1nc(Nc2nc(N3CCCCC3)nc3c2CCN(c2ncccc2C(F)(F)F)CC3)ccc1C(F)(F)F]

MS: mass calcd. for $C_{26}H_{27}F_6N_7O$, 567.2181; m/z found, 568.2 [M+H]$^+$. $^1$H NMR (CDCl$_3$): 8.43-8.39 (m, 1H), 7.93-7.87 (m, 2H), 7.83 (d, J=8;5 Hz, 1H), 7.16 (s, 1H), 6.98-6.94

(m, 1H), 4.00 (s, 3H), 3.81-3.75 (m, 4H), 3.65-3.55 (m, 4H), 3.14-3.09 (m, 2H), 2.96-2.92 (m, 2H), 1.73-1.60 (m, 6H).

Example 387

4-[2-Piperidin-1-yl-7-(3-trifluoromethyl-pyridin-2-yl)-6,7,8,9-tetrahydro-5H-pyrimido[4,5-d]azepin-4-ylamino]-benzoic acid methyl-ester

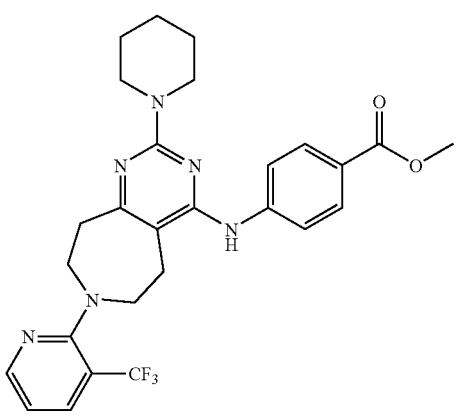 [SMILES: COC(=O)c1ccc(Nc2nc(N3CCCCC3)nc3c2CCN(c2ncccc2C(F)(F)F)CC3)cc1]

MS: mass calcd. for $C_{27}H_{29}F_3N_6O_2$, 526.2304; m/z found, 527.2 [M+H]$^+$. $^1$H NMR (CDCl$_3$): 8.41-8.39 (m, 1H), 8.04-7.99 (m, 2H), 7.88 (dd, J=1.8, 7.8 Hz, 1H), 7.67-7.60 (m, 2H), 6.97-6.92 (m, 1H), 6.56 (s, 1H), 3.92 (s, 3H), 3.79-3.73 (m, 4H), 3.63-3.55 (m, 4H), 3.12-3.07 (m, 2H), 2.91-2.86 (m, 2H), 1.71-1.58 (m, 6H).

Example 388

4-[2-Piperidin-1-yl-7-(3-trifluoromethyl-pyridin-2-yl)-6,7,8,9-tetrahydro-5H-pyrimido[4,5-d]azepin-4-ylamino]-benzoic acid

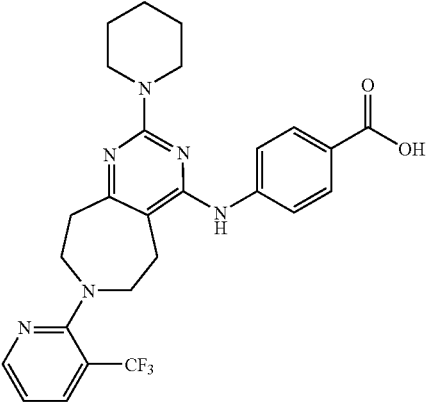 [SMILES: O=C(O)c1ccc(Nc2nc(N3CCCCC3)nc3c2CCN(c2ncccc2C(F)(F)F)CC3)cc1]

MS: mass calcd. for $C_{26}H_{27}F_3N_6O_2$, 512.2148; m/z found, 513.2 [M+H]$^+$. $^1$H NMR (CD$_3$OD): 8.47-8.42 (m, 1H), 8.03-8.00 (m, 1H), 7.93-7.88 (m, 2H), 7.62-7.58 (m, 2H), 7.14-

7.09 (m, 1H), 3.76-3.69 (m, 4H), 3.49-3.44 (m, 4H), 3.07-3.03 (m, 2H), 3.02-2.97 (m, 2H), 1.72-1.65 (m, 2H), 1.63-1.55 (m, 4H).

Example 389

2-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-propan-2-ol

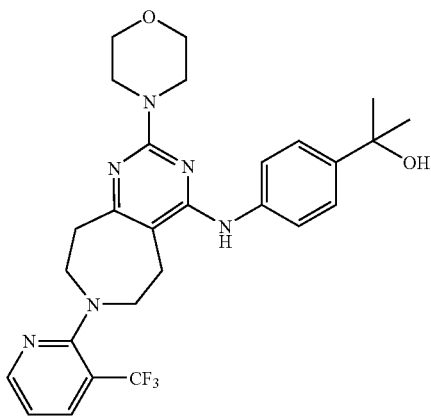 [SMILES: CC(C)(O)c1ccc(Nc2nc(N3CCOCC3)nc3c2CCN(c2ncccc2C(F)(F)F)CC3)cc1]

MS: mass calcd. for $C_{27}H_{31}F_3N_6O_2$, 528.246; m/z found, 529.2 [M+H]$^+$. $^1$H NMR (CDCl$_3$): 8.42-8.38 (m, 1H), 7.88 (dd, J=1.8, 7.8 Hz, 1H), 7.53-7.49 (m, 2H), 7.48-7.44 (m, 2H), 6.97-6.93 (m, 1H), 6.40 (s, 1H), 3.82-3.72 (m, 8H), 3.67-3.56 (m, 4H), 3.12-3.07 (m, 2H), 2.90-2.86 (m, 2H), 1.62 (s, 6H).

Example 390

(6-Chloro-5-trifluoromethyl-pyridin-2-yl)-[2-piperidin-1-yl-7-(3-trifluoromethyl-pyridin-2-yl)-6,7,8,9-tetrahydro-5H-pyrimido[4,5-d]azepin-4-yl]-amine

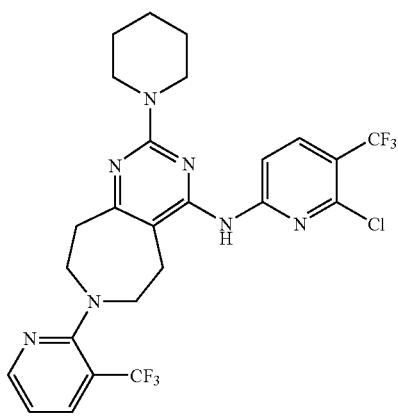 [SMILES: FC(F)(F)c1ccc(Nc2nc(N3CCCCC3)nc3c2CCN(c2ncccc2C(F)(F)F)CC3)nc1Cl]

MS: mass calcd. for $C_{25}H_{24}ClF_6N_7$, 571.1686; m/z found, 572.2 [M+H]$^+$. $^1$H NMR (CDCl$_3$): 8.44-8.39 (m, 1H), 8.34 (d, J=8.7 Hz, 1H), 7.95 (d, J=8.7 Hz, 1H), 7.89 (dd, J=1.8, 7.8 Hz, 1H), 7.43 (s, 1H), 7.00-6.95 (m, 1H), 3.81-3.73 (m, 4H), 3.57-3.52 (m, 4H), 3.13-3.09 (m, 2H), 2.94-2.90 (m, 2H), 1.74-1.59 (m, 6H).

Example 391

2-{2-Fluoro-4-[2-piperidin-1-yl-7-(3-trifluoromethyl-pyridin-2-yl)-6,7,8,9-tetrahydro-5H-pyrimido[4,5-d]azepin-4-ylamino]-phenyl}-propan-2-ol

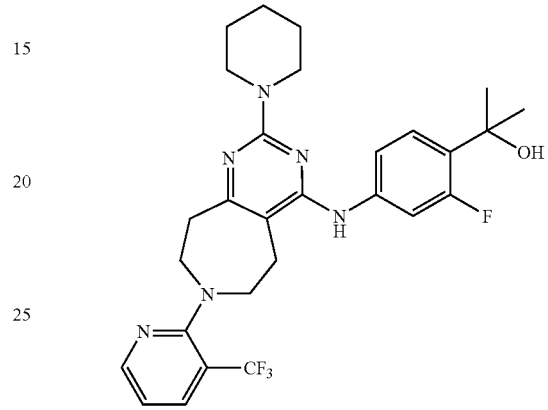

MS: mass calcd. for $C_{28}H_{32}F_4N_6O$, 544.2574; m/z found, 545.3 [M+H]$^+$. $^1$H NMR (CDCl$_3$): 8.41-8.35 (m, 1H), 7.86 (dd, J=1.8, 7.8 Hz, 1H), 7.61 (dd, J=2.2, 14.9 Hz, 1H), 7.45-7.40 (m, 1H), 7.08 (dd, J=2.2, 8.5 Hz, 1H), 6.95-6.90 (m, 1H), 6.38 (s, 1H), 3.78-3.71 (m, 4H), 3.62-3.53 (m, 4H), 3.10-3.03 (m, 2H), 2.87-2.80 (m, 2H), 2.09 (d, J=3.5 Hz, 1H), 1.69-1.57 (m, 12H).

Example 392

2-Methyl-2-{4-[2-morpholin-4-yl-7-(3-trifluoromethyl-pyridin-2-yl)-6,7,8,9-tetrahydro-5H-pyrimido[4,5-d]azepin-4-ylamino]-phenyl}-propionic acid

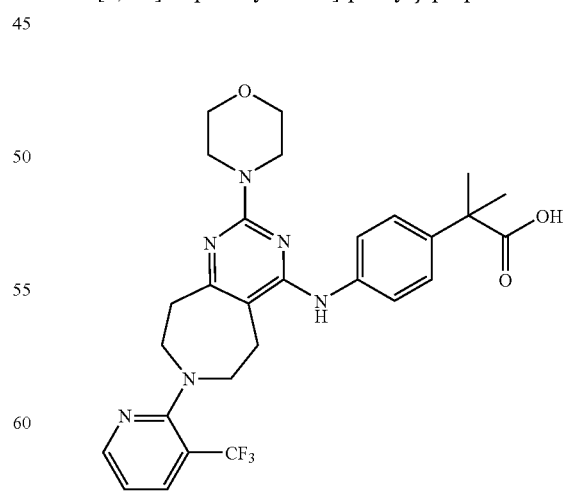

MS: mass calcd. for $C_{28}H_{31}F_3N_6O_3$, 556.241; m/z found, 557.2 [M+H]$^+$. $^1$H NMR (CDCl$_3$): 8.46-8.42 (m, 1H), 8.02 (dd, J=1.8, 7.8 Hz, 1H), 7.55-7.51 (m, 2H), 7.35-7.32 (m, 2H), 7.13-7.10 (m, 1H), 3.76-3.65 (m, 8H), 3.49-3.44 (m, 4H), 3.08-3.03 (m, 2H), 3.01-2.97 (m, 2H), 1.55 (s, 6H).

Example 393

5-Chloro-6-[2-piperidin-1-yl-4-(4-trifluoromethyl-phenylamino)-5,6,8,9-tetrahydro-pyrimido[4,5-d]azepin-7-yl]-nicotinic acid methyl ester

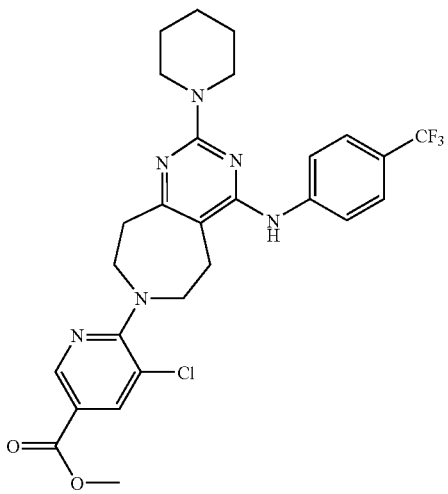 [SMILES: COC(=O)c1cnc(N2CCc3nc(N4CCCCC4)nc(Nc4ccc(C(F)(F)F)cc4)c3CC2)c(Cl)c1]

MS: mass calcd. for $C_{27}H_{28}ClF_3N_6O_2$, 560.1914; m/z found, 561.2 [M+H]$^+$. $^1$H NMR (CDCl$_3$): 8.77-8.62 (m, 1H), 8.38-7.86 (m, 1H), 7.73-7.63 (m, 2H), 7.61-7.55 (m, 1H), 7.35-7.28 (m, 1H), 6.62-6.37 (m, 1H), 4.03-3.79 (m, 7H), 3.80-3.70 (m, 4H), 3.21-3.04 (m, 2H), 2.98-2.88 (m, 2H), 1.74-1.61 (m, 6H).

Example 394

{5-Chloro-6-[2-piperidin-1-yl-4-(4-trifluoromethyl-phenylamino)-5,6,8,9-tetrahydro-pyrimido[4,5-d]azepin-7-yl]-pyridin-3-yl}-methanol

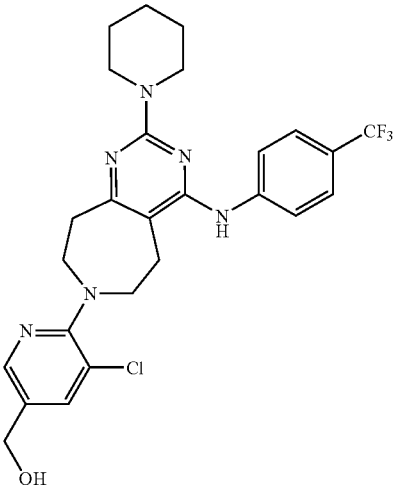 [SMILES: OCc1cnc(N2CCc3nc(N4CCCCC4)nc(Nc4ccc(C(F)(F)F)cc4)c3CC2)c(Cl)c1]

MS: mass calcd. for $C_{26}H_{28}ClF_3N_6O$, 532.1965; m/z found, 533.2 [M+H]$^+$. $^1$H NMR ((CD$_3$)$_2$CO): 8.20-8.09 (m, 2H), 7.96-7.88 (m, 2H), 7.71 (d, J=2.0 Hz, 1H), 7.61 (d, J=8.7 Hz, 2H), 4.66-4.48 (m, 2H), 3.84-3.69 (m, 4H), 3.60-3.47 (m, 4H), 3.13-2.97 (m, 4H), 1.75-1.49 (m, 6H).

The compounds in Examples 395-518 are prepared using methods analogous to those described in the preceding examples.

| Example | Chemical Name |
|---|---|
| 395 | $N^2,N^2$-Dimethyl-$N^6$-[2-piperidin-1-yl-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 396 | 2-{4-[2-Isopropyl-7-(3-trifluoromethyl-pyridin-2-yl)-6,7,8,9-tetrahydro-5H-pyrimido[4,5-d]azepin-4-ylamino]-phenyl}-N-methyl-isobutyramide |
| 397 | [2-Morpholin-4-yl-7-(3-trifluoromethyl-pyridin-2-yl)-6,7,8,9-tetrahydro-5H-pyrimido[4,5-d]azepin-4-yl]-[4-(piperazine-1-sulfonyl)-phenyl]-amine |
| 398 | (4-Methanesulfonyl-phenyl)-[2-morpholin-4-yl-7-(3-trifluoromethyl-pyridin-2-yl)-6,7,8,9-tetrahydro-5H-pyrimido[4,5-d]azepin-4-yl]-amine |
| 399 | [4-(2-Amino-1,1-dimethyl-ethyl)-phenyl]-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 400 | [2-Morpholin-4-yl-7-(3-trifluoromethyl-pyridin-2-yl)-6,7,8,9-tetrahydro-5H-pyrimido[4,5-d]azepin-4-yl]-(4-trifluoromethanesulfonyl-phenyl)-amine |
| 401 | 1,1,1-Trifluoro-2-{4-[2-morpholin-4-yl-7-(3-trifluoromethyl-pyridin-2-yl)-6,7,8,9-tetrahydro-5H-pyrimido[4,5-d]azepin-4-ylamino]-phenyl}-propan-2-ol |
| 402 | 2-{2-Fluoro-4-[2-morpholin-4-yl-7-(3-trifluoromethyl-pyridin-2-yl)-6,7,8,9-tetrahydro-5H-pyrimido[4,5-d]azepin-4-ylamino]-phenyl}-propan-2-ol |
| 403 | 2-Methyl-2-{4-[2-morpholin-4-yl-7-(3-trifluoromethyl-pyridin-2-yl)-6,7,8,9-tetrahydro-5H-pyrimido[4,5-d]azepin-4-ylamino]-phenyl}-propan-1-ol |
| 404 | [4-(2-Amino-1,1-dimethyl-ethyl)-phenyl]-[2-morpholin-4-yl-7-(3-trifluoromethyl-pyridin-2-yl)-6,7,8,9-tetrahydro-5H-pyrimido[4,5-d]azepin-4-yl]-amine |
| 405 | $N^6$-[2-Isopropyl-7-(3-trifluoromethyl-pyridin-2-yl)-6,7,8,9-tetrahydro-5H-pyrimido[4,5-d]azepin-4-yl]-$N^2$-methyl-3-trifluoromethyl-pyridine-2,6-diamine |
| 406 | 2-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-isobutyramide |
| 407 | $N^6$-[2-Isopropyl-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |

| Example | Chemical Name |
|---|---|
| 408 | [2-Morpholin-4-yl-7-(3-trifluoromethyl-pyridin-2-yl)-6,7,8,9-tetrahydro-5H-pyrimido[4,5-d]azepin-4-yl]-(6-trifluoromethyl-pyridin-3-yl)-amine |
| 409 | 2-{4-[2-(2-Methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-isobutyramide |
| 410 | (3-Fluoro-4-trifluoromethyl-phenyl)-[2-morpholin-4-yl-7-(3-trifluoromethyl-pyridin-2-yl)-6,7,8,9-tetrahydro-5H-pyrimido[4,5-d]azepin-4-yl]-amine |
| 411 | 1-{4-[2-Isopropyl-7-(3-trifluoromethyl-pyridin-2-yl)-6,7,8,9-tetrahydro-5H-pyrimido[4,5-d]azepin-4-ylamino]-phenyl}-cyclopropanecarboxylic acid methyl ester |
| 412 | [2-(2-Methyl-pyrrolidin-1-yl)-7-(3-trifluoromethyl-pyridin-2-yl)-6,7,8,9-tetrahydro-5H-pyrimido[4,5-d]azepin-4-yl]-[4-(morpholine-4-sulfonyl)-phenyl]-amine |
| 413 | 1-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid dimethylamide |
| 414 | [4-(2-Dimethylamino-1,1-dimethyl-ethyl)-phenyl]-[2-piperidin-1-yl-7-(3-trifluoromethyl-pyridin-2-yl)-6,7,8,9-tetrahydro-5H-pyrimido[4,5-d]azepin-4-yl]-amine |
| 415 | 2-{4-[2-Isopropyl-7-(3-trifluoromethyl-pyridin-2-yl)-6,7,8,9-tetrahydro-5H-pyrimido[4,5-d]azepin-4-ylamino]-phenyl}-isobutyramide |
| 416 | $N^6$-[2-Piperidin-1-yl-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 417 | (6-Chloro-5-trifluoromethyl-pyridin-2-yl)-[2-morpholin-4-yl-7-(3-trifluoromethyl-pyridin-2-yl)-6,7,8,9-tetrahydro-5H-pyrimido[4,5-d]azepin-4-yl]-amine |
| 418 | [2-Morpholin-4-yl-7-(3-trifluoromethyl-pyridin-2-yl)-6,7,8,9-tetrahydro-5H-pyrimido[4,5-d]azepine-4-yl]-(4-trifluoromethoxy-phenyl)-amine |
| 419 | [4-(1,1-Dimethyl-2-methylamino-ethyl)-phenyl]-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 420 | (4-Bromo-phenyl)-[2-morpholin-4-yl-7-(3-trifluoromethyl-pyridin-2-yl)-6,7,8,9-tetrahydro-5H-pyrimido[4,5-d]azepin-4-yl]-amine |
| 421 | (4-Chloro-phenyl)-[2-morpholin-4-yl-7-(3-trifluoromethyl-pyridin-2-yl)-6,7,8,9-tetrahydro-5H-pyrimido[4,5-d]azepin-4-yl]-amine |
| 422 | (1-Methyl-1,2,3,4-tetrahydro-quinolin-7-yl)-[2-morpholin-4-yl-7-(3-trifluoromethyl-pyridin-2-yl)-6,7,8,9-tetrahydro-5H-pyrimido[4,5-d]azepin-4-yl]-amine |
| 423 | [2-Morpholin-4-yl-7-(3-trifluoromethyl-pyridin-2-yl)-6,7,8,9-tetrahydro-5H-pyrimido[4,5-d]azepin-4-yl]-(1,4,4-trimethyl-1,2,3,4-tetrahydro-quinolin-7-yl)-amine |
| 424 | 2-Methyl-2-{4-[2-(2-methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-propionitrile |
| 425 | 4-[2-Morpholin-4-yl-7-(3-trifluoromethyl-pyridin-2-yl)-6,7,8,9-tetrahydro-5H-pyrimido[4,5-d]azepin-4-ylamino]-benzoic acid methyl ester |
| 426 | 4-[2-Morpholin-4-yl-7-(3-trifluoromethyl-pyridin-2-yl)-6,7,8,9-tetrahydro-5H-pyrimido[4,5-d]azepin-4-ylamino]-benzoic acid |
| 427 | $N^2$-Methyl-$N^6$-[2-piperidin-1-yl-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 428 | 2-Fluoro-4-[2-morpholin-4-yl-7-(3-trifluoromethyl-pyridin-2-yl)-6,7,8,9-tetrahydro-5H-pyrimido[4,5-d]azepin-4-ylamino]-benzoic acid methyl ester |
| 429 | 2-Fluoro-4-[2-morpholin-4-yl-7-(3-trifluoromethyl-pyridin-2-yl)-6,7,8,9-tetrahydro-5H-pyrimido[4,5-d]azepin-4-ylamino]-benzoic acid |
| 430 | 1-{4-[2-Piperidin-1-yl-7-(3-trifluoromethyl-pyridin-2-yl)-6,7,8,9-tetrahydro-5H-pyrimido[4,5-d]azepin-4-ylamino]-phenyl}-cyclopropanol |
| 431 | [4-(2-Dimethylamino-1,1-dimethyl-ethyl)-phenyl]-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 432 | N,N-Dimethyl-2-{4-[2-(2-methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-isobutyramide |
| 433 | 1-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid methyl ester |
| 434 | (6-Chloro-5-trifluoromethyl-pyridin-2-yl)-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 435 | 1-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid |
| 436 | (1-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-cyclopropyl)-methanol |
| 437 | [4-(1-Dimethylaminomethyl-cyclopropyl)-phenyl]-[2-piperidin-1-yl-7-(3-trifluoromethyl-pyridin-2-yl)-6,7,8,9-tetrahydro-5H-pyrimido[4,5-d]azepin-4-yl]-amine |

-continued

| Example | Chemical Name |
|---|---|
| 438 | [4-(1-Aminomethyl-cyclopropyl)-phenyl]-[2-morpholin-4-yl-7-(3-trifluoromethyl-pyridin-2-yl)-6,7,8,9-tetrahydro-5H-pyrimido[4,5-d]azepin-4-yl]-amine |
| 439 | 1-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid amide |
| 440 | 1-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid methylamide |
| 441 | N-Methyl-2-{4-[2-morpholin-4-yl-7-(3-trifluoromethyl-pyridin-2-yl)-6,7,8,9-tetrahydro-5H-pyrimido[4,5-d]azepin-4-ylamino]-phenyl}-isobutyramide |
| 442 | N,N-Dimethyl-2-{4-[2-morpholin-4-yl-7-(3-trifluoromethyl-pyridin-2-yl)-6,7,8,9-tetrahydro-5H-pyrimido[4,5-d]azepin-4-ylamino]-phenyl}-isobutyramide |
| 443 | [4-(2-Dimethylamino-1,1-dimethyl-ethyl)-phenyl]-[2-morpholin-4-yl-7-(3-trifluoromethyl-pyridin-2-yl)-6,7,8,9-tetrahydro-5H-pyrimido[4,5-d]azepin-4-yl]-amine |
| 444 | [4-(1,1-Dimethyl-2-methylamino-ethyl)-phenyl]-[2-morpholin-4-yl-7-(3-trifluoromethyl-pyridin-2-yl)-6,7,8,9-tetrahydro-5H-pyrimido[4,5-d]azepin-4-yl]-amine |
| 445 | $N^6$-[2-Morpholin-4-yl-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 446 | $N^2$-Methyl-$N^6$-[2-morpholin-4-yl-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 447 | $N^2,N^2$-Dimethyl-$N^6$-[2-morpholin-4-yl-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 448 | [2-(2-Methyl-pyrrolidin-1-yl)-7-(3-trifluoromethyl-pyridin-2-yl)-6,7,8,9-tetrahydro-5H-pyrimido[4,5-d]azepin-4-yl]-[4-(piperazine-1-sulfonyl)-phenyl]-amine |
| 449 | [2-Isopropyl-7-(3-trifluoromethyl-pyridin-2-yl)-6,7,8,9-tetrahydro-5H-pyrimido[4,5-d]azepin-4-yl]-[4-(morpholine-4-sulfonyl)-phenyl]-amine |
| 450 | [2-Isopropyl-7-(3-trifluoromethyl-pyridin-2-yl)-6,7,8,9-tetrahydro-5H-pyrimido[4,5-d]azepin-4-yl]-[4-(piperazine-1-sulfonyl)-phenyl]-amine |
| 451 | [4-(Morpholine-4-sulfonyl)-phenyl]-[2-piperidin-1-yl-7-(3-trifluoromethyl-pyridin-2-yl)-6,7,8,9-tetrahydro-5H-pyrimido[4,5-d]azepin-4-yl]-amine |
| 452 | [4-(Piperazine-1-sulfonyl)-phenyl]-[2-piperidin-1-yl-7-(3-trifluoromethyl-pyridin-2-yl)-6,7,8,9-tetrahydro-5H-pyrimido[4,5-d]azepin-4-yl]-amine |
| 453 | $N^6$-[2-Isopropyl-7-(3-trifluoromethyl-pyridin-2-yl)-6,7,8,9-tetrahydro-5H-pyrimido[4,5-d]azepin-4-yl]-$N^2,N^2$-dimethyl-3-trifluoromethyl-pyridine-2,6-diamine |
| 454 | $N^6$-[2-(2-Methyl-pyrrolidin-1-yl)-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 455 | [4-(1-Methylaminomethyl-cyclopropyl)-phenyl]-[2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 456 | $N^2$-Methyl-$N^6$-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 457 | $N^2,N^2$-Dimethyl-$N^6$-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-3-trifluoromethyl-pyridine-2,6-diamine |
| 458 | 1,1,1-Trifluoro-2-{4-[2-(2-methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-propan-2-ol |
| 459 | [4-(2-Amino-1,1-dimethyl-ethyl)-phenyl]-[2-piperidin-1-yl-7-(3-trifluoromethyl-pyridin-2-yl)-6,7,8,9-tetrahydro-5H-pyrimido[4,5-d]azepin-4-yl]-amine |
| 460 | [2-(2-Methyl-pyrrolidin-1-yl)-7-(3-trifluoromethyl-pyridin-2-yl)-6,7,8,9-tetrahydro-5H-pyrimido[4,5-d]azepin-4-yl]-(5-trifluoromethyl-pyrazin-2-yl)-amine |
| 461 | (6-Methoxy-5-trifluoromethyl-pyridin-2-yl)-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 462 | 2-{2-Fluoro-4-[2-(2-methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-propan-2-ol |
| 463 | 2-Fluoro-4-[2-(2-methyl-pyrrolidin-1-yl)-7-(3-trifluoromethyl-pyridin-2-yl)-6,7,8,9-tetrahydro-5H-pyrimido[4,5-d]azepin-4-ylamino]-benzoic acid |
| 464 | 2-Fluoro-4-[2-(2-methyl-pyrrolidin-1-yl)-7-(3-trifluoromethyl-pyridin-2-yl)-6,7,8,9-tetrahydro-5H-pyrimido[4,5-d]azepin-4-ylamino]-benzoic acid methyl ester |
| 465 | (3-Fluoro-4-trifluoromethyl-phenyl)-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |

-continued

| Example | Chemical Name |
|---|---|
| 466 | 2-{4-[2-Piperidin-1-yl-7-(3-trifluoromethyl-pyridin-2-yl)-6,7,8,9-tetrahydro-5H-pyrimido[4,5-d]azepin-4-ylamino]-phenyl}-isobutyramide |
| 467 | N-Methyl-2-{4-[2-piperidin-1-yl-7-(3-trifluoromethyl-pyridin-2-yl)-6,7,8,9-tetrahydro-5H-pyrimido[4,5-d]azepin-4-ylamino]-phenyl}-isobutyramide |
| 468 | N,N-Dimethyl-2-{4-[2-piperidin-1-yl-7-(3-trifluoromethyl-pyridin-2-yl)-6,7,8,9-tetrahydro-5H-pyrimido[4,5-d]azepin-4-ylamino]-phenyl}-isobutyramide |
| 469 | 2-{2-Fluoro-4-[2-isopropyl-7-(3-trifluoromethyl-pyridin-2-yl)-6,7,8,9-tetrahydro-5H-pyrimido[4,5-d]azepin-4-ylamino]-phenyl}propan-2-ol |
| 470 | 2-Fluoro-4-[2-isopropyl-7-(3-trifluoromethyl-pyridin-2-yl)-6,7,8,9-tetrahydro-5H-pyrimido[4,5-d]azepin-4-ylamino]-benzoic acid |
| 471 | 2-Fluoro-4-[2-isopropyl-7-(3-trifluoromethyl-pyridin-2-yl)-6,7,8,9-tetrahydro-5H-pyrimido[4,5-d]azepin-4-ylamino]-benzoic acid methyl ester |
| 472 | 2-{4-[2-Isopropyl-7-(3-trifluoromethyl-pyridin-2-yl)-6,7,8,9-tetrahydro-5H-pyrimido[4,5-d]azepin-4-ylamino]-phenyl}-N,N-dimethyl-isobutyramide |
| 473 | N-Methyl-2-{4-[2-(2-methyl-pyrrolidin-yl)-7-(3-trifluoromethyl-pyridin-2-yl)-6,7,8,9-tetrahydro-5H-pyrimido[4,5-d]azepin-4-ylamino]-phenyl}-isobutyramide |
| 474 | (6-Methoxy-5-trifluoromethyl-pyridin-2-yl)-[2-morpholin-4-yl-7-(3-trifluoromethyl-pyridin-2-yl)-6,7,8,9-tetrahydro-5H-pyrimido[4,5-d]azepin-4-yl]-amine |
| 475 | (4-Bromo-phenyl)-[2-piperidin-1-yl-7-(3-trifluoromethyl-pyridin-2-yl)-6,7,8,9-tetrahydro-5H-pyrimido[4,5-d]azepin-4-yl]-amine |
| 476 | [2-Piperidin-1-yl-7-(3-trifluoromethyl-pyridin-2-yl)-6,7,8,9-tetrahydro-5H-pyrimido[4,5-d]azepin-4-yl]-(4-trifluoromethoxy-phenyl)-amine |
| 477 | [2-(2-Methyl-pyrrolidin-1-yl)-7-(3-trifluoromethyl-pyridin-2-yl)-6,7,8,9-tetrahydro-5H-pyrimido[4,5-d]azepin-4-yl-]-(4-trifluoromethoxy-phenyl)-amine |
| 478 | [2-Morpholin-4-yl-7-(3-trifluoromethyl-pyridin-2-yl)-6,7,8,9-tetrahydro-5H-pyrimido[4,5-d]azepin-4-yl-]-(5-trifluoromethyl-pyrazin-2-yl)-amine |
| 479 | 1-{4-[2-Isopropyl-7-(3-trifluoromethyl-pyridin-2-yl)-6,7,8,9-tetrahydro-5H-pyrimido[4,5-d]azepin-4-ylamino]-phenyl}-cyclopropanecarboxylic acid methylamide |
| 480 | 1-{4-[2-Morpholin-4-yl-7-(3-trifluoromethyl-pyridin-2-yl)-6,7,8,9-tetrahydro-5H-pyrimido[4,5-d]azepin-4-ylamino]-phenyl}-cyclopropanol |
| 481 | 1-{4-[2-Piperidin-1-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid amide |
| 482 | (4-Bromo-phenyl)-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 483 | (4-Methanesulfonyl-phenyl)-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 484 | (1-{4-[2-Piperidin-1-yl-7-(3-trifluoromethyl-pyridin-2-yl)-6,7,8,9-tetrahydro-5H-pyrimido[4,5-d]azepin-4-ylamino]-phenyl}cyclopropyl)-methanol |
| 485 | [2-(2-Methyl-pyrrolidin-1-yl)-7-(3-trifluoromethyl-pyridin-2-yl)-6,7,8,9-tetrahydro-5H-pyrimido[4,5-d]azepin-4-yl]-(4-trifluoromethanesulfonyl-phenyl)-amine |
| 486 | [4-(2-Dimethylamino-1,1-dimethyl-ethyl)-phenyl]-[2-isopropyl-7-(3-trifluoromethyl-pyridin-2-yl)-6,7,8,9-tetrahydro-5H-pyrimido[4,5-d]azepin-4-yl]amine |
| 487 | [4-(1,1-Dimethyl-2-methylamino-ethyl)-phenyl]-[2-isopropyl-7-(3-trifluoromethyl-pyridin-2-yl)-6,7,8,9-tetrahydro-5H-pyrimido[4,5-d]azepin-4-yl]-amine |
| 488 | [4-(2-Amino-1,1-dimethyl-ethyl)-phenyl]-[2-isopropyl-7-(3-trifluoromethyl-pyridin-2-yl)-6,7,8,9-tetrahydro-5H-pyrimido[4,5-d]azepin-4-yl]-amine |
| 489 | 2-Methyl-2-{4-[2-(2-methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-propan-1-ol |
| 490 | 1-{4-[2-Isopropyl-7-(3-trifluoromethyl-pyridin-2-yl)-6,7,8,9-tetrahydro-5H-pyrimido[4,5-d]azepin-4-ylamino]-phenyl}-cyclopropanecarboxylic acid |
| 491 | [4-(1,1-Dimethyl-2-methylamino-ethyl)-phenyl]-[2-piperidin-1-yl-7-(3-trifluoromethyl-pyridin-2-yl)-6,7,8,9-tetrahydro-5H-pyrimido[4,5-d]azepin-4-yl]-amine |
| 492 | 1-{4-[2-(2-Methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-cyclopropanecarboxylic acid methylamide |
| 493 | [4-(1-Methylaminomethyl-cyclopropyl)-phenyl]-[2-piperidin-1-yl-7-(3-trifluoromethyl-pyridin-2-yl)-6,7,8,9-tetrahydro-5H-pyrimido[4,5-d]azepin-4-yl]-amine |
| 494 | [4-(1-Aminomethyl-cyclopropyl)-phenyl]-[2-piperidin-1-yl-7-(3-trifluoromethyl-pyridin-2-yl)-6,7,8,9-tetrahydro-5H-pyrimido[4,5-d]azepin-4-yl]-amine |
| 495 | [4-(1-Aminomethyl-cyclopropyl)-phenyl]-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |

| Example | Chemical Name |
|---|---|
| 496 | [4-(1-Dimethylaminomethyl-cyclopropyl)-phenyl]-[2-(2-methyl-pyrrolidin-1-yl)-7-(3-trifluoromethyl-pyridin-2-yl)-6,7,8,9-tetrahydro-5H-pyrimido[4,5-d]azepin-4-yl]-amine |
| 497 | 1-{4-[2-(2-Methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-cyclopropanecarboxylic acid dimethylamide |
| 498 | 1-{4-[2-(2-Methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-cyclopropanecarboxylic acid amide |
| 499 | 1-{4-[2-(2-Methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-cyclopropanecarboxylic acid methyl ester |
| 500 | 1-{4-[2-(2-Methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-cyclopropanecarboxylic acid |
| 501 | [2-Morpholin-4-yl-7-(3-trifluoromethyl-pyridin-2-yl)-6,7,8,9-tetrahydro-5H-pyrimido[4,5-d]azepin-4-yl]-[4-(pyrrolidine-1-sulfonyl)-phenyl]-amine |
| 502 | (1-{4-[2-(2-Methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-cyclopropyl)-methanol |
| 503 | 1-{4-[2-(2-Methyl-pyrrolidin-1-yl)-7-(3-trifluoromethyl-pyridin-2-yl)-6,7,8,9-tetrahydro-5H-pyrimido[4,5-d]azepin-4-ylamino]-phenyl}-cyclopropanol |
| 504 | [2-(2-Methyl-pyrrolidin-1-yl)-7-(3-trifluoromethyl-pyridin-2-yl)-6,7,8,9-tetrahydro-5H-pyrimido[4,5-d]azepin-4-yl]-(1,4,4-trimethyl-1,2,3,4-tetrahydro-quinolin-7-yl)-amine |
| 505 | [2-(2-Methyl-pyrrolidin-1-yl)-7-(3-trifluoromethyl-pyridin-2-yl)-6,7,8,9-tetrahydro-5H-pyrimido[4,5-d]azepin-4-yl]-(1-methyl-1,2,3,4-tetrahydro-quinolin-7-yl)-amine |
| 506 | [2-(2-Methyl-pyrrolidin-1-yl)-7-(3-trifluoromethyl-pyridin-2-yl)-6,7,8,9-tetrahydro-5H-pyrimido[4,5-d]azepin-4-yl]-(6-trifluoromethyl-pyridin-3-yl)-amine |
| 507 | [4-(1-Aminomethyl-cyclopropyl)-phenyl]-[2-isopropyl-7-(3-trifluoromethyl-pyridin-2-yl)-6,7,8,9-tetrahydro-5H-pyrimido[4,5-d]azepin-4-yl]-amine |
| 508 | [2-Isopropyl-7-(3-trifluoromethyl-pyridin-2-yl)-6,7,8,9-tetrahydro-5H-pyrimido[4,5-d]azepin-4-yl]-[4-(1-methylaminomethyl-cyclopropyl)-phenyl]-amine |
| 509 | [4-(1-Dimethylaminomethyl-cyclopropyl)-phenyl]-[2-isopropyl-7-(3-trifluoromethyl-pyridin-2-yl)-6,7,8,9-tetrahydro-5H-pyrimido[4,5-d]azepin-4-yl]-amine |
| 510 | 1-{4-[2-Isopropyl-7-(3-trifluoromethyl-pyridin-2-yl)-6,7,8,9-tetrahydro-5H-pyrimido[4,5-d]azepin-4-ylamino]-phenyl}-cyclopropanecarboxylic acid dimethylamide |
| 511 | 1-{4-[2-Isopropyl-7-(3-trifluoromethyl-pyridin-2-yl)-6,7,8,9-tetrahydro-5H-pyrimido[4,5-d]azepin-4-ylamino]phenyl}-cyclopropanecarboxylic acid amide |
| 512 | (1-{4-[2-Isopropyl-7-(3-trifluoromethyl-pyridin-2-yl)-6,7,8,9-tetrahydro-5H-pyrimido[4,5-d]azepin-4-ylamino]-phenyl}-cyclopropyl)-methanol |
| 513 | 1-{4-[2-Isopropyl-7-(3-trifluoromethyl-pyridin-2-yl)-6,7,8,9-tetrahydro-5H-pyrimido[4,5-d]azepin-4-ylamino]-phenyl}-cyclopropanol |
| 514 | 1-{4-[2-Piperidin-1-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid methyl ester |
| 515 | [4-(Morpholine-4-sulfonyl)-phenyl]-[2-morpholin-4-yl-7-(3-trifluoromethyl-pyridin-2-yl)-6,7,8,9-tetrahydro-5H-pyrimido[4,5-d]azepin-4-yl]-amine |
| 516 | 1-{4-[2-Piperidin-1-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid |
| 517 | 1-{4-[2-Piperidin-1-yl-7-(3-trifluoromethyl-pyridin-2-yl)-6,7,8,9-tetrahydro-5H-pyrimido[4,5-d]azepin-4-ylamino]phenyl}-cyclopropanecarboxylic acid methylamide |
| 518 | 1-{4-[2-Piperidin-1-yl-7-(3-trifluoromethyl-pyridin-2-yl)-6,7,8,9-tetrahydro-5H-pyrimido[4,5-d]azepin-4-ylamino]-phenyl}-cyclopropanecarboxylic acid dimethylamide |

Biological Testing:
Functional Assay: Block of Capsaicin-induced $Ca^{2+}$ Influx
A. Human Assay HEK293 cells were transfected with human TRPV1 cloned in pcDNA3.1zeo(+) using the Effectene non-liposomal lipid based transfection kit (Qiagen) (hTRPV1/HEK293). hTRPV1/HEK293 cells were routinely grown as monolayers under selection in zeocin (200 μg/mL; Invitrogen) in Dulbecco's Modified Eagle Medium (DMEM, Gibco BRL) supplemented with 10% fetal bovine serum, and penicillin/streptomycin (50 units/mL) in 5% $CO_2$ at 37° C. Cells were passaged frequently, every 3-5 days, to avoid overgrowth, depletion of essential medium components, or acidic medium exposure. Cells were passaged using a brief wash in 0.05% trypsin with 1 mM EDTA, followed by dissociation in divalent-free phosphate-buffered saline (Hyclone #SH30028.02). Dissociated cells were seeded onto poly-D-lysine coated black-walled 96-well plates (Biocoat; Becton Dickinson #354640) at about 40,000 cells per well and grown for approximately 1 day in culture medium to near confluency. The assay buffer was composed of 130 mM NaCl 2 mM KCl, 2 mM $MgCl_2$, 10 mM HEPES, 5 mM glucose, and either 2 mM or 20 μM $CaCl_2$. On the day of the experiment, the culture medium was replaced with 2 mM calcium assay buffer using an automated plate washer (ELx405; Biotek, VT). The cells were incubated in 100 µL/well Fluo-3/AM (2 µM; TEFLabs #0116) with Pluronic $F_{127}$ (100 µg/mL; Sigma #P2443) for 1 h at rt in the dark. After loading the cells, the dye solution was replaced with 50 µL/well of 20 µM calcium assay buffer using the ELx405 plate washer. Test compounds (50 µL/well) were added to the plate and incubated for 30 min. Intracellular $Ca^{2+}$ levels were subsequently assayed using a Fluorometric Imaging Plate Reader (FLIPR™ instrument, Molecular Devices, CA) to simultaneously monitor Fluo-3 fluorescence in all wells ($\lambda_{excitation}$=488 nm, $\lambda_{emission}$=540 nm) during challenge with agonist (capsaicin). The $IC_{50}$ values were determined. Cells were challenged with 150 nM capsaicin and the fluorescence counts were captured following agonist addition at a sampling rate of 0.33 Hz. The contents of the wells were mixed 3 times (40 µL mix volume) immediately after the additions were made. Concentration dependence of block was determined by exposing each well of cells in duplicate rows of a 96 well plate to a serial dilution of test compound. The concentration series usually started at 10 µM with a three-fold serial decrement in concentration. The magnitude of the capsaicin response was determined by measuring the change in fluo3 fluorescence before and 100 seconds after the addition of the agonist. Data were analyzed using a non-linear regression program (Origin; OriginLab, MA). Results for the compounds tested in this assay are presented in Table 1. $IC_{50}$ values shown are the average (mean) of the results obtained.

B. Rat Assay

The assay was performed as described above, using HEK293 cells transfected with rat TRPV1 (rTRPV1/HEK293). These cells had a geneticin selection marker and were grown in Dulbecco's Modified Eagle Medium (DMEM, Gibco BRL) supplemented with 10% fetal bovine serum, penicillin/streptomycin (50 units/mL), and 500 µg/mL geneticin 5% $CO_2$ at 37° C. Results for the compounds tested in this assay are also presented in Table 1. $IC_{50}$ values shown are the average (mean) of the results obtained. Where activity is shown as greater than (>) a particular value, the value is the solubility limit of the compound in the assay medium.

TABLE 1

| Ex. | Human $IC_{50}$ (µM) | Rat $IC_{50}$ (µM) |
| --- | --- | --- |
| 1 | 0.029 | 0.090 |
| 1A | 0.016 | 0.049 |
| 2 | 0.072 | 0.79 |
| 2A | 0.075 | 0.42 |
| 3 | 0.019 | 0.095 |
| 4 | 0.20 | 0.50 |
| 5 | 0.060 | 0.15 |
| 5A | 0.042 | 0.19 |
| 6 | 0.0059 | 0.49 |
| 7 | 0.018 | 0.14 |
| 8 | 0.018 | 0.025 |
| 9 | 0.078 | 0.092 |
| 9A | 0.051 | 0.052 |
| 10 | 0.63 | 0.93 |
| 11 | 0.20 | 0.20 |
| 12 | 0.53 | 0.95 |
| 13 | 0.46 | 1.3 |
| 14 | 0.010 | 0.040 |
| 15 | 0.082 | 0.046 |
| 16 | 0.041 | 0.10 |
| 17 | 0.081 | NT |
| 18 | >6.7 | >6.7 |
| 19 | 0.36 | 0.51 |
| 20 | 0.050 | 0.032 |

TABLE 1-continued

| Ex. | Human $IC_{50}$ (µM) | Rat $IC_{50}$ (µM) |
| --- | --- | --- |
| 20A | 0.17 | 0.25 |
| 21 | 0.82 | 1.1 |
| 22 | 0.075 | 0.13 |
| 23 | 0.14 | 0.31 |
| 24 | 0.18 | 0.29 |
| 25 | >6.7 | 0.77 |
| 26 | >6.7 | >6.7 |
| 27 | 5.2 | 10 |
| 28 | >6.7 | >6.7 |
| 29 | 0.70 | 0.34 |
| 30 | 0.51 | 1.3 |
| 31 | 0.39 | 0.53 |
| 32 | 1.74 | 0.013 |
| 33 | 1.1 | 0.11 |
| 34 | 1.5 | 0.36 |
| 35 | 1.5 | 2.4 |
| 36 | 0.17 | 0.37 |
| 37 | 0.41 | 0.15 |
| 38 | 1.1 | 1.4 |
| 39 | 0.0060 | 0.018 |
| 39A | 0.0095 | 0.023 |
| 40 | 0.0037 | 0.056 |
| 40A | 0.0053 | 0.019 |
| 41 | 0.038 | 0.049 |
| 42 | 0.018 | 0.049 |
| 43B | 0.061 | 0.39 |
| 44 | 0.12 | 0.25 |
| 45 | 0.042 | 0.090 |
| 46 | 0.20 | 0.38 |
| 47 | 0.0068 | 0.023 |
| 48 | 0.018 | 0.074 |
| 49 | 0.027 | 0.24 |
| 50B | 0.18 | 0.91 |
| 51 | 0.93 | 1.2 |
| 52 | 0.028 | 0.053 |
| 53 | 0.50 | >6.7 |
| 54 | 0.15 | 0.23 |
| 55B | 0.14 | 0.15 |
| 56B | 0.024 | 0.064 |
| 57B | 3.3 | 5.5 |
| 58B | 0.34 | 1.5 |
| 59B | 0.073 | 0.38 |
| 60B | 0.031 | 0.14 |
| 61B | 0.11 | 0.23 |
| 62 | 0.037 | 0.053 |
| 63B | 0.44 | 2.5 |
| 64 | >6.7 | >6.7 |
| 65B | 0.030 | 0.65 |
| 66B | 0.42 | 0.93 |
| 67B | 0.090 | 0.034 |
| 68B | 3.6 | 3.2 |
| 69 | 0.37 | 0.50 |
| 70B | >20 | 4.4 |
| 71B | >20 | >20 |
| 72B | 0.064 | 0.18 |
| 73B | >20 | 6.7 |
| 74B | >6.7 | 3.9 |
| 75B | NT | 0.040 |
| 76B | 0.090 | 0.091 |
| 77B | 0.66 | 0.58 |
| 78B | 0.69 | 1.8 |
| 79B | NT | 1.3 |
| 80B | 0.065 | 0.13 |
| 81B | NT | 0.97 |
| 82B | NT | 2.8 |
| 83 | 0.62 | 0.99 |
| 84 | NT | >20 |
| 85 | >2.2 | >6.7 |
| 86 | 0.37 | 0.85 |
| 87 | 0.84 | 0.35 |
| 88 | 1.8 | 0.96 |
| 89 | >6.7 | >6.7 |
| 90B | NT | >6.7 |
| 91B | NT | 0.24 |
| 92B | 0.16 | 0.27 |
| 93B | 0.0089 | 0.037 |
| 94B | 0.086 | 0.19 |

TABLE 1-continued

| Ex. | Human IC$_{50}$ (µM) | Rat IC$_{50}$ (µM) |
|---|---|---|
| 95B | 0.062 | 0.082 |
| 96 | 0.28 | 0.34 |
| 97 | 0.55 | 0.49 |
| 98 | >6.7 | >6.7 |
| 99B | 3.3 | 7.2 |
| 100 | 0.022 | 0.031 |
| 101B | >2.2 | 0.99 |
| 102 | 0.046 | 0.17 |
| 103 | 0.37 | 0.34 |
| 104 | 0.47 | 0.32 |
| 105 | 14 | >20 |
| 106 | 0.0054 | 0.062 |
| 107 | >20 | >20 |
| 108 | 1.9 | 0.94 |
| 109 | 0.45 | 0.58 |
| 115 | >6.67 | 3.79 |
| 116 | >20 | 7.03 |
| 117 | >20 | 13.49 |
| 118 | 0.65 | 0.50 |
| 119 | 1.09 | 1.22 |
| 120 | >20 | 12.05 |
| 121 | >20 | >20 |
| 122 | 1.96 | 0.19 |
| 123 | 1.02 | 0.99 |
| 124 | 0.63 | 0.57 |
| 125 | 0.52 | 0.61 |
| 126 | 2.06 | 1.19 |
| 127 | >20 | 19.20 |
| 128 | 0.13 | 0.15 |
| 129 | 0.58 | 0.23 |
| 130 | >20 | >20 |
| 131 | >6.67 | NT |
| 132 | >6.67 | NT |
| 133 | 0.47 | NT |
| 134 | >6.67 | NT |
| 135 | 0.07 | NT |
| 136 | 0.07 | 0.11 |
| 137 | 0.09 | 0.06 |
| 138 | 0.06 | 0.03 |
| 139 | 0.65 | 0.62 |
| 140 | 0.10 | 0.19 |
| 141 | 0.42 | 0.13 |
| 142 | 1.66 | 2.09 |
| 143 | 0.08 | 0.13 |
| 144 | 0.06 | 0.24 |
| 145 | 0.08 | 0.24 |
| 146 | 0.20 | 0.72 |
| 147 | 0.10 | 0.11 |
| 148 | 0.48 | 2.17 |
| 149 | 0.02 | 0.15 |
| 150 | 0.02 | 0.20 |
| 151 | 2.31 | 0.82 |
| 152 | 0.62 | 0.55 |
| 153 | 0.11 | 0.14 |
| 154 | 0.45 | 1.14 |
| 155 | 0.62 | 3.28 |
| 156 | 0.06 | 0.59 |
| 157 | 0.004 | 0.07 |
| 158 | 0.02 | 0.06 |
| 159 | 0.004 | 0.03 |
| 160 | 0.02 | 0.10 |
| 161 | 0.29 | 0.13 |
| 162 | 0.09 | 0.03 |
| 163 | 0.08 | 0.12 |
| 164 | 0.03 | 0.02 |
| 165 | 3.51 | 2.25 |
| 166 | 0.04 | 0.38 |
| 167 | 0.06 | 0.37 |
| 168 | 0.02 | 0.03 |
| 169 | 0.28 | 1.01 |
| 170 | 0.15 | 0.06 |
| 171 | 0.10 | 0.08 |
| 172 | 0.06 | 0.13 |
| 173 | 0.15 | 0.21 |
| 174 | 0.39 | 2.01 |
| 175 | 0.06 | 0.08 |
| 176 | 0.54 | 0.81 |
| 177 | 0.02 | 0.09 |
| 178 | 0.09 | 0.11 |
| 179 | 0.23 | 1.34 |
| 180 | 0.03 | >6.67 |
| 181 | 0.70 | 0.82 |
| 182 | 0.87 | 0.79 |
| 183 | 2.06 | 2.37 |
| 184 | 1.42 | 1.95 |
| 185 | >20 | >20 |
| 186 | 0.05 | 0.14 |
| 187 | 1.60 | 2.85 |
| 188 | 0.24 | 1.59 |
| 189 | 1.94 | 1.93 |
| 190 | 0.60 | 1.16 |
| 191 | 0.11 | 0.26 |
| 192 | 0.02 | 0.07 |
| 193 | 1.39 | 2.11 |
| 194 | 0.05 | 0.07 |
| 195 | 4.42 | 4.32 |
| 196 | 0.13 | 0.10 |
| 197 | 0.13 | 0.15 |
| 198 | >20 | 9.16 |
| 199 | 0.39 | 1.36 |
| 200 | 0.03 | 0.11 |
| 201 | 0.56 | 0.32 |
| 202 | 2.93 | 12.42 |
| 203 | >20 | >6.67 |
| 204 | 1.22 | 0.56 |
| 205 | 0.17 | 2.28 |
| 206 | 0.13 | 0.29 |
| 207 | 0.51 | 0.77 |
| 208 | >20 | >20 |
| 209 | >6.67 | 3.45 |
| 210 | 0.90 | NT |
| 211 | >20 | 11.40 |
| 212 | 0.09 | 0.22 |
| 213 | 0.15 | 0.11 |
| 214 | 0.01 | 0.01 |
| 215 | 0.02 | 0.01 |
| 216 | 0.06 | 0.05 |
| 217 | 0.20 | 0.39 |
| 218 | 0.09 | 0.12 |
| 219 | 2.92 | 3.38 |
| 220 | 0.65 | 1.52 |
| 221 | 0.28 | 0.72 |
| 222 | 0.01 | 0.02 |
| 223 | 0.01 | 0.03 |
| 224 | 0.01 | 0.02 |
| 225 | 3.43 | 4.67 |
| 226 | 1.71 | 1.73 |
| 227 | >20 | >20 |
| 228 | 0.09 | 0.04 |
| 229 | 0.04 | 0.06 |
| 230 | 2.13 | 0.94 |
| 231 | 0.07 | 0.10 |
| 232 | >6.67 | >6.67 |
| 233 | 0.04 | 0.17 |
| 234 | 0.05 | 0.08 |
| 235 | 0.01 | 0.01 |
| 236 | 0.01 | 0.01 |
| 237 | 0.01 | 0.01 |
| 238 | 0.02 | 0.04 |
| 239 | 0.03 | 0.03 |
| 240 | 0.01 | 0.02 |
| 241 | 0.01 | 0.17 |
| 242 | 0.01 | 0.09 |
| 243 | 0.31 | 0.45 |
| 244 | 0.002 | 0.01 |
| 245 | 0.01 | 0.02 |
| 246 | 0.003 | 0.05 |
| 247 | >20 | >20 |
| 248 | 0.25 | 0.53 |
| 249 | 0.12 | 0.83 |
| 250 | 0.05 | 0.09 |
| 251 | >6.67 | 1.98 |
| 252 | 0.47 | 0.45 |
| 253 | 0.01 | 0.01 |

TABLE 1-continued

| Ex. | Human IC$_{50}$ (μM) | Rat IC$_{50}$ (μM) |
|---|---|---|
| 254 | 0.18 | 0.10 |
| 255 | 4.29 | 0.70 |
| 256 | >6.67 | >6.67 |
| 257 | 0.04 | 0.02 |
| 258 | 0.02 | NT |
| 259 | 0.03 | 0.09 |
| 260 | 0.02 | 0.05 |
| 261 | 0.15 | 0.34 |
| 262 | 0.56 | 1.64 |
| 263 | 1.13 | 1.46 |
| 264 | 0.43 | 1.30 |
| 265 | 0.20 | 0.39 |
| 266 | 0.12 | 0.45 |
| 267 | 2.48 | 1.87 |
| 268 | 0.05 | 0.15 |
| 269 | 0.13 | 0.18 |
| 270 | 0.38 | 0.83 |
| 271 | 0.18 | 0.84 |
| 272 | 0.04 | 0.20 |
| 273 | 0.57 | 0.68 |
| 274 | 0.04 | 0.26 |
| 275 | 0.17 | 0.19 |
| 276 | 0.01 | 0.04 |
| 277 | 0.02 | 0.05 |
| 278 | 0.63 | 0.67 |
| 279 | 0.38 | >6.67 |
| 280 | >6.67 | >6.67 |
| 281 | 1.78 | 2.62 |
| 282 | 0.31 | 0.13 |
| 283 | 2.99 | 8.52 |
| 284 | 1.67 | 0.55 |
| 285 | >6.67 | >6.67 |
| 286 | >6.67 | >6.67 |
| 287 | >6.67 | >6.67 |
| 288 | 2.99 | 2.02 |
| 289 | 2.84 | 0.29 |
| 290 | 0.41 | 0.10 |
| 291 | 0.27 | 0.17 |
| 292 | 0.12 | 0.05 |
| 293 | 9.34 | 3.49 |
| 294 | 3.39 | 2.94 |
| 295 | 4.66 | 10.43 |
| 296 | 0.42 | 0.12 |
| 297 | 0.45 | 1.08 |
| 298 | 0.45 | 0.37 |
| 299 | >6.67 | 3.00 |
| 300 | 4.07 | 2.00 |
| 301 | 3.43 | 8.97 |
| 302 | 0.84 | 9.46 |
| 303 | 2.03 | >6.67 |
| 304 | >6.67 | NT |
| 305 | 1.78 | 1.12 |
| 306 | 0.61 | 1.21 |
| 307 | 0.02 | 0.03 |
| 308 | 0.34 | 0.36 |
| 309 | >6.67 | 1.42 |
| 310 | 0.28 | 0.07 |
| 311 | 5.00 | >20 |
| 312 | 0.22 | 0.45 |
| 313 | 0.83 | 0.56 |
| 314 | 0.19 | 0.16 |
| 315 | 1.54 | 5.52 |
| 316 | 0.09 | 1.18 |
| 317 | 0.13 | 0.61 |
| 318 | 0.003 | >6.67 |
| 319 | 0.03 | 0.24 |
| 320 | 0.005 | 0.02 |
| 321 | 0.33 | 0.18 |
| 322 | 0.16 | 0.01 |
| 323 | 0.56 | 0.67 |
| 324 | 0.81 | 0.10 |
| 325 | 0.05 | 0.30 |
| 326 | 0.21 | 0.60 |
| 327 | 0.26 | 0.89 |
| 328 | 0.08 | 0.25 |
| 329 | 1.12 | 0.12 |
| 330 | 0.01 | 0.05 |
| 331 | 0.07 | 0.50 |
| 332 | 0.01 | 2.04 |
| 333 | 0.01 | 0.04 |
| 334 | 0.04 | 0.04 |
| 335 | 0.03 | 0.15 |
| 336 | 0.05 | 1.64 |
| 337 | 0.02 | 0.17 |
| 338 | 0.03 | 0.40 |
| 339 | 0.03 | 0.19 |
| 340 | 0.05 | 0.26 |
| 341 | 0.06 | 0.15 |
| 342 | 0.18 | 0.06 |
| 343 | 0.04 | 0.06 |
| 344 | >20 | >20 |
| 345 | 0.08 | 0.19 |
| 346 | 1.38 | >6.67 |
| 347 | 1.86 | 1.32 |
| 348 | 3.02 | 3.22 |
| 349 | 0.50 | 2.35 |
| 350 | 0.06 | 0.03 |
| 351 | >6.67 | 0.75 |
| 352 | 1.01 | >6.67 |
| 353 | 0.01 | 0.24 |
| 354 | 0.01 | 0.25 |
| 355 | 0.03 | 0.06 |
| 356 | 0.11 | 0.29 |
| 357 | 0.02 | 0.14 |
| 358 | 0.07 | 0.07 |
| 359 | 0.63 | 0.32 |
| 360 | 0.65 | 0.25 |
| 361 | 0.10 | 1.53 |
| 362 | 0.003 | 0.19 |
| 363 | 0.01 | 0.06 |
| 364 | >6.67 | 1.18 |
| 365 | 1.09 | >6.67 |
| 366 | 0.23 | 0.13 |
| 367 | 1.30 | >6.67 |
| 368 | 0.13 | 0.02 |
| 369 | 0.19 | 0.01 |
| 370 | NT | 2.61 |
| 371 | 2.19 | >6.67 |
| 372 | 0.03 | 0.33 |
| 373 | 0.07 | 0.18 |
| 374 | 0.19 | 0.004 |
| 375 | 0.07 | >6.67 |
| 376 | 0.07 | 0.11 |
| 377 | 2.69 | 1.41 |
| 378 | 0.04 | 0.04 |
| 379 | 0.04 | 0.07 |
| 380 | 0.05 | 0.23 |
| 381 | 0.01 | 0.04 |
| 382 | 0.02 | 0.04 |
| 383 | 0.14 | 0.16 |
| 384 | 0.02 | 0.04 |
| 385 | 0.13 | 0.82 |
| 386 | >6.67 | >6.67 |
| 387 | 0.10 | 0.55 |
| 388 | NT | NT |
| 389 | 0.05 | 0.32 |
| 390 | 0.01 | 0.09 |
| 391 | NT | NT |
| 392 | 0.12 | 1.54 |
| 393 | 0.05 | 0.12 |
| 394 | 0.17 | 0.29 |

NT = not tested

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. A compound selected from the group consisting of:
[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine;
(4-tert-Butyl-phenyl)-[2-piperidin-1-yl-7-(3-trifluoromethyl-pyridin-2-yl)-6,7,8,9-tetrahydro-5H-pyrimido[4,5-d]azepin-4-yl]-amine;
1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidine-4-carboxylic acid;
1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-4-ol;
(R)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol;
(S)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol;
1-[4-({2-Piperidin-1-yl-7-[3-(trifluoromethyl)pyridin-2-yl]-6,7,8,9-tetrahydro-5H-pyrimido[4,5-d]azepin-4-yl}amino)phenyl]ethanone;
N-[3-Fluoro-4-(trifluoromethyl)phenyl]-2-piperidin-1-yl-7-[3-(trifluoromethyl)pyridin-2-yl]-6,7,8,9-tetrahydro-5H-pyrimido[4,5-d]azepin-4-amine;
N,N-Dimethyl-4-({2-piperidin-1-yl-7-[3-(trifluoromethyl)pyridin-2-yl]-6,7,8,9-tetrahydro-5H-pyrimido[4,5-d]azepin-4-yl}amino)benzenesulfonamide;
N-[4-(1,1-Dimethylethyl)-3-nitrophenyl]-2-piperidin-1-yl-7-[3-(trifluoromethyl)pyridin-2-yl]-6,7,8,9-tetrahydro-5H-pyrimido[4,5-d]azepin-4-amine;
N-[4-(Methylsulfanyl)phenyl]-2-piperidin-1-yl-7-[3-(trifluoromethyl)pyridin-2-yl]-6,7,8,9-tetrahydro-5H-pyrimido[4,5-d]azepin-4-amine;
(2-Fluoro-4-trifluoromethyl-phenyl)-[2-piperidin-1-yl-7-(3-trifluoromethyl-pyridin-2-yl)-6,7,8,9-tetrahydro-5H-pyrimido[4,5-d]azepin-4-yl]-amine;
Methyl 2-methyl-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propanoate;
2-[4-({2-Piperidin-1-yl-7-[3-(trifluoromethyl)pyridin-2-yl]-6,7,8,9-tetrahydro-5H-pyrimido[4,5-d]azepin-4-yl}amino) phenyl]propan-2-ol;
1,1,1-Trifluoro-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propan-2-ol;
2-Methyl-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propanoic acid;
4(1,1-Dimethylethyl)-N1-{2-piperidin-1-yl-7-[3-(trifluoromethyl)pyridin-2-yl]-6,7,8,9-tetrahydro-5H-pyrimido[4,5-d]azepin-4-yl}benzene-1,3-diamine;
2-[3-(Methyloxy)piperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine;
N-[3-Chloro-4-(trifluoromethyl)phenyl]-2-piperidin-1-yl-7-[3-(trifluoromethyl)pyridin-2-yl]-6,7,8,9-tetrahydro-5H-pyrimido[4,5-d]azepin-4-amine;
2-(3,3-Difluoropiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine;
2-(4-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine;
2-(3-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine;
2-(4,4-Difluoropiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine;
[1-(4-{[4-(Trifluoromethyl)phenyl]amino}-7-[3-(trifluoromethyl)pyridin-2-yl]-6,7,8,9-tetrahydro-5H-pyrimido[4,5-d]azepin-2-yl)piperidin-2-yl]methanol;
2-[(2S)-2-Methylpiperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine;
2-[(2R)-2-Methylpiperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine;
7-[3-(Ethylsulfonyl)pyridin-2-yl]-2-piperidin-1-yl-N-[4-(trifluoromethyl)phenyl]-6,7,8,9-tetrahydro-5H-pyrimido[4,5-d]azepin-4-amine;
2-(2-Piperidin-1-yl-4-{[4-(trifluoromethyl)phenyl]amino}-5,6,8,9-tetrahydro-7H-pyrimido[4,5-d]azepin-7-yl)pyridine-3-sulfonamide;
N-Cyclopropyl-2-(2-piperidin-1-yl-4-{[4-(trifluoromethyl)phenyl]amino}-5,6,8,9-tetrahydro-7H-pyrimido[4,5-d]azepin-7-yl)pyridine-3-sulfonamide;
N-(1-Methylethyl)-2-(2-piperidin-1-yl-4-{[4-(trifluoromethyl)phenyl]amino}-5,6,8,9-tetrahydro-7H-pyrimido[4,5-d]azepin-7-yl)pyridine-3-sulfonamide;
2-Piperidin-1-yl-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine;
2-Methyl-2-{4-[2-piperidin-1-yl-7-(3-trifluoromethyl-pyridin-2-yl)-6,7,8,9-tetrahydro-5H-pyrimido[4,5-d]azepin-4-ylamino]-phenyl}-propan-1-ol;
2-Methyl-2-{4-[2-piperidin-1-yl-7-(3-trifluoromethyl-pyridin-2-yl)-6,7,8,9-tetrahydro-5H-pyrimido[4,5-d]azepin-4-ylamino]-phenyl}-propionitrile;
2-Fluoro-4-[2-piperidin-1-yl-7-(3-trifluoromethyl-pyridin-2-yl)-6,7,8,9-tetrahydro-5H-pyrimido[4,5-d]azepin-4-ylamino]-benzoic acid methyl ester;
4-[2-Piperidin-1-yl-7-(3-trifluoromethyl-pyridin-2-yl)-6,7,8,9-tetrahydro-5H-pyrimido[4,5-d]azepin-4-ylamino]-benzoic acid methyl ester;
4-[2-Piperidin-1-yl-7-(3-trifluoromethyl-pyridin-2-yl)-6,7,8,9-tetrahydro-5H-pyrimido[4,5-d]azepin-4-ylamino]-benzoic acid;
2-{2-Fluoro-4-[2-piperidin-1-yl-7-(3-trifluoromethyl-pyridin-2-yl)-6,7,8,9-tetrahydro-5H-pyrimido[4,5-d]azepin-4-ylamino]-phenyl}-propan-2-ol;
5-Chloro-6-[2-piperidin-1-yl-4-(4-trifluoromethyl-phenylamino)-5,6,8,9-tetrahydro-pyrimido[4,5-d]azepin-7-yl]-nicotinic acid methyl ester; and pharmaceutically acceptable salts thereof.

2. A pharmaceutical composition, comprising:
(a) a therapeutically effective amount of a compound selected from the group consisting of:
[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine;
(4-tert-Butyl-phenyl)-[2-piperidin-1-yl-7-(3-trifluoromethyl-pyridin-2-yl)-6,7,8,9-tetrahydro-5H-pyrimido[4,5-d]azepin-4-yl]-amine;
1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidine-4-carboxylic acid;
1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-4-ol;

(R)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol;
(S)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol;
1-[4-({2-Piperidin-1-yl-7-[3-(trifluoromethyl)pyridin-2-yl]-6,7,8,9-tetrahydro-5H-pyrimido[4,5-d]azepin-4-yl}amino)phenyl]ethanone;
N-[3-Fluoro-4-(trifluoromethyl)phenyl]-2-piperidin-1-yl-7-[3-(trifluoromethyl)pyridin-2-yl]-6,7,8,9-tetrahydro-5H-pyrimido[4,5-d]azepin-4-amine;
N,N-Dimethyl-4-({2-piperidin-1-yl-7-[3-(trifluoromethyl)pyridin-2-yl]-6,7,8,9-tetrahydro-5H-pyrimido[4,5-d]azepin-4-yl}amino)benzenesulfonamide;
N-[4-(1,1-Dimethylethyl)-3-nitrophenyl]-2-piperidin-1-yl-7-[3-(trifluoromethyl)pyridin-2-yl]-6,7,8,9-tetrahydro-5H-pyrimido[4,5-d]azepin-4-amine;
N-[4-(Methylsulfanyl)phenyl]-2-piperidin-1-yl-7-[3-(trifluoromethyl)pyridin-2-yl]-6,7,8,9-tetrahydro-5H-pyrimido[4,5-d]azepin-4-amine;
(2-Fluoro-4-trifluoromethyl-phenyl)-[2-piperidin-1-yl-7-(3-trifluoromethyl-pyridin-2-yl)-6,7,8,9-tetrahydro-5H-pyrimido[4,5-d]azepin-4-yl]-amine;
Methyl 2-methyl-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propanoate;
2-[4-({2-Piperidin-1-yl-7-[3-(trifluoromethyl)pyridin-2-yl]-6,7,8,9-tetrahydro-5H-pyrimido[4,5-d]azepin-4-yl}amino)phenyl]propan-2-ol;
1,1,1-Trifluoro-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propan-2-ol;
2-Methyl-2-[4-({2-piperidin-1-yl-7-[3-(trifluoromethyl)pyridin-2-yl]-6,7,8,9-tetrahydro-5H-pyrimido[4,5-d]azepin-4-yl}amino)phenyl]propanoic acid;
4(1,1-Dimethylethyl)-N1-{2-piperidin-1-yl-7-[3-(trifluoromethyl)pyridin-2-yl]-6,7,8,9-tetrahydro-5H-pyrimido[4,5-d]azepin-4-yl}benzene-1,3-diamine;
2-[3-(Methyloxy)piperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine;
N-[3-Chloro-4-(trifluoromethyl)phenyl]-2-piperidin-1-yl-7-[3-(trifluoromethyl)pyridin-2-yl]-6,7,8,9-tetrahydro-5H-pyrimido[4,5-d]azepin-4-amine;
2-(3,3-Difluoropiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine;
2-(4-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine;
2-(3-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine;
2-(4,4-Difluoropiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine;
[1-(4-{[4-(Trifluoromethyl)phenyl]amino}-7-[3-(trifluoromethyl)pyridin-2-yl]-6,7,8,9-tetrahydro-5H-pyrimido[4,5-d]azepin-2-yl)piperidin-2-yl]methanol;
2-[(2S)-2-Methylpiperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine;
2-[(2R)-2-Methylpiperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine;
7-[3-(Ethylsulfonyl)pyridin-2-yl]-2-piperidin-1-yl-N-[4-(trifluoromethyl)phenyl]-6,7,8,9-tetrahydro-5H-pyrimido[4,5-d]azepin-4-amine;
2-(2-Piperidin-1-yl-4-{[4-(trifluoromethyl)phenyl]amino}-5,6,8,9-tetrahydro-7H-pyrimido[4,5-d]azepin-7-yl)pyridine-3-sulfonamide;
N-Cyclopropyl-2-(2-piperidin-1-yl-4-{[4-(trifluoromethyl)phenyl]amino}-5,6,8,9-tetrahydro-7H-pyrimido[4,5-d]azepin-7-yl)pyridine-3-sulfonamide;
N-(1-Methylethyl)-2-(2-piperidin-1-yl-4-{[4-(trifluoromethyl)phenyl]amino}-5,6,8,9-tetrahydro-7H-pyrimido[4,5-d]azepin-7-yl)pyridine-3-sulfonamide;
2-Piperidin-1-yl-7-[3-(trifluoromethyl)pyridin-2-yl]-N-{4-[(trifluoromethyl)sulfonyl]phenyl}-6,7,8,9-tetrahydro-5H-pyrimido[4,5-d]azepin-4-amine;
2-Methyl-2-{4-[2-piperidin-1-yl-7-(3-trifluoromethyl-pyridin-2-yl)-6,7,8,9-tetrahydro-5H-pyrimido[4,5-d]azepin-4-ylamino]-phenyl}-propan-1-ol;
2-Methyl-2-{4-[2-piperidin-1-yl-7-(3-trifluoromethyl-pyridin-2-yl)-6,7,8,9-tetrahydro-5H-pyrimido[4,5-d]azepin-4-ylamino]-phenyl}-propionitrile;
2-Fluoro-4-[2-piperidin-1-yl-7-(3-trifluoromethyl-pyridin-2-yl)-6,7,8,9-tetrahydro-5H-pyrimido[4,5-d]azepin-4-ylamino]-benzoic acid methyl ester;
4-[2-Piperidin-1-yl-7-(3-trifluoromethyl-pyridin-2-yl)-6,7,8,9-tetrahydro-5H-pyrimido[4,5-d]azepin-4-ylamino]-benzoic acid methyl ester;
4-[2-Piperidin-1-yl-7-(3-trifluoromethyl-pyridin-2-yl)-6,7,8,9-tetrahydro-5H-pyrimido[4,5-d]azepin-4-ylamino]-benzoic acid;
2-{2-Fluoro-4-[2-piperidin-1-yl-7-(3-trifluoromethyl-pyridin-2-yl)-6,7,8,9-tetrahydro-5H-pyrimido[4,5-d]azepin-4-ylamino]-phenyl}-propan-2-ol;
5-Chloro-6-[2-piperidin-1-yl-4-(4-trifluoromethyl-phenylamino)-5,6,8,9-tetrahydro-pyrimido [4,5-d]azepin-7-yl]-nicotinic acid methyl ester; and pharmaceutically acceptable salts thereof; and
(b) a pharmaceutically acceptable excipient.

3. A compound which is any one of [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine and pharmaceutically acceptable salts thereof.

4. A compound of claim 3 which is [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine.

5. A compound of claim 3 which is [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine hydrochloride salt.

6. A compound of claim 3 which is [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine sulfate salt.

7. A pharmaceutical composition, comprising:
(a) a therapeutically effective amount of a compound where the compound is any one of [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine and pharmaceutically acceptable salts thereof; and
(b) a pharmaceutically acceptable excipient.

8. A pharmaceutical composition of claim 7, where the compound is [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine.

9. A pharmaceutical composition of claim 7, where the compound is [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine hydrochloride salt.

10. A pharmaceutical composition of claim 7, where the compound is [2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine sulfate salt.

11. A compound selected from the group consisting of:
[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine hydrochloride salt;
[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine sulfate salt;
1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidine-4-carboxylic acid trifluoro acetic acid salt;
1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-4-ol trifluoro acetic acid salt;
(R)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol trifluoro acetic acid salt;
(S)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol trifluoro acetic acid salt;
N-(1-Methyl-1,2,3,4-tetrahydroquinolin-7-yl)-2-piperidin-1-yl-7-[3-(trifluoromethyl)pyridin-2-yl]-6,7,8,9-tetrahydro-5H-pyrimido[4,5-d]azepin-4-amine hydrochloride salt;
2-Piperidin-1-yl-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine hydrochloride salt;
2-[3-(Methyloxy)piperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt;
N-[3-Chloro-4-(trifluoromethyl)phenyl]-2-piperidin-1-yl-7-[3-(trifluoromethyl)pyridin-2-yl]-6,7,8,9-tetrahydro-5H-pyrimido[4,5-d]azepin-4-amine trifluoroacetic acid salt;
2-(3,3-Difluoropiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt;
2-(4-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt;
2-(3-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt; and
2-(2-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine hydrochloride salt.

12. A pharmaceutical composition, comprising:
(a) a therapeutically effective amount of a compound selected from the group consisting of:
[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine hydrochloride salt;
[2-Piperidin-1-yl-7-(3-trifluoromethyl-pyridin-2-yl)-6,7,8,9-tetrahydro-5H-pyrimido[4,5-d]azepin-4-yl]-(4-trifluoromethyl-phenyl)-amine sulfate salt;
1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidine-4-carboxylic acid trifluoro acetic acid salt;
1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-4-ol trifluoro acetic acid salt;
(R)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol trifluoro acetic acid salt;
(S)-1-[4-(4-Trifluoromethyl-phenylamino)-7-(3-trifluoromethyl-pyridin-2-yl)-6,7,8,9-tetrahydro-5H-pyrimido[4,5-d]azepin-2-yl]-piperidin-3-ol trifluoro acetic acid salt;
N-(1-Methyl-1,2,3,4-tetrahydroquinolin-7-yl)-2-piperidin-1-yl-7-[3-(trifluoromethyl)pyridin-2-yl]-6,7,8,9-tetrahydro-5H-pyrimido[4,5-d]azepin-4-amine hydrochloride salt;
2-Piperidin-1-yl-7-[3-(trifluoromethyl)pyridin-2-yl]-N-(1,4,4-trimethyl-1,2,3,4-tetrahydroquinolin-7-yl)-6,7,8,9-tetrahydro-5H-pyrimido[4,5-d]azepin-4-amine hydrochloride salt;
2-[3-(Methyloxy)piperidin-1-yl]-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt;
N-[3-Chloro-4-(trifluoromethyl)phenyl]-2-piperidin-1-yl-7-[3-(trifluoromethyl)pyridin-2-yl]-6,7,8,9-tetrahydro-5H-pyrimido[4,5-d]azepin-4-amine trifluoroacetic acid salt;
2-(3,3-Difluoropiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt;
2-(4-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt;
2-(3-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine trifluoroacetic acid salt; and
2-(2-Methylpiperidin-1-yl)-N-[4-(trifluoromethyl)phenyl]-7-[3-(trifluoromethyl)pyridin-2-yl]-6,7,8,9-tetrahydro-5H-pyrimido[4,5-d]azepin-4-amine hydrochloride salt; and
(b) a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 8,673,895 B2 | Page 1 of 1 |
| APPLICATION NO. | : 11/726756 | |
| DATED | : March 18, 2014 | |
| INVENTOR(S) | : Branstetter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1766 days.

Signed and Sealed this
Eleventh Day of August, 2015

Michelle K. Lee
*Director of the United States Patent and Trademark Office*